US012686661B2

(12) United States Patent
Suh et al.

(10) Patent No.: US 12,686,661 B2
(45) Date of Patent: Jul. 21, 2026

(54) COMPOUND AND ORGANIC LIGHT EMITTING DEVICE COMPRISING THE SAME

(71) Applicant: LG CHEM, LTD., Seoul (KR)

(72) Inventors: Sang Duk Suh, Daejeon (KR); Min Woo Jung, Daejeon (KR); Jungha Lee, Daejeon (KR); Su Jin Han, Daejeon (KR); Seulchan Park, Daejeon (KR); Sunghyun Hwang, Daejeon (KR); Dong Hoon Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 1014 days.

(21) Appl. No.: 17/632,875

(22) PCT Filed: Nov. 6, 2020

(86) PCT No.: PCT/KR2020/015464
§ 371 (c)(1),
(2) Date: Feb. 4, 2022

(87) PCT Pub. No.: WO2021/125552
PCT Pub. Date: Jun. 24, 2021

(65) Prior Publication Data

US 2022/0306616 A1 Sep. 29, 2022

(30) Foreign Application Priority Data

Dec. 20, 2019 (KR) ........................ 10-2019-0172476
Nov. 3, 2020 (KR) ........................ 10-2020-0145518

(51) Int. Cl.
*C07D 209/86* (2006.01)
*C07D 403/04* (2006.01)
(Continued)

(52) U.S. Cl.
CPC ......... *C07D 209/86* (2013.01); *C07D 403/04* (2013.01); *C07D 405/14* (2013.01);
(Continued)

(58) Field of Classification Search
CPC ........... H10K 85/6572; H10K 85/6574; H10K 85/6576; C08B 2200/05; C07D 405/04; C07D 405/14; C07D 409/14
See application file for complete search history.

(56) References Cited

U.S. PATENT DOCUMENTS

2014/0158992 A1 6/2014 Xia et al.
2014/0332793 A1 11/2014 Park et al.
(Continued)

FOREIGN PATENT DOCUMENTS

EP 1995292 A1 11/2008
EP 3808744 A1 4/2021
(Continued)

OTHER PUBLICATIONS

Machine-generated English-language translation of WO-2018174682-A1.*
(Continued)

*Primary Examiner* — Vu A Nguyen
(74) *Attorney, Agent, or Firm* — Bryan Cave Leighton Paisner LLP

(57) ABSTRACT

Provided is a compound of Chemical Formula 1:

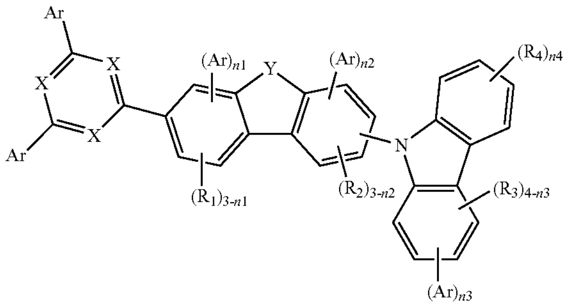

wherein:
each X is independently N or CH, provided that at least one X is N;
(Continued)

Y is O or S;
each Ar is independently substituted or unsubstituted: $C_{6-60}$ aryl or $C_{5-60}$ heteroaryl containing N, O or S;
each $R_1$, $R_2$, $R_3$, and $R_4$ independently is hydrogen, deuterium, halogen, cyano, or substituted or unsubstituted: $C_{1-60}$ alkyl, $C_{1-60}$ alkoxy, $C_{2-60}$ alkenyl, $C_{2-60}$ alkynyl, $C_{3-60}$ cycloalkyl, $C_{6-60}$ aryl, or $C_{2-60}$ heteroaryl containing N, O or S, or two adjacent $R_4s$ combine to form a $C_{4-60}$ aliphatic or aromatic ring;
n1, n2, and n3 are each independently 0 or 1, and
n4 is 1 to 4,
provided that at least one of Ar is substituted with deuterium, or at least one of $R_1$, $R_2$, $R_3$, or $R_4$ is, or is substituted with, one or more deuterium, and an organic light-emitting diode comprising same.

15 Claims, 1 Drawing Sheet

(51) Int. Cl.

| | |
|---|---|
| ***C07D 405/14*** | (2006.01) |
| ***C07D 409/14*** | (2006.01) |
| ***C07D 487/04*** | (2006.01) |
| ***C07D 491/048*** | (2006.01) |
| ***C07D 495/04*** | (2006.01) |
| ***H10K 50/11*** | (2023.01) |
| ***H10K 50/15*** | (2023.01) |
| ***H10K 50/16*** | (2023.01) |
| ***H10K 85/60*** | (2023.01) |

(52) U.S. Cl.
CPC ......... *C07D 409/14* (2013.01); *C07D 487/04* (2013.01); *C07D 491/048* (2013.01); *C07D 495/04* (2013.01); *H10K 50/11* (2023.02); *H10K 50/157* (2023.02); *H10K 50/16* (2023.02); *H10K 85/6572* (2023.02); *H10K 85/6574* (2023.02); *H10K 85/6576* (2023.02); *C07B 2200/05* (2013.01)

(56) References Cited

U.S. PATENT DOCUMENTS

| | | | | |
|---|---|---|---|---|
| 2017/0117488 | A1 | 4/2017 | Ahn et al. | |
| 2018/0010040 | A1 * | 1/2018 | Pan | ...................... C07D 209/86 |
| 2018/0019410 | A1 | 1/2018 | Sim et al. | |
| 2019/0047991 | A1 | 2/2019 | Jung et al. | |
| 2019/0067597 | A1 | 2/2019 | Takeda | |
| 2020/0119285 | A1 | 4/2020 | No et al. | |
| 2020/0266355 | A1 | 8/2020 | Park et al. | |
| 2020/0381629 | A1 | 12/2020 | No et al. | |
| 2021/0184131 | A1 | 6/2021 | Jung et al. | |
| 2021/0273164 | A1 | 9/2021 | Song et al. | |
| 2022/0006022 | A1 | 1/2022 | Suh et al. | |
| 2022/0396568 | A1 | 12/2022 | Yang et al. | |

FOREIGN PATENT DOCUMENTS

| | | | | |
|---|---|---|---|---|
| EP | 4056566 | A1 | 9/2022 | |
| JP | 2009-277790 | A | 11/2009 | |
| JP | 2017-513220 | A | 5/2017 | |
| JP | 6319228 | | 5/2018 | |
| JP | 2019-513131 | A | 5/2019 | |
| JP | 7102679 | B2 | 7/2022 | |
| JP | 2023-500009 | A | 1/2023 | |
| KR | 10-2000-0051826 | | 8/2000 | |
| KR | 10-2013-0084963 | | 7/2013 | |
| KR | 10-2015-0111534 | | 10/2015 | |
| KR | 10-2017-0111387 | | 10/2017 | |
| KR | 10-2018-0008293 | | 1/2018 | |
| KR | 10-2018-0027468 | | 3/2018 | |
| KR | 10-2018-0051355 | | 5/2018 | |
| KR | 10-1857632 | B1 | 5/2018 | |
| KR | 10-2018-008427 | | 10/2018 | |
| KR | 10-2018-0108425 | | 10/2018 | |
| KR | 10-2019-0007789 | | 1/2019 | |
| KR | 10-2019-0030963 | | 3/2019 | |
| KR | 10-1961334 | | 3/2019 | |
| KR | 10-2054806 | B1 | 12/2019 | |
| WO | WO-2018174682 | A1 * | 9/2018 | ........... C07D 209/86 |
| WO | 2020-022860 | | 1/2020 | |
| WO | 2021/091259 | A1 | 5/2021 | |

OTHER PUBLICATIONS

Tsuji et al., "The hydrogen/deuterium isotope effect of the host material on the lifetime of organic light-emitting diodes," Chem. Commun. 50(94):14870-14872 (2014).

* cited by examiner

【FIG. 1】
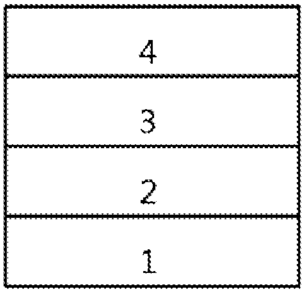
【FIG. 2】
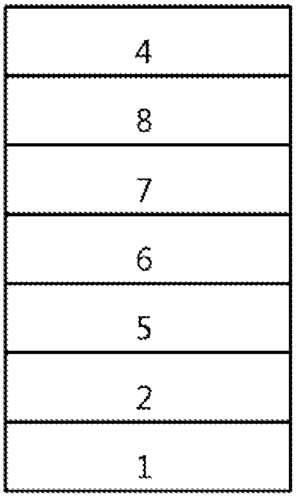

COMPOUND AND ORGANIC LIGHT EMITTING DEVICE COMPRISING THE SAME

CROSS-REFERENCE TO RELATED APPLICATION(S)

The present application is a National Stage Application of International Application No. PCT/KR2020/015464 filed on Nov. 6, 2020, which claims priority to Korean Patent Application No. 10-2019-0172476, filed on Dec. 20, 2019, and Korean Patent Application No. 10-2020-0145518, filed on Nov. 3, 2020 in the Korean Intellectual Property Office, respectively, the disclosures of which are incorporated herein by reference in their entirety.

TECHNICAL FIELD

The present disclosure relates to a novel compound and an organic light emitting device including the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer can be formed of a hole injection layer, a hole transport layer, a light emitting layer, an electron transport layer, an electron injection layer, and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in the organic light emitting devices as described above.

Meanwhile, recently, an organic light emitting device manufactured by using a solution process, particularly an inkjet process, instead of the existing deposition process has been developed in order to reduce process costs. In the early days, it was attempted to develop an organic light emitting device by coating all organic light emitting device layers using a solution process. However, there is a limitation in development with the current technology, so a hybrid process in which only HIL, HTL, and EML are subjected to the solution process in the normal-type structure, and subsequent processes are subjected to the existing deposition process is being studied.

Accordingly, in the present disclosure, there is provided a novel material for an organic light emitting device that can be used in an organic light emitting device and can be deposited by a solution process at the same time.

Background Art Literature

PATENT LITERATURE (Patent Literature 0001) Korean Unexamined Patent Publication No. 10-2000-0051826

BRIEF DESCRIPTION

Technical Problem

The present disclosure relates to a novel compound and an organic light emitting device including the same.

Technical Solution

In the present disclosure, there is provided a compound of the following Chemical Formula 1:

<Chemical Formula 1>

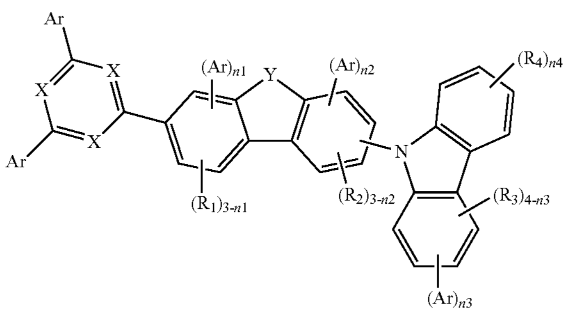

wherein in the Chemical Formula 1:

each X is independently N or CH, provided that at least one of X is N;

Y is O or S;

each Ar is independently substituted or unsubstituted $C_{6-60}$ aryl, or substituted or unsubstituted $C_{5-60}$ heteroaryl containing at least one heteroatom selected from the group consisting of N, O and S;

$R_1$, $R_2$, and $R_3$ are each independently hydrogen, deuterium, halogen, cyano, substituted or unsubstituted $C_{1-60}$ alkyl, substituted or unsubstituted $C_{1-60}$ alkoxy, substituted or unsubstituted $C_{2-60}$ alkenyl, substituted or unsubstituted $C_{2-60}$ alkynyl, substituted or unsubstituted $C_{3-60}$ cycloalkyl, substituted or unsubstituted $C_{6-60}$ aryl, or substituted or unsubstituted $C_{2-60}$ heteroaryl containing at least one heteroatom selected from the group consisting of N, O and S;

each $R_4$ is independently hydrogen, deuterium, halogen, cyano, substituted or unsubstituted $C_{1-60}$ alkyl, substituted or unsubstituted $C_{1-60}$ alkoxy, substituted or unsubstituted $C_{2-60}$ alkenyl, substituted or unsubstituted $C_{2-60}$ alkynyl, substituted or unsubstituted $C_{3-60}$ cycloalkyl, substituted or unsubstituted $C_{6-60}$ aryl, or substituted or unsubstituted $C_{2-60}$ heteroaryl containing at least one heteroatom selected from the group consisting of N, O and S, or two adjacent $R_4$s combine with each other to form a $C_{4-60}$ aliphatic or aromatic ring;

n1, n2, and n3 are each independently 0 or 1; and n4 is an integer of 1 to 4, provided that at least one of Ar is substituted with one or more deuterium, at least one of $R_1$, $R_2$, $R_3$, or $R_4$ is substituted with one or more deuterium, or at least one of $R_1$, $R_2$, $R_3$, and $R_4$ is deuterium.

In addition, there is also provided an organic light emitting device including: a first electrode; a second electrode that is provided opposite to the first electrode; and one or more organic material layers that are provided between the first electrode and the second electrode, wherein at least one layer of the organic material layers includes the compound of Chemical Formula 1.

Advantageous Effects

The compound of Chemical Formula 1 can be used as a material of an organic material layer of an organic light emitting device, and can improve the efficiency, achieve low driving voltage and/or improve lifetime characteristics in the organic light emitting device. In particular, the compound of Chemical Formula 1 can be applied to a solution process, and can be used as a material for hole injection, hole transport, hole injection and transport, light emission, electron transport, or electron injection.

BRIEF DESCRIPTION OF THE DRAWINGS

FIG. 1 shows an example of an organic light emitting device including a substrate 1, an anode 2, a light emitting layer 3, and a cathode 4.

FIG. 2 shows an example of an organic light emitting device including a substrate 1, an anode 2, a hole injection layer 5, a hole transport layer 6, a light emitting layer 7, an electron transport layer 8, and a cathode 4.

DETAILED DESCRIPTION

Hereinafter, embodiments of the present disclosure will be described in more detail to facilitate understanding of the invention.

As used herein, the notation

or means a bond linked to another substituent group.

As used herein, the term "substituted or unsubstituted" means being unsubstituted or substituted with one or more substituents selected from the group consisting of deuterium, a halogen group, a nitrile group, a nitro group, a hydroxyl group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group containing at least one of N, O and S atoms, or being unsubstituted or substituted with a substituent in which two or more substituents of the above-exemplified substituents are connected. For example, "a substituent in which two or more substituents are connected" can be a biphenyl group. That is, a biphenyl group can be an aryl group, or it can also be interpreted as a substituent in which two phenyl groups are connected.

In the present disclosure, the carbon number of a carbonyl group is not particularly limited, but is preferably 1 to 40. Specifically, the carbonyl group can be a compound having the following structural formulae, but is not limited thereto:

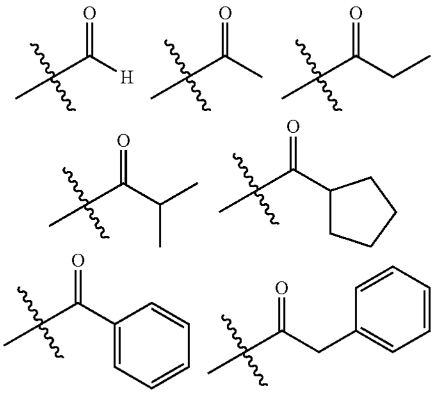

.

In the present disclosure, for an ester group, the oxygen of the ester group can be substituted with a straight-chain, branched-chain, or cyclic alkyl group having 1 to 25 carbon atoms, or an aryl group having 6 to 25 carbon atoms. Specifically, the ester group can be a compound having the following structural formulae, but is not limited thereto:

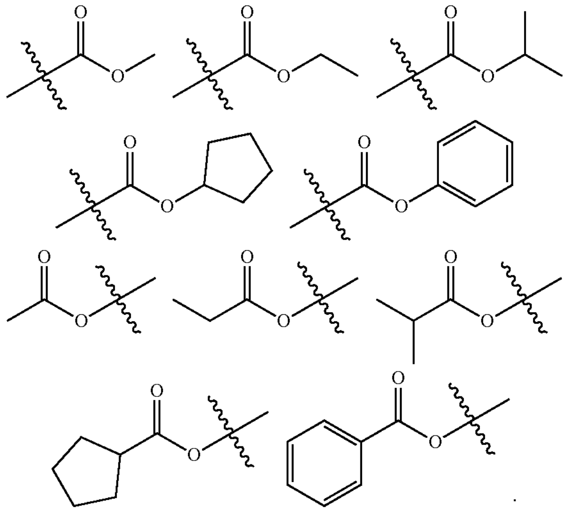

.

In the present disclosure, the carbon number of an imide group is not particularly limited, but is preferably 1 to 25. Specifically, the imide group can be a compound having the following structural formulae, but is not limited thereto:

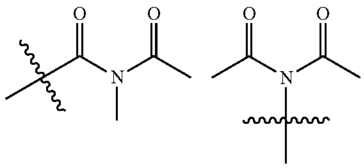

-continued

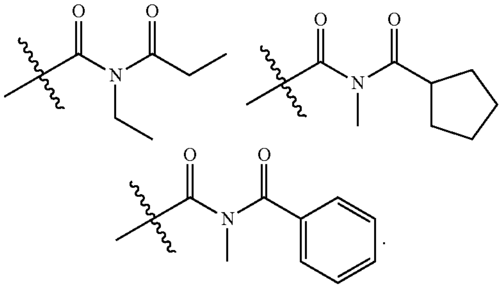

In the present disclosure, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present disclosure, a boron group specifically includes a trimethylboron group, a triethylboron group, a t-butyldimethylboron group, a triphenylboron group, a phenylboron group and the like, but is not limited thereto.

In the present disclosure, examples of a halogen group include fluorine, chlorine, bromine, or iodine.

In the present disclosure, the alkyl group can be straight-chain, or branched-chain, and the carbon number thereof is not particularly limited, but is preferably 1 to 40. According to one embodiment, the carbon number of the alkyl group is 1 to 20. According to another embodiment, the carbon number of the alkyl group is 1 to 10. According to another embodiment, the carbon number of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cycloheptylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methyl-hexyl, and the like, but are not limited thereto.

In the present disclosure, the alkenyl group can be straight-chain or branched-chain, and the carbon number thereof is not particularly limited, but is preferably 2 to 40. According to one embodiment, the carbon number of the alkenyl group is 2 to 20. According to another embodiment, the carbon number of the alkenyl group is 2 to 10. According to another embodiment, the carbon number of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but the carbon number thereof is preferably 3 to 60. According to one embodiment, the carbon number of the cycloalkyl group is 3 to 30. According to another embodiment, the carbon number of the cycloalkyl group is 3 to 20. According to another embodiment, the carbon number of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present disclosure, an aryl group is not particularly limited, but the carbon number thereof is preferably 6 to 60, and it can be a monocyclic aryl group or a polycyclic aryl group. According to one embodiment, the carbon number of the aryl group is 6 to 30. According to one embodiment, the carbon number of the aryl group is 6 to 20. The monocyclic aryl group includes a phenyl group, a biphenyl group, a terphenyl group and the like, but is not limited thereto. The polycyclic aryl group includes a naphthyl group, an anthracenyl group, a phenanthryl group, a pyrenyl group, a perylenyl group, a chrysenyl group, a fluorenyl group, and the like, but is not limited thereto.

In the present disclosure, a fluorenyl group can be substituted, and two substituents can be bonded to each other to form a spiro structure. In the case where the fluorenyl group is substituted,

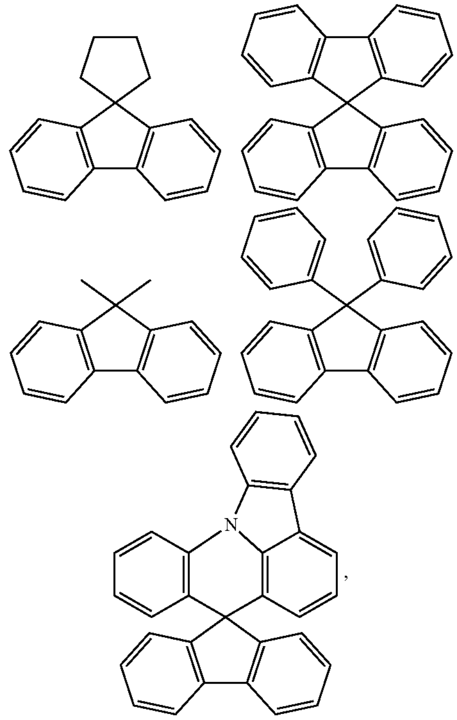
, and the like can be formed. However, the structure is not limited thereto.

In the present disclosure, a heterocyclic group is a heterocyclic group containing at least one of N, O, Si and S as a heterogeneous element, and the carbon number thereof is not particularly limited, but is preferably 2 to 60. Examples of the heterocyclic include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazol group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present disclosure, the aryl group in the aralkyl group, the aralkenyl group, the alkylaryl group, and the arylamine group is the same as the aforementioned examples of the aryl group. In the present disclosure, the alkyl group in the aralkyl group, the alkylaryl group and the alkylamine group is the same as the aforementioned examples of the alkyl group. In the present disclosure, the heteroaryl in the heteroarylamine can apply the aforementioned description of the heterocyclic group. In the present disclosure, the alkenyl group in the aralkenyl group is the same as the aforementioned examples of the alkenyl group. In the present disclosure, the aforementioned description of the aryl group can be applied except that the arylene is a divalent group. In the present disclosure, the aforementioned description of the heterocyclic group can be applied except that the heteroarylene is a divalent group. In the present disclosure, the aforementioned description of the aryl group or cycloalkyl group can be applied except that the hydrocarbon ring is not a monovalent group but formed by combining two substituent groups. In the present disclosure, the aforementioned description of the heterocyclic group can be applied, except that the heterocycle is not a monovalent group but formed by combining two substituent groups.

In the present disclosure, there is provided a compound of Chemical Formula 1.

The compound of Chemical Formula 1 has a structure in which a carbazole group is bonded to a hexagonal ring containing at least one N through a tricyclic heterocyclic ring containing O or S, wherein at least one deuterium is substituted. Thus, it is possible to improve characteristics of the organic light emitting device. In particular, the compound of Chemical Formula 1 includes a polycyclic aromatic core in which a plurality of aromatic rings are connected, thereby increasing molecular rigidity. Therefore, it can exhibit better light emitting properties, and improve quantum efficiency and lifespan.

In particular, the compound of Chemical Formula 1 has a structure in which a nitrogen-containing heterocyclic ring serving as an electron acceptor and a carbazole derivative serving as an electron donor are connected through dibenzofuran or dibenzothiophene, wherein at least one deuterium is substituted therein. Furthermore, this nitrogen-containing heterocyclic ring is connected at the 3rd position of the dibenzofuran/dibenzothiophene, which is the position where conjugation is most likely to occur. Further, this helps to transfer electrons from the opposite ring to which the carbazole derivative serving as an electron donor is substituted to the nitrogen-containing heterocyclic ring, thereby enhancing charge-transfer (CT) properties of the compound. In addition, substituting deuterium in such a structure lowers vibration energy to increase stability of the material, and can help transfer energy to the dopant even in an unstable triplet state. Accordingly, the compound of Chemical Formula 1 has excellent properties in terms of low voltage, high efficiency, and long lifespan when applied to an organic light emitting device.

Specifically, the compound of Chemical Formula 1 can be substituted with at least 4 of deuterium, or 4 to 26 of deuterium.

In addition, according to the specific structure of the carbazole group bonded through a tricyclic heterocyclic ring containing O or S in the Chemical Formula 1, the compound of Chemical Formula 1 can be the following Chemical Formula 1-1 or 1-2:

<Chemical Formula 1-1>

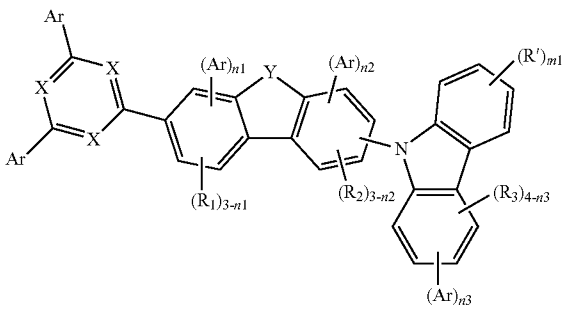

<Chemical Formula 1-2>

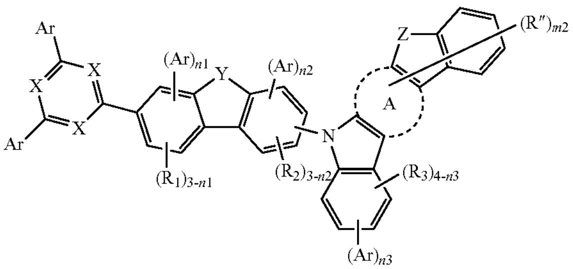

wherein in the Chemical Formulae 1-1 and 1-2:

X, Y, Ar, $R_1$, $R_2$, $R_3$, n1, n2, and n3 are as defined in Chemical Formula 1;

A is a benzene ring fused with two adjacent pentagonal rings;

Z is $C(R_5)_2$, O, S, or N—($R_6$);

each $R_5$ is independently substituted or unsubstituted $C_{1-60}$ alkyl, or substituted or unsubstituted $C_{6-60}$ aryl;

$R_6$ is substituted or unsubstituted $C_{6-60}$ aryl;

R' and R" are each independently hydrogen, deuterium, halogen, cyano, substituted or unsubstituted $C_{1-60}$ alkyl, substituted or unsubstituted $C_{1-60}$ alkoxy, substituted or unsubstituted $C_{2-60}$ alkenyl, substituted or unsubstituted $C_{2-60}$ alkynyl, substituted or unsubstituted $C_{3-60}$ cycloalkyl, substituted or unsubstituted $C_{6-60}$ aryl, or substituted or unsubstituted $C_{2-60}$ heteroaryl containing at least one heteroatom selected from the group consisting of N, O and S;

m1 is an integer of 1 to 4; and m2 is an integer of 1 to 6, provided that at least one of Ar is substituted with one or more deuterium, or at least one of $R_1$, $R_2$, $R_3$, R', and R" is deuterium.

Specifically, all of X can be N.

Specifically, Ar can independently be $C_{6-30}$ aryl, $C_{6-28}$ aryl, or $C_{6-25}$ aryl, or substituted or unsubstituted $C_{5-30}$ heteroaryl, $C_{8-20}$ heteroaryl, or $C_{12-18}$ heteroaryl containing at least one heteroatom selected from the group consisting of N, O and S.

For example, Ar can independently be any one of phenyl, biphenylyl, terphenylyl, quaterphenylyl, naphthyl, phenanthrenyl, triphenylenyl, dimethylfluorenyl, diphenylfluorenyl, 9,9'-spirobifluorenyl, benzofluorenyl, dibenzofuranyl, dibenzothiophenyl, 9-phenyl-9H-carbazolyl, or deuterium-substituted phenyl.

Preferably, in the Chemical Formula 1, at least one of Ar is phenyl, biphenylyl, or phenyl substituted with five deuteriums, and the rest of Ar can be any one of phenyl, biphenylyl, dibenzofuranyl, or dibenzothiophenyl.

Specifically, $R_1$, $R_2$, and $R_3$ can each independently be hydrogen; deuterium; halogen; cyano; substituted or unsubstituted $C_{1-20}$ alkyl, $C_{1-12}$ alkyl, or $C_{1-6}$ alkyl; substituted or unsubstituted $C_{1-20}$ alkoxy, $C_{1-12}$ alkoxy, or $C_{1-6}$ alkoxy; substituted or unsubstituted $C_{2-20}$ alkenyl, $C_{2-12}$ alkenyl, or $C_{2-6}$ alkenyl; substituted or unsubstituted $C_{2-20}$ alkynyl, $C_{2-12}$ alkynyl, or $C_{2-6}$ alkynyl; substituted or unsubstituted $C_{3-30}$ cycloalkyl, $C_{3-25}$ cycloalkyl, or $C_{3-20}$ cycloalkyl; substituted or unsubstituted $C_{6-30}$ aryl, $C_{6-28}$ aryl, or $C_{6-25}$ aryl; or substituted or unsubstituted $C_{5-30}$ heteroaryl, $C_{8-20}$ heteroaryl, or $C_{12-18}$ heteroaryl containing at least one heteroatom selected from the group consisting of N, O and S.

For example, $R_1$, $R_2$, and $R_3$ can each independently be hydrogen or deuterium.

Specifically, each $R_4$ can independently be hydrogen; deuterium; halogen; cyano; substituted or unsubstituted $C_{1-20}$ alkyl, $C_{1-12}$ alkyl, or $C_{1-6}$ alkyl; substituted or unsubstituted $C_{1-20}$ alkoxy, $C_{1-12}$ alkoxy, or $C_{1-6}$ alkoxy; substituted or unsubstituted $C_{2-20}$ alkenyl, $C_{2-12}$ alkenyl, or $C_{2-6}$ alkenyl; substituted or unsubstituted $C_{2-20}$ alkynyl, $C_{2-12}$ alkynyl, or $C_{2-6}$ alkynyl; substituted or unsubstituted $C_{3-30}$ cycloalkyl, $C_{3-25}$ cycloalkyl, or $C_{3-20}$ cycloalkyl; substituted or unsubstituted $C_{6-30}$ aryl, $C_{6-28}$ aryl, or $C_{6-25}$ aryl; or substituted or unsubstituted $C_{5-30}$ heteroaryl, $C_{8-20}$ heteroaryl, or $C_{12-18}$ heteroaryl containing at least one heteroatom selected from the group consisting of N, O and S, or two adjacent $R_4s$ can combine with each other to form a $C_{4-30}$ aliphatic or aromatic ring in which deuterium is substituted or unsubstituted, a $C_{4-28}$ aliphatic or aromatic ring in which deuterium is substituted or unsubstituted, or a $C_{4-25}$ aliphatic or aromatic ring in which deuterium is substituted or unsubstituted.

For example, each $R_4$ can independently be hydrogen or deuterium.

In particular, the compound of Chemical Formula 1-1 does not include a case in which adjacent $R_4$s combine with each other, that is, it corresponds to a case in which two adjacent $R_4$s do not form a ring by combining with each other.

Alternatively, as another example, in the Chemical Formula 1, two adjacent $R_4$s can combine with each other to form a 1,1'-dimethyl-indene, benzofuran, benzothiophene, 1-phenyl-indole, deuterium-substituted 1,1'-dimethyl-indene, deuterium-substituted benzofuran, deuterium-substituted benzothiophene, or deuterium-substituted 1-phenyl-indole ring, and the rest of $R_4$ can be hydrogen or deuterium.

In particular, the compound of Chemical Formula 1-2 corresponds to a case in which two adjacent $R_4$s of the above-described $R_4$ combine with each other to form a deuterium-substituted or unsubstituted $C_{4-60}$ aliphatic or aromatic ring.

Preferably, in the Chemical Formula 1, at least one of Ar is phenyl, biphenylyl, or phenyl substituted with five deuteriums, and the rest of Ar are any one of phenyl, biphenylyl, dibenzofuranyl, or dibenzothiophenyl; $R_1$, $R_2$, and $R_3$ are each hydrogen or deuterium; and each $R_4$ is hydrogen or deuterium, or two adjacent $R_4$s combine with each other to form a 1,1'-dimethyl-indene, benzofuran, benzothiophene, 1-phenyl-indole, deuterium-substituted 1,1'-dimethyl-indene, deuterium-substituted benzofuran, deuterium-substituted benzothiophene, or deuterium-substituted 1-phenyl-indole ring, and the rest of $R_4$ are hydrogen or deuterium; provided that at least one of Ar is phenyl substituted with five deuteriums, at least one of $R_1$, $R_2$, $R_3$, and $R_4$ is deuterium, or at least a pair of two adjacent $R_4$s can combine with each other to form a deuterium-substituted benzofuran, deuterium-substituted benzothiophene, or deuterium-substituted 1-phenyl-indole ring.

Meanwhile, in the Chemical Formula 1-2, R' and R" can each independently be hydrogen; deuterium; halogen; cyano; substituted or unsubstituted $C_{1-20}$ alkyl, $C_{1-12}$ alkyl, or $C_{1-6}$ alkyl; substituted or unsubstituted $C_{1-20}$ alkoxy, $C_{1-12}$ alkoxy, or $C_{1-6}$ alkoxy; substituted or unsubstituted $C_{2-20}$ alkenyl, $C_{2-12}$ alkenyl, or $C_{2-6}$ alkenyl; substituted or unsubstituted $C_{2-20}$ alkynyl, $C_{2-12}$ alkynyl, or $C_{2-6}$ alkynyl; substituted or unsubstituted $C_{3-30}$ cycloalkyl, $C_{3-25}$ cycloalkyl, or $C_{3-20}$ cycloalkyl; substituted or unsubstituted $C_{6-30}$ aryl, $C_{6-28}$ aryl, or $C_{6-25}$ aryl; or substituted or unsubstituted $C_{5-30}$ heteroaryl, $C_{8-20}$ heteroaryl, or $C_{12-18}$ heteroaryl containing at least one heteroatom selected from the group consisting of N, O and S.

For example, R' and R" can each independently be hydrogen or deuterium.

In addition, in the Chemical Formula 1-2, Z can be C-(methyl)$_2$, C-(phenyl)$_2$, O, S, or N-(phenyl). For example, in the Chemical Formula 1-2, each $R_5$ can independently be methyl or phenyl, and each $R_6$ can independently be phenyl.

Meanwhile, the compound of Chemical Formula 1 can include all stereo-isomers in which left and right positions of both ends of a carbazole ring are changed by rotation of Ar, $R_3$, and $R_4$ substituted in the carbazole group bonded to a tricyclic heterocyclic ring containing O or S.

Representative examples of the compound of Chemical Formula 1 are as follows:

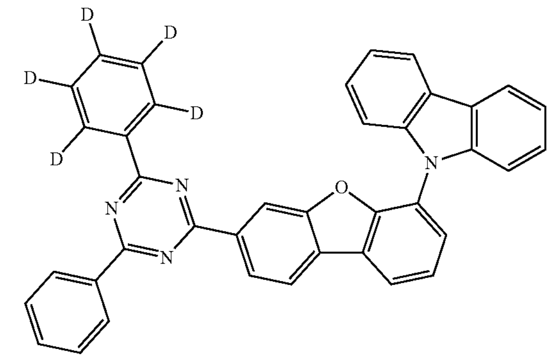

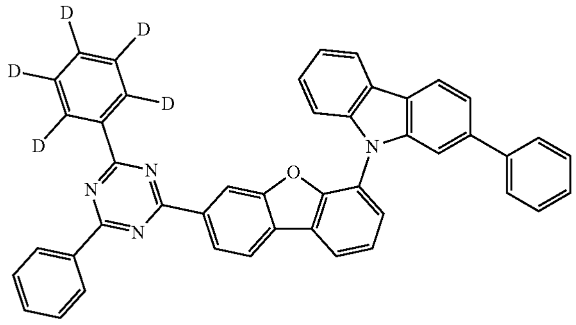

-continued
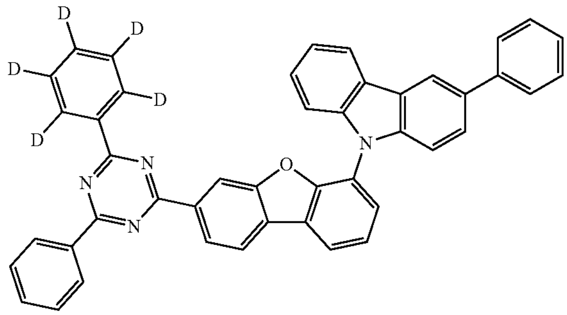
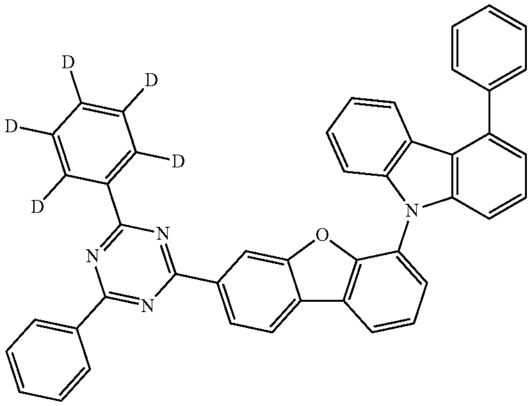
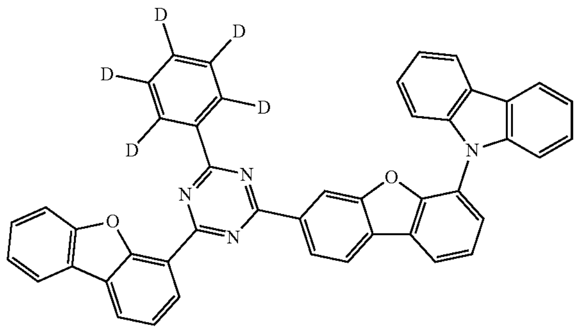
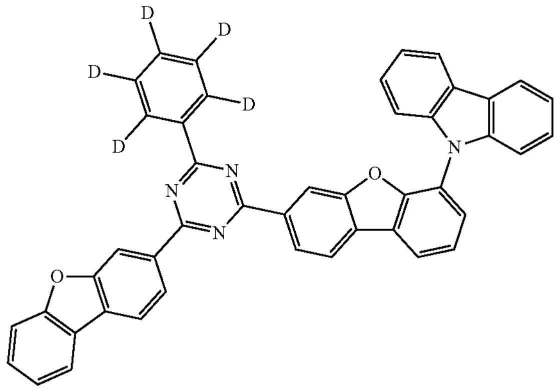
-continued
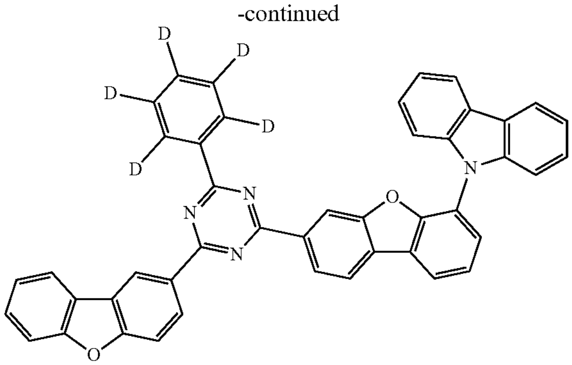
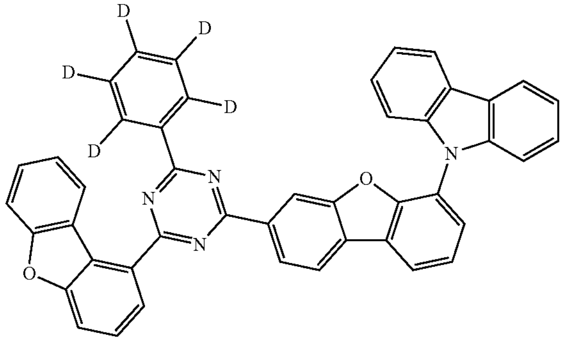
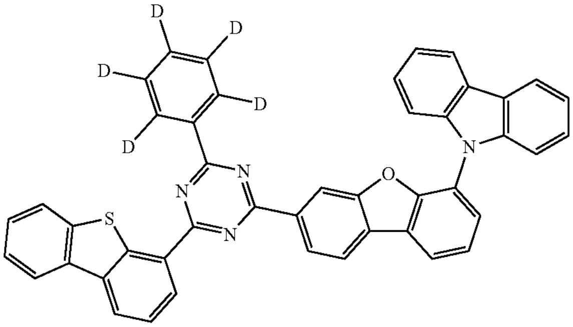
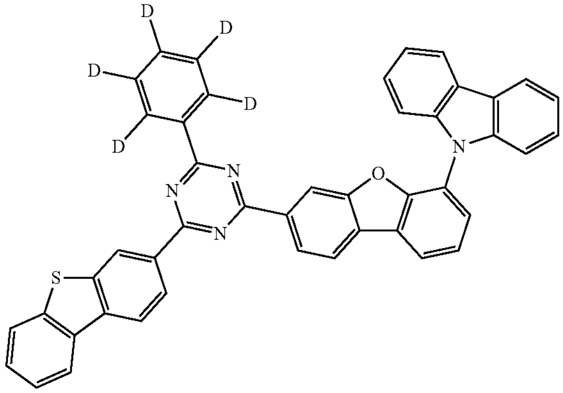
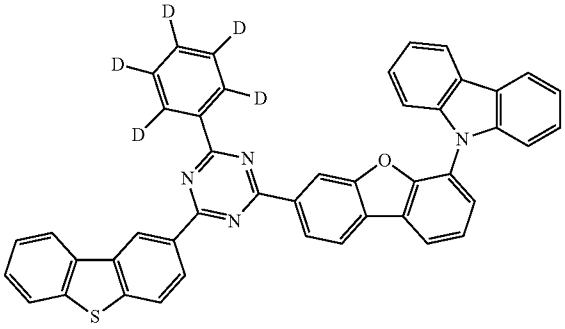

-continued
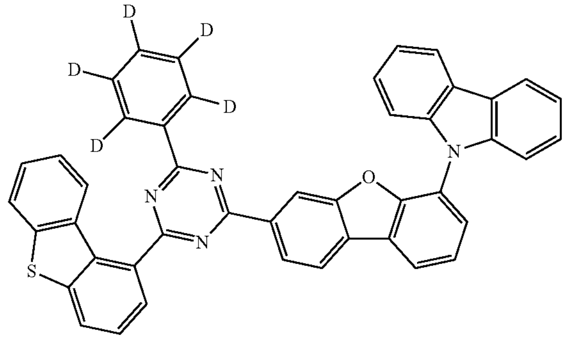
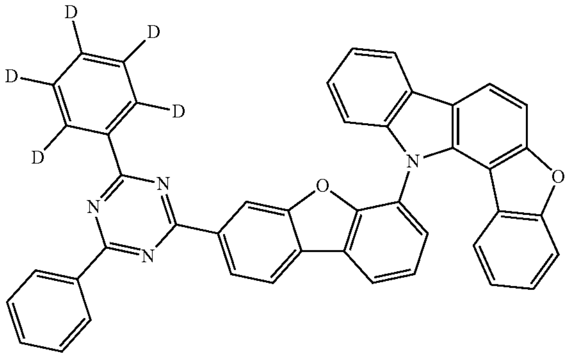
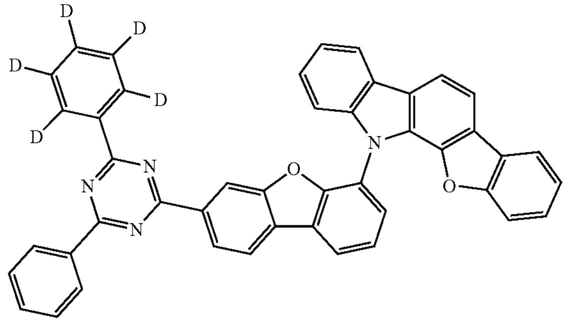
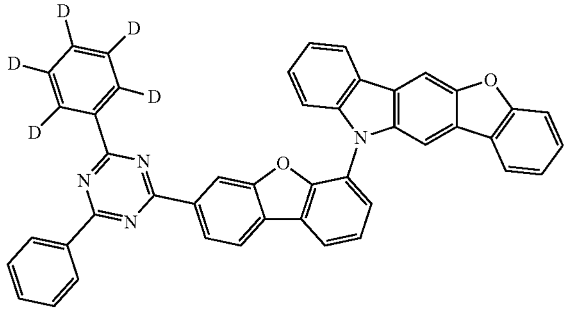
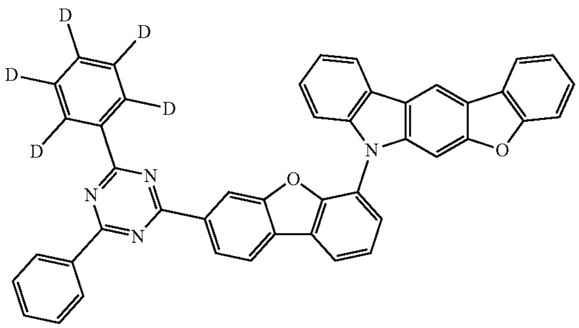
-continued
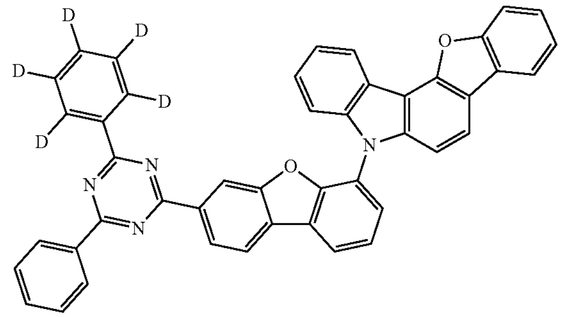
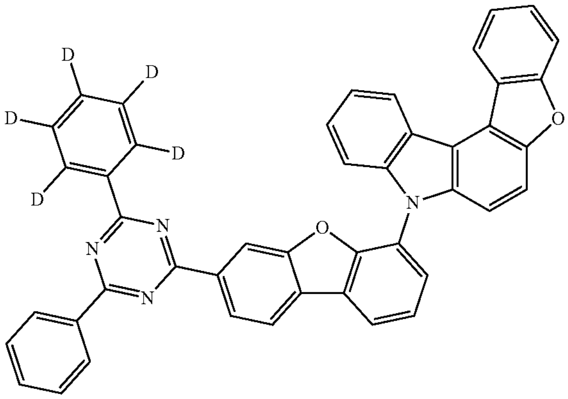
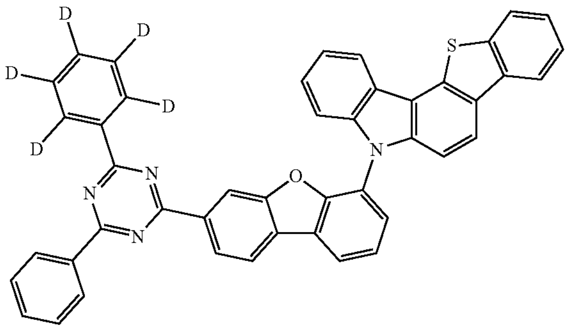
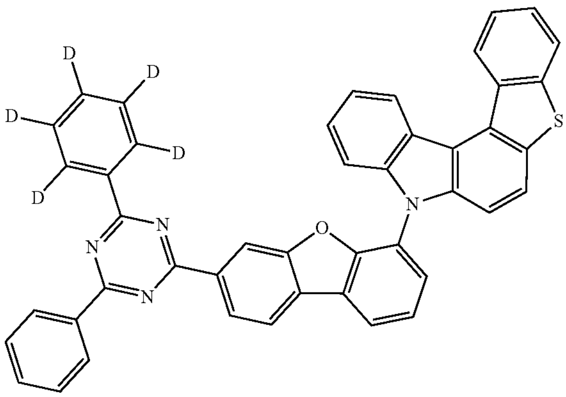

-continued
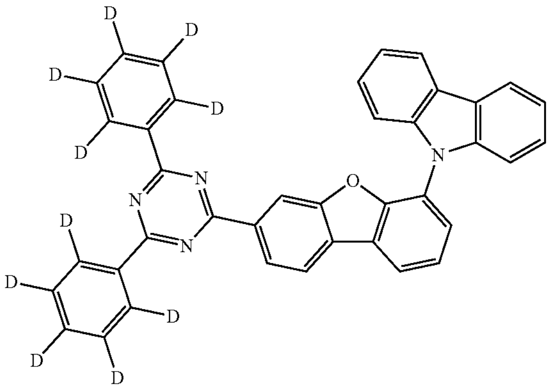
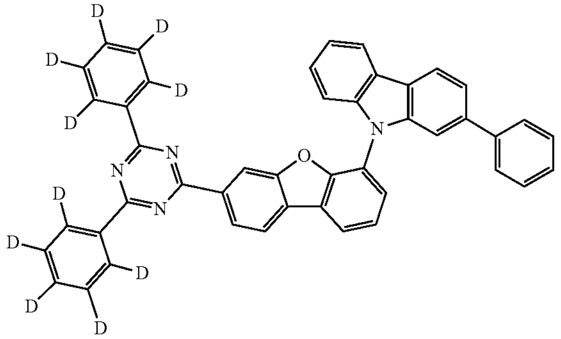
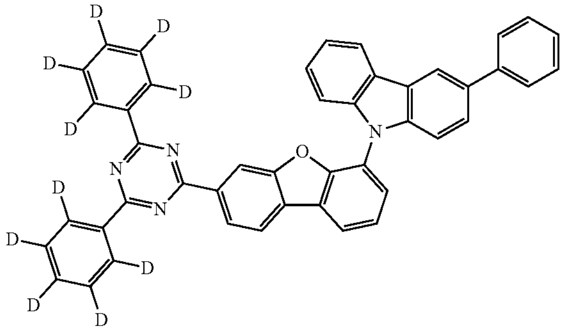
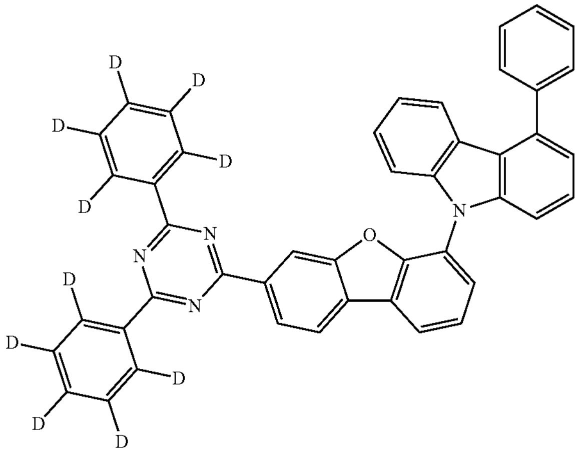
-continued
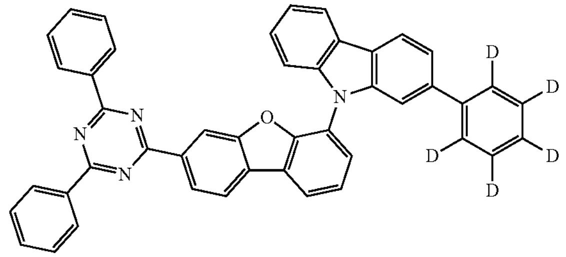
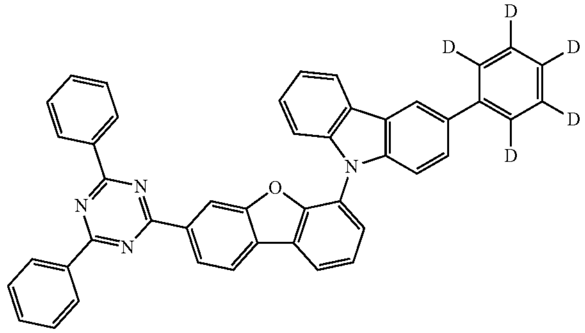
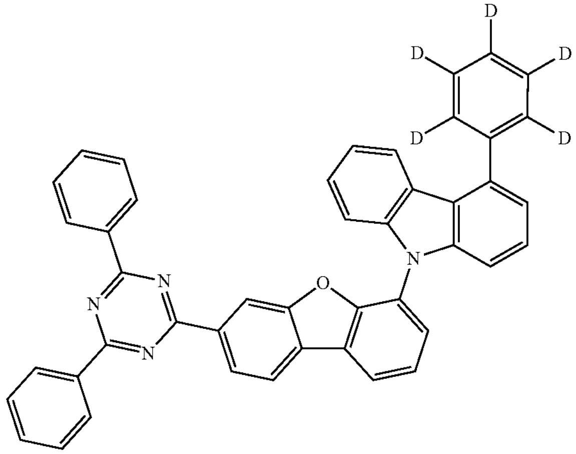
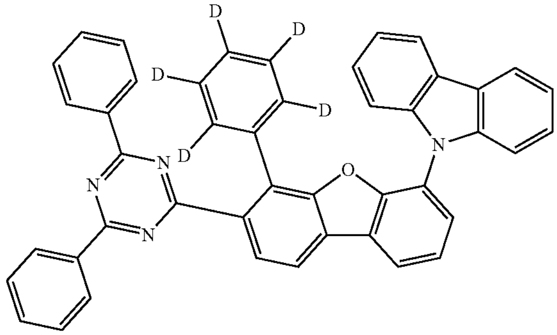
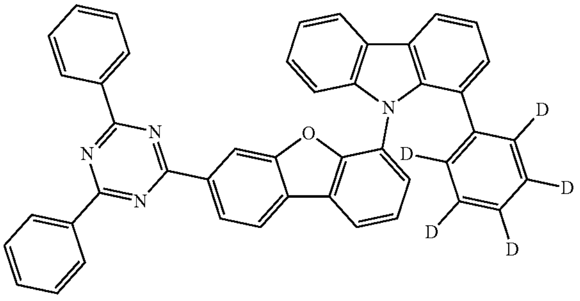

-continued
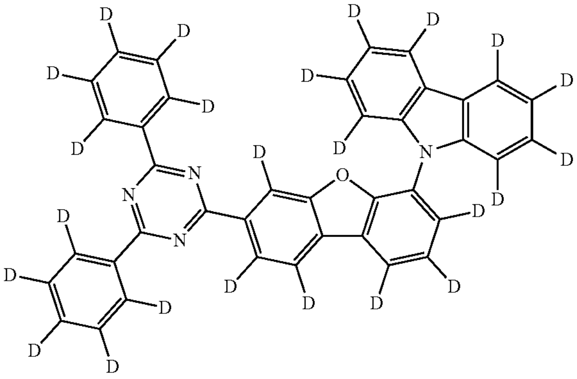
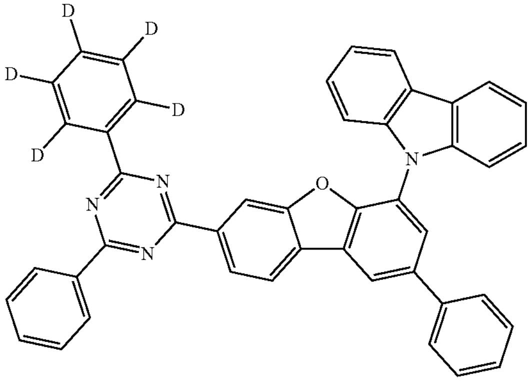
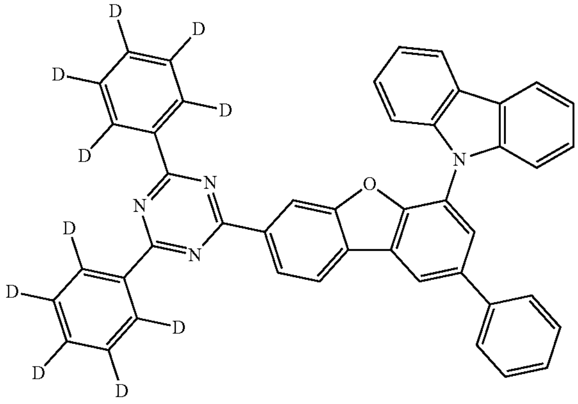
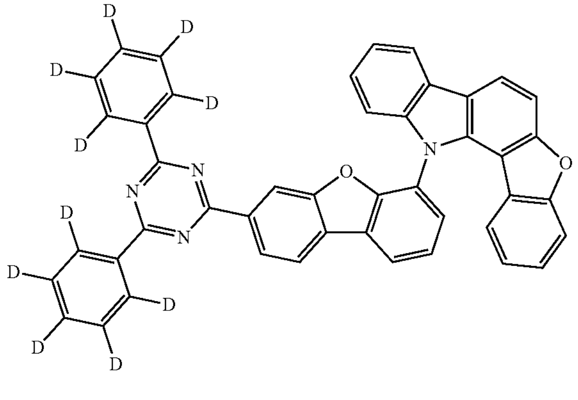
-continued
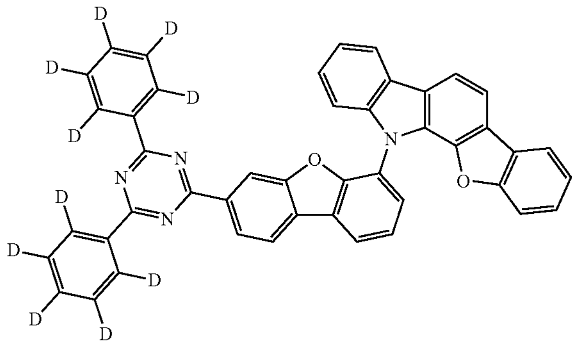
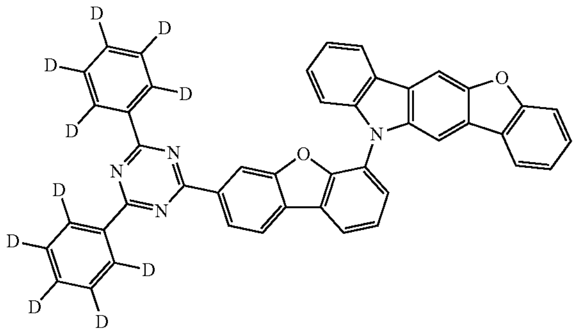
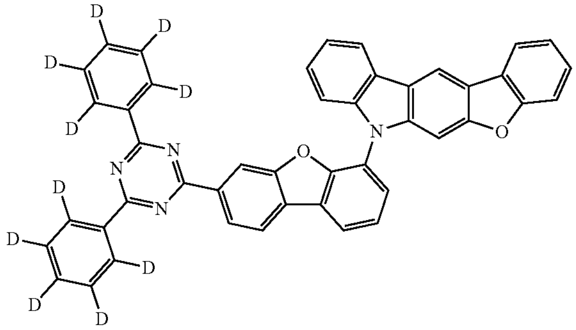
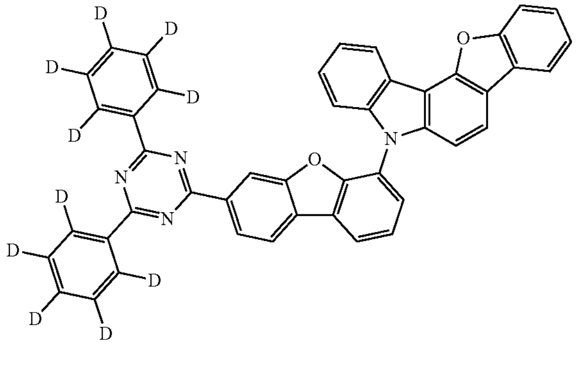

-continued
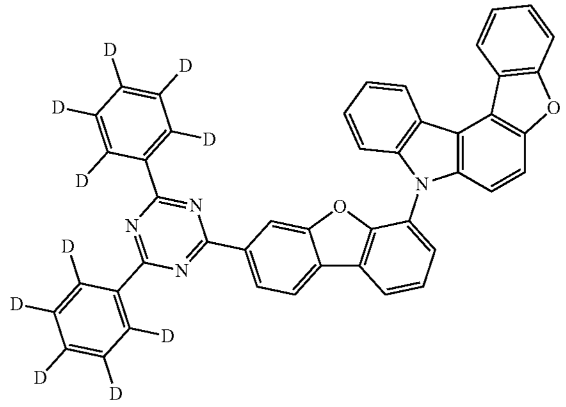
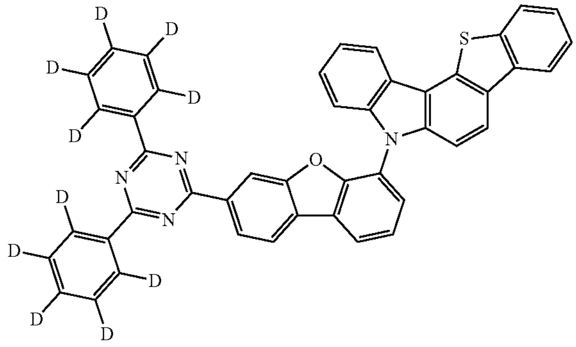
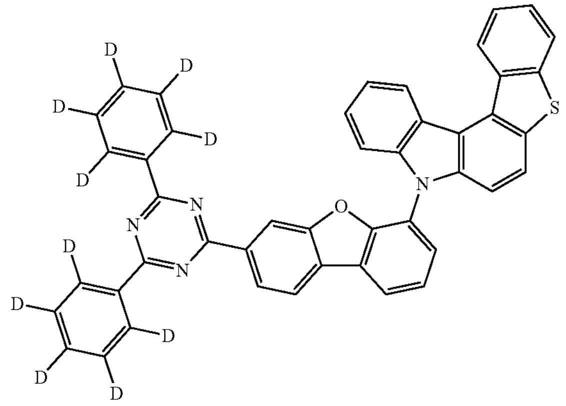
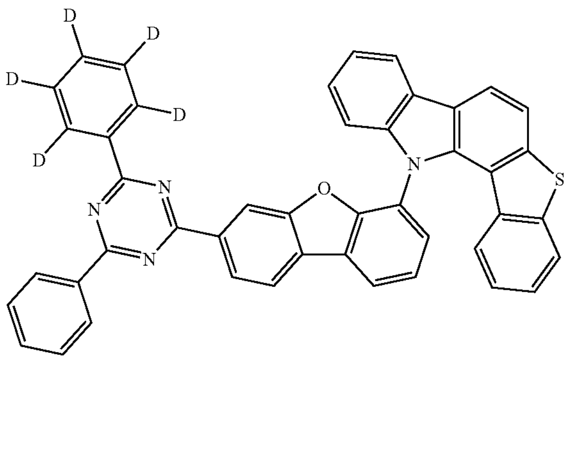
-continued
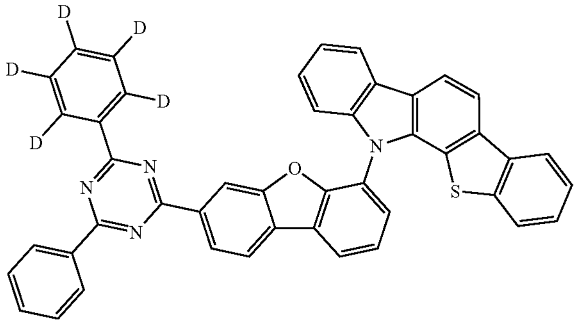
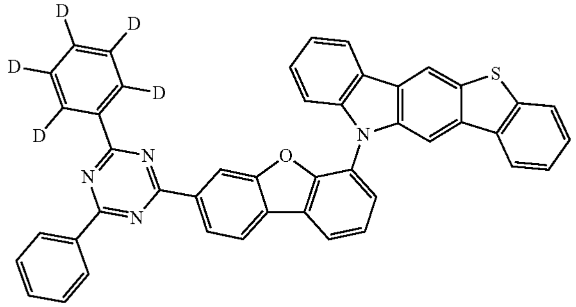
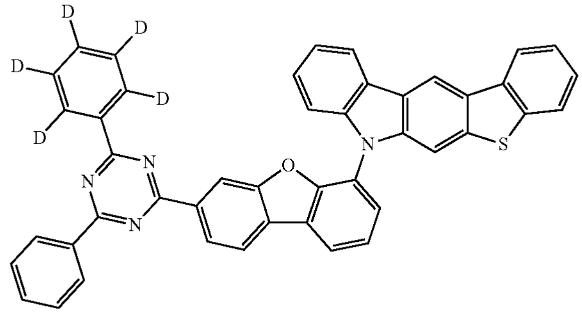
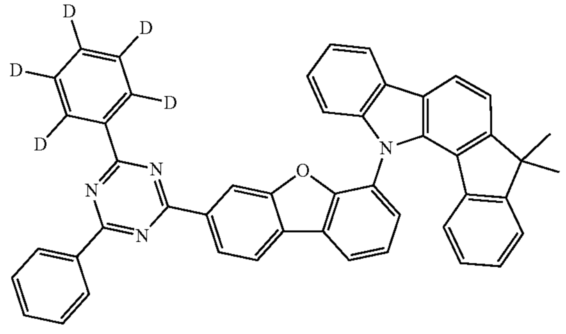
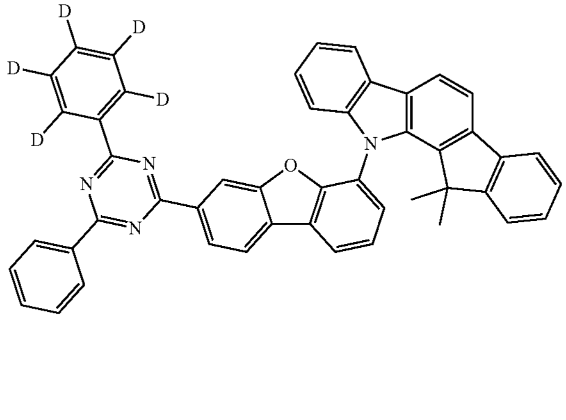

-continued
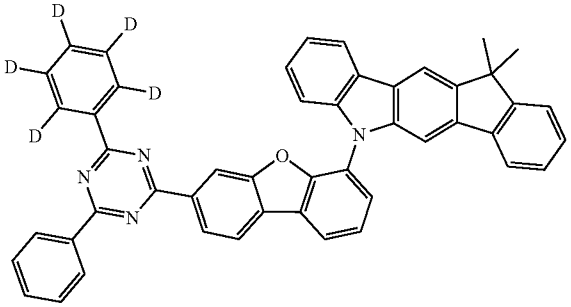
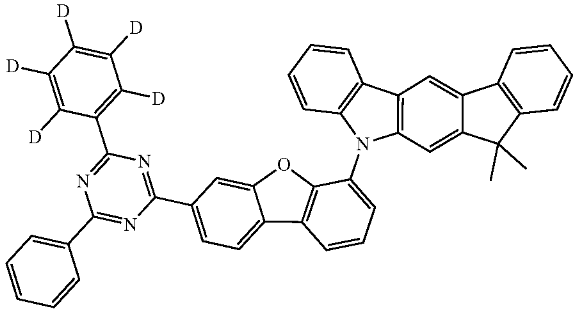
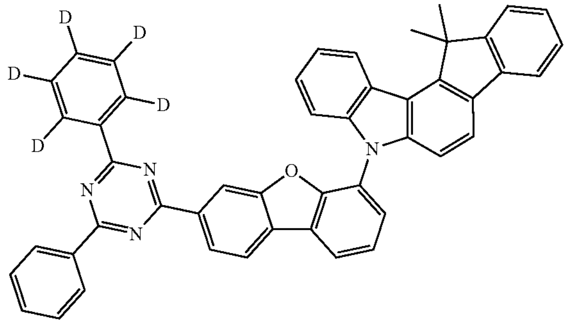
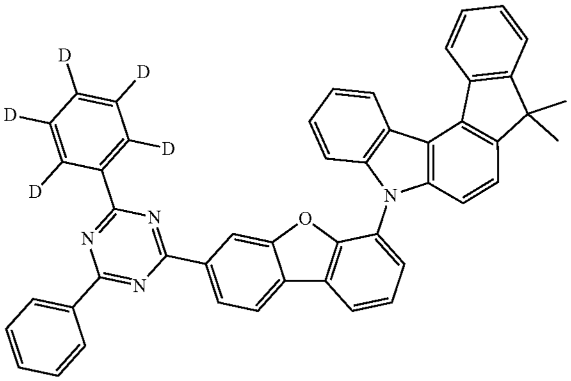
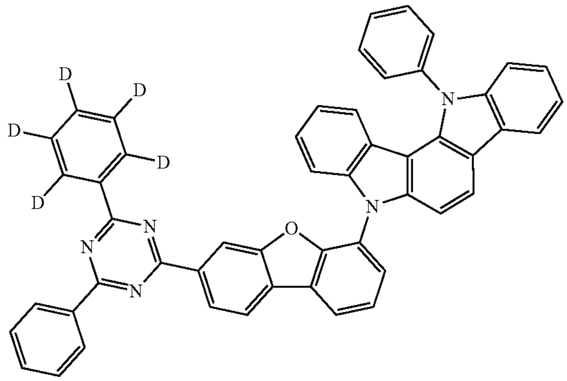
-continued
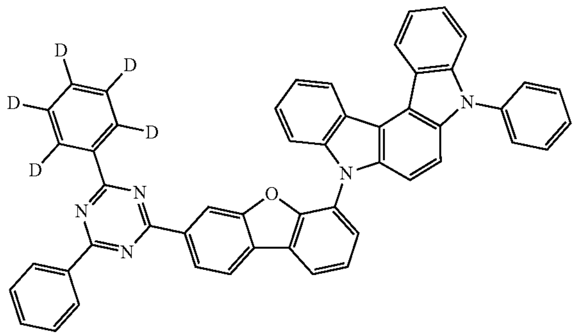
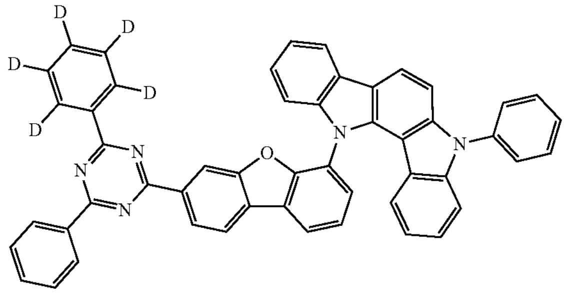
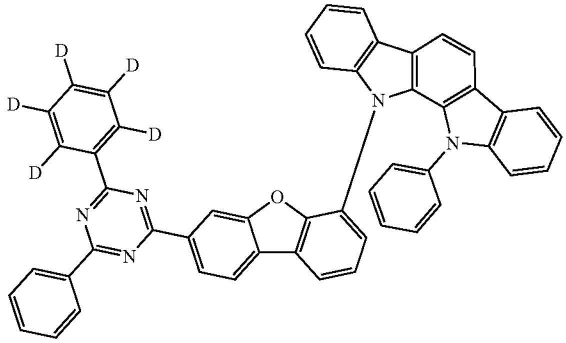
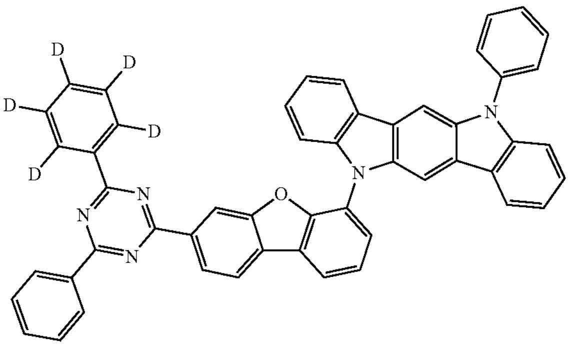
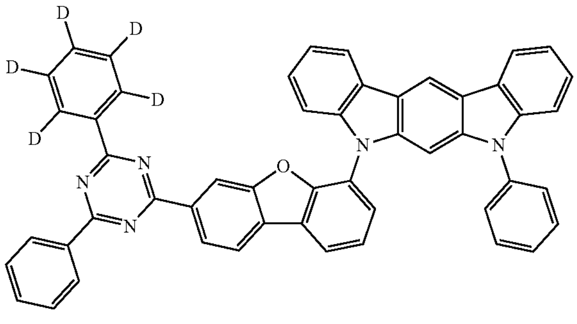

-continued
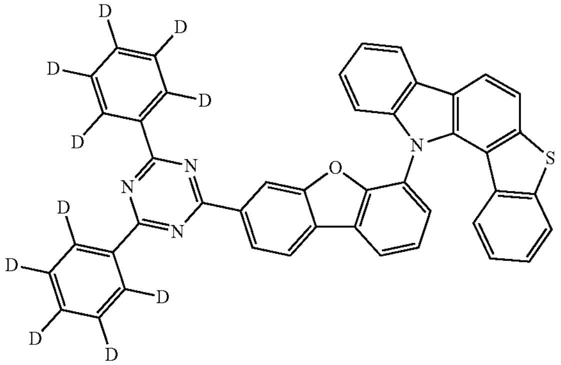
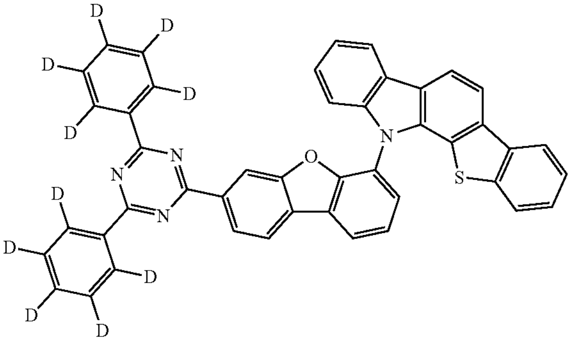
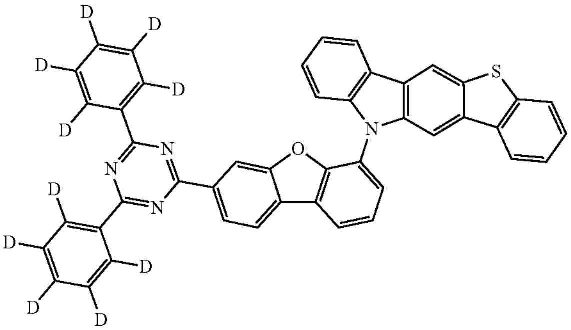
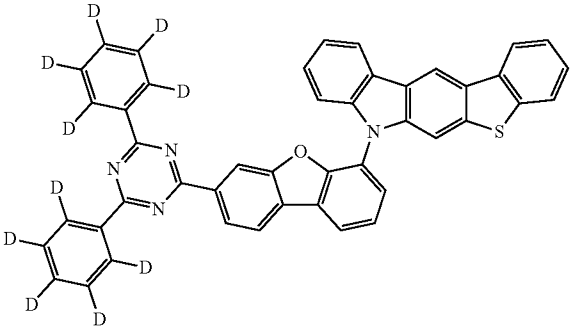
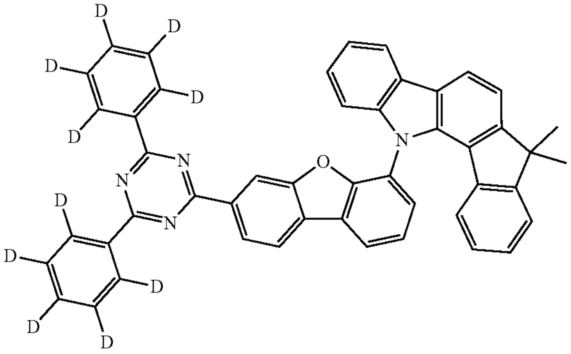
-continued
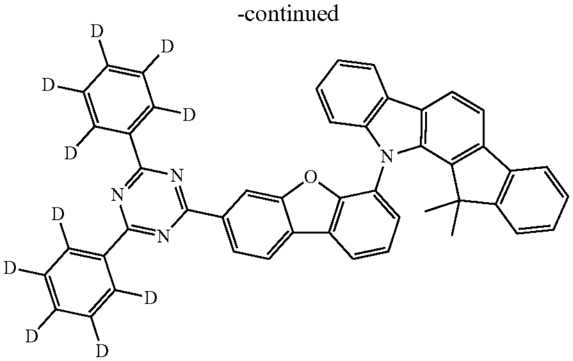
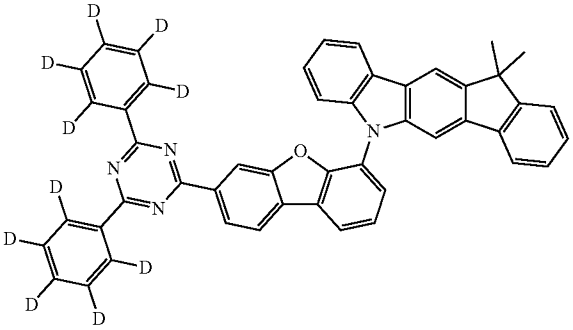
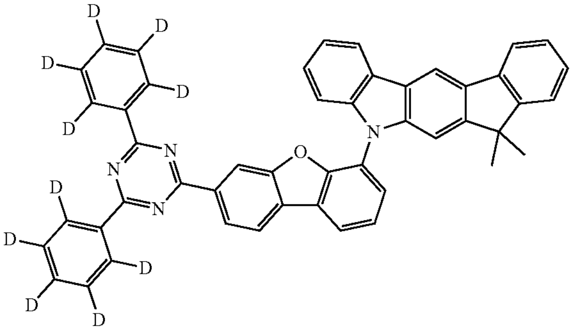
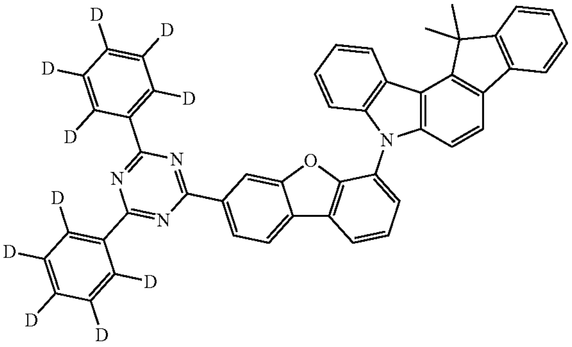
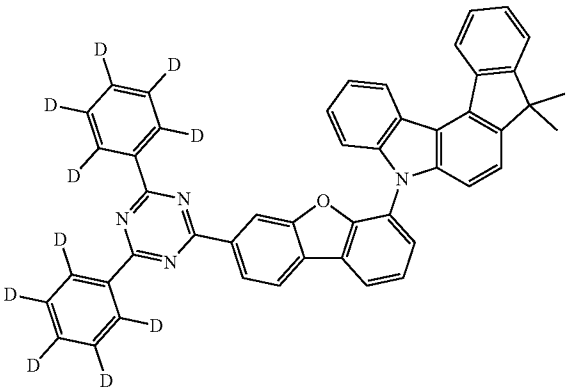

-continued
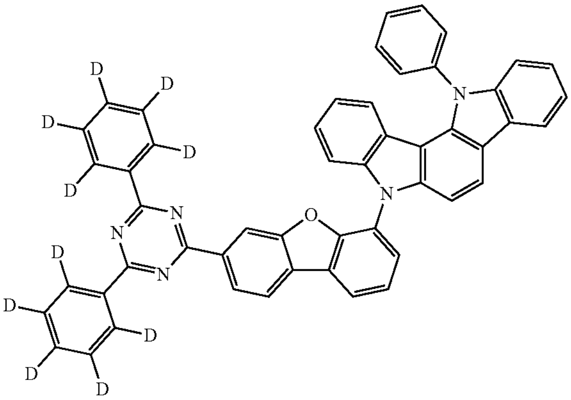
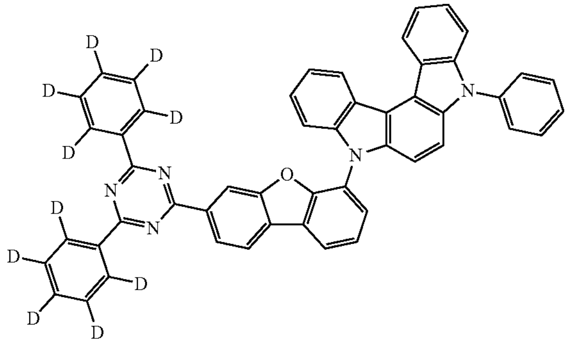
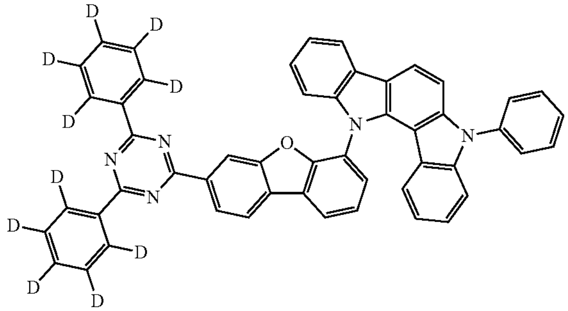
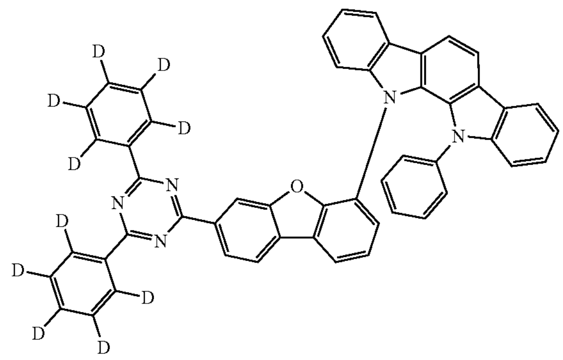
-continued
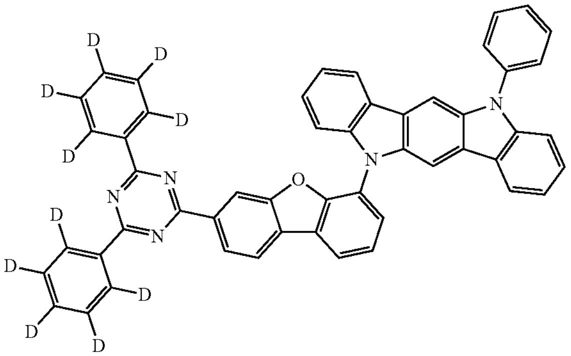
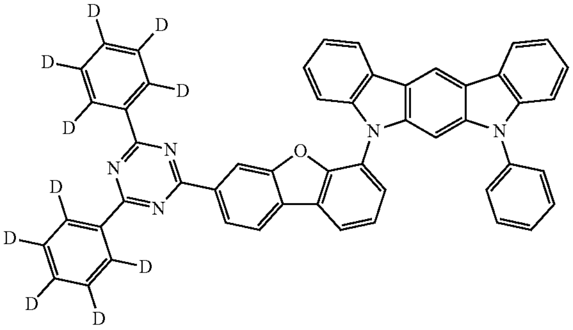
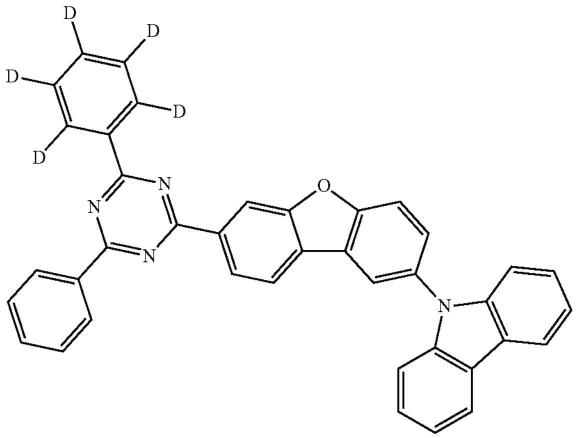
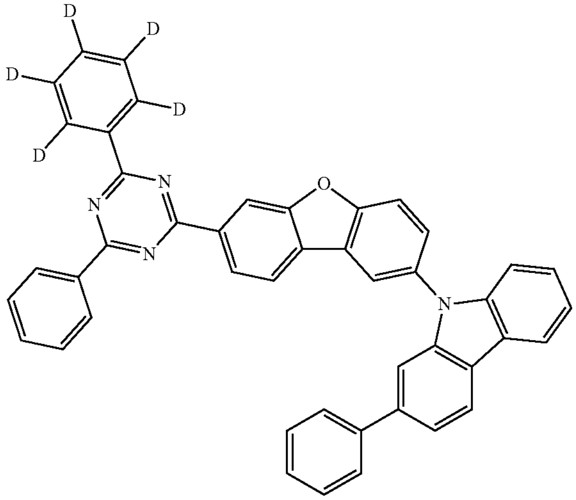

-continued
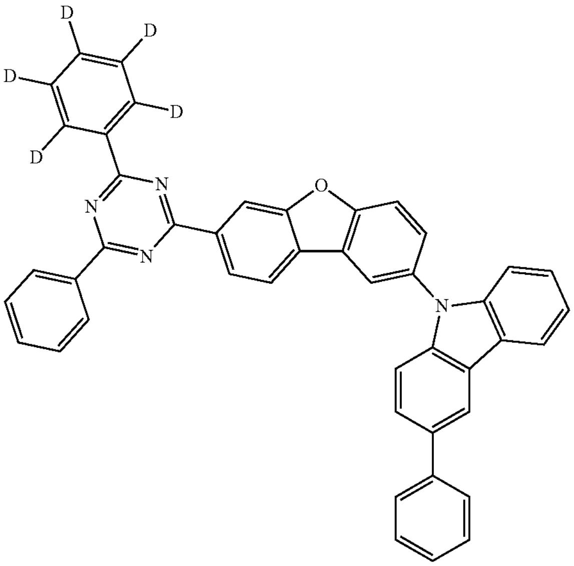
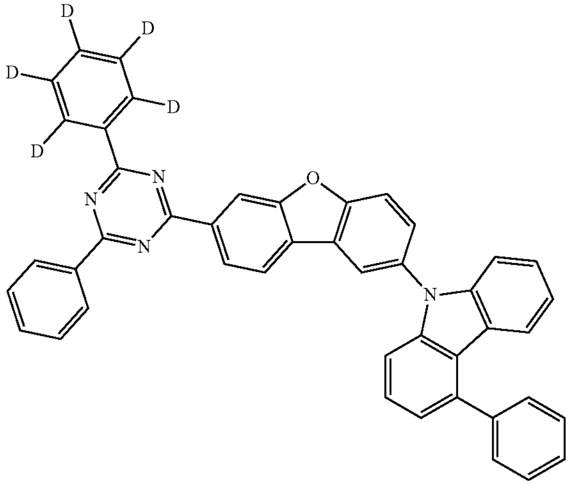
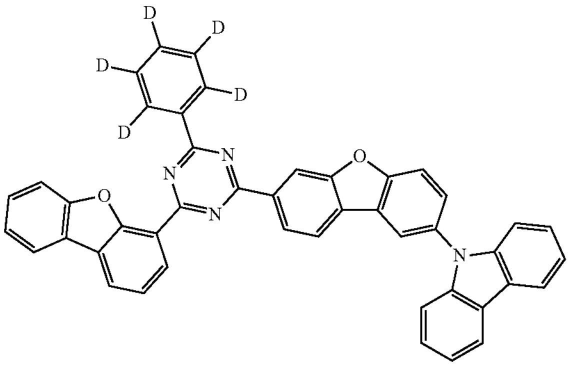
-continued
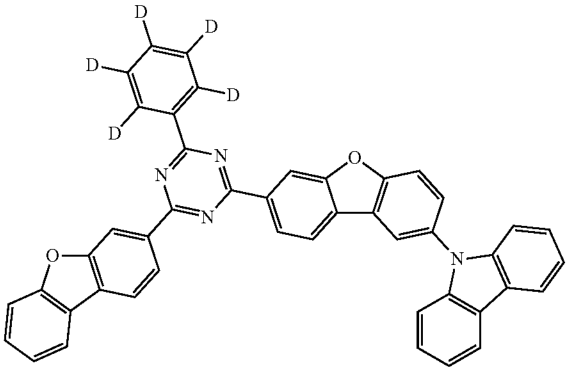
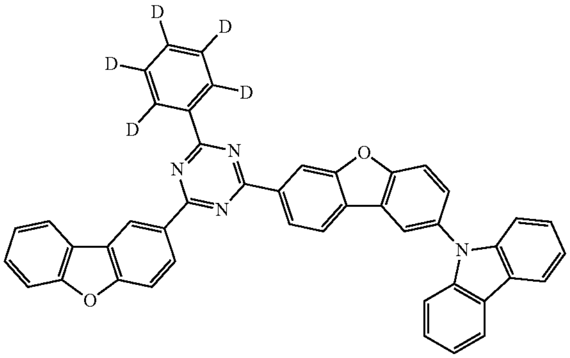
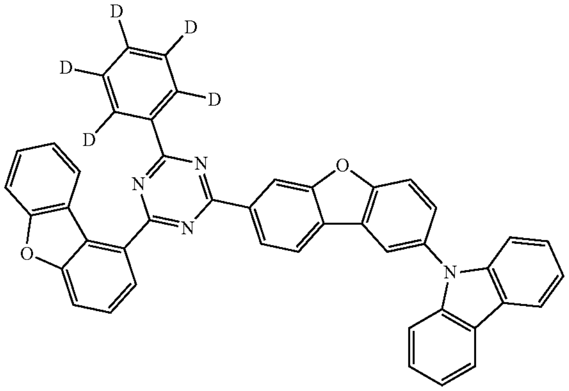
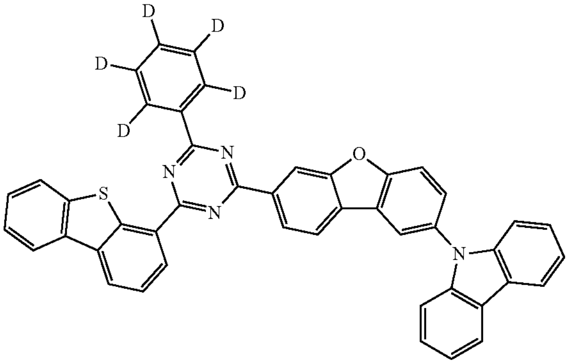

-continued
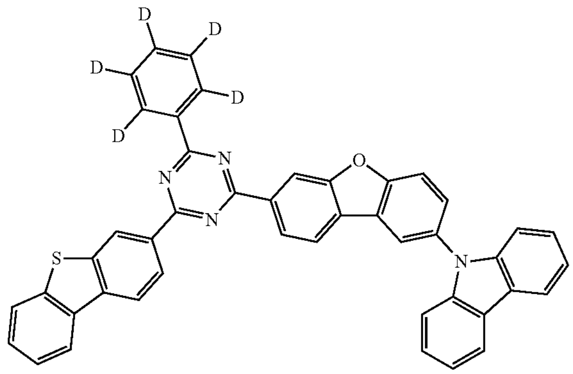
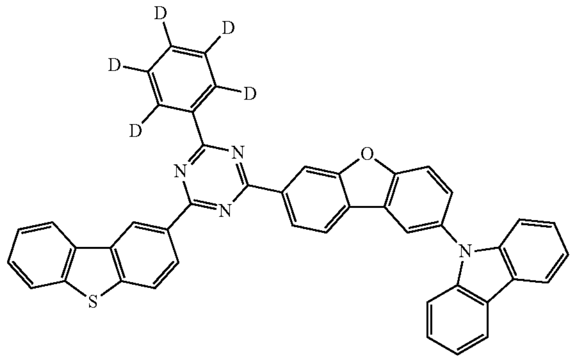
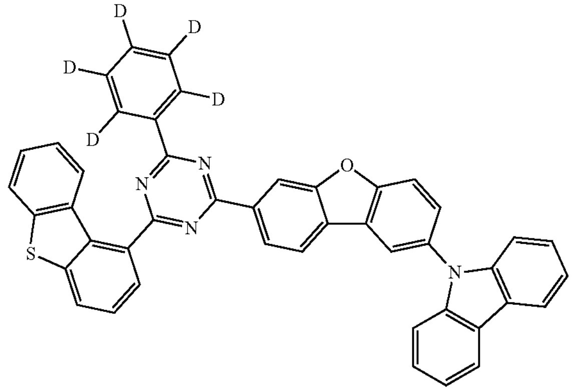
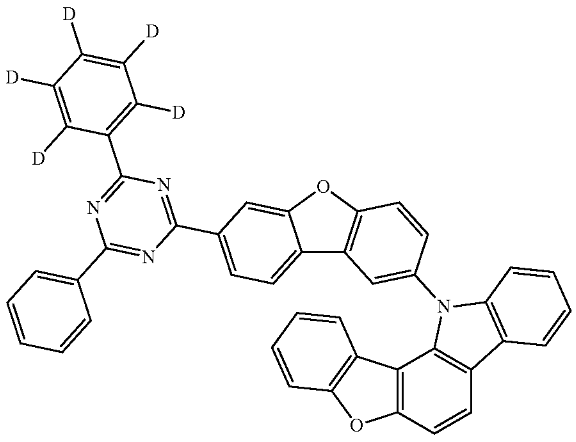
-continued
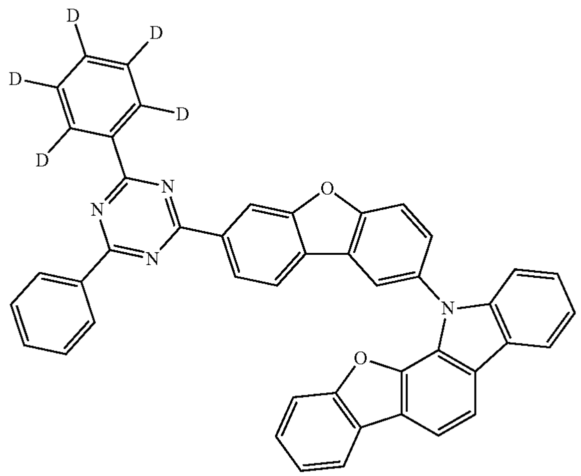
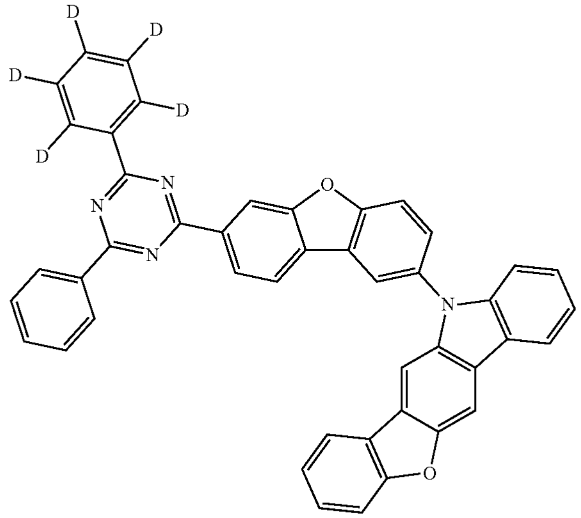
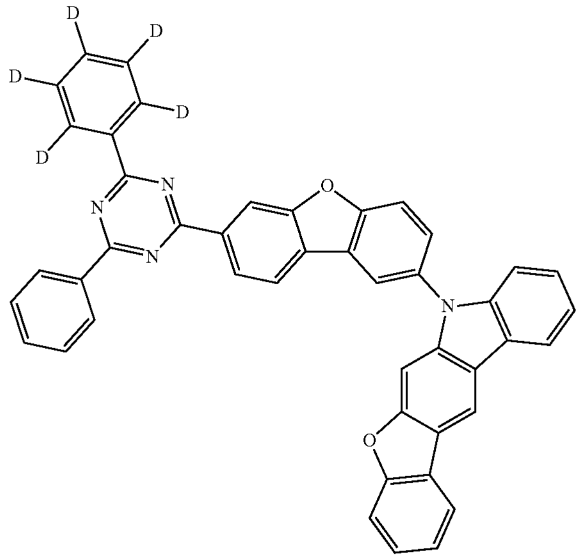

-continued
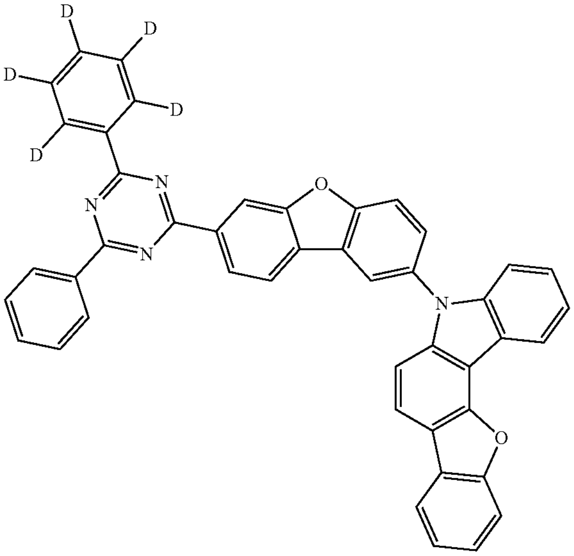
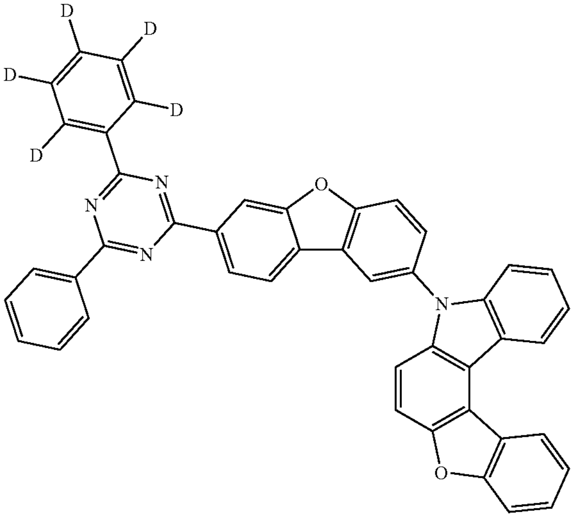
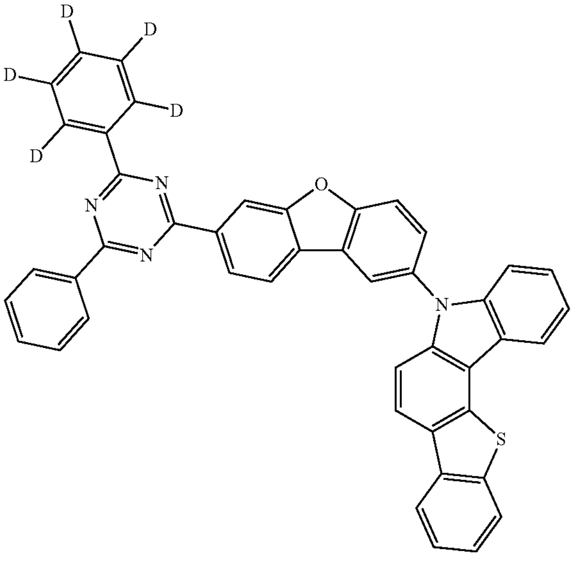
-continued
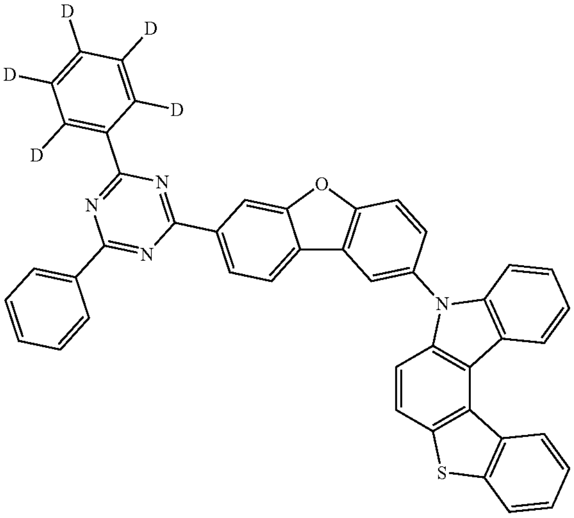
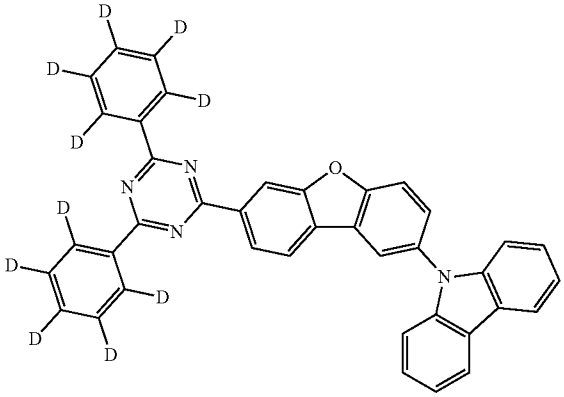
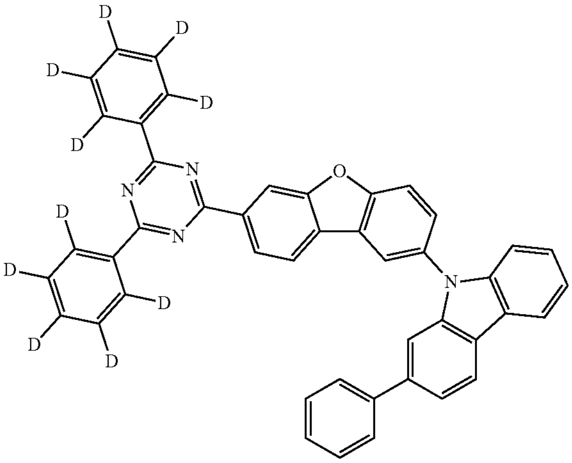

-continued
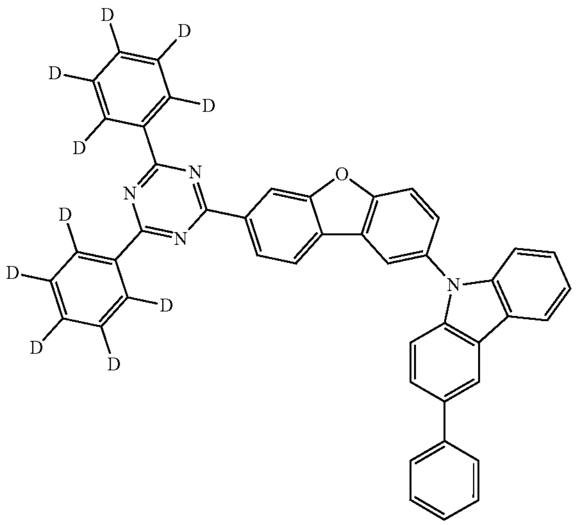
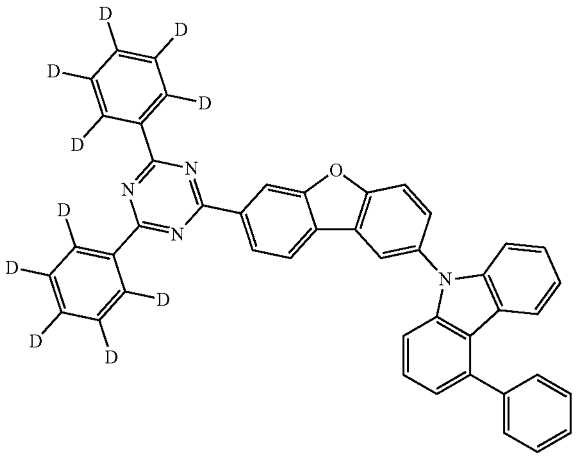
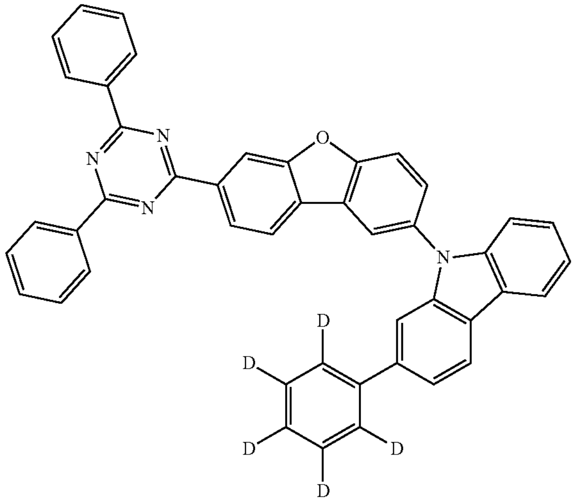
-continued
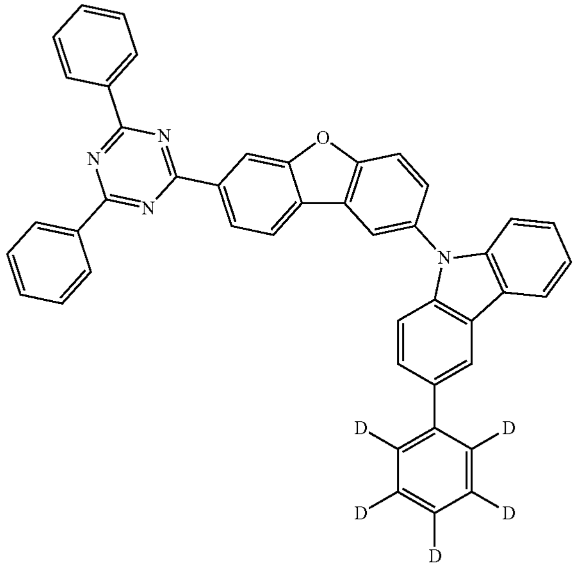
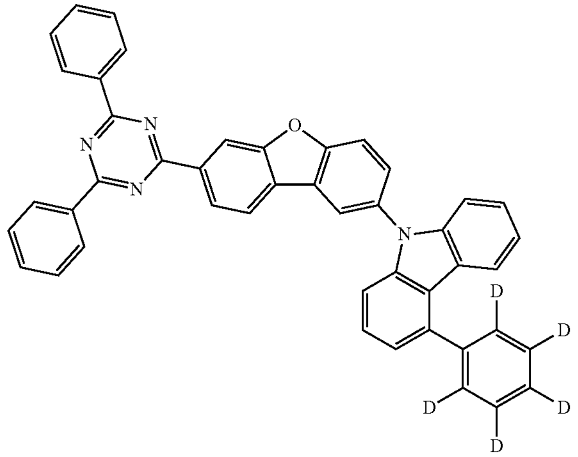
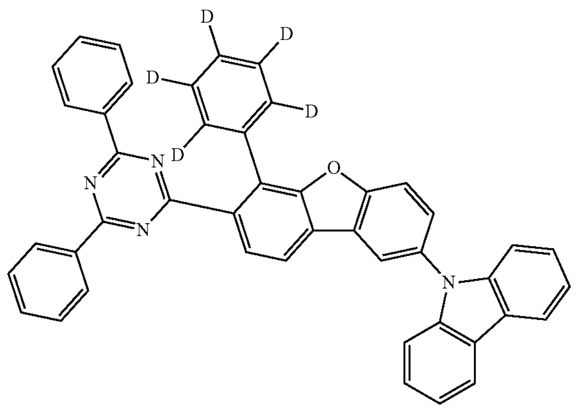

-continued
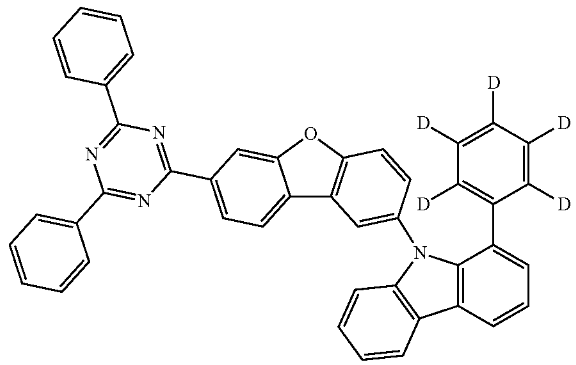
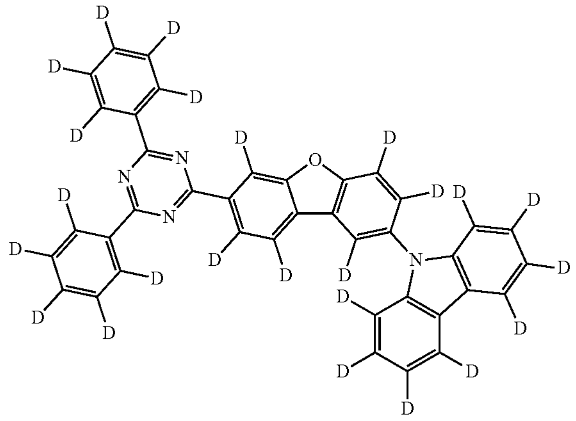
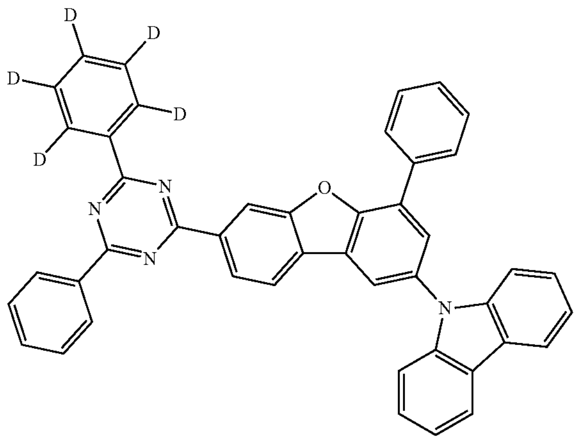
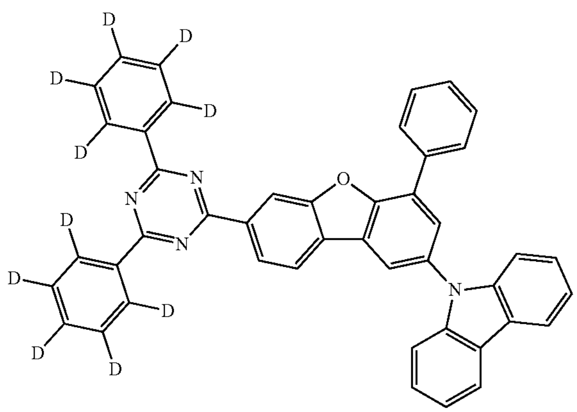
-continued
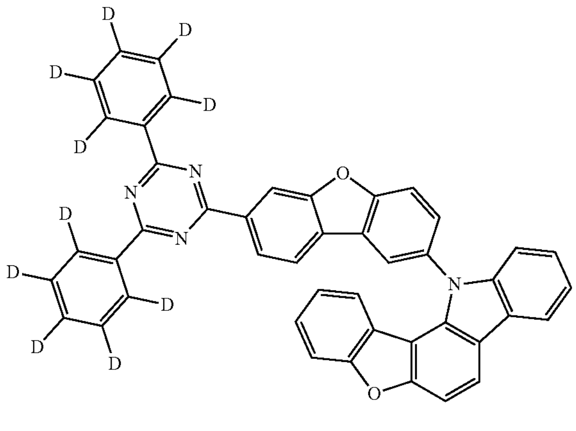
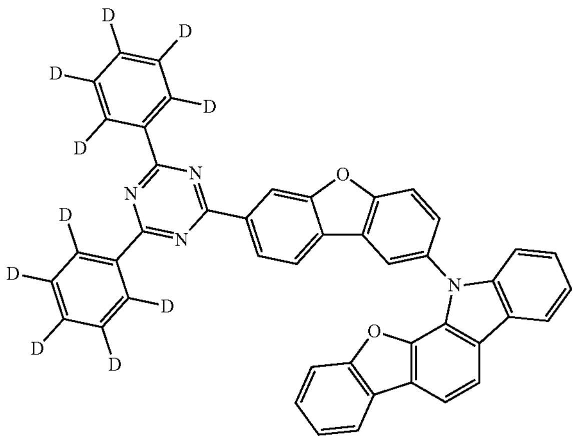
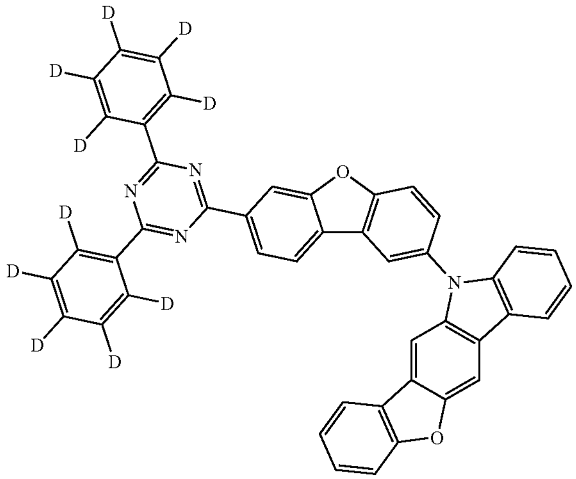

-continued
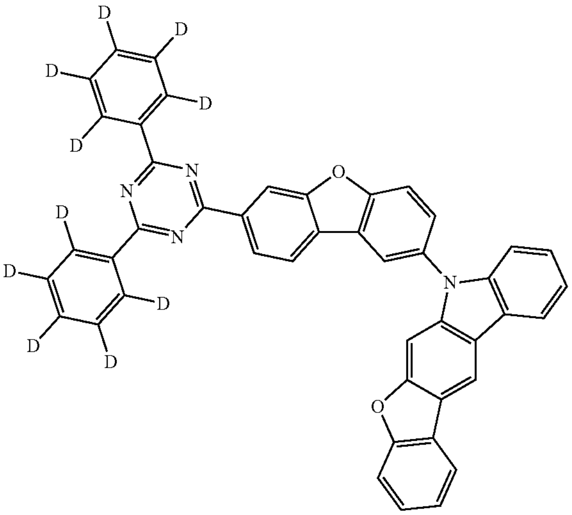
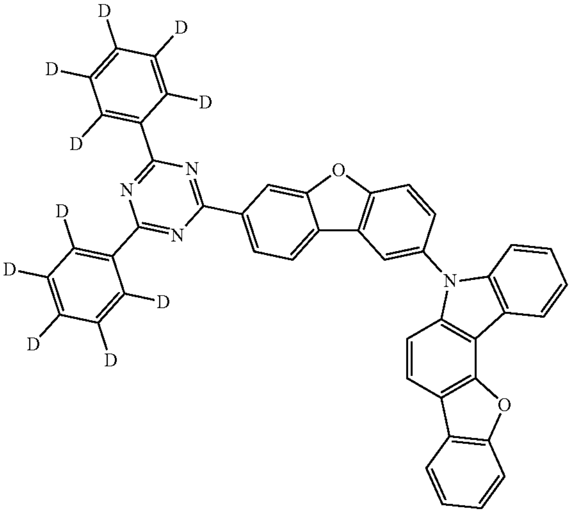
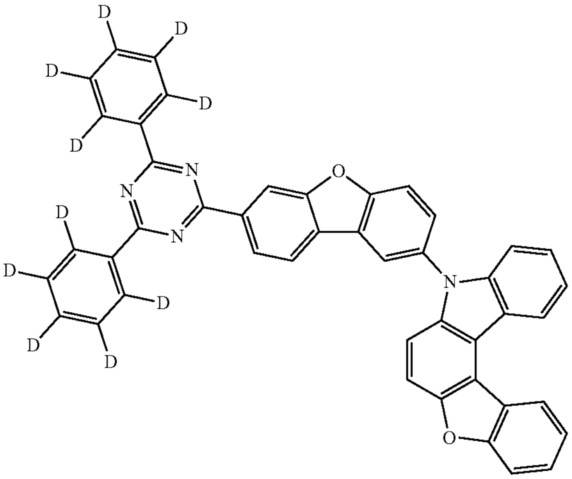
-continued
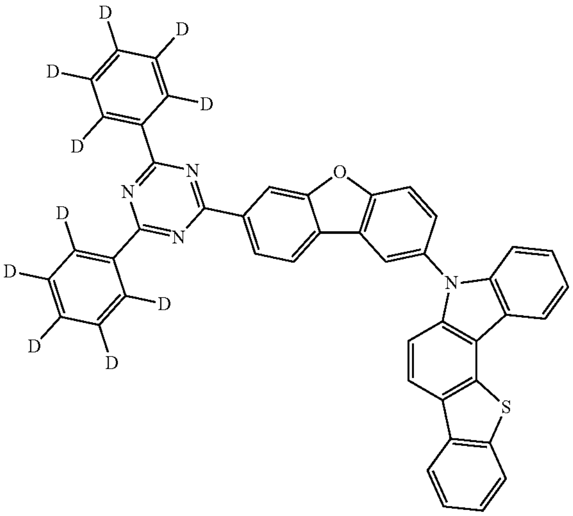
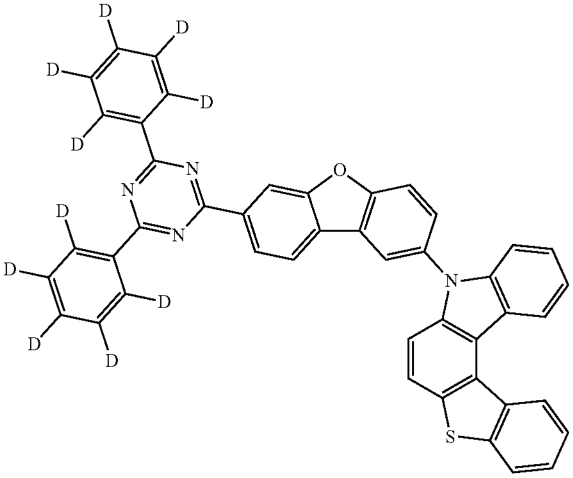
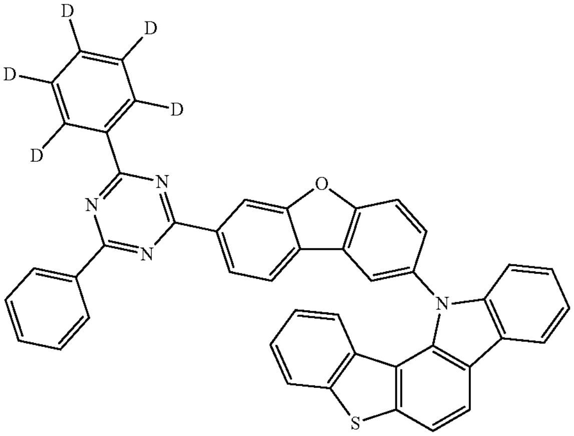

-continued
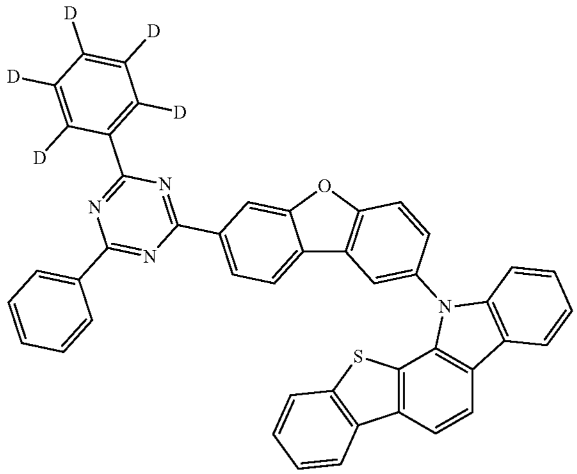
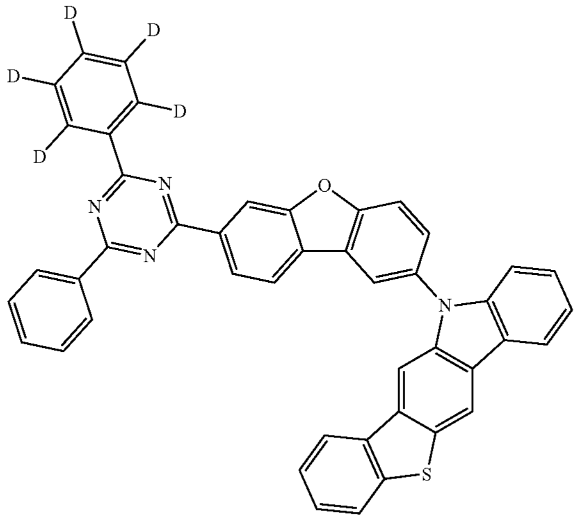
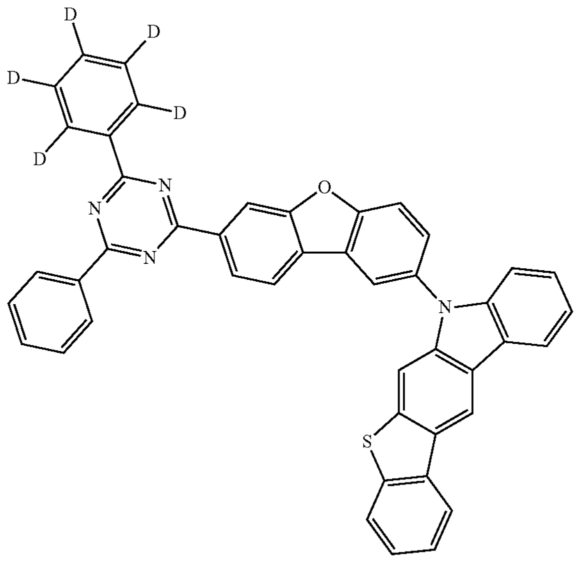
-continued
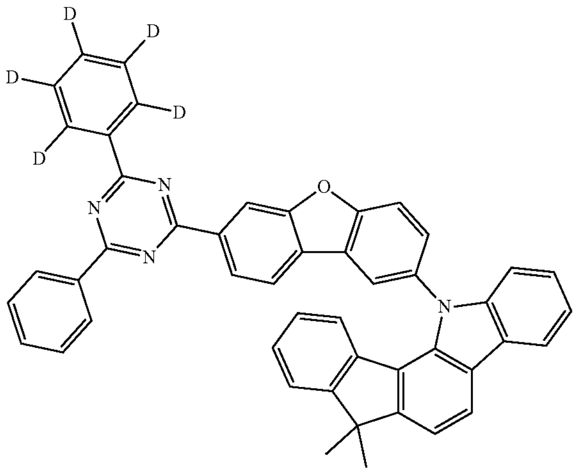
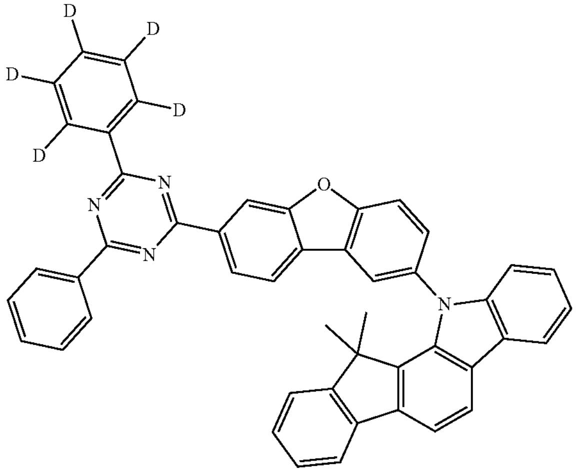
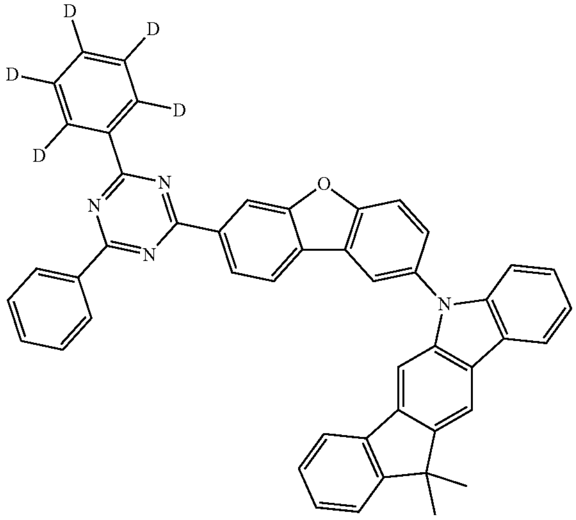

-continued
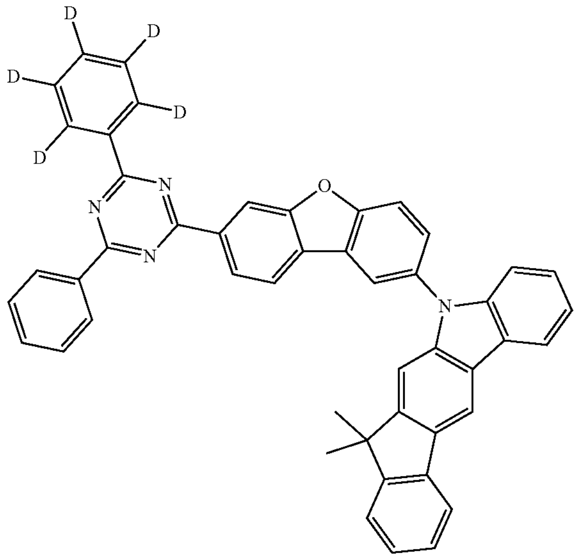
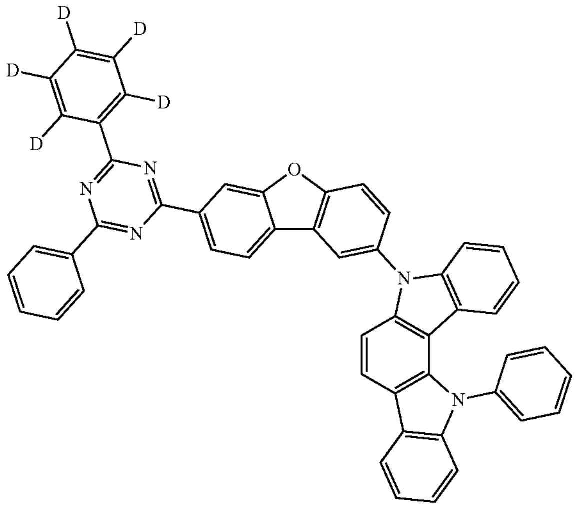
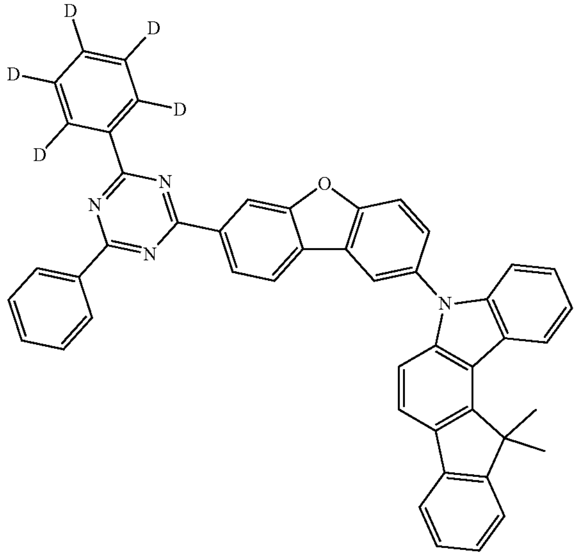
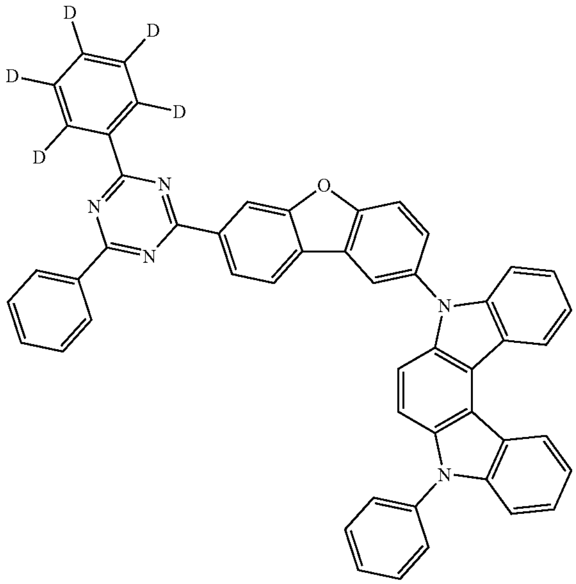
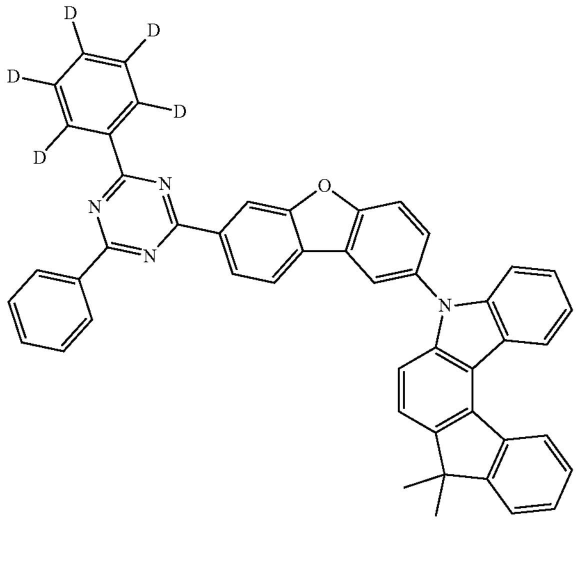
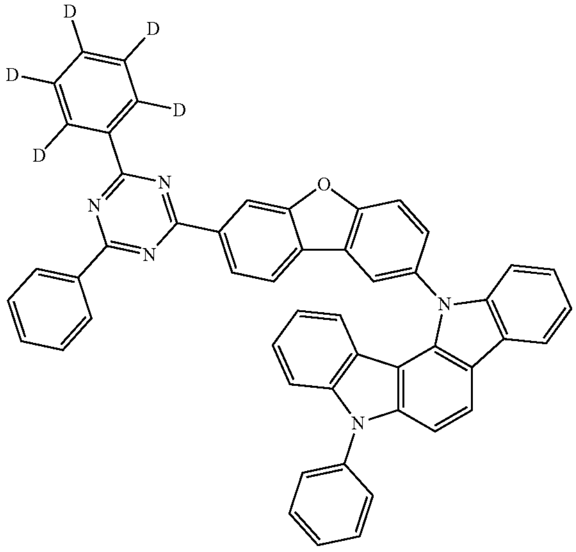
-continued -continued
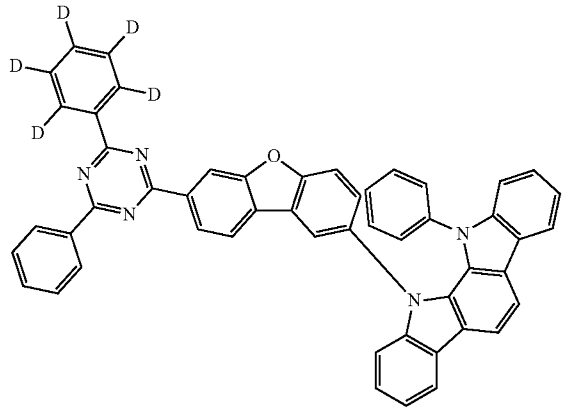
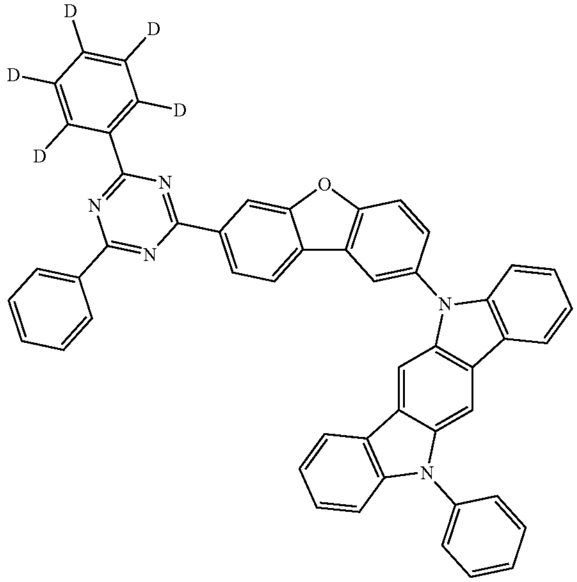
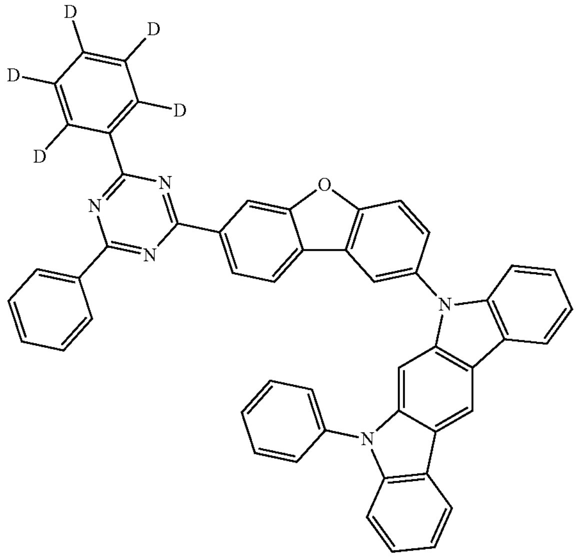
-continued
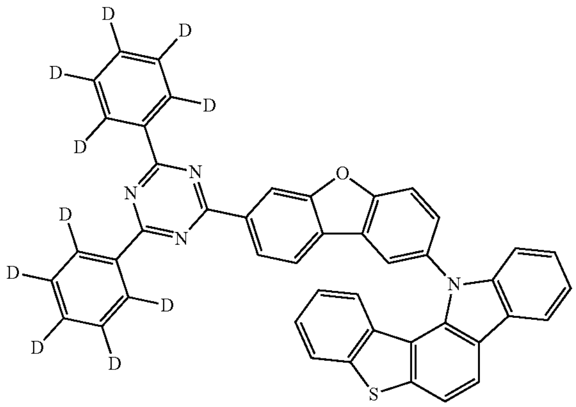
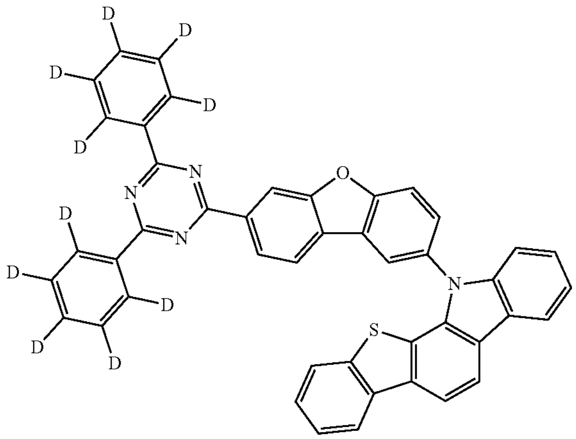
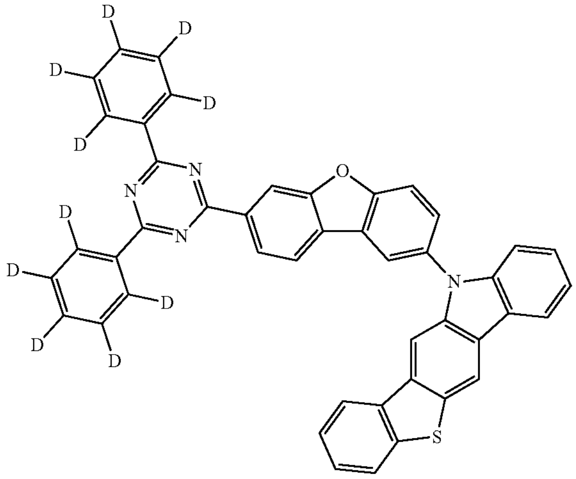

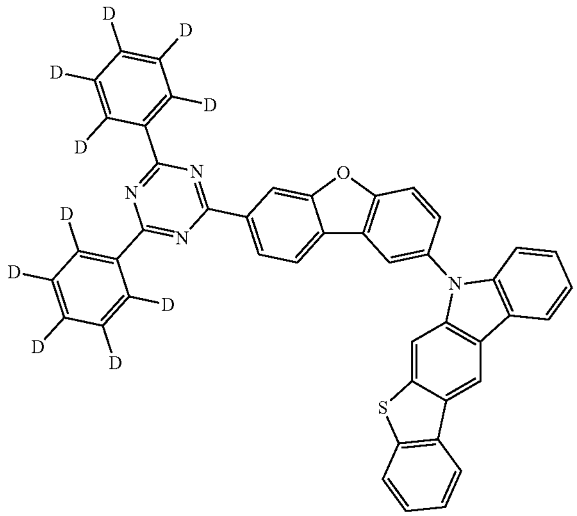
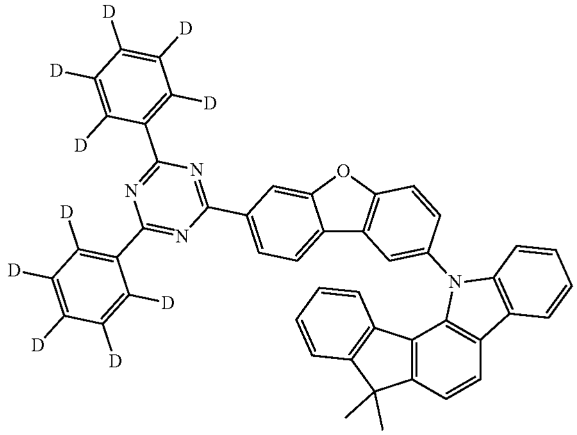
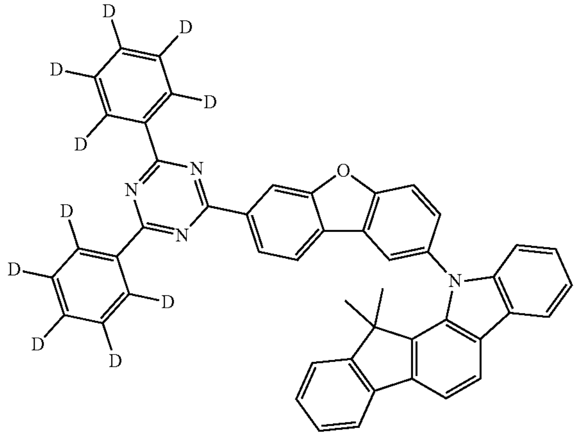
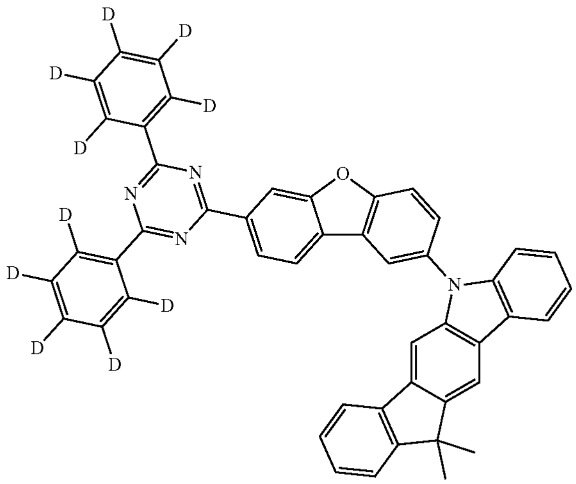
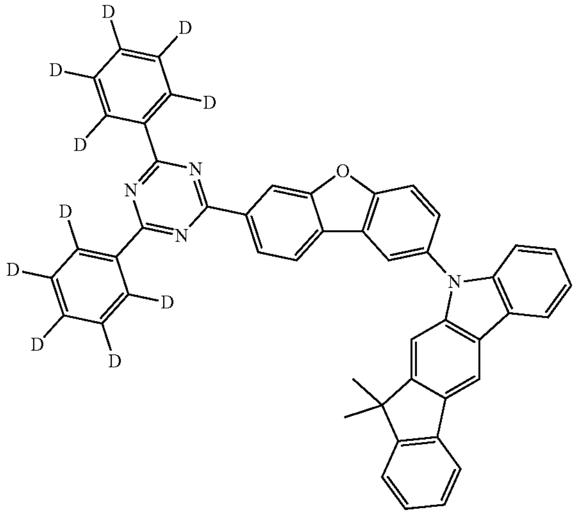
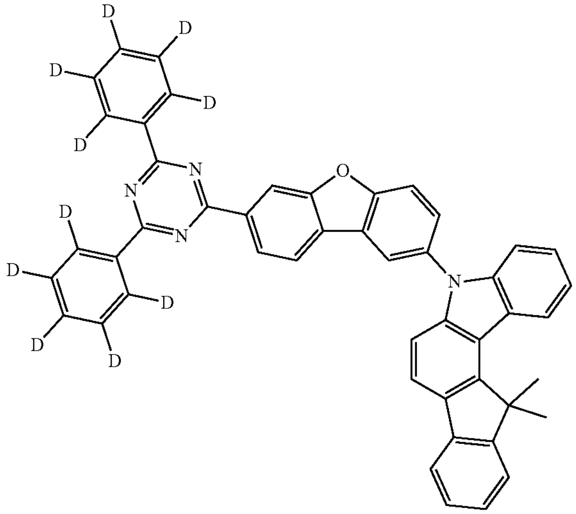

-continued
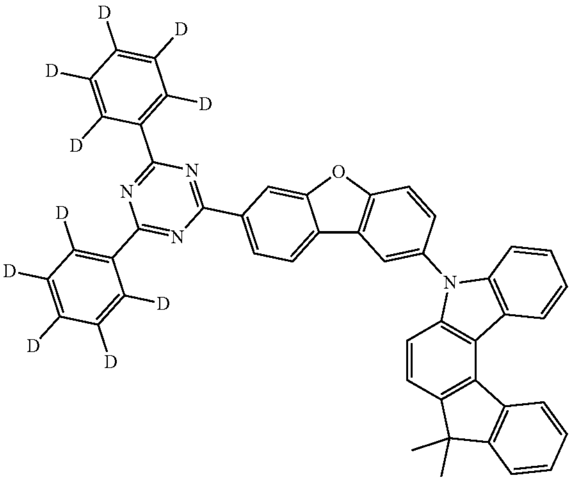
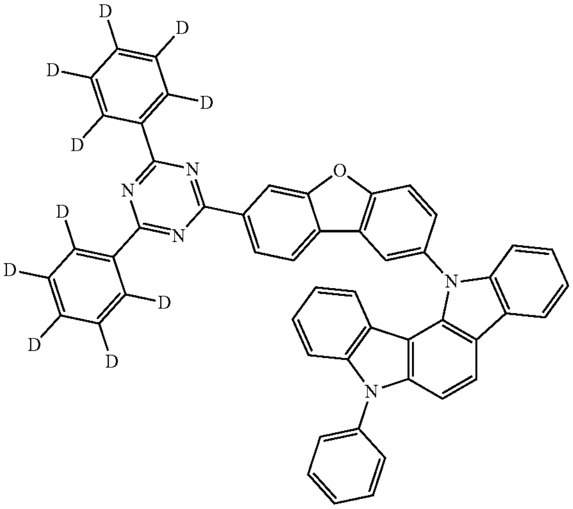
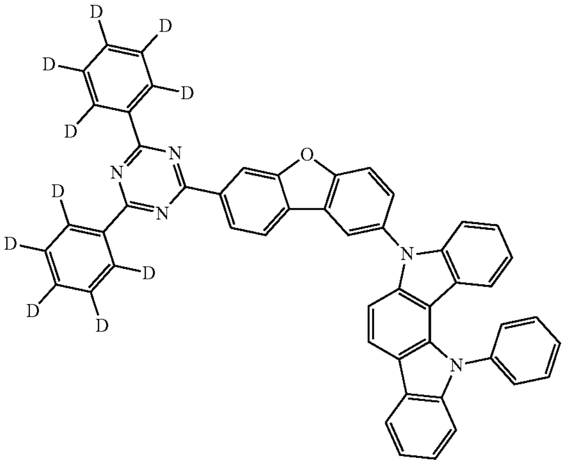
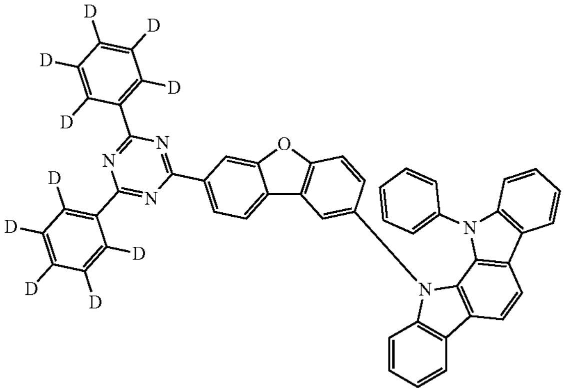
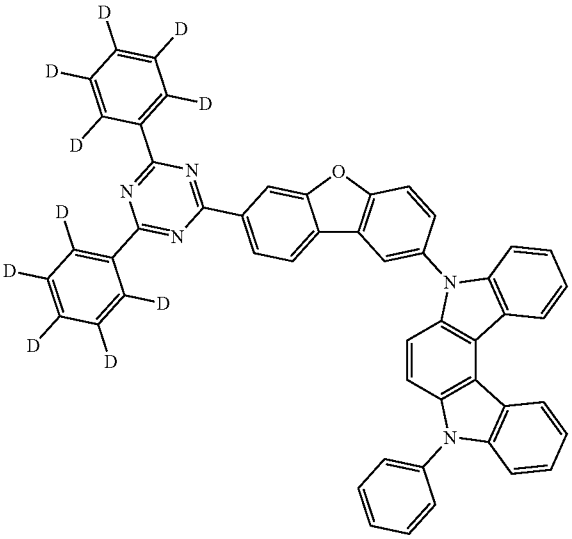
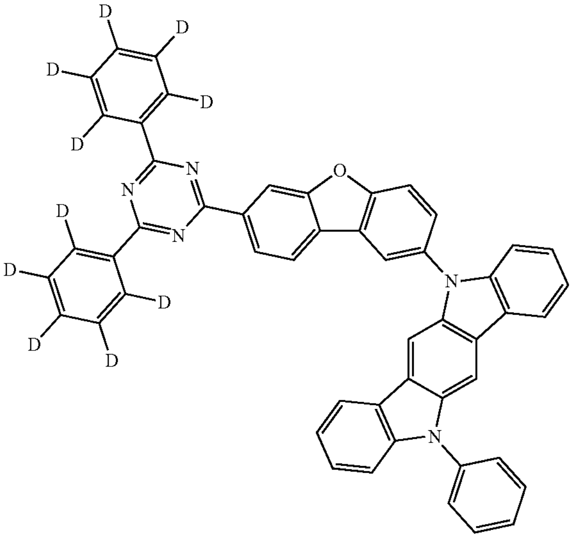
-continued -continued
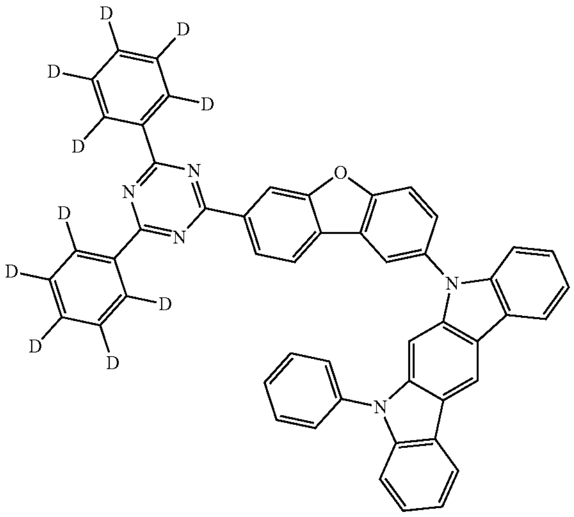
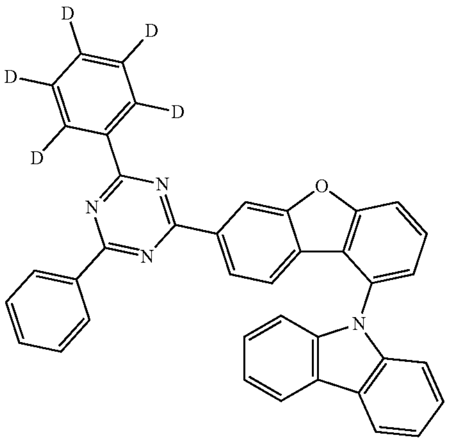
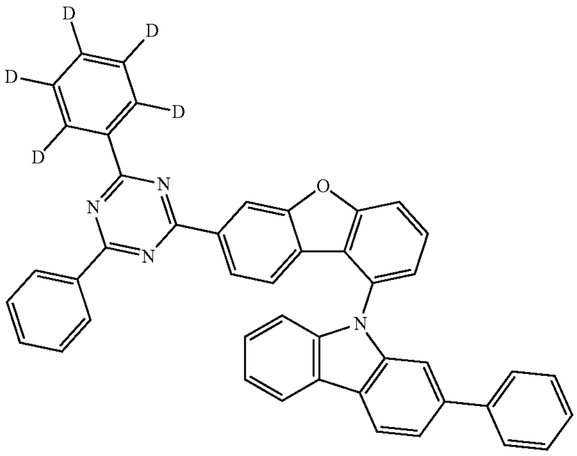
-continued
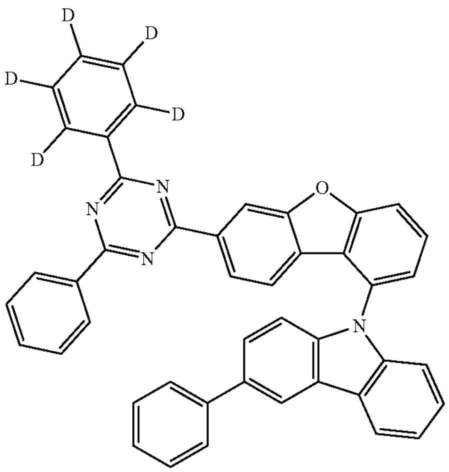
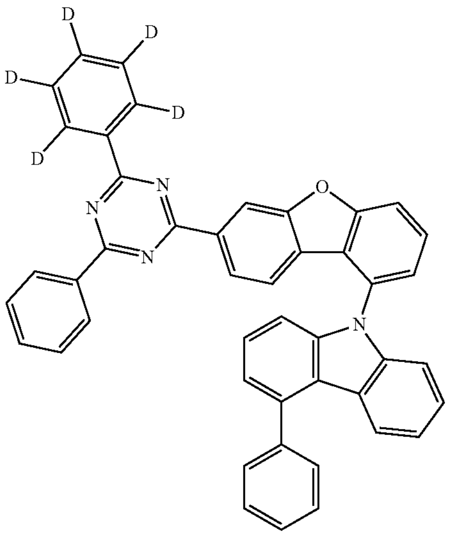
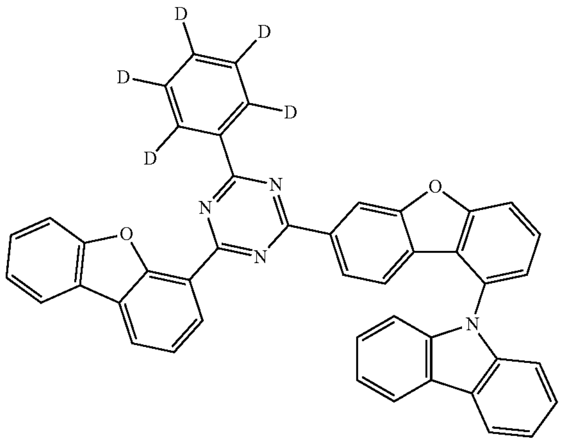

-continued
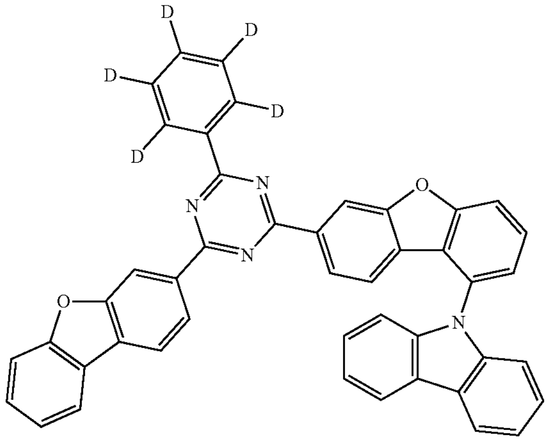
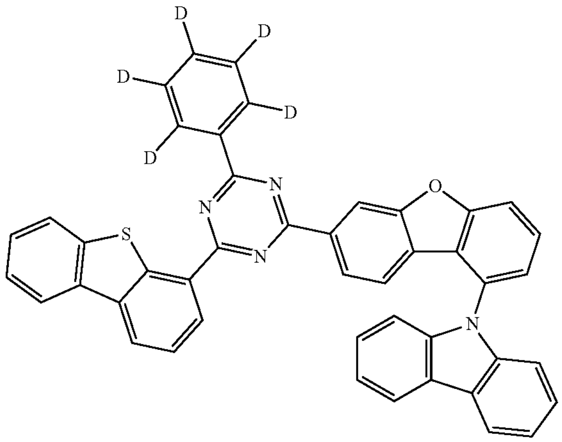
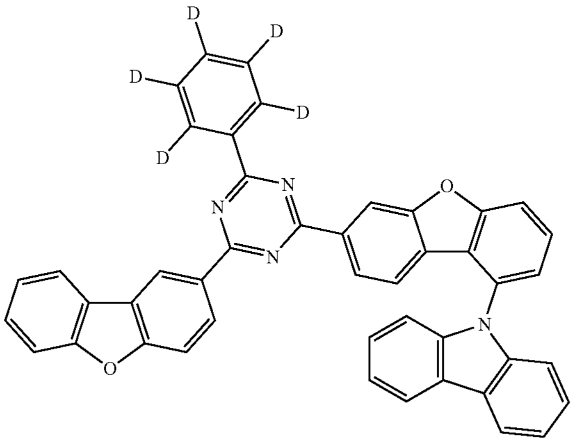
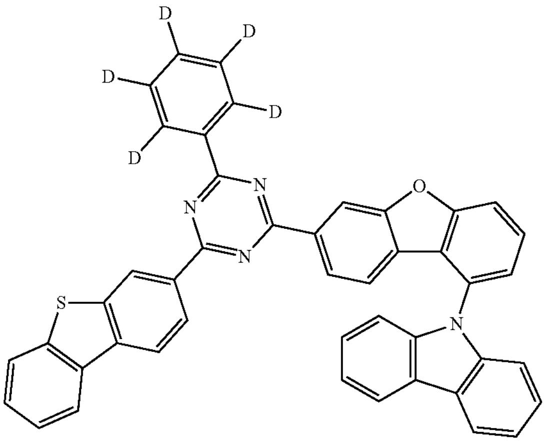
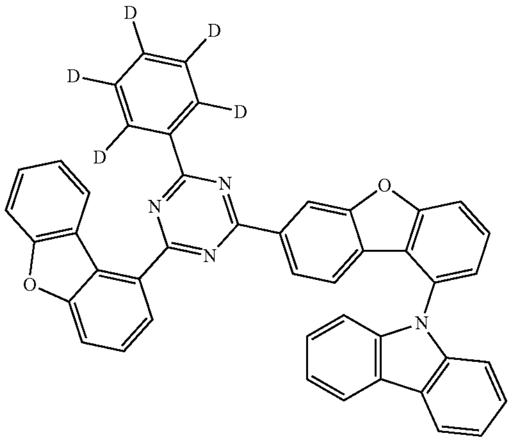
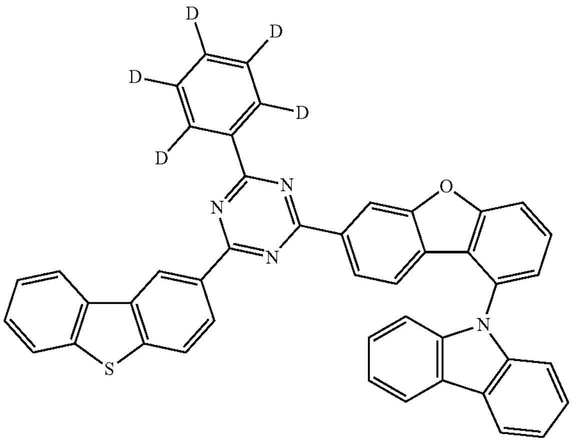
-continued -continued
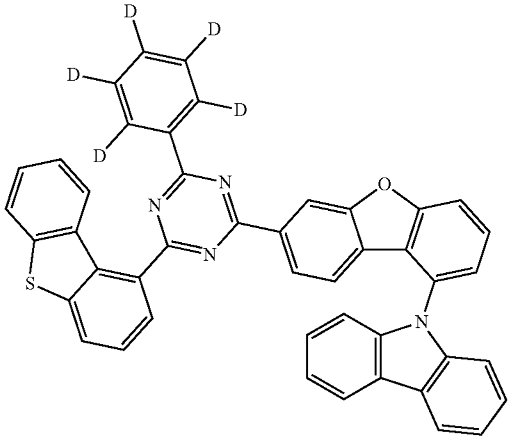
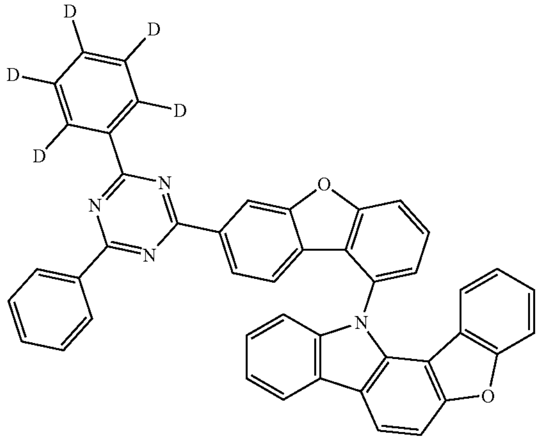
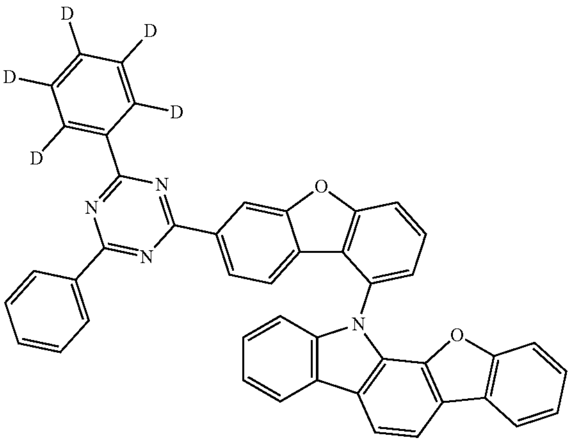
-continued
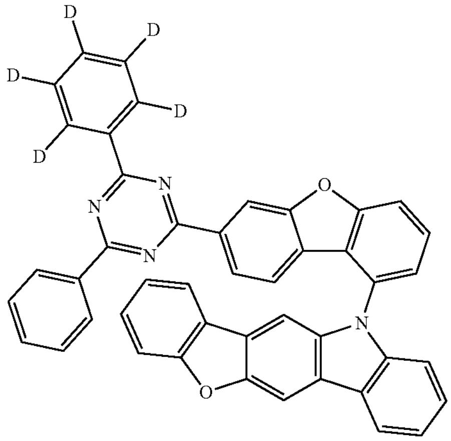
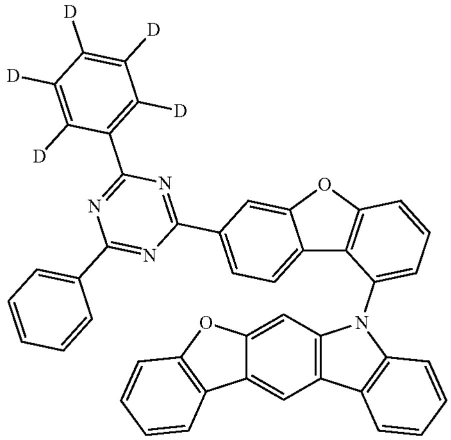
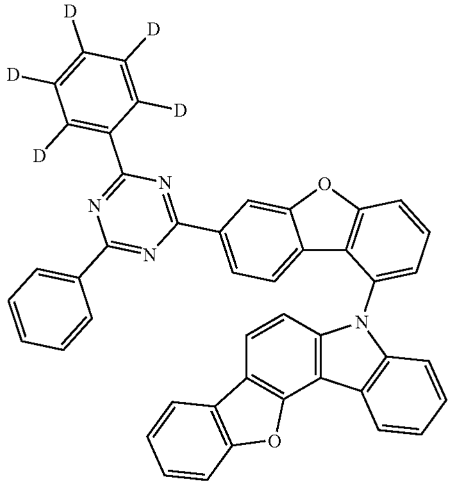

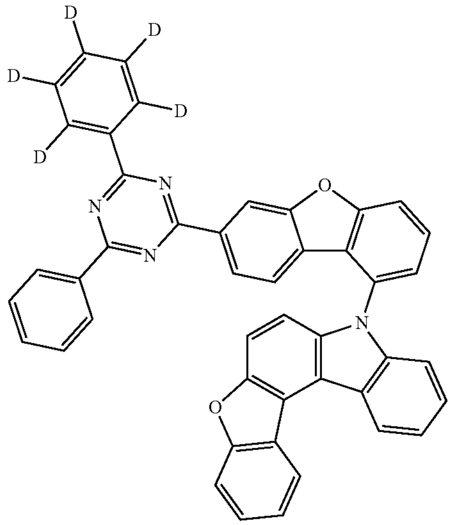
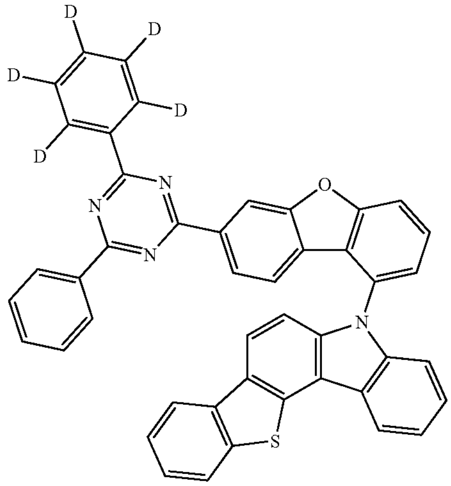
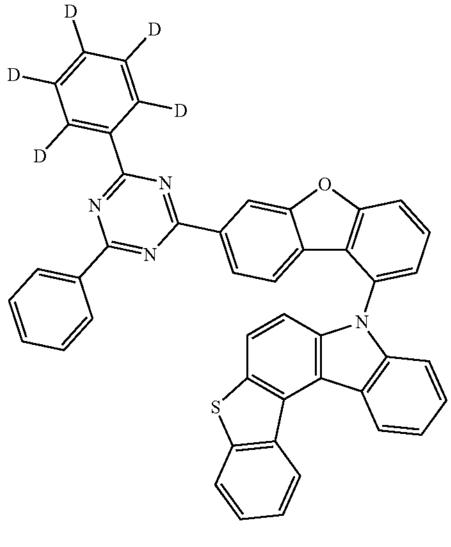
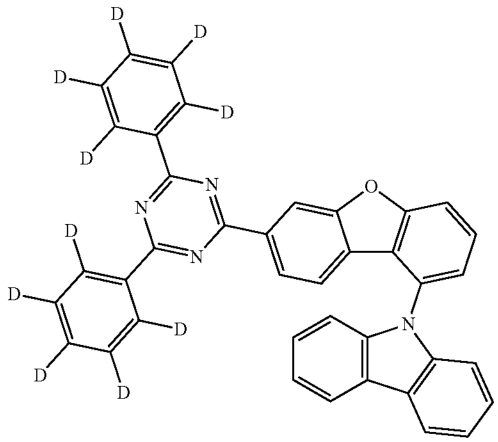
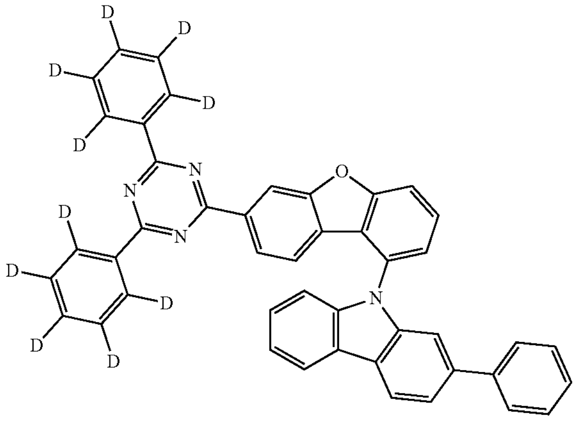
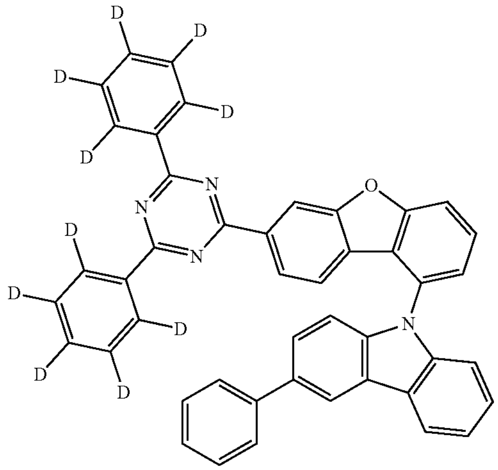

-continued
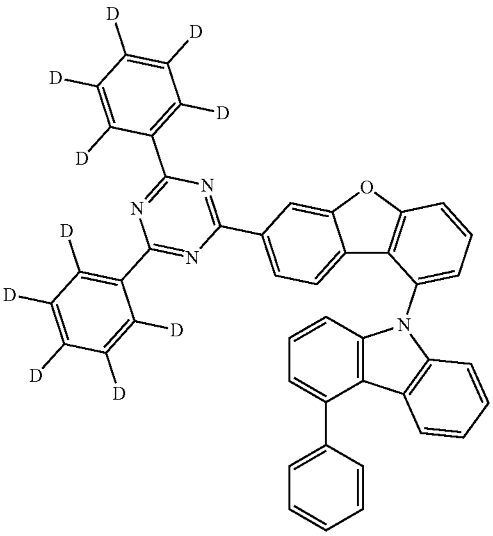
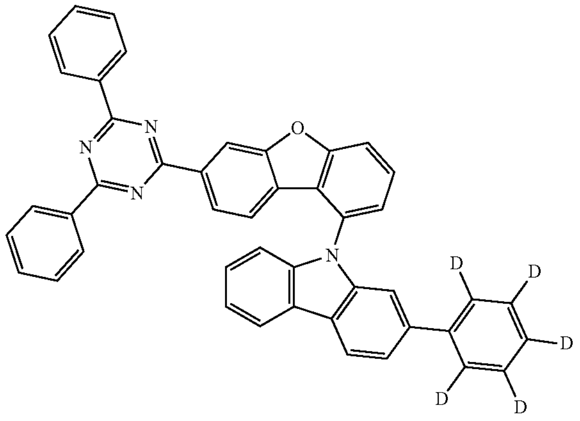
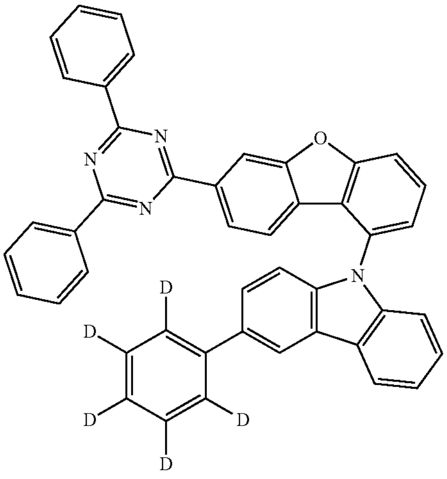
-continued
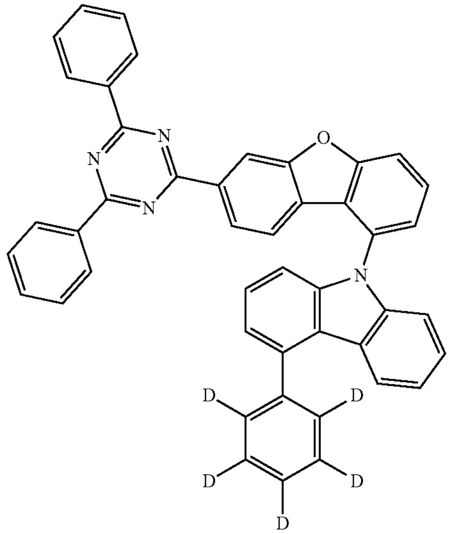
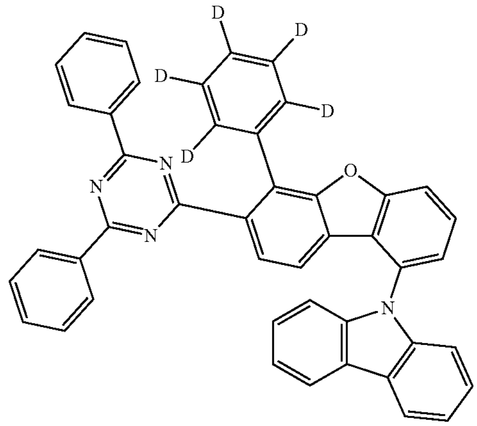
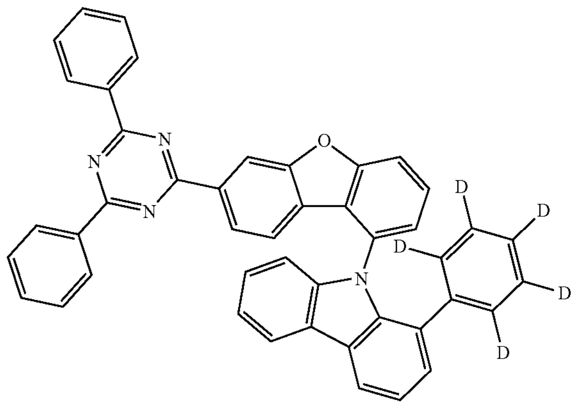

-continued
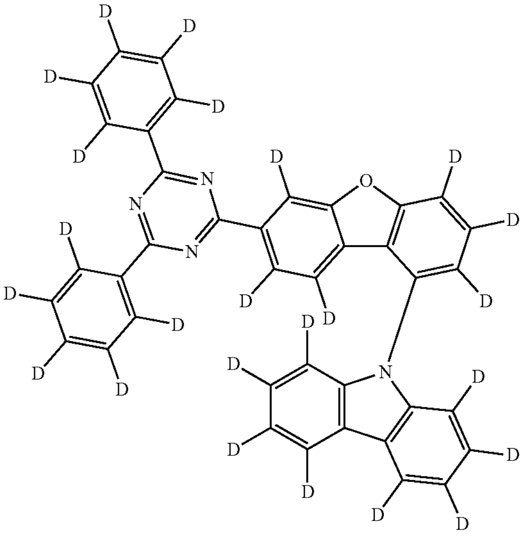
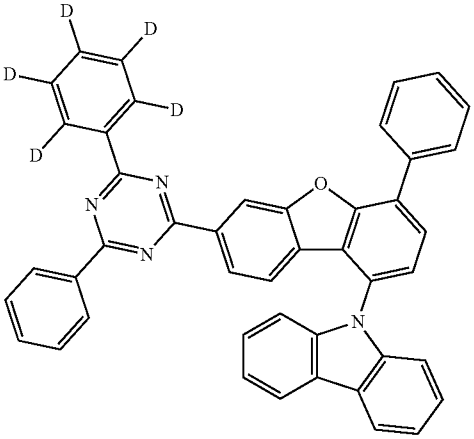
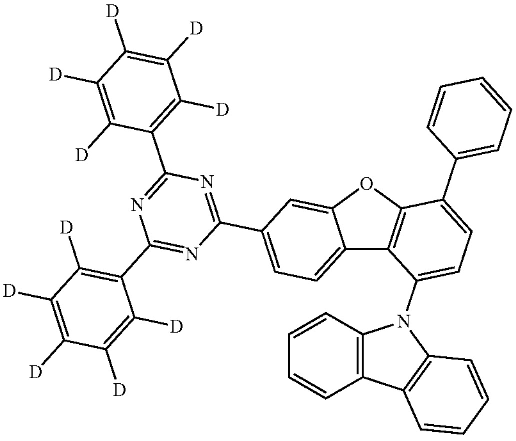
-continued
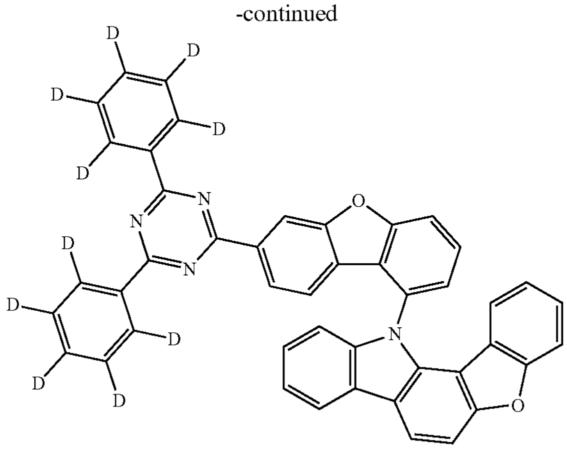
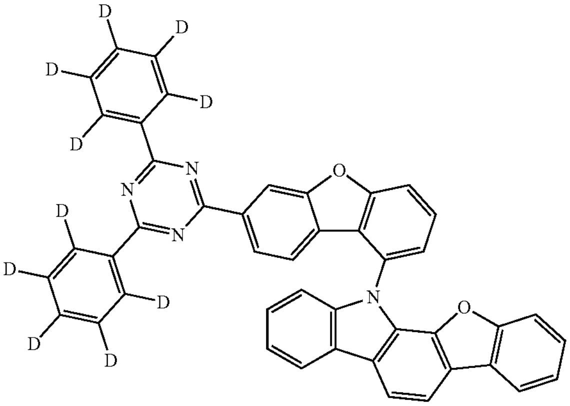
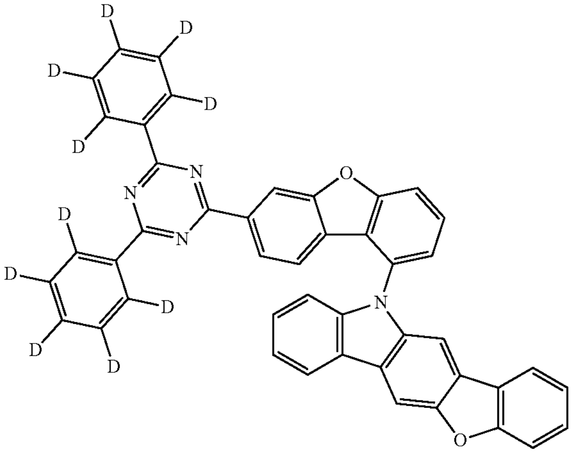
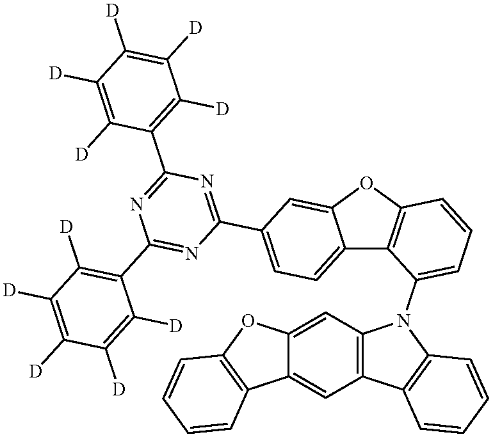

-continued
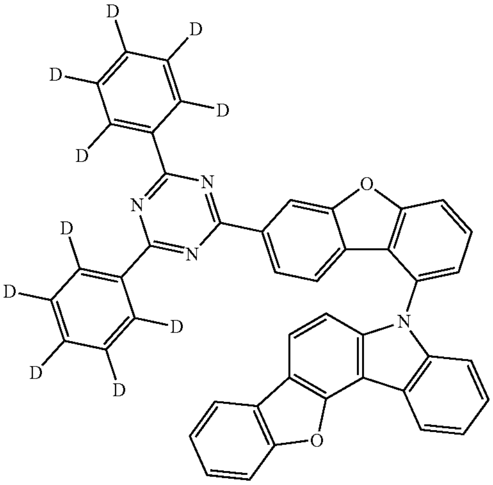
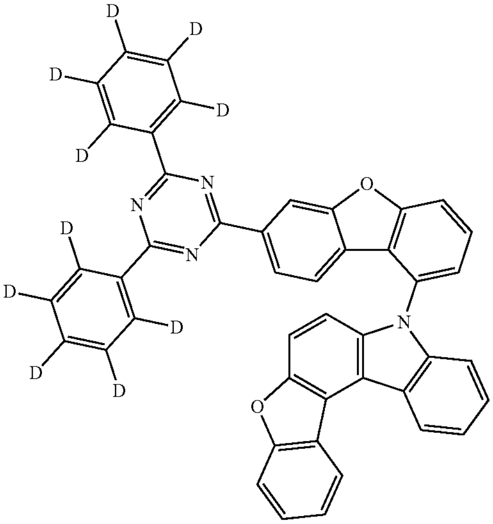
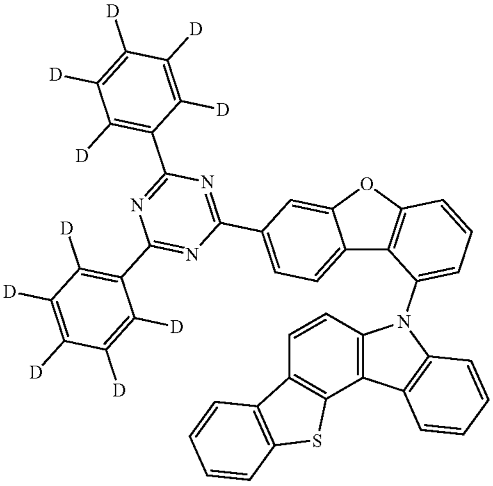
-continued
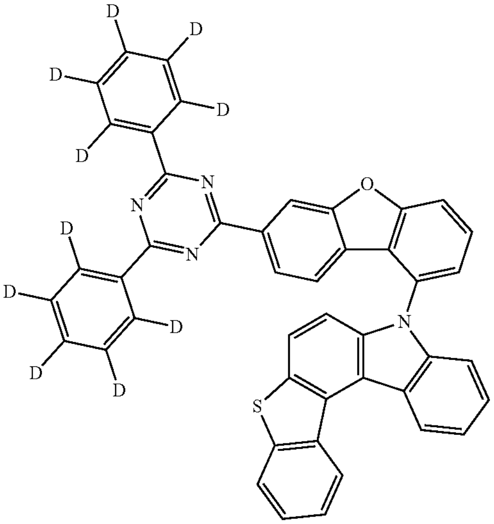
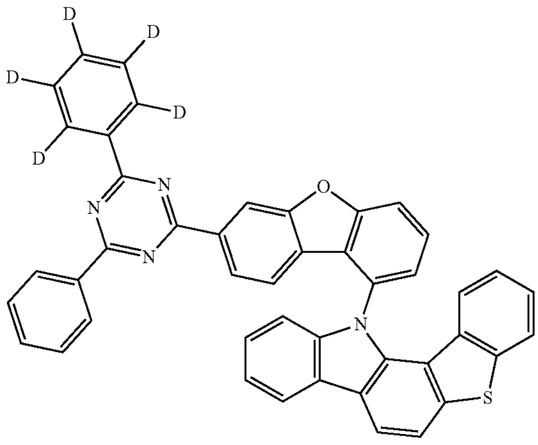
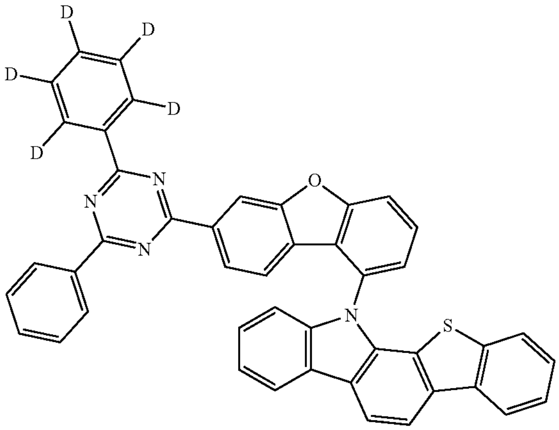

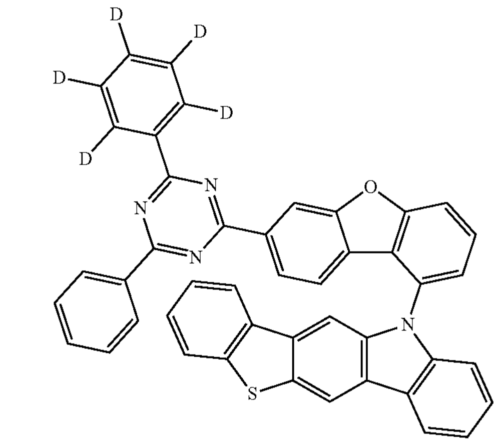
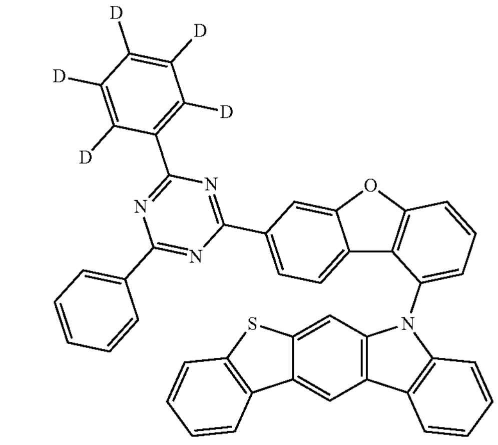
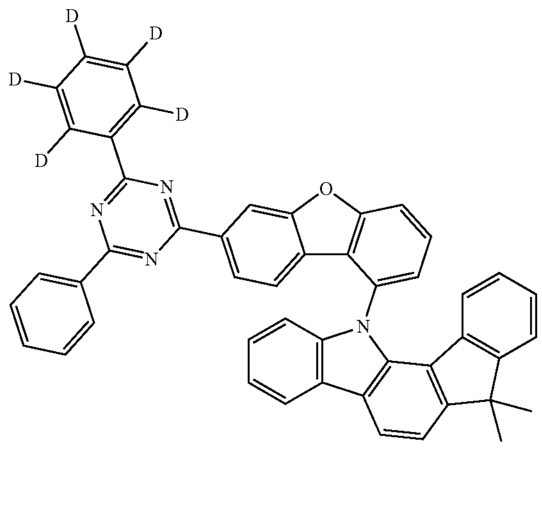
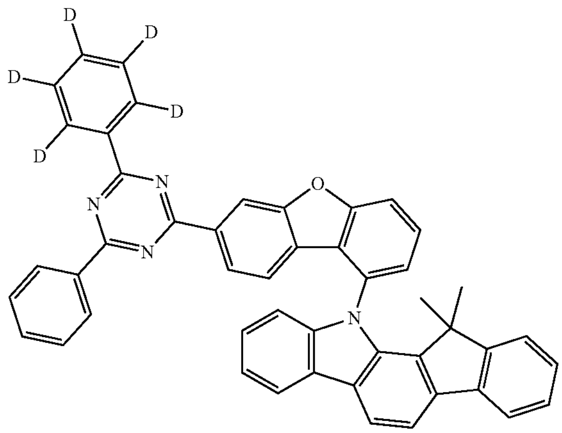
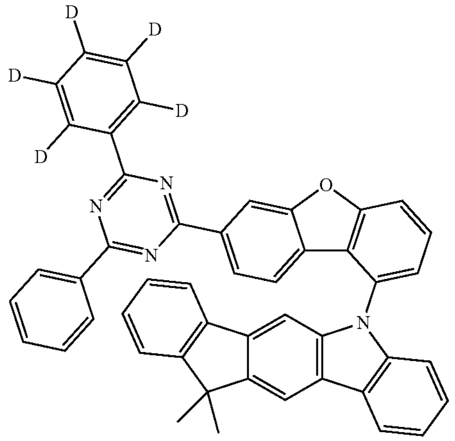
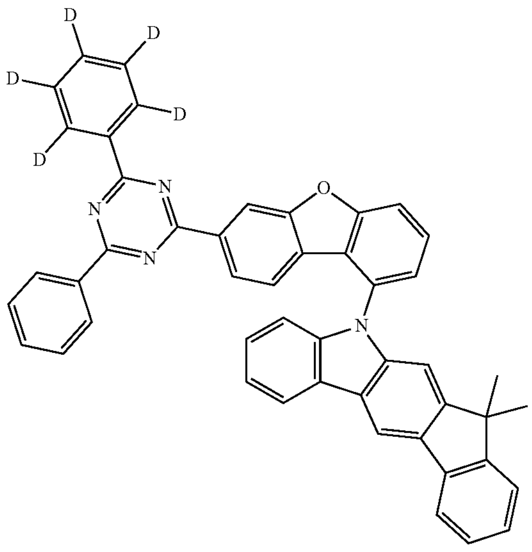

-continued
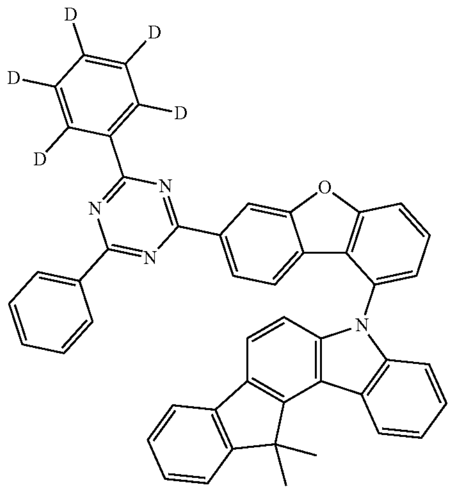
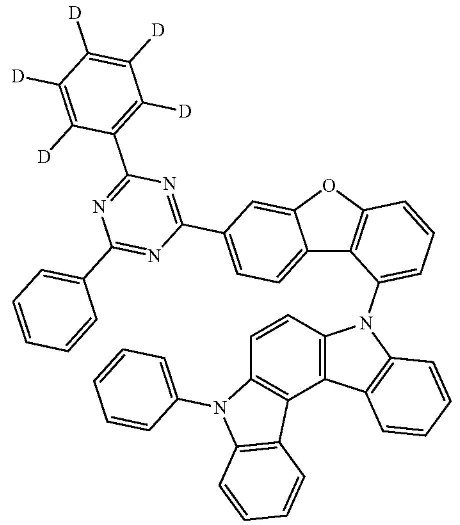
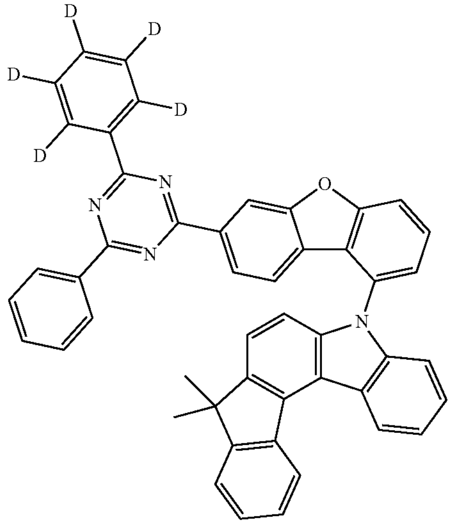
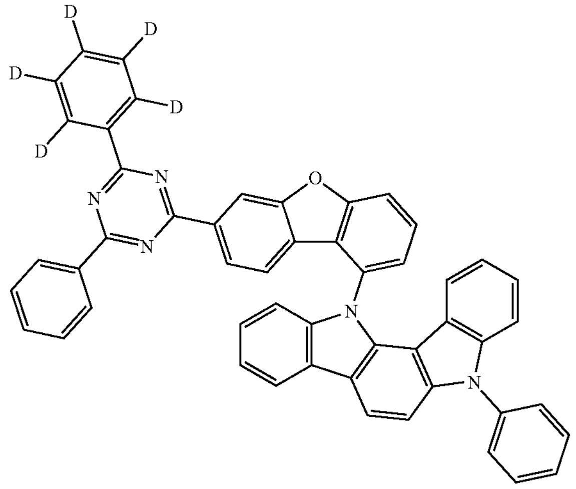
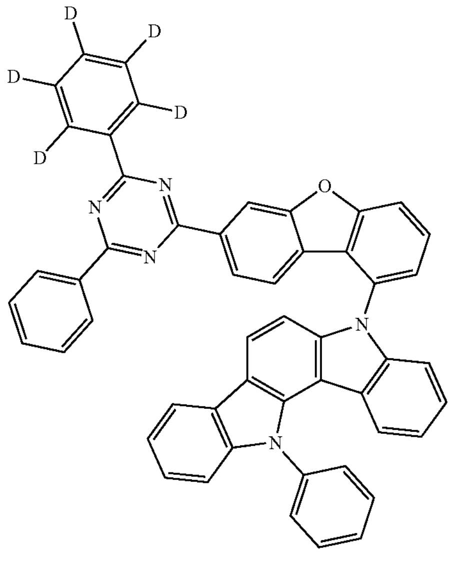
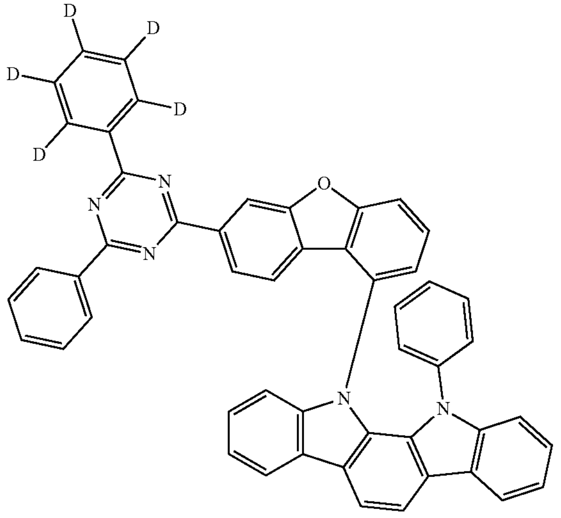
-continued -continued
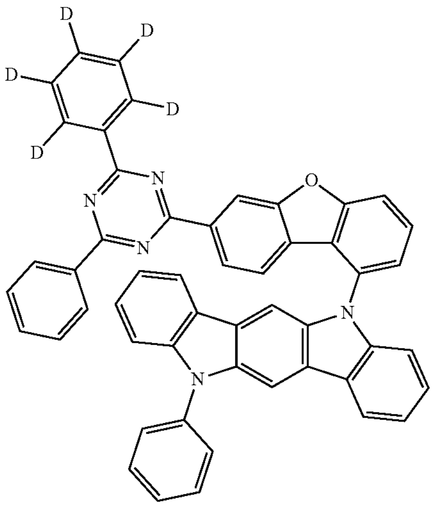
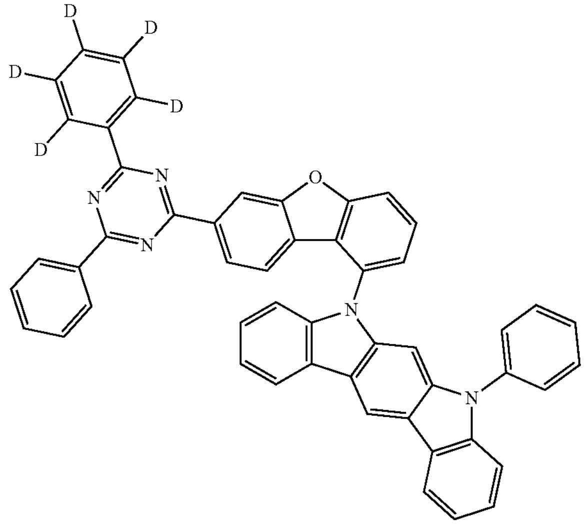
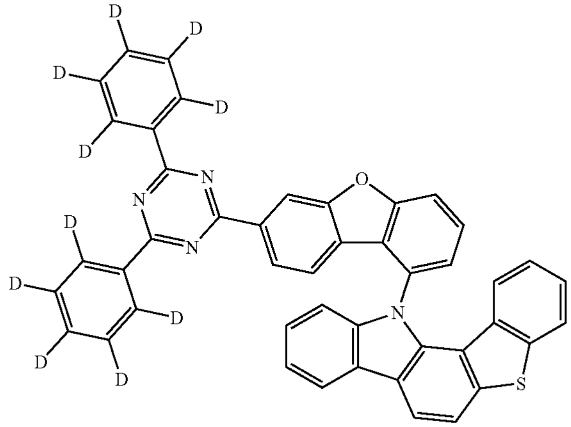
-continued
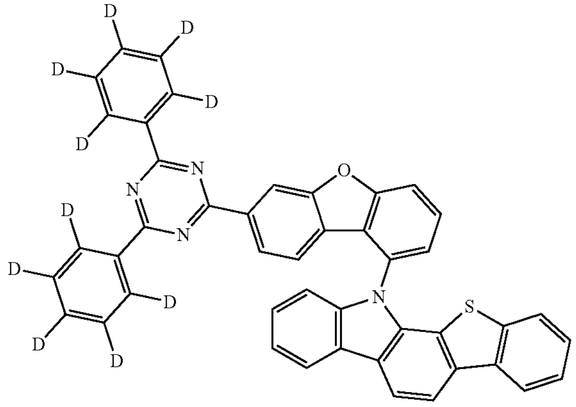
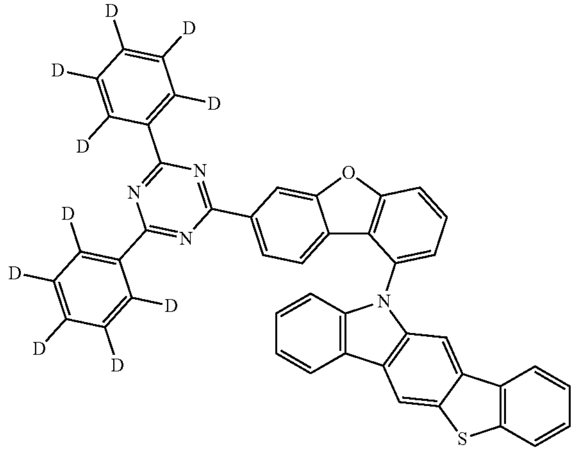
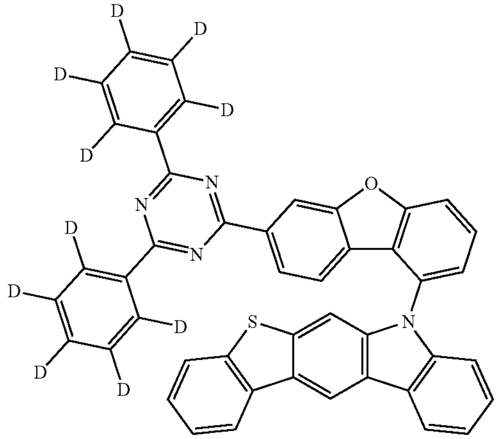
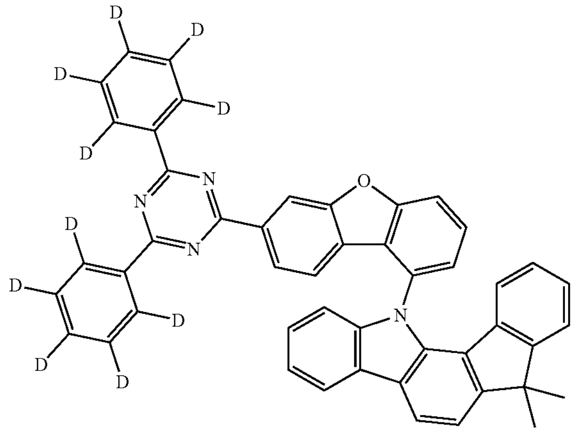

-continued
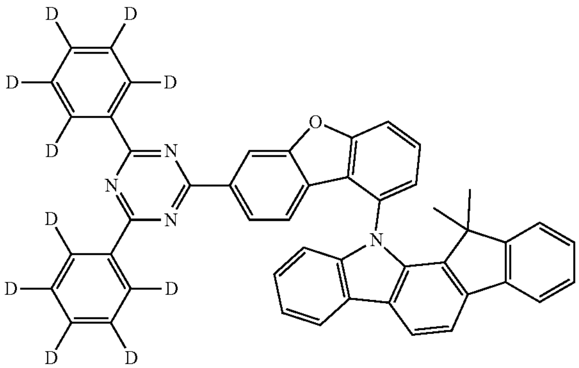
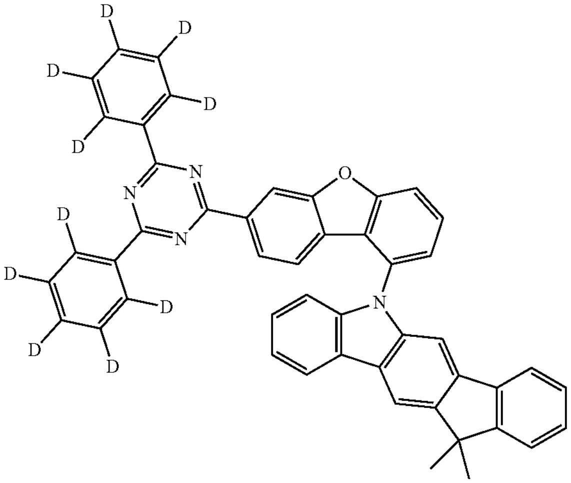
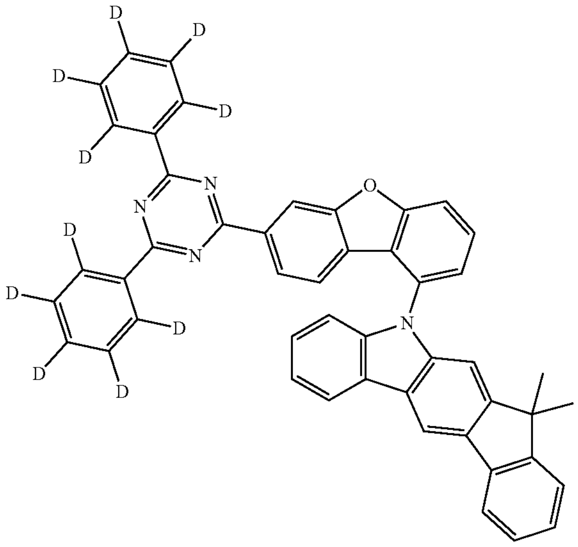
-continued
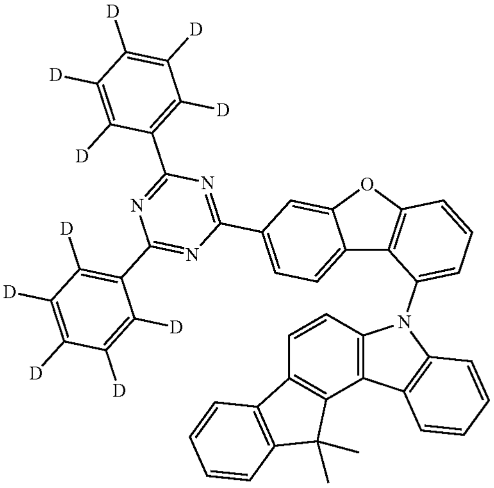
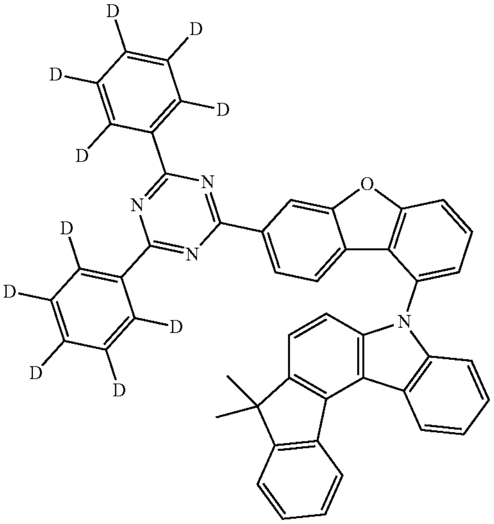
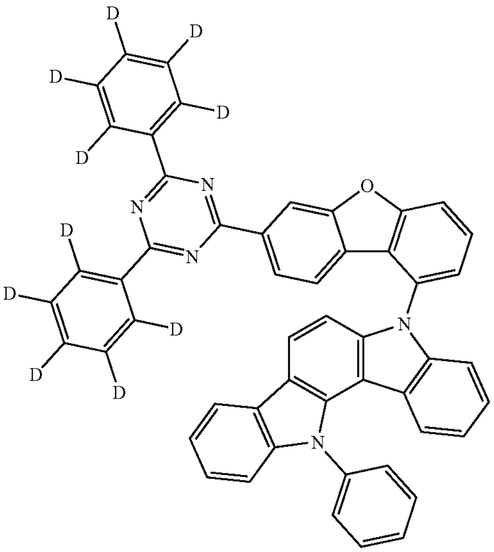

-continued
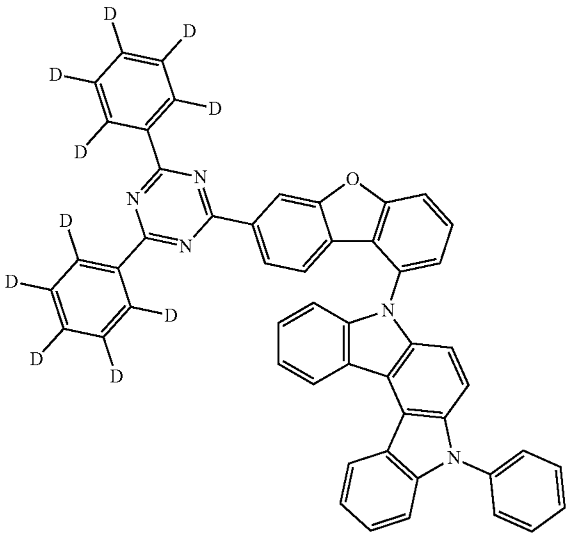
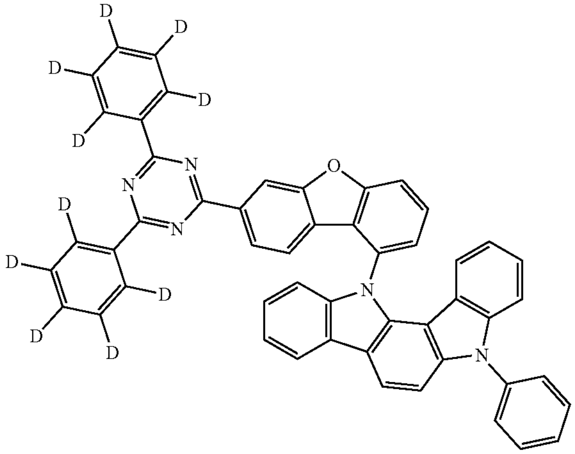
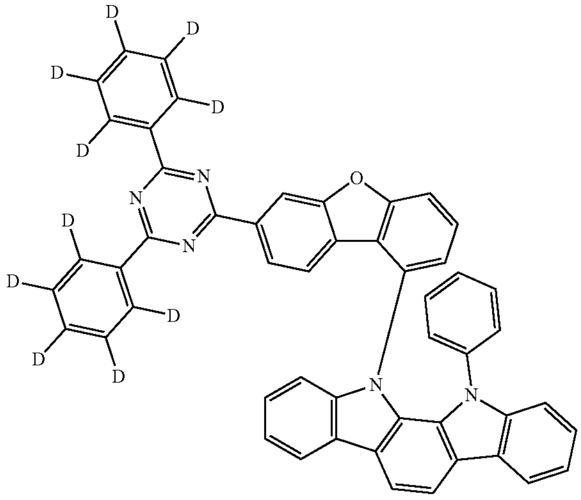
-continued
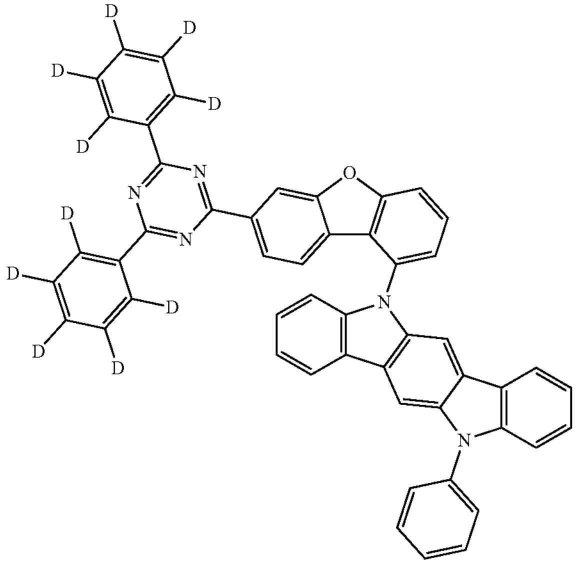
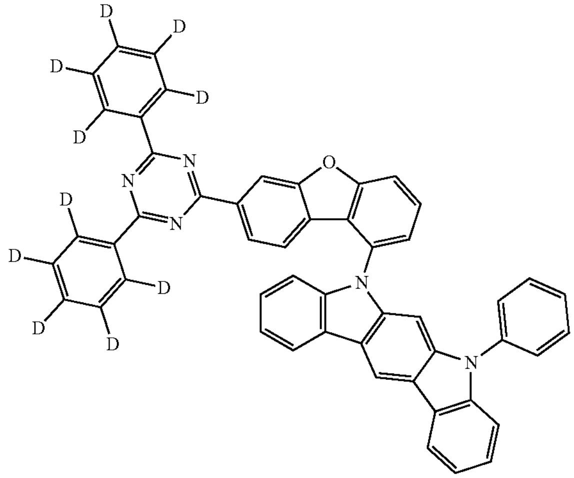
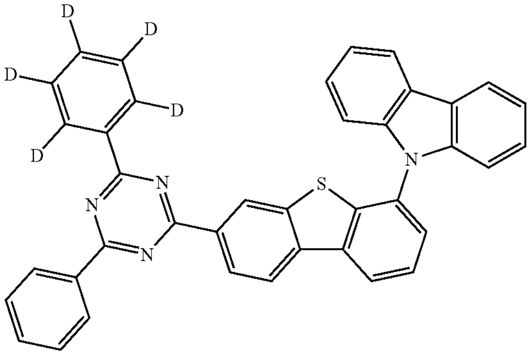
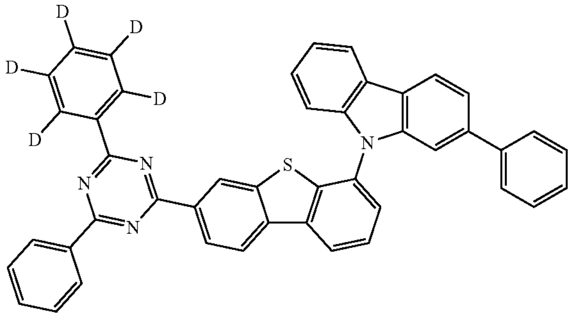

-continued
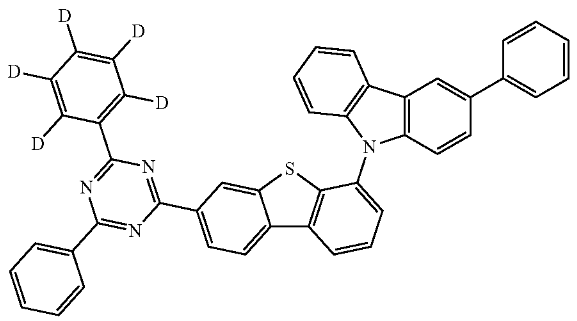
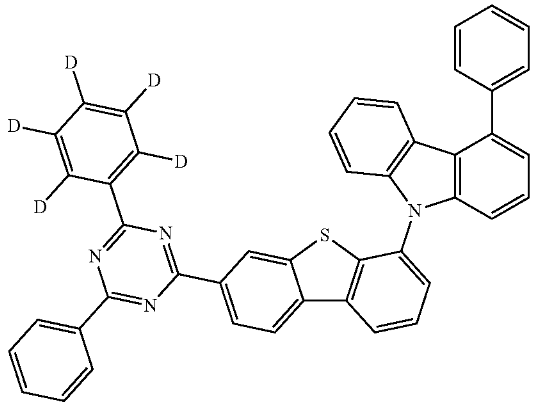
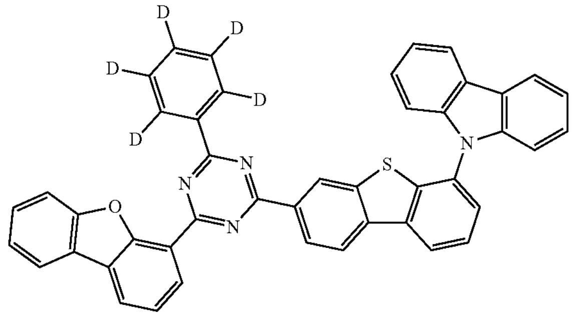
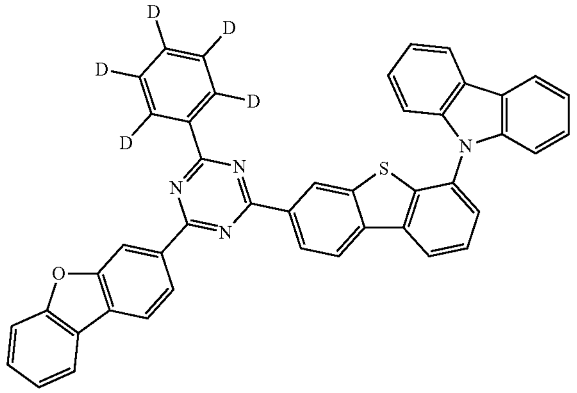
-continued
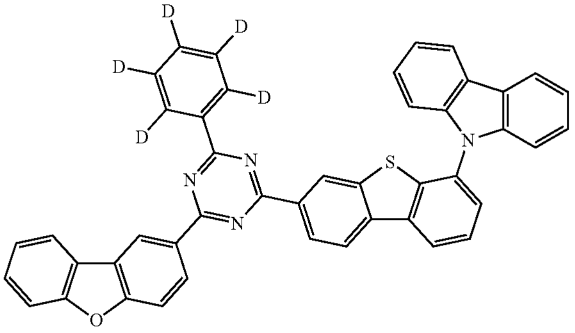
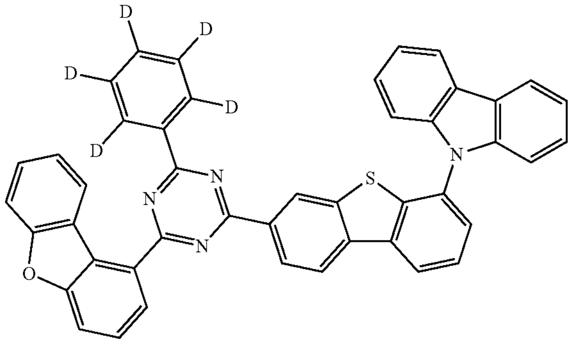
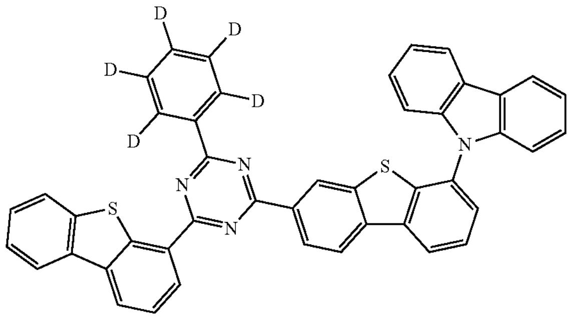
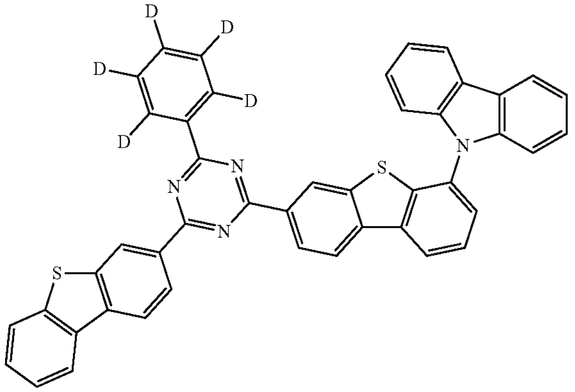
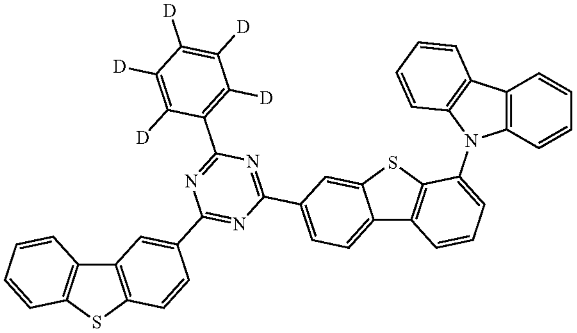

-continued
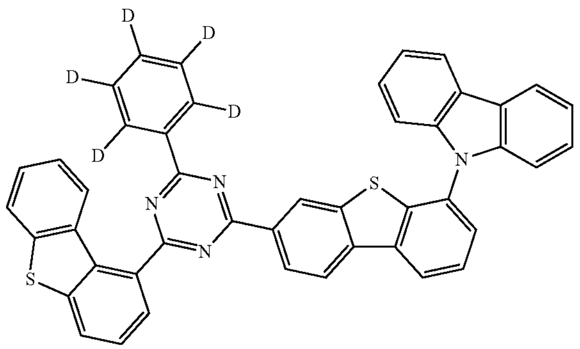
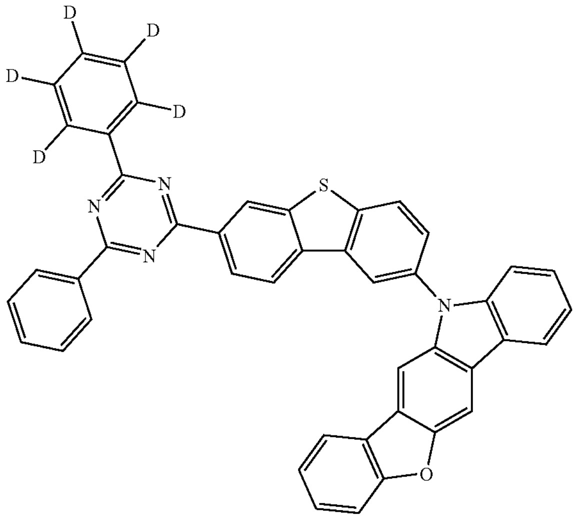
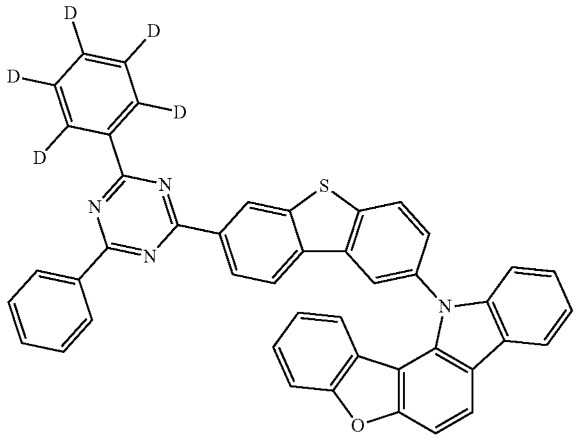
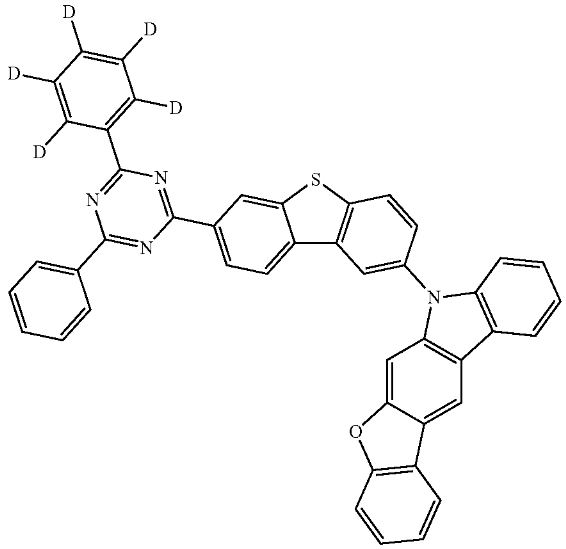
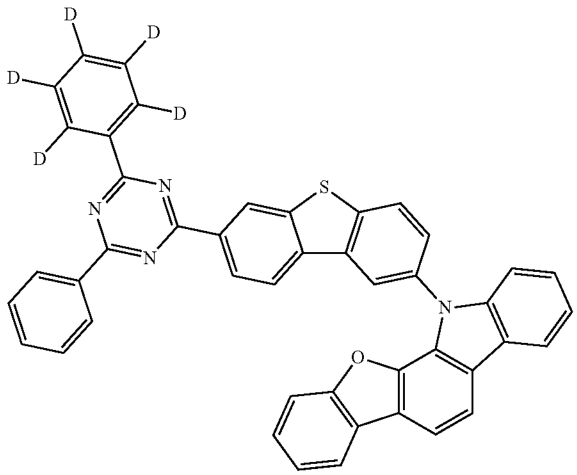
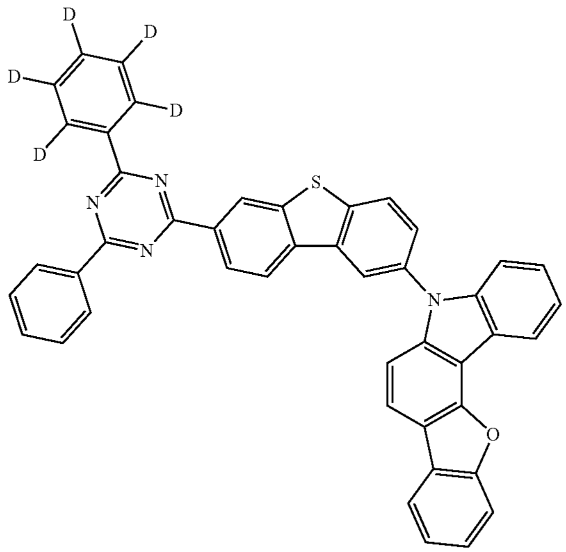
-continued -continued
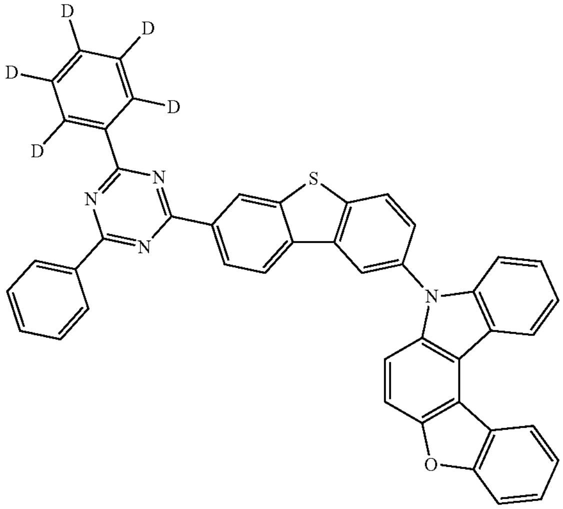
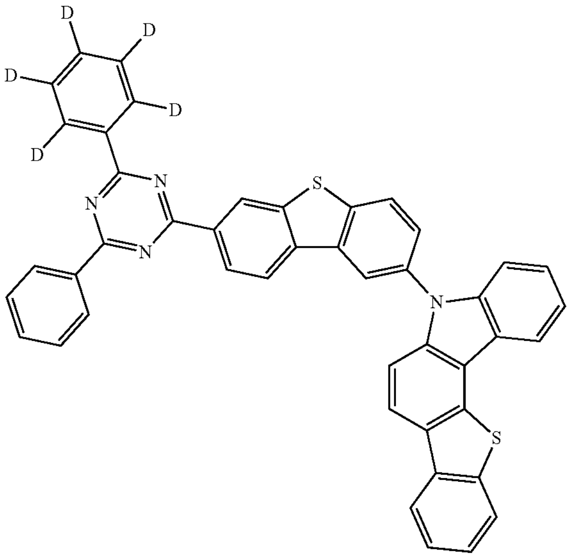
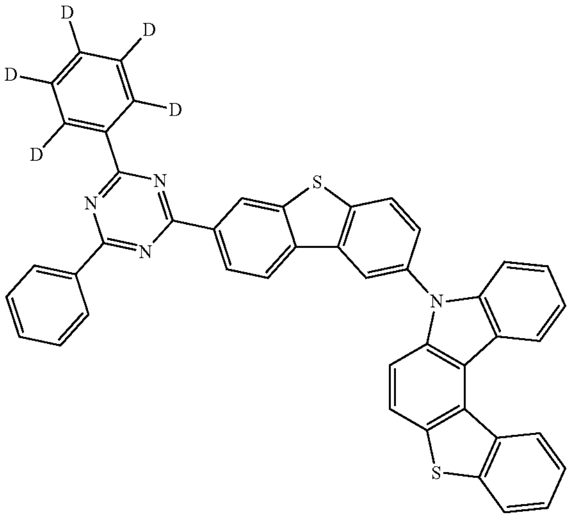
-continued
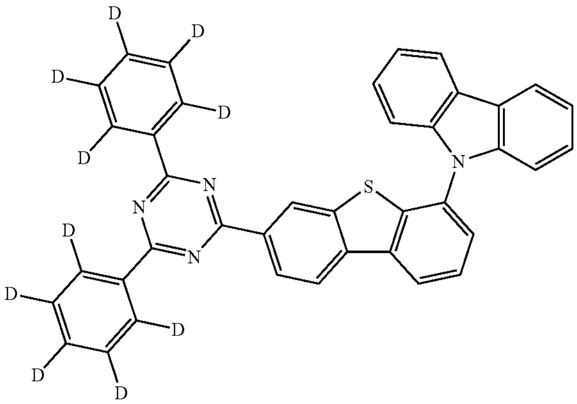
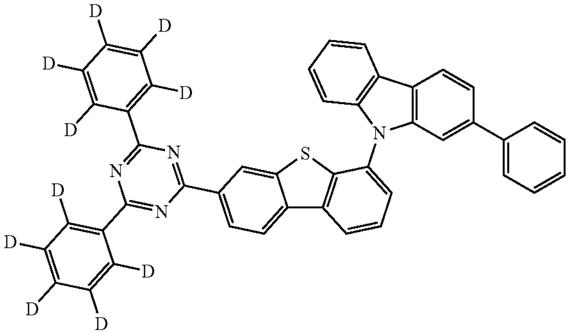
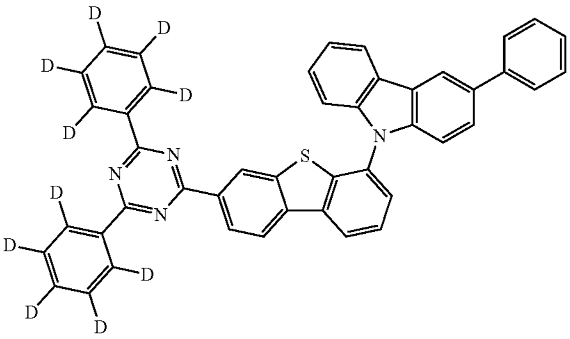
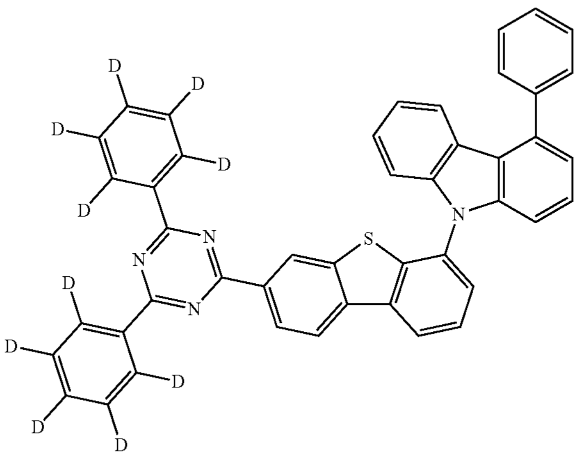

-continued
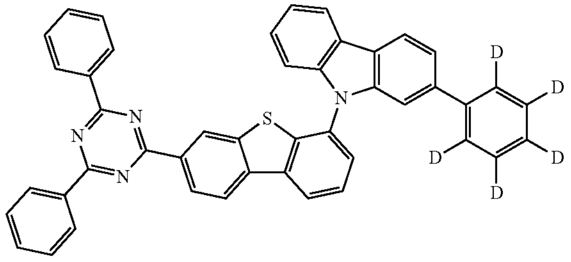
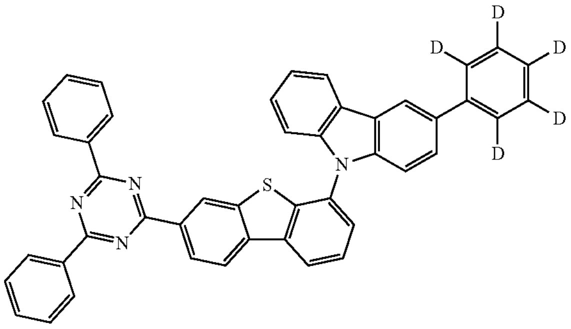
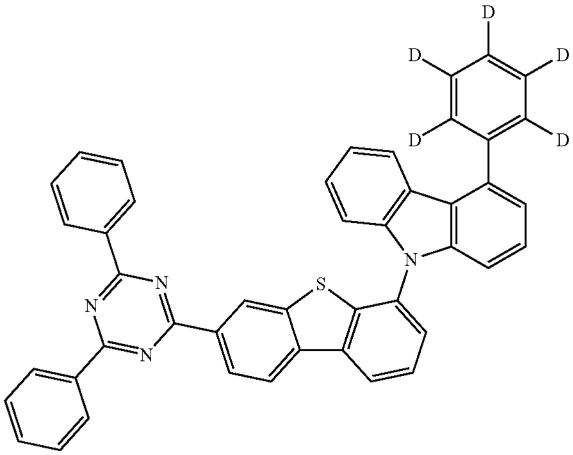
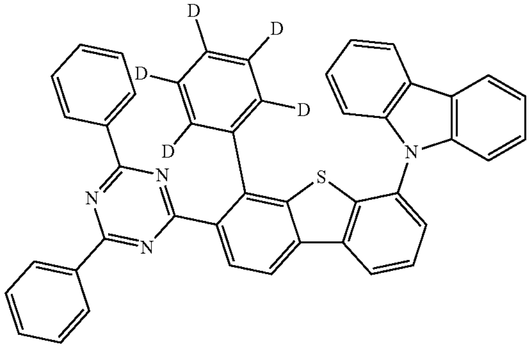
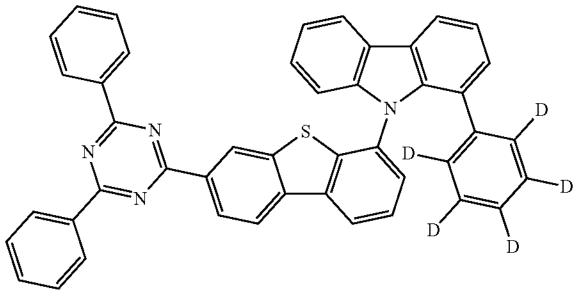
-continued
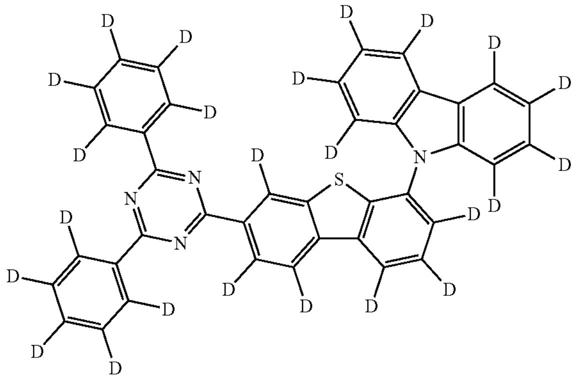
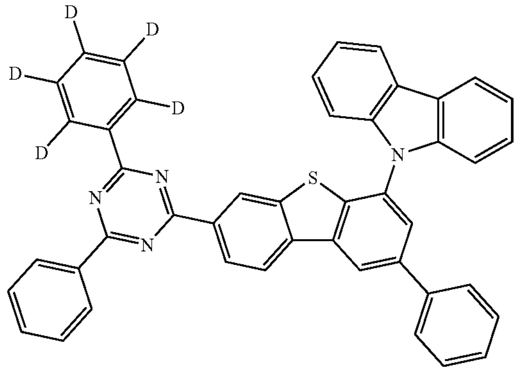
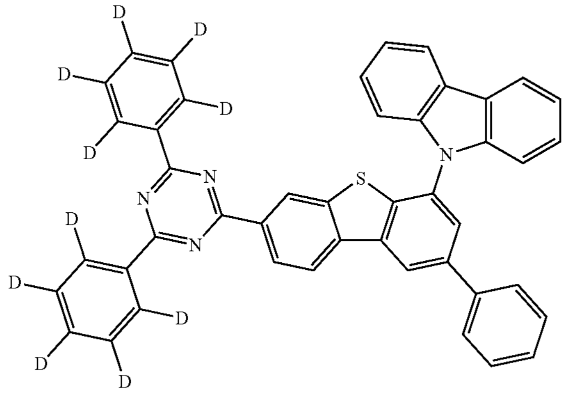
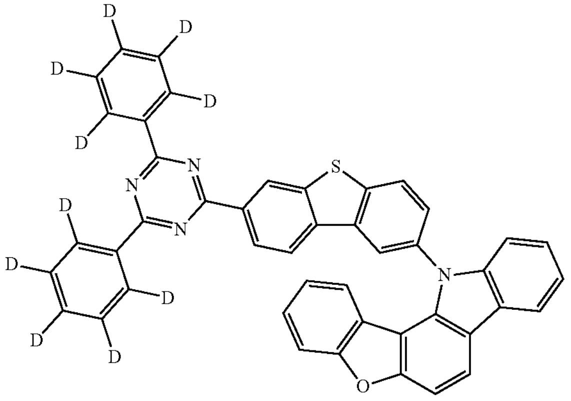

-continued
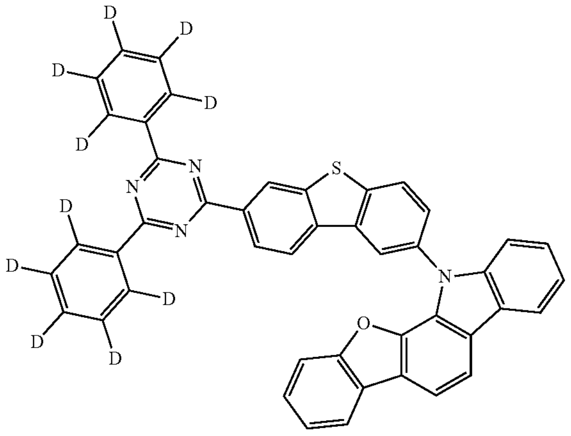
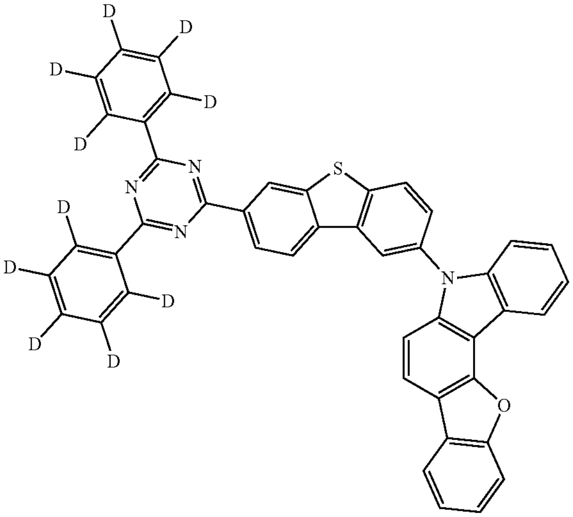
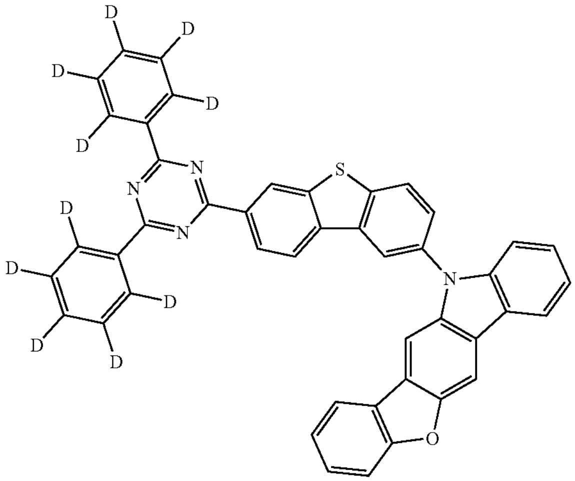
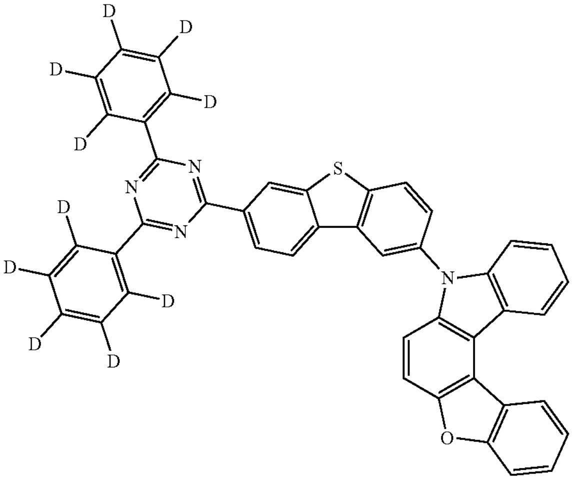
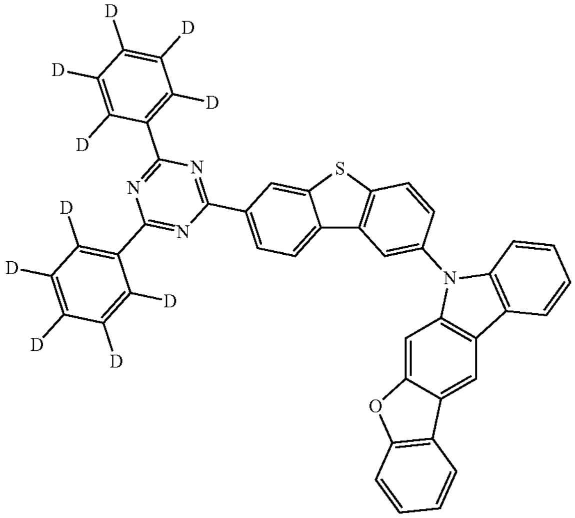
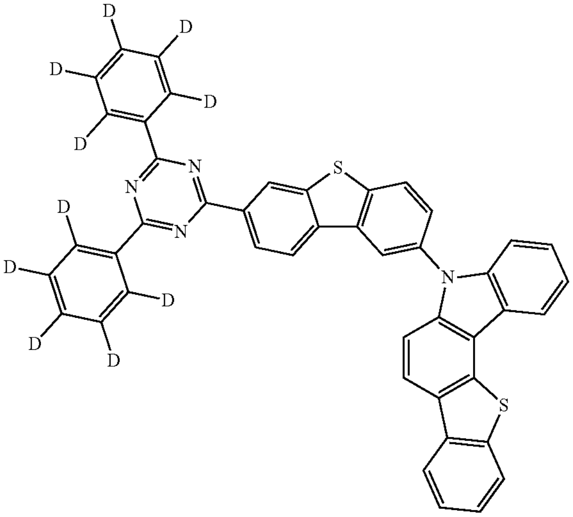
-continued -continued
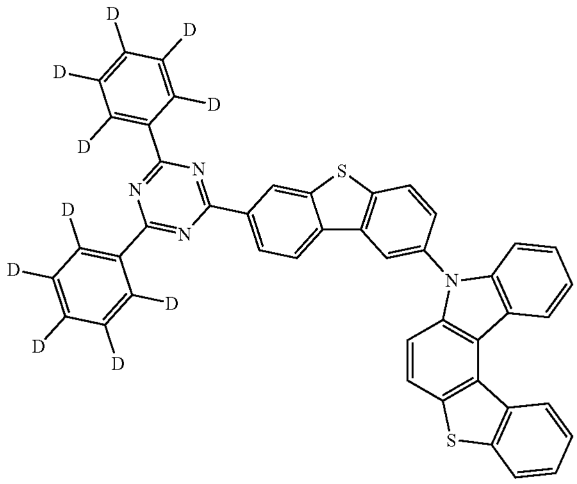
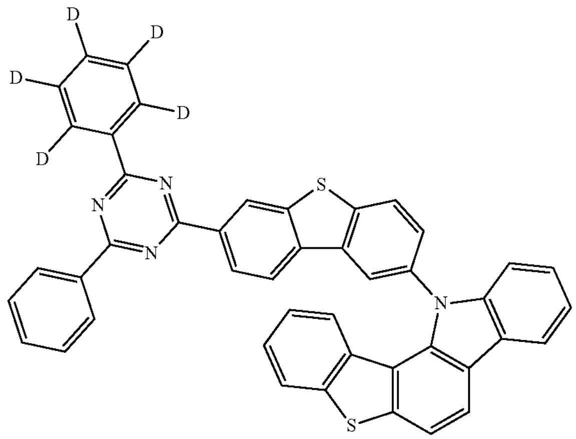
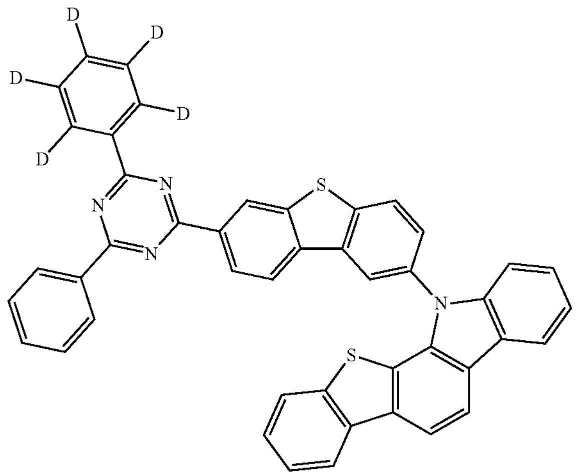 [SMILES: [2H]c1c([2H])c([2H])c(-c2nc(-c3ccccc3)nc(-c3ccc4c(c3)sc3ccc(-n5c6ccccc6c6ccc7c8ccccc8sc7c65)cc34)n2)c([2H])c1[2H]]
-continued
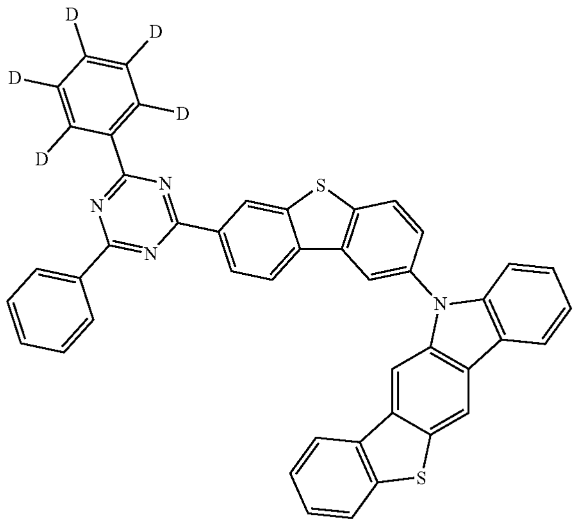
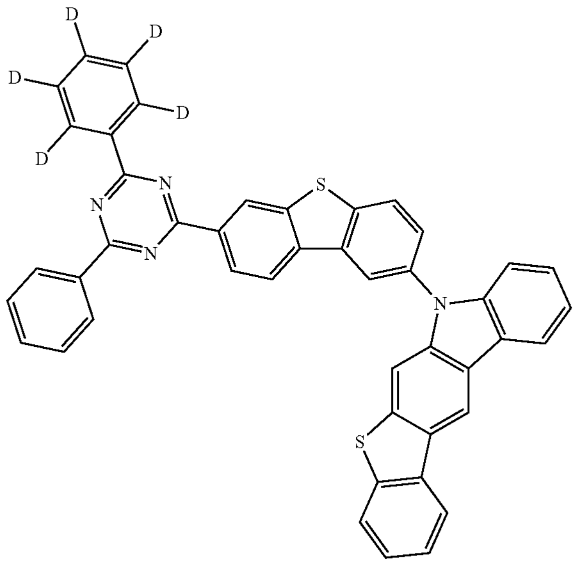
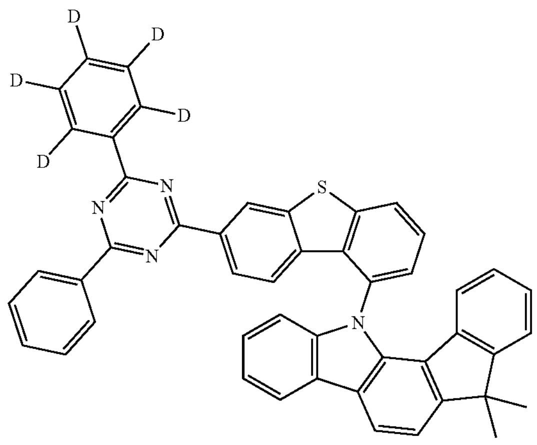

-continued
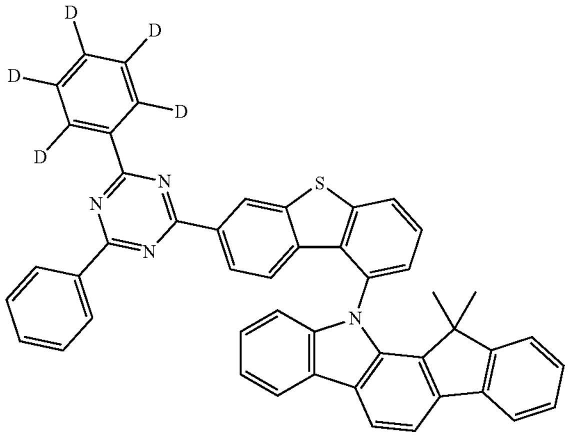
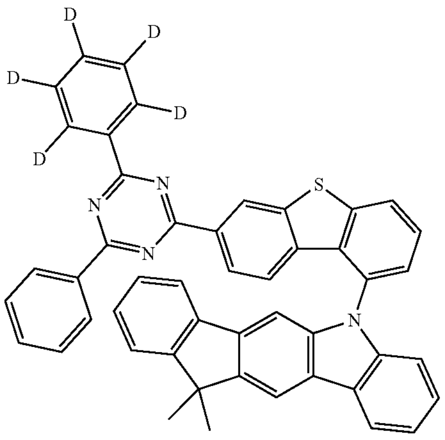
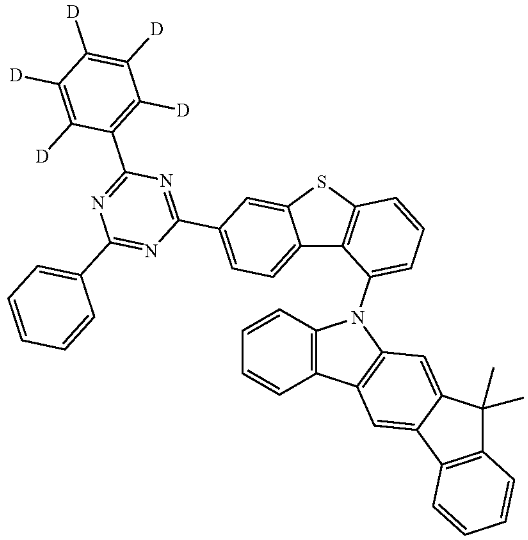
-continued
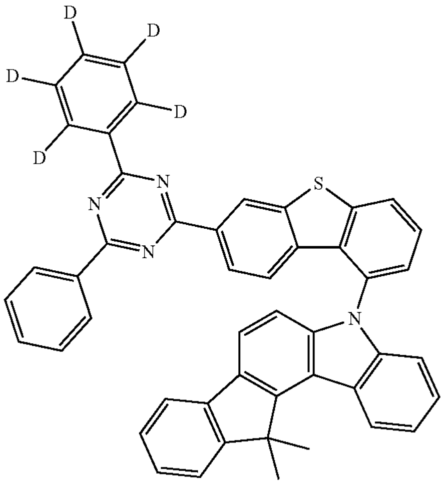
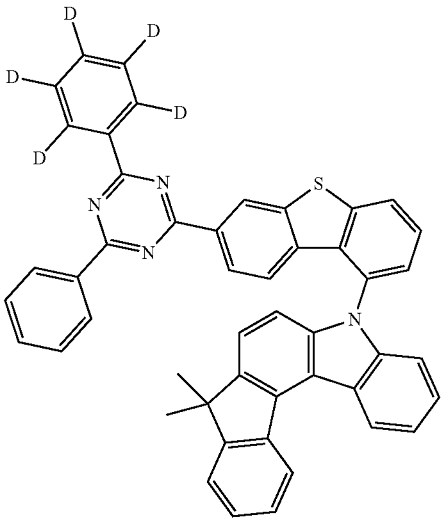
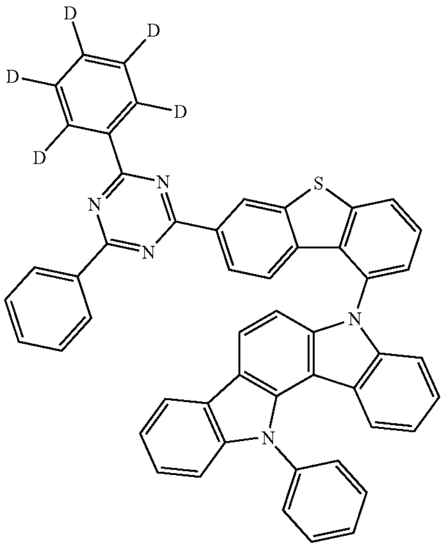

-continued
-continued
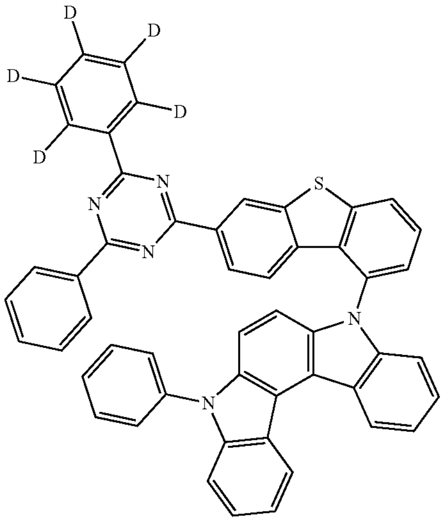
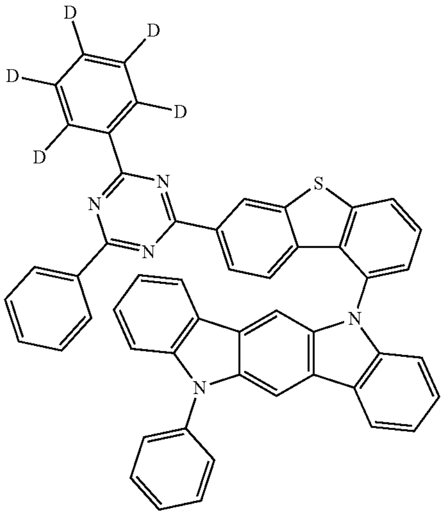
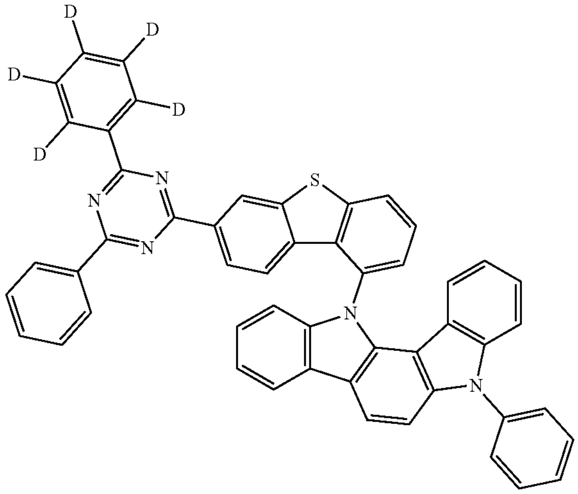
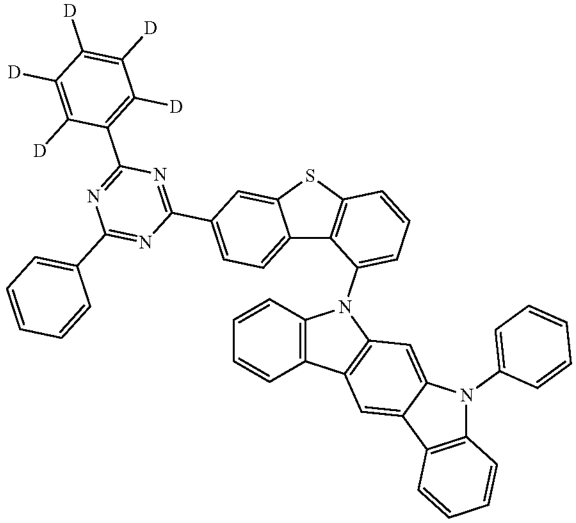
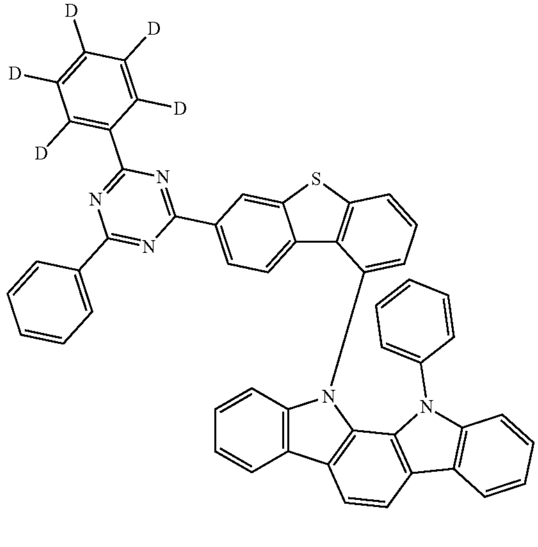
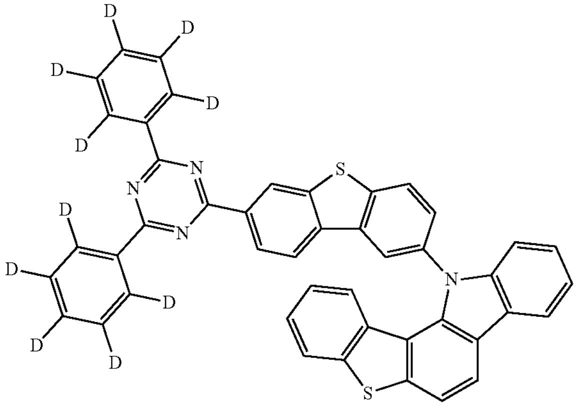

-continued
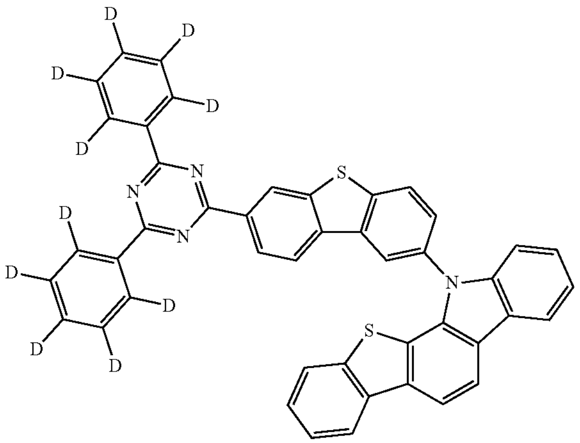
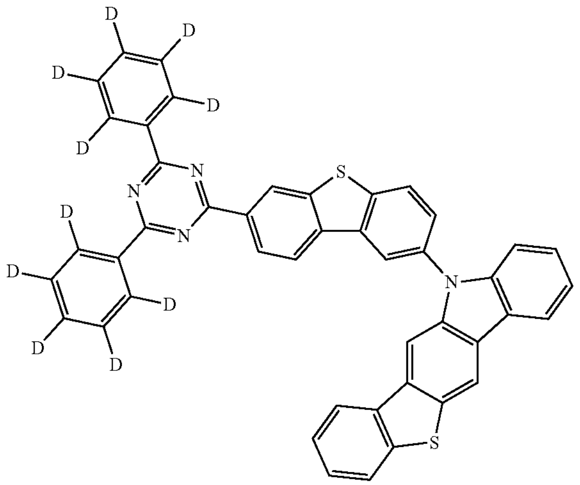
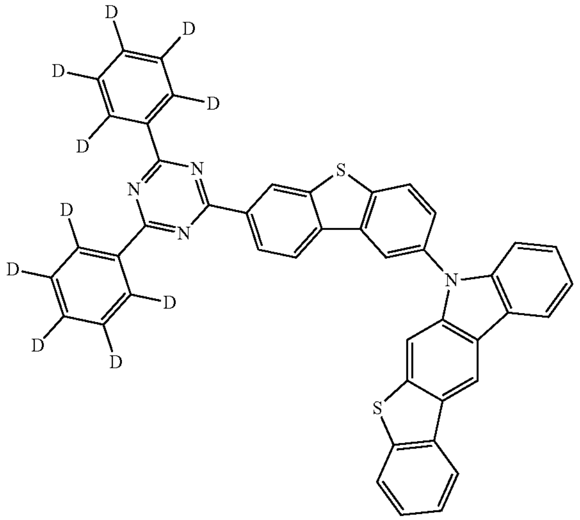
-continued
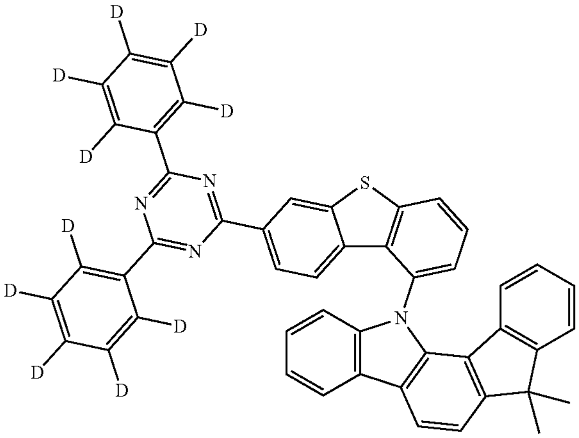
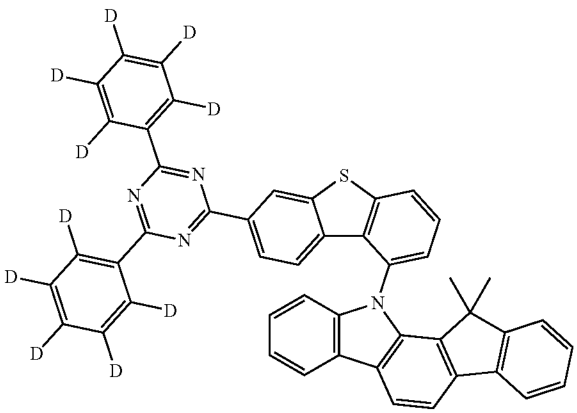
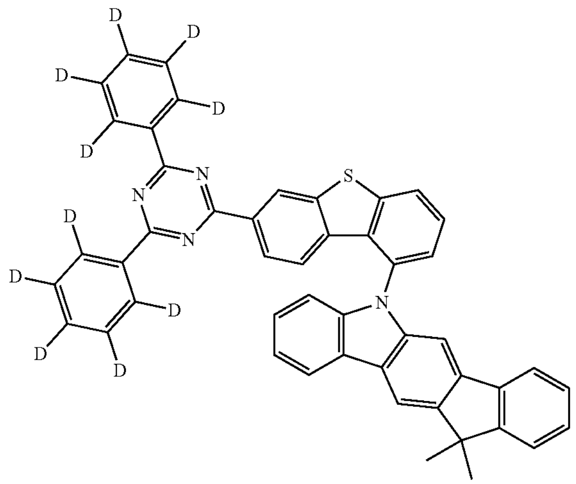

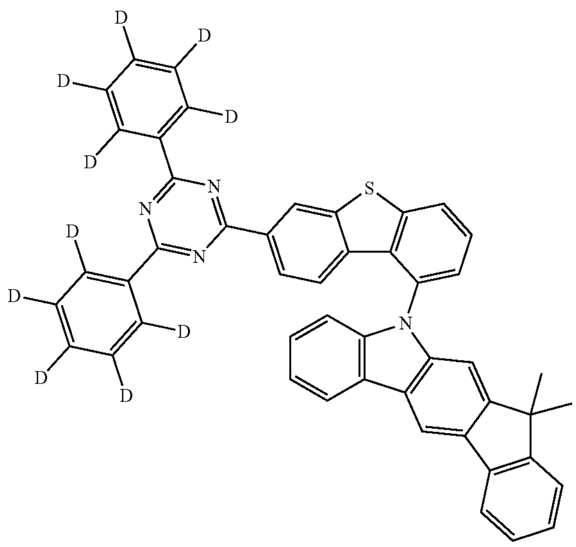
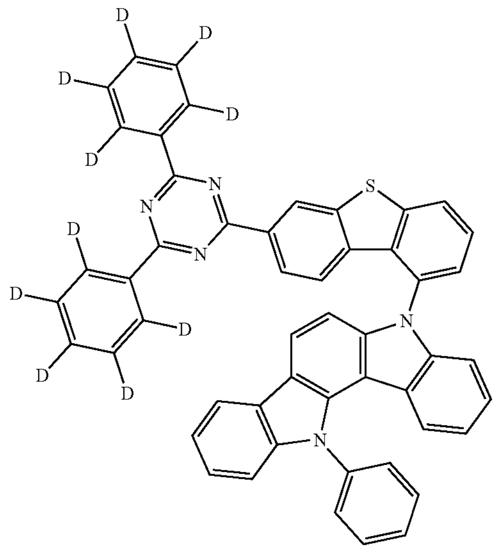
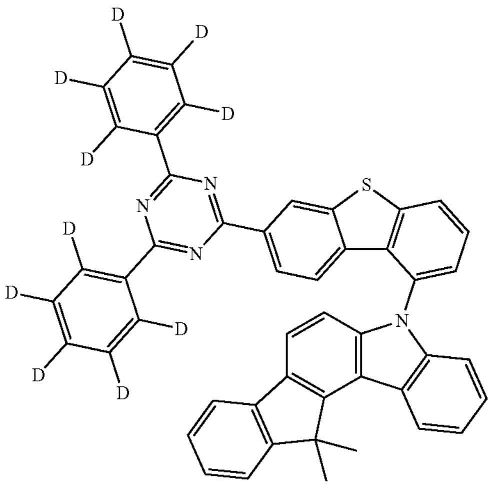
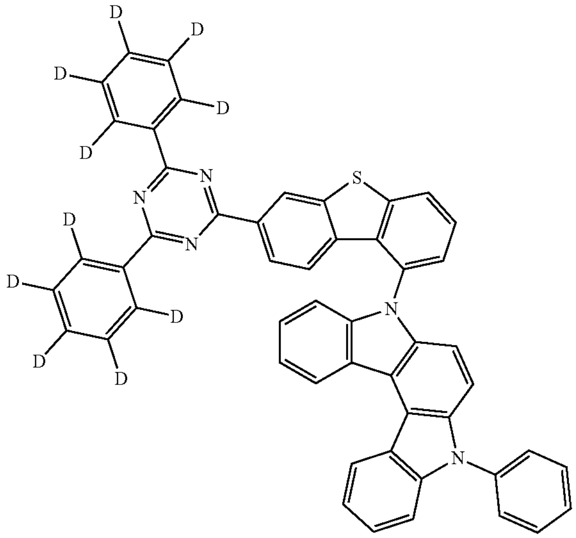
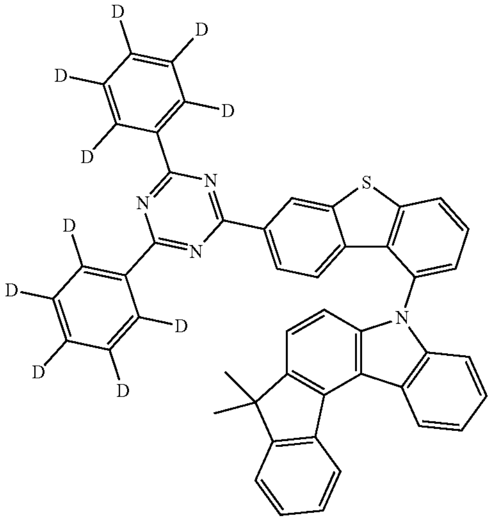
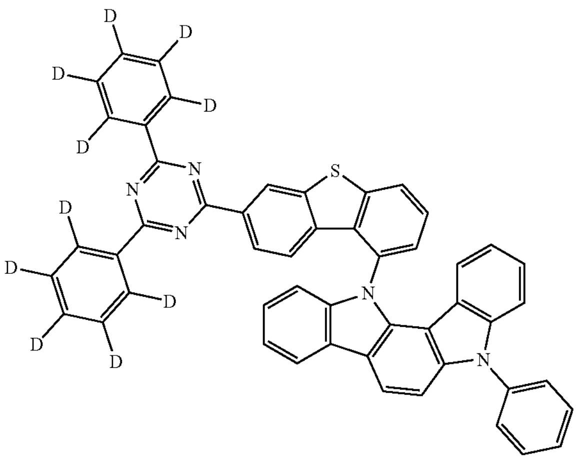

-continued
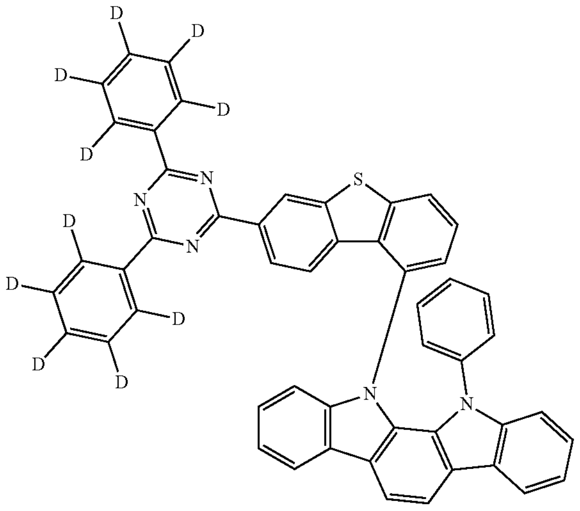
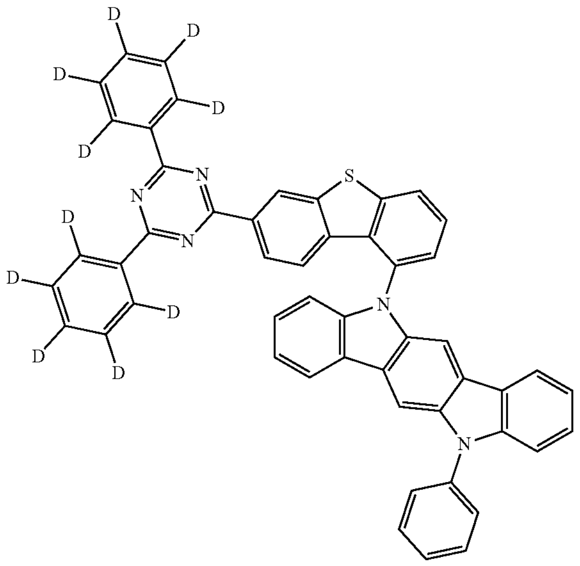
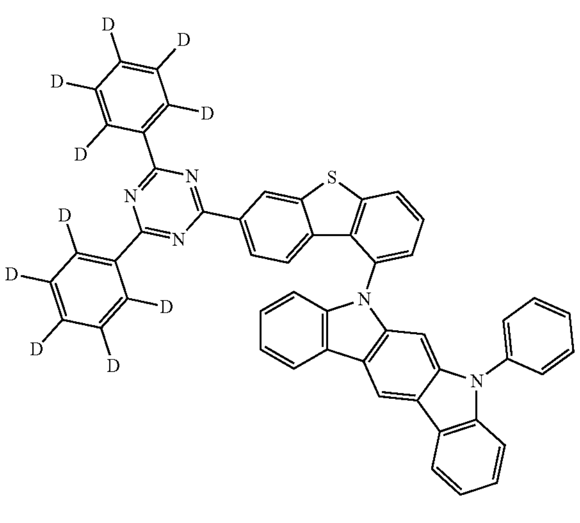
-continued
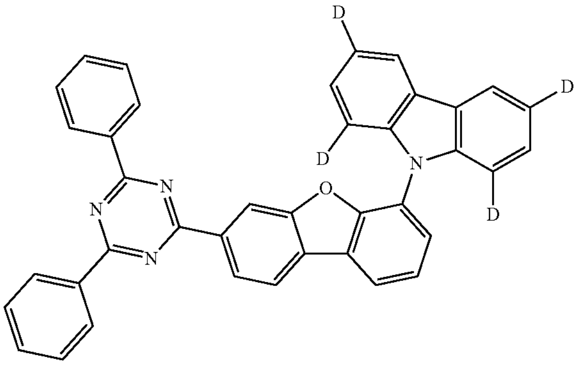
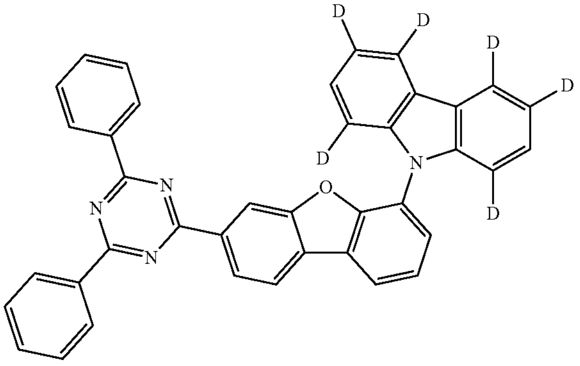
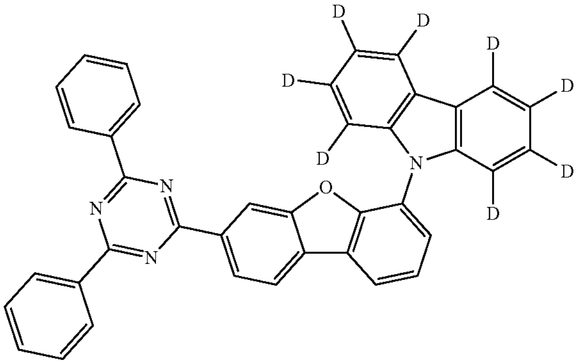
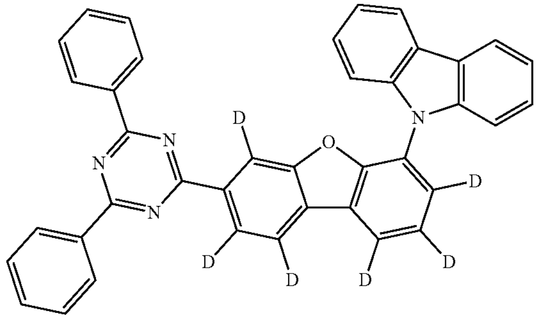
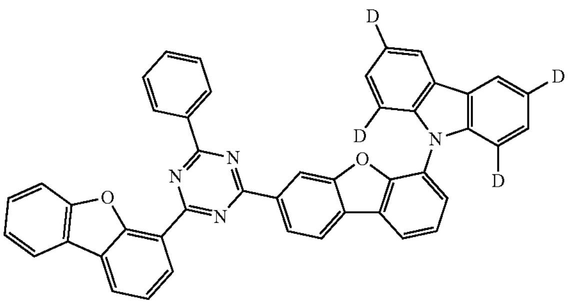

-continued
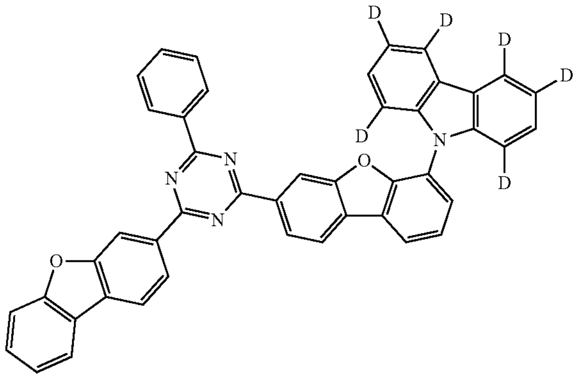
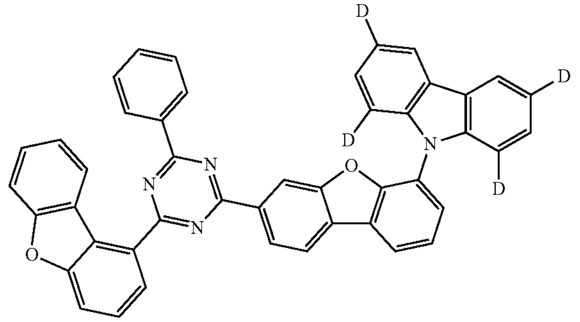
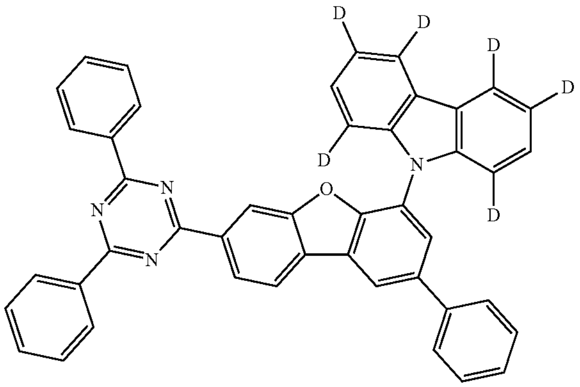
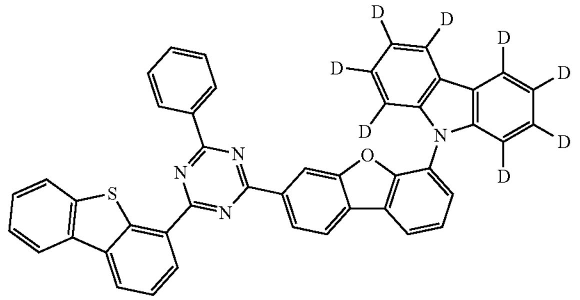
-continued
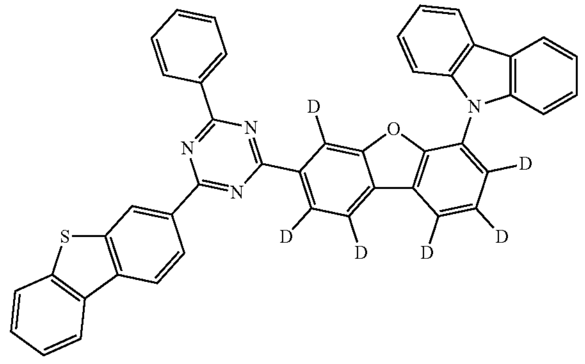
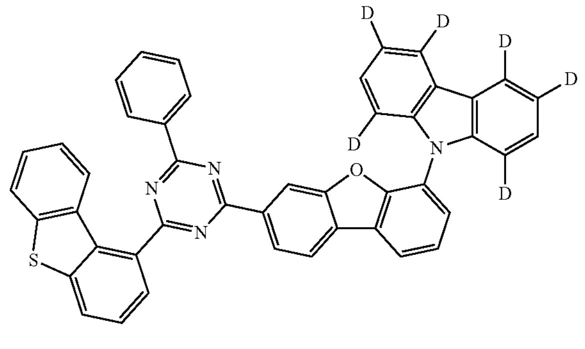
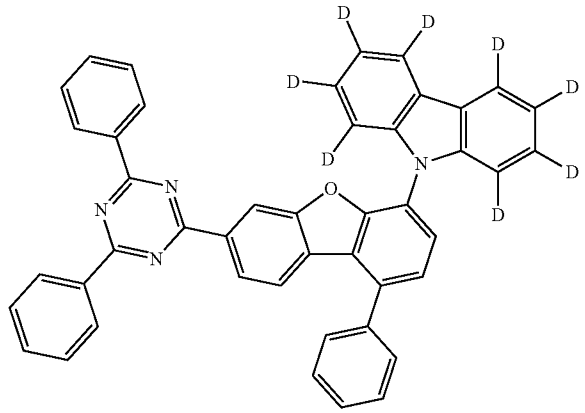
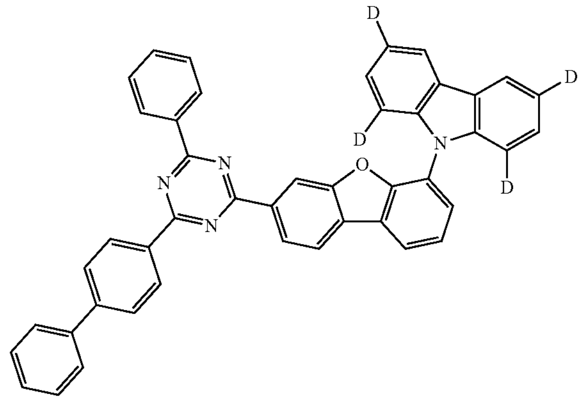

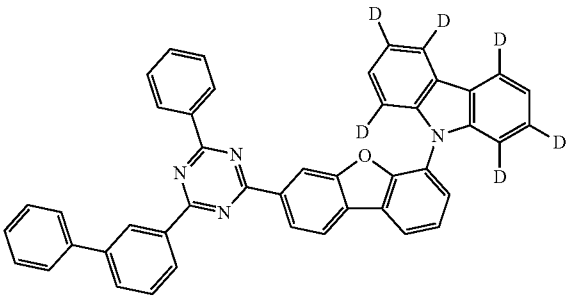
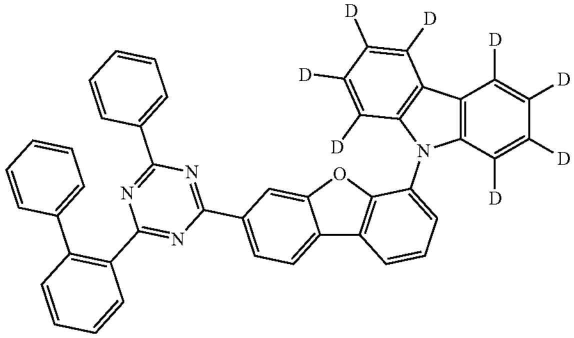
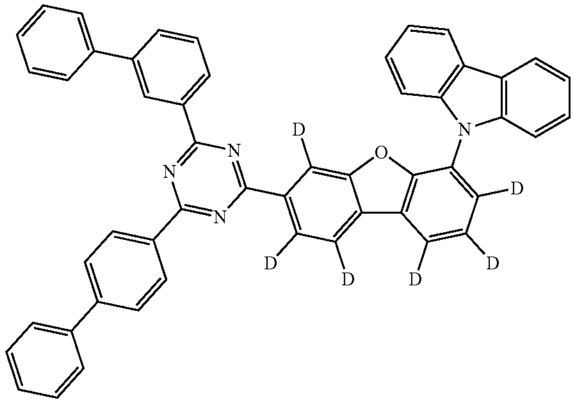
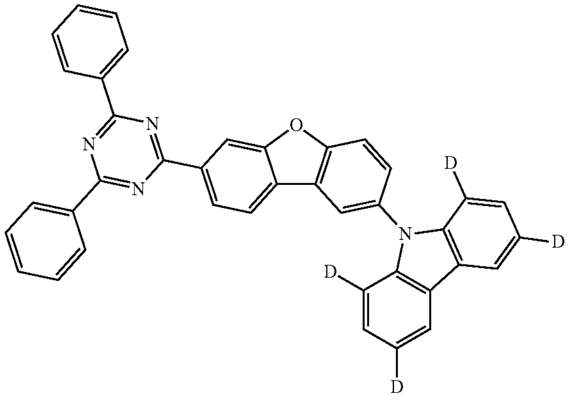
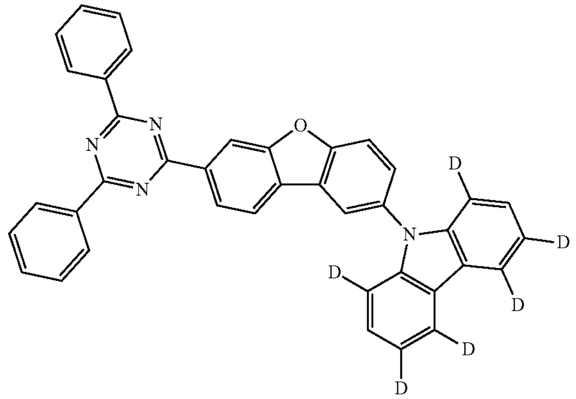
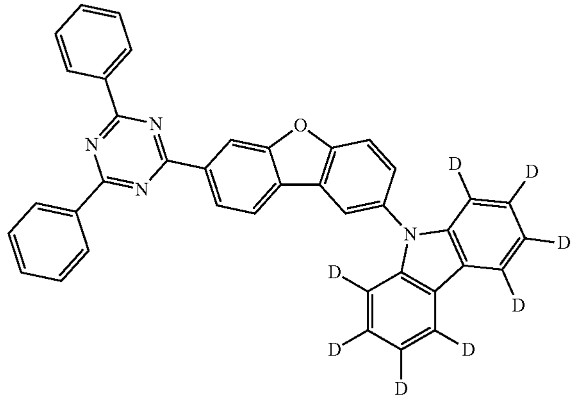
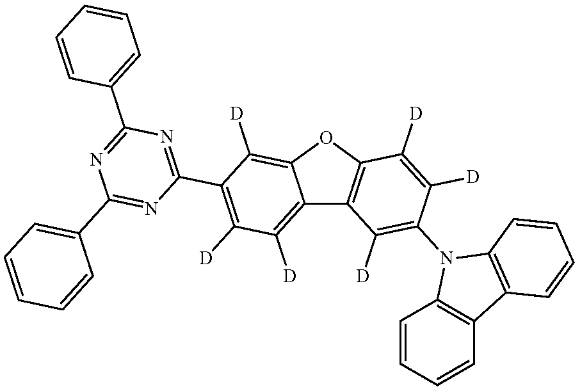
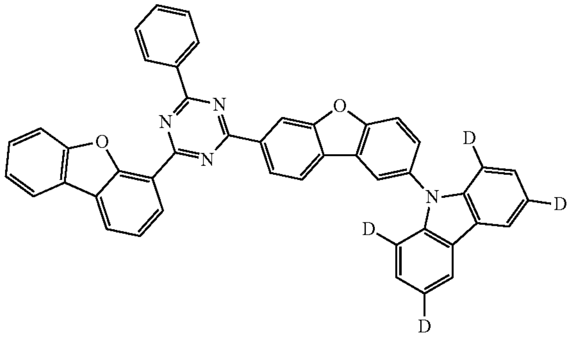

-continued
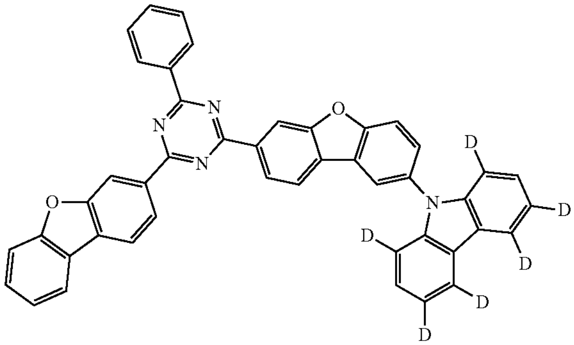
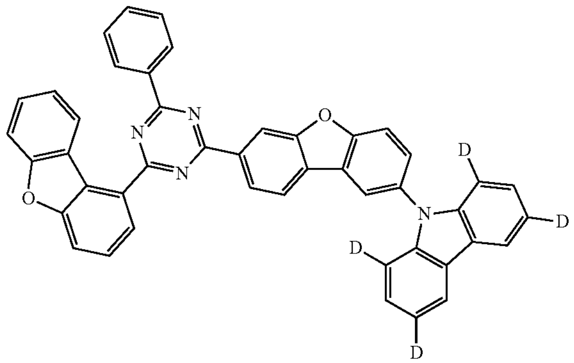
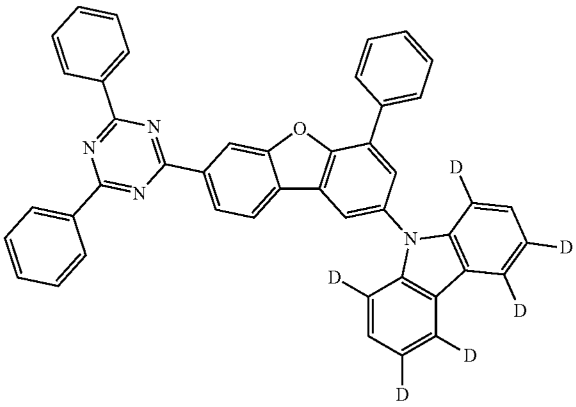
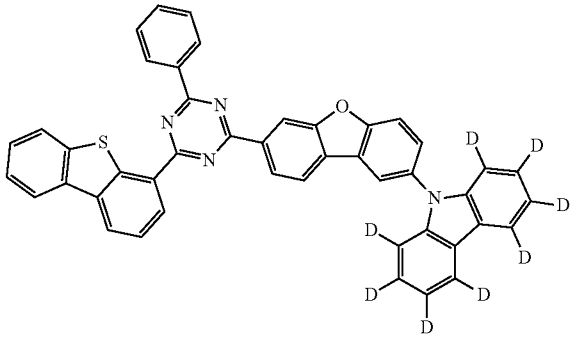
-continued
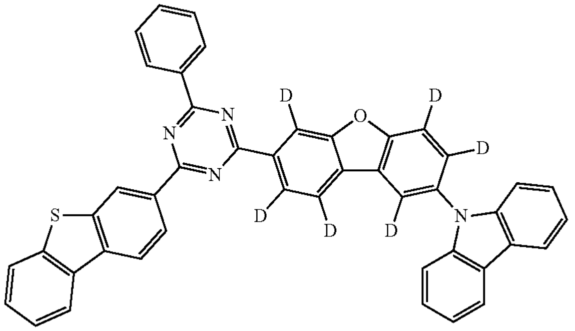
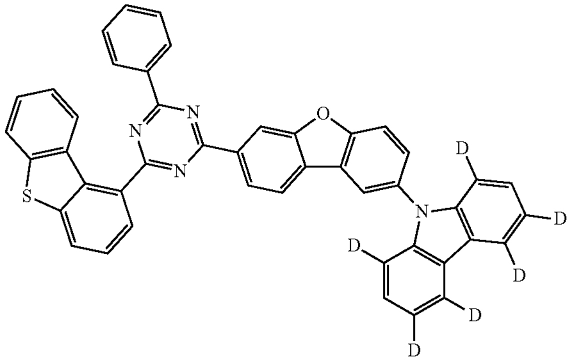
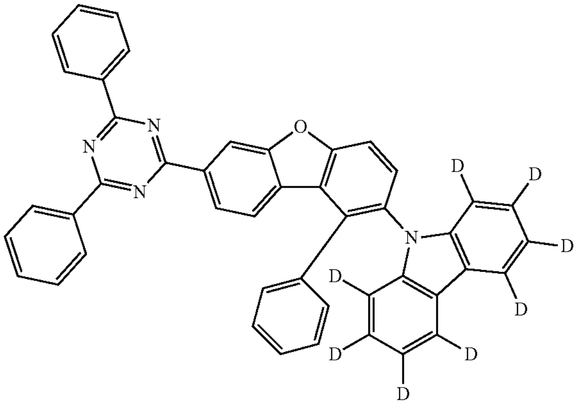
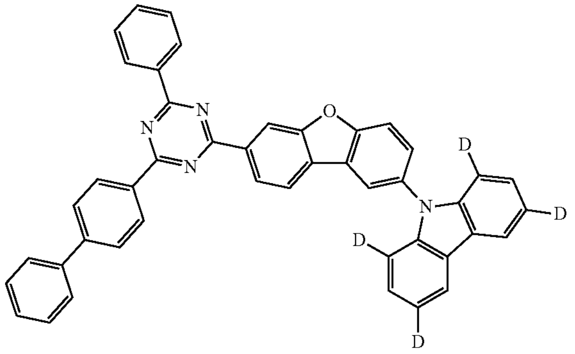

-continued
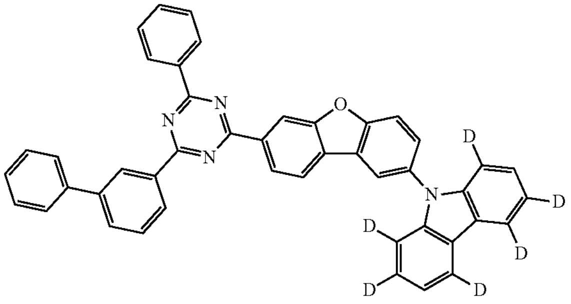
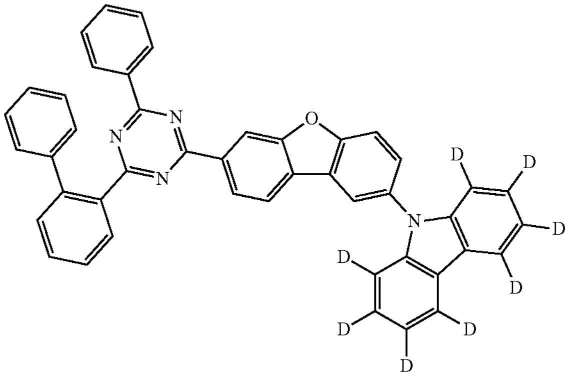
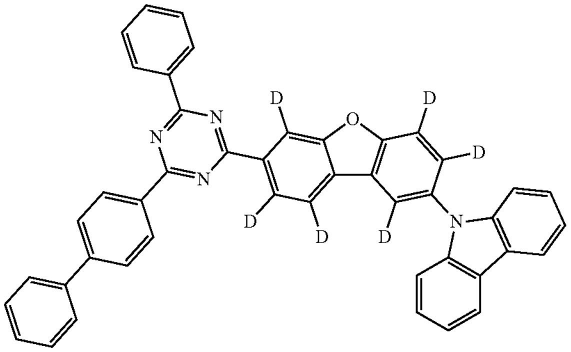
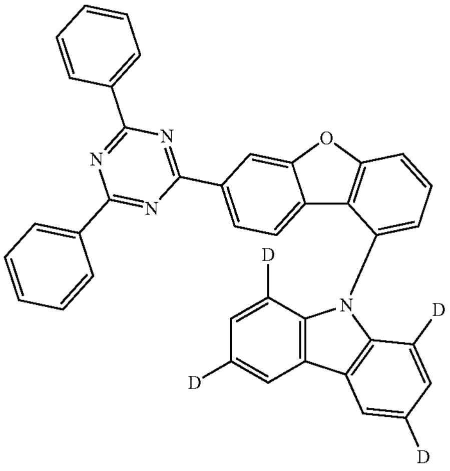
-continued
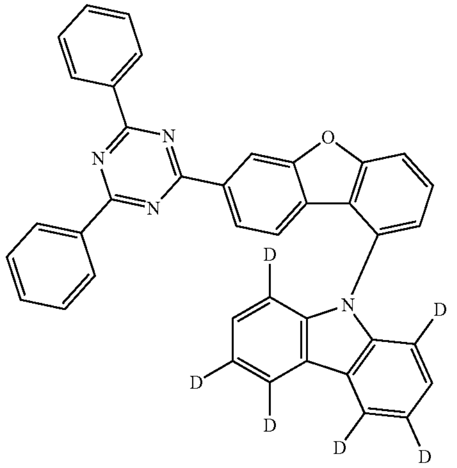
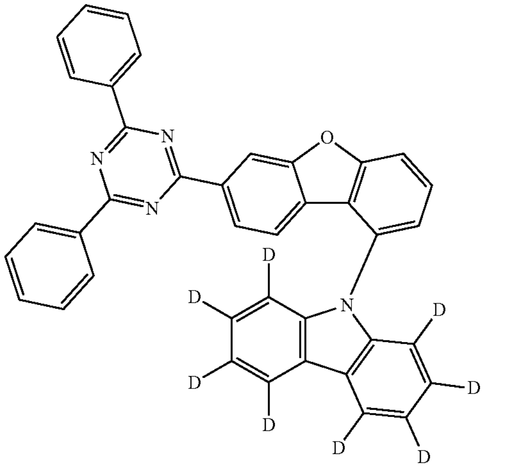
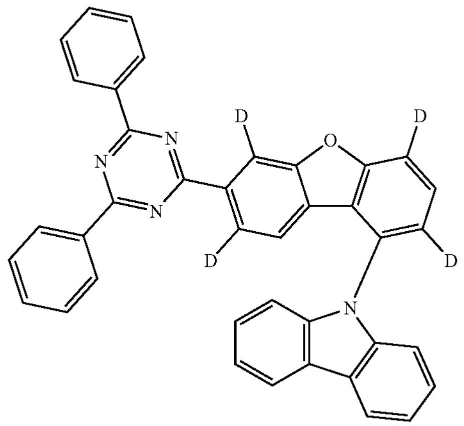

-continued
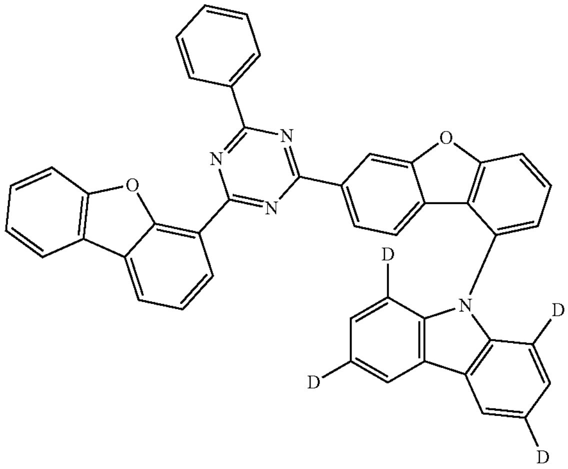
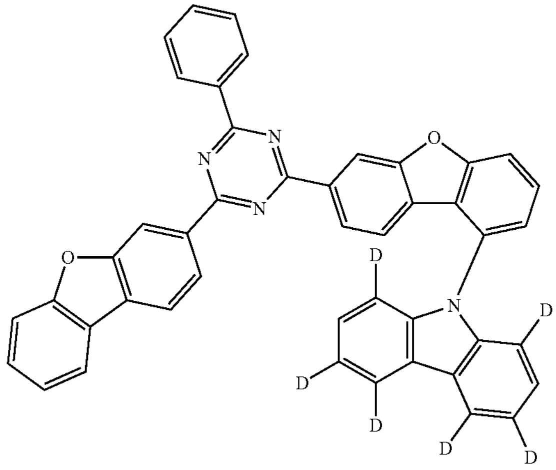
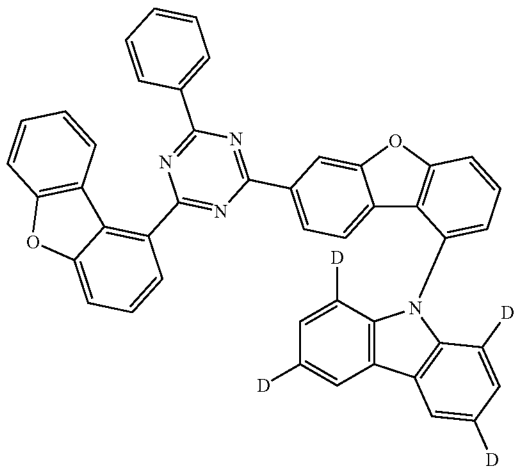
-continued
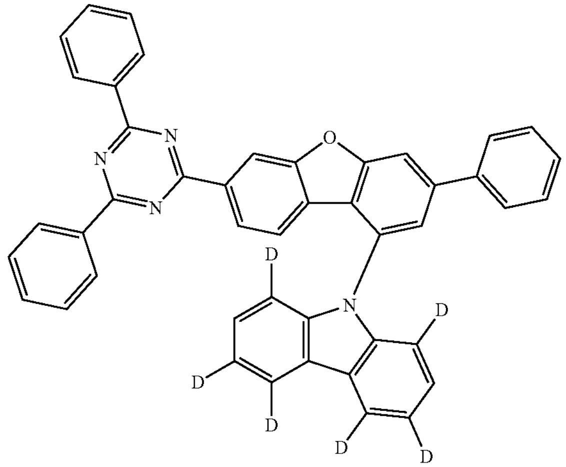
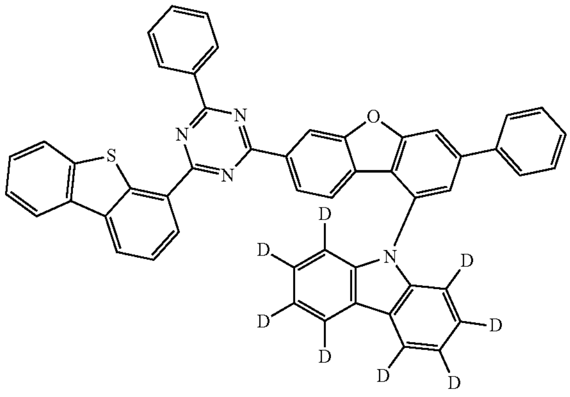
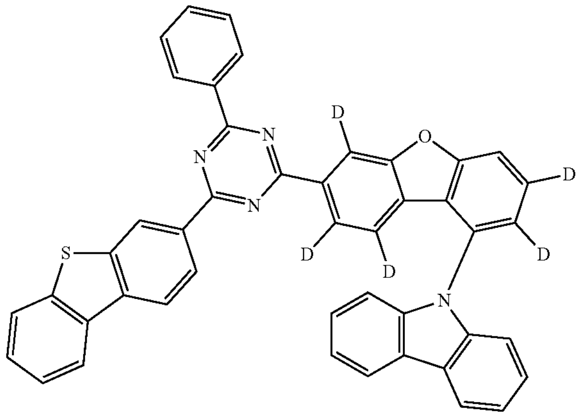

-continued
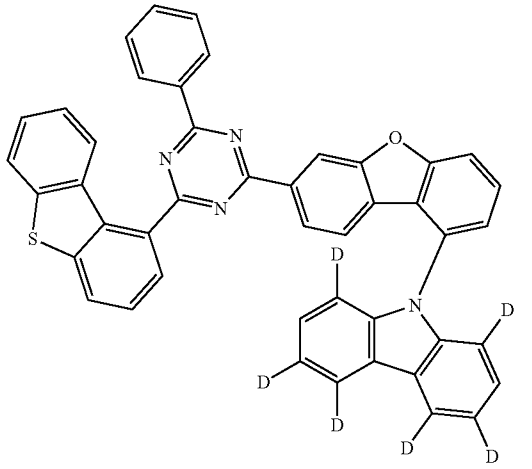
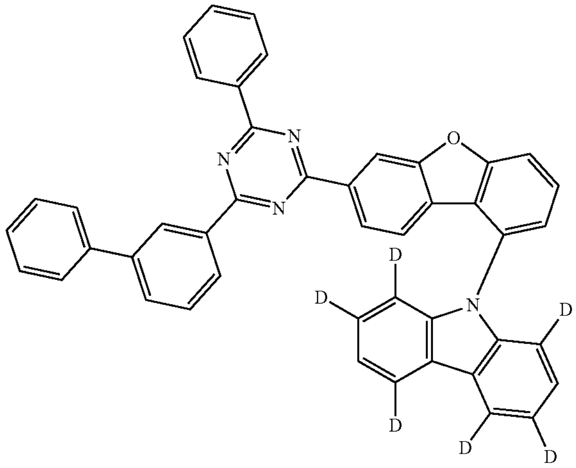
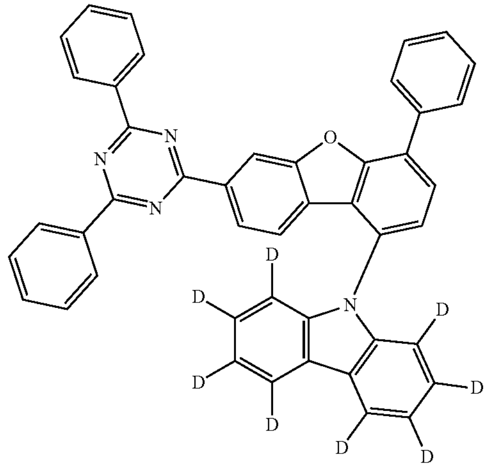
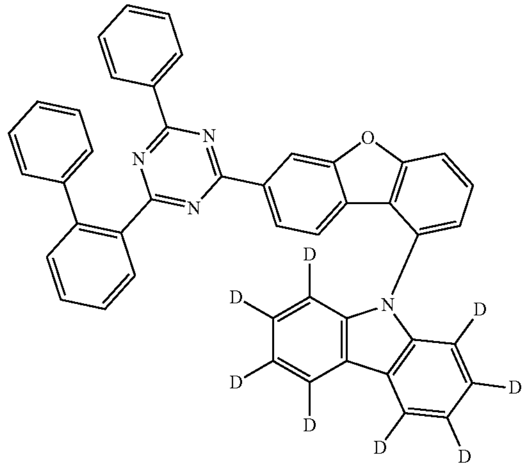
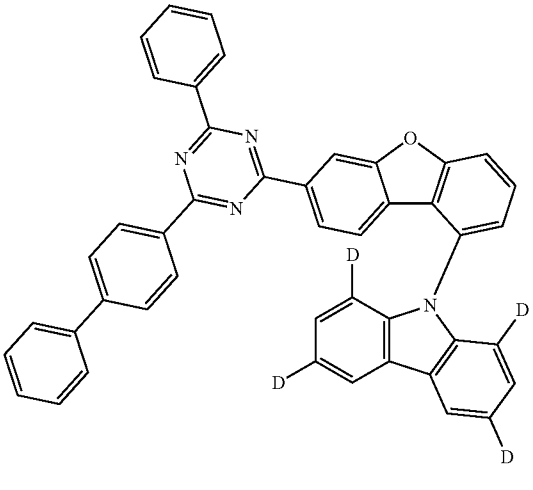
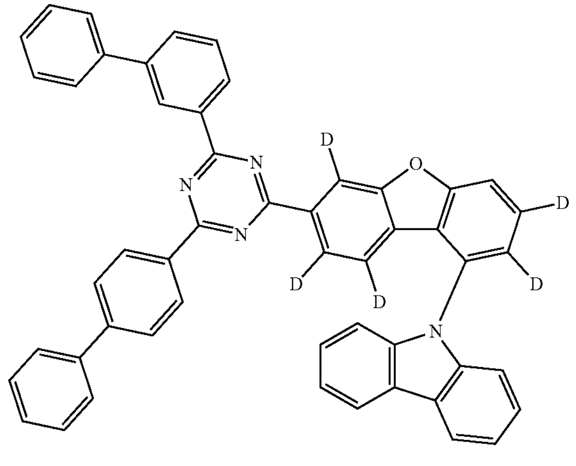

-continued
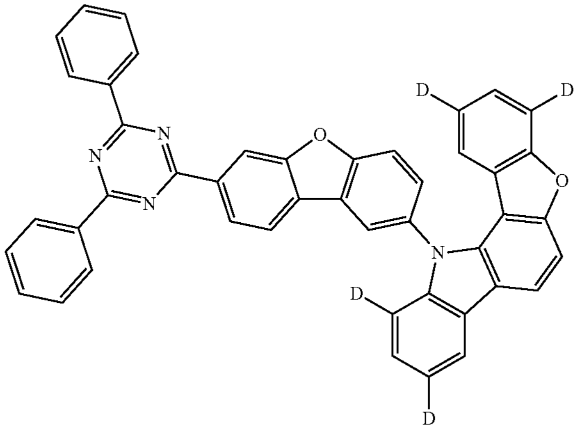
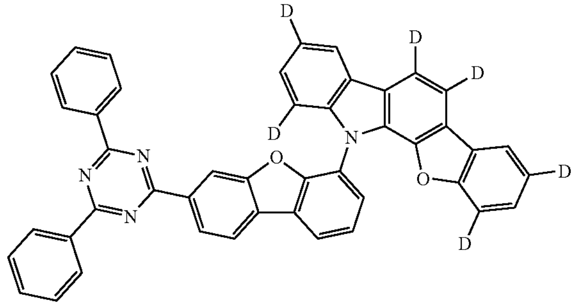
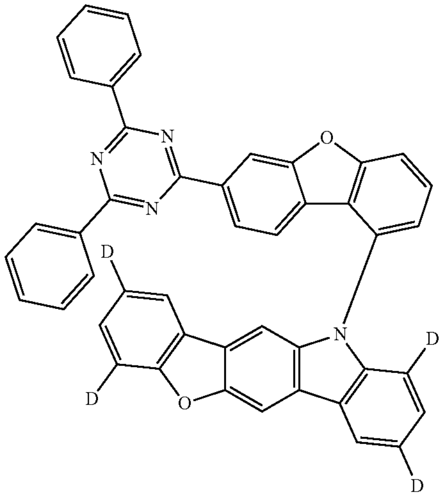
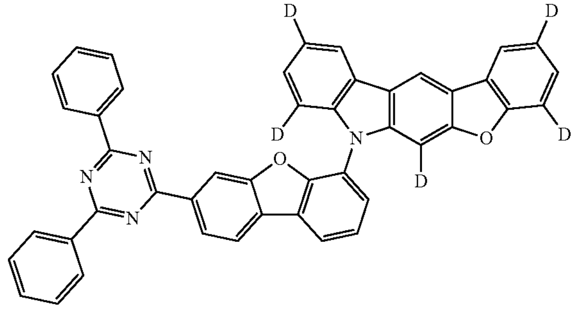
-continued
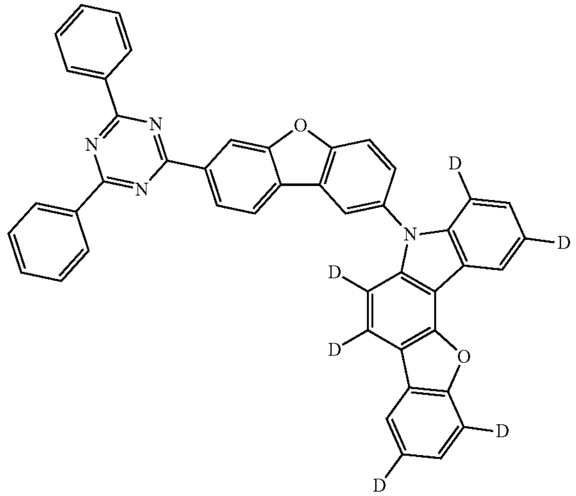
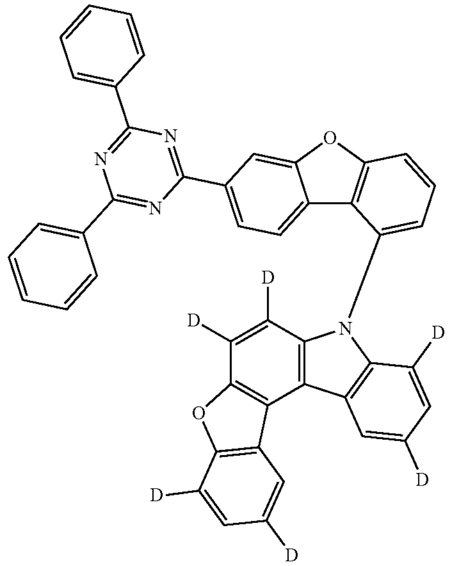
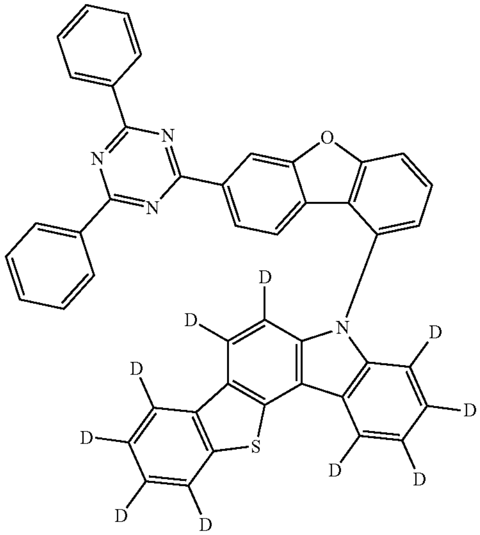

-continued
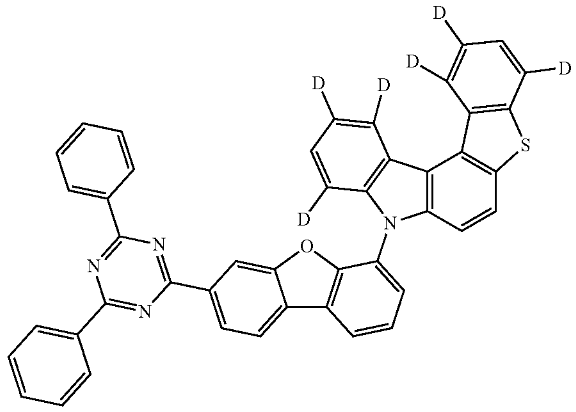
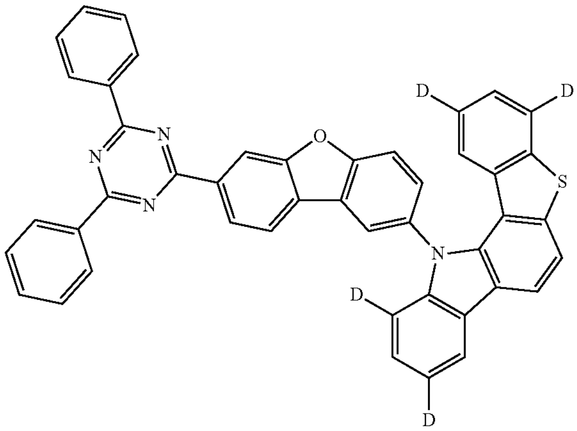
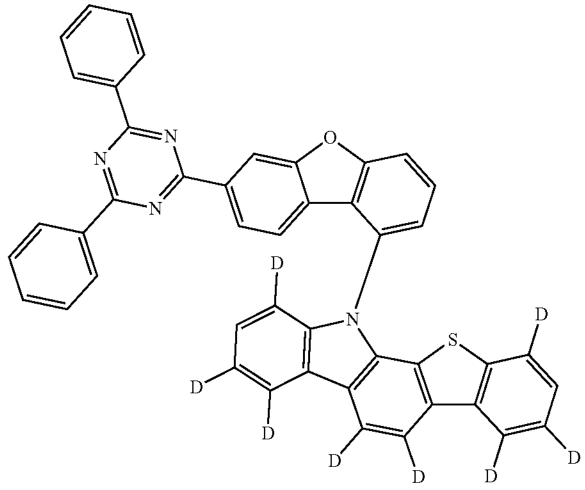
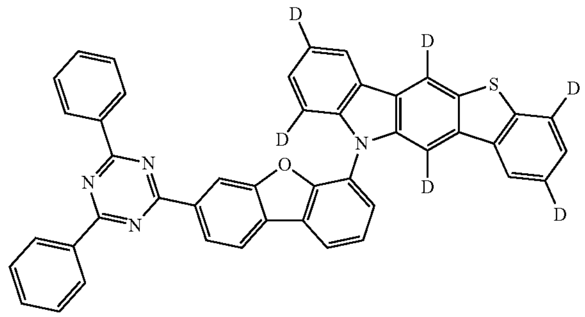
-continued
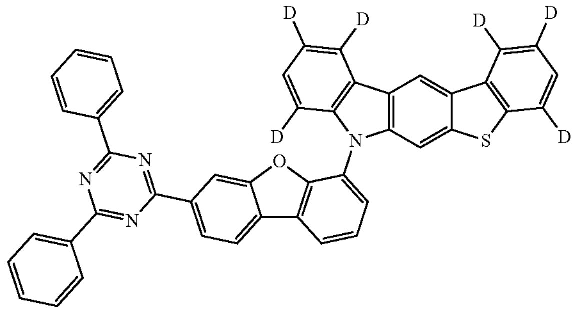
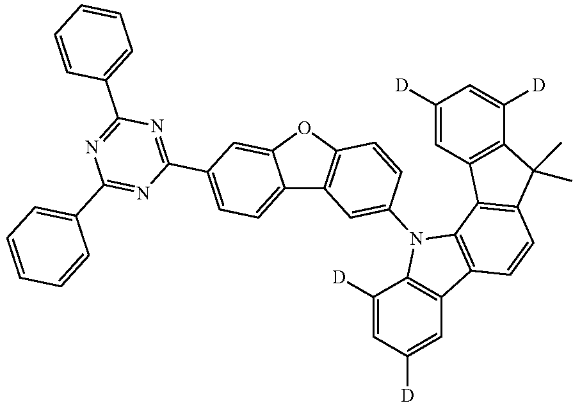
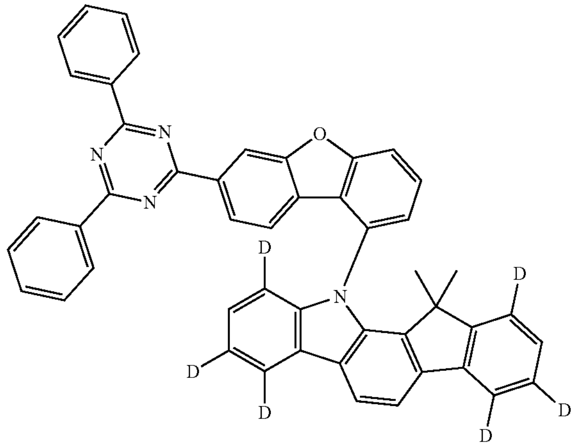
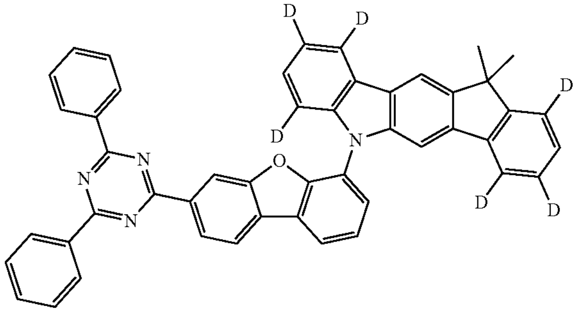

-continued
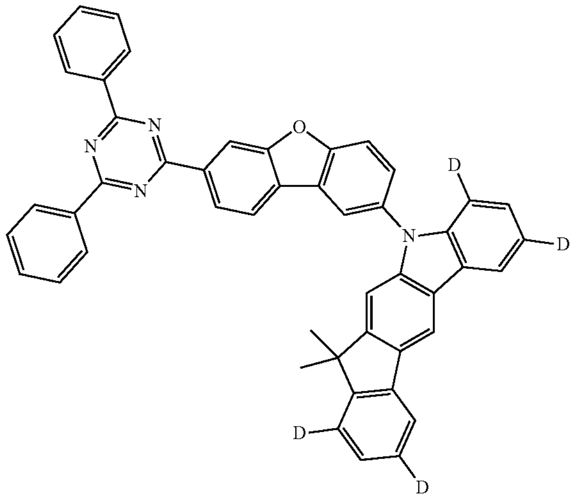
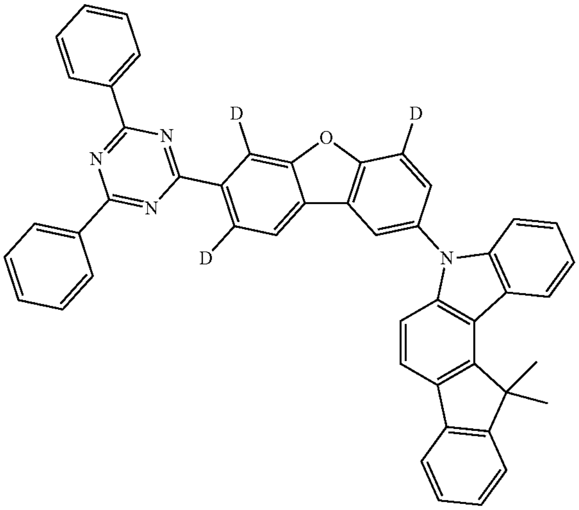
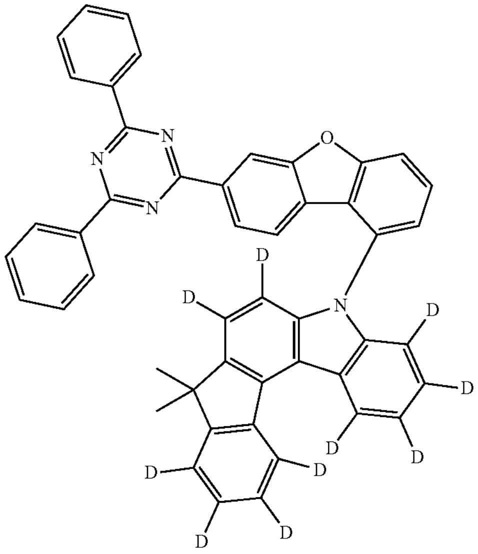
-continued
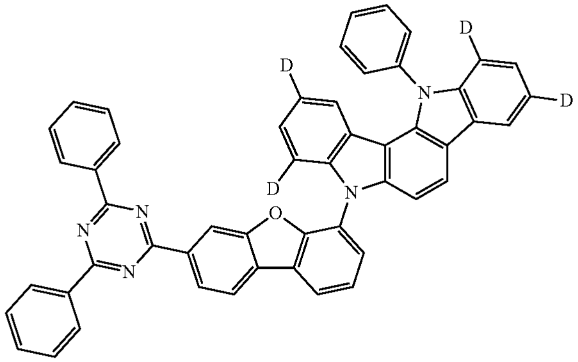
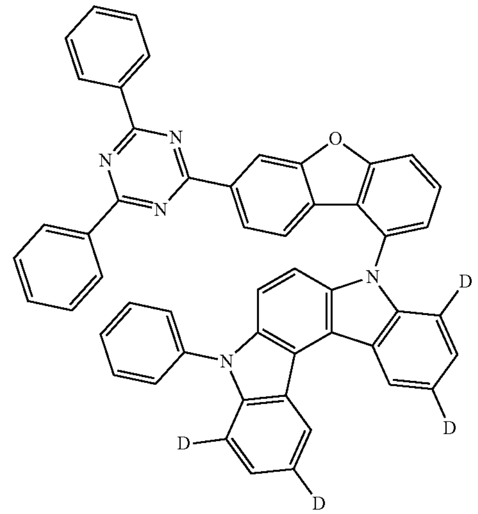
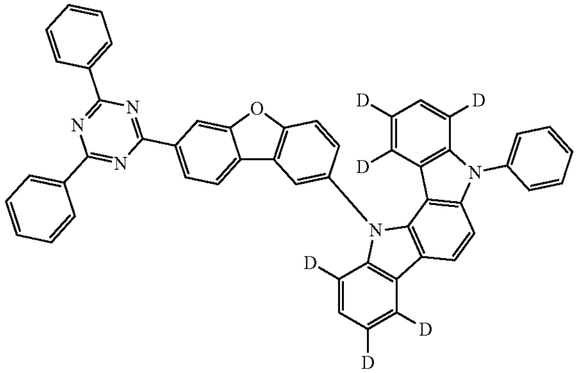

-continued
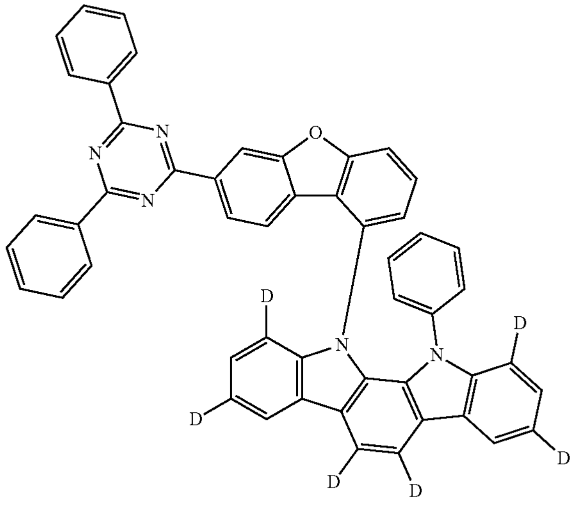
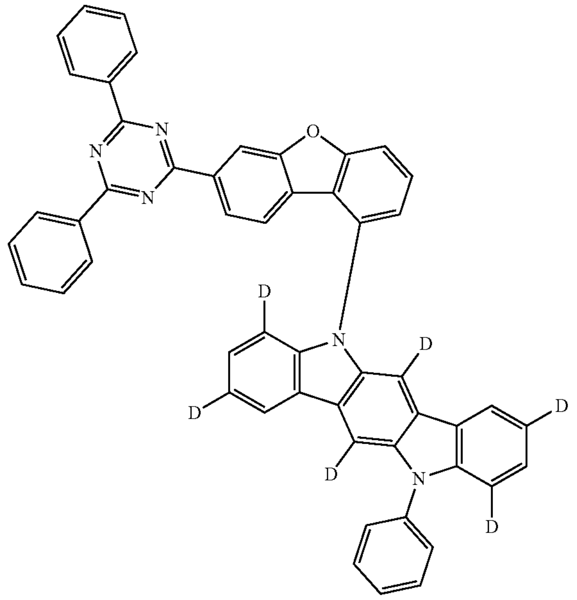
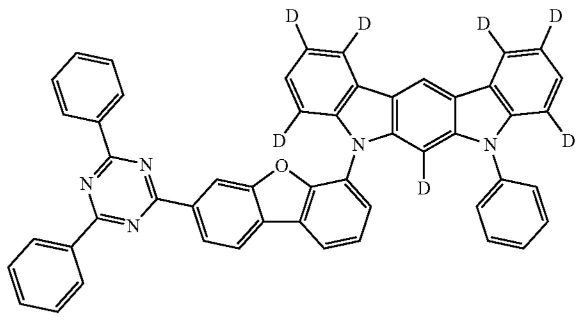
-continued
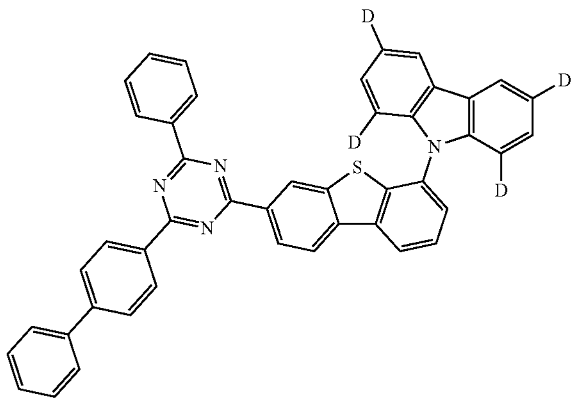
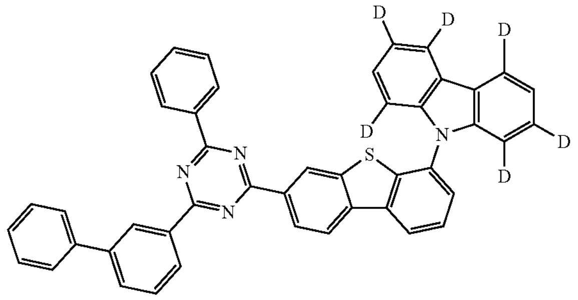
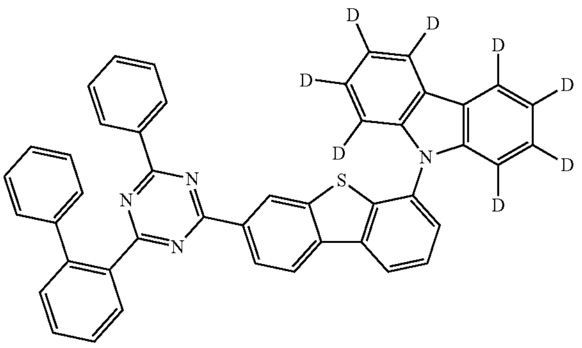
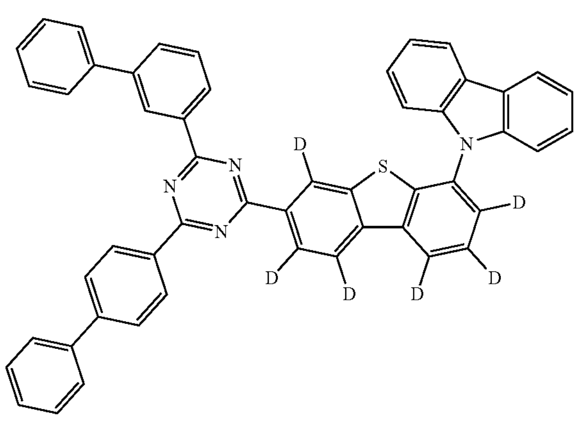

-continued
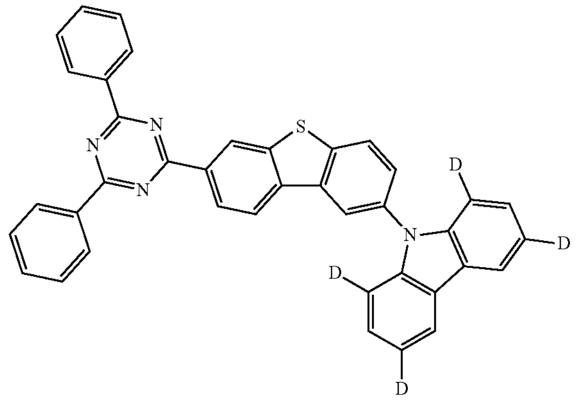
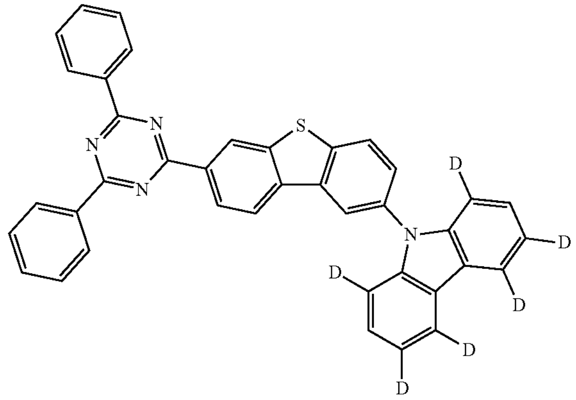
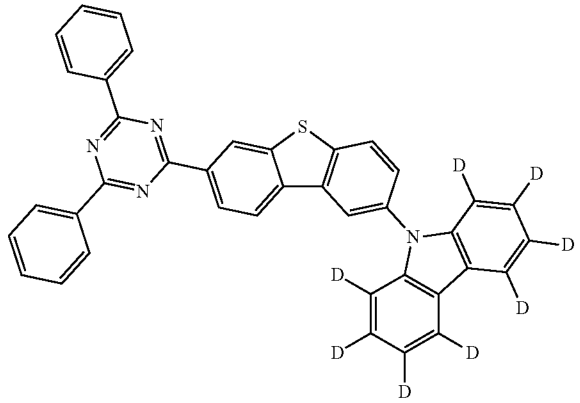
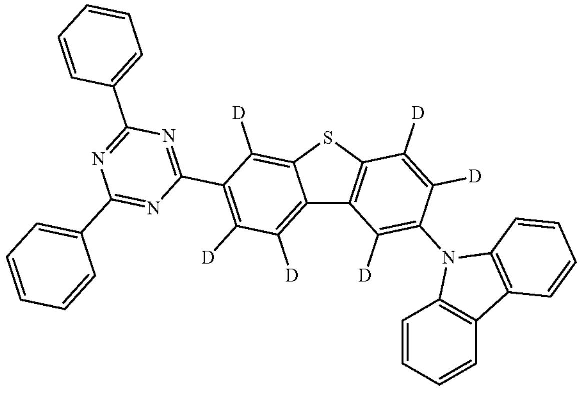
-continued
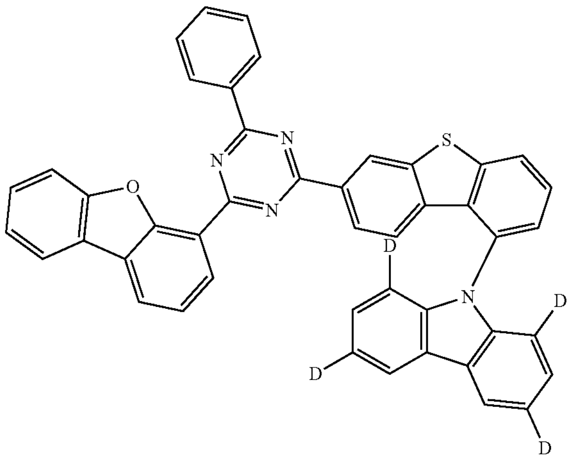
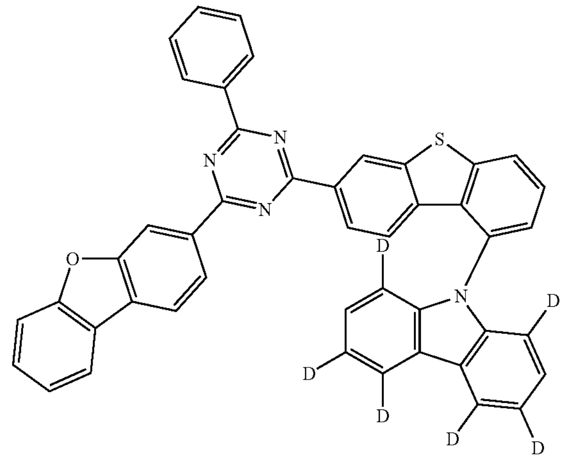
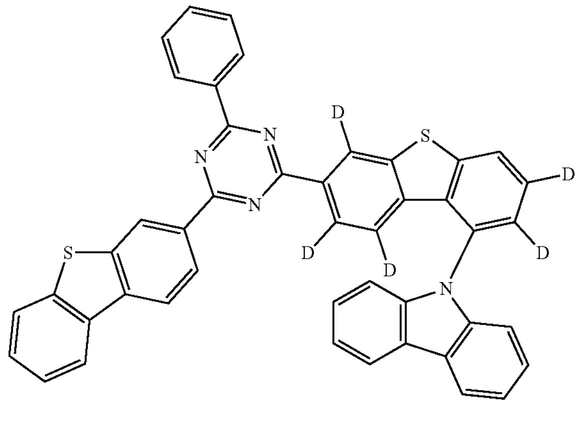

-continued

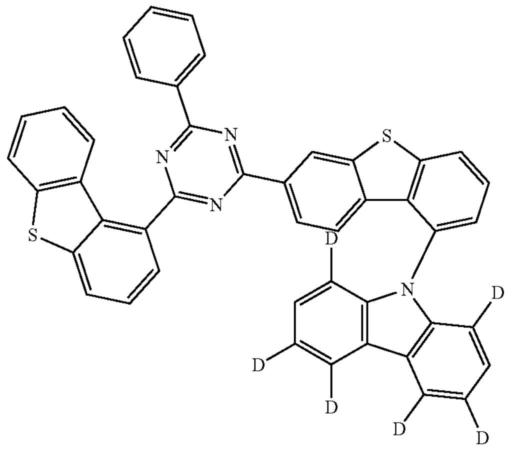

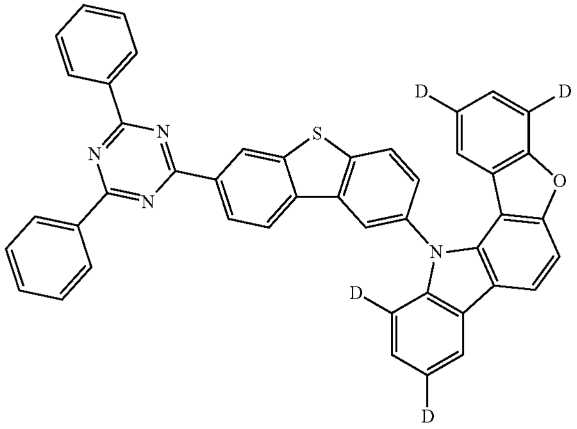

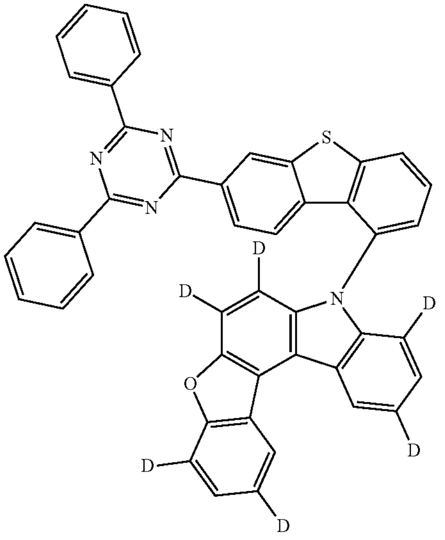

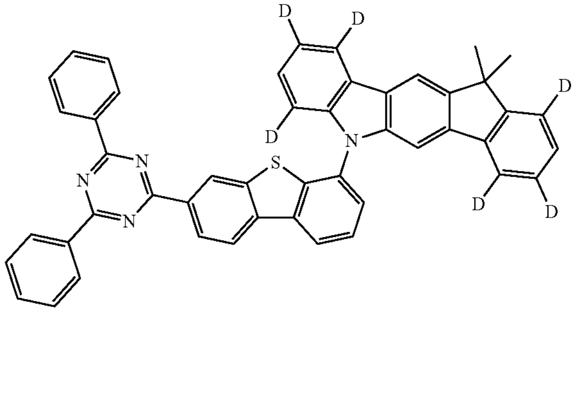

-continued

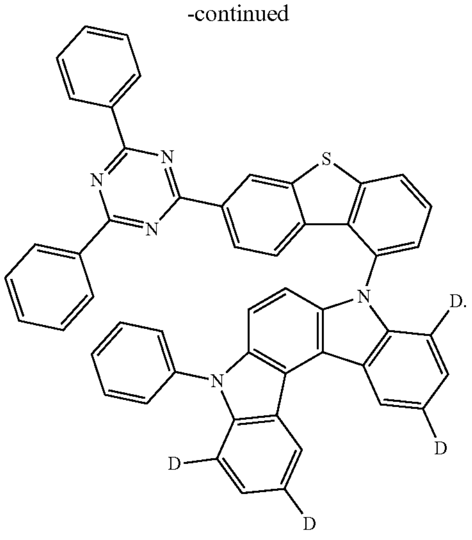

Meanwhile, the compound of Chemical Formula 1 can be used in an organic light emitting device together with the compound of the following Chemical Formula 2:

<Chemical Formula 2>

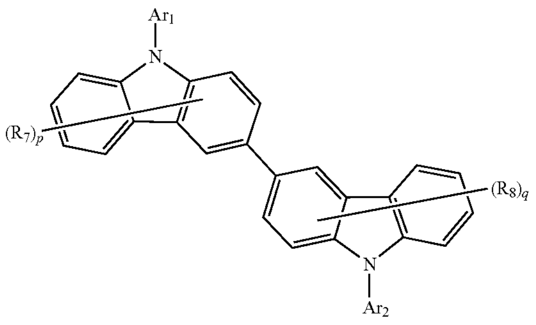

wherein in the Chemical Formula 2:

$Ar_1$ and $Ar_2$ are independently substituted or unsubstituted $C_{6-60}$ aryl, or substituted or unsubstituted $C_{5-60}$ heteroaryl containing at least one heteroatom selected from the group consisting of N, O and S;

$R_7$ and $R_8$ are each independently hydrogen, deuterium, halogen, cyano, nitro, amino, substituted or unsubstituted $C_{1-60}$ alkyl, substituted or unsubstituted $C_{3-60}$ cycloalkyl, substituted or unsubstituted $C_{2-60}$ alkenyl, substituted or unsubstituted $C_{6-60}$ aryl, or substituted or unsubstituted $C_{5-60}$ heteroaryl containing at least one heteroatom selected from the group consisting of N, O and S; and p and q are each independently an integer of 0 to 7.

In particular, using the compound of Chemical Formula 2 in an organic light emitting device together with the compound of Chemical Formula 1 is advantageous even in forming an exciplex, so that characteristics of low voltage, high efficiency, and long lifespan can be further improved.

Specifically, in the Chemical Formula 2, $Ar_1$ and $Ar_2$ can each independently be phenyl, biphenylyl, terphenylyl, naphthyl, dibenzofuranyl, dibenzothiophenyl, or dimethylfluorenyl.

In addition, $R_7$ and $R_8$ can each be hydrogen or phenyl.

In addition, p and q can each be 0 or 1.

Representative examples of the compound of Chemical Formula 2 are as follows:
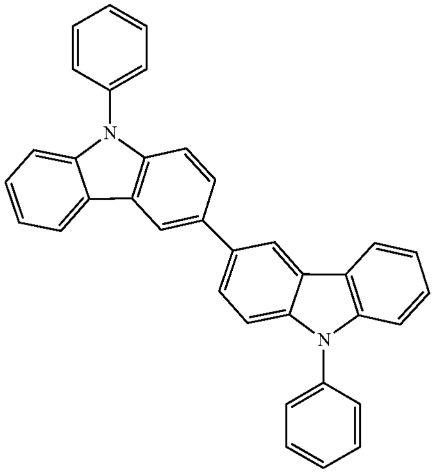
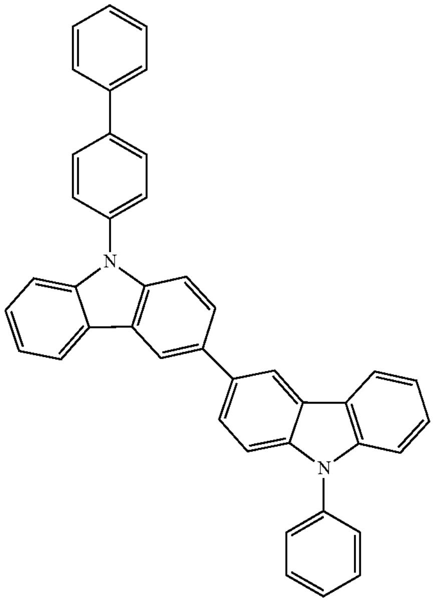
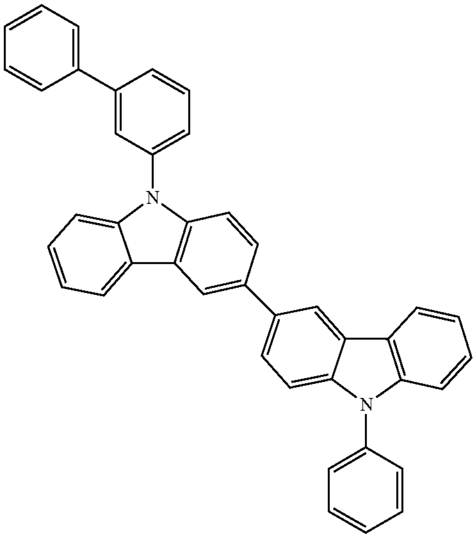
-continued
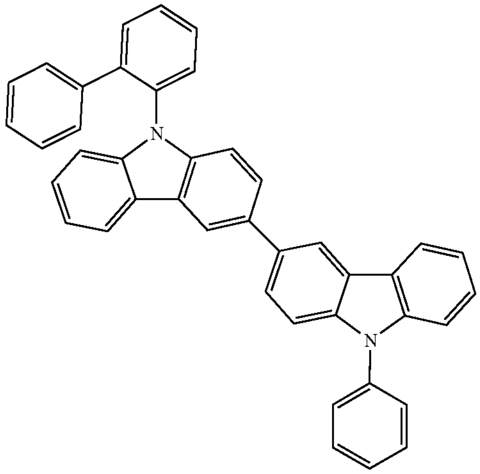
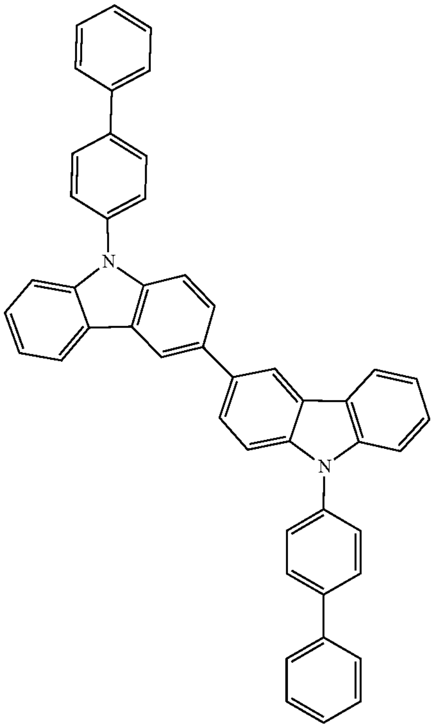

-continued
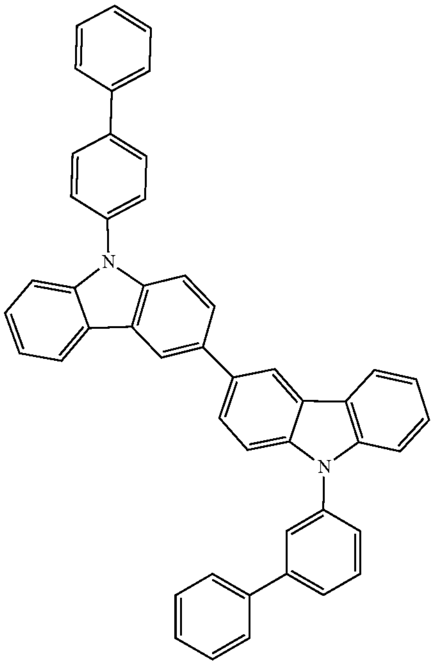
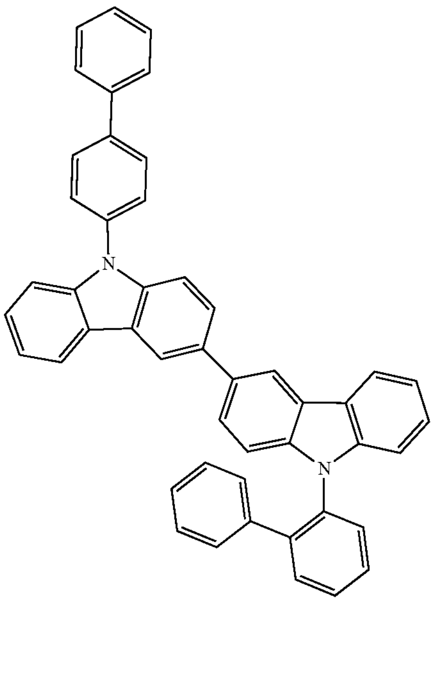
-continued
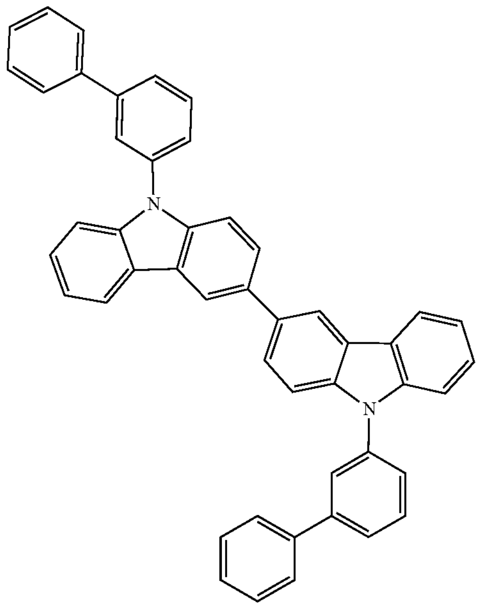
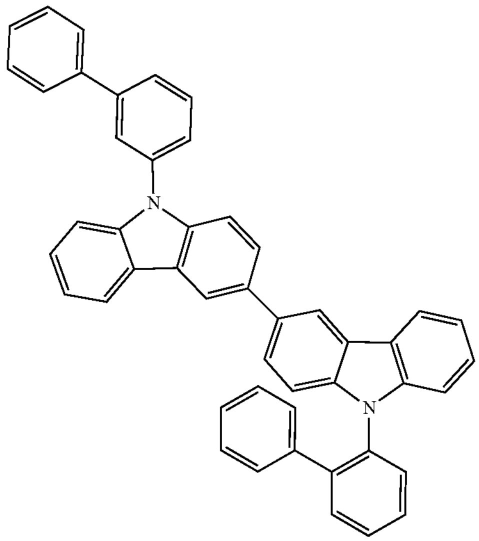
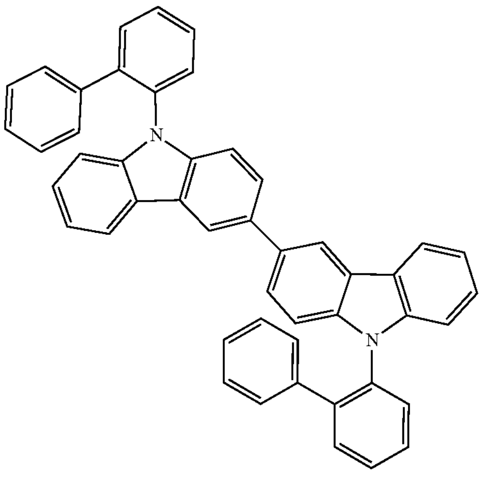

-continued
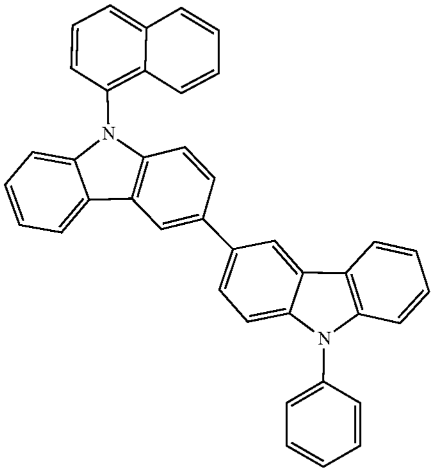
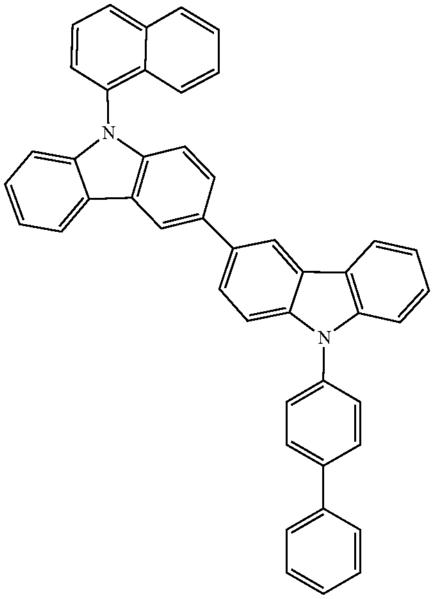
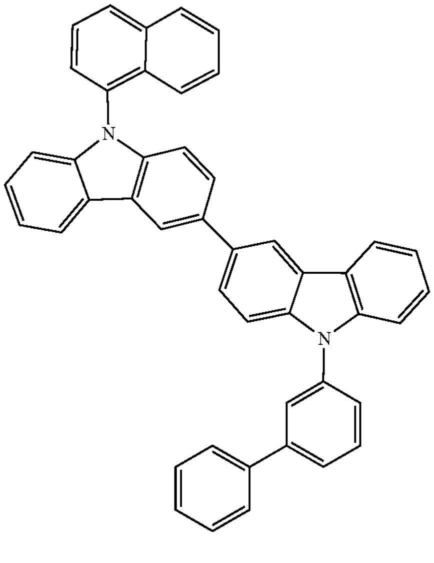
-continued
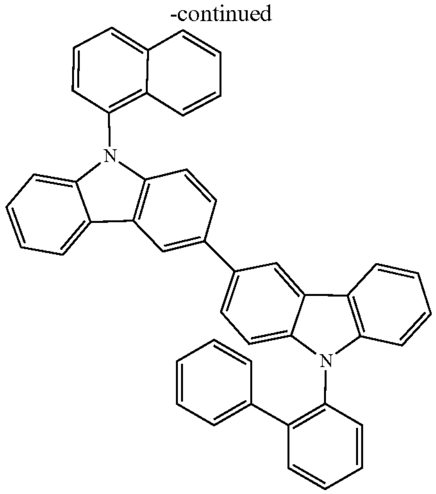
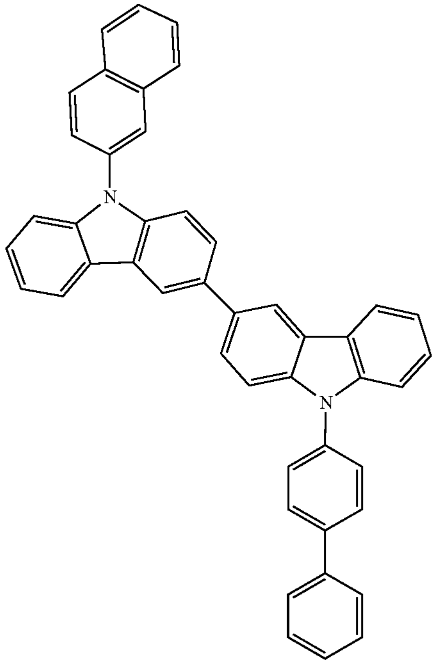
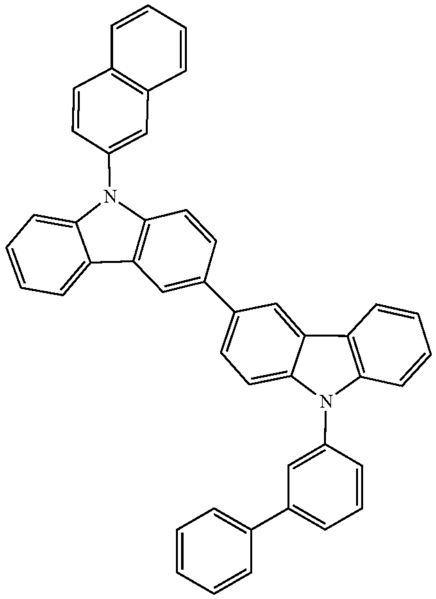

-continued
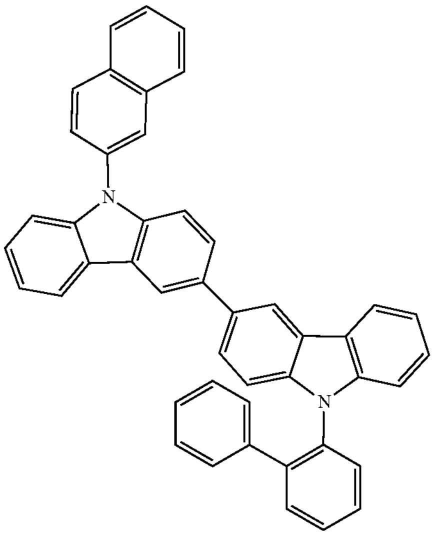
-continued
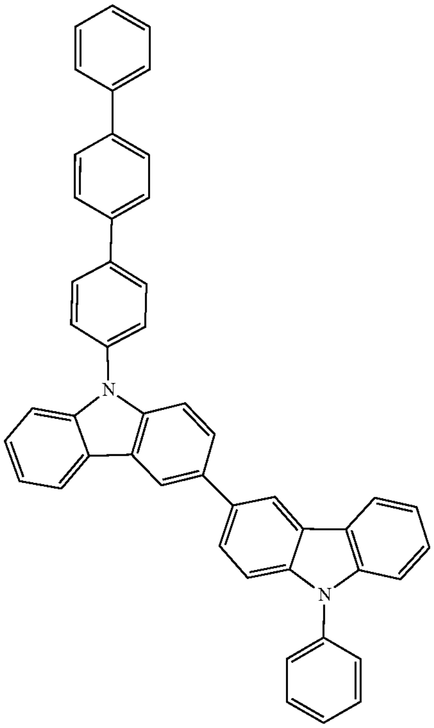
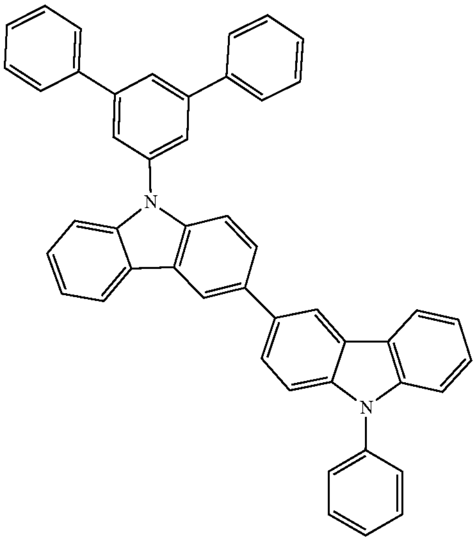
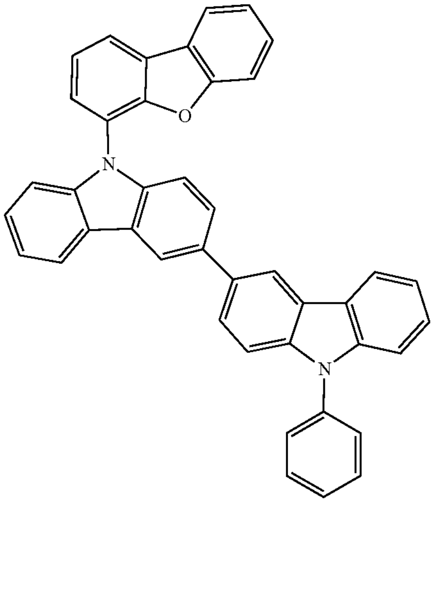

-continued
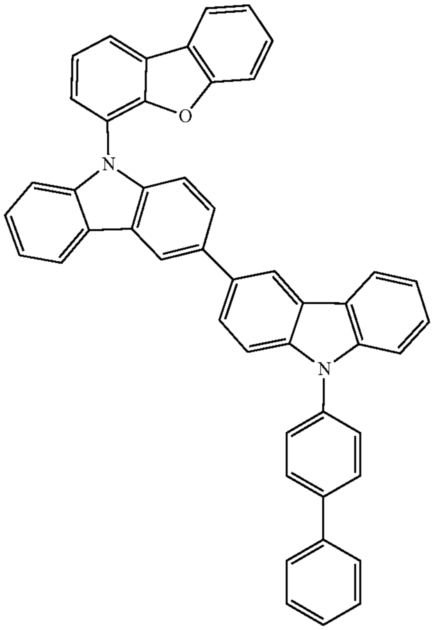
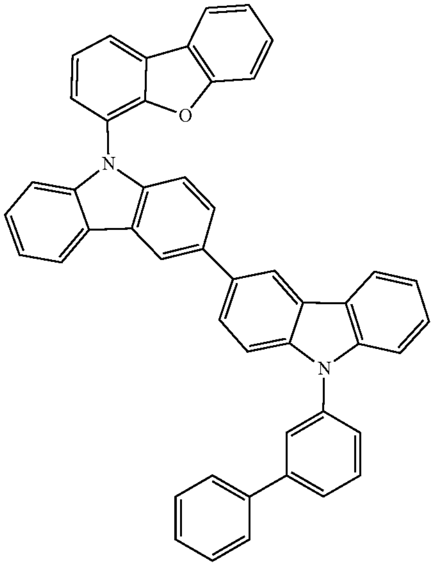
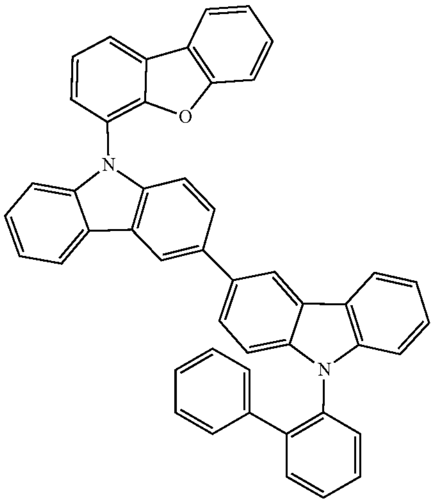
-continued
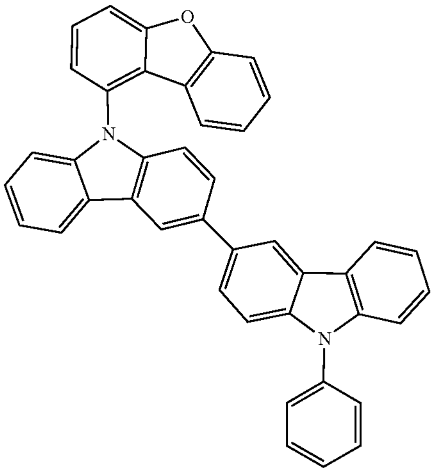
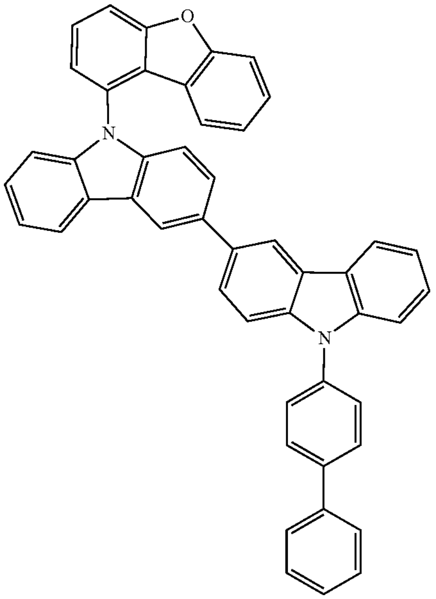
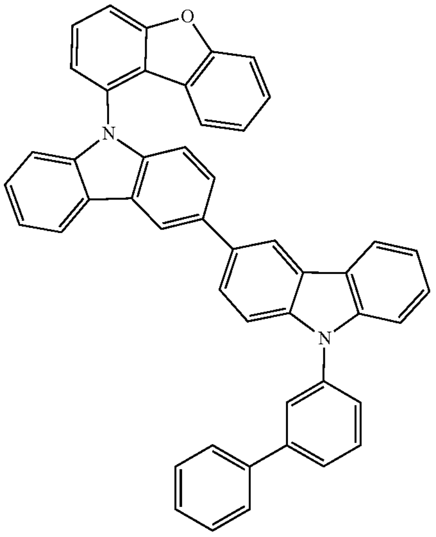

-continued
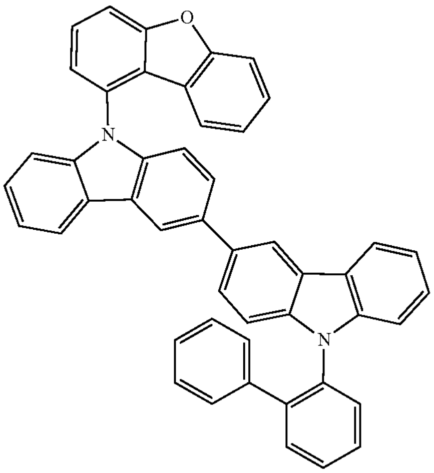
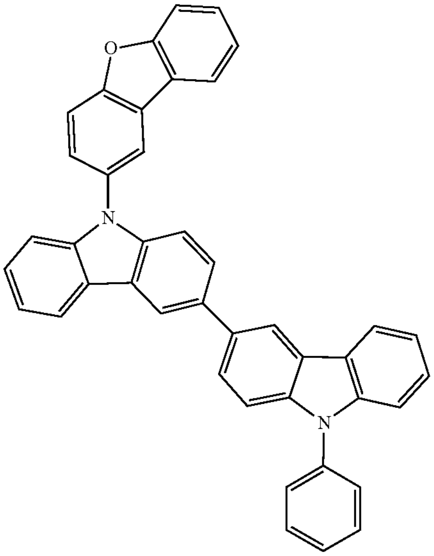
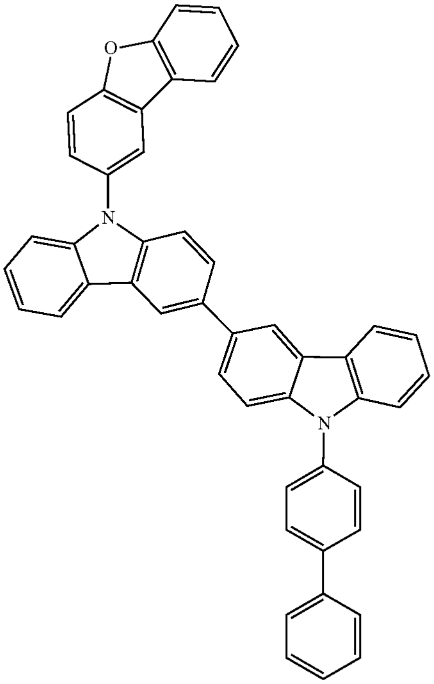
-continued
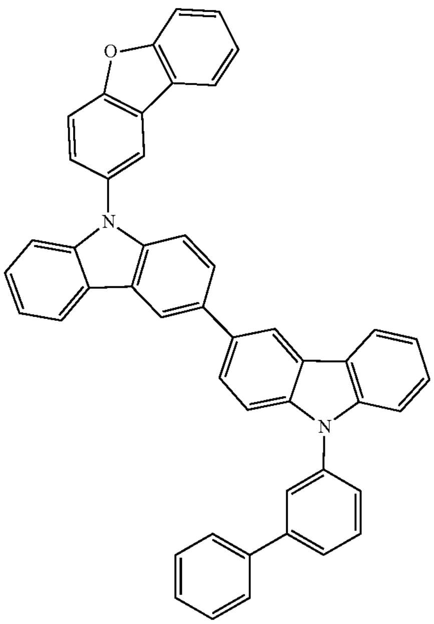
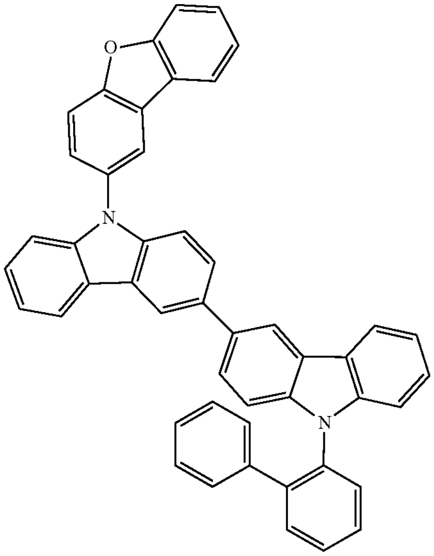

-continued
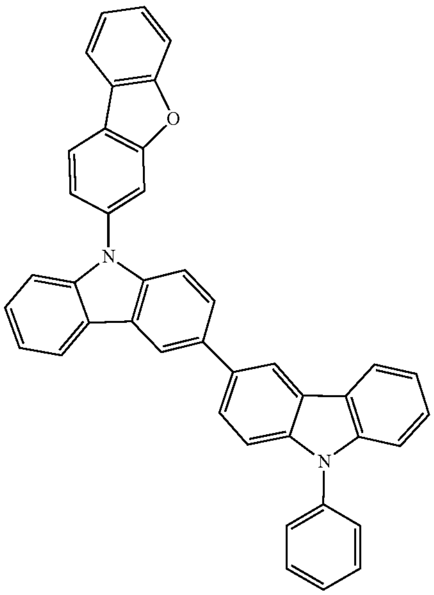
-continued
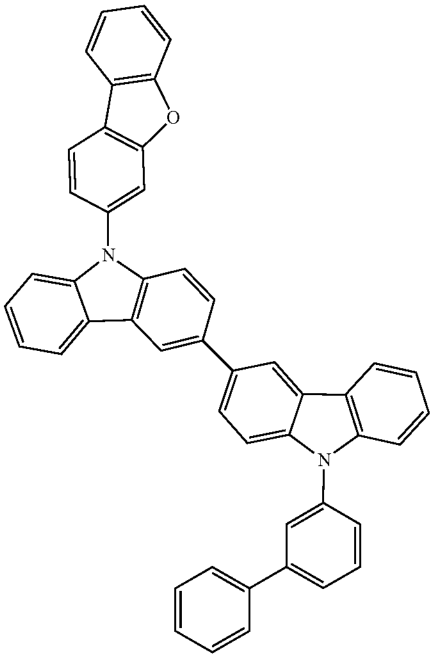
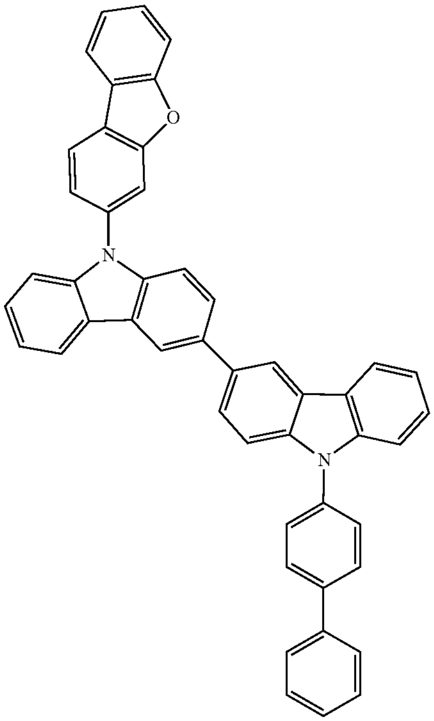
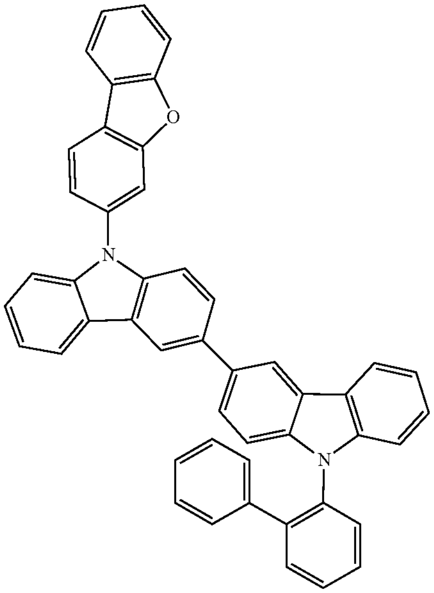

-continued
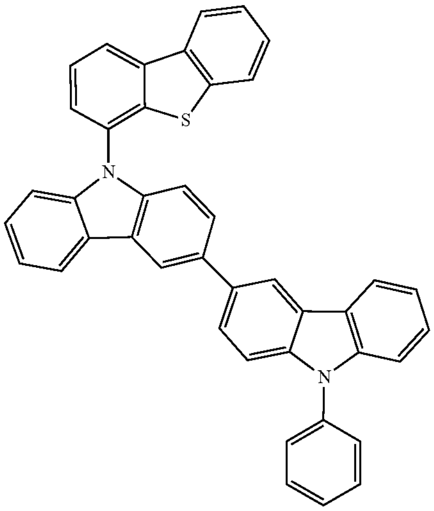
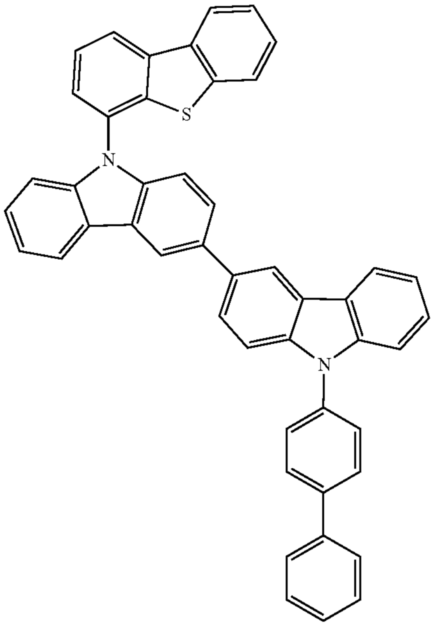
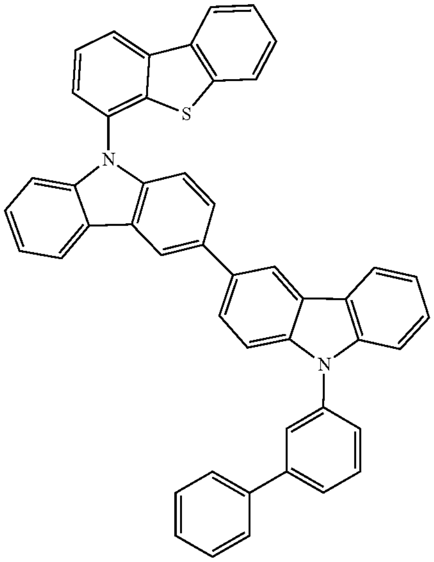
-continued
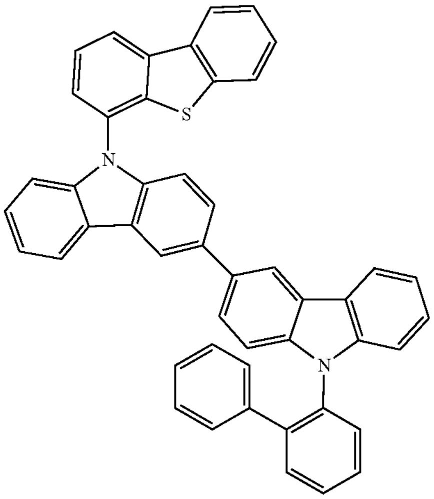
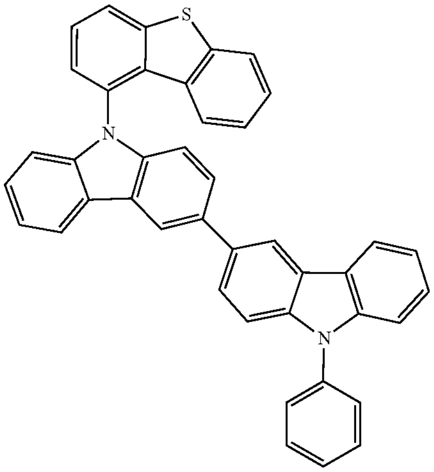
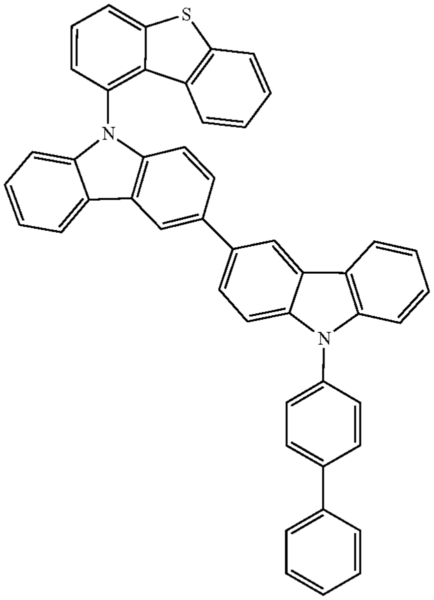

-continued
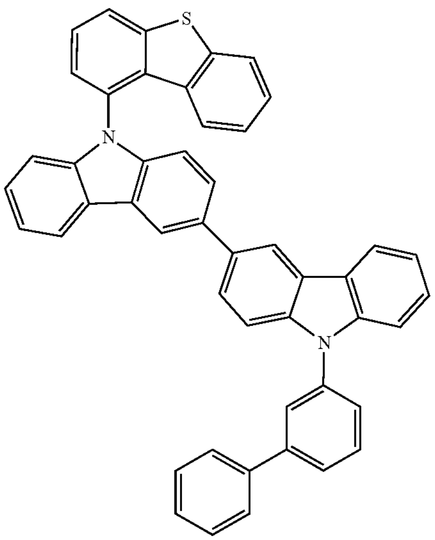
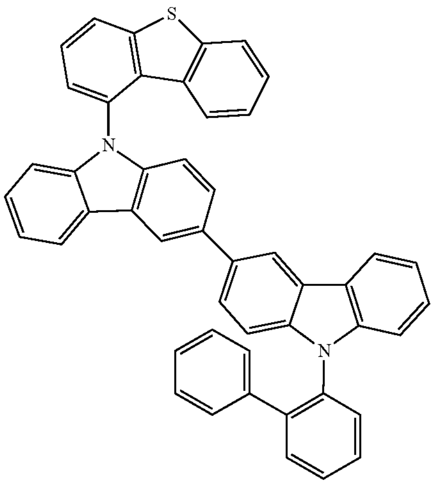
-continued
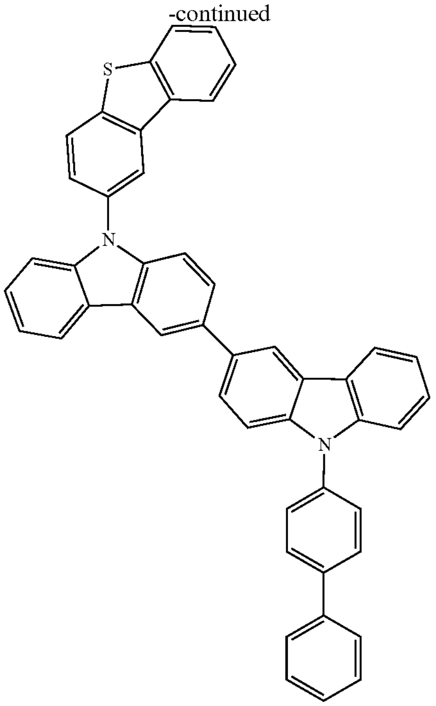
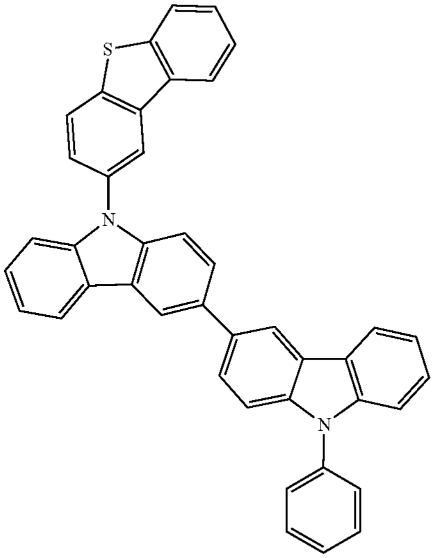
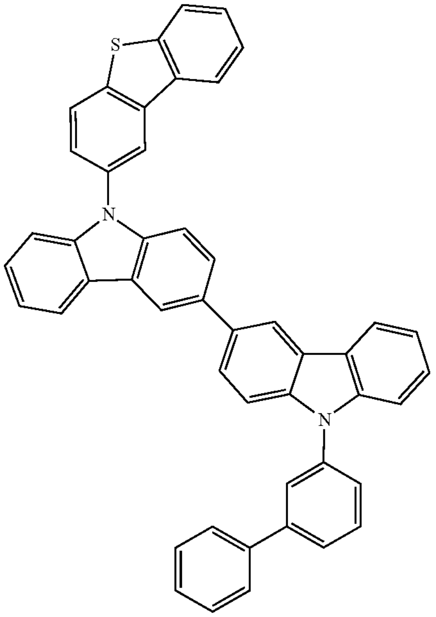

-continued
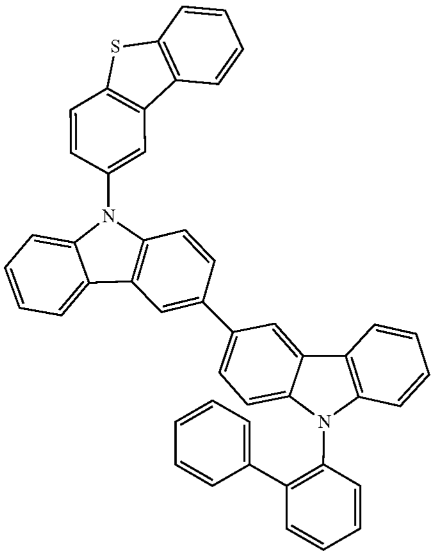
-continued
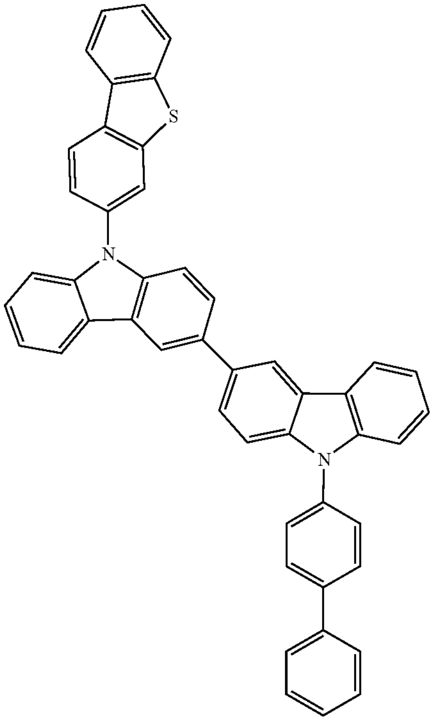
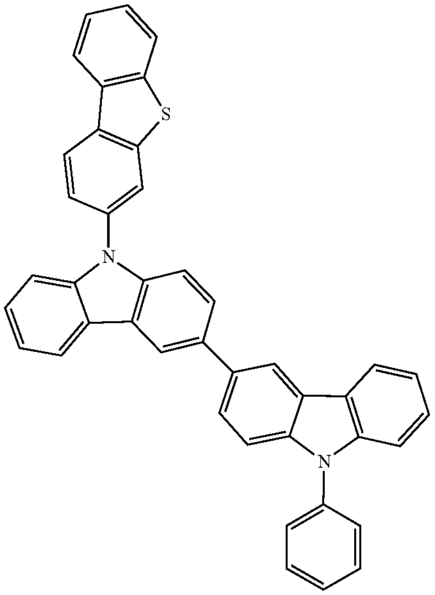
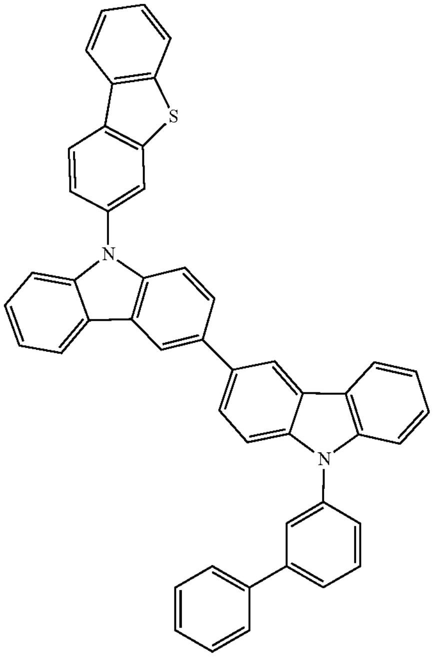

-continued
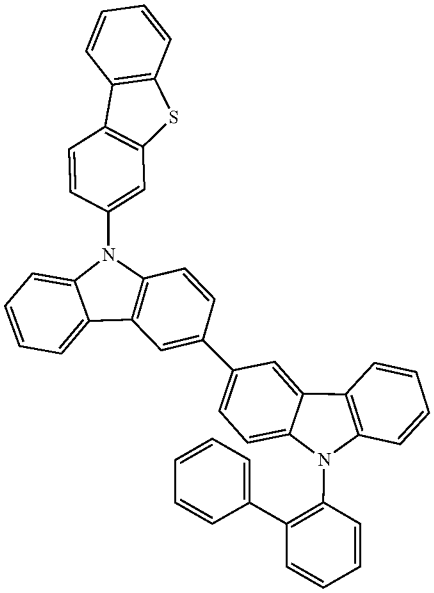
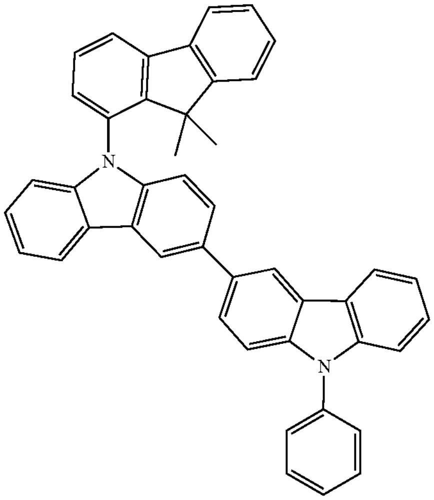
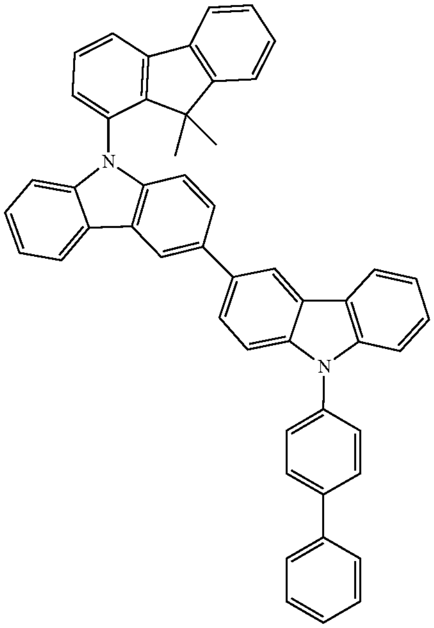
-continued
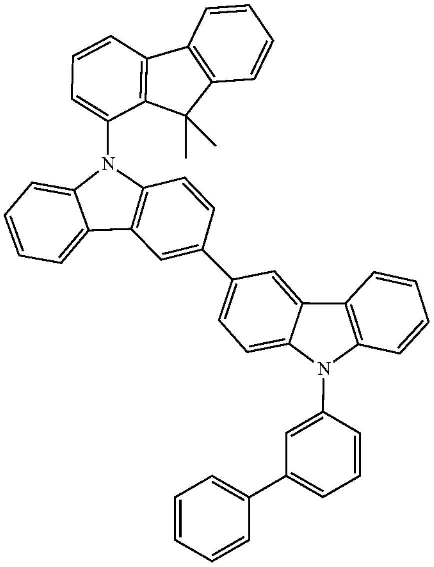
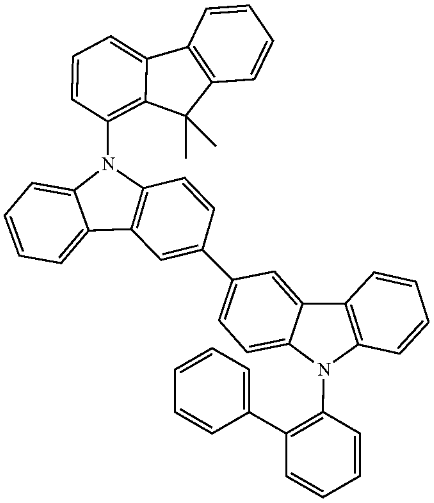
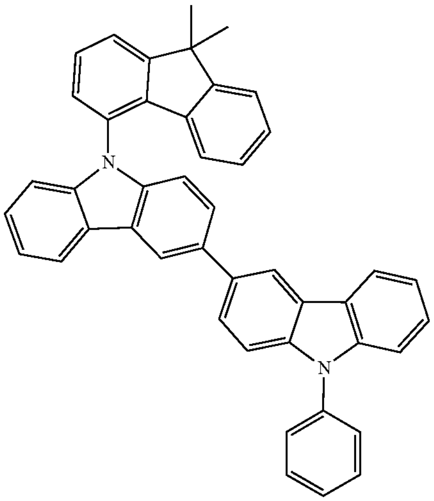

-continued
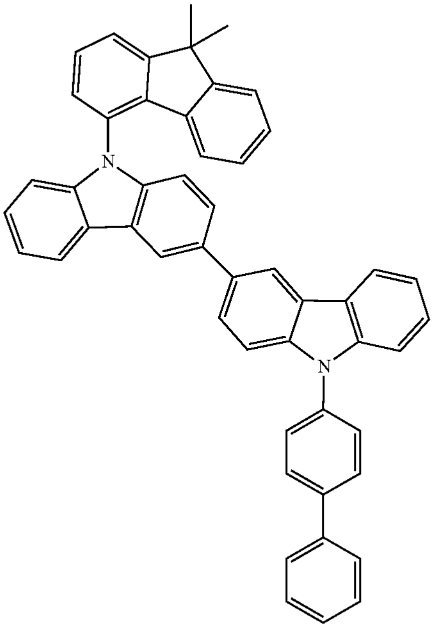
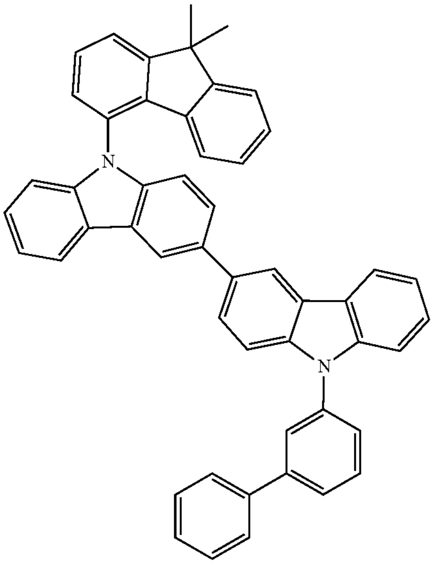
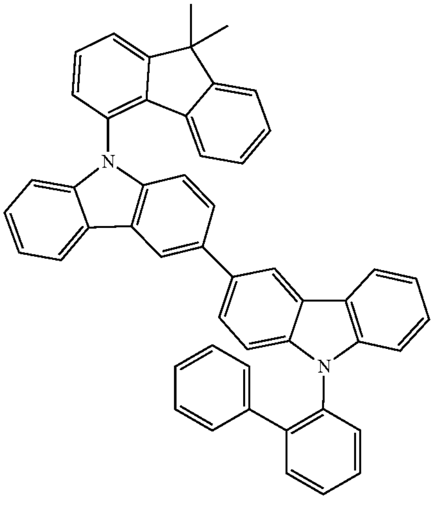
-continued
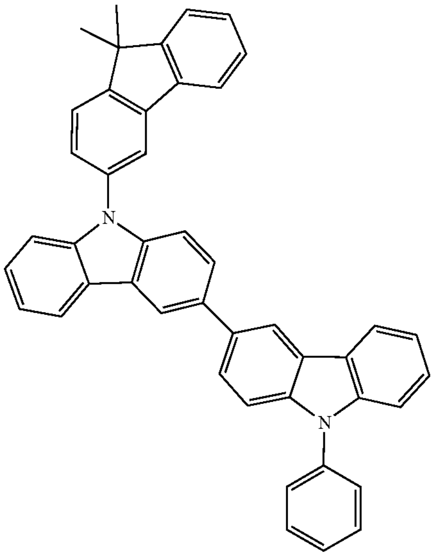
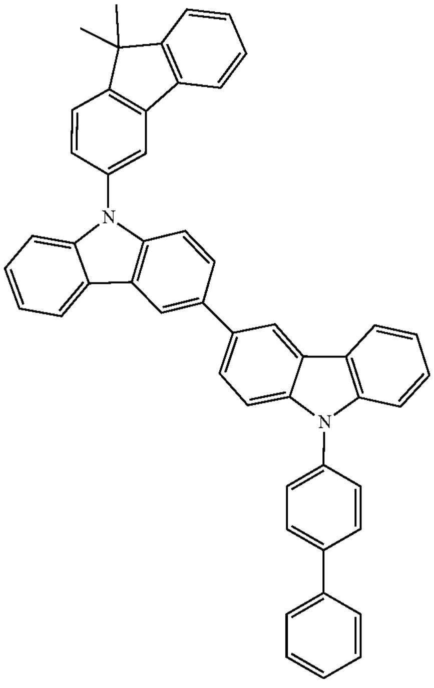

-continued
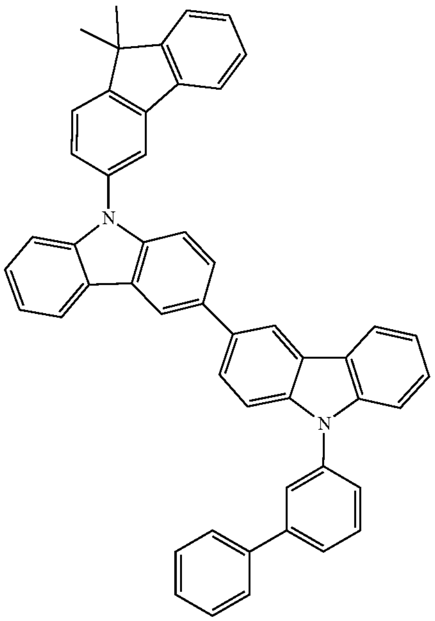
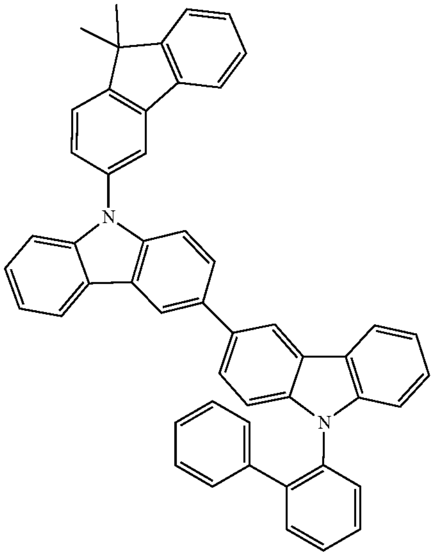
-continued
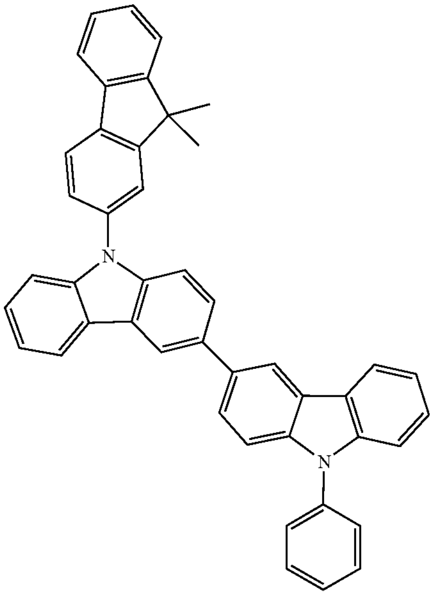
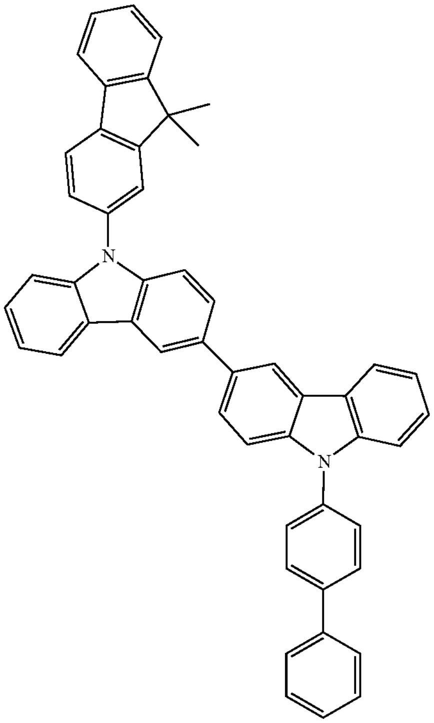 [SMILES: CC1(C)c2ccccc2-c2ccc(-n3c4ccccc4c4cc(-c5ccc6c(c5)c5ccccc5n6-c5ccc(-c6ccccc6)cc5)ccc43)cc21]

-continued
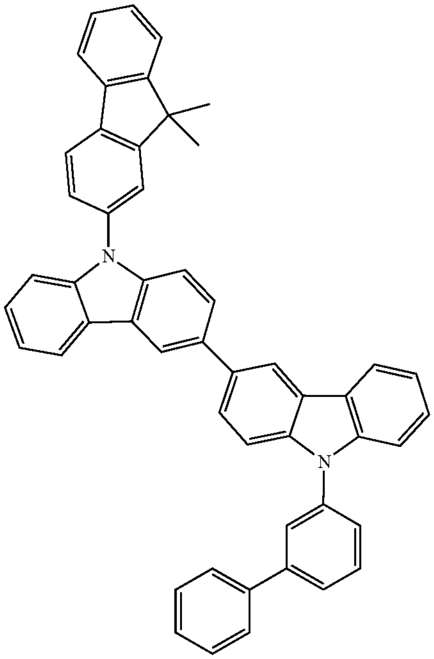
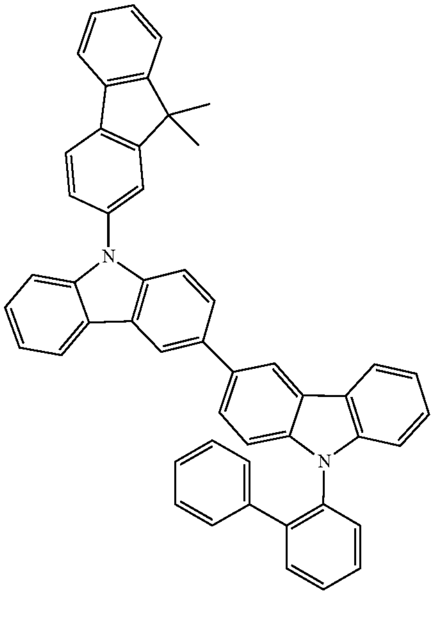
-continued
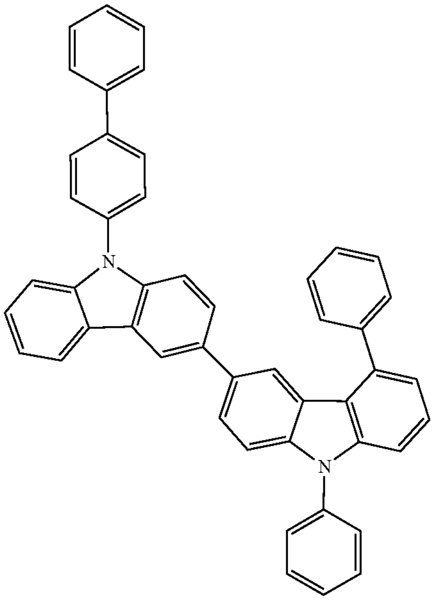
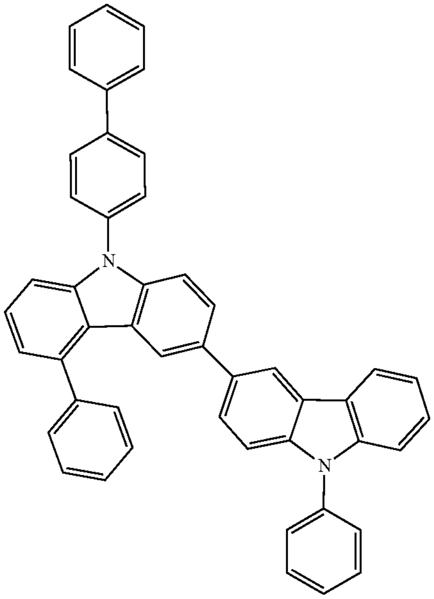

-continued
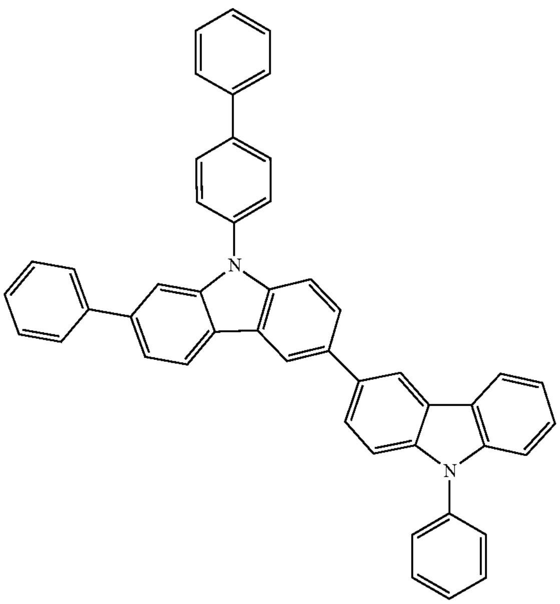
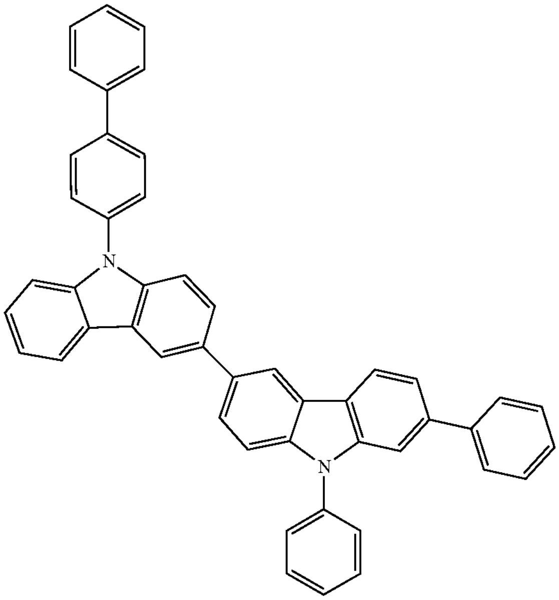
-continued
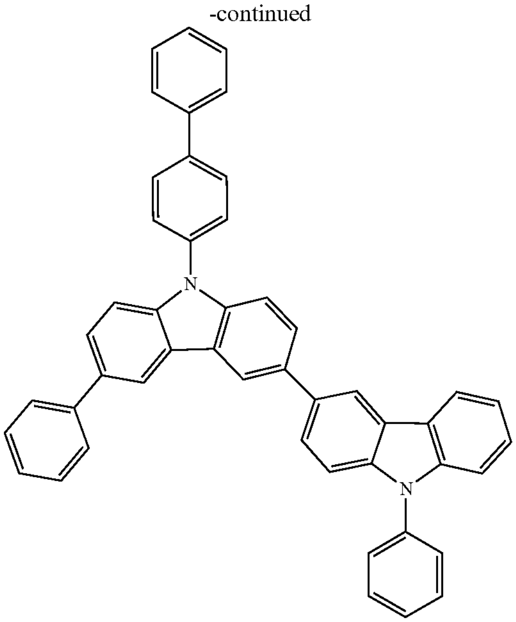
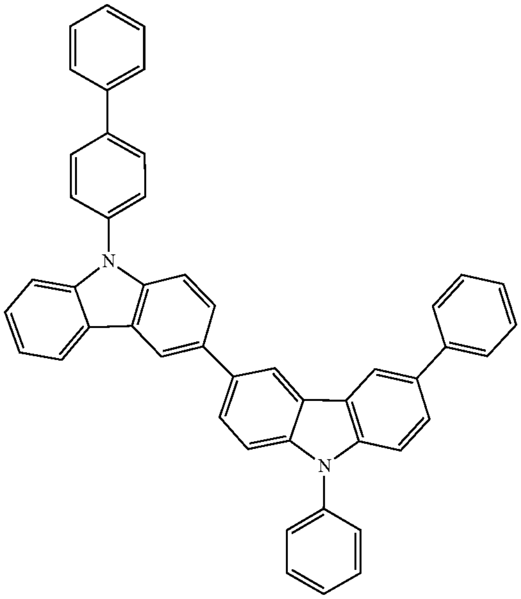
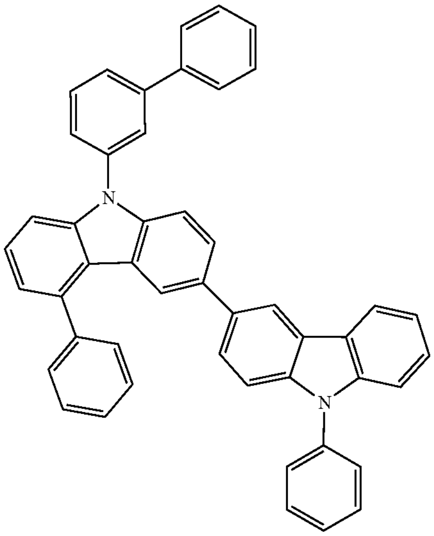

-continued

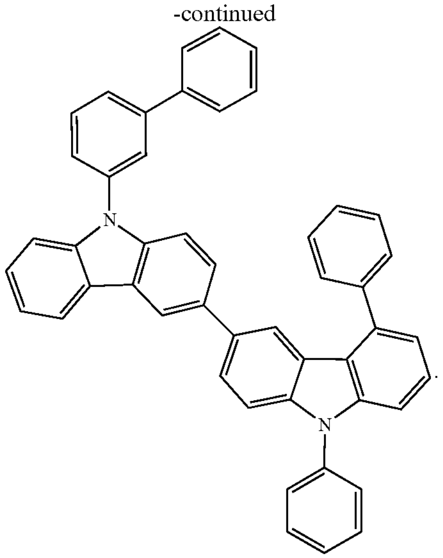

In addition, when the compound of Chemical Formula 2 is used in one or more organic material layers of the organic light emitting device together with the compound of Chemical Formula 1, a weight ratio of the compound of Chemical Formula 1 to the compound of Chemical Formula 2 can be 20:80 to 50:50, or 35:65 to 45:55, and preferably 40:60.

Meanwhile, the compound of Chemical Formula 1 can be prepared by a preparation method as shown in Reaction Scheme 1 below. The preparation method can be more specifically described in Synthesis Examples described below.

<Reaction Scheme 1>

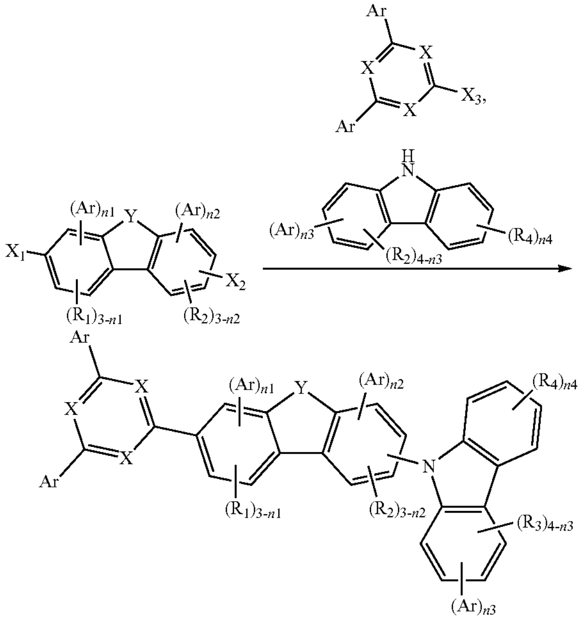

In Reaction Scheme 1,

X, Y, Ar, $R_1$, $R_2$, $R_3$, n1, n2, n3, and n4 are as defined in the Chemical Formula 1, and $X_1$ to $X_3$ are each independently a halogen group.

In particular, in the Reaction Scheme 1, $X_1$ to $X_3$ are different from each other, and can each be fluorine, chlorine, bromine or iodine.

The Reaction Scheme 1 is a reaction in which a hexagonal ring containing at least one N and a carbazole group are introduced into a tricyclic heterocyclic ring containing O or S.

In the Reaction Scheme 1, the reaction step of introducing a hexagonal ring containing at least one N, and the reaction step of introducing a carbazole group into a tricyclic heterocyclic ring containing O or S can be performed using a Pd catalyst or without a separate transition metal catalyst, in the presence of a base, respectively. In particular, when any one of $X_1$ or $X_2$ is fluorine, the Reaction Scheme 1 can be performed only in the presence of a base without a separate catalyst.

For example, sodium tert-butoxide (NaOtBu), sodium ethoxide (NaOEt), potassium carbonate ($K_2CO_3$), sodium bicarbonate ($NaHCO_3$), cesium carbonate ($Cs_2CO_3$), sodium acetate (NaOAc), potassium acetate (KOAc), triethylamine ($Et_3N$), or the like can be used as the base. Preferably, the base can be sodium tert-butoxide (NaOtBu), potassium acetate (KOAc), potassium carbonate ($K_2CO_3$), or cesium carbonate ($Cs_2CO_3$).

Tris(dibenzylideneacetone)-dipalladium (0) ($Pd_2(dba)_3$), bis(tri-(tert-butyl)phosphine)palladium (0) (BTP, $Pd(t\text{-}Bu_3P)_2$), bis(dibenzylidene-acetone)palladium (0), tetrakis (triphenylphosphine)palladium (0), or palladium(II) acetate ($Pd(OAc)_2$) can be used as the palladium catalyst. Preferably, the palladium catalyst can be bis(tri-(tert-butyl)phosphine)-palladium (0) (BTP, $Pd(t\text{-}Bu_3P)_2$), bis(dibenzylideneacetone)palladium (0), or tetrakis(triphenylphosphine) palladium (0).

In addition, the palladium catalyst can also be used in combination with a ligand compound such as tricyclohexylphosphine, tri-tert-butylphosphine ($P(tBu)_3$), or triphenylphosphine ($P(Ph)_3$). For example, a palladium catalyst such as bis(dibenzylideneacetone)palladium (0) can be used together with a ligand compound such as tricyclohexylphosphine.

Specifically, the Reaction Scheme 1 can proceed in the same manner as in the following Reaction Scheme 1-1 or 1-2 according to the order of introducing the hexagonal ring containing at least one N and the carbazole group into the tricyclic heterocyclic ring containing O or S.

<Reaction Scheme 1-1>

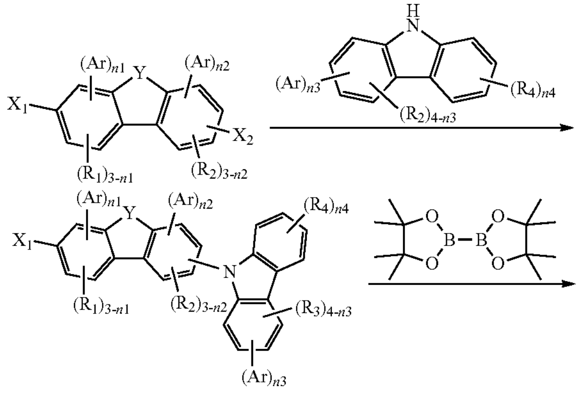

-continued

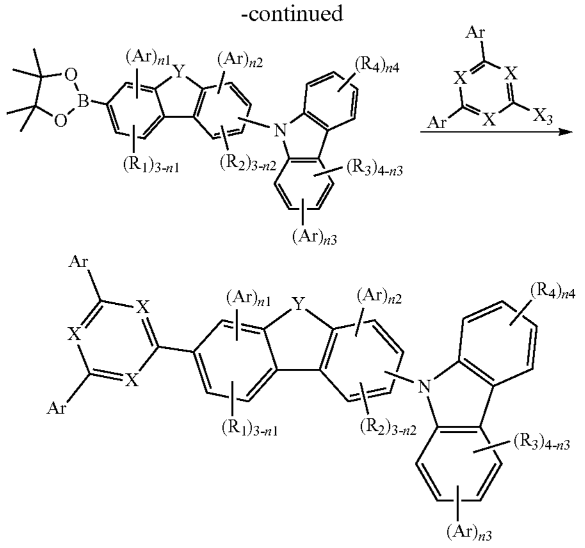

<Reaction Scheme 1-2>

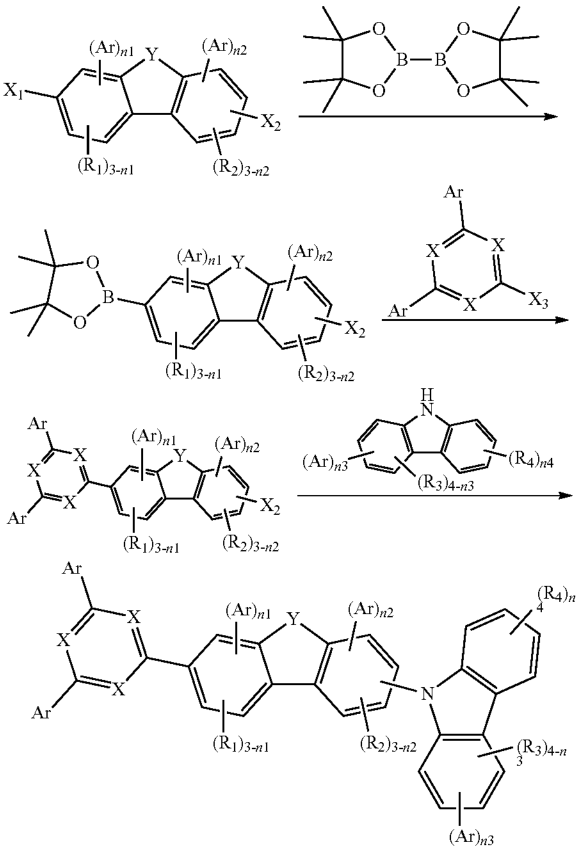

In the Reaction Schemes 1-1 and 1-2, X, Y, Ar, $R_1$, $R_2$, $R_3$, n1, n2, n3, n4, and $X_1$ to $X_3$ are as defined in the Reaction Scheme 1.

The Reaction Scheme 1-1 is a reaction in which a carbazole group is first introduced into a tricyclic heterocyclic ring containing O or S, and then a hexagonal ring containing at least one N is introduced.

Specifically, in the Reaction Scheme 1-1, a carbazole group is introduced into a tricyclic heterocyclic compound containing O or S and halogen groups of $X_1$ and $X_2$ at the $X_2$ position using a Pd catalyst in the presence of a base. Thereafter, bis(pinacolato)diboron is reacted in the presence of a base and a Pd catalyst, and a hexagonal ring containing at least one N is introduced at the remaining $X_1$ position using a Pd catalyst in the presence of a base. In particular, in the Reaction Scheme 1-1, $X_1$ can be chlorine, and $X_2$ can be bromine.

In addition, the Reaction Scheme 1-2 is a reaction in which a hexagonal ring containing at least one N is first introduced into a tricyclic heterocyclic ring containing O or S, and then a carbazole group is introduced.

Specifically, in the Reaction Scheme 1-2, bis(pinacolato) diboron is reacted with a tricyclic heterocyclic compound containing O or S and halogen groups of $X_1$ and $X_2$ in the presence of a base and a Pd catalyst, and then a hexagonal ring containing at least one N is first introduced at the $X_1$ position using a Pd catalyst in the presence of a base. Thereafter, a carbazole group is introduced at the $X_2$ position using a Pd catalyst or without a separate transition metal catalyst in the presence of a base. In particular, in the Reaction Scheme 1-2, $X_1$ can be bromine and $X_2$ can be chlorine, or $X_1$ can be chlorine and $X_2$ can be bromine.

In addition, the preparation method of the compound of Chemical Formula 1 can further include a step of performing an addition reaction or a substitution reaction for converting hydrogen or a substituent included in each reactant or reaction product used in the Reaction Scheme 1 to another substituent. For example, a reaction step of substituting at least one hydrogen included in the hexagonal ring containing at least one N, the tricyclic heterocyclic ring containing O or S, and the carbazole group constituting the polycyclic structure of Chemical Formula 1 with deuterium, or substituting halogen or the like with aryl, heteroaryl or the like can be further included.

This addition reaction or substitution reaction of deuterium or the substituent such as aryl and heteroaryl can be performed individually with respect to each reactant used in the Reaction Scheme 1 or in the preparation step of each reactant, performed as an additional step with respect to the intermediate product produced in each step of the Reaction Scheme 1, or performed as an additional step with respect to the final product obtained by the Reaction Scheme 1. Specific reaction conditions and method can be more specifically described in Synthesis Examples described below.

For example, the reaction of substituting at least one of hydrogens included in the Chemical Formula 1 with deuterium can be performed using heavy water ($D_2O$, deuterium oxide) in the presence of a platinum catalyst such as platinum (IV) oxide ($PtO_2$, platinum(IV) oxide). In addition, the addition reaction of the substituent such as aryl or heteroaryl can be performed using a Pd catalyst or the like in the presence of a base, and the types of the base component and the Pd catalyst are as described above.

In addition, in the preparation method according to the Reaction Scheme 1, each reactive group for the reaction of introducing a hexagonal ring containing at least one N and a carbazole group into a tricyclic heterocyclic ring containing O or S, an additional addition reaction of a substituent, or an additional substitution reaction can be modified as known in the art. The preparation method can be more specifically described in Synthesis Examples described below.

Meanwhile, in the present disclosure, there is provided an organic light emitting device including the above-mentioned compound of Chemical Formula 1. As an example, there is provided an organic light emitting device including: a first electrode; a second electrode that is provided opposite to the first electrode; and one or more organic material layers that are provided between the first electrode and the second electrode, wherein at least one layer of the organic material layers includes the compound of Chemical Formula 1.

The organic material layer of the organic light emitting device of the present disclosure can have a single-layer structure, or a multilayered structure in which two or more organic material layers are stacked. For example, the organic light emitting device of the present disclosure can have a structure including a hole injection layer, a hole transport layer, a light emitting layer, an electron transport layer, an electron injection layer and the like as the organic material layer. However, the structure of the organic light emitting device is not limited thereto, and it can include a smaller number of organic layers.

In addition, the organic material layer can include a hole injection layer, a hole transport layer, or a layer that simultaneously injects and transports holes, and the hole injection layer, the hole transport layer, or the layer that simultaneously injects and transports holes includes the compound of Chemical Formula 1.

In addition, the organic material layer can include a light emitting layer, and the light emitting layer includes the compound of Chemical Formula 1.

In addition, the organic material layer can include an electron transport layer or an electron injection layer, and the electron transport layer or the electron injection layer includes the compound of Chemical Formula 1.

In addition, the electron transport layer, the electron injection layer, or the layer that simultaneously transports and injects electrons includes the compound of Chemical Formula 1.

In addition, the organic material layer can include a light emitting layer and an electron transport layer, and the electron transport layer can include a compound of Chemical Formula 1.

Meanwhile, the organic light emitting device of the present disclosure can further include a compound of Chemical Formula 2 together with the compound of Chemical Formula 1. For example, the organic light emitting device of the present disclosure includes a first electrode; a second electrode that is provided opposite to the first electrode; and one or more organic material layers that are provided between the first electrode and the second electrode, wherein at least one layer of the organic material layers can further include a compound of Chemical Formula 2 together with the compound of Chemical Formula 1.

Further, the organic light emitting device according to the present disclosure can be a normal type organic light emitting device in which an anode, one or more organic material layers and a cathode are sequentially stacked on a substrate. Further, the organic light emitting device according to the present disclosure can be an inverted type organic light emitting device in which a cathode, one or more organic material layers and an anode are sequentially stacked on a substrate. For example, the structure of an organic light emitting device according to an embodiment of the present disclosure is illustrated in FIGS. 1 and 2.

FIG. 1 shows an example of an organic light emitting device including a substrate 1, an anode 2, a light emitting layer 3, and a cathode 4. In this structure, the compound of Chemical Formula 1 can be included in the light emitting layer.

FIG. 2 shows an example of an organic light emitting device including a substrate 1, an anode 2, a hole injection layer 5, a hole transport layer 6, a light emitting layer 7, an electron transport layer 8, and a cathode 4. In this structure, the compound of Chemical Formula 1 can be included in one or more layers of the hole injection layer, the hole transport layer, the light emitting layer, and the electron transport layer. Specifically, the compound of Chemical Formula 1 can be included in the light emitting layer, for example, can be included as a dopant material of the light emitting layer.

The organic light emitting device according to the present disclosure can be manufactured by materials and methods known in the art, except that one or more layers of the organic material layers include the compound of Chemical Formula 1 or the compound of Chemical Formula 2 together with the compound of Chemical Formula 1. Moreover, when the organic light emitting device includes a plurality of organic material layers, the organic material layers can be formed of the same material or different materials.

For example, the organic light emitting device according to the present disclosure can be manufactured by sequentially stacking a first electrode, an organic material layer and a second electrode on a substrate. In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device can be manufactured by sequentially depositing a cathode material, an organic material layer and an anode material on a substrate.

Further, the compound of Chemical Formula 1 can be formed into an organic material layer by a solution coating method as well as a vacuum deposition method at the time of manufacturing an organic light emitting device. In particular, the compound of Chemical Formula 1 has excellent solubility in a solvent used for the solution coating method, and thus it is easy to apply the solution coating method. Herein, the solution coating method means a spin coating, a dip coating, a doctor blading, an inkjet printing, a screen printing, a spray method, a roll coating, or the like, but is not limited thereto.

Accordingly, in the present disclosure, there is provided a coating composition including the compound of Chemical Formula 1 and a solvent.

The solvent is not particularly limited as long as it is a solvent capable of dissolving or dispersing the compound according to the present disclosure. Examples thereof can include a chlorine-based solvent such as chloroform, methylene chloride, 1,2-dichloroethane, 1,1,2-trichloroethane, chlorobenzene and o-dichlorobenzene; an ether-based solvent such as tetrahydrofuran and dioxane; an aromatic hydrocarbon-based solvent such as toluene, xylene, trimethylbenzene, and mesitylene; an aliphatic hydrocarbon-based solvent such as cyclohexane, methylcyclohexane, n-pentane, n-hexane, n-heptane, n-octane, n-nonane, and n-decane; a ketone-based solvent such as acetone, methyl ethyl ketone, and cyclohexanone; an ester-based solvent such as ethyl acetate, butyl acetate, and ethyl cellosolve acetate; a polyhydric alcohol and derivatives thereof such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin, and 1,2-hexanediol; an alcohol-based solvent such as methanol, ethanol, propanol, isopropanol and cyclohexanol; a sulfoxide-based solvent such as dimethyl sulfoxide; and an amide-based solvent such as N-methyl-2-pyrrolidone and N,N-dimethylformamide; a benzoate-based solvent such as butyl benzoate and methyl-2-methoxy benzoate; tetralin; 3-phenoxy-toluene and the like. In addition, the above-mentioned solvents can be used alone or in mixture of two or more.

In addition, a viscosity of the coating composition is preferably 1 cP to 10 cP, and coating is easy within the above range. In addition, a concentration of the compound according to the present disclosure in the coating composition is preferably 0.1 wt/v % to 20 wt/v %.

In addition, there is also provided a method for forming a functional layer using the above-described coating composition. Specifically, it includes the steps of coating the coating composition according to the present disclosure in a solution process; and heat-treating the coated coating composition.

The heat-treatment in the heat-treatment step is preferably performed at 150 to 230° C. In addition, the heat-treatment is performed for 1 minute to 3 hours, more preferably for 10 minutes to 1 hour. In addition, the heat-treatment is preferably performed under an inert gas atmosphere such as argon or nitrogen.

For example, the first electrode is an anode, and the second electrode is a cathode, or alternatively, the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides such as ZnO:Al or $SnO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof, a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole-injecting effect to the light emitting layer or the light emitting material, prevents excitons produced in the light emitting layer from moving to an electron injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which can receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is suitably a material capable of emitting light in a visible ray region by receiving holes and electrons from the hole transport layer and the electron transport layer, respectively, to combine them, and having good quantum efficiency to fluorescence or phosphorescence. Specific examples thereof include 8-hydroxy-quinoline aluminum complex ($Alq_3$); a carbazole-based compound; a dimerized styryl compound; BAlq; a 10-hydroxybenzo quinoline-metal compound; a benzoxazole-, benzothiazole- and benzimidazole-based compound; a poly(p-phenylenevinylene) (PPV)-based polymer; a spiro compound; polyfluorene, rubrene, and the like, but are not limited thereto.

The light emitting layer can include a host material and a dopant material. The host material can be a fused aromatic ring derivative, a heterocycle-containing compound or the like. Specific examples of the fused aromatic ring derivative include anthracene derivatives, pyrene derivatives, naphthalene derivatives, pentacene derivatives, phenanthrene compounds, fluoranthene compounds, and the like. Examples of the heterocyclic-containing compound include carbazole derivatives, dibenzofuran derivatives, ladder-type furan compounds, pyrimidine derivatives, and the like, but are not limited thereto.

The dopant material includes an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto. Preferably, the compound of Chemical Formula 1 according to the present disclosure is used as the dopant material. Meanwhile, as the dopant material, the compound of Chemical Formula 2 can be further used together with the compound of Chemical Formula 1.

The electron transport layer is a layer which receives electrons from an electron injection layer and transports the electrons to a light emitting layer, and an electron transport material is suitably a material which can receive electrons well from a cathode and transfer the electrons to a light emitting layer and has large mobility for electrons. Specific examples thereof include an Al complex of 8-hydroxyquinoline; a complex including $Alq_3$ (tris(8-hydroxyquinolino)

aluminum); an organic radical compound; a hydroxyflavone-metal complex, and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)-gallium, bis(10-hydroxybenzo[h]quinolinato)beryllium, bis(10-hydroxybenzo-[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)-aluminum, bis(2-methyl-8-quinolinato)(2-naphtholato)gallium, and the like, but are not limited thereto.

The organic light emitting device according to the present disclosure can be a front side emission type, a backside emission type, or a double-sided emission type according to the used material.

In addition, the compound of Chemical Formula 1 can be included in an organic solar cell or an organic transistor in addition to an organic light emitting device.

The preparation of the compound of Chemical Formula 1 and the organic light emitting device containing the same will be described in detail in the following examples. However, these examples are presented for illustrative purposes only, and are not intended to limit the scope of the present disclosure.

SYNTHESIS EXAMPLES

Synthesis Example 1: Synthesis of Compound 1

Step 1) Synthesis of Compound 1-1

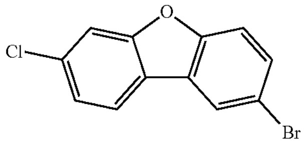

+

-continued

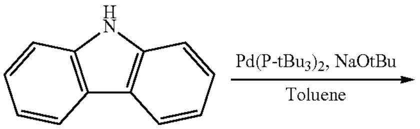

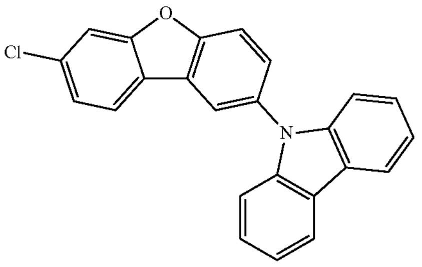

1-1

2-bromo-7-chlorodibenzo[b,d]furan (15 g, 53.3 mmol) and 9H-carbazole (9.8 g, 58.6 mmol) were added to 300 ml of toluene under a nitrogen atmosphere, and the mixture was stirred and refluxed. Then, sodium tert-butoxide (7.7 g, 79.9 mmol) and bis(tri-tert-butylphosphine)palladium(0) (0.8 g, 1.6 mmol) were added thereto. After 2 hours of reaction, it was cooled to room temperature and the organic layer was separated using chloroform and water, and then the organic layer was distilled. Then, this was dissolved again in chloroform, and washed twice with water. Thereafter, the organic layer was separated, treated with anhydrous magnesium sulfate, stirred, then filtered, and the filtrate was distilled under reduced pressure. The concentrated compound was purified by silica gel column chromatography to prepare 15.7 g of Compound 1-1 (yield 80%, MS: $[M+H]^+$=369).

Step 2) Synthesis of Compound 1-2

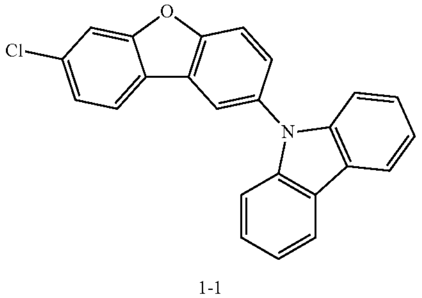

+

1-1

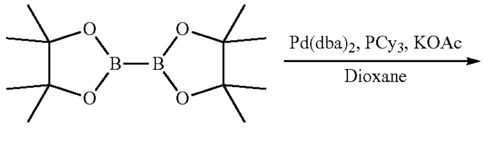

-continued

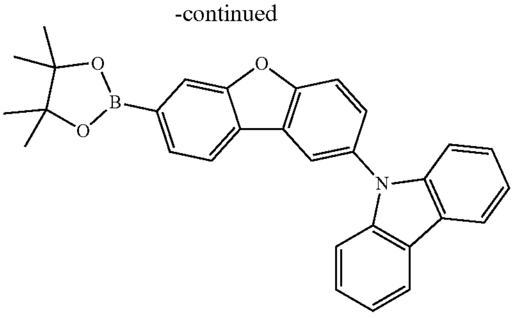

1-2

Compound 1-1 (15 g, 40.8 mmol) and bis(pinacolato) diboron (11.4 g, 44.9 mmol) were added to 300 ml of 1,4-dioxane under a nitrogen atmosphere, and the mixture was stirred and refluxed. Then, potassium acetate (6 g, 61.2 mmol) was added thereto and sufficiently stirred, followed by adding bis(dibenzylideneacetone)palladium(0) (0.7 g, 1.2 mmol) and tricyclohexylphosphine (0.7 g, 2.4 mmol). After 7 hours of reaction, it was cooled to room temperature and the organic layer was separated using chloroform and water, and then the organic layer was distilled. Then, this was dissolved again in chloroform, and washed twice with water. Thereafter, the organic layer was separated, treated with anhydrous magnesium sulfate, stirred, then filtered, and the filtrate was distilled under reduced pressure. The concentrated compound was purified by silica gel column chromatography to prepare 12.7 g of Compound 1-2 (yield 68%, MS: $[M+H]^+=460$).

Step 3) Synthesis of Compound 1

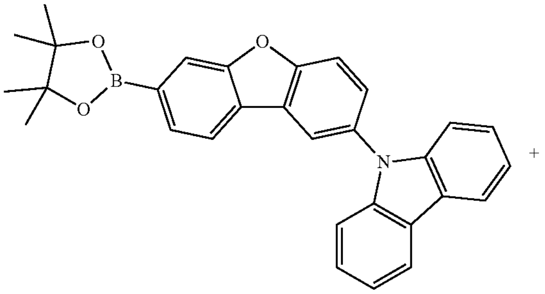

1-2

-continued

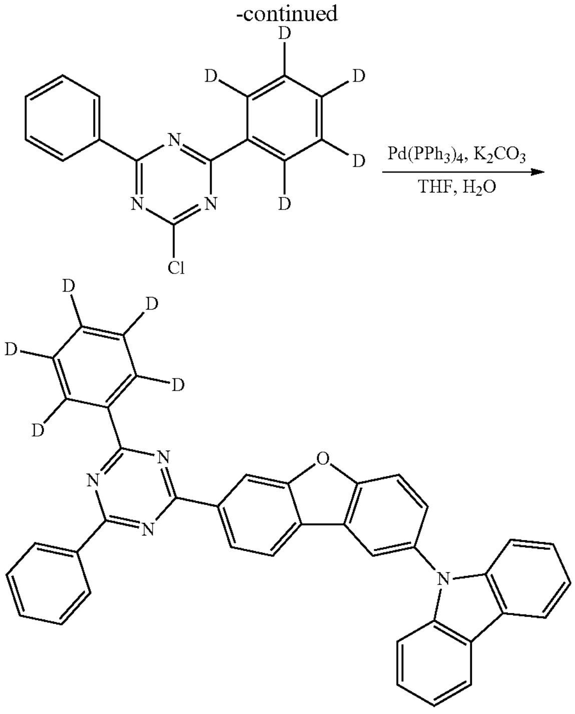

1

Compound 1-2 (15 g, 32.7 mmol) and 2-chloro-4-phenyl-6-(phenyl-d5)-1,3,5-triazine (9.8 g, 35.9 mmol) were added to 300 ml of THF under a nitrogen atmosphere, and the mixture was stirred and refluxed. Then, potassium carbonate (18.1 g, 130.6 mmol) was dissolved in 54 ml of water, and then added thereto. Thereafter, it was sufficiently stirred, followed by adding tetrakis(triphenylphosphine)palladium (0) (1.1 g, 1 mmol). After 11 hours of reaction, it was cooled to room temperature and the organic layer was separated from the water layer, and then the organic layer was distilled. Then, this was dissolved again in chloroform, and washed twice with water. Thereafter, the organic layer was separated, treated with anhydrous magnesium sulfate, stirred, then filtered, and the filtrate was distilled under reduced pressure. The concentrated compound was purified by silica gel column chromatography, and then 6.7 g of Compound 1 was prepared through sublimation purification (yield 36%, MS: $[M+H]^+=571$).

Synthesis Example 2: Synthesis of Compound 2

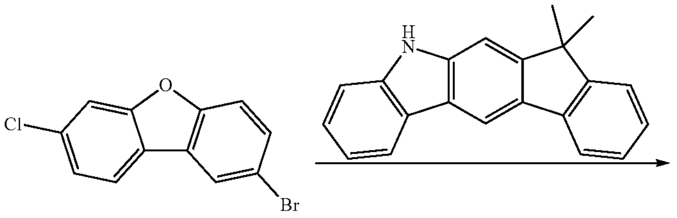

-continued

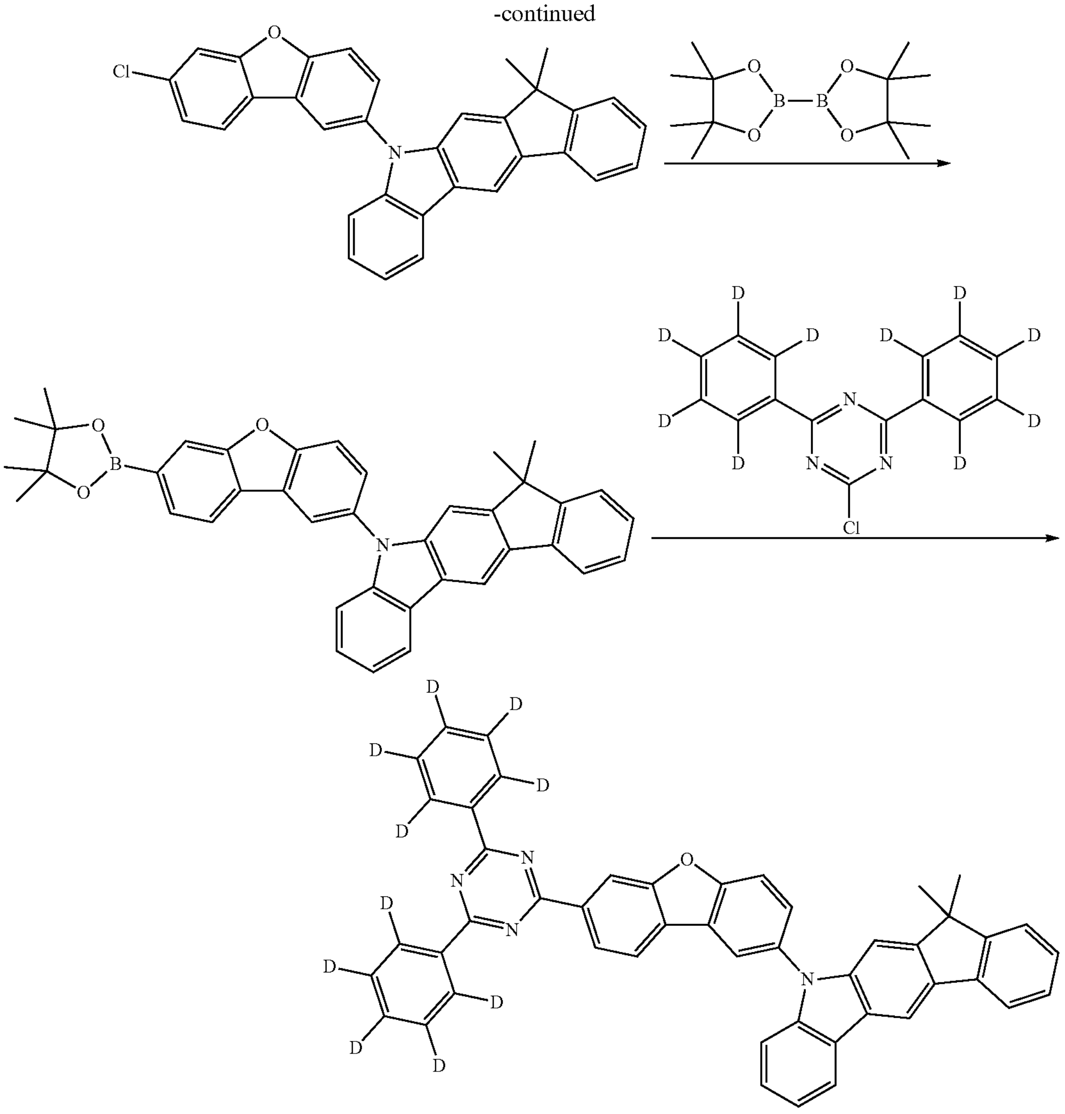

2

Compound 2 was prepared in the same manner as in the preparation method of Compound 1, except that 9H-carbazole was changed to 7,7-dimethyl-5,7-dihydroindeno[2,1-b] carbazole and 2-chloro-4-phenyl-6-(phenyl-d5)-1,3,5-triazine was changed to 2-chloro-4,6-bis(phenyl-d5)-1,3,5-triazine in Synthesis Example 1 (MS: $[M+H]^+$=692).

Synthesis Example 3: Synthesis of Compound 3

Step 1) Synthesis of Compound 3-1

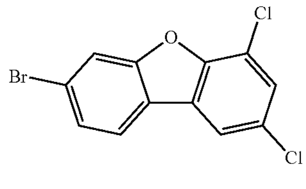

+

-continued

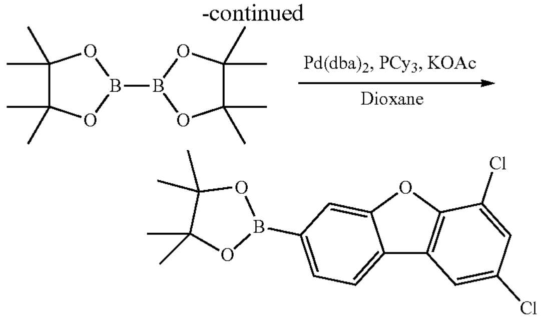

3-1

7-bromo-2,4-dichlorodibenzo[b,d]furan (15 g, 47.5 mmol) and bis(pinacolato)diboron (13.3 g, 52.2 mmol) were added to 300 ml of 1,4-dioxane under a nitrogen atmosphere, and the mixture was stirred and refluxed. Then, potassium acetate (7 g, 71.2 mmol) was added thereto and sufficiently stirred, followed by adding bis(dibenzylideneacetone)palladium(0) (0.8 g, 1.4 mmol) and tricyclohexylphosphine (0.8 g, 2.8 mmol). After 7 hours of reaction, it was cooled to room temperature and the organic layer was separated using chloroform and water, and then the organic layer was distilled. Then, this was dissolved again in chloroform, and washed twice with water. Thereafter, the organic layer was separated, treated with anhydrous magnesium sulfate, stirred, then filtered, and the filtrate was distilled under reduced pressure. The concentrated compound was purified by silica gel column chromatography to prepare 12.4 g of Compound 3-1 (yield 72%, MS: $[M+H]^+=364$).

Step 2) Synthesis of Compound 3-2

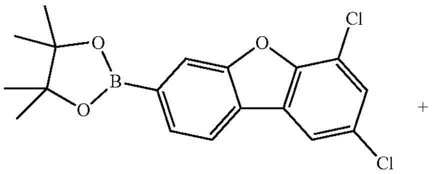

3-1

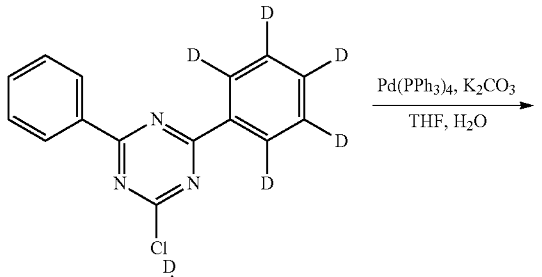

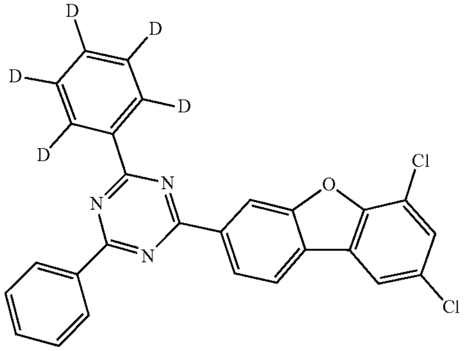

3-2

Compound 3-1 (15 g, 41.3 mmol) and 2-chloro-4-phenyl-6-(phenyl-d5)-1,3,5-triazine (12.4 g, 45.4 mmol) were added to 300 ml of THF under a nitrogen atmosphere, and the mixture was stirred and refluxed. Then, potassium carbonate (22.8 g, 165.3 mmol) was dissolved in 69 ml of water, and then added thereto. Thereafter, it was sufficiently stirred, followed by adding tetrakis(triphenylphosphine)palladium (0) (1.4 g, 1.2 mmol). After 11 hours of reaction, it was cooled to room temperature and the organic layer was separated from the water layer, and then the organic layer was distilled. Then, this was dissolved again in chloroform, and washed twice with water. Thereafter, the organic layer was separated, treated with anhydrous magnesium sulfate, stirred, then filtered, and the filtrate was distilled under reduced pressure. The concentrated compound was purified by silica gel column chromatography to prepare 12.9 g of Compound 3-2 (yield 66%, MS: $[M+H]^+=474$).

Step 3) Synthesis of Compound 3-3

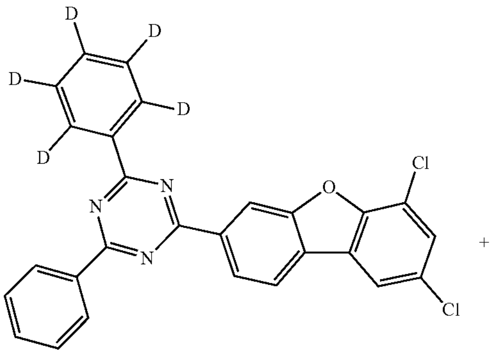

3-2

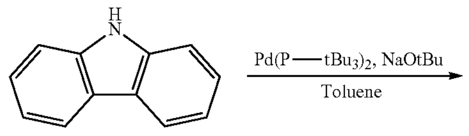

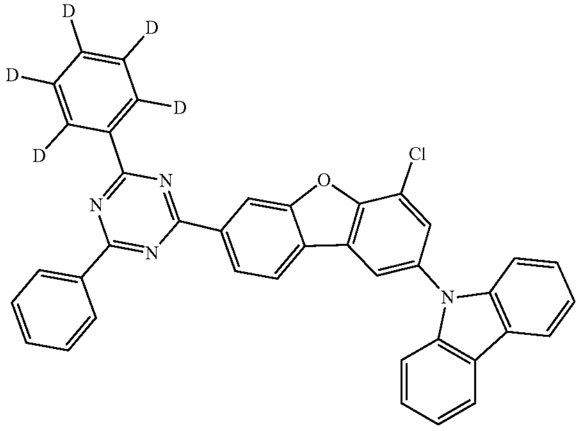

3-3

Compound 3-2 (15 g, 31.7 mmol) and 9H-carbazole (5.8 g, 34.9 mmol) were added to 300 ml of toluene under a nitrogen atmosphere, and the mixture was stirred and refluxed. Then, sodium tert-butoxide (4.6 g, 47.5 mmol) and bis(tri-tert-butylphosphine)palladium(0) (0.5 g, 1 mmol) were added thereto. After 4 hours of reaction, it was cooled to room temperature and the organic layer was separated using chloroform and water, and then the organic layer was distilled. Then, this was dissolved again in chloroform, and washed twice with water. Thereafter, the organic layer was separated, treated with anhydrous magnesium sulfate, stirred, then filtered, and the filtrate was distilled under reduced pressure. The concentrated compound was purified by silica gel column chromatography to prepare 14.9 g of Compound 3-3 (yield 78%, MS: $[M+H]^+=605$).

Step 4) Synthesis of Compound 3

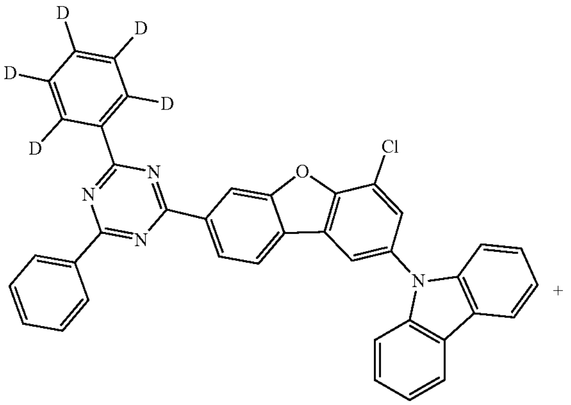

3-3

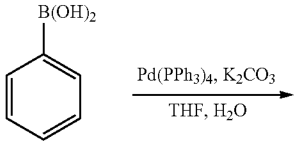

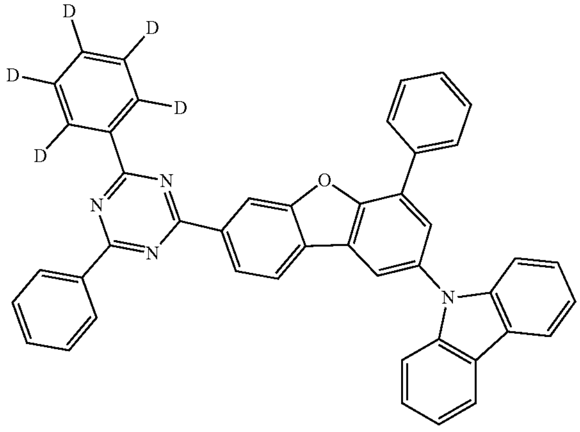

3

Compound 3-3 (15 g, 24.8 mmol) and phenylboronic acid (3.3 g, 27.3 mmol) were added to 300 ml of THF under a nitrogen atmosphere, and the mixture was stirred and refluxed. Then, potassium carbonate (13.7 g, 99.3 mmol) was dissolved in 41 ml of water, and then added thereto. Thereafter, it was sufficiently stirred, followed by adding tetrakis(triphenylphosphine)-palladium(0) (0.9 g, 0.7 mmol). After 11 hours of reaction, it was cooled to room temperature and the organic layer was separated from the water layer, and then the organic layer was distilled. Then, this was dissolved again in chloroform, and washed twice with water. Thereafter, the organic layer was separated, treated with anhydrous magnesium sulfate, stirred, then filtered, and the filtrate was distilled under reduced pressure. The concentrated compound was purified by silica gel column chromatography, and then 7.7 g of Compound 3 was prepared through sublimation purification (yield 48%, MS: $[M+H]^+=647$).

Synthesis Example 4: Synthesis of Compound 4

Step 1) Synthesis of Compound 4-1

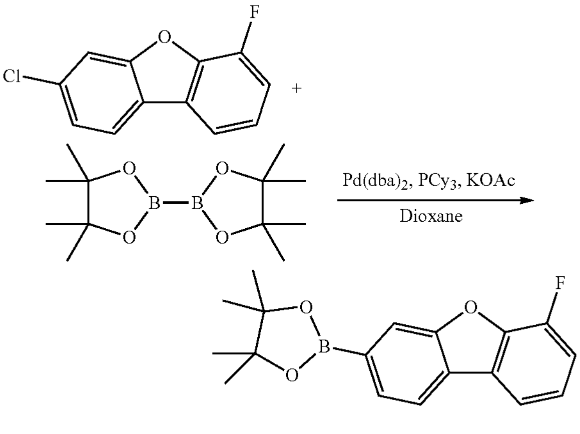

4-1

3-chloro-6-fluorodibenzo[b,d]furan (15 g, 68 mmol) and bis(pinacolato)diboron (19 g, 74.8 mmol) were added to 300 ml of 1,4-dioxane under a nitrogen atmosphere, and the mixture was stirred and refluxed. Then, potassium acetate (10 g, 102 mmol) was added thereto and sufficiently stirred, followed by adding bis(dibenzylideneacetone)palladium(0) (1.2 g, 2 mmol) and tricyclohexylphosphine (1.1 g, 4.1 mmol). After 6 hours of reaction, it was cooled to room temperature and the organic layer was separated using chloroform and water, and then the organic layer was distilled. Then, this was dissolved again in chloroform, and washed twice with water. Thereafter, the organic layer was separated, treated with anhydrous magnesium sulfate, stirred, then filtered, and the filtrate was distilled under reduced pressure. The concentrated compound was purified by silica gel column chromatography to prepare 12.7 g of Compound 4-1 (yield 60%, MS: $[M+H]^+=313$).

Step 2) Synthesis of Compound 4-2

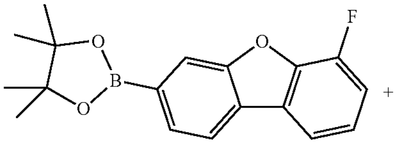

4-1

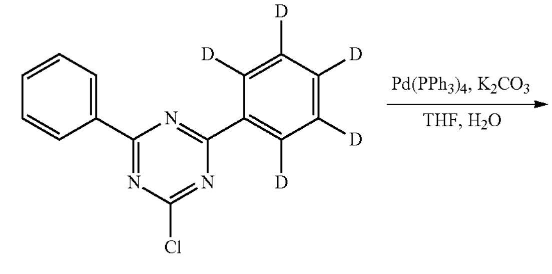

-continued

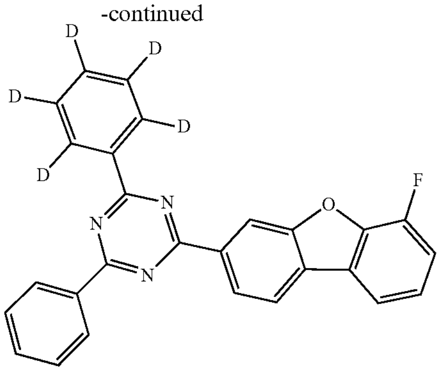

4-2

Compound 4-1 (15 g, 48.1 mmol) and 2-chloro-4-phenyl-6-(phenyl-d5)-1,3,5-triazine (14.4 g, 52.9 mmol) were added to 300 ml of THF under a nitrogen atmosphere, and the mixture was stirred and refluxed. Then, potassium carbonate (26.6 g, 192.2 mmol) was dissolved in 80 ml of water, and then added thereto. Thereafter, it was sufficiently stirred, followed by adding tetrakis(triphenylphosphine)palladium (0) (1.7 g, 1.4 mmol). After 10 hours of reaction, it was cooled to room temperature and the organic layer was separated using chloroform and water, and then the organic layer was distilled. Then, this was dissolved again in chloroform, and washed twice with water. Thereafter, the organic layer was separated, treated with anhydrous magnesium sulfate, stirred, then filtered, and the filtrate was distilled under reduced pressure. The concentrated compound was purified by silica gel column chromatography to prepare 13.8 g of Compound 4-2 (yield 68%, MS: $[M+H]^+=423$).

Step 3) Synthesis of Compound 4

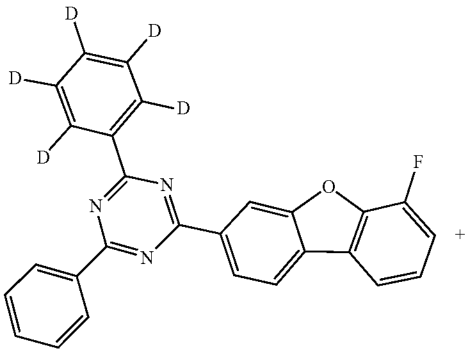

4-2

-continued

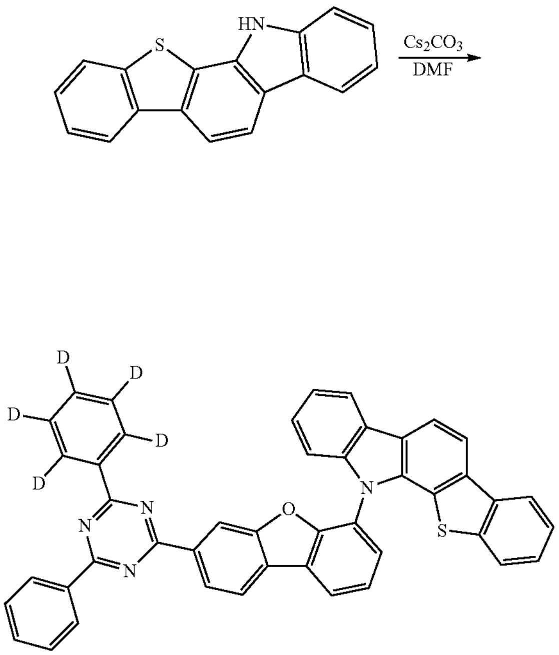

4

Compound 4-2 (20 g, 47.3 mmol) and 12H-benzo[4,5]thieno[2,3-a]carbazole (14.2 g, 52.1 mmol) were added to 400 ml of DMF under a nitrogen atmosphere, and the mixture was stirred and refluxed. Then, cesium carbonate (46.3 g, 142 mmol) was added thereto, and stirred. After 3 hours of reaction, it was cooled to room temperature and the organic layer was separated using chloroform and water, and then the organic layer was distilled. Then, this was dissolved again in chloroform, and washed twice with water. Thereafter, the organic layer was separated, treated with anhydrous magnesium sulfate, stirred, then filtered, and the filtrate was distilled under reduced pressure. The concentrated compound was purified by silica gel column chromatography, and then 14.4 g of Compound 4 was prepared through sublimation purification (yield 45%, MS: $[M+H]^+=677$).

Synthesis Example 5: Synthesis of Compound 5

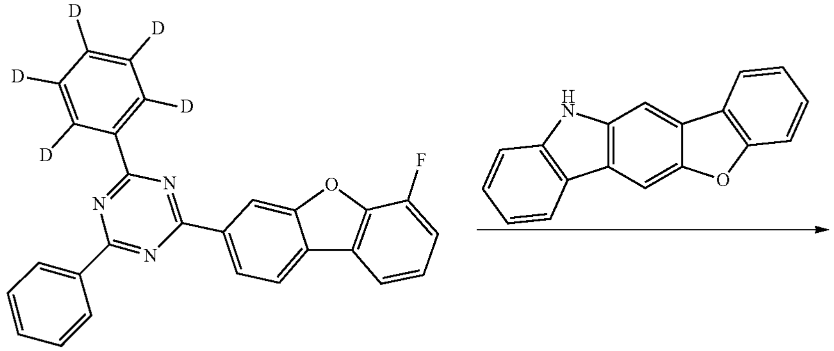

4-2

-continued

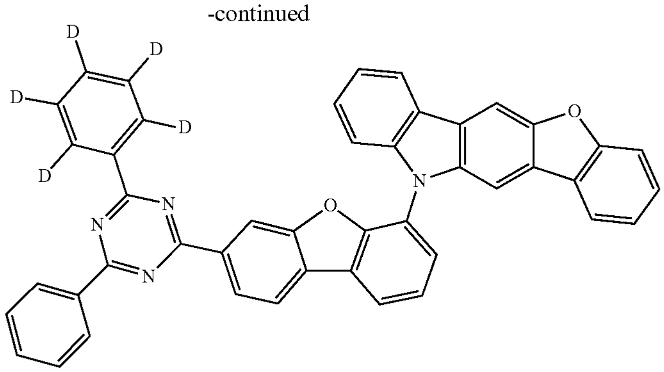

5

Compound 5 was prepared in the same manner as in the preparation method of Compound 4, except that 12H-benzo[4,5]thieno[2,3-a]carbazole was changed to 11H-benzofuro[3,2-b]carbazole in Step 3 of Synthesis Example 4 (MS: $[M+H]^+=661$).

Synthesis Example 6: Synthesis of Compound 6

Step 1) Synthesis of Compound 6-1

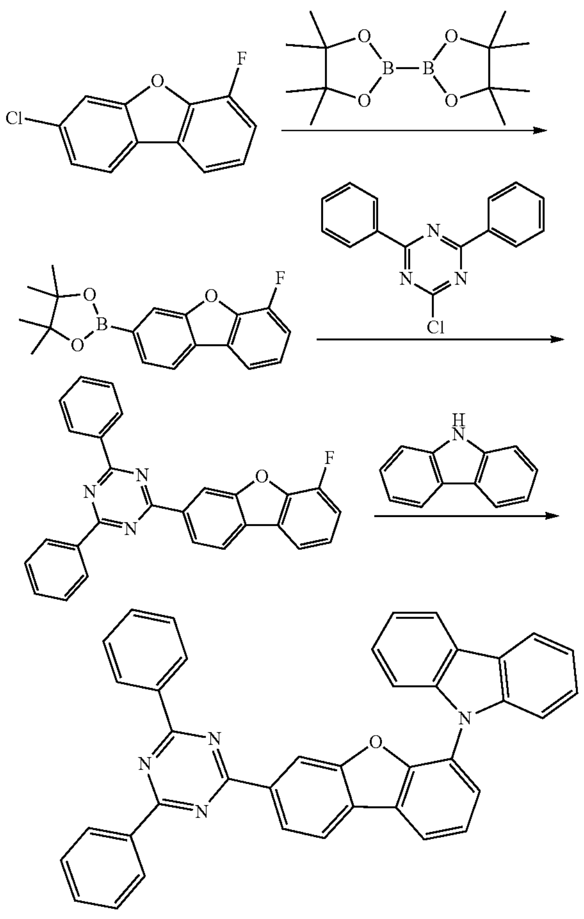

6-1

Compound 6-1 was prepared in the same manner as in the preparation method of Compound 4, except that 2-chloro-4-phenyl-6-(phenyl-d5)-1,3,5-triazine was changed to 2-chloro-4,6-diphenyl-1,3,5-triazine and 12H-benzo[4,5]thieno[2,3-a]carbazole was changed to 9H-carbazole in Synthesis Example 4 (MS: $[M+H]^+=566$).

Step 2) Synthesis of Compound 6

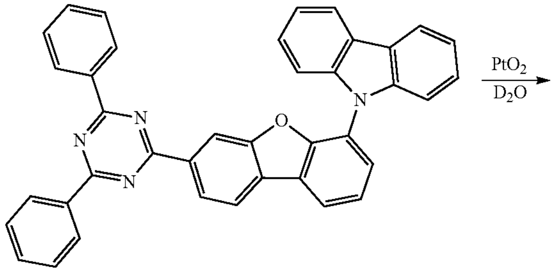

6-1

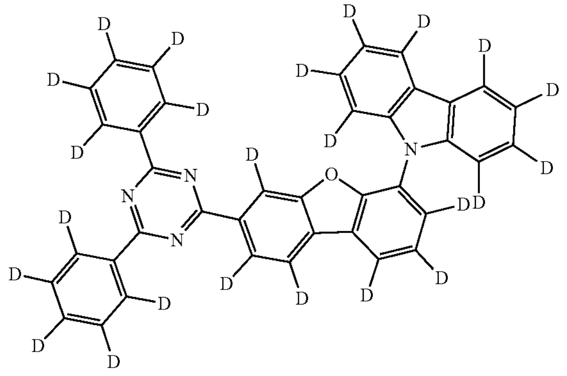

6

Compound 6-1 (10 g, 17.7 mmol), $PtO_2$ (1.2 g, 5.3 mmol), and 89 mL of $D_2O$ were placed in a shaker tube, and then the tube was sealed and heated at 250° C. and 600 psi for 12 hours. When the reaction was completed, chloroform was added thereto, and the reaction solution was transferred to a separatory funnel for extraction. The extract was dried with $MgSO_4$, and concentrated. Thereafter, the sample was purified by silica gel column chromatography, and then 4.6 g of Compound 6 was prepared through sublimation purification (yield 44%, MS: $[M+H]^+=590$).

Synthesis Example 7: Synthesis of Compound 7
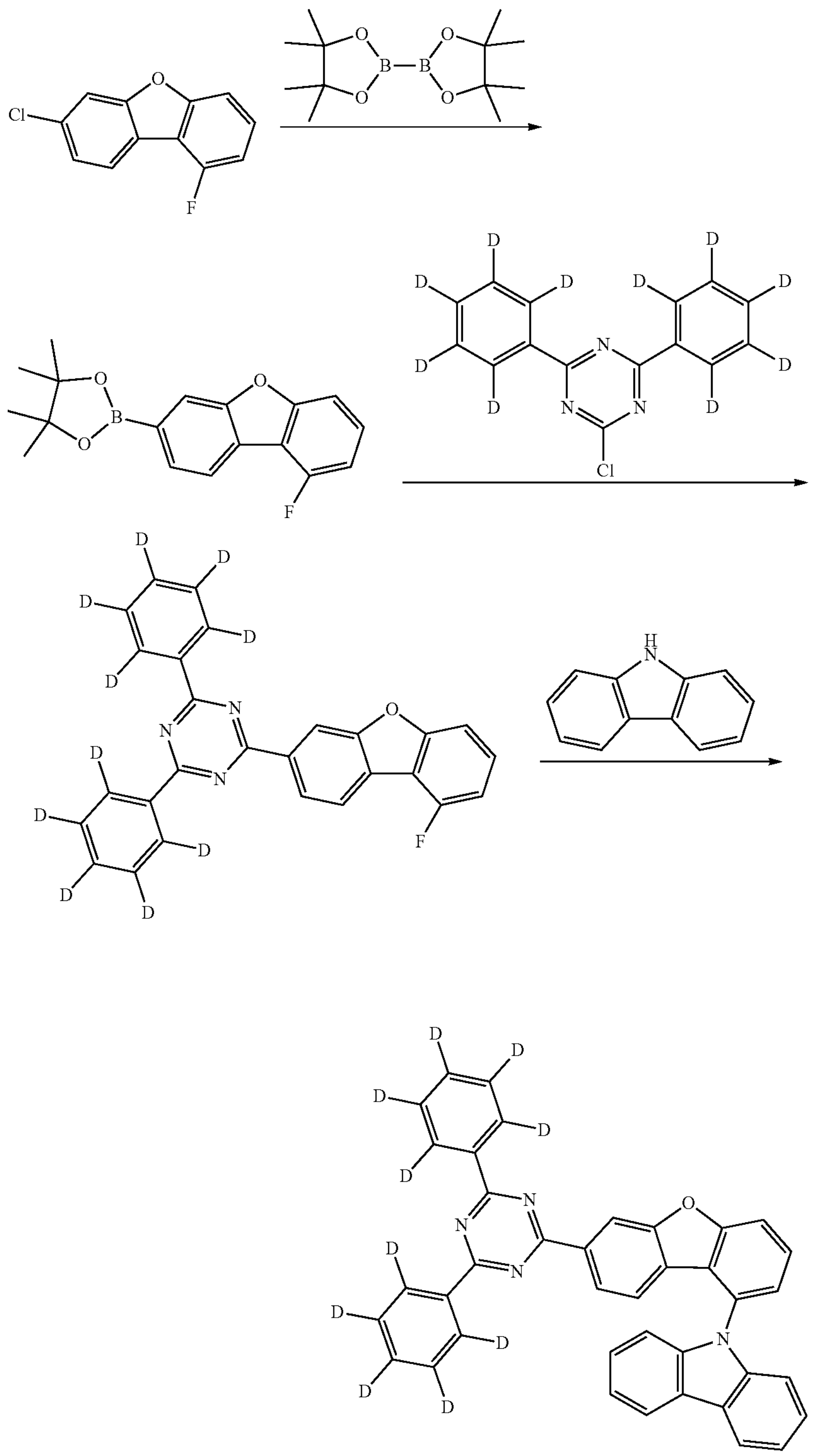
7

Compound 7 was prepared in the same manner as in the preparation method of Compound 4, except that 3-chloro-6-fluorodibenzo[b,d]furan was changed to 7-chloro-1-fluorodibenzo[b,d]furan, 2-chloro-4-phenyl-6-(phenyl-d5)-1,3,5-triazine was changed to 2-chloro-4,6-bis(phenyl-d5)-1,3,5-triazine, and 12H-benzo[4,5]thieno[2,3-a]carbazole was changed to 9H-carbazole in Synthesis Example 4 (MS: [M+H]$^+$=576).

Synthesis Example 8: Synthesis of Compound 8

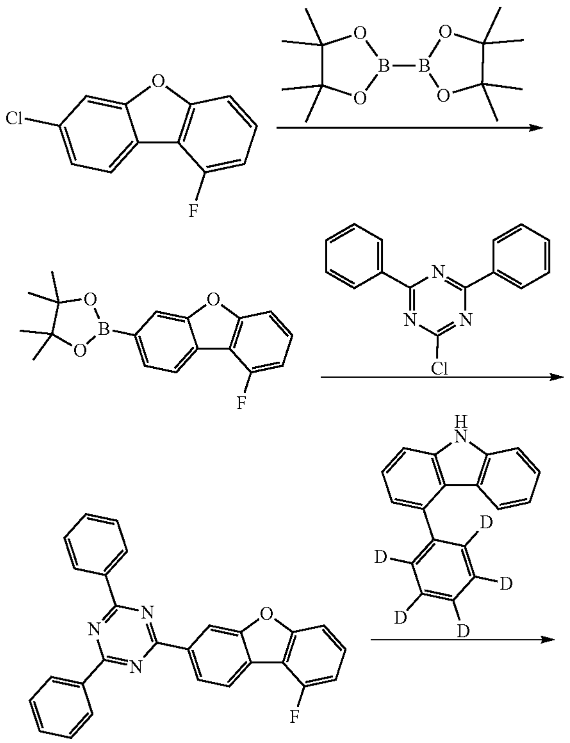

-continued

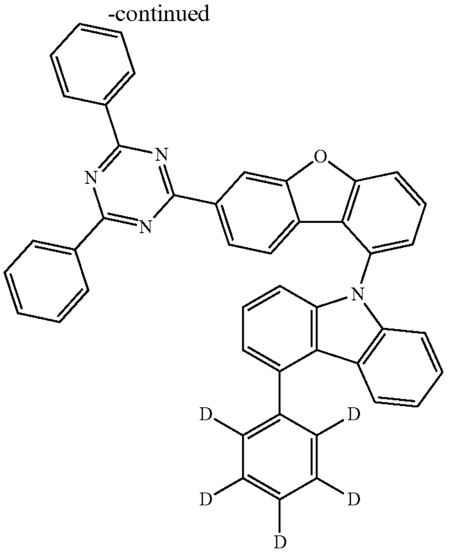

8

Compound 8 was prepared in the same manner as in the preparation method of Compound 4, except that 3-chloro-6-fluorodibenzo[b,d]furan was changed to 7-chloro-1-fluorodibenzo[b,d]furan, 2-chloro-4-phenyl-6-(phenyl-d5)-1,3,5-triazine was changed to 2-chloro-4,6-diphenyl-1,3,5-triazine, and 12H-benzo[4,5]thieno[2,3-a]carbazole was changed to 4-(phenyl-d5)-9H-carbazole in Synthesis Example 4 (MS: [M+H]$^+$=647).

Synthesis Example 9: Synthesis of Compound 9

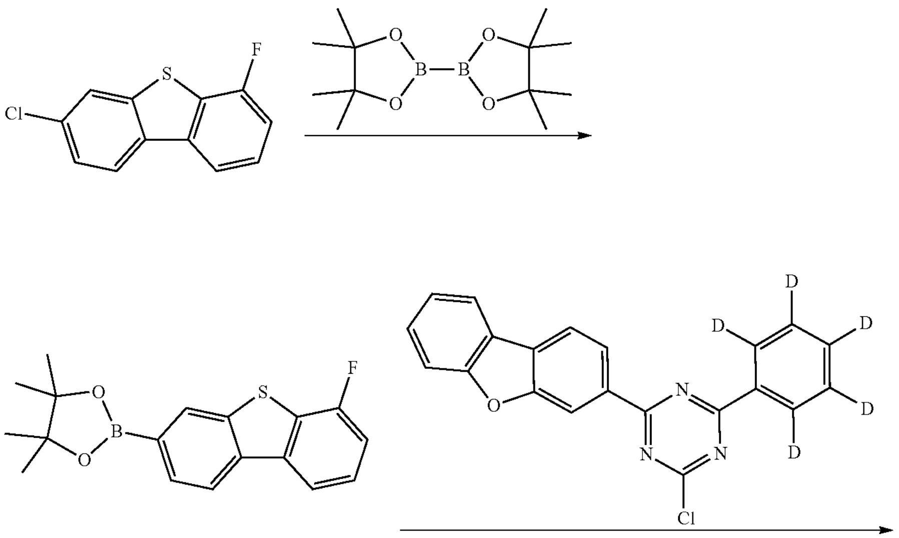

-continued

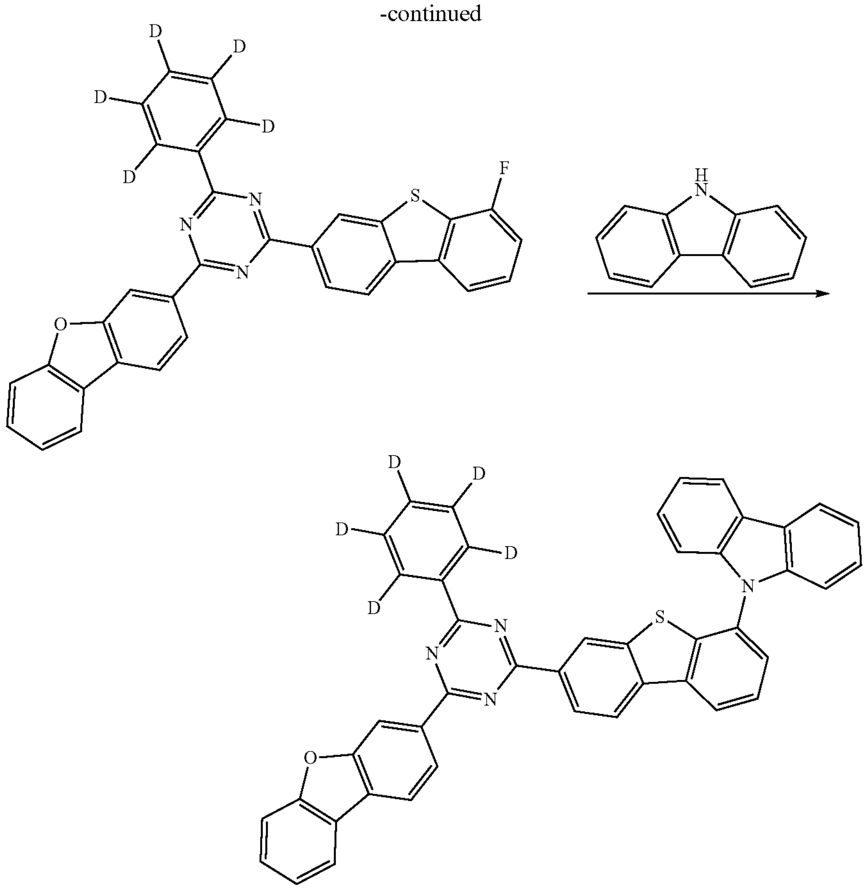

9

Compound 9 was prepared in the same manner as in the preparation method of Compound 4, except that 3-chloro-6-fluorodibenzo[b,d]furan was changed to 3-chloro-6-fluorodibenzo[b,d]thiophene, 2-chloro-4-phenyl-6-(phenyl-d5)-1,3,5-triazine was changed to 2-chloro-4-(dibenzo[b,d]furan-3-yl)-6-(phenyl-d5)-1,3,5-triazine, and 12H-benzo[4,5]thieno[2,3-a]carbazole was changed to 9H-carbazole in Synthesis Example 4 (MS: $[M+H]^+=677$).

Synthesis Example 10: Synthesis of Compound 10

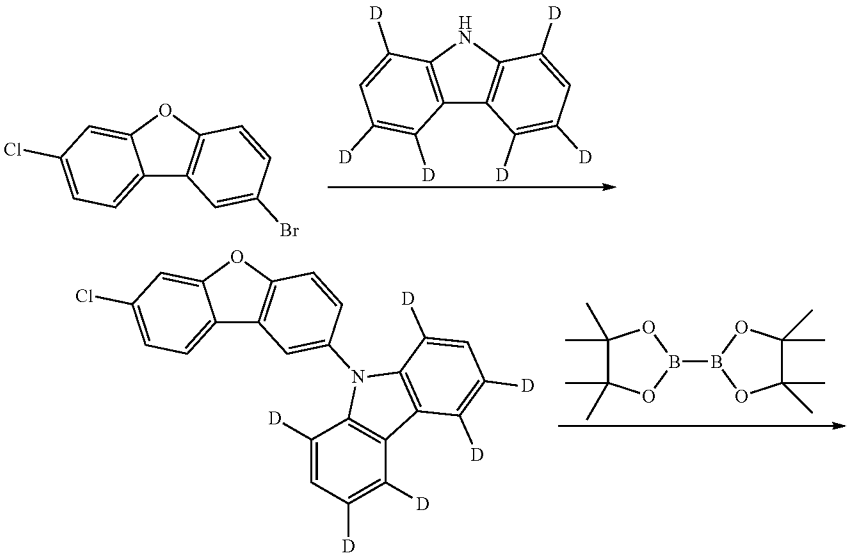

-continued
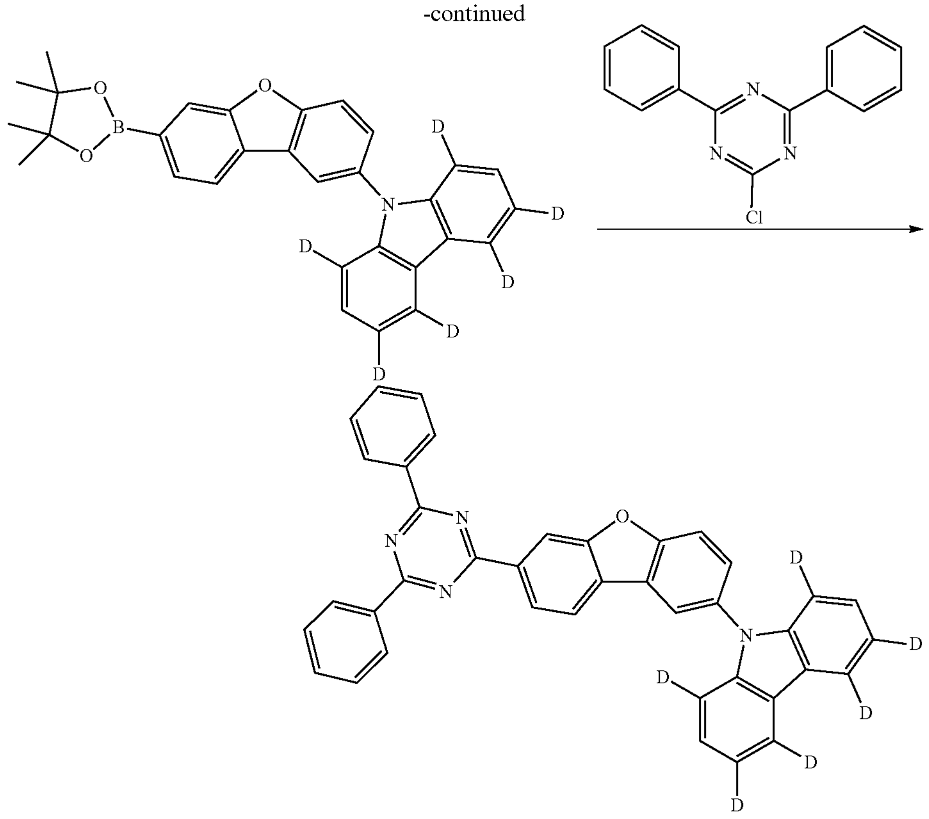
10
Compound 10 was prepared in the same manner as in the preparation method of Compound 1, except that 9H-carbazole was changed to 9H-carbazole-1,3,4,5,6,8-d6 and 2-chloro-4-phenyl-6-(phenyl-d5)-1,3,5-triazine was changed to 2-chloro-4,6-diphenyl-1,3,5-triazine in Synthesis Example 1 (MS: $[M+H]^+=572$).
Synthesis Example 11: Synthesis of Compound 11
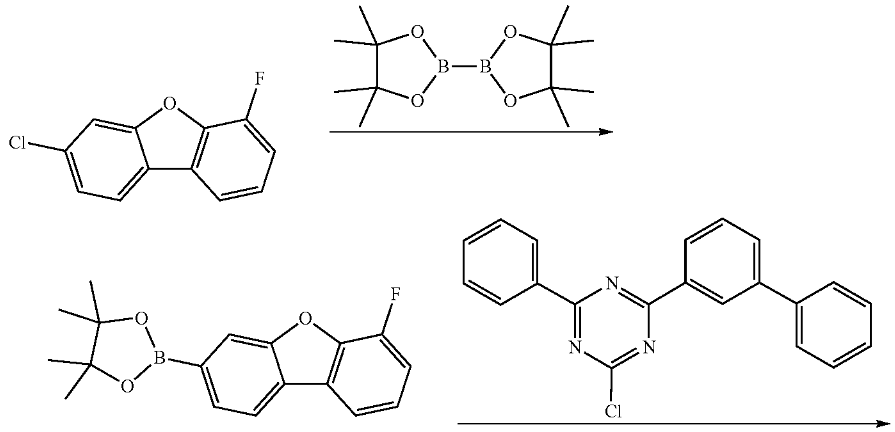

-continued

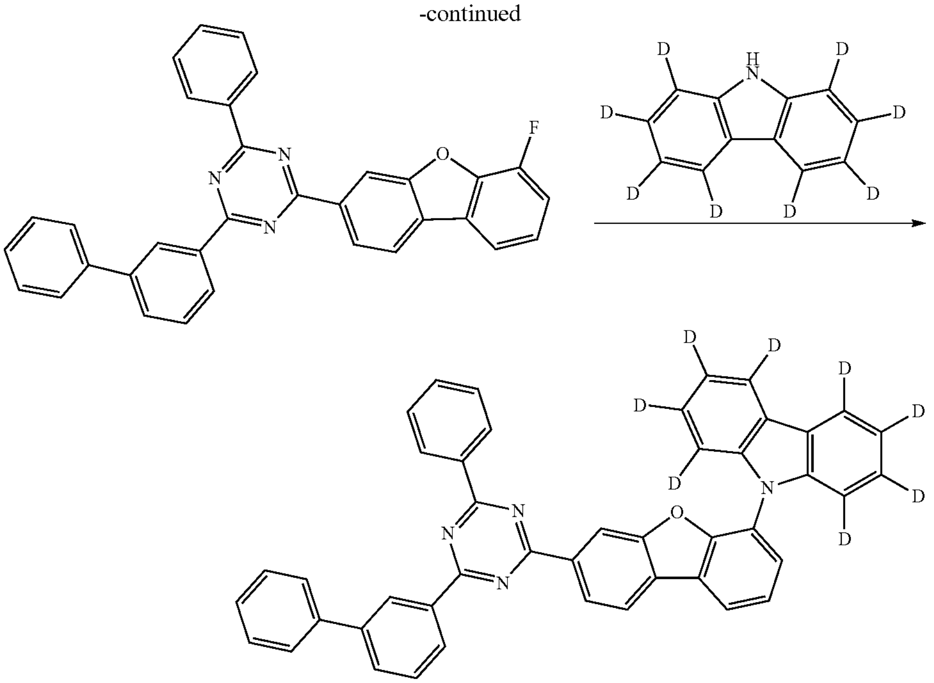

11

Compound 11 was prepared in the same manner as in the preparation method of Compound 4, except that 2-chloro-4-phenyl-6-(phenyl-d5)-1,3,5-triazine was changed to 2-([1, 1'-biphenyl]-3-yl)-4-chloro-6-phenyl-1,3,5-triazine and 12H-benzo[4,5]thieno[2,3-a]carbazole was changed to 9H-carbazole-1, 2, 3, 4, 5, 6, 7, 8-d8 in Synthesis Example 4 (MS: $[M+H]^+=650$).

EXPERIMENTAL EXAMPLES

Example 1

A glass substrate on which ITO (Indium Tin Oxide) was coated as a thin film to a thickness of 1,400 Å (angstrom) was put into distilled water in which a detergent was dissolved, and ultrasonically cleaned. At this time, a product manufactured by Fischer Co. was used as the detergent, and distilled water filtered twice using a filter manufactured by Millipore Co. was used as the distilled water. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. The substrate was cleaned for 5 minutes using oxygen plasma and then transferred to a vacuum depositor.

On the prepared ITO transparent electrode, the following Compound HT-A and the following Compound PD were thermally vacuum-deposited to a thickness of 100 Å in a weight ratio of 95:5, and then only the following Compound HT-A was deposited thereon to a thickness of 1150 Å to form a hole transport layer. The following Compound HT-B was thermally vacuum-deposited on the hole transport layer to a thickness of 450 Å to form an electron blocking layer. The Compound 1 prepared above and the following Compound GD were vacuum-deposited on the electron blocking layer to a thickness of 400 Å in a weight ratio of 85:15 to form a light emitting layer. The following Compound ET-A was vacuum-deposited on the light emitting layer to a thickness of 50 Å to form a hole blocking layer. On the hole blocking layer, the following Compound ET-B and the following Compound Liq were thermally vacuum-deposited to a thickness of 250 Å in a weight ratio of 2:1, and then LiF and magnesium were vacuum-deposited thereon to a thickness of 30 Å in a weight ratio of 1:1 to form an electron transport and injection layer. Magnesium and silver were deposited on the electron transport and injection layer to a thickness of 160 Å in a weight ratio of 1:4 to form a cathode, thereby manufacturing an organic light emitting device.

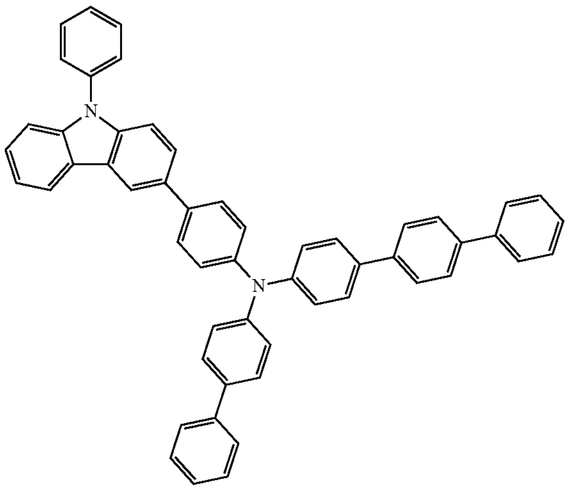

HT-A

-continued

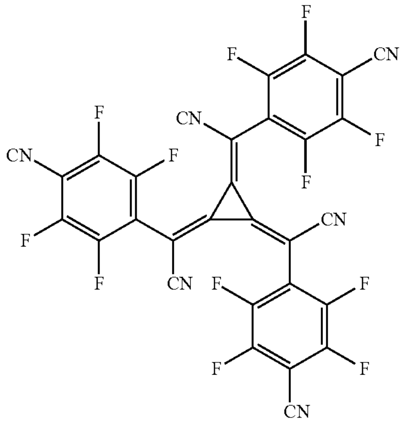

PD

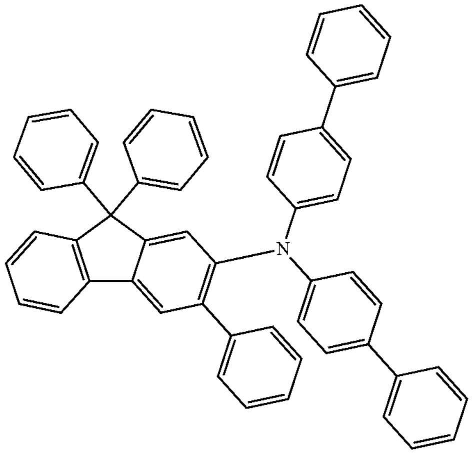

HT-B

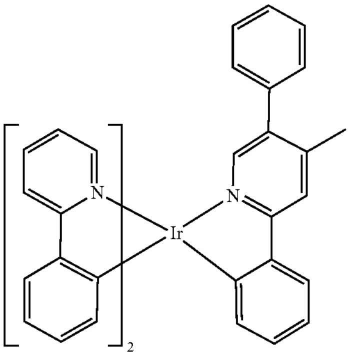

GD

-continued

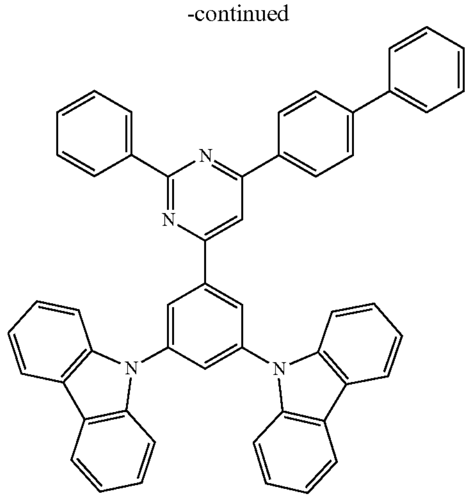

ET-A

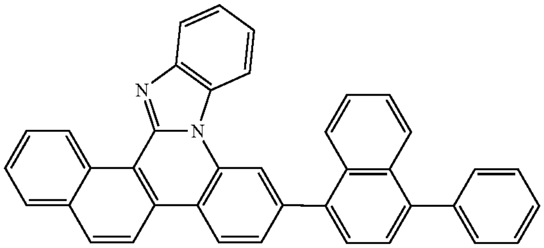

ET-B

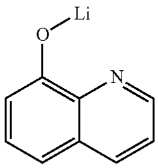

Liq

In the above process, the deposition rate of the organic material was maintained at 0.4 to 0.7 Å/sec, the deposition rate of lithium fluoride of cathode was maintained at 0.3 Å/sec, the deposition rate of silver and magnesium was maintained at 2 Å/sec, and the degree of vacuum during the deposition was maintained at $2\times10^{-7}$ to $5\times10^{-6}$ torr, thereby manufacturing an organic light emitting device.

Example 2 to Example 11

An organic light emitting device was manufactured in the same manner as in Example 1, except that the compound shown in Table 1 was used instead of Compound 1.

Example 12 to Example 16

An organic light emitting device was manufactured in the same manner as in Example 1, except that the compound shown in Table 1 was used instead of Compound 1. In Table 1 below, the ratio of compounds is represented by a weight ratio, and the Compounds PGH-1 and PGH-2 are as follows, respectively.

PGH-1
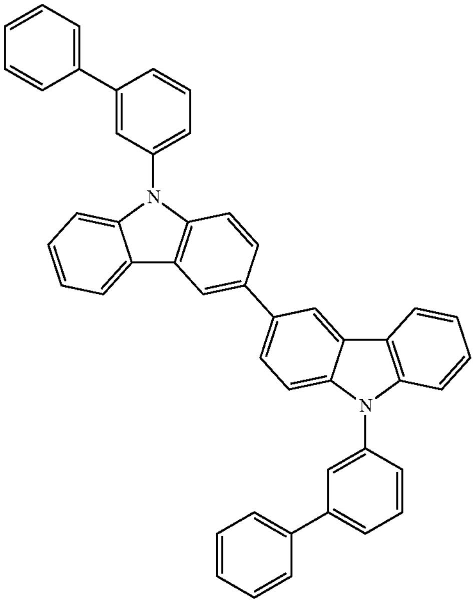
PGH-2
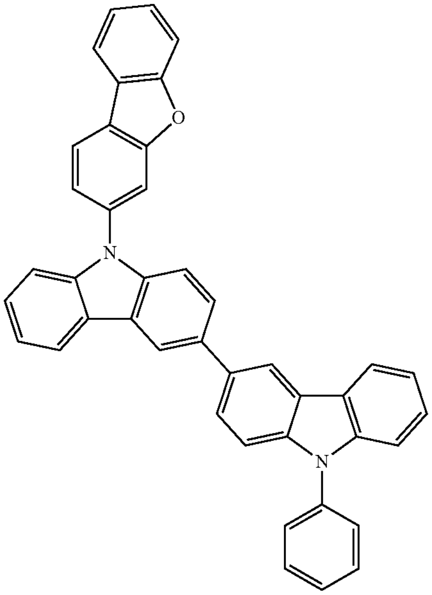
Comparative Example 1 to Comparative Example 5
An organic light emitting device was manufactured in the same manner as in Example 1, except that the compound shown in Table 1 was used instead of Compound 1. In Table 1 below, the Compounds GH-A, GH-B, GH-C, GH-D, and GH-E are as follows, respectively.
GH-A
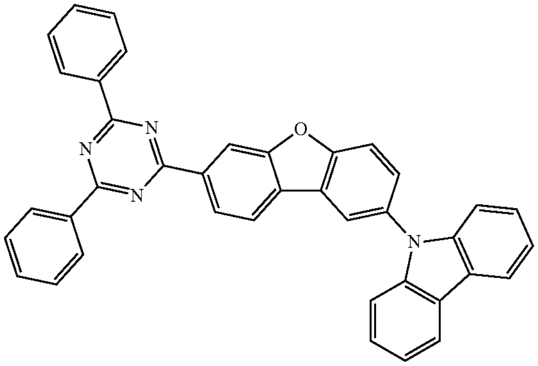
GH-B
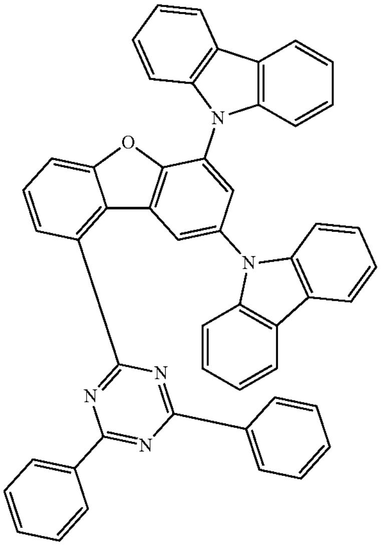
GH-C
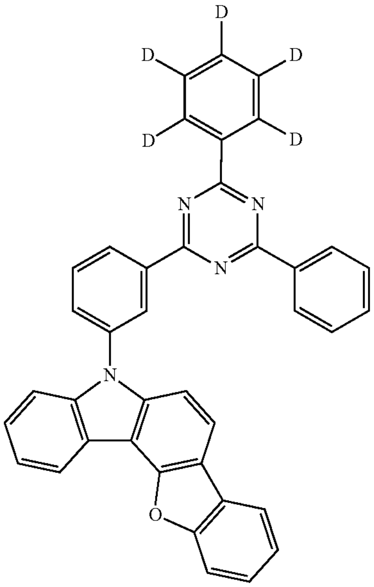

-continued

GH-D

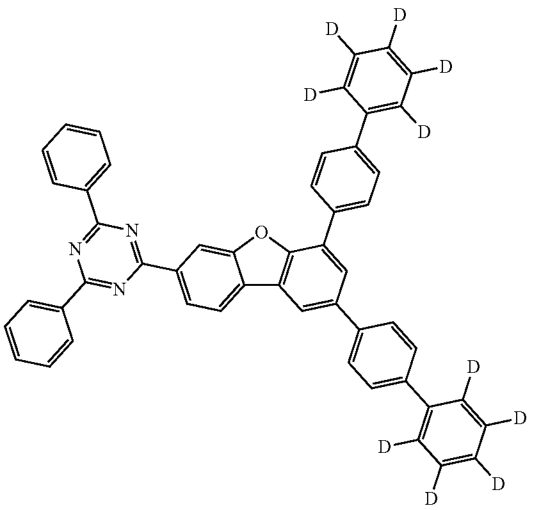

GH-E

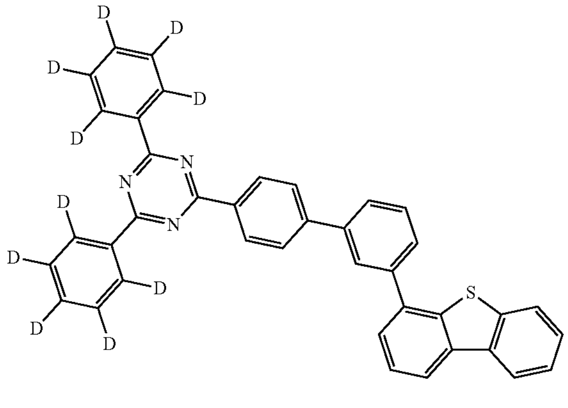

Comparative Example 6 and Comparative Example 7

An organic light emitting device was manufactured in the same manner as in Example 1, except that the compound shown in Table 1 was used instead of Compound 1. In Table 1 below, the ratio of compounds is represented by a weight ratio, and the Compounds GH-A, GH-D, PGH-1 and PGH-2 are as described above, respectively.

The organic light emitting devices prepared in Examples and Comparative Examples were heat-treated by storing them in an oven at 110° C. for 30 minutes. Then, the voltage, efficiency, and lifespan (T95) were measured by applying a current, and the results are shown in Table 1 below. Herein, the voltage and efficiency were measured by applying a current density of 10 mA/cm$^2$. In addition, T95 in Table 1 below means the time taken until the initial luminance decreases to 95% at a current density of 20 mA/cm$^2$.

TABLE 1

| | Light emitting layer (Host) | Voltage (V) | Efficiency (cd/A) | Lifespan (T95, hr) |
|---|---|---|---|---|
| Example 1 | Compound 1 | 4.81 | 36.1 | 65 |
| Example 2 | Compound 2 | 4.80 | 36.5 | 71 |
| Example 3 | Compound 3 | 4.82 | 36.6 | 66 |
| Example 4 | Compound 4 | 4.92 | 38.4 | 73 |
| Example 5 | Compound 5 | 4.93 | 39.1 | 70 |
| Example 6 | Compound 6 | 4.91 | 38.7 | 89 |
| Example 7 | Compound 7 | 4.97 | 37.1 | 84 |
| Example 8 | Compound 8 | 4.97 | 37.3 | 78 |
| Example 9 | Compound 9 | 4.81 | 35.7 | 67 |
| Example 10 | Compound 10 | 4.81 | 36.1 | 76 |
| Example 11 | Compound 11 | 4.92 | 37.4 | 85 |
| Example 12 | PGH-1:Compound 1(60:40) | 4.23 | 51.5 | 121 |
| Example 13 | PGH-1:Compound 4(60:40) | 4.32 | 51.4 | 130 |
| Example 14 | PGH-2:Compound 6(60:40) | 4.33 | 52.1 | 143 |
| Example 15 | PGH-2:Compound 8(60:40) | 4.34 | 51.8 | 131 |
| Example 16 | PGH-1:Compound 11(60:40) | 4.33 | 51.5 | 138 |
| Comparative Example 1 | GH-A | 4.81 | 36.0 | 48 |
| Comparative Example 2 | GH-B | 4.85 | 27.1 | 52 |
| Comparative Example 3 | GH-C | 5.38 | 31.6 | 51 |
| Comparative Example 4 | GH-D | 5.88 | 12.3 | 5 |
| Comparative Example 5 | GH-E | 5.72 | 14.4 | 16 |
| Comparative Example 6 | PGH-1:GH-A(60:40) | 4.23 | 50.3 | 77 |
| Comparative Example 7 | PGH-2:GH-D(60:40) | 4.88 | 28.8 | 10 |

Referring to Table 1, it can be seen that when Compounds 1 to 11 having a specific polycyclic structure in which at least one deuterium is substituted in the structure in which a carbazole group is bonded to a hexagonal ring containing at least one N through a tricyclic heterocyclic ring containing O or S according to the present disclosure are applied as the host of an organic light emitting device, the characteristics of low voltage, high efficiency, and long lifespan are better than those to which the compounds of Comparative Examples are applied.

In particular, it can be confirmed that these characteristics are advantageous even in forming an exciplex using Compounds PGH-1 and PGH-2, which are of Chemical Formula 2, together as the host as in Examples 12 to 16, so that the characteristics of low voltage, high efficiency, and long lifespan are further improved.

DESCRIPTION OF SYMBOLS

1: Substrate
2: Anode
3: Light emitting layer
4: Cathode
5: Hole injection layer
6: Hole transport layer
7: Light emitting layer
8: Electron transport layer

The invention claimed is:

1. An organic light emitting device, comprising:

a first electrode;

a second electrode that is provided opposite to the first electrode; and one or more organic material layers that are provided between the first electrode and the second electrode, wherein at least one layer of the organic material layers comprises a compound of Chemical Formula 1, and the organic material layer comprising the compound is a light emitting layer:

<Chemical Formula 1>

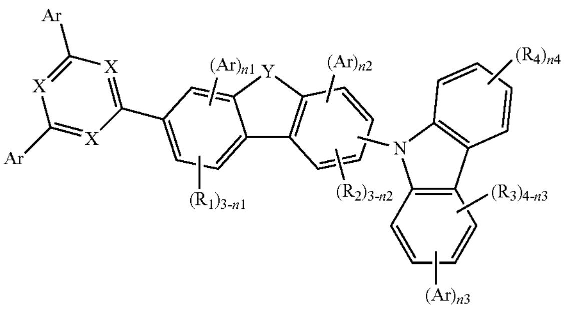

wherein in the Chemical Formula 1:

each X is independently N or CH, provided that at least one of X is N;

Y is O or S;

each Ar is independently substituted or unsubstituted $C_{6-60}$ aryl; or substituted or unsubstituted $C_{5-60}$ heteroaryl containing at least one heteroatom selected from the group consisting of N, O and S;

$R_1$, $R_2$, and $R_3$ are each independently hydrogen, deuterium, halogen, cyano, substituted or unsubstituted $C_{1-60}$ alkyl, substituted or unsubstituted $C_{1-60}$ alkoxy, substituted or unsubstituted $C_{2-60}$ alkenyl, substituted or unsubstituted $C_{2-60}$ alkynyl, substituted or unsubstituted $C_{3-60}$ cycloalkyl, substituted or unsubstituted $C_{6-60}$ aryl, or substituted or unsubstituted $C_{2-60}$ heteroaryl containing at least one heteroatom selected from the group consisting of N, O and S;

each $R_4$ is independently hydrogen, deuterium, halogen, cyano, substituted or unsubstituted $C_{1-60}$ alkyl, substituted or unsubstituted $C_{1-60}$ alkoxy, substituted or unsubstituted $C_{2-60}$ alkenyl, substituted or unsubstituted $C_{2-60}$ alkynyl, substituted or unsubstituted $C_{3-60}$ cycloalkyl, substituted or unsubstituted $C_{6-60}$ aryl, or substituted or unsubstituted $C_{2-60}$ heteroaryl containing at least one heteroatom selected from the group consisting of N, O and S, or two adjacent Ras combine with each other to form a $C_{4-60}$ aliphatic or aromatic ring;

n1, n2, and n3 are each independently 0 or 1; and n4 is an integer of 1 to 4, provided that at least one of Ar is substituted with one or more deuterium, at least one of $R_1$, $R_2$, $R_3$, or $R_4$ is substituted with one or more deuterium, or at least one of $R_1$, $R_2$, $R_3$, and $R_4$ is deuterium;

wherein the light emitting layer further comprises a compound of the following Chemical Formula 2:

<Chemical Formula 2>

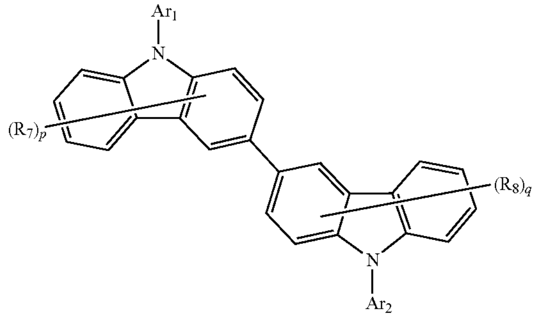

wherein in the Chemical Formula 2:

$Ar_1$ and $Ar_2$ are independently substituted or unsubstituted $C_{6-60}$ aryl or substituted or unsubstituted $C_{5-60}$ heteroaryl containing at least one heteroatom selected from the group consisting of N, O and S;

$R_7$ and $R_8$ are each independently hydrogen, deuterium, halogen, cyano, nitro, amino, substituted or unsubstituted $C_{1-60}$ alkyl, substituted or unsubstituted $C_{3-60}$ cycloalkyl, substituted or unsubstituted $C_{2-60}$ alkenyl, substituted or unsubstituted $C_{6-60}$ aryl, or substituted or unsubstituted $C_{5-60}$ heteroaryl containing at least one heteroatom selected from the group consisting of N, O and S; and p and q are each independently an integer of 0 to 7.

2. The organic light emitting device of claim 1, wherein $Ar_1$ and $Ar_2$ are each independently phenyl, biphenylyl, terphenylyl, naphthyl, dibenzofuranyl, dibenzothiophenyl, or dimethylfluorenyl.

3. The organic light emitting device of claim 1, wherein the compound of Chemical Formula 2 is any one compound selected from the group consisting of the following compounds:

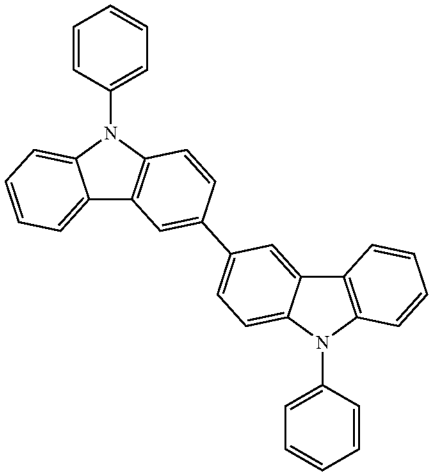

-continued
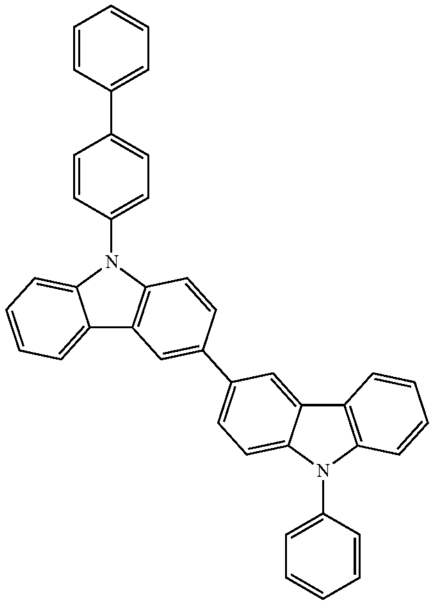
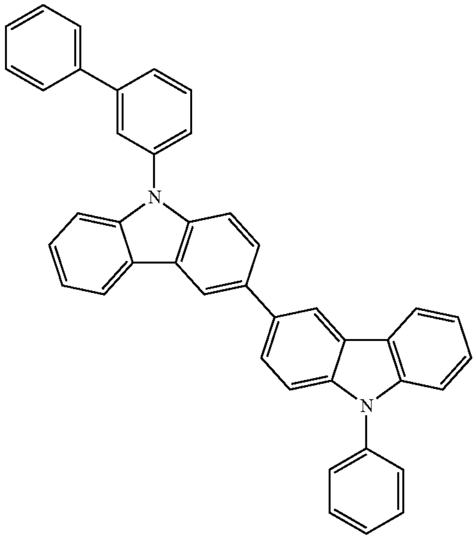
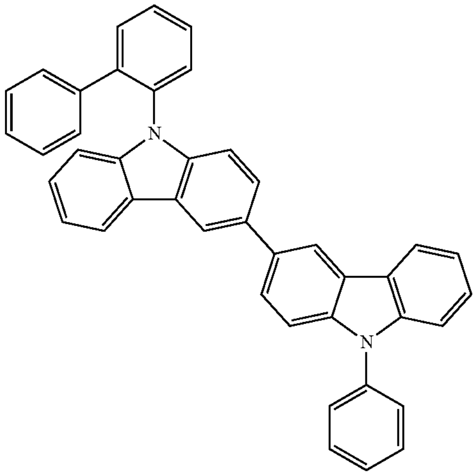
-continued
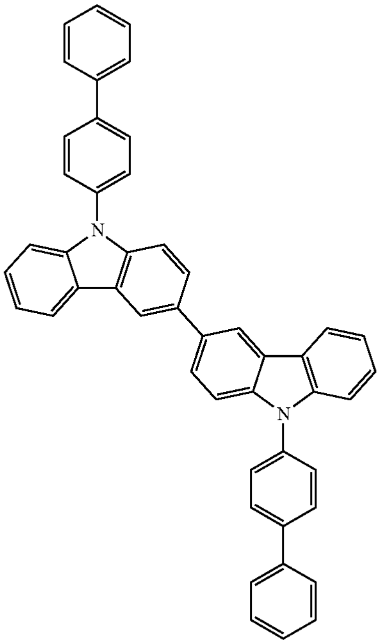
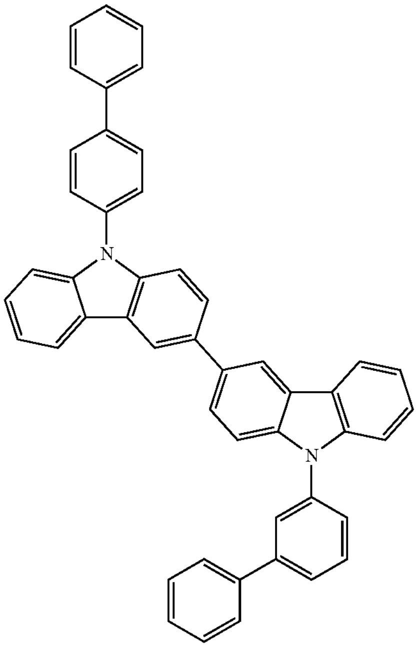

-continued
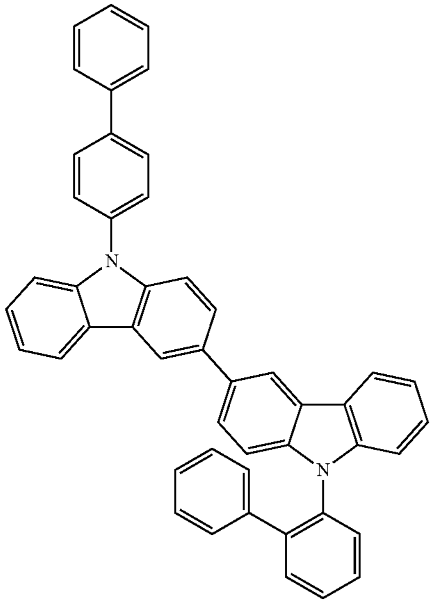
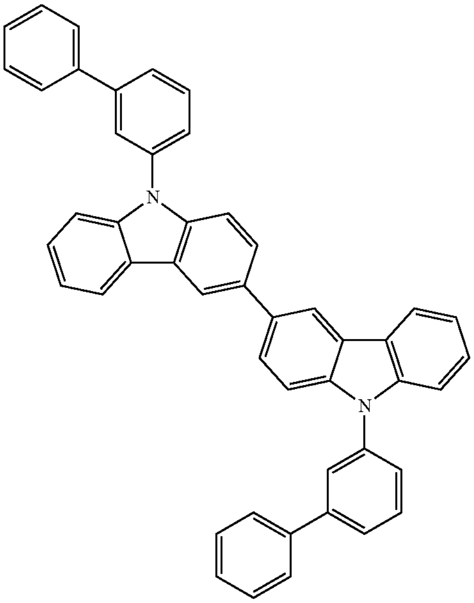
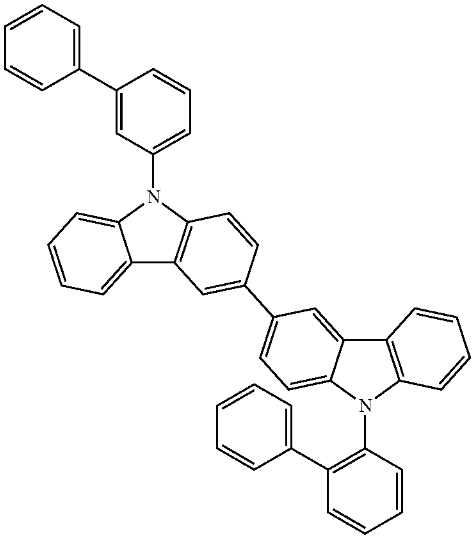
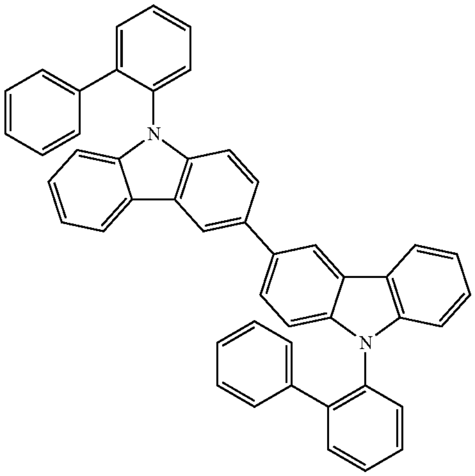
-continued
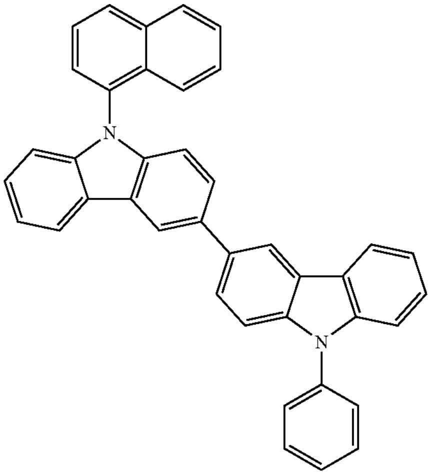

-continued
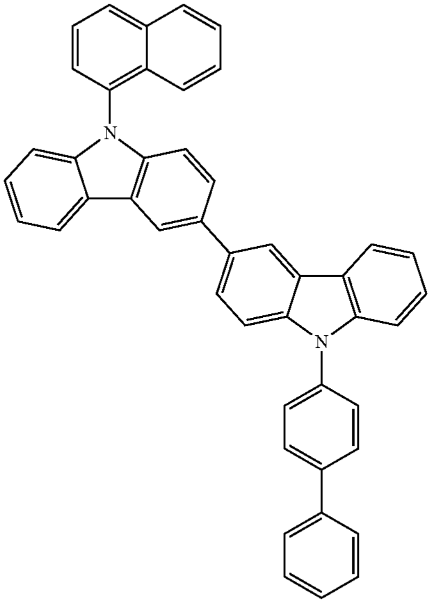
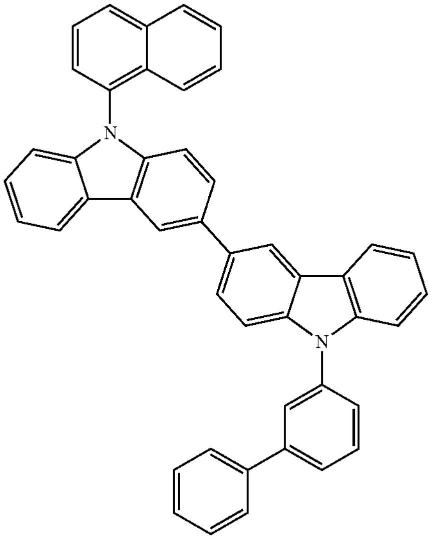
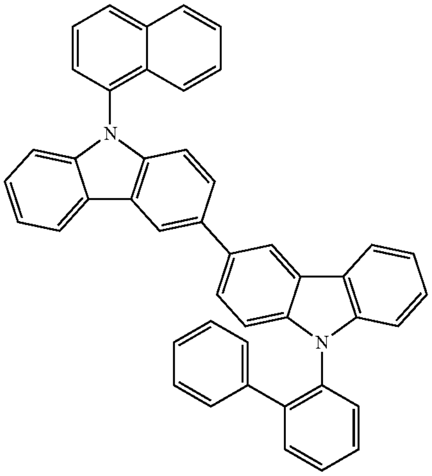
-continued
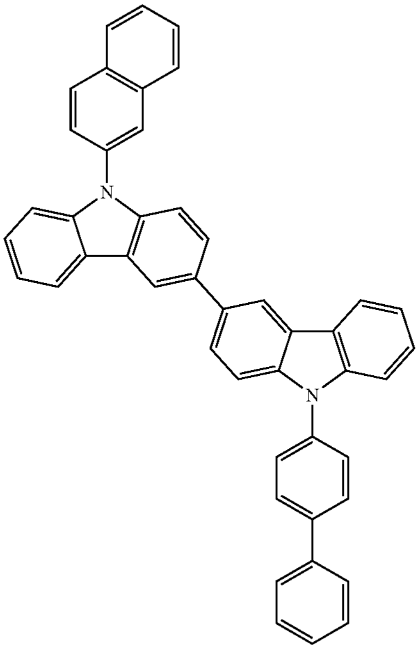
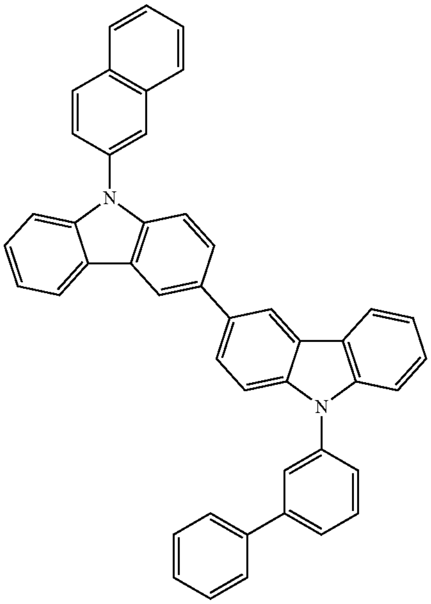

-continued
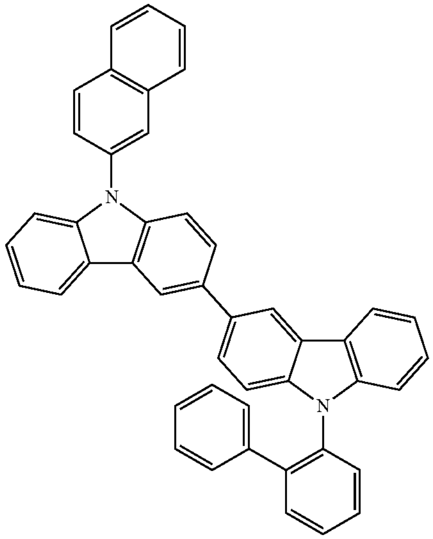
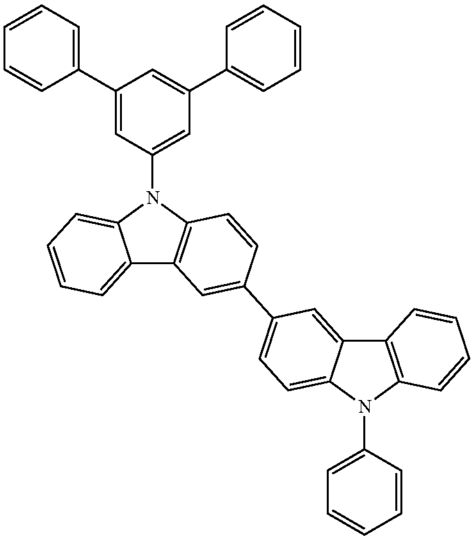
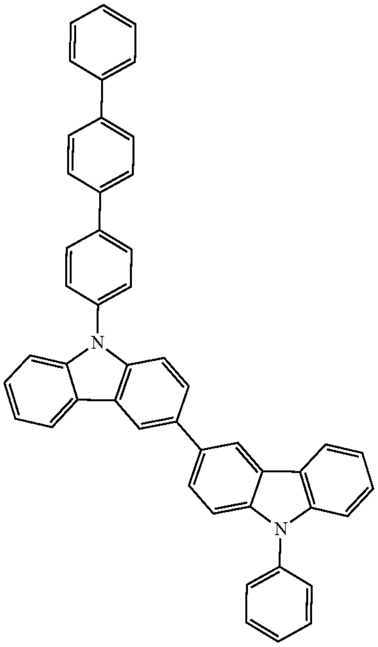
-continued
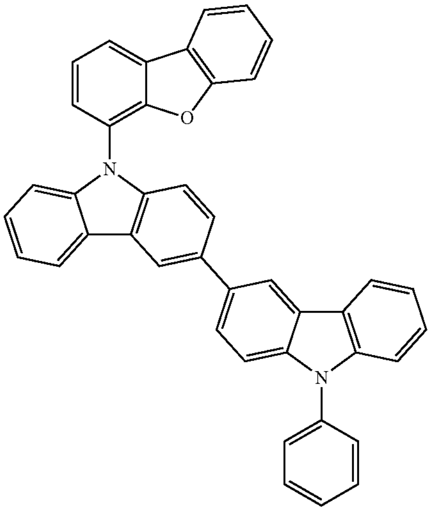
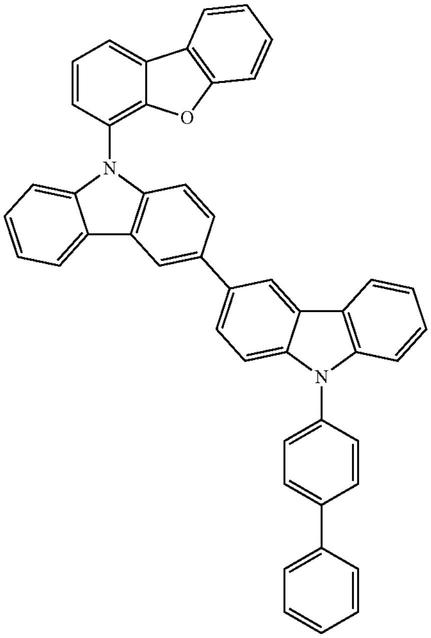
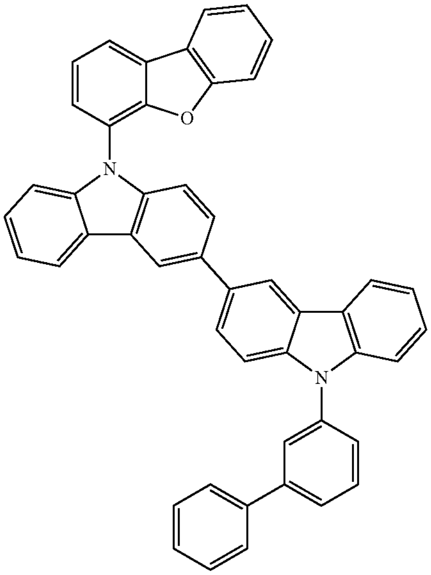

-continued
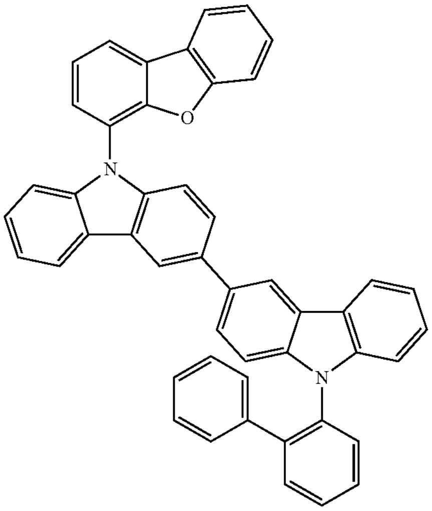
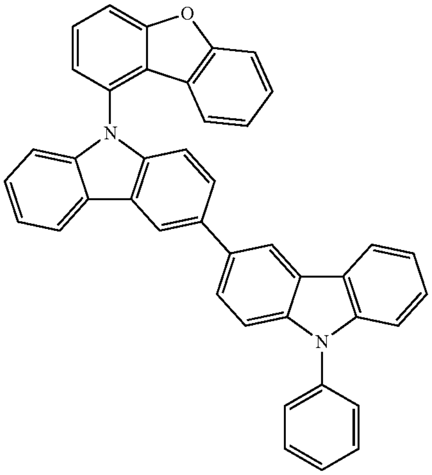
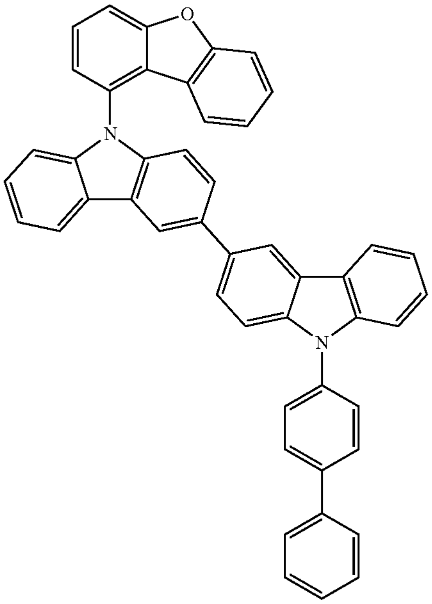
-continued
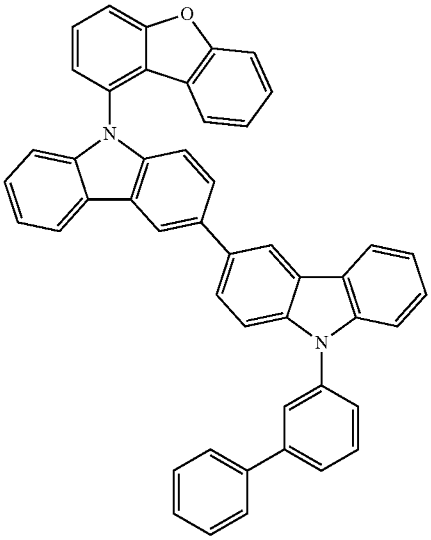
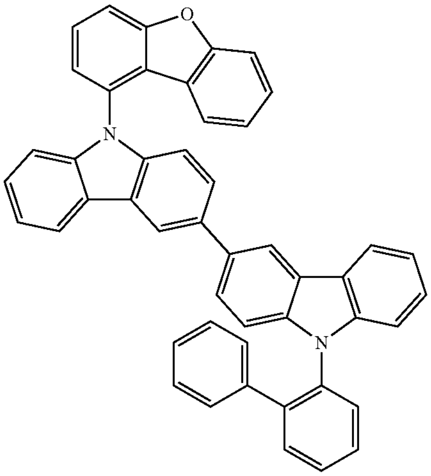
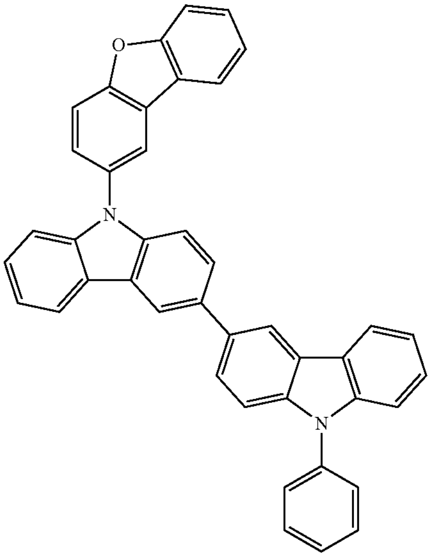

-continued
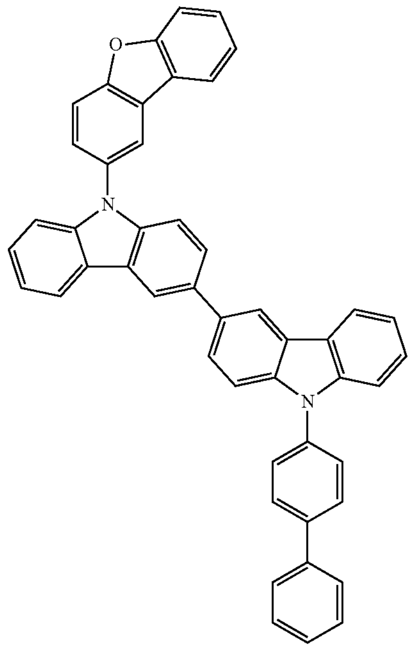
-continued
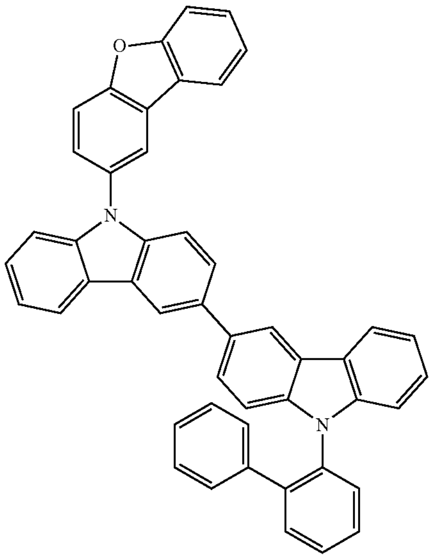
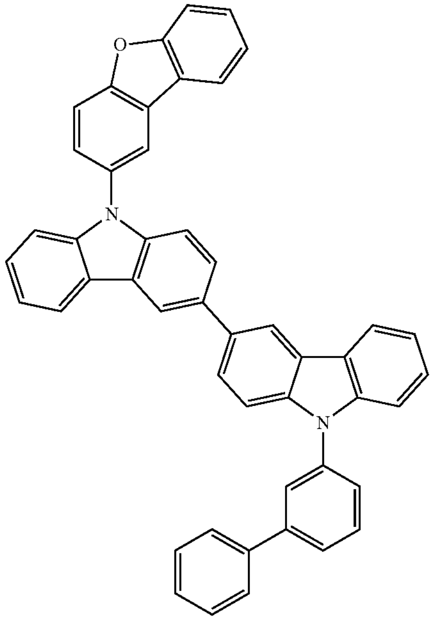
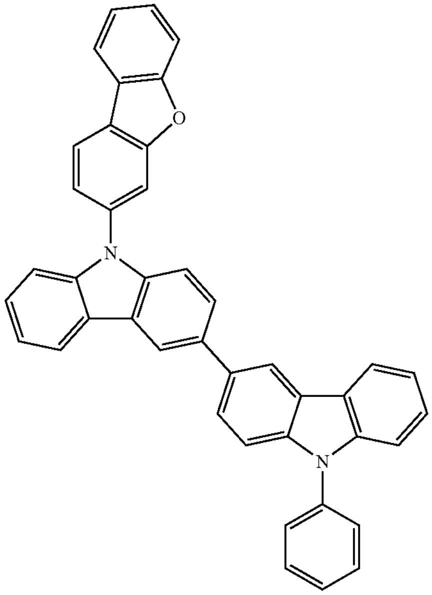

-continued
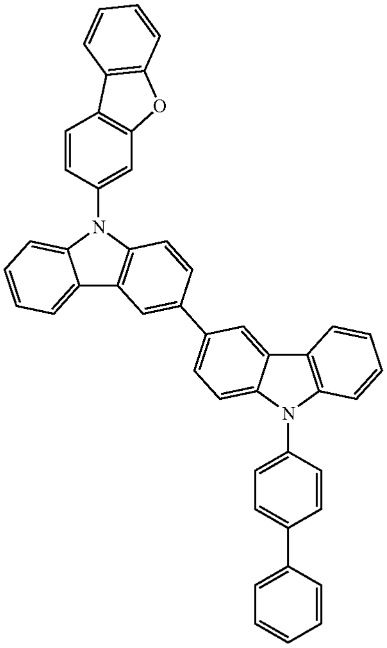
-continued
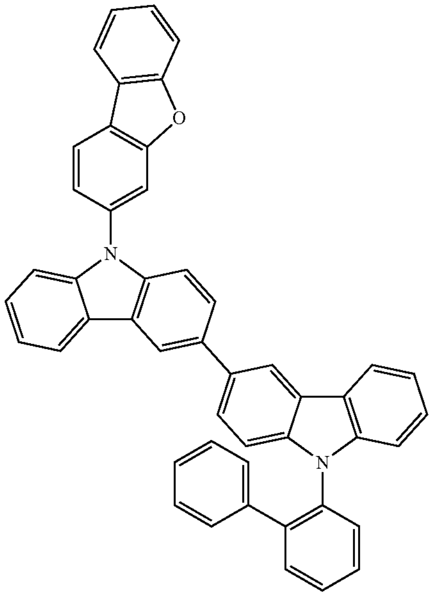
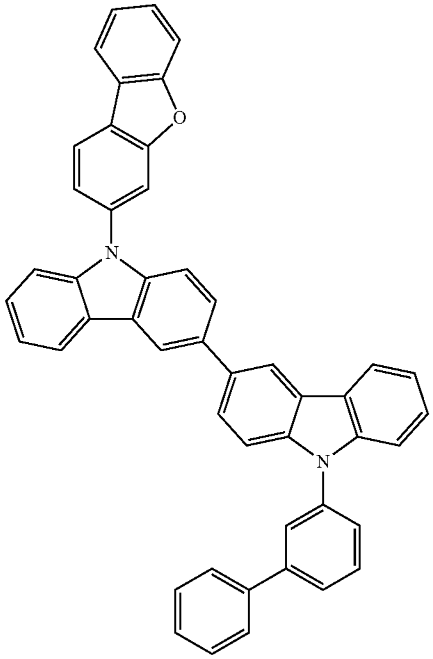
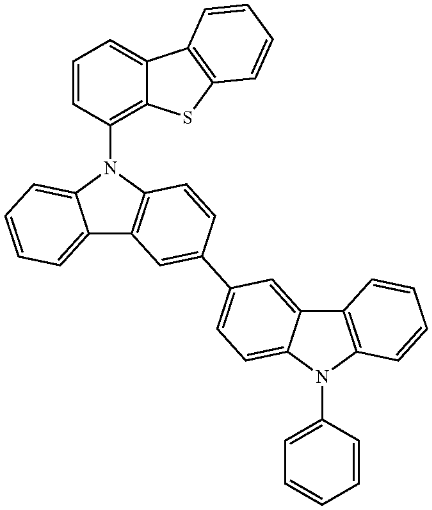

-continued
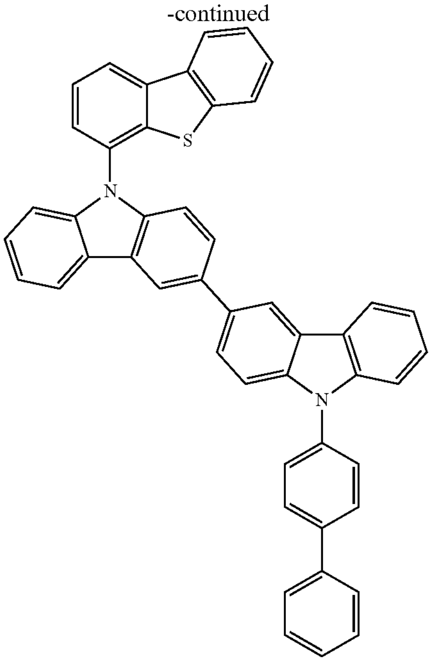
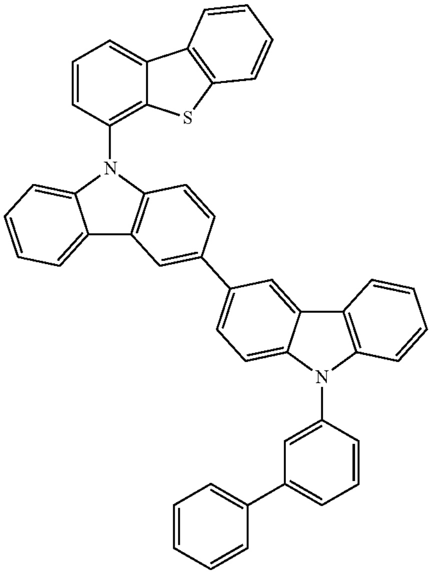
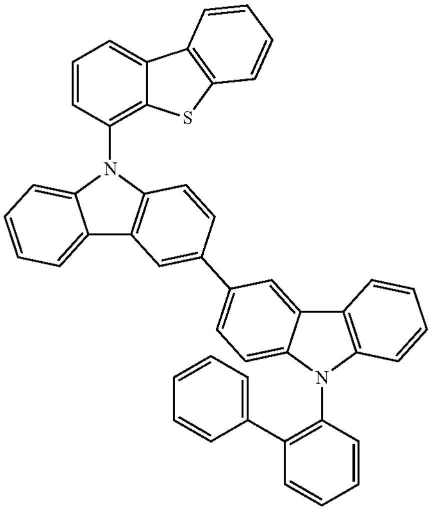
-continued
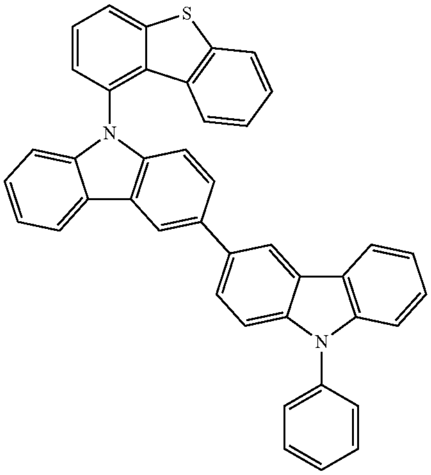
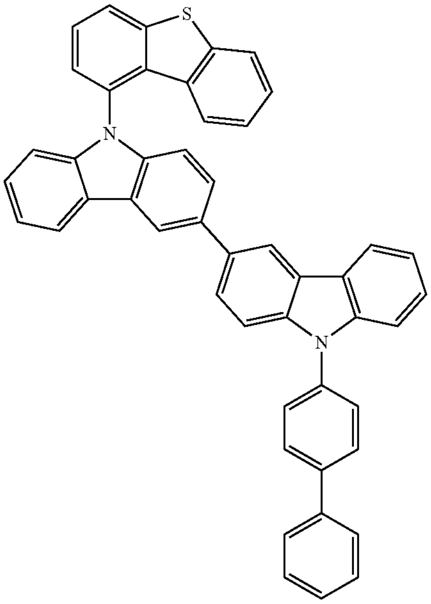
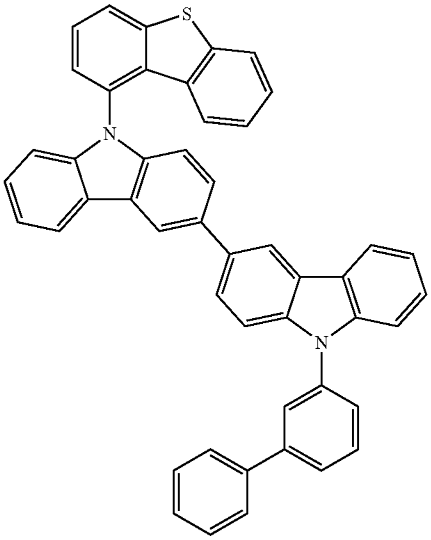

-continued
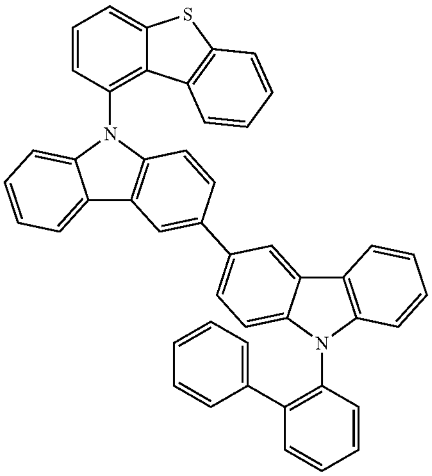
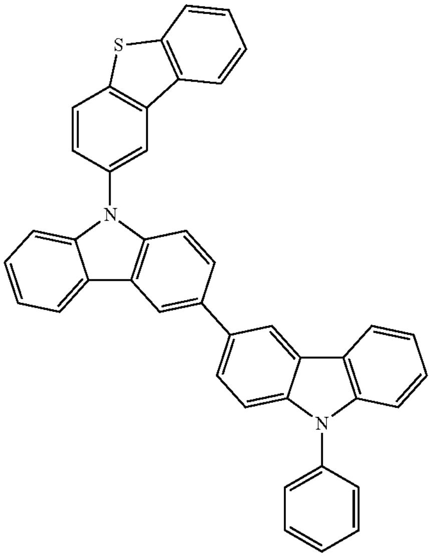
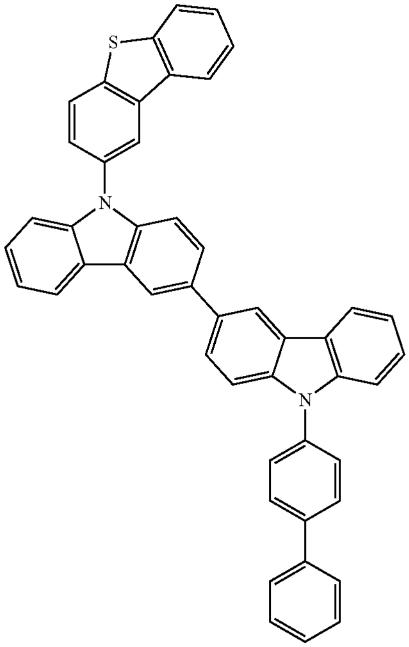
-continued
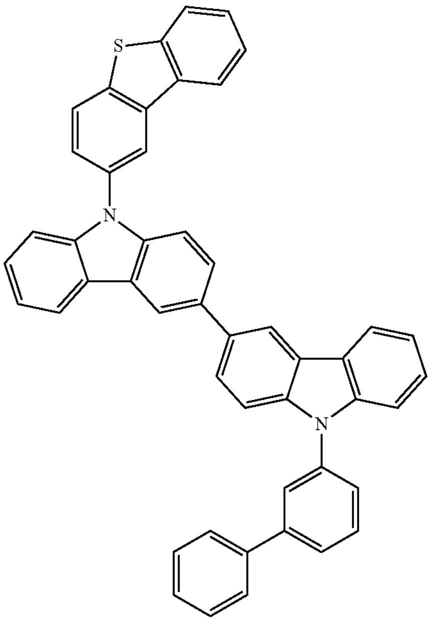
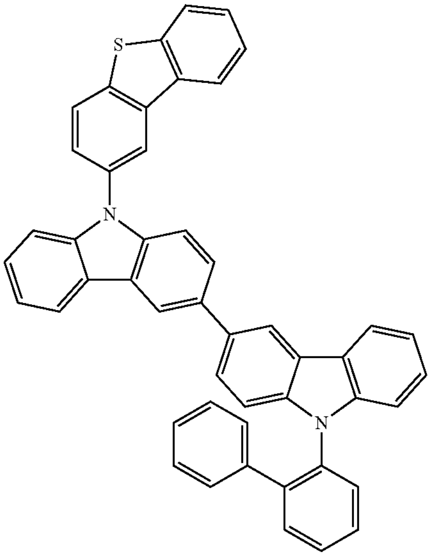

-continued
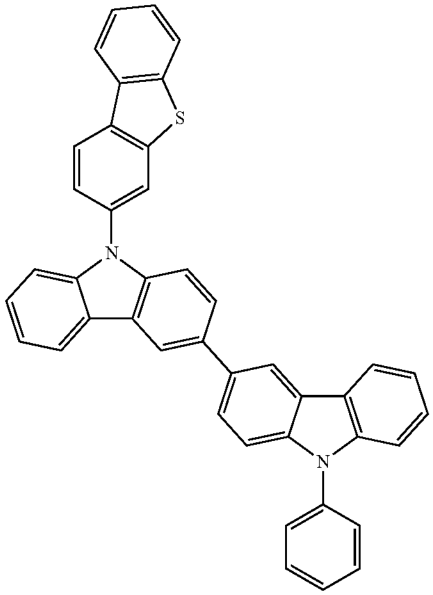
-continued
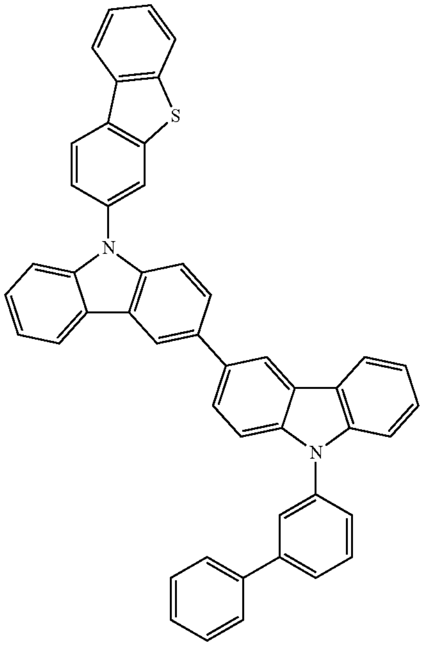
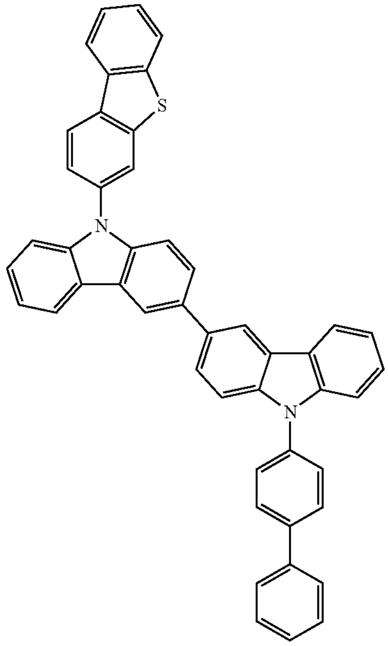
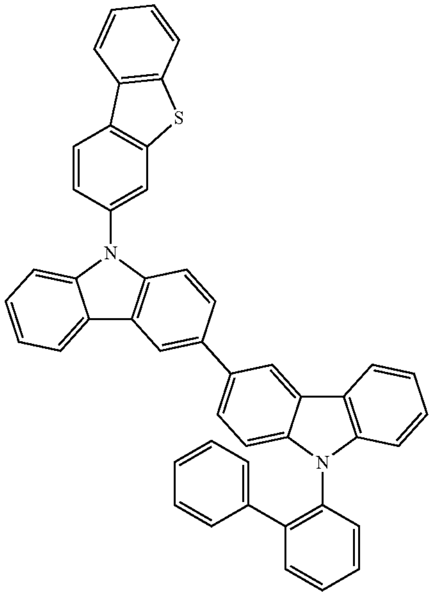

-continued
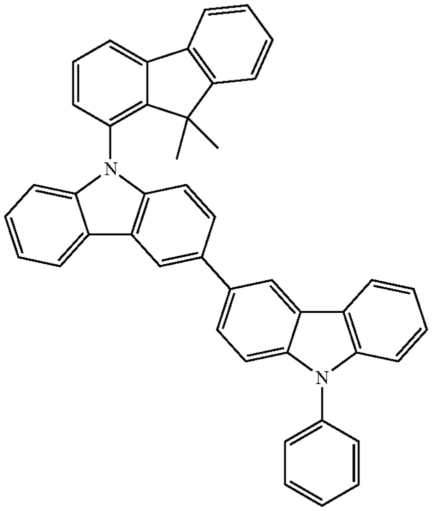
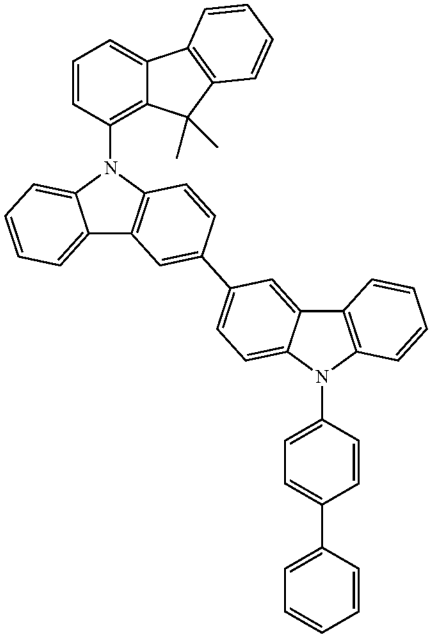
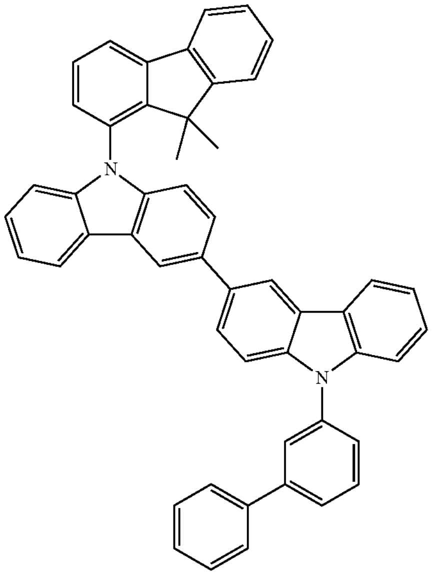
-continued
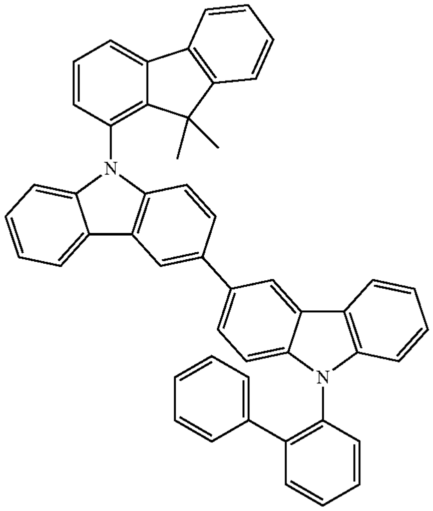
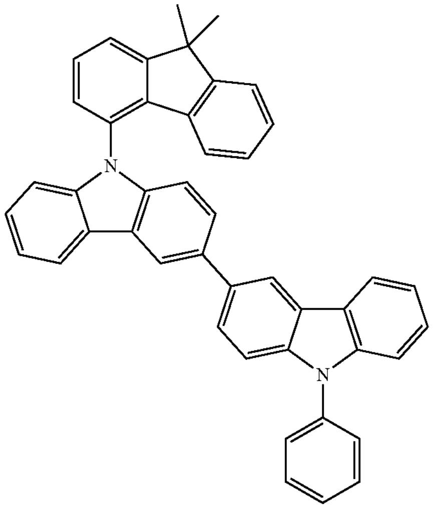
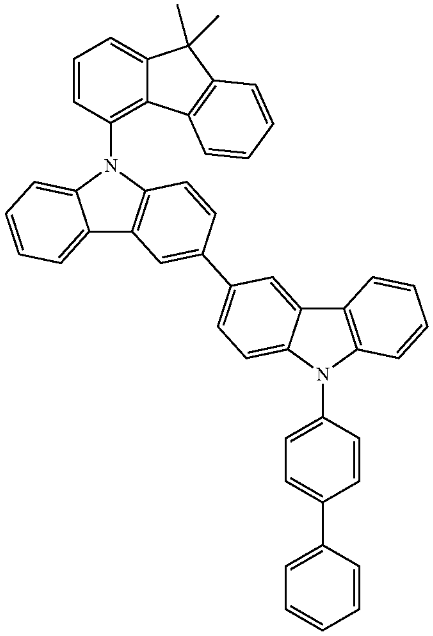

-continued
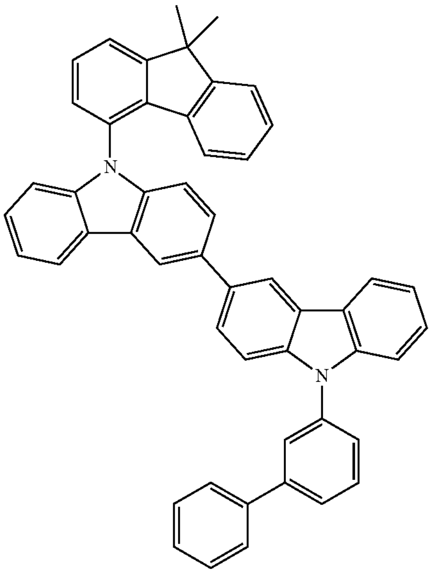
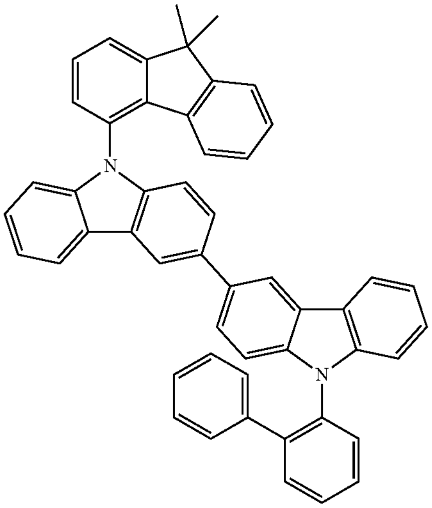
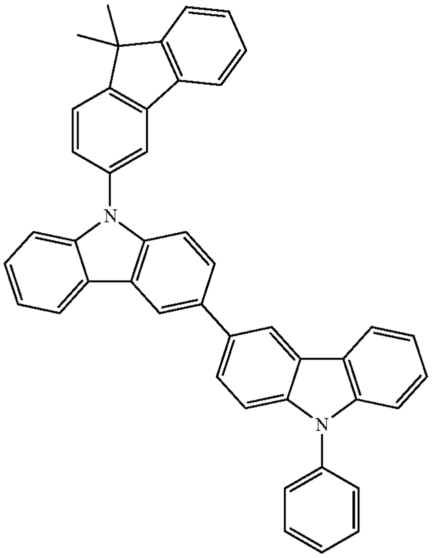
-continued
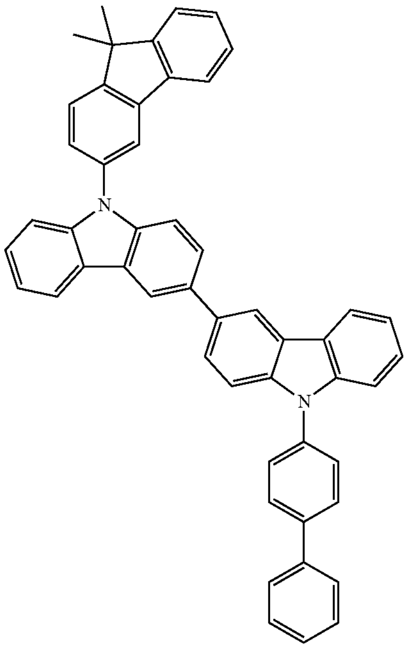
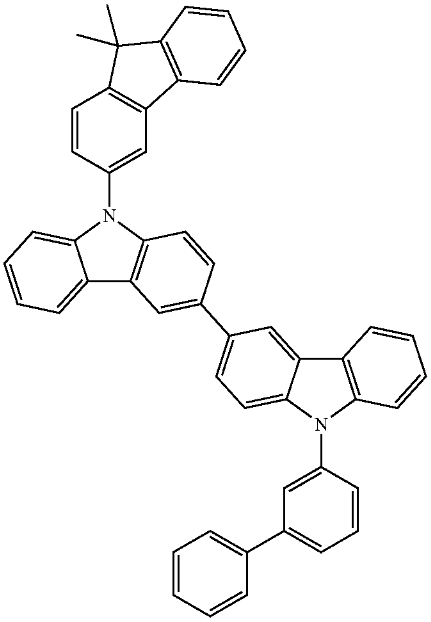

-continued
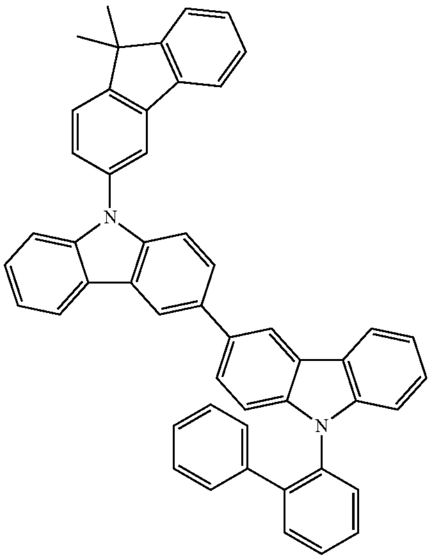
-continued
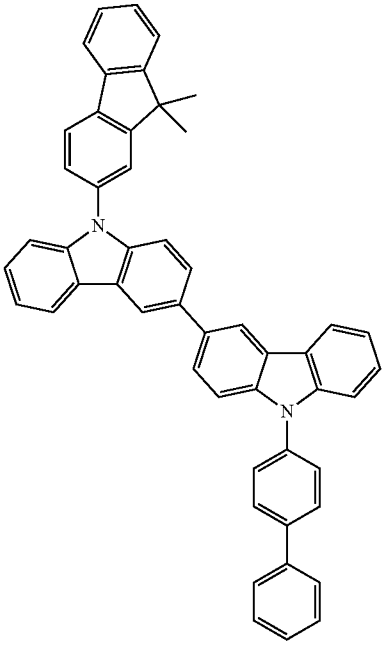
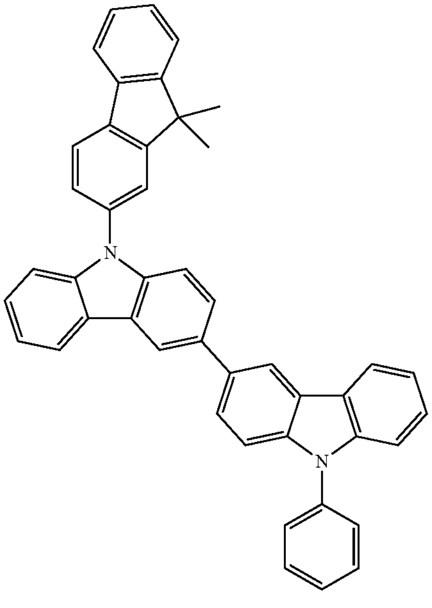
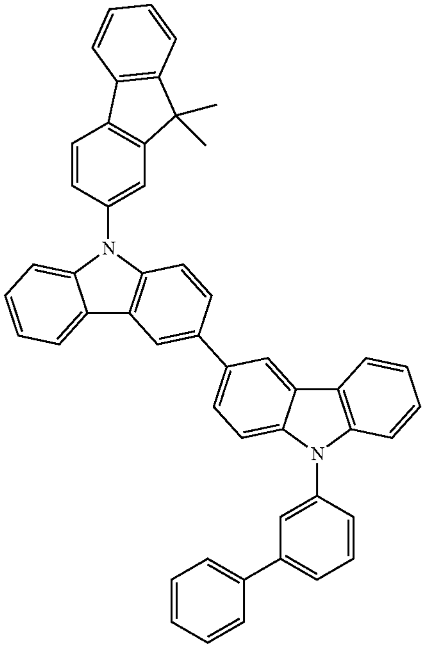

-continued
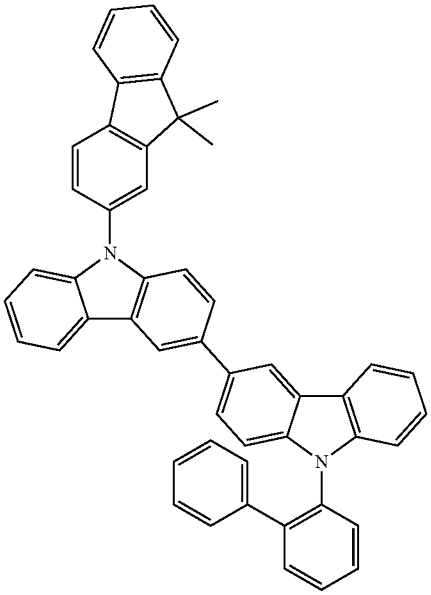
-continued
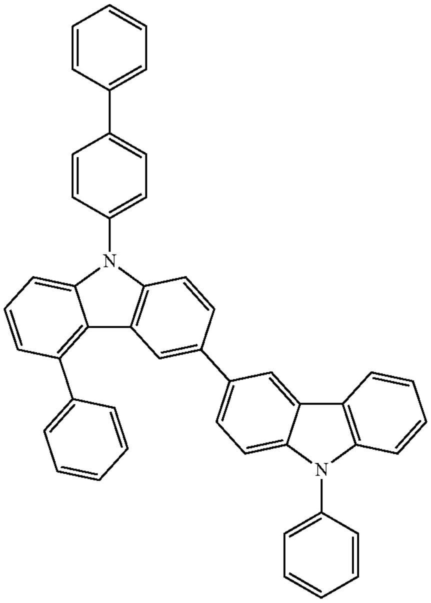
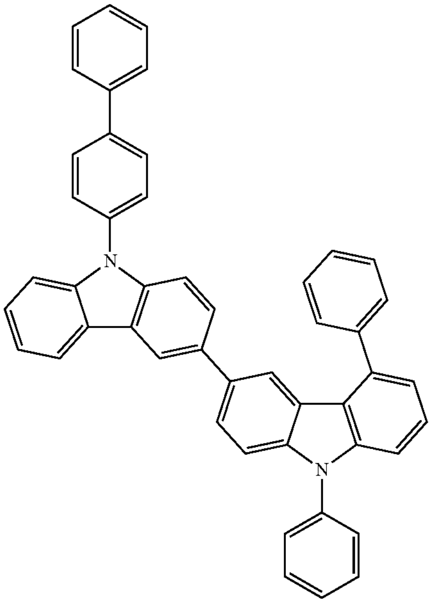
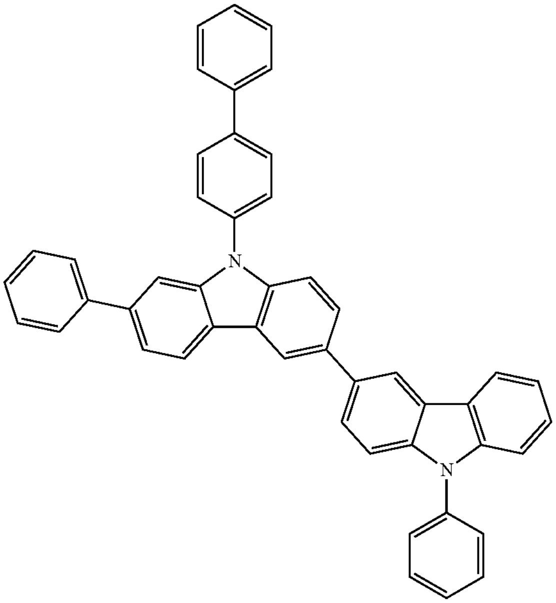

-continued
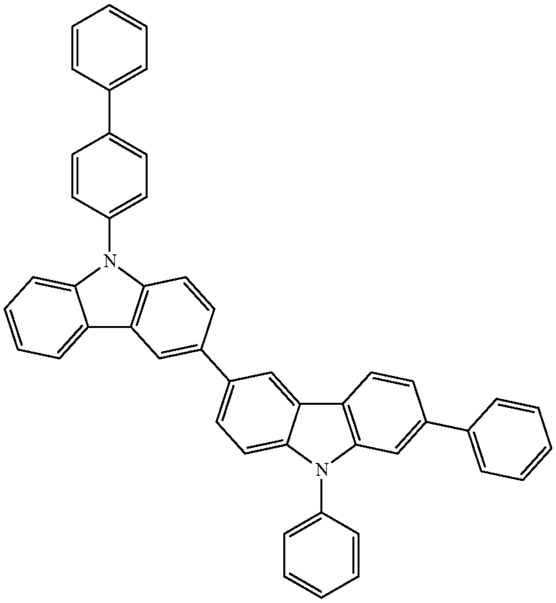
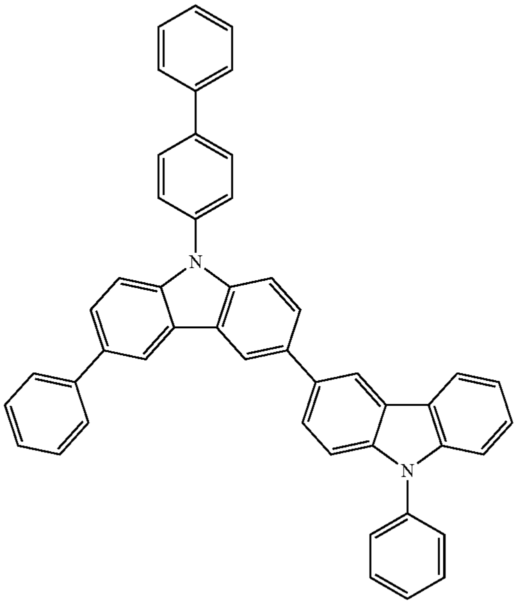
-continued
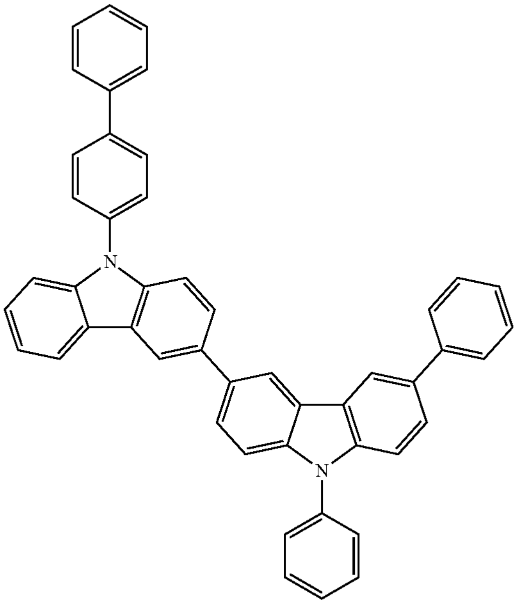
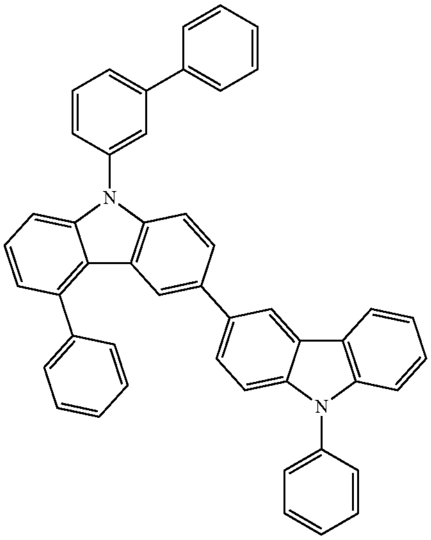
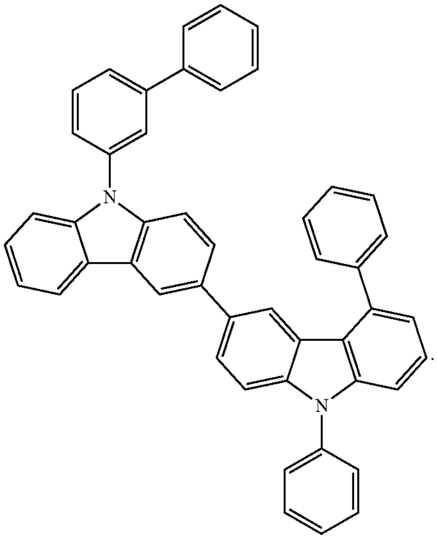 [SMILES: c1ccc(-c2cccc(-n3c4ccccc4c4cc(-c5ccc6c(c5)c5c(-c7ccccc7)cccc5n6-c5ccccc5)ccc43)c2)cc1]
.

4. An organic light emitting device comprising:

a first electrode;

a second electrode that is provided opposite to the first electrode; and one or more organic material layers that are provided between the first electrode and the second electrode, wherein at least one layer of the one or more organic material layers is a light emitting layer comprising a compound of Chemical Formula 1:

<Chemical Formula 1>

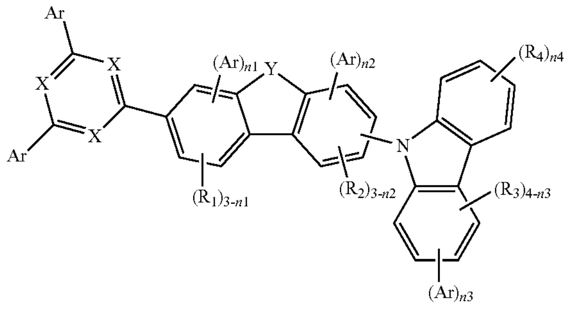

wherein in the Chemical Formula 1:

each X is independently N or CH, provided that at least one of X is N;

Y is O or S;

at least one of Ar is phenyl, biphenylyl, or phenyl substituted with five deuteriums, and the rest of Ar are any one of phenyl, biphenylyl, dibenzofuranyl, or dibenzothiophenyl;

$R_1$, $R_2$, and $R_3$ are each independently hydrogen or deuterium;

each $R_4$ is independently hydrogen or deuterium, or two adjacent Ras combine with each other to form a 1,1'-dimethyl-indene, benzofuran, benzothiophene, 1-phenyl-indole, deuterium-substituted 1,1'-dimethyl-indene, deuterium-substituted benzofuran, deuterium-substituted benzothiophene, or deuterium-substituted 1-phenyl-indole ring, and the rest of $R_4$ are hydrogen or deuterium;

n1, n2, and n3 are each independently 0 or 1; and n4 is an integer of 1 to 4, provided that at least one of Ar is phenyl substituted with five deuteriums, or the compound of Chemical Formula 1 is substituted with at least four deuterium;

wherein the light emitting layer further comprises a compound of the following Chemical Formula 2:

<Chemical Formula 2>

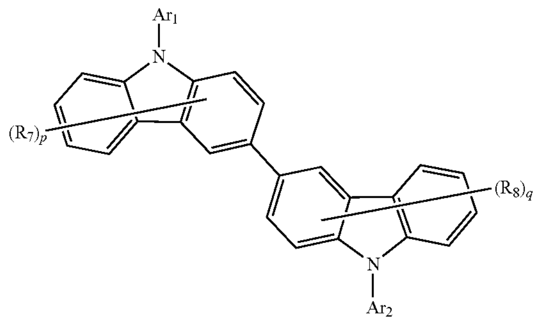

wherein in the Chemical Formula 2:

$Ar_1$ and $Ar_2$ are independently substituted or unsubstituted $C_{6-60}$ aryl or substituted or unsubstituted $C_{5-60}$ heteroaryl containing at least one heteroatom selected from the group consisting of N, O and S;

$R_7$ and $R_8$ are each independently hydrogen, deuterium, halogen, cyano, nitro, amino, substituted or unsubstituted $C_{1-60}$ alkyl, substituted or unsubstituted $C_{3-60}$ cycloalkyl, substituted or unsubstituted $C_{2-60}$ alkenyl, substituted or unsubstituted $C_{6-60}$ aryl, or substituted or unsubstituted $C_{5-60}$ heteroaryl containing at least one heteroatom selected from the group consisting of N, O and S; and p and q are each independently an integer of 0 to 7.

5. The organic light emitting device of claim 4, wherein $Ar_1$ and $Ar_2$ are each independently phenyl, biphenylyl, terphenylyl, naphthyl, dibenzofuranyl, dibenzothiophenyl, or dimethylfluorenyl.

6. The organic light emitting device of claim 4, wherein the compound of Chemical Formula 2 is any one compound selected from the group consisting of the following compounds:

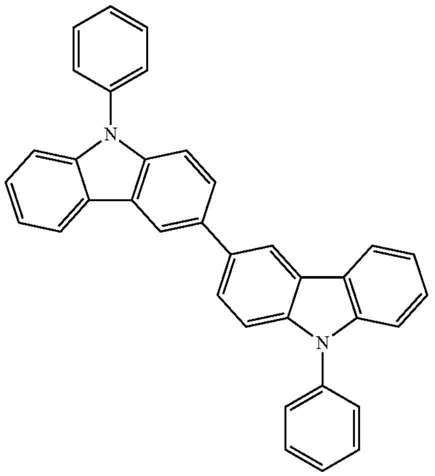

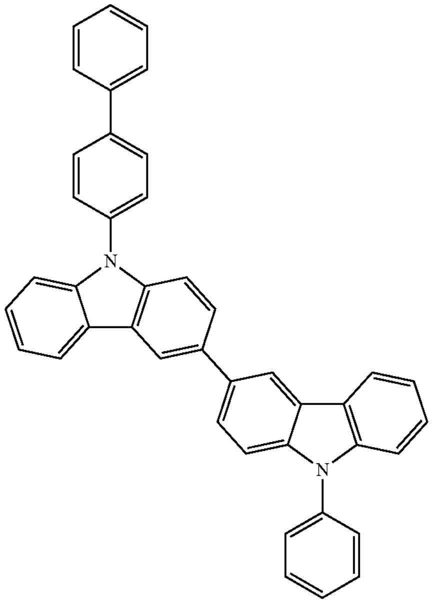

-continued
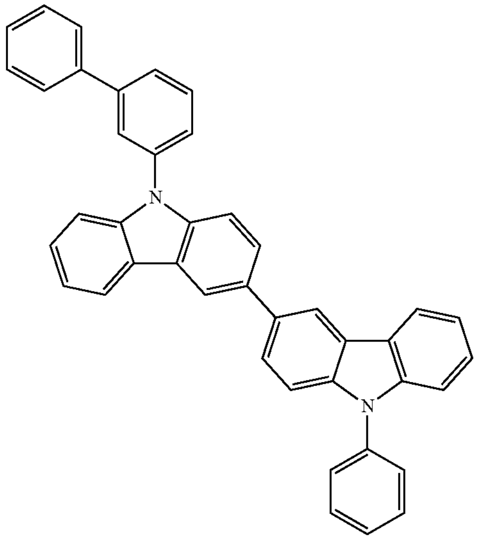
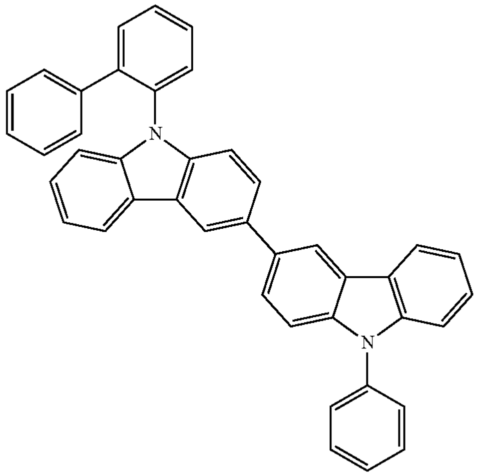
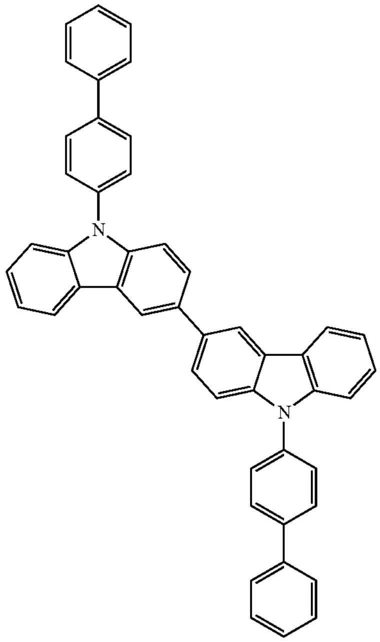
-continued
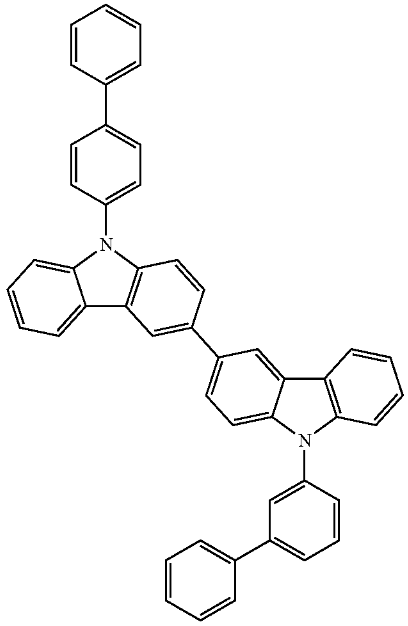
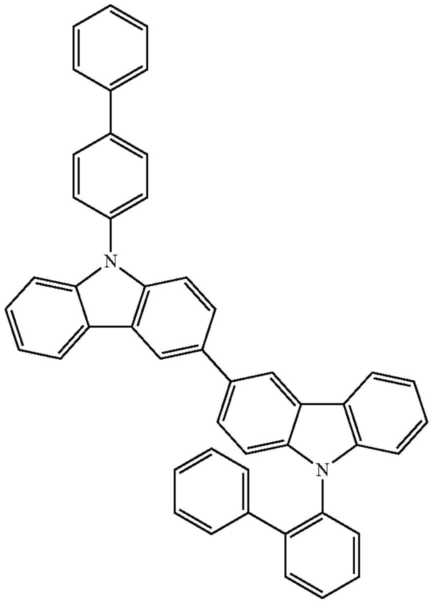

-continued
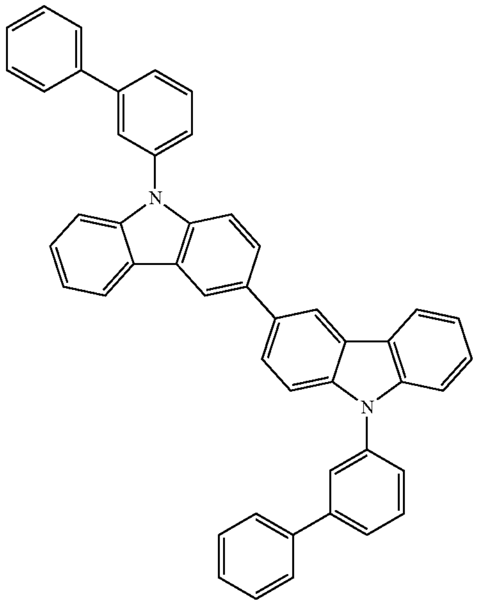
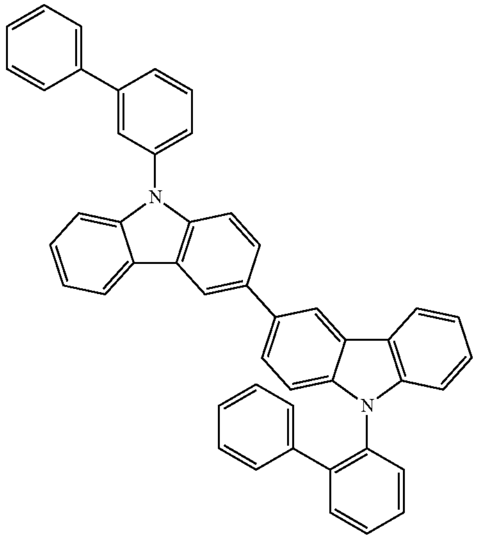
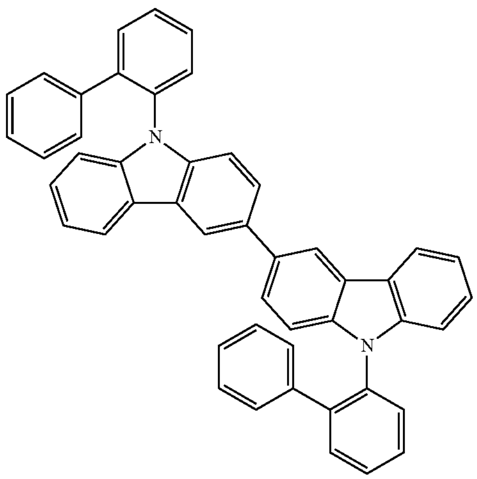
-continued
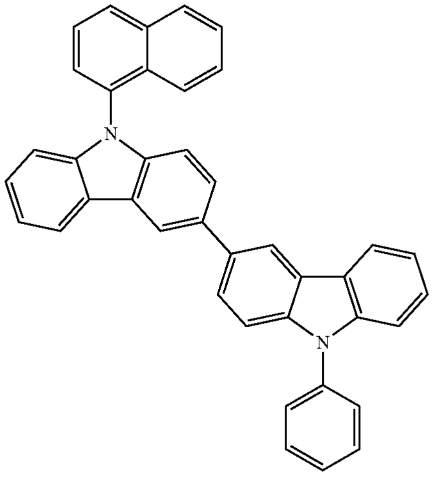
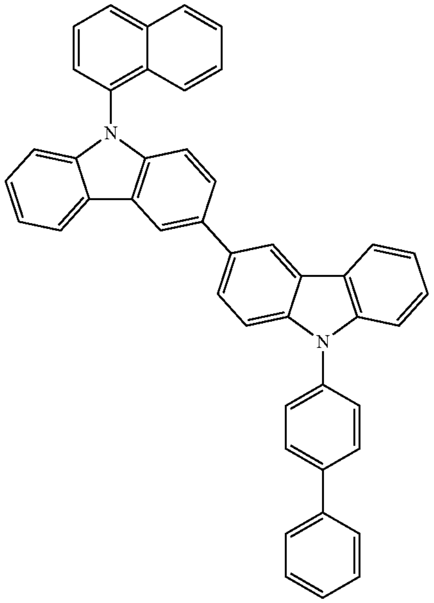
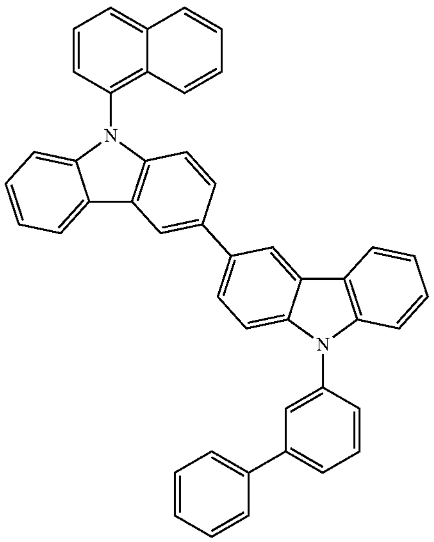

-continued
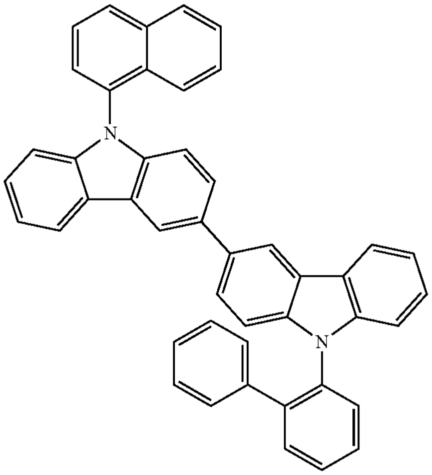
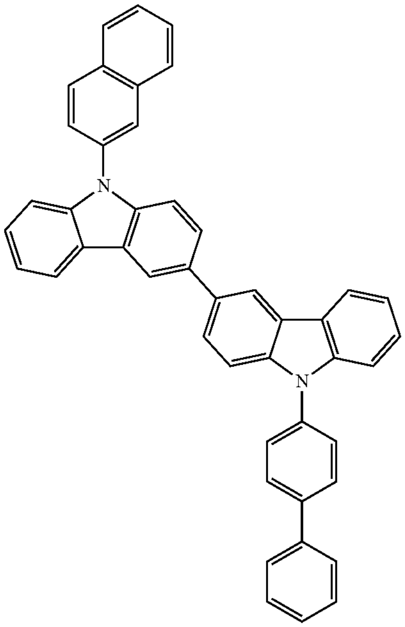
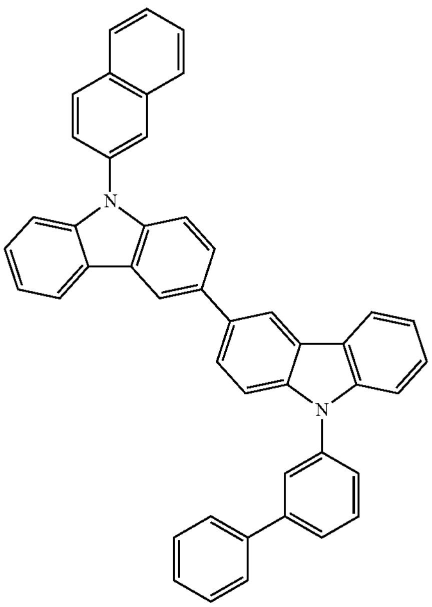
-continued
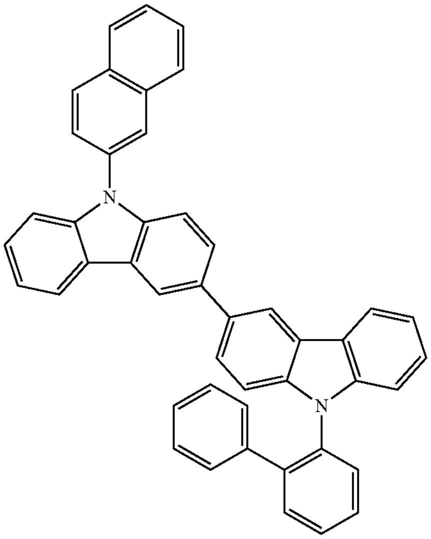
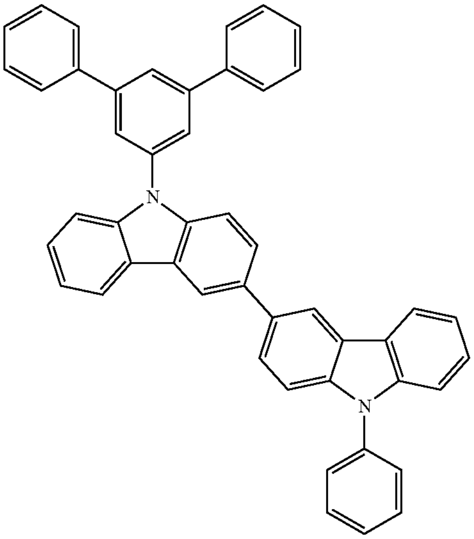
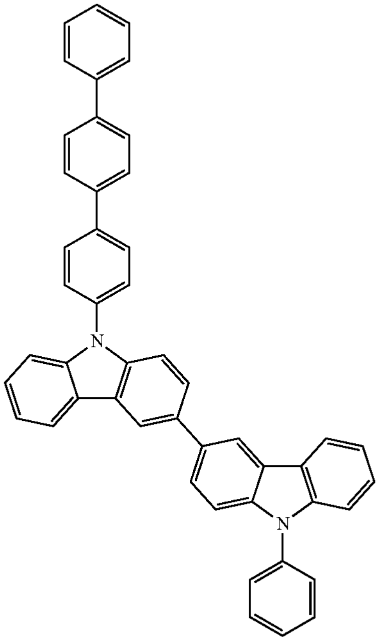

-continued
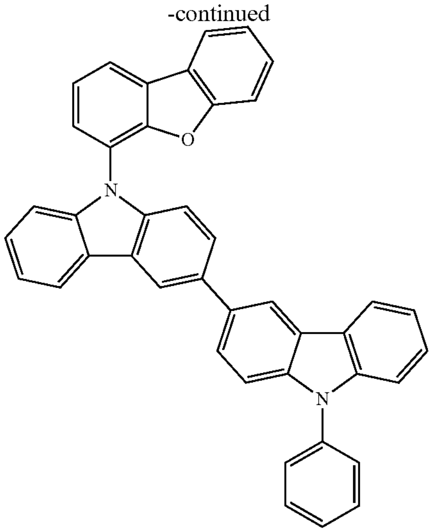
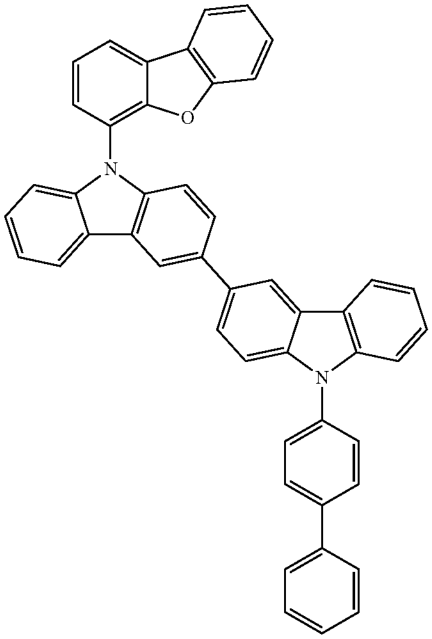
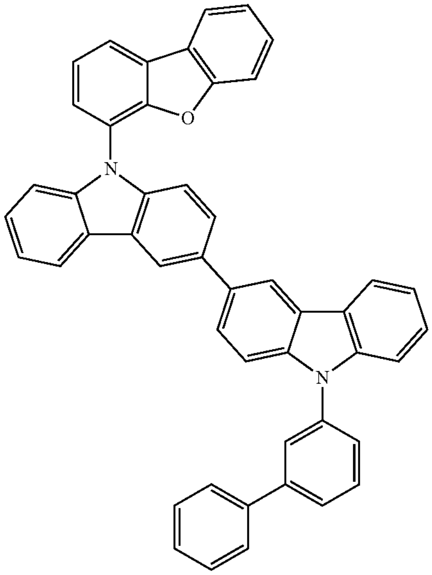
-continued
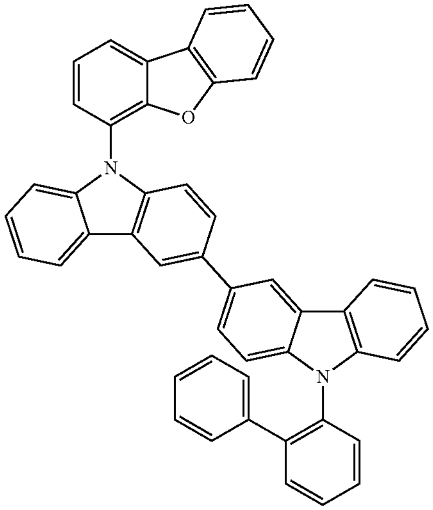
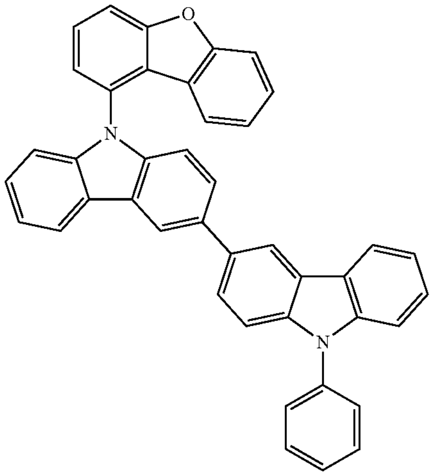
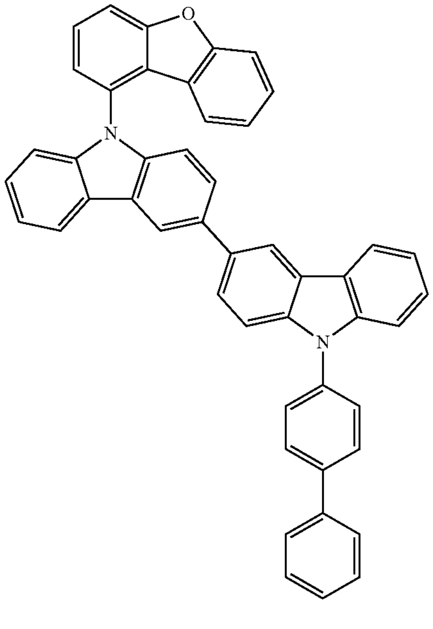

-continued
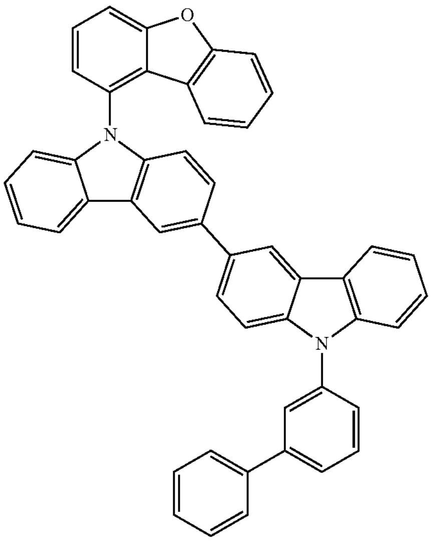
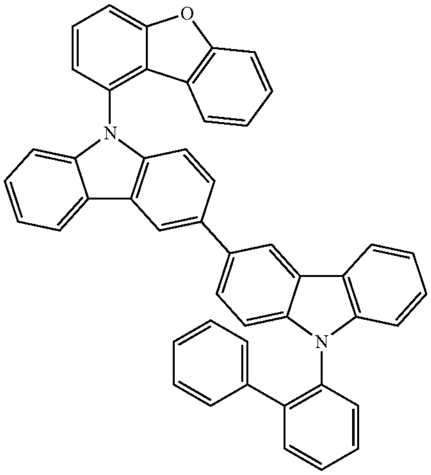
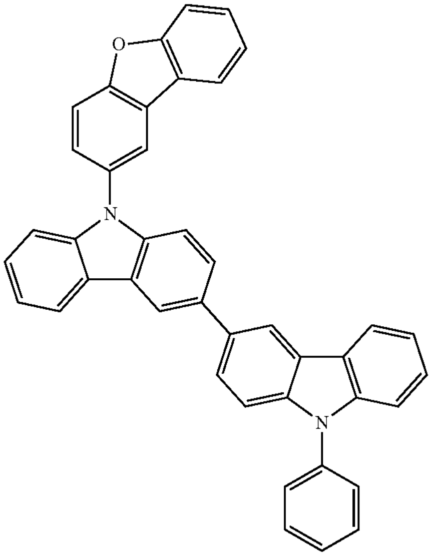
-continued
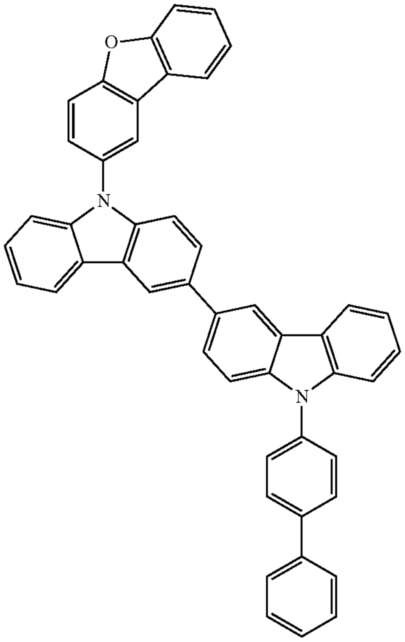
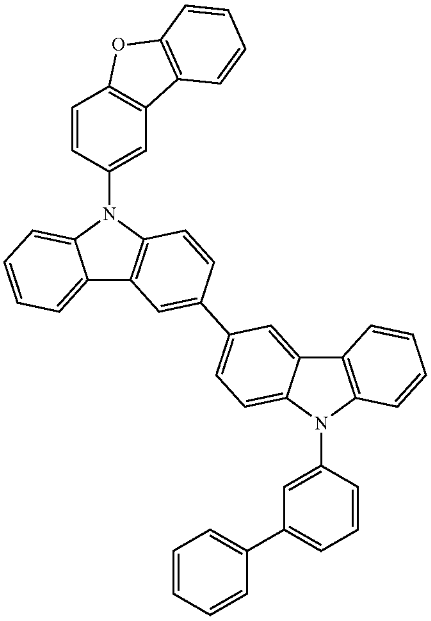

-continued
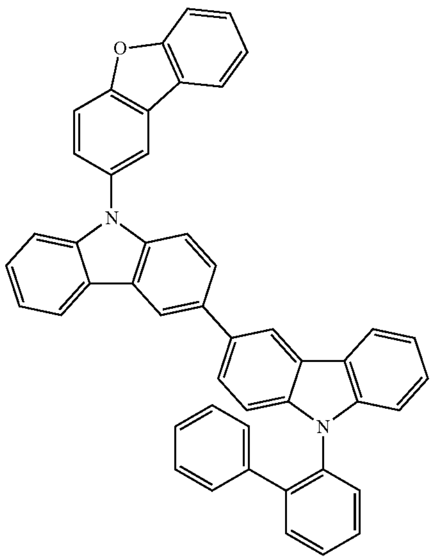
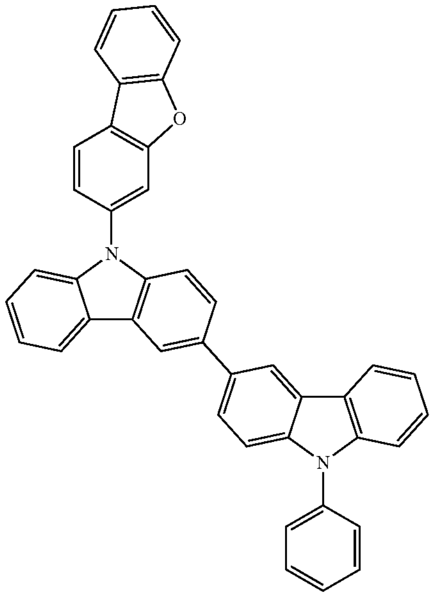
-continued
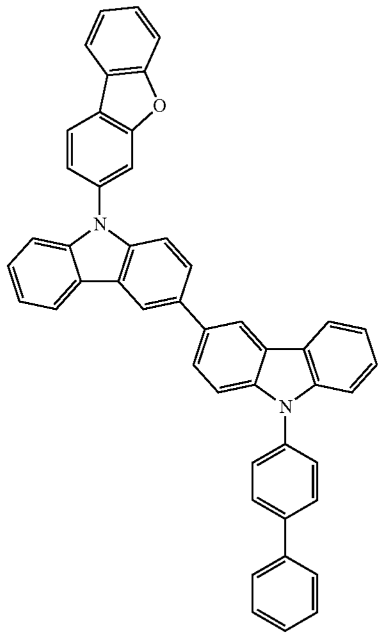
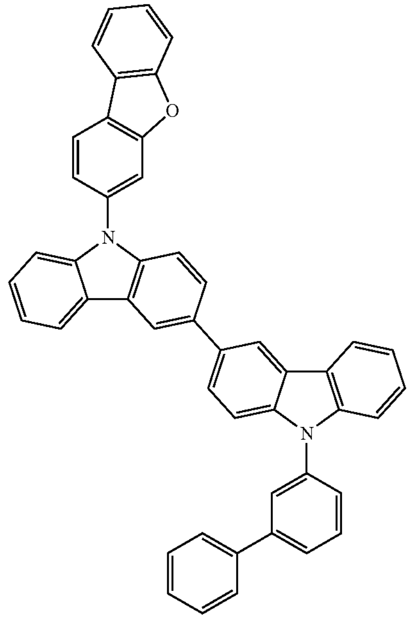

-continued
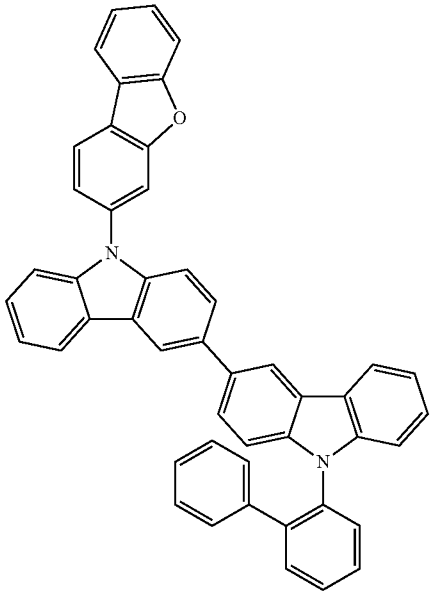
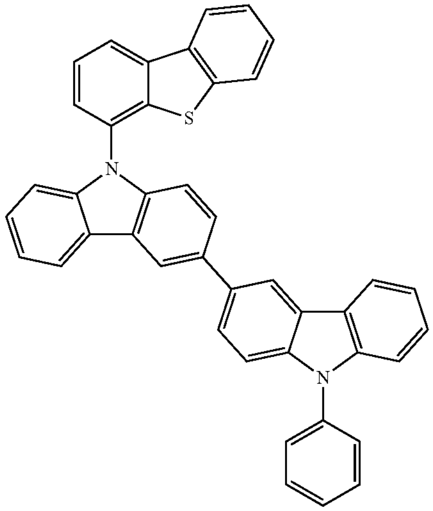
-continued
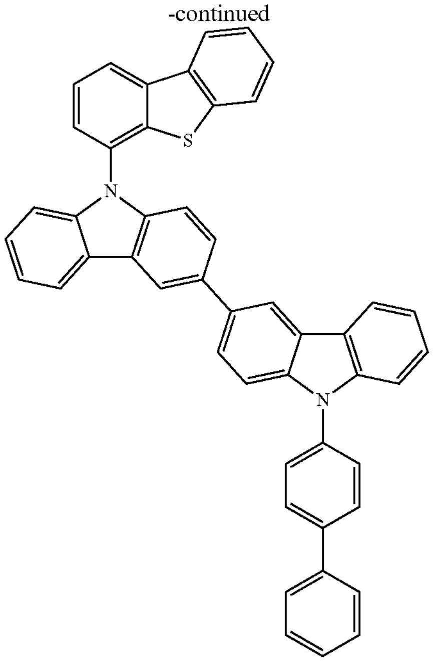
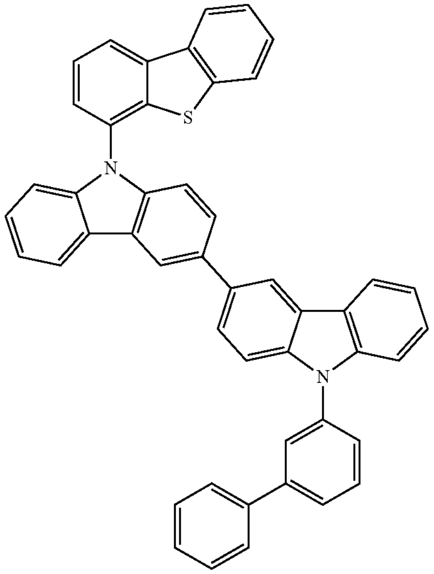
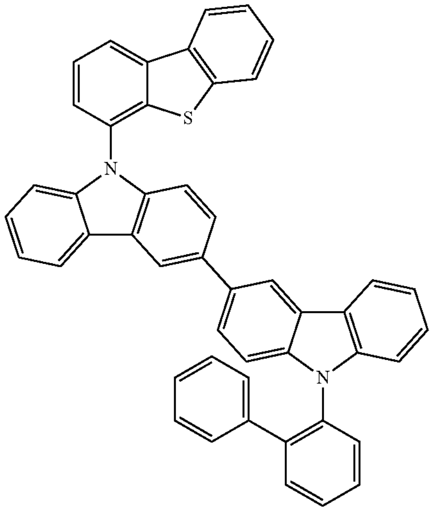

-continued
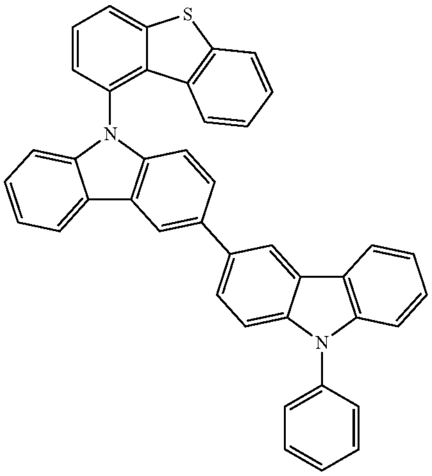
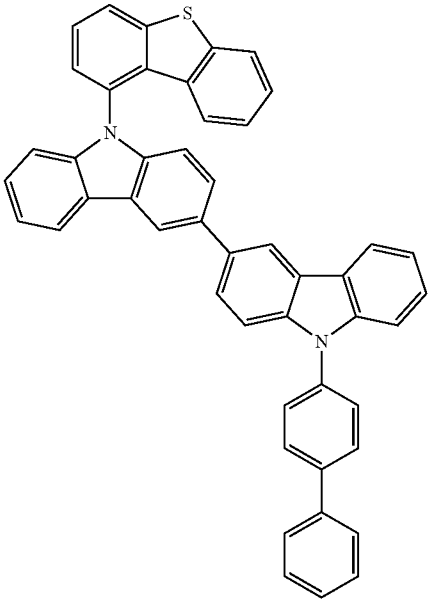
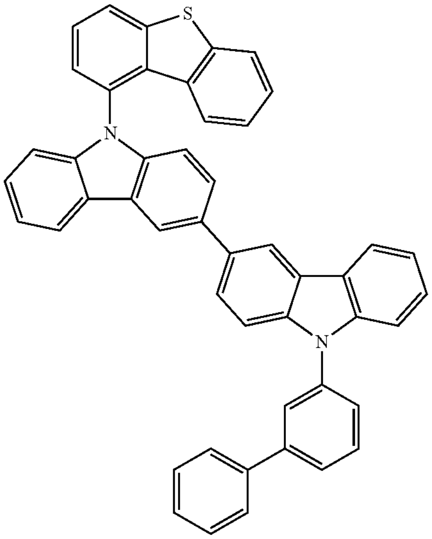
-continued
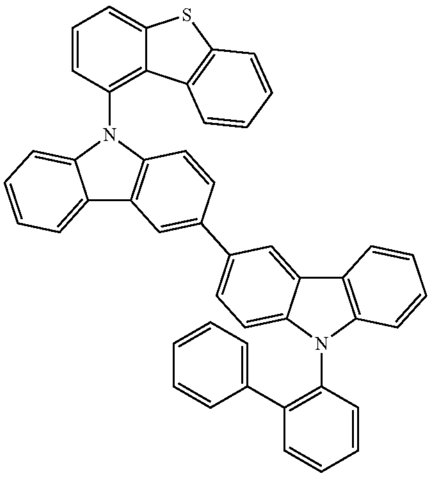
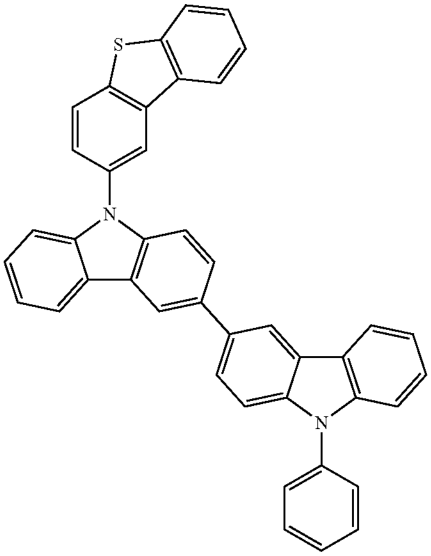
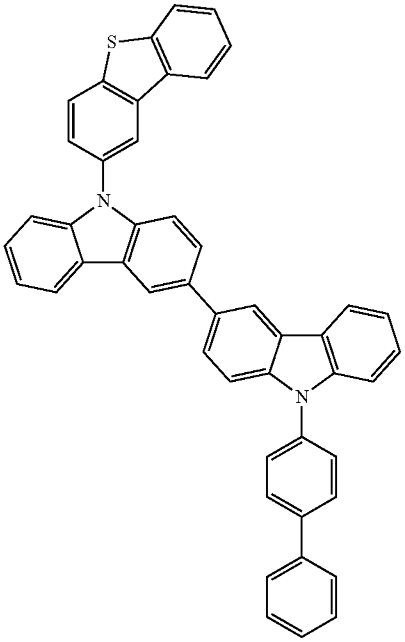

-continued
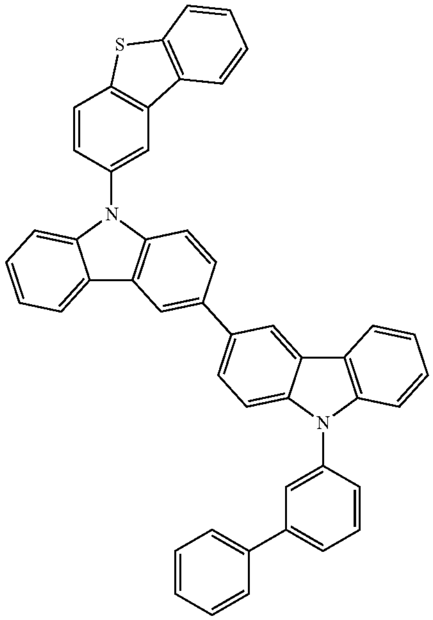
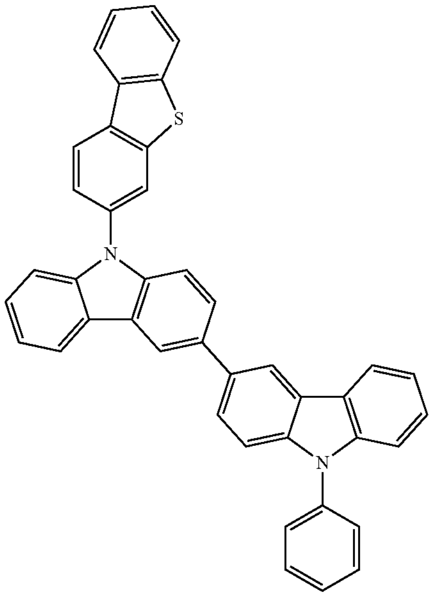
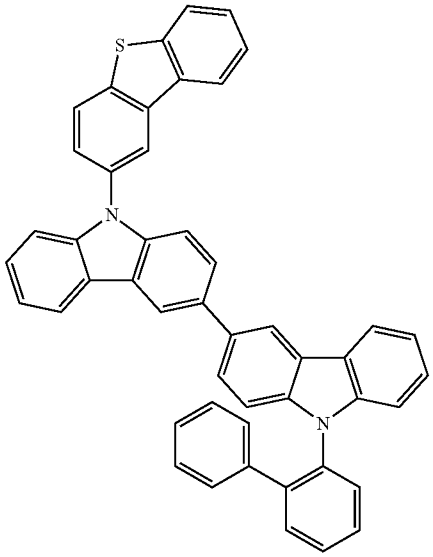
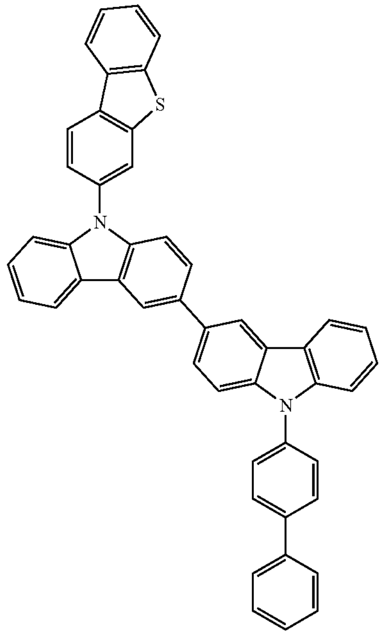

-continued
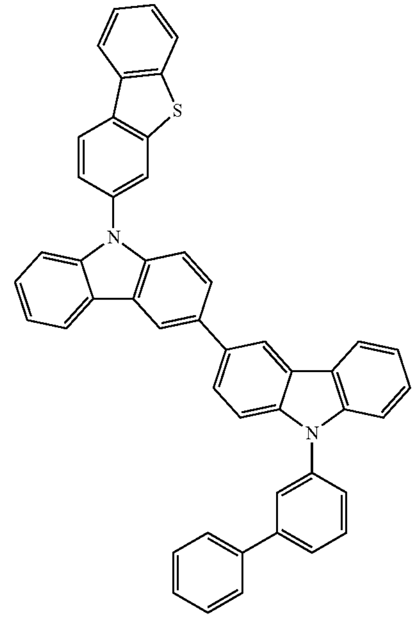
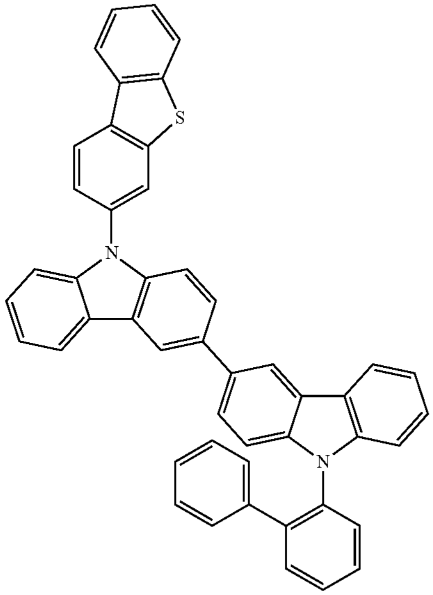
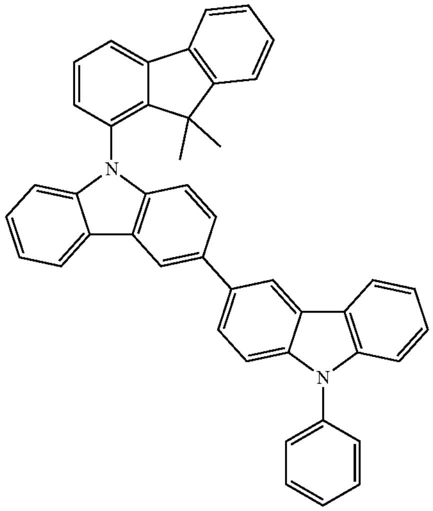
-continued
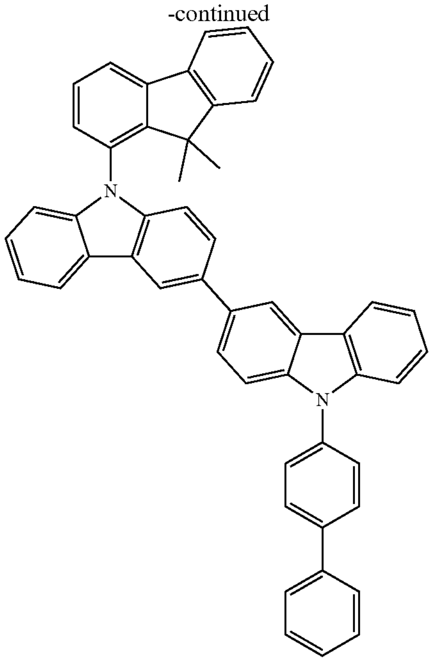
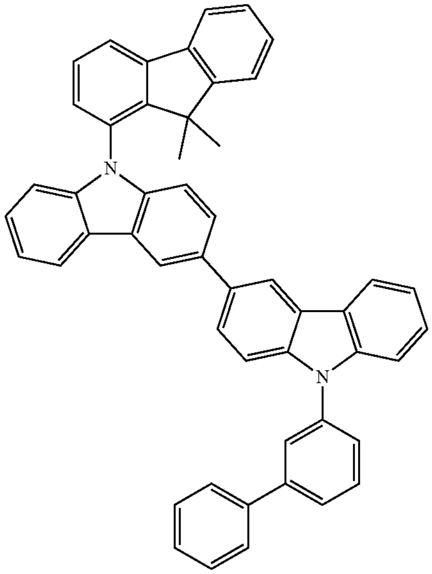
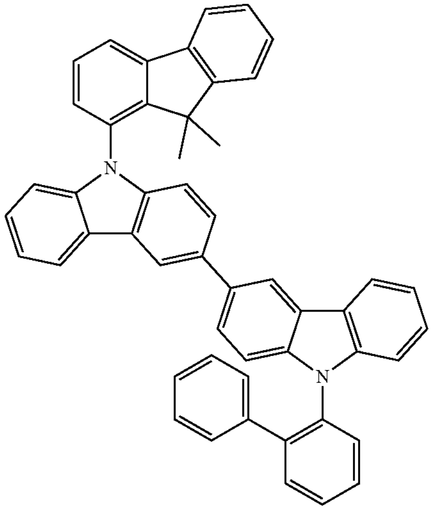

-continued
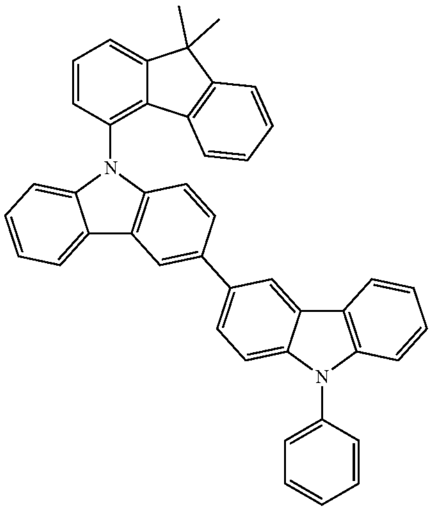
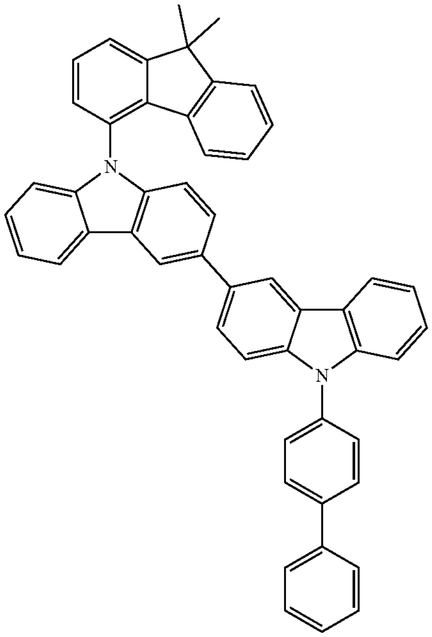
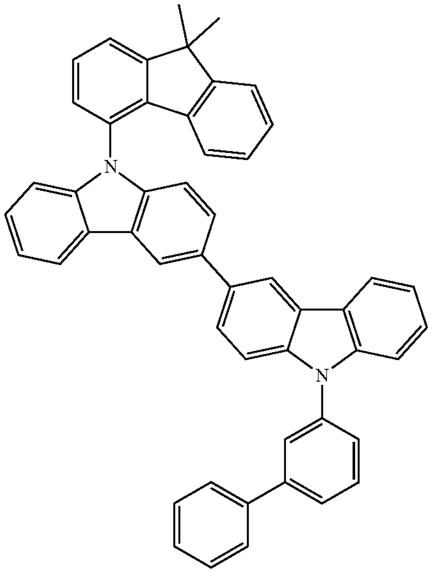
-continued
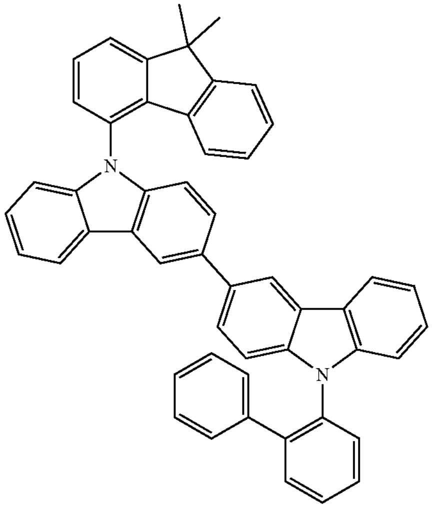 [SMILES: CC1(C)c2ccccc2-c2c(-n3c4ccccc4c4cc(-c5ccc6c(c5)c5ccccc5n6-c5ccccc5-c5ccccc5)ccc43)cccc21]
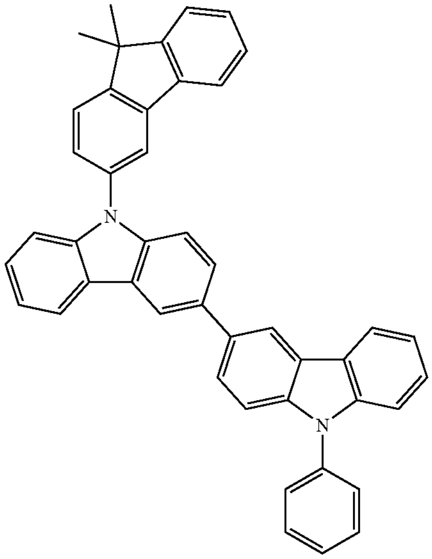
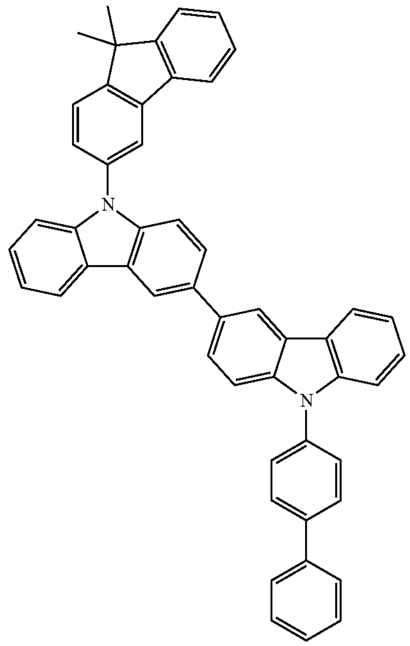

-continued
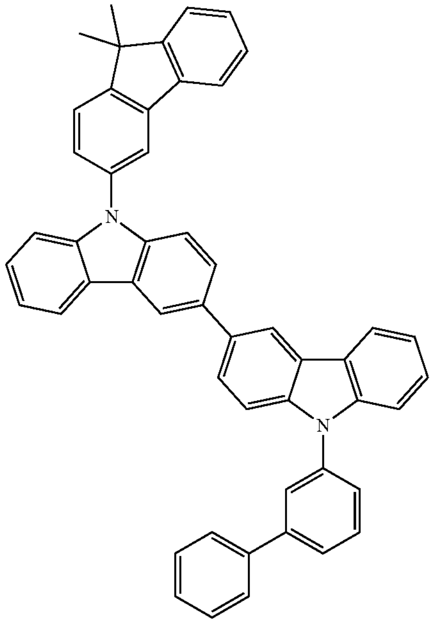
-continued
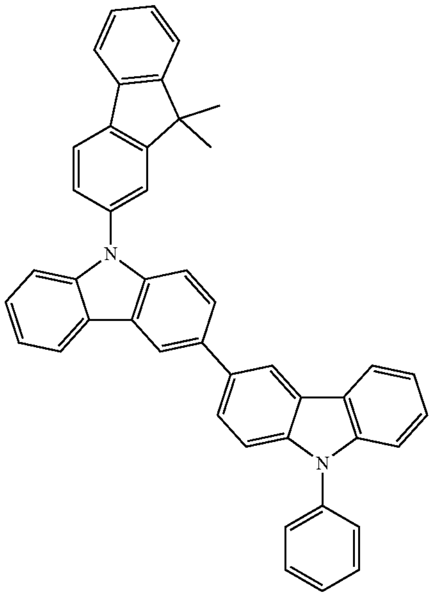
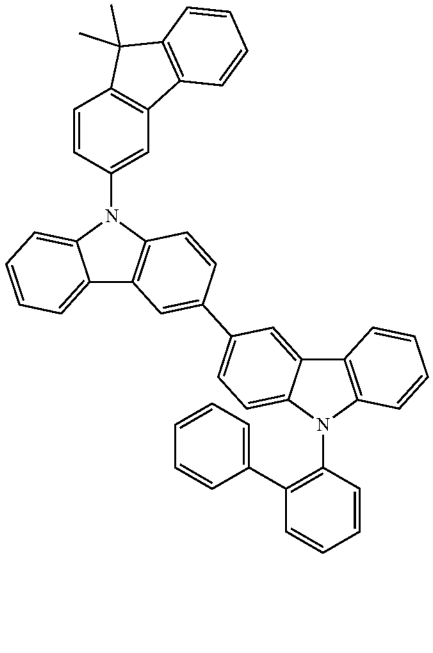
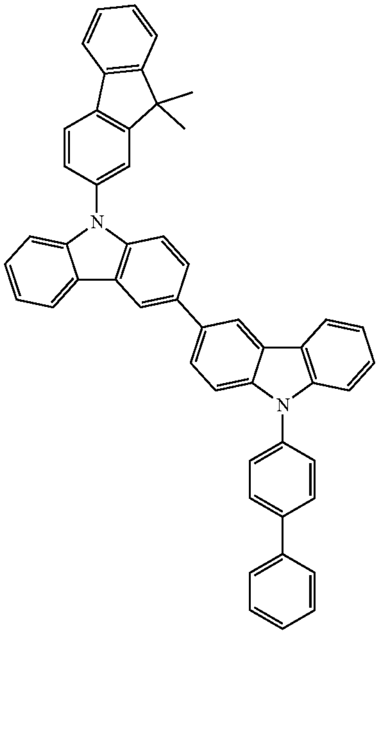

-continued
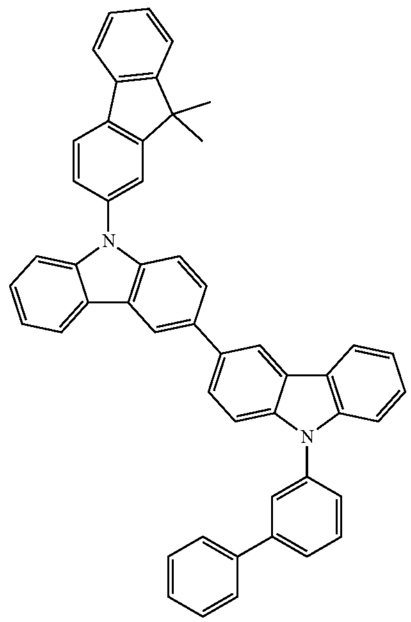
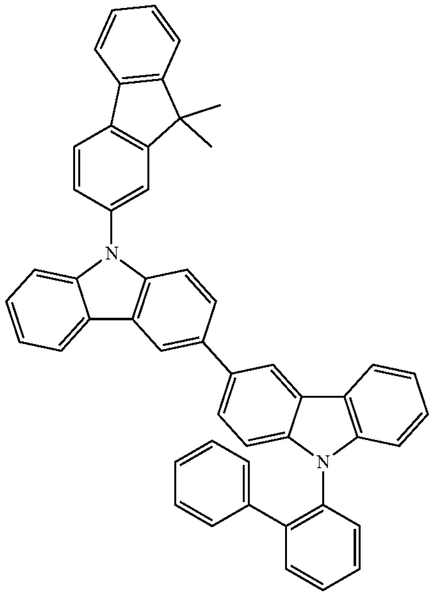
-continued
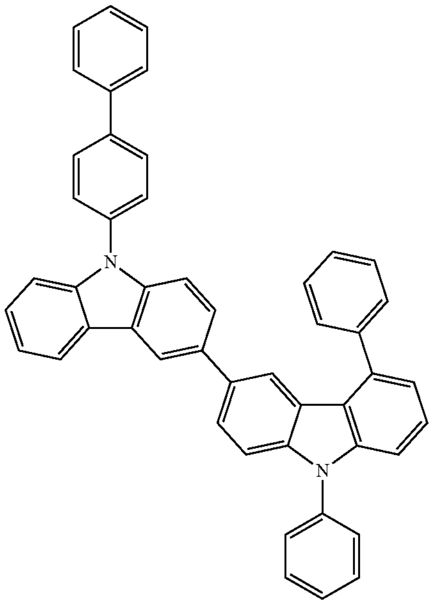
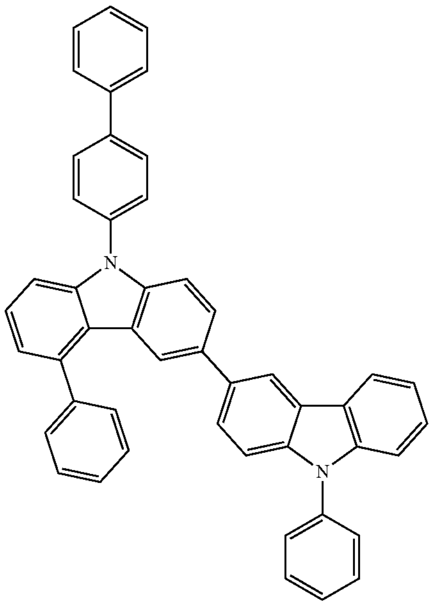

-continued
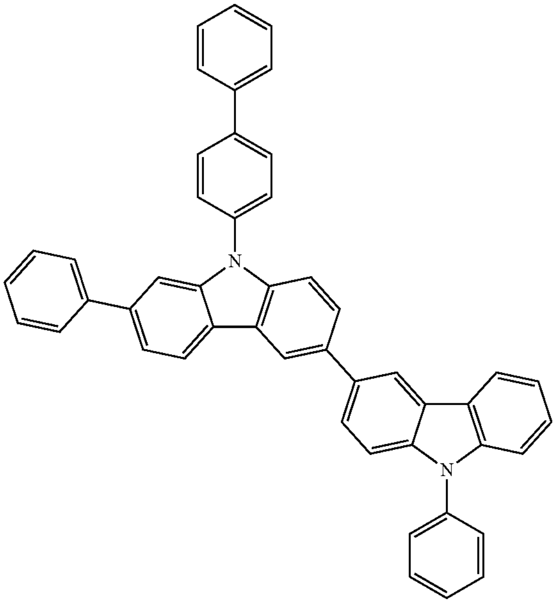
-continued
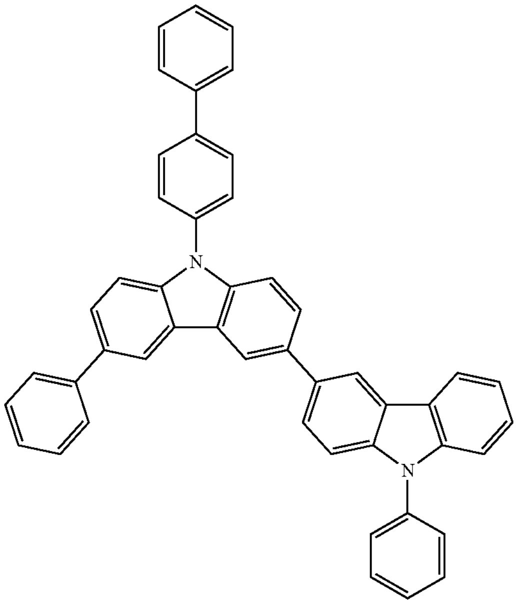
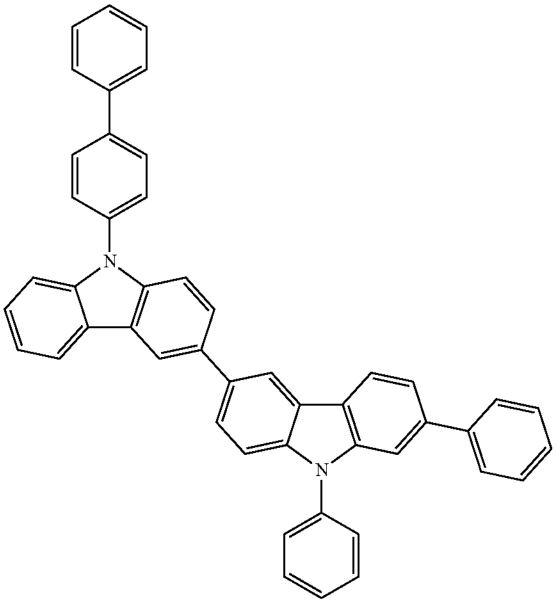
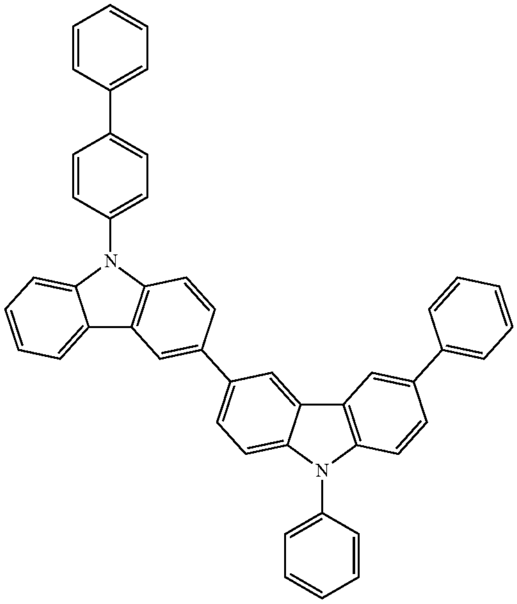

-continued

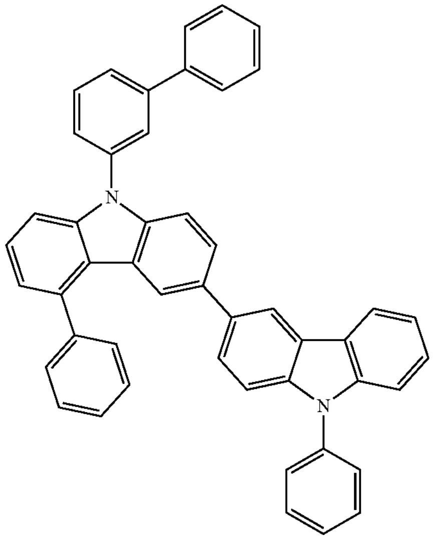

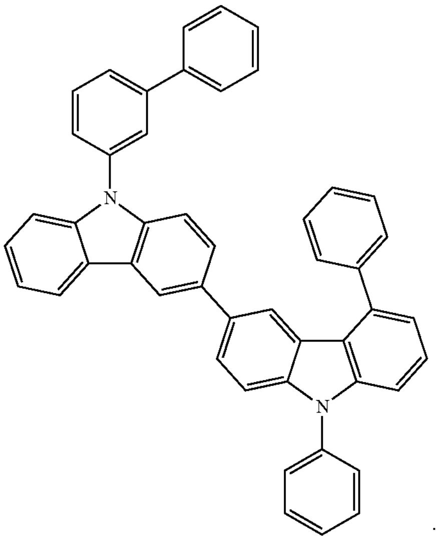

.

7. The organic light emitting device of claim 1, wherein the compound of Chemical Formula 1 is the following Chemical Formula 1-1 or Chemical Formula 1-2:

<Chemical Formula 1-1>

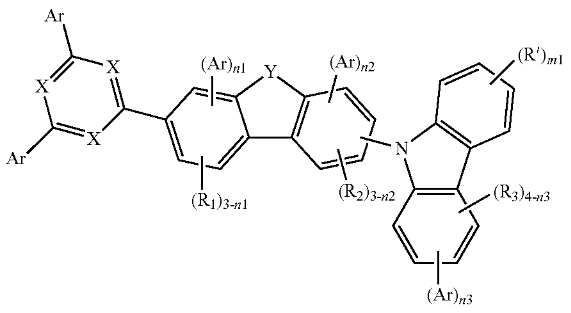

-continued

<Chemical Formula 1-2>

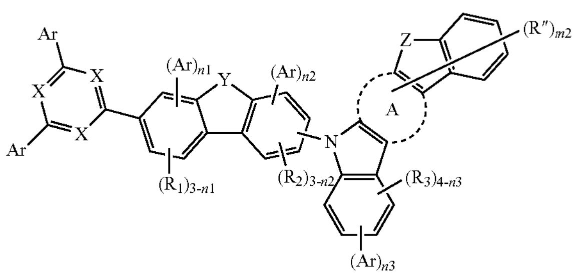

wherein in the Chemical Formulae 1-1 and 1-2:

X, Y, Ar, $R_1$, $R_2$, $R_3$, n1, n2, and n3 are as defined in claim 1;

A is a benzene ring;

Z is $C(R_5)_2$, O, S, or N—($R_6$);

each $R_5$ is independently a $C_{1-10}$ alkyl that is unsubstituted or substituted with deuterium, or a $C_{6-20}$ aryl that is unsubstituted or substituted with deuterium;

$R_6$ is a $C_{6-60}$ aryl that is unsubstituted or substituted with deuterium;

R' and R" are each independently hydrogen or deuterium;

m1 is an integer of 1 to 4; and m2 is an integer of 1 to 6, provided that at least one of Ar is phenyl substituted with five deuteriums, or at least one of $R_1$, $R_2$, $R_3$, R', and R" is deuterium.

8. The organic light emitting device of claim 1, wherein the compound of Chemical Formula 1 is any one compound selected from among the following compounds:

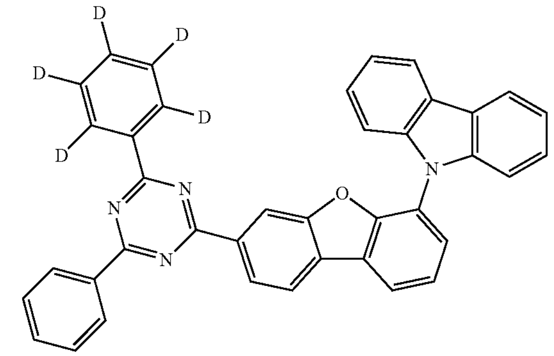

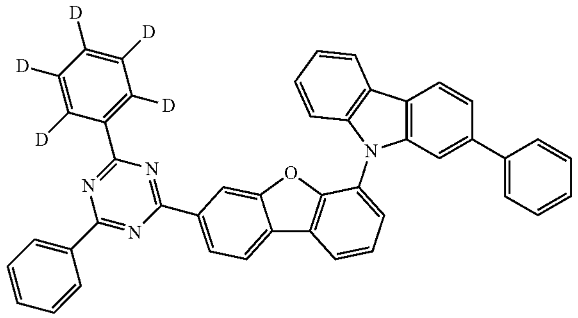

-continued
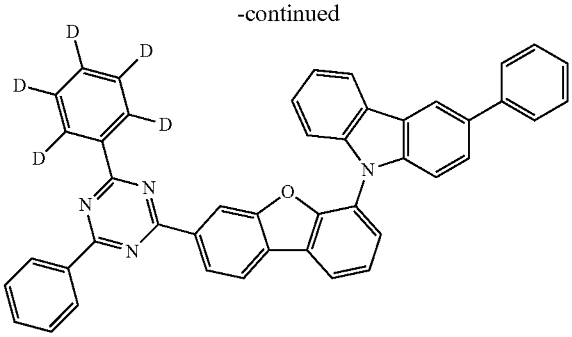
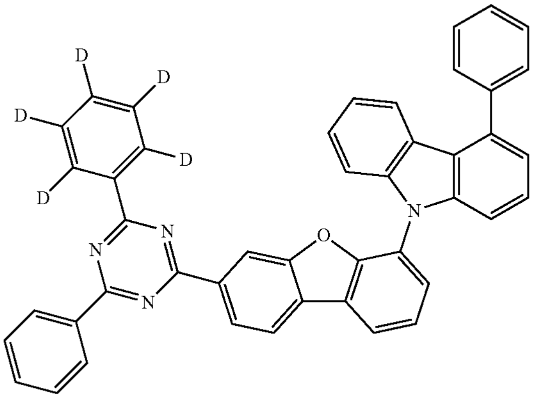
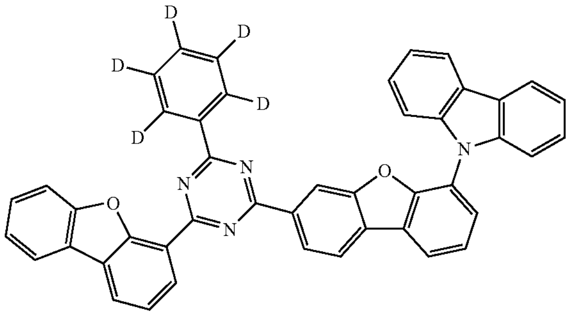
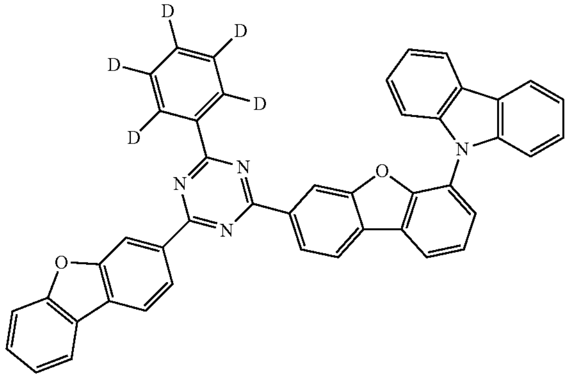
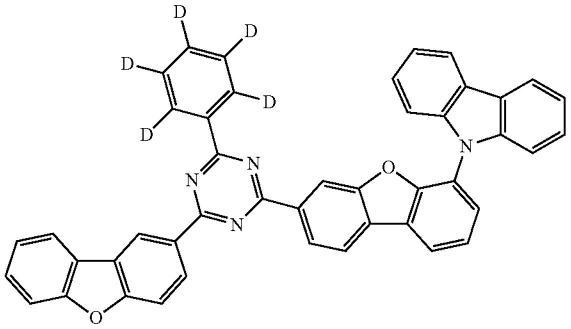
-continued
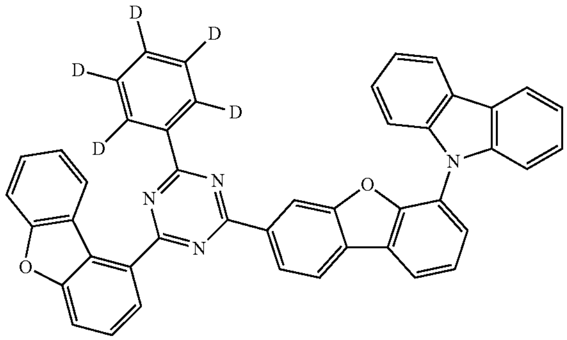
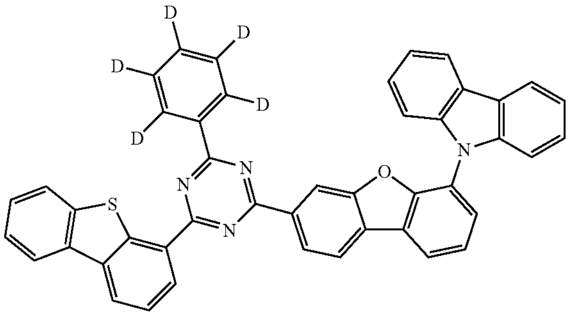
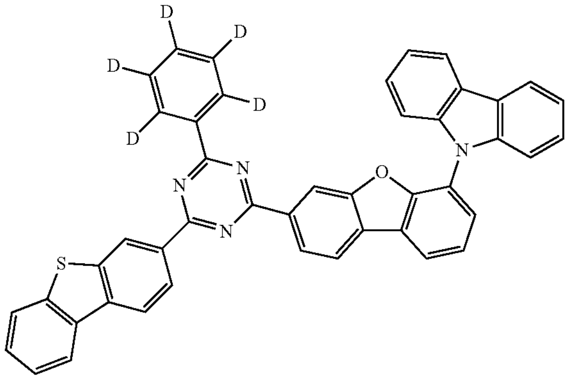
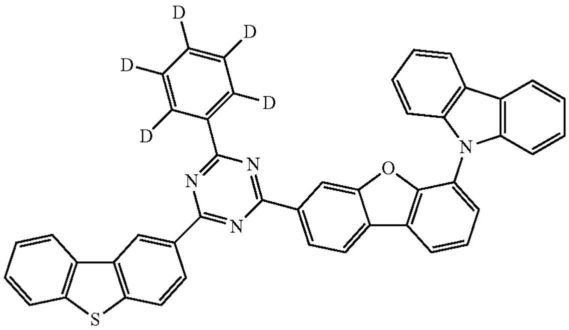
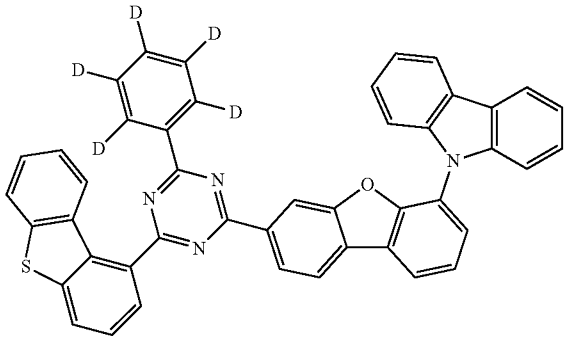

-continued
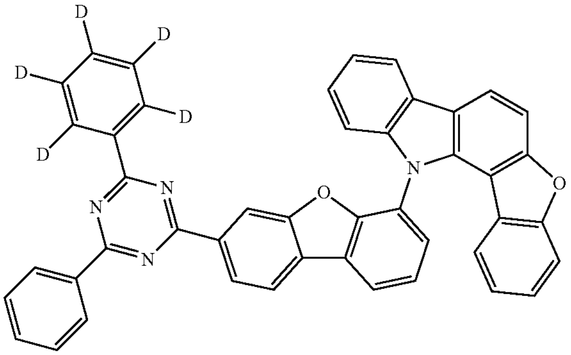
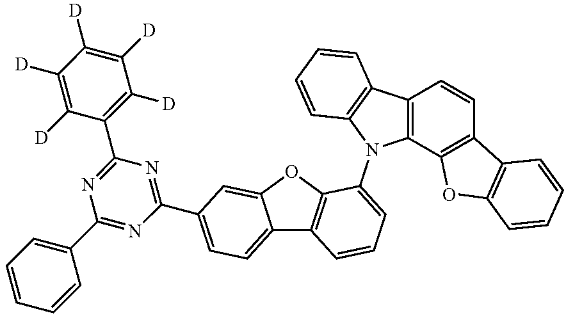
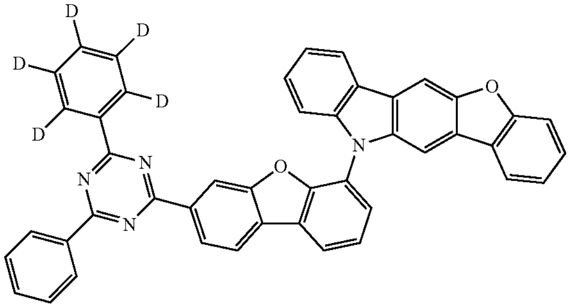
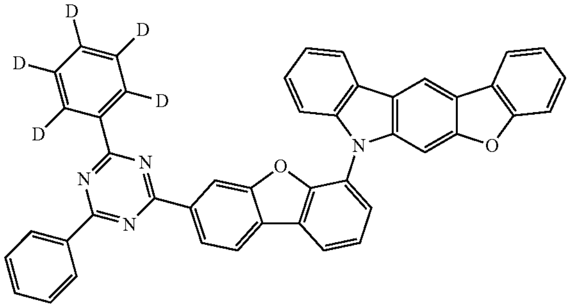
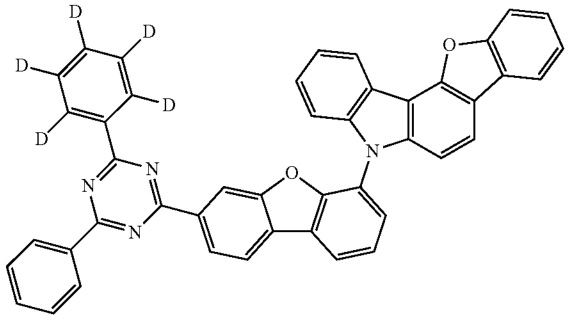
-continued
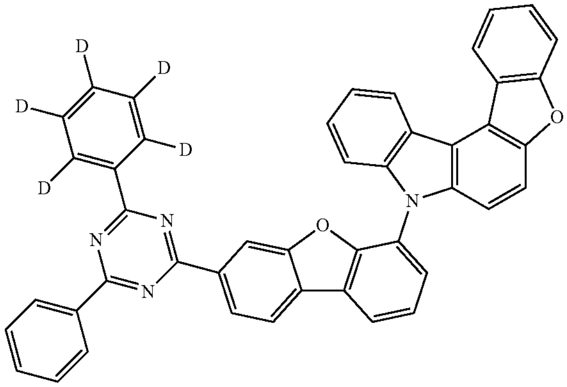
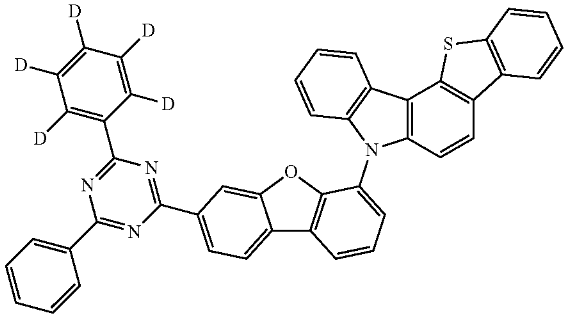
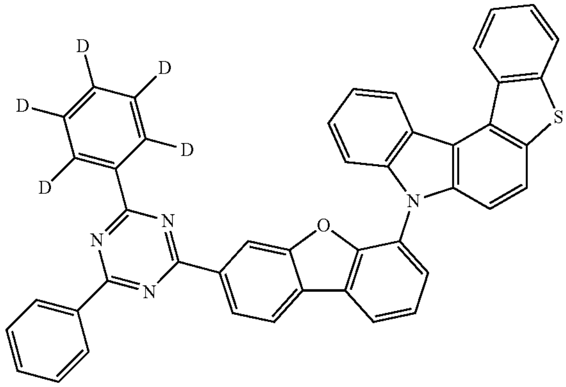
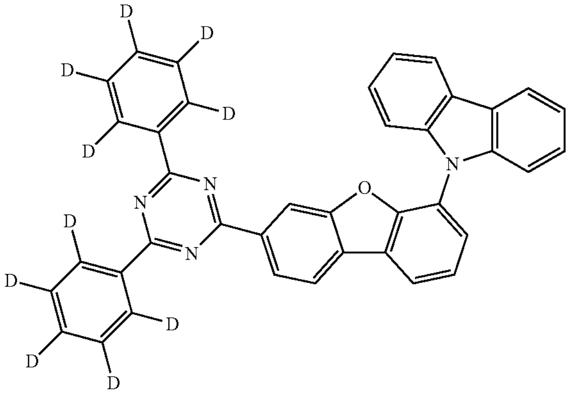

-continued
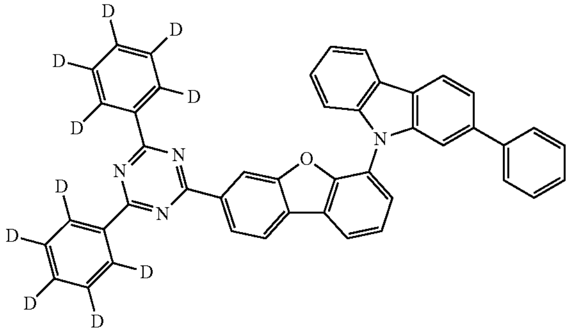
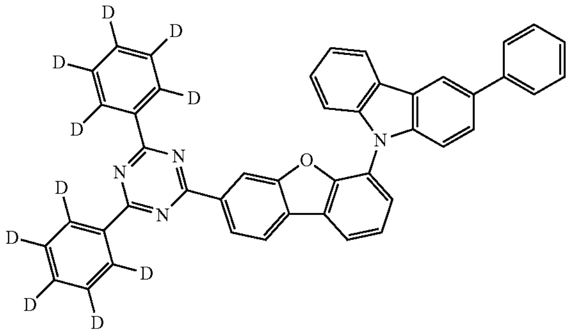
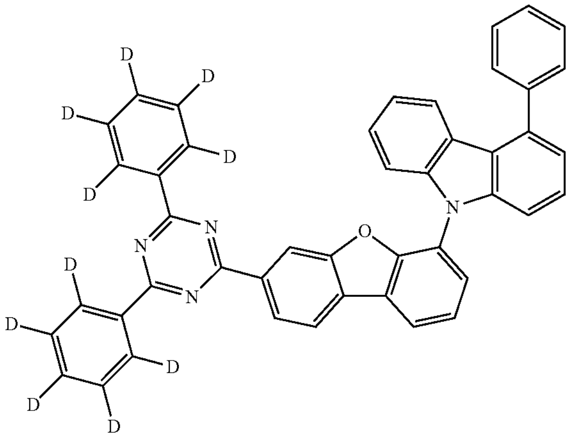
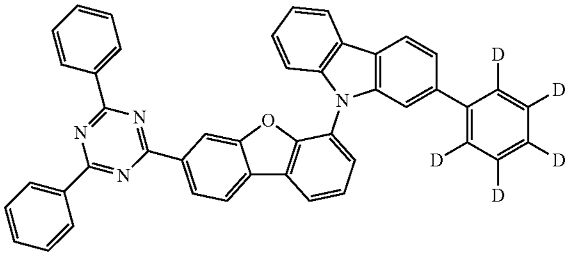
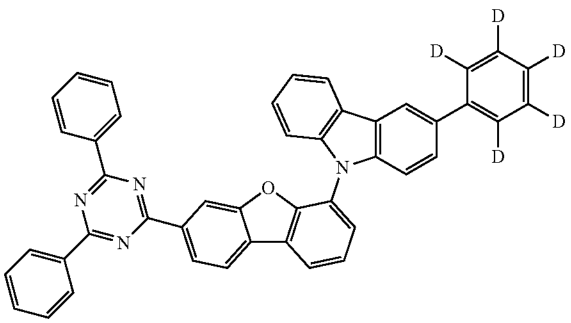
-continued
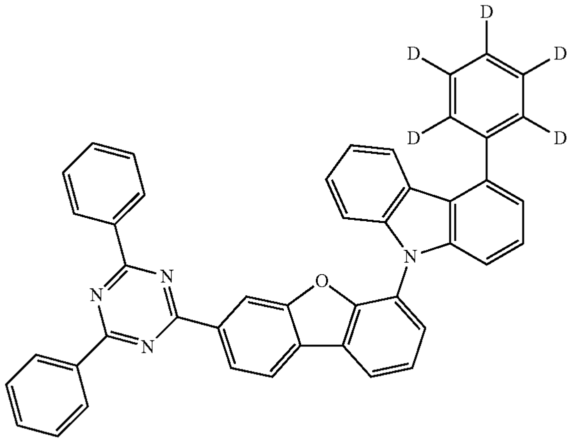
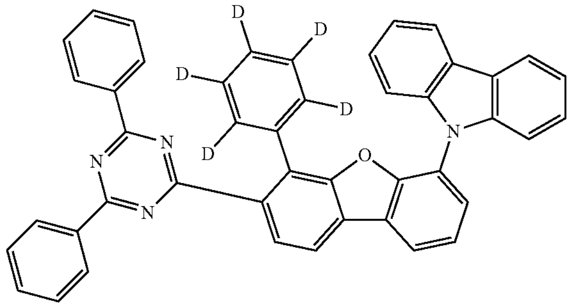
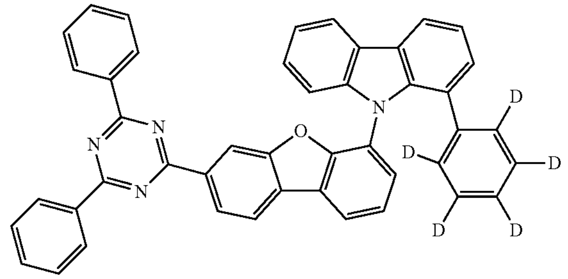
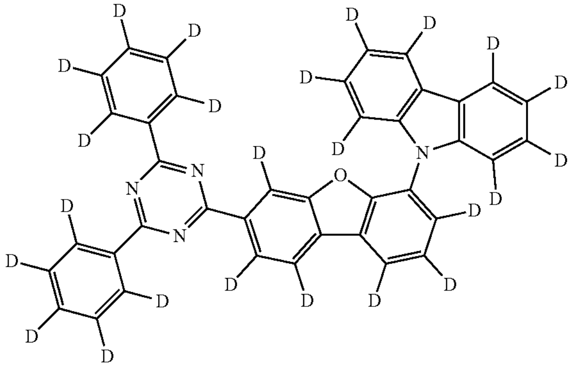

-continued
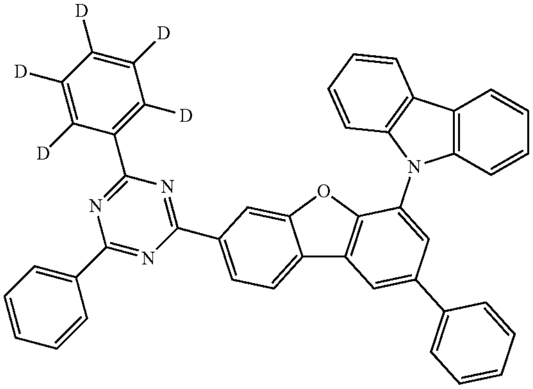
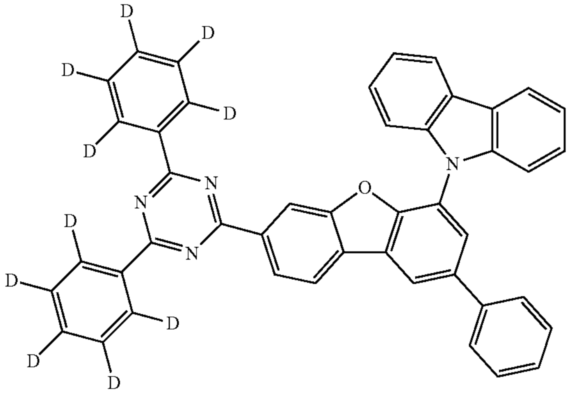
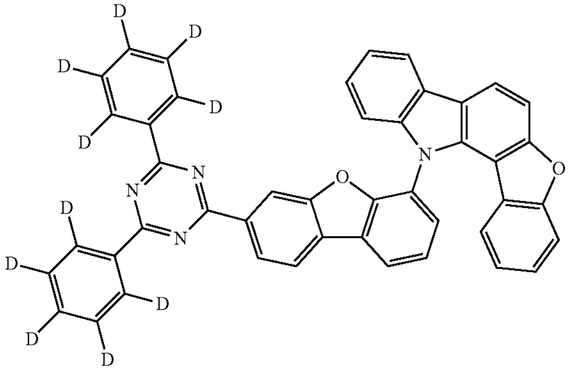
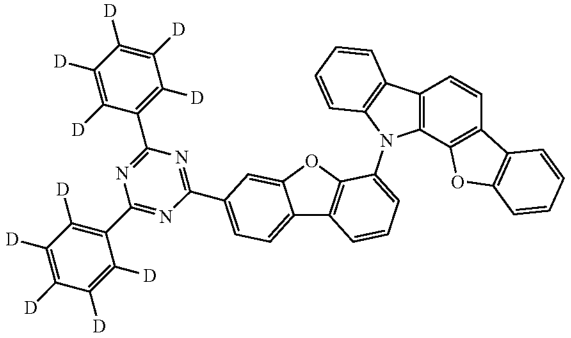
-continued
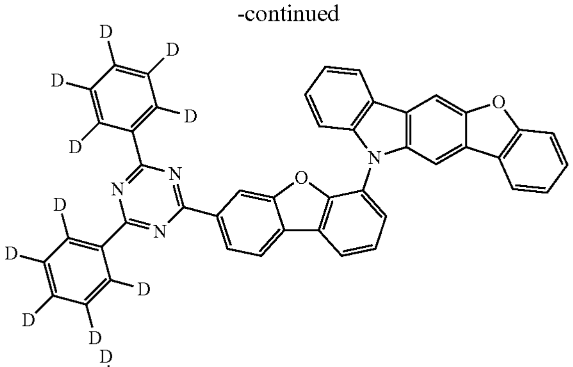
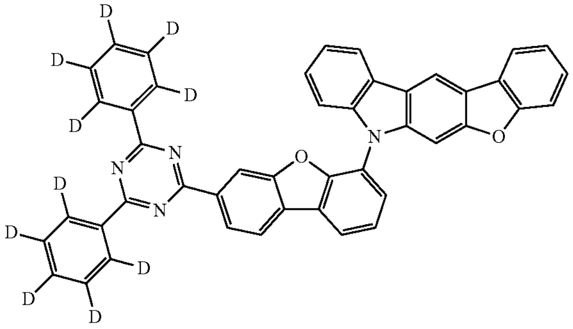
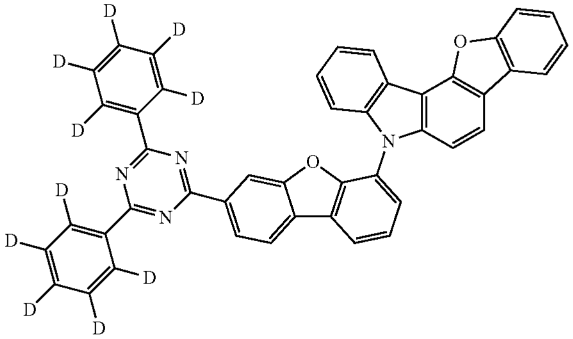
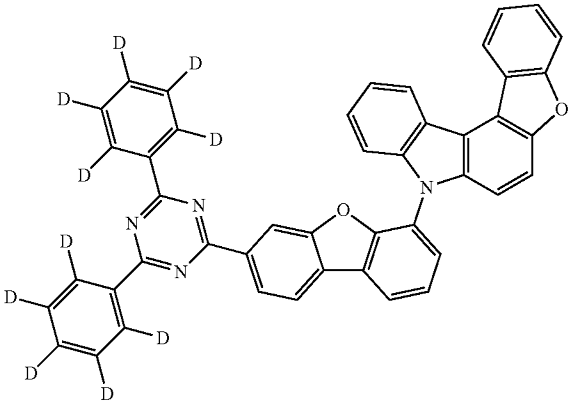
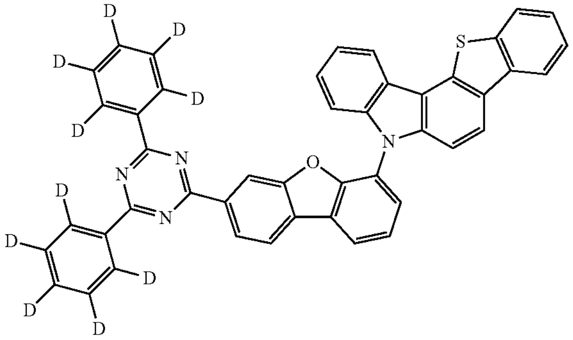

-continued
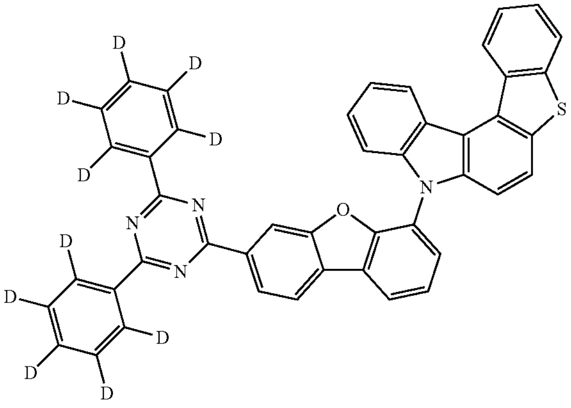
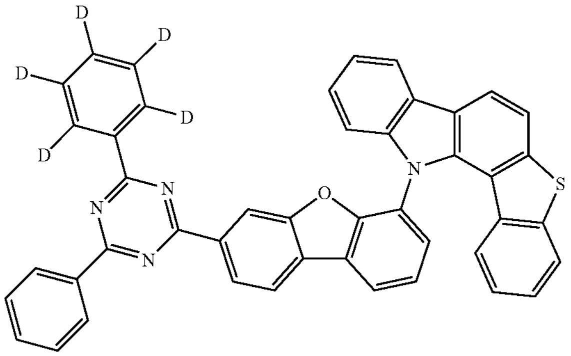
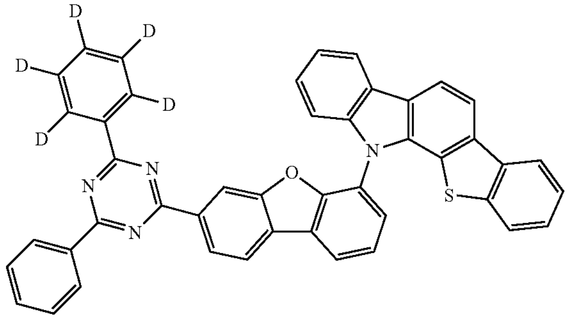
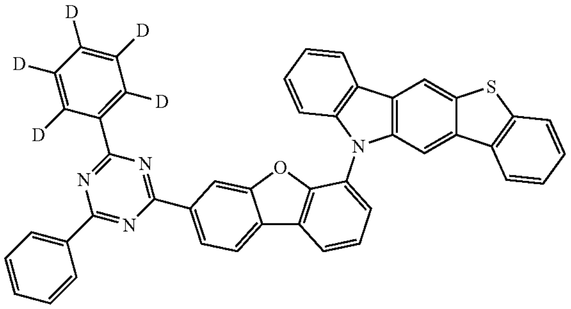
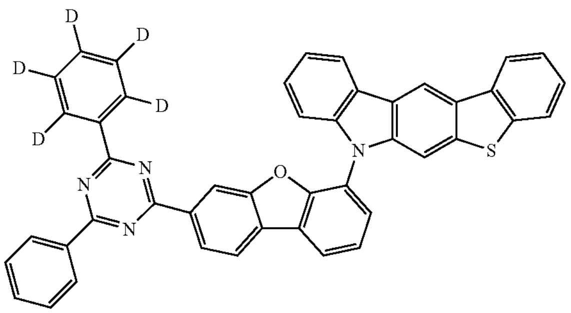
-continued
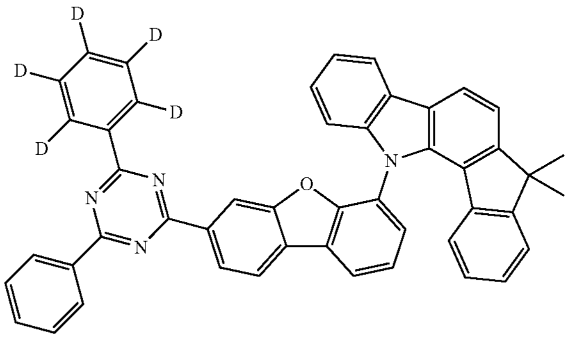
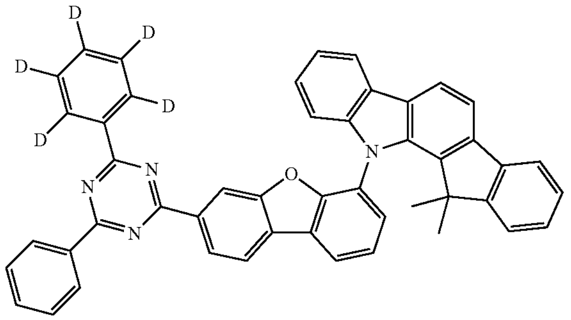
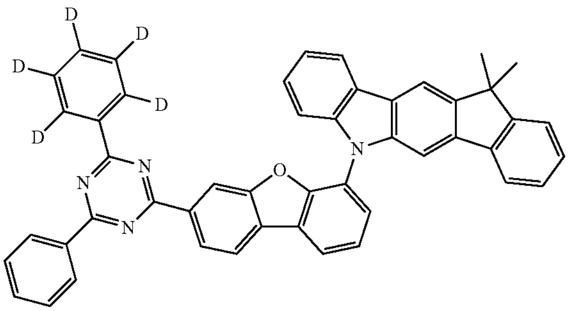
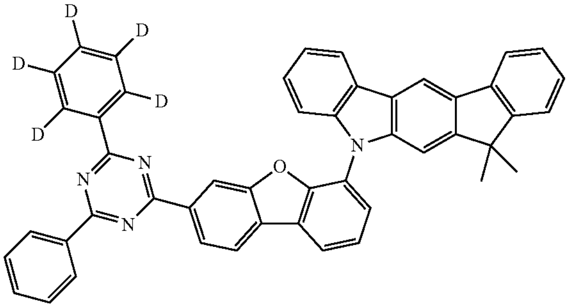
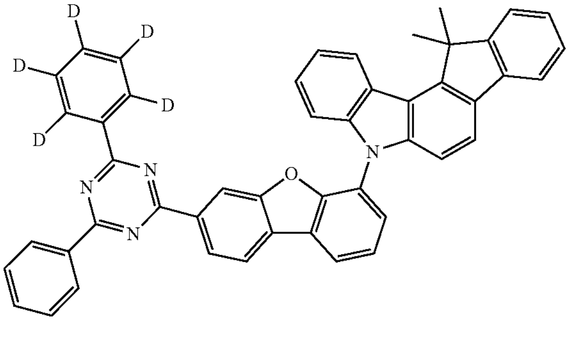

-continued
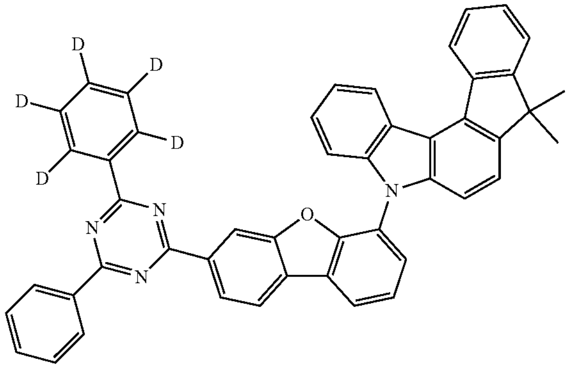
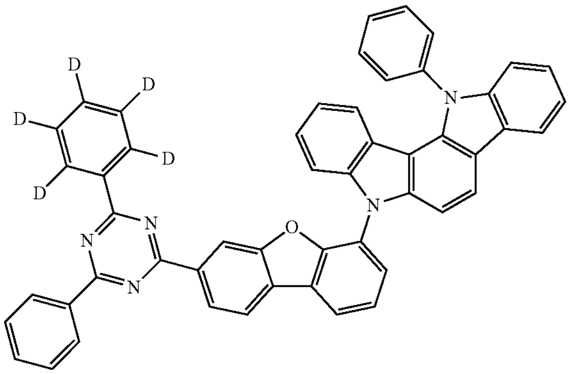
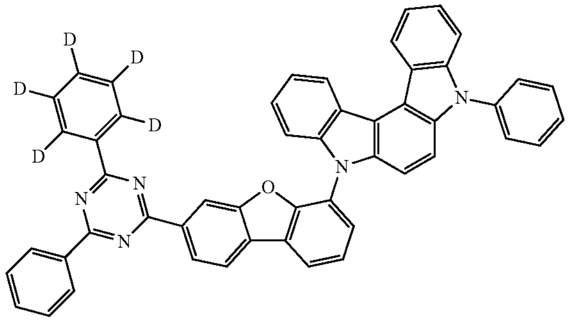
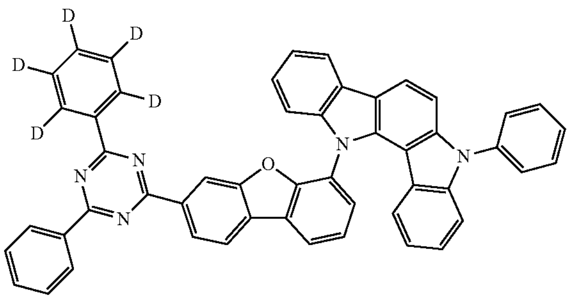
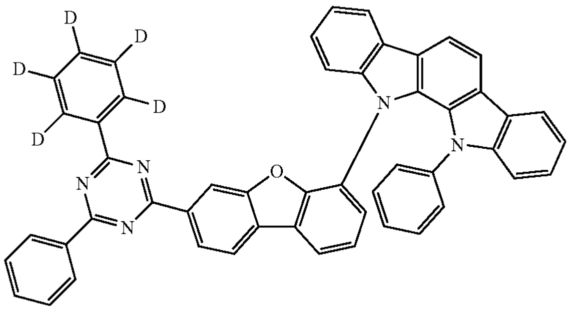
-continued
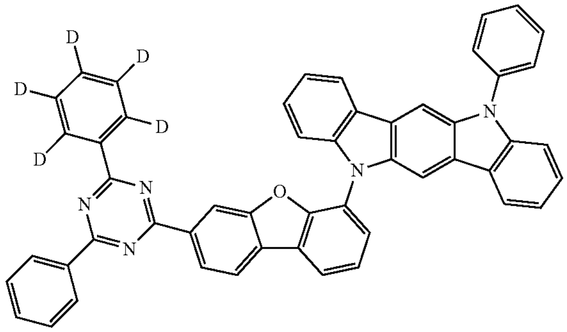
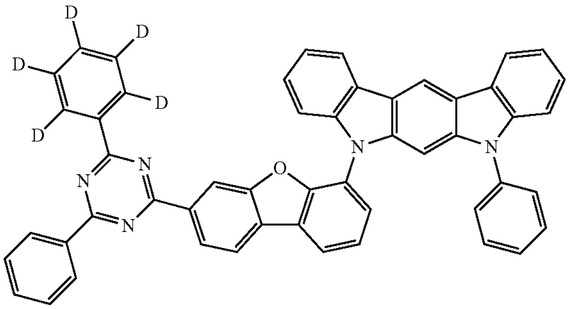
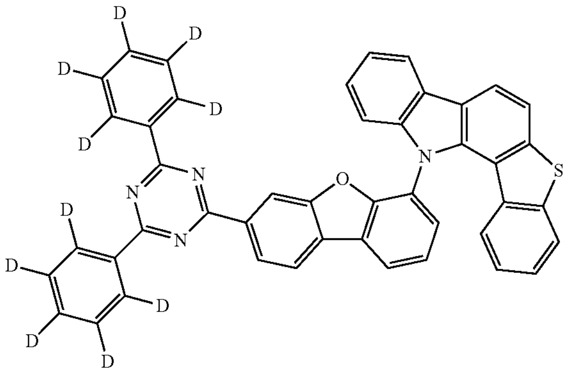
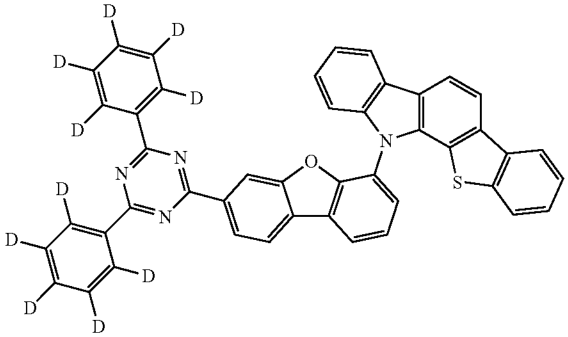
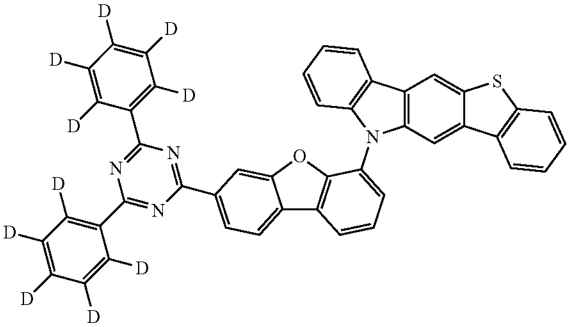

-continued
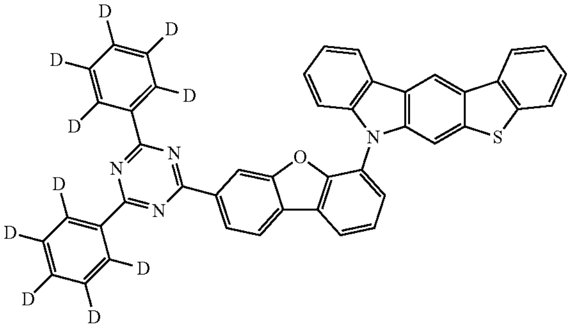
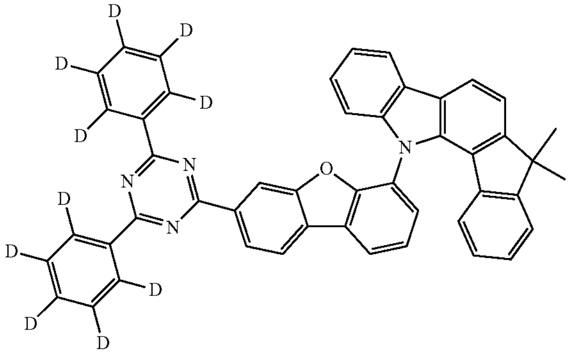
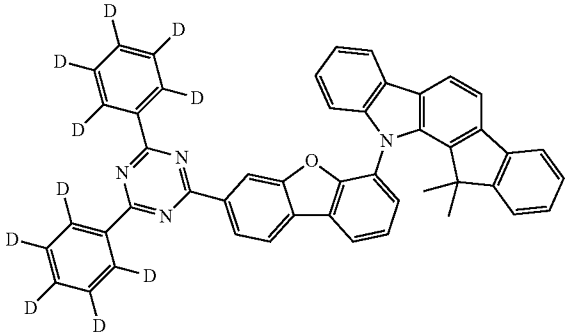
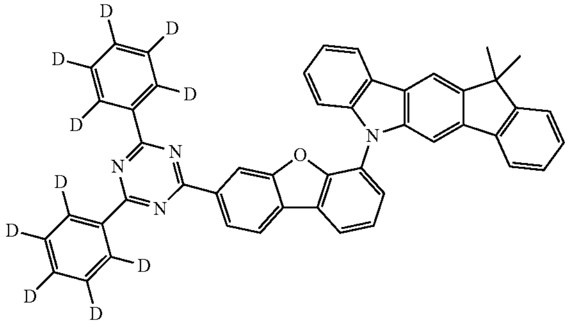
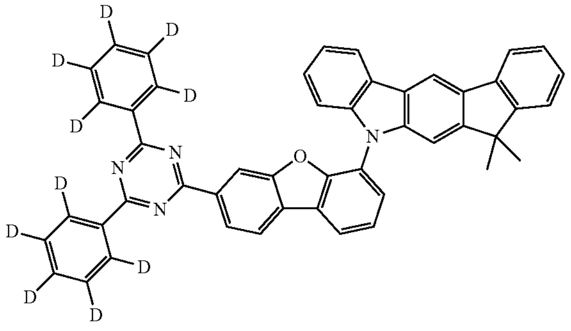
-continued
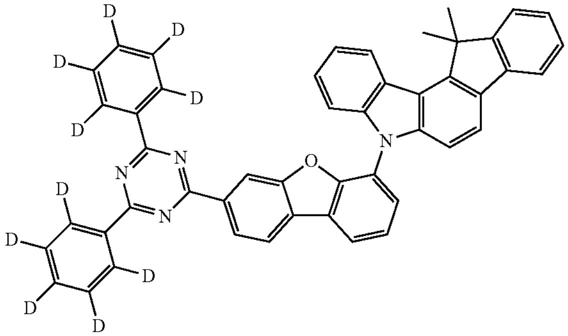
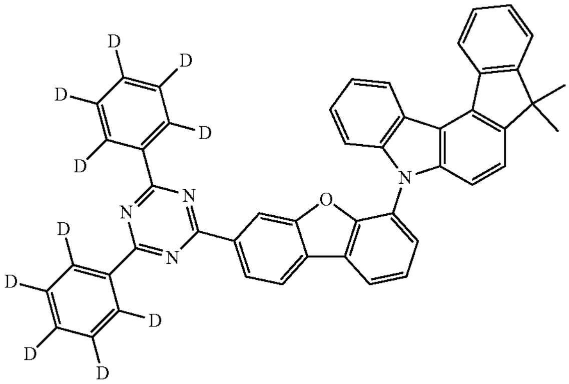
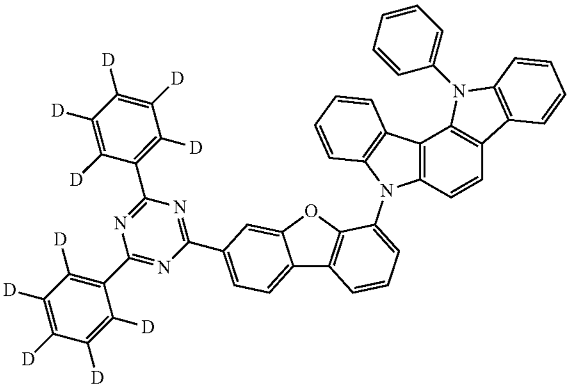
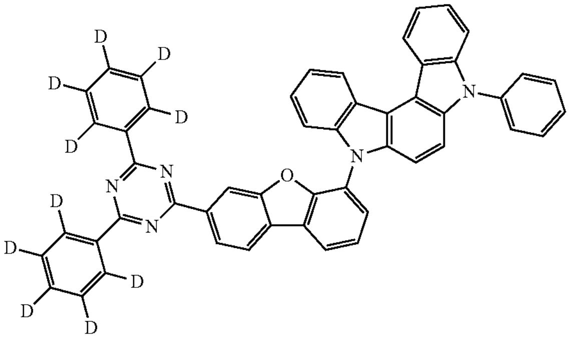

-continued
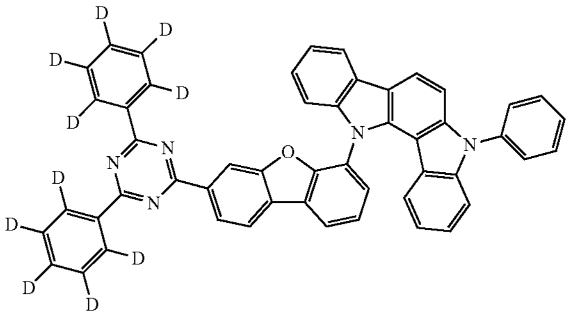
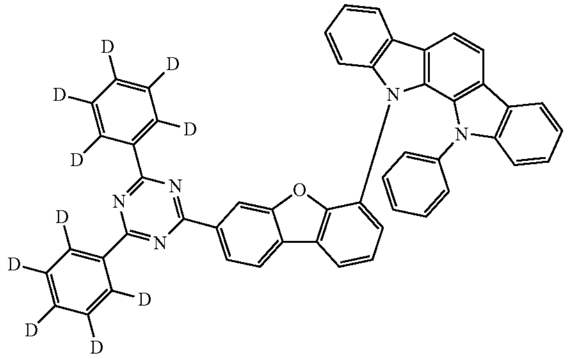
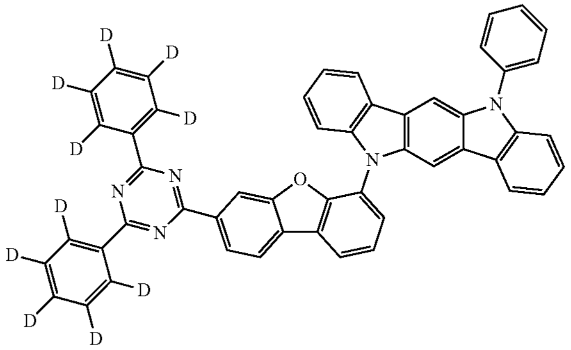
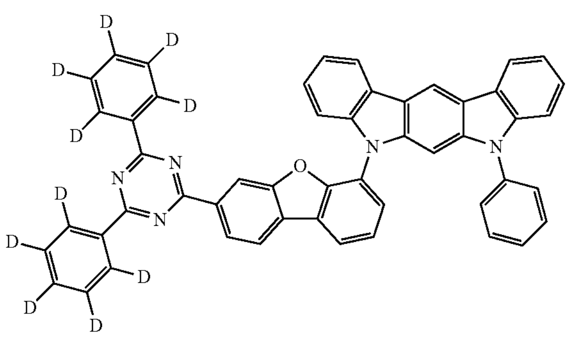
-continued
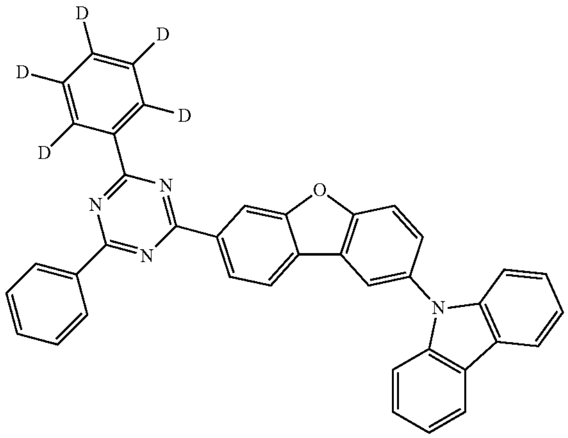
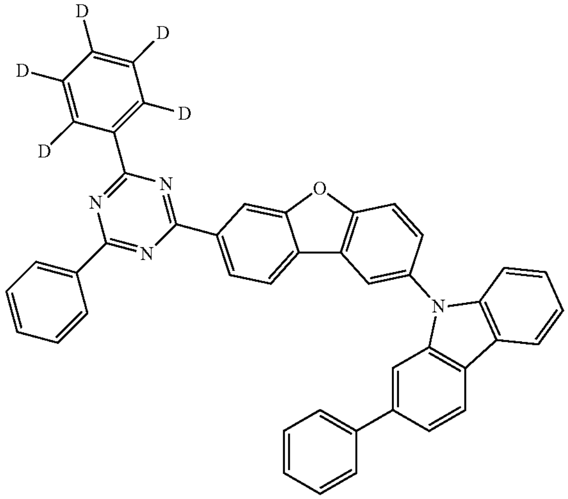
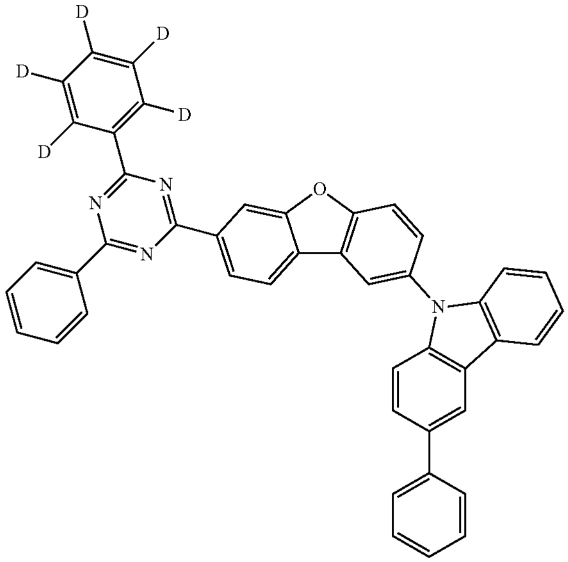

-continued
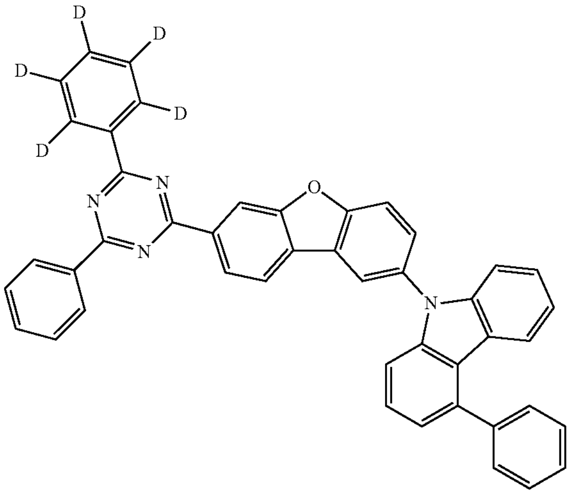
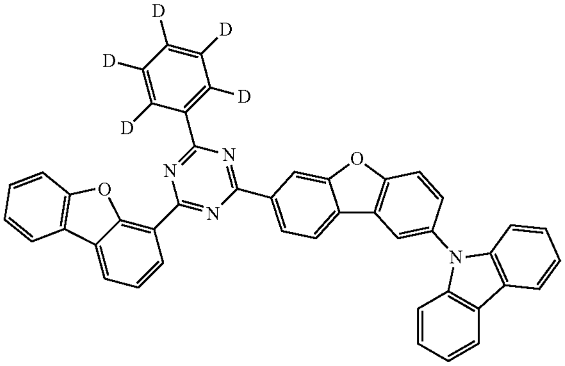
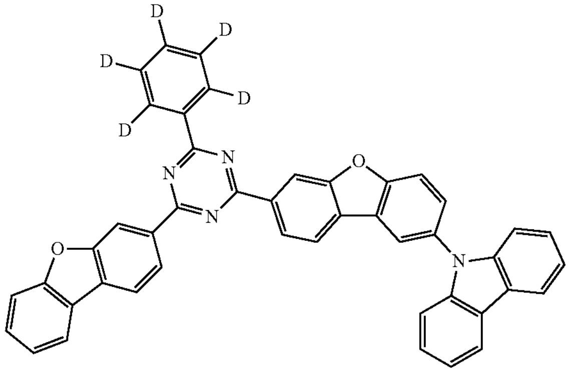
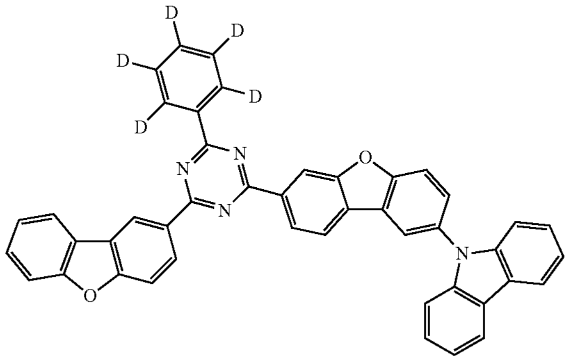
-continued
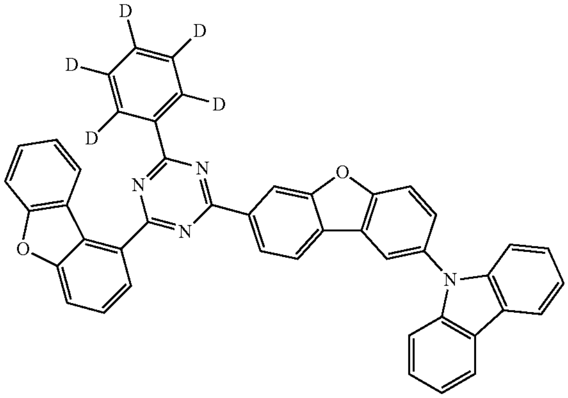
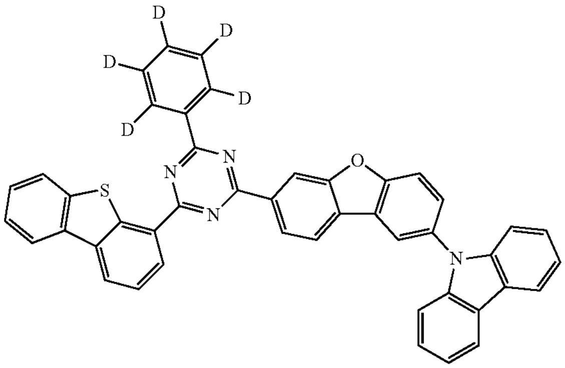
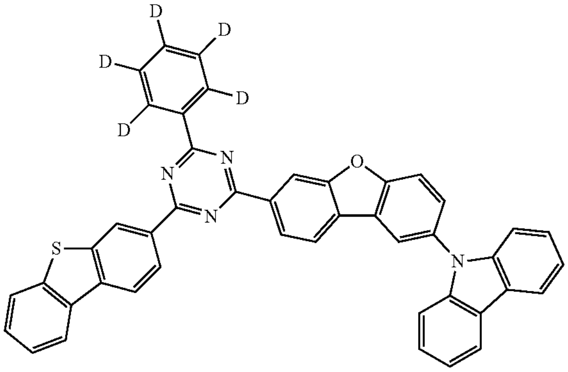
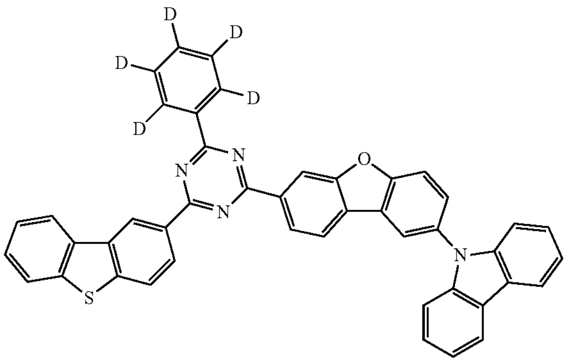

-continued
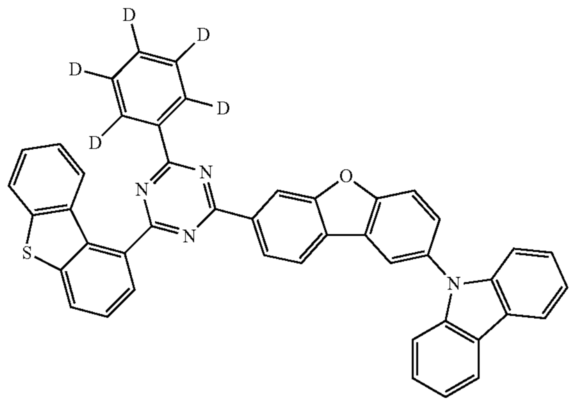
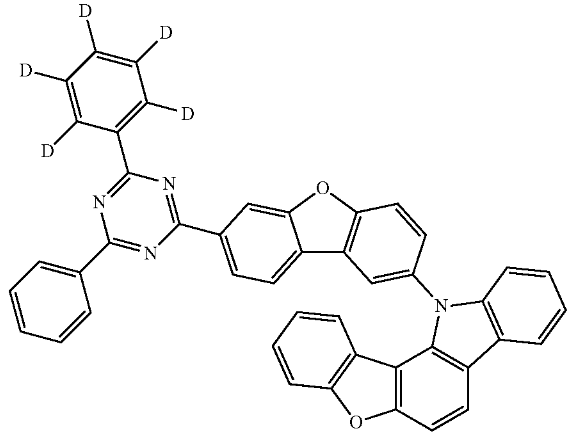
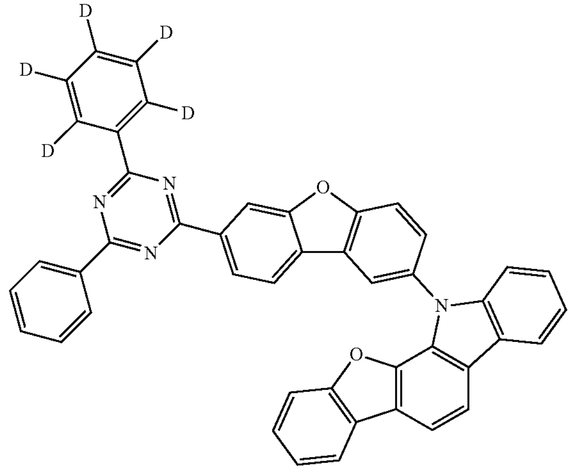
-continued
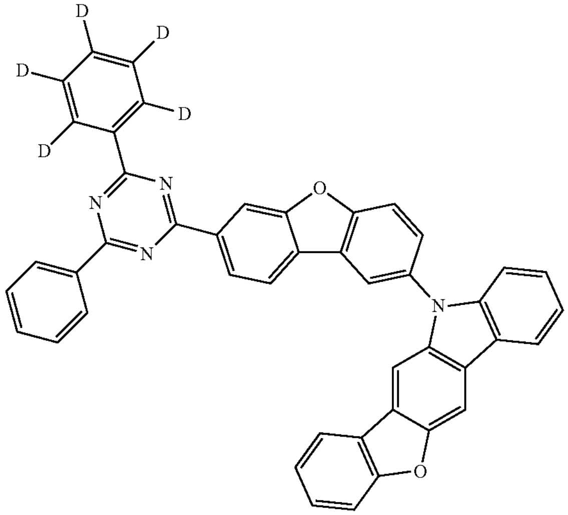
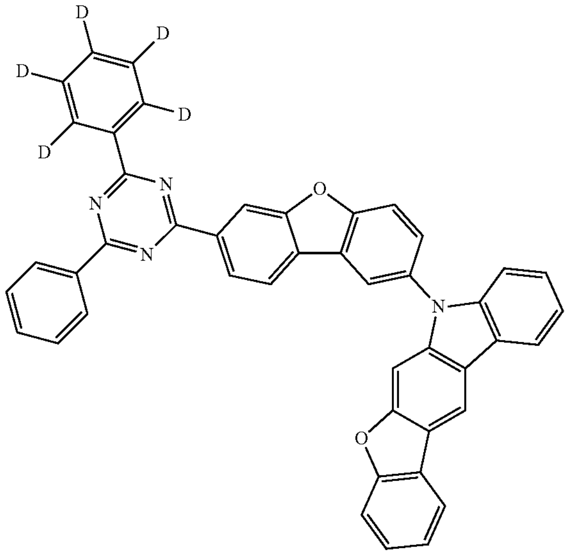
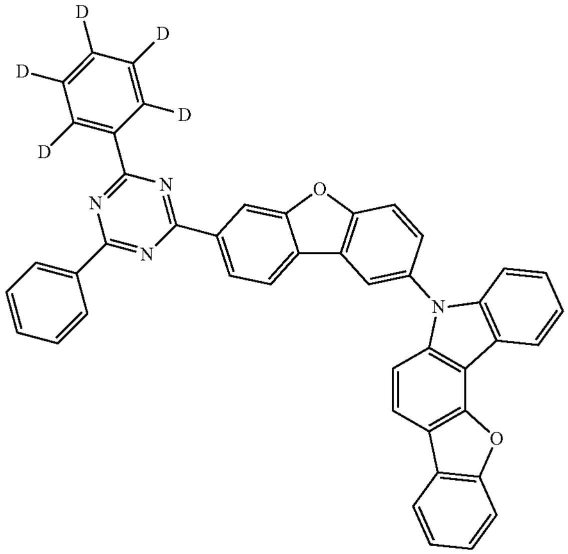

-continued
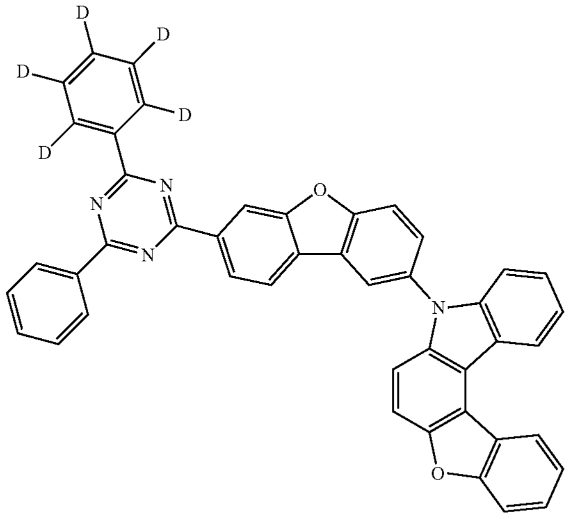
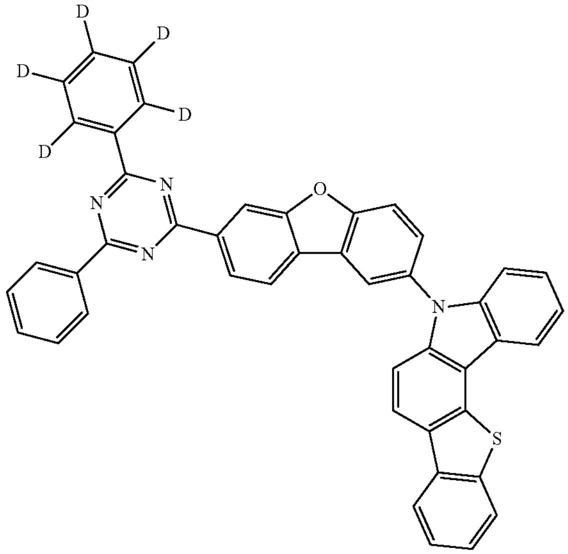
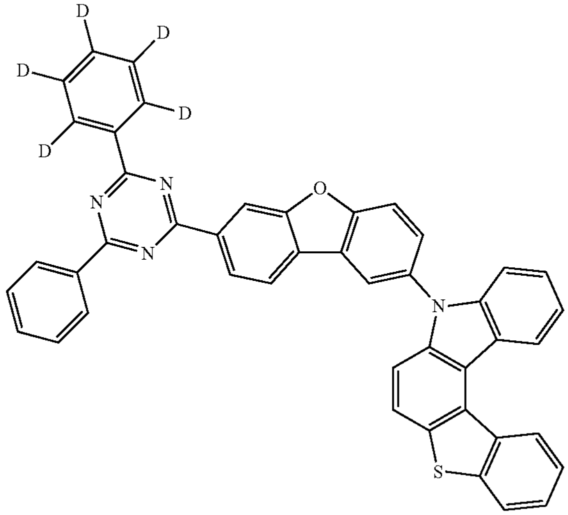
-continued
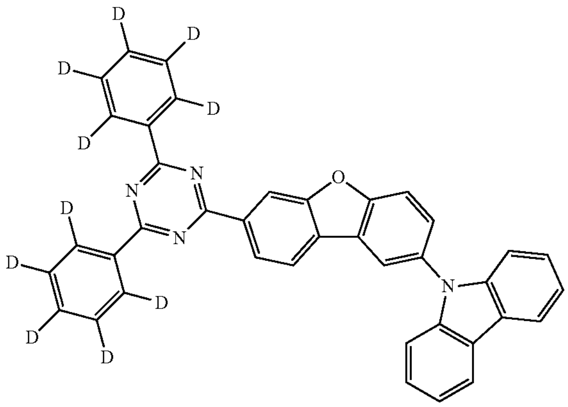
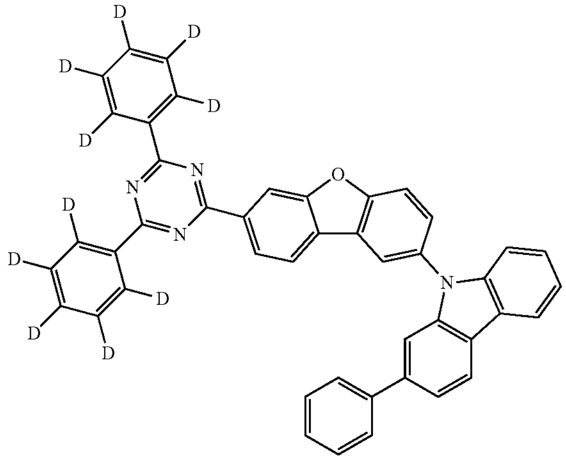
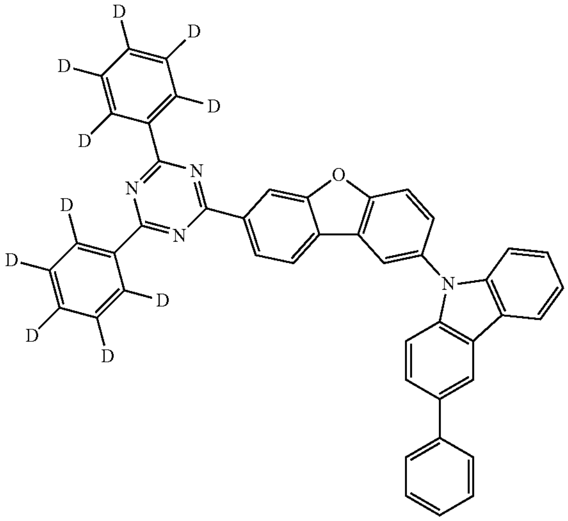

-continued
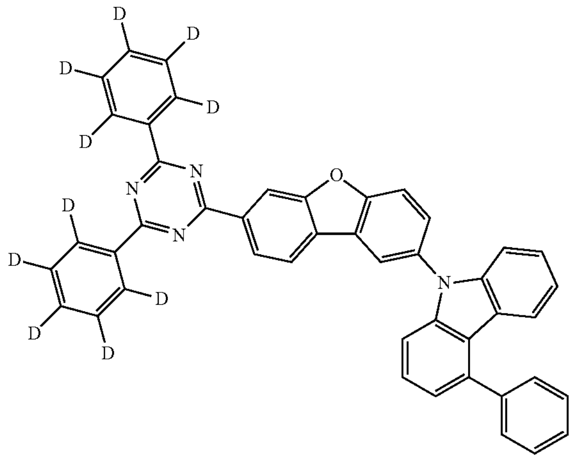
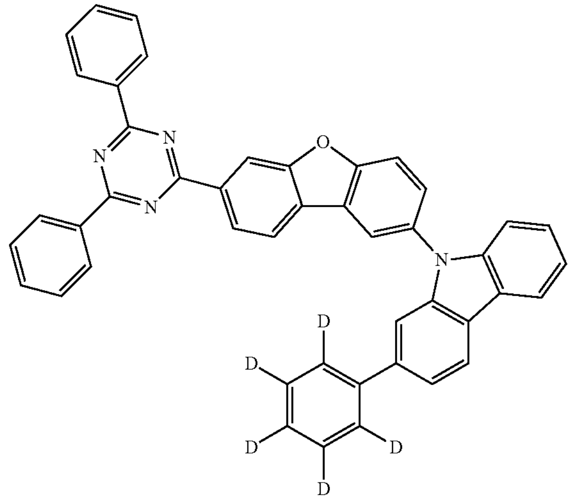
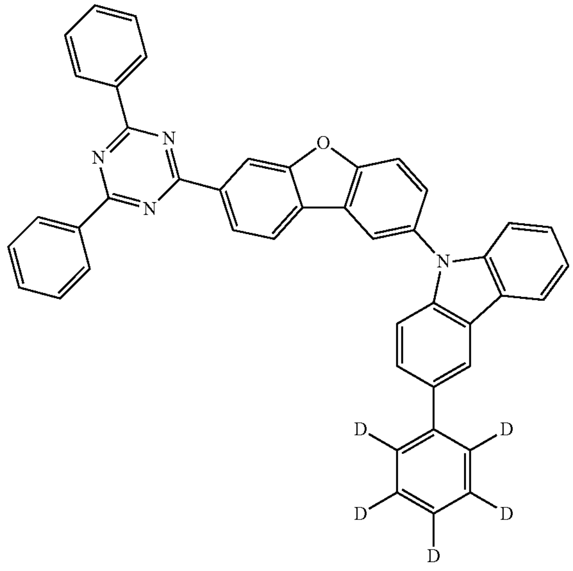
-continued
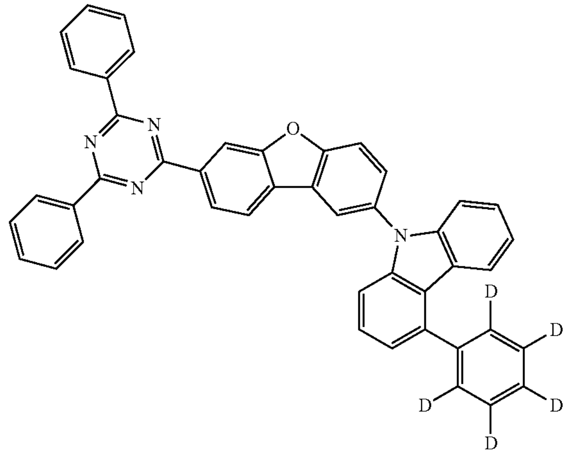
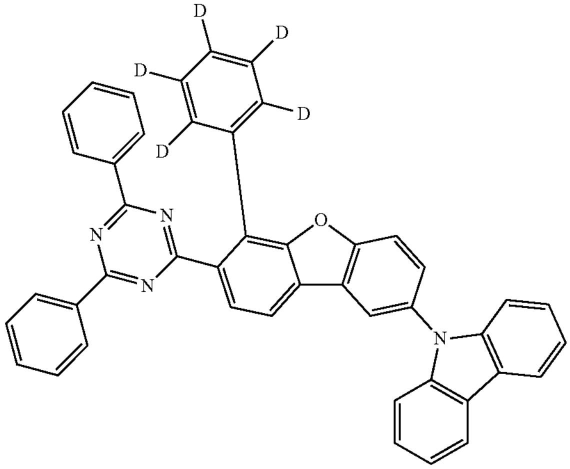
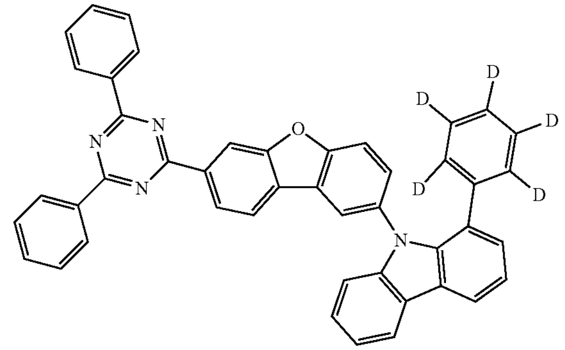
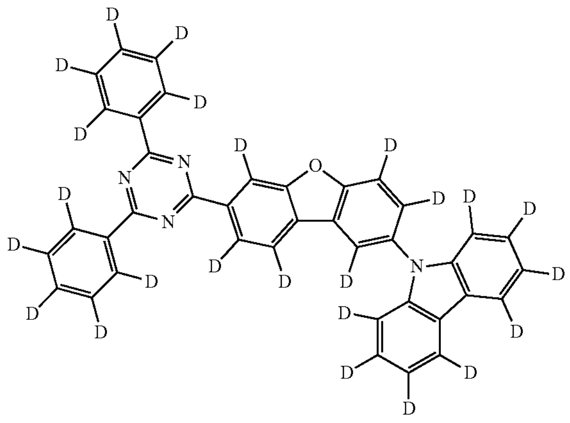

-continued
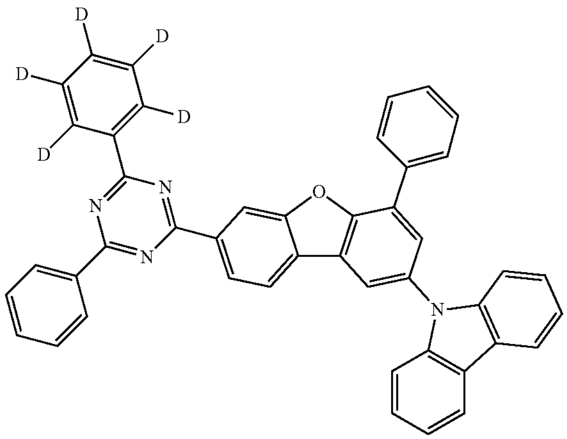
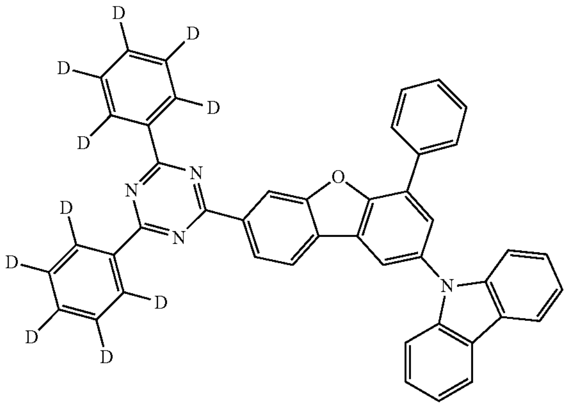
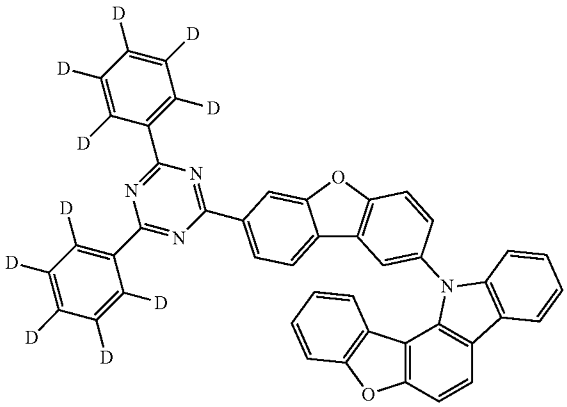
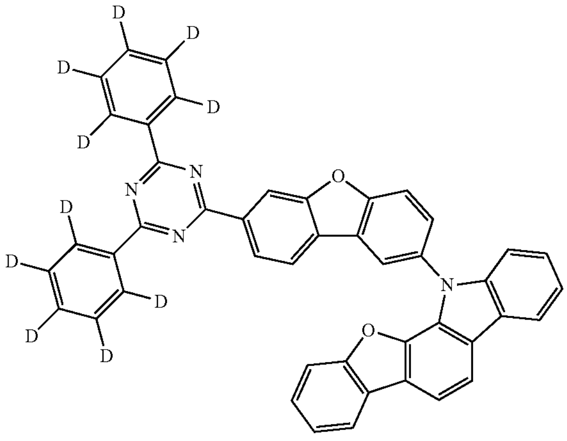
-continued
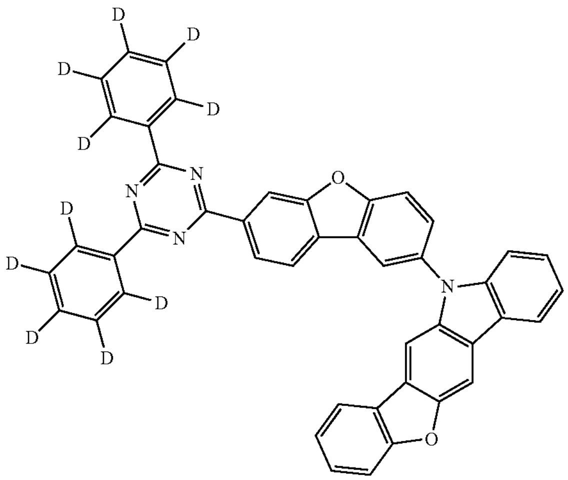
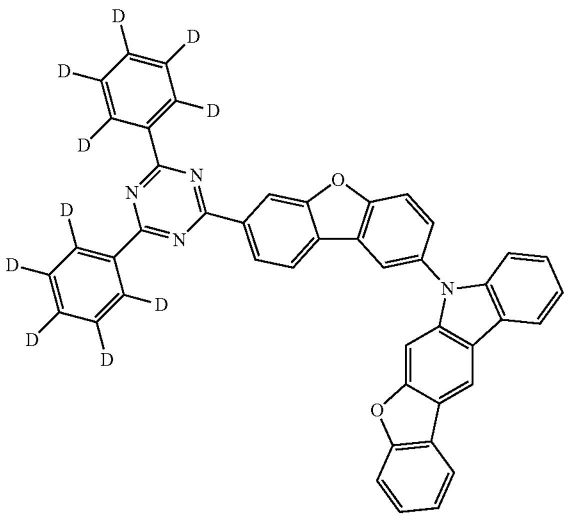
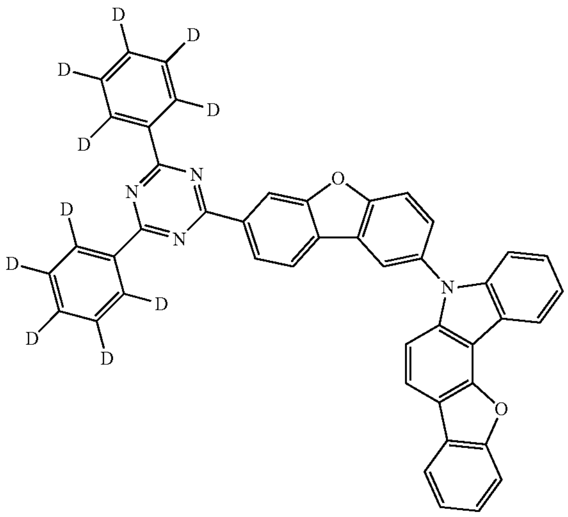

-continued
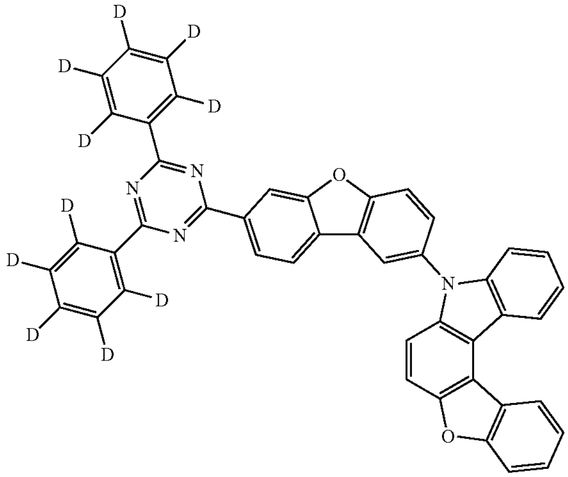
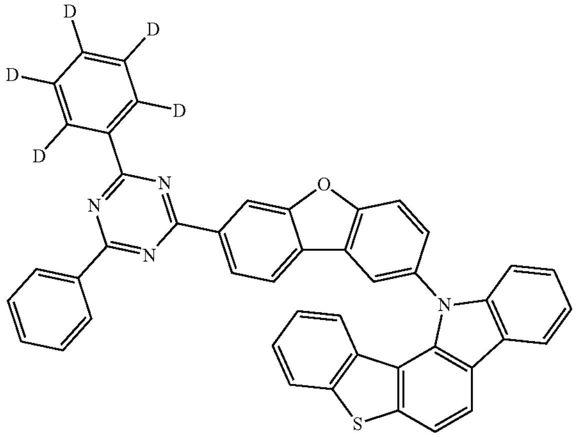
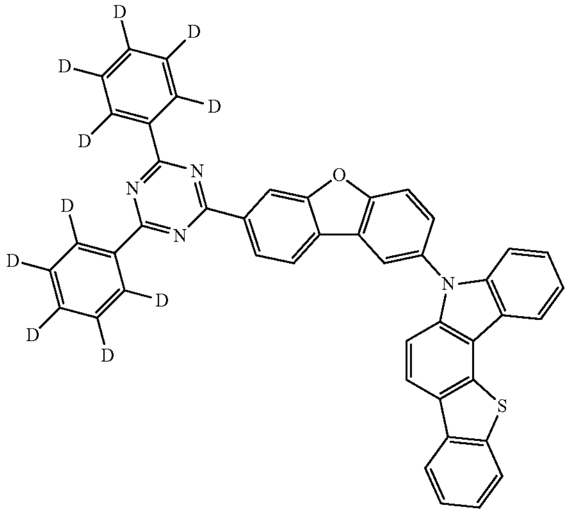
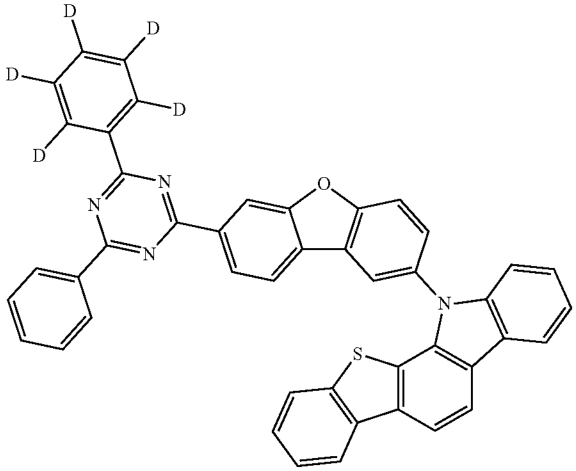
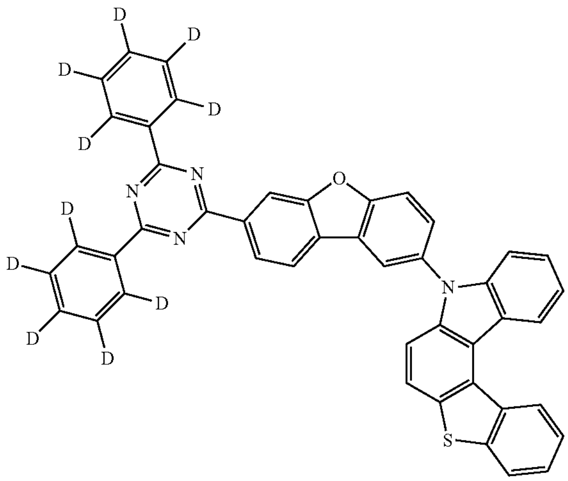
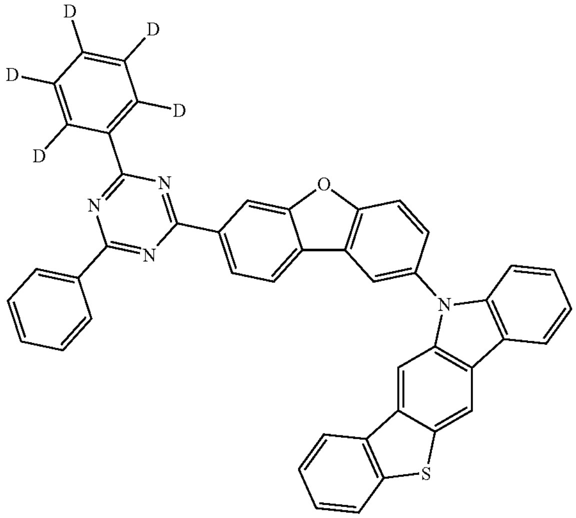

-continued
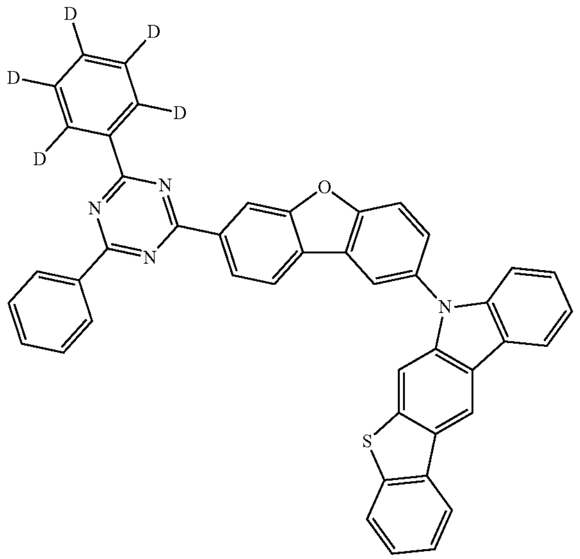
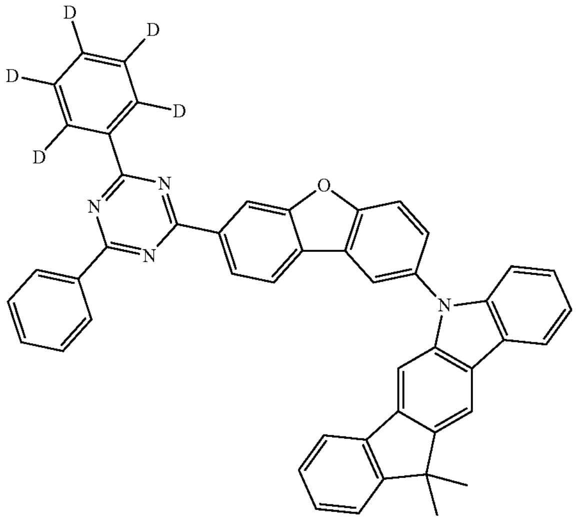
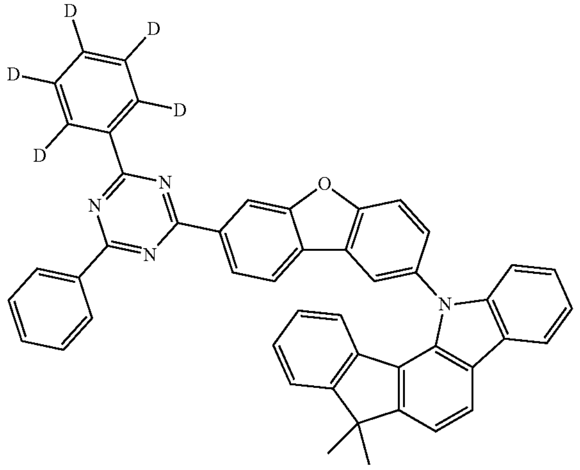
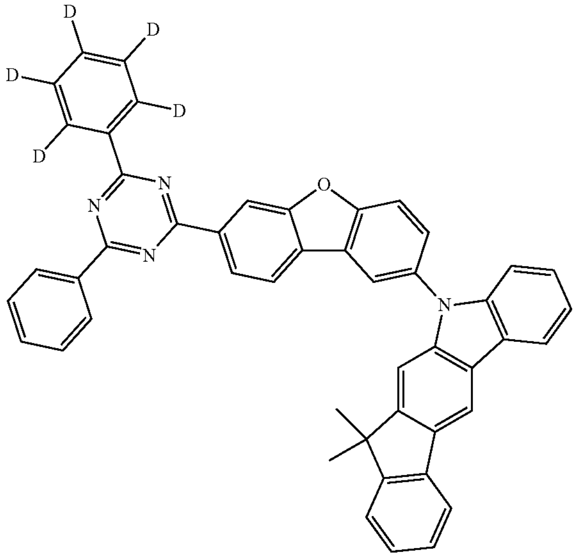
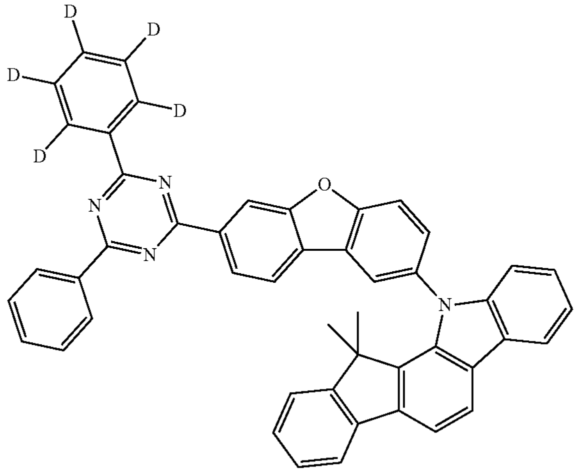
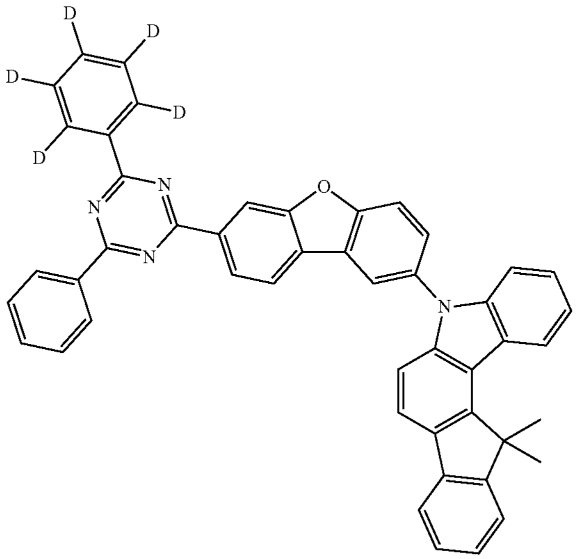
-continued -continued
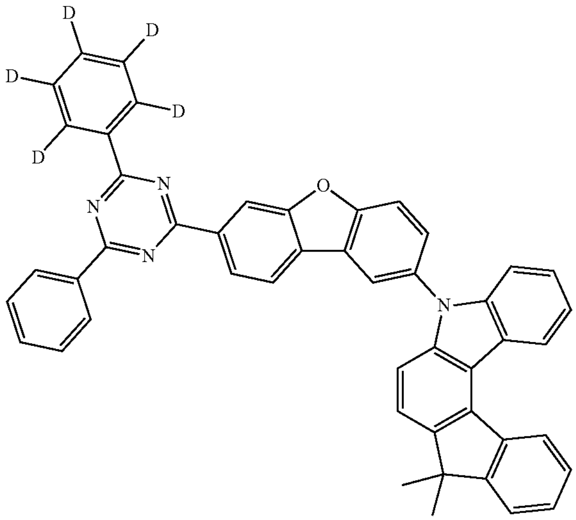
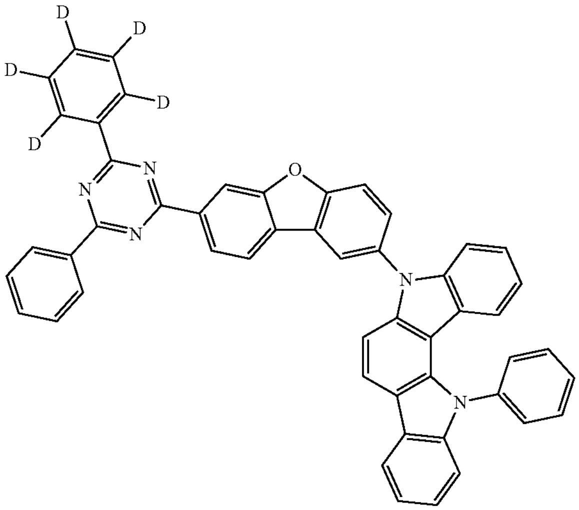
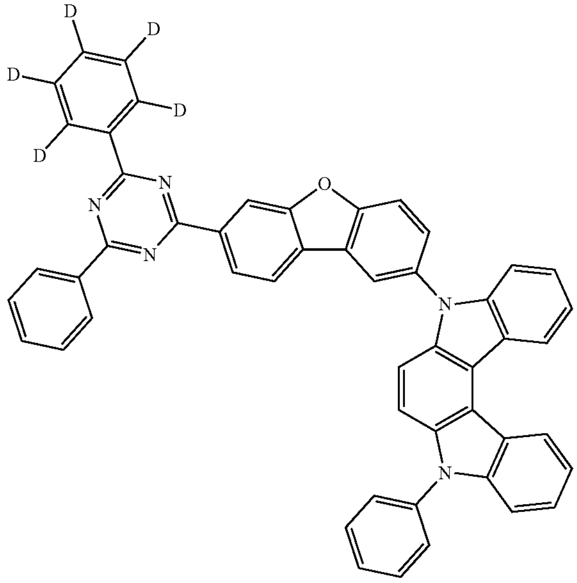
-continued
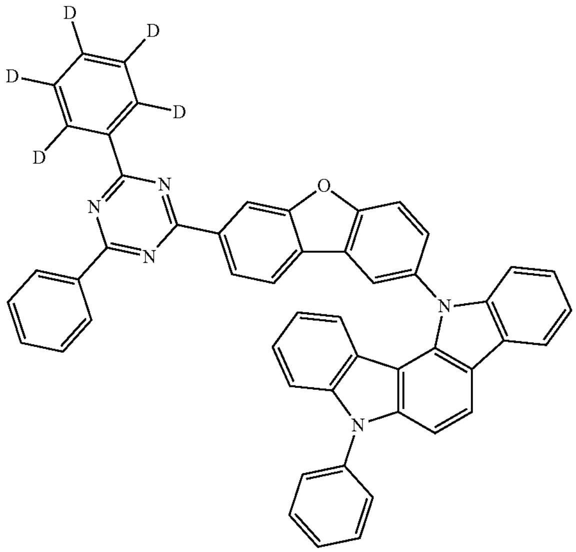
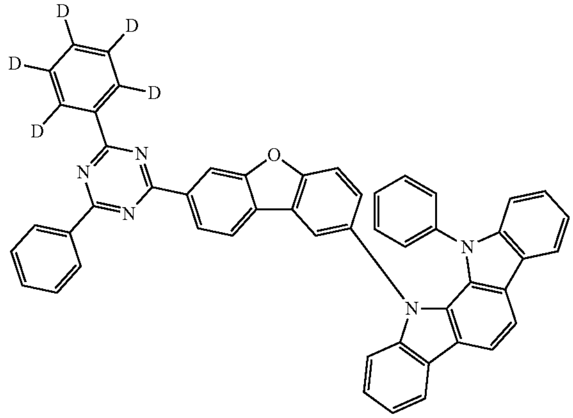
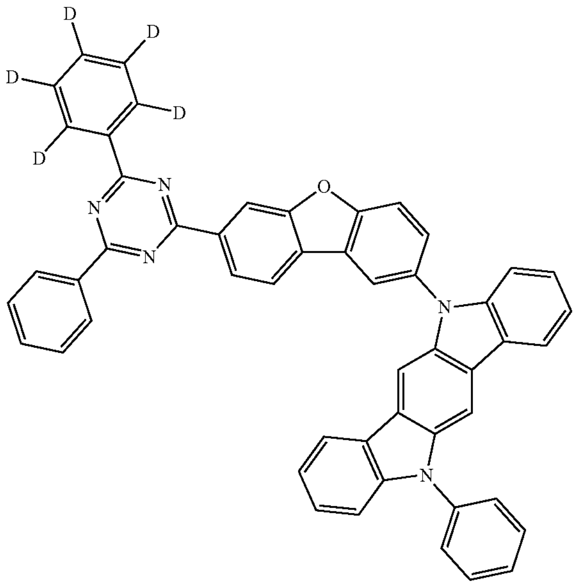

-continued
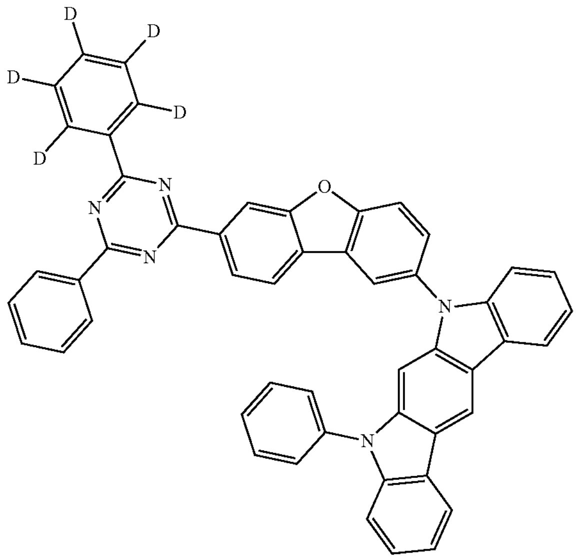
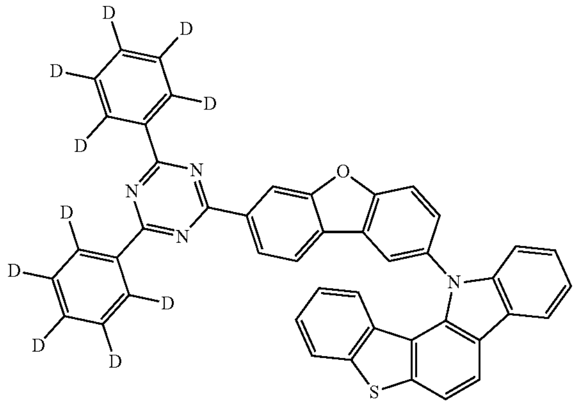
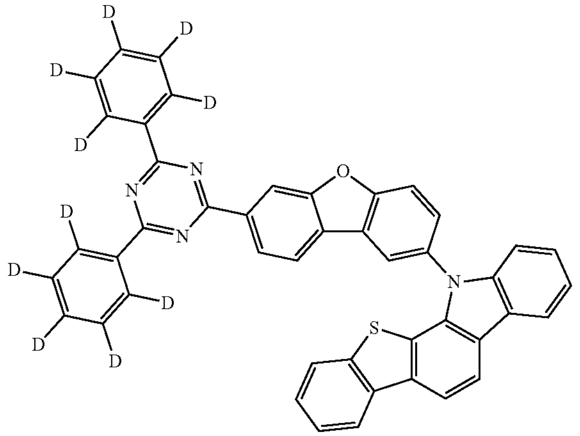
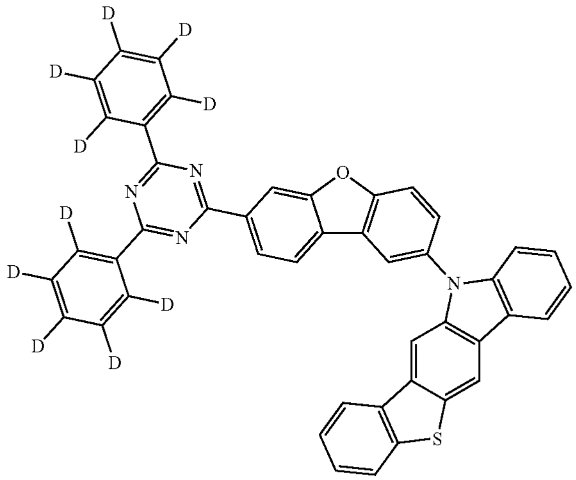
-continued
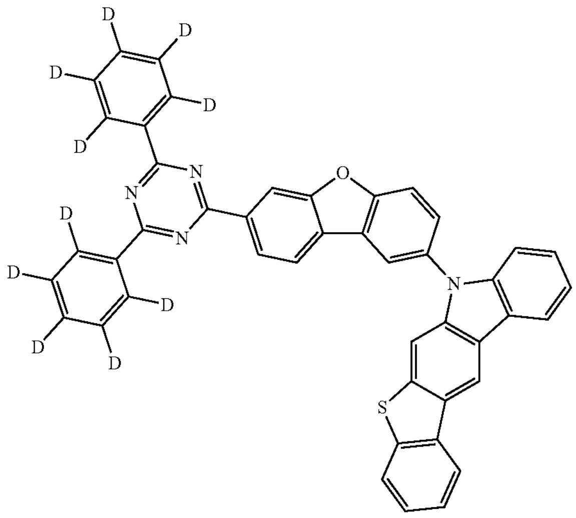
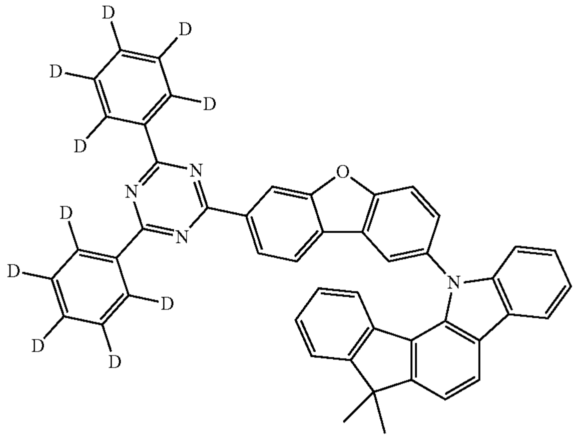

-continued
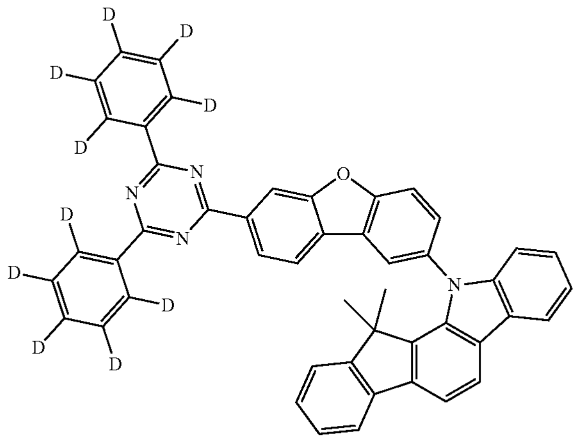
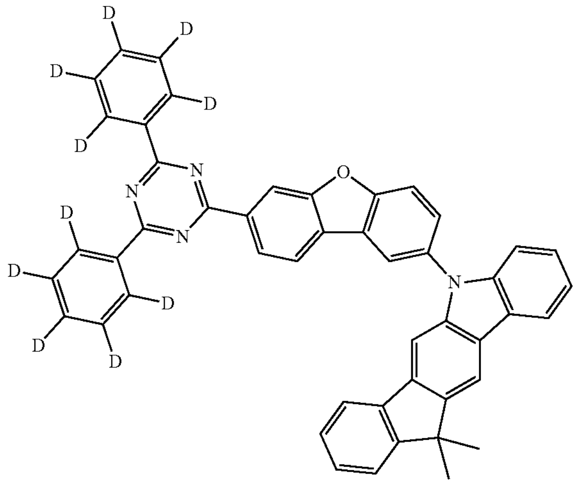
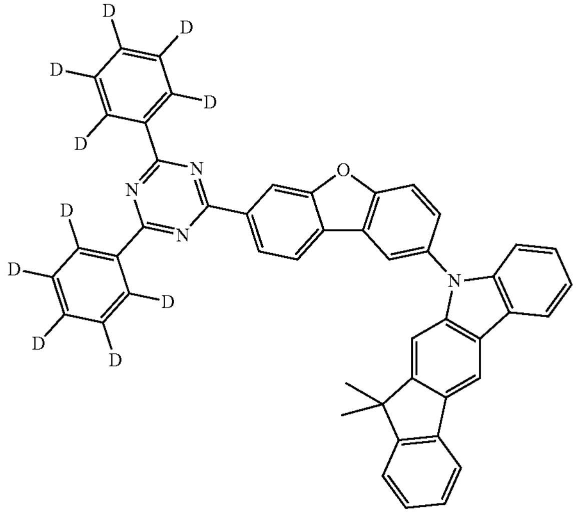
-continued
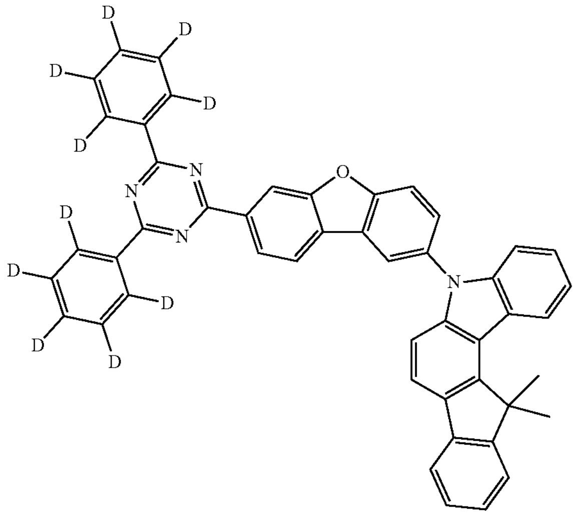
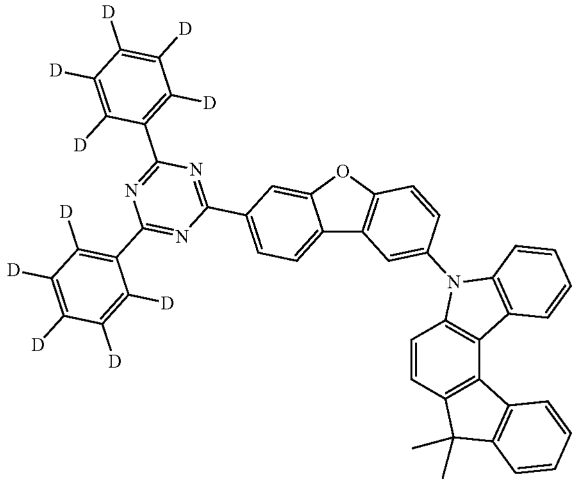
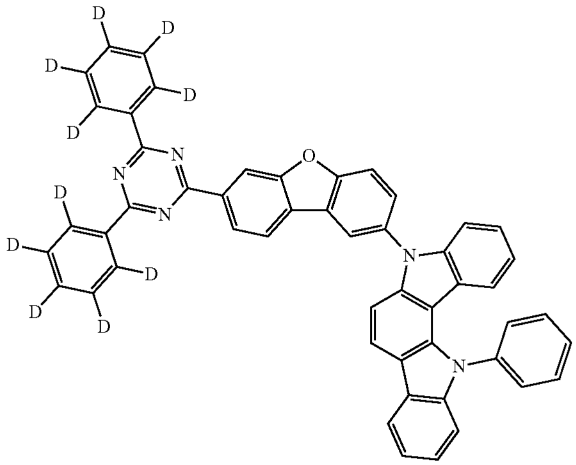

-continued
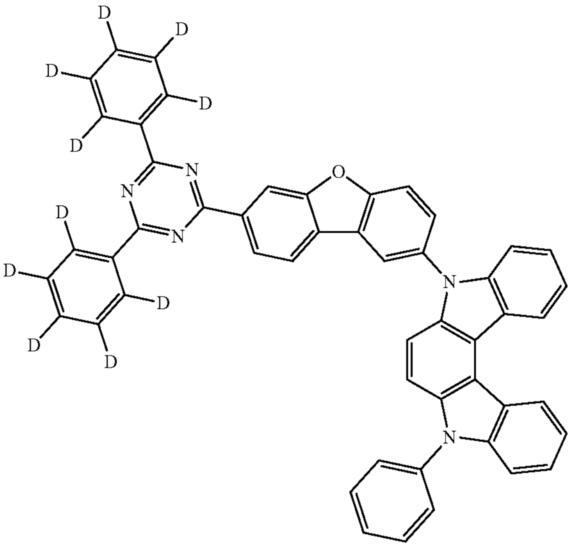
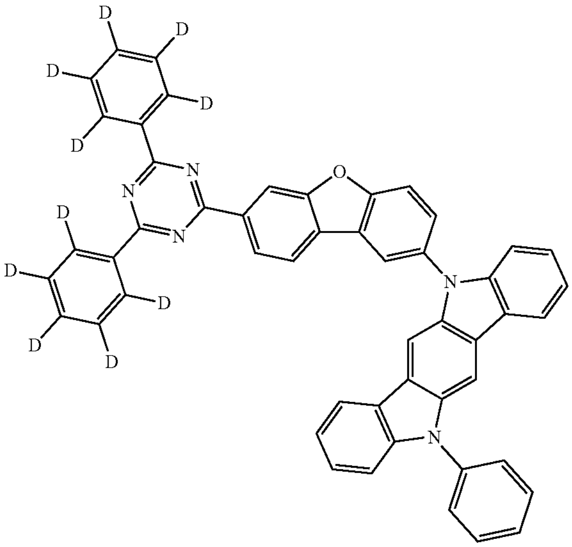
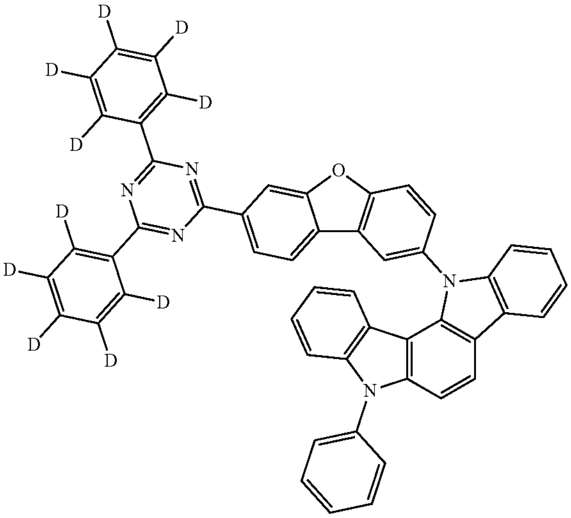
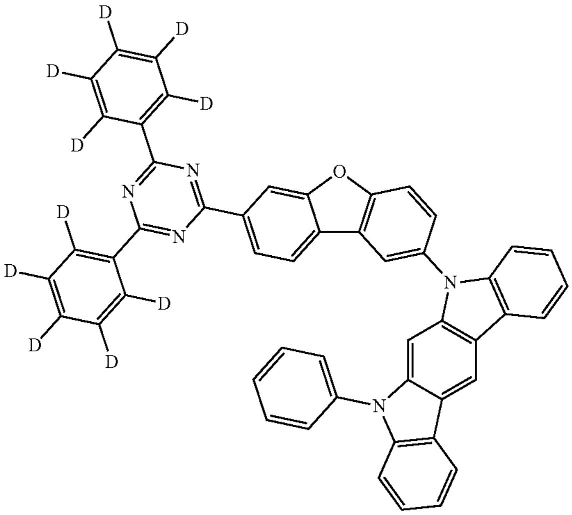
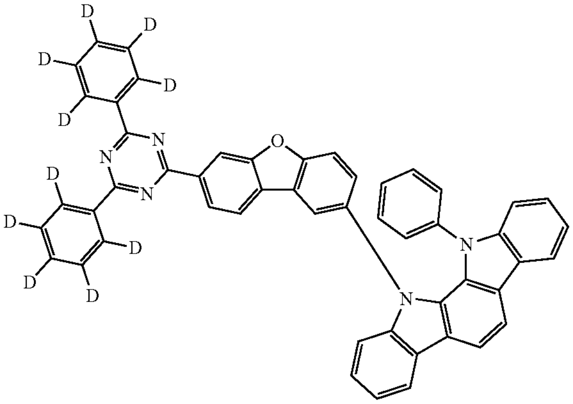
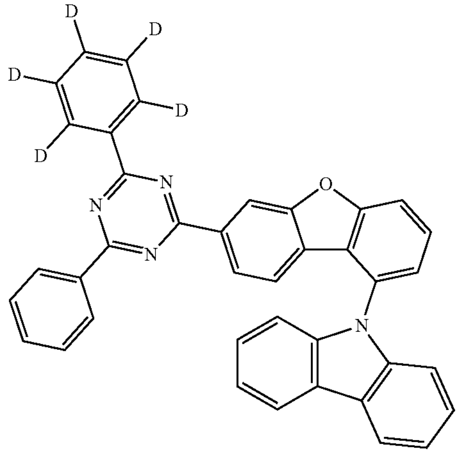
-continued -continued
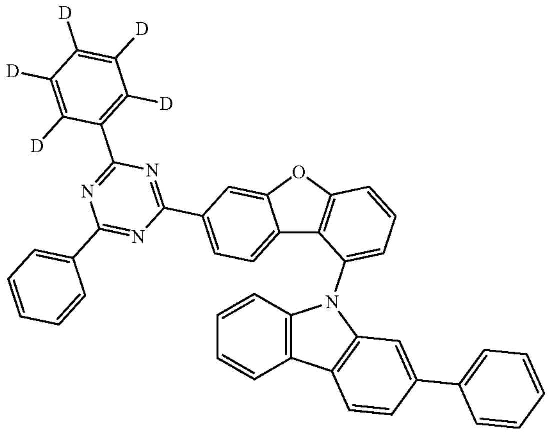
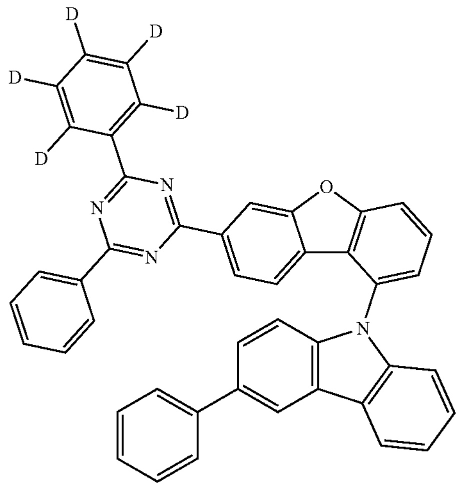
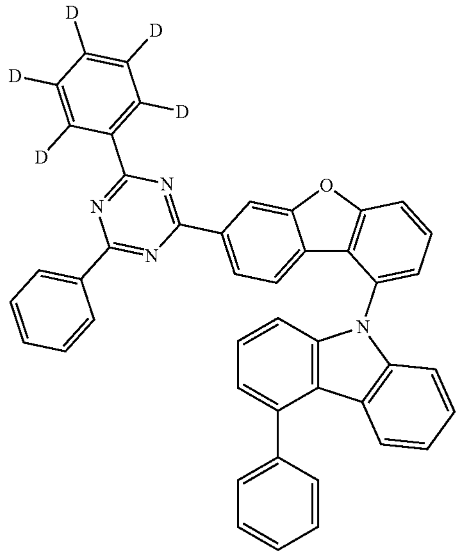
-continued
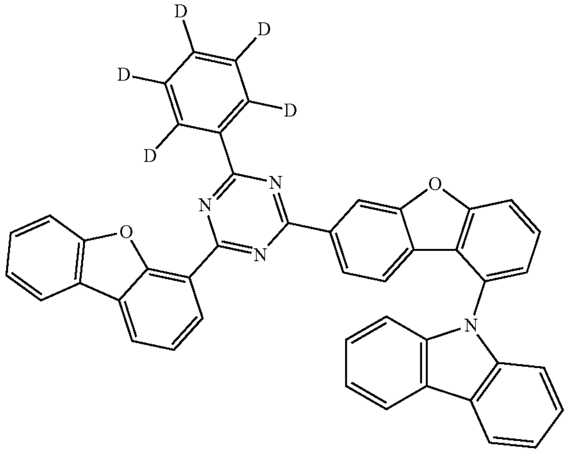
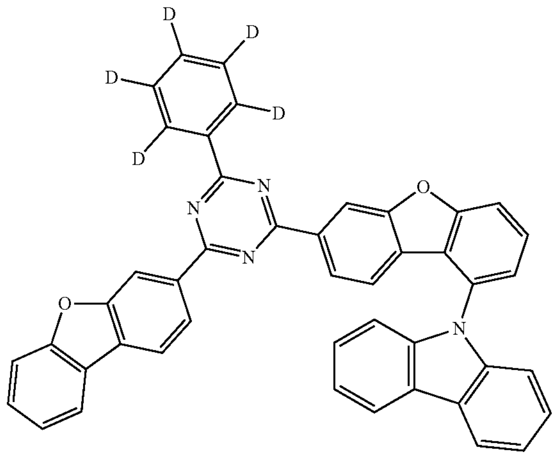
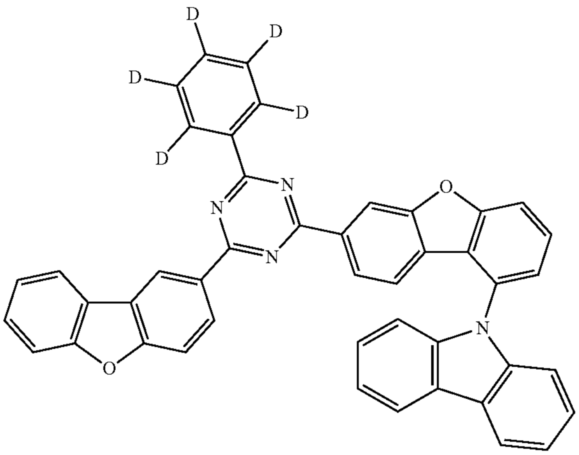

-continued
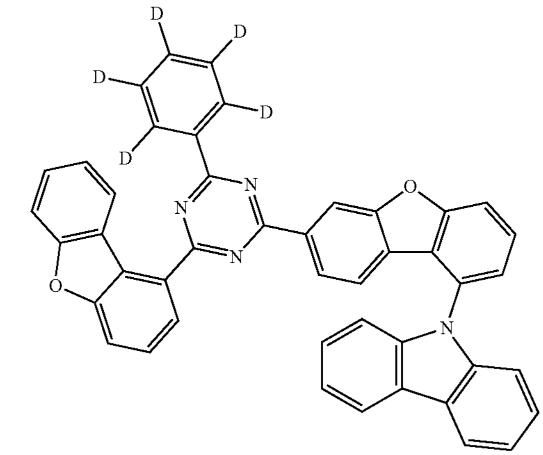
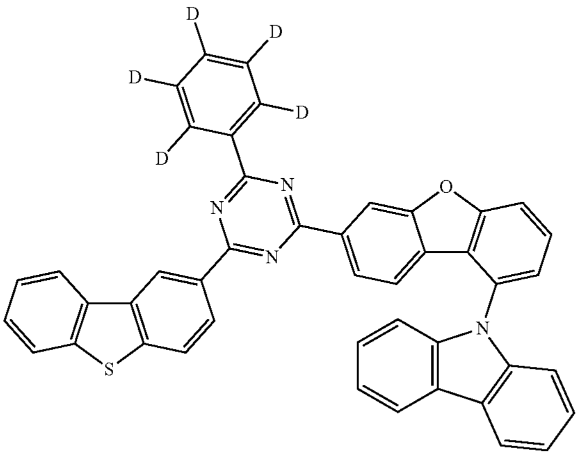
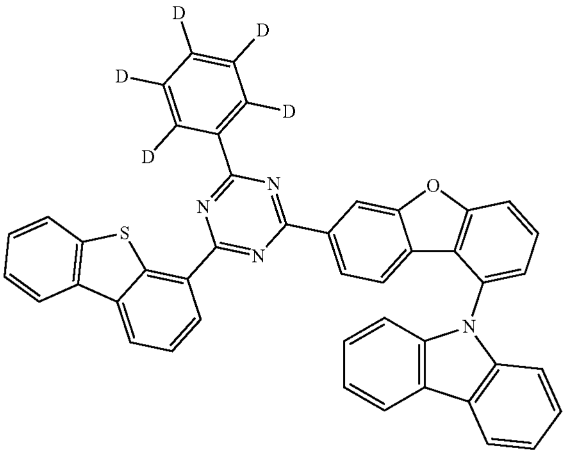
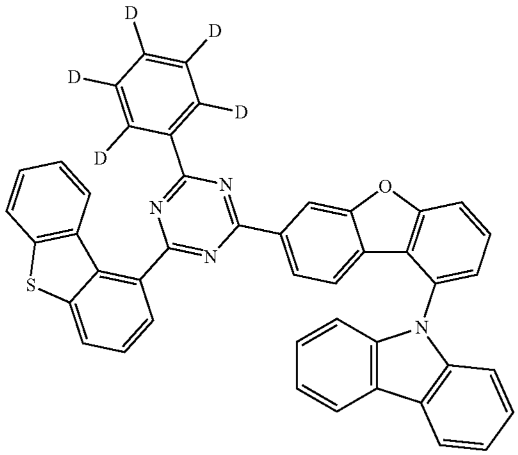
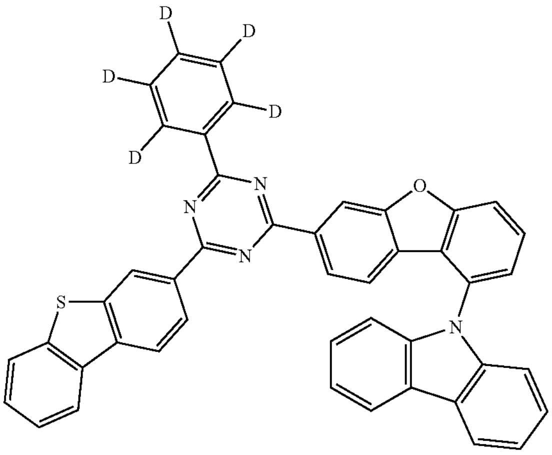
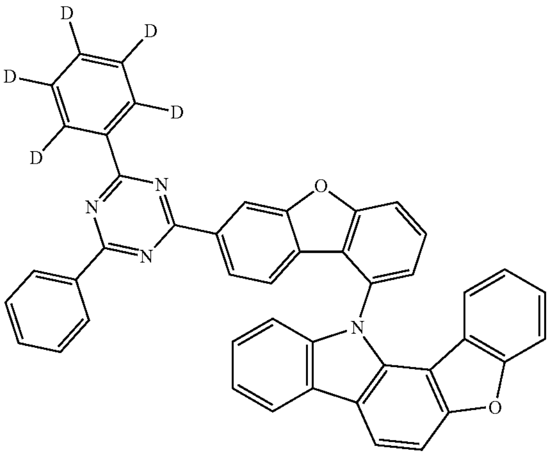
-continued -continued
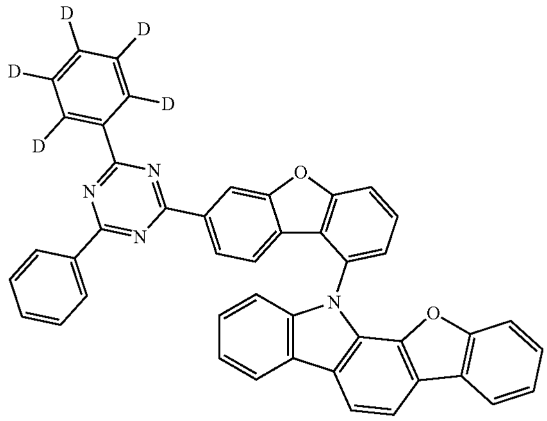
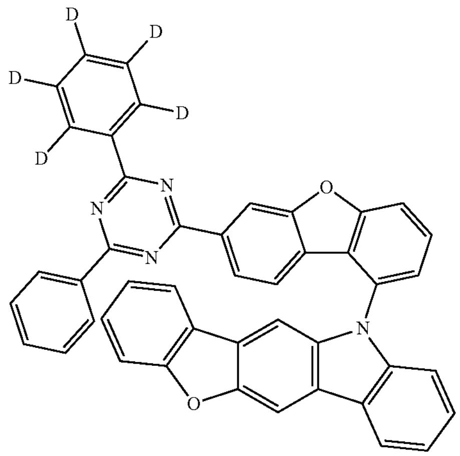
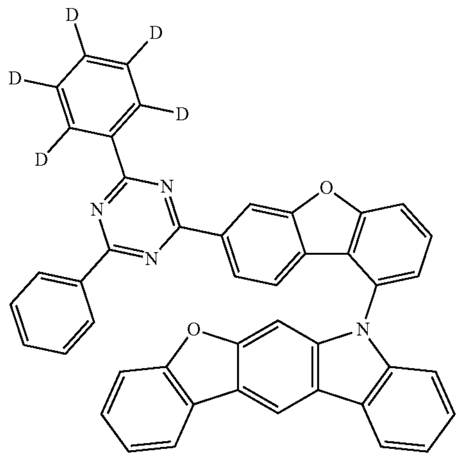
-continued
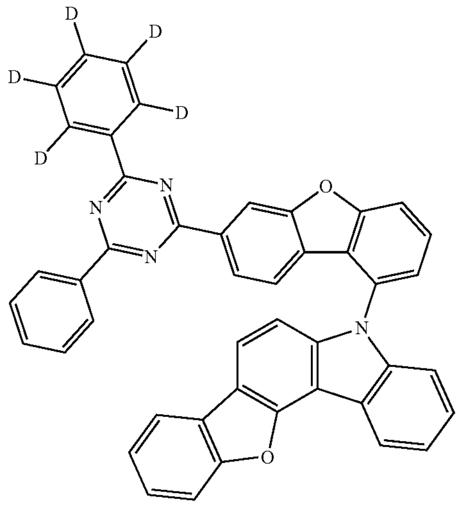
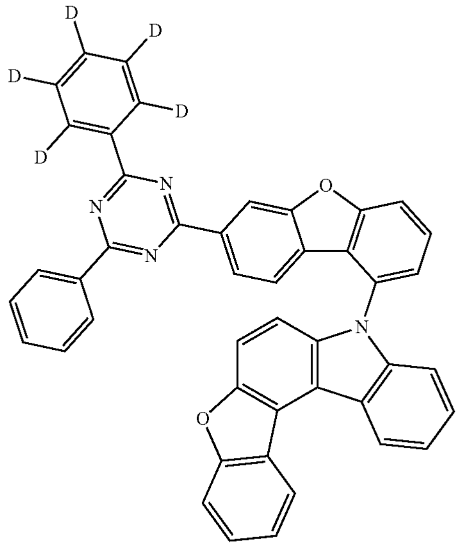
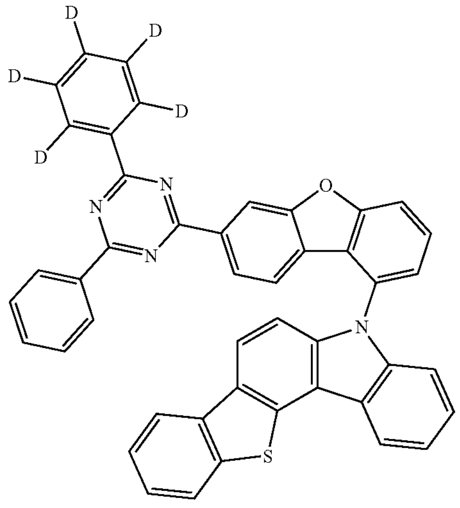

-continued
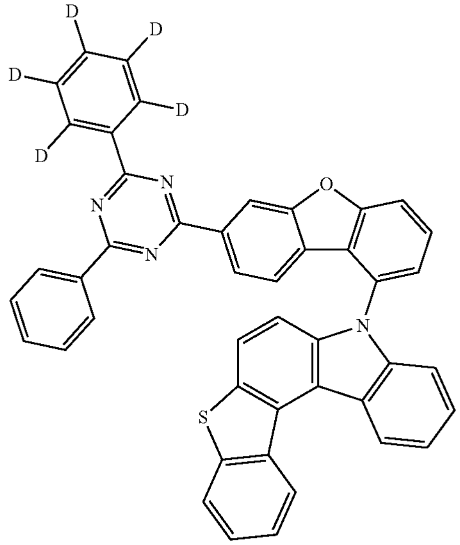
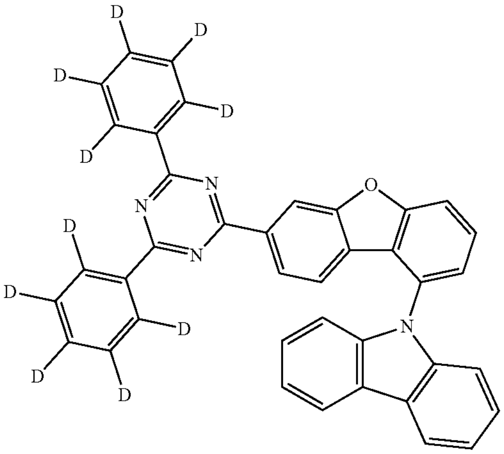
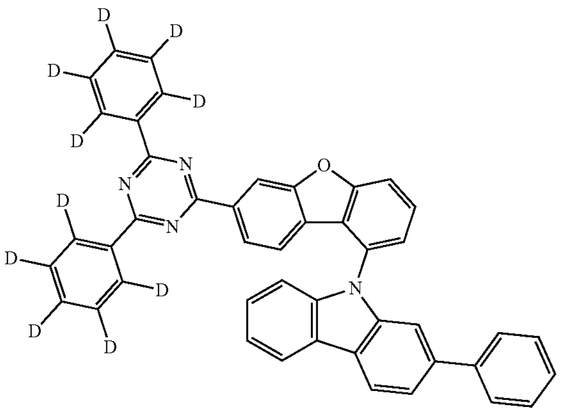
-continued
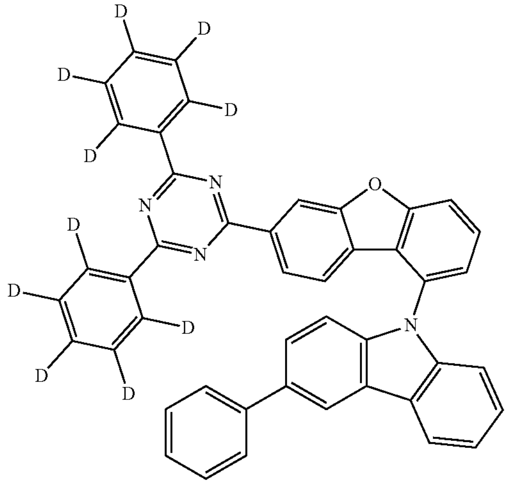
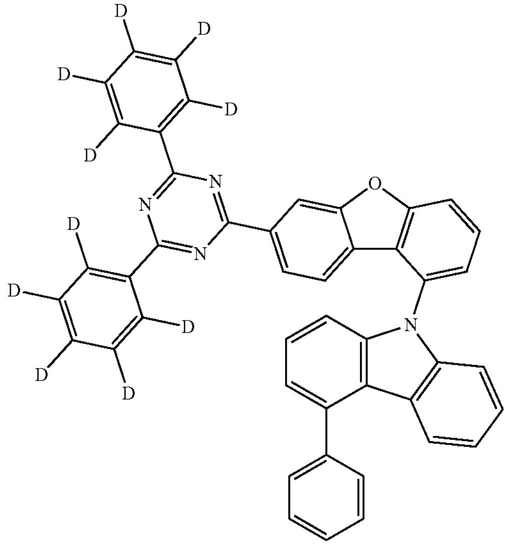
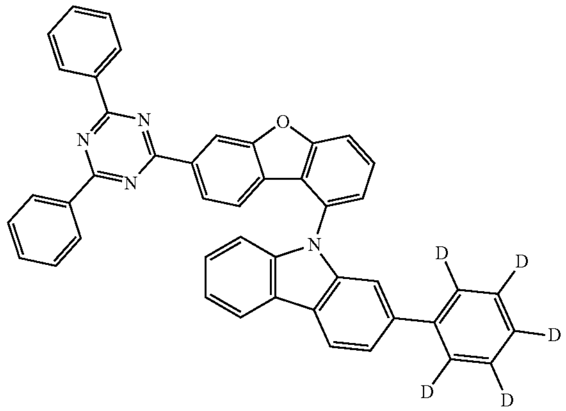

-continued
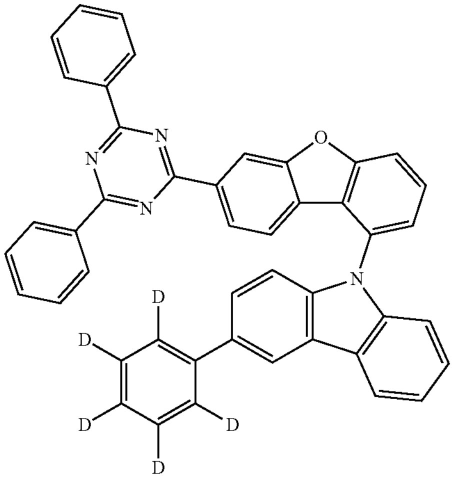
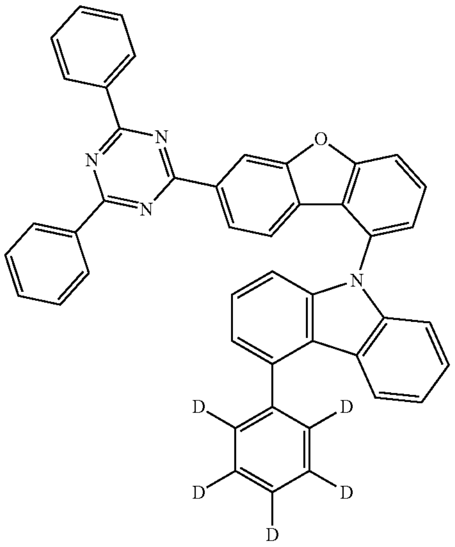
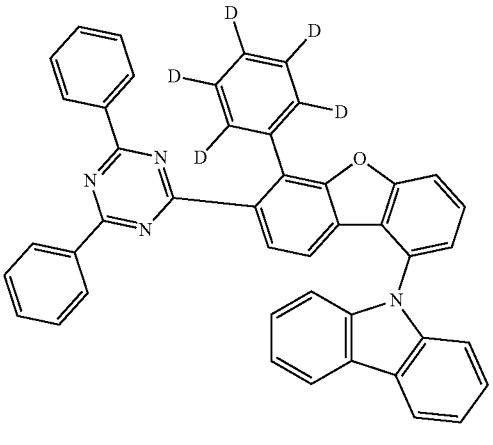
-continued
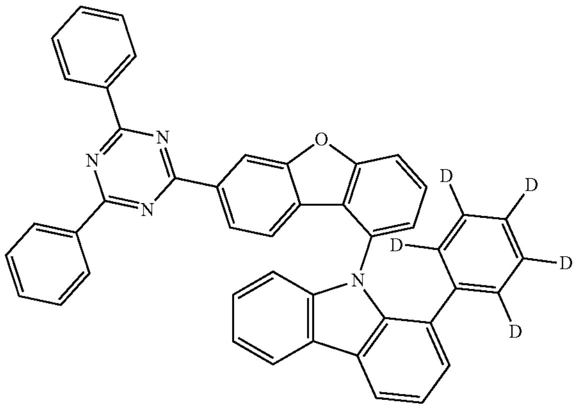
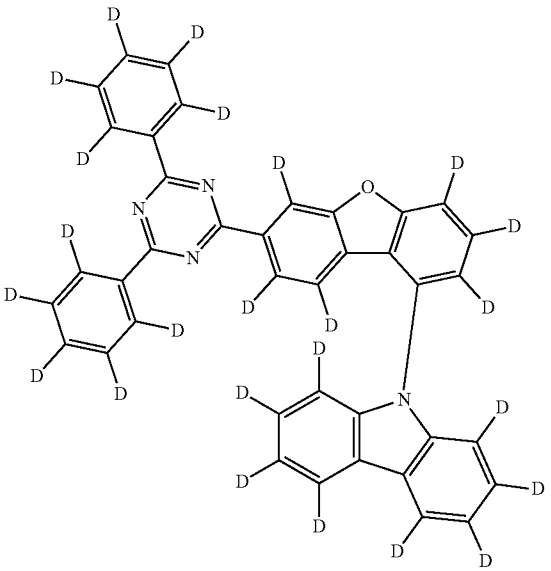
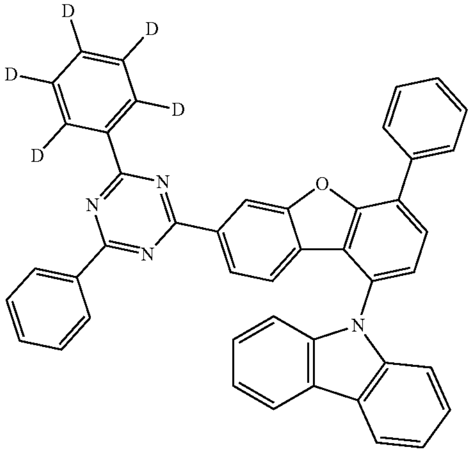

-continued
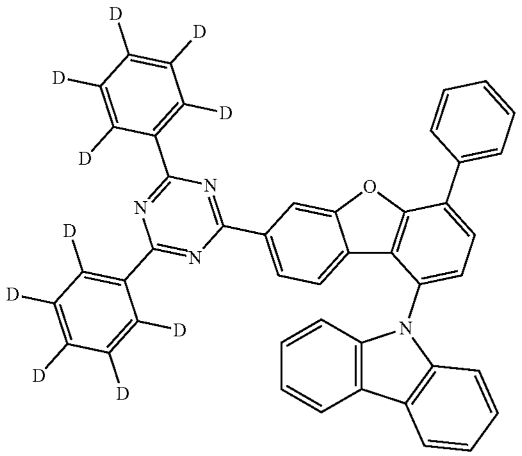
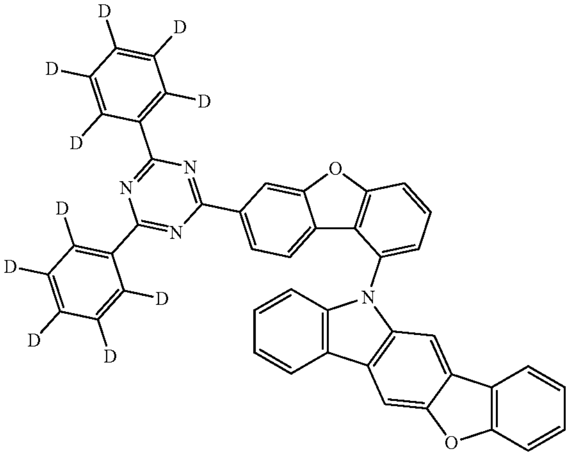
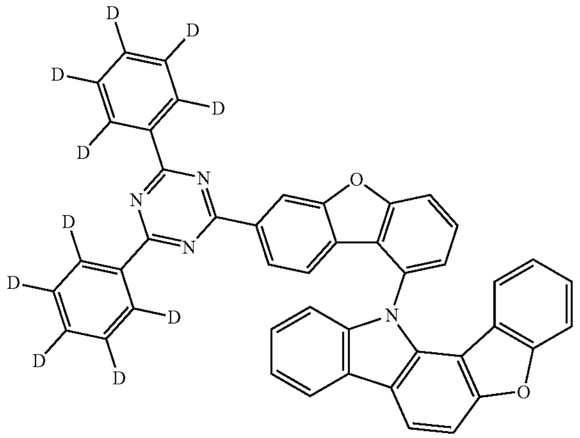
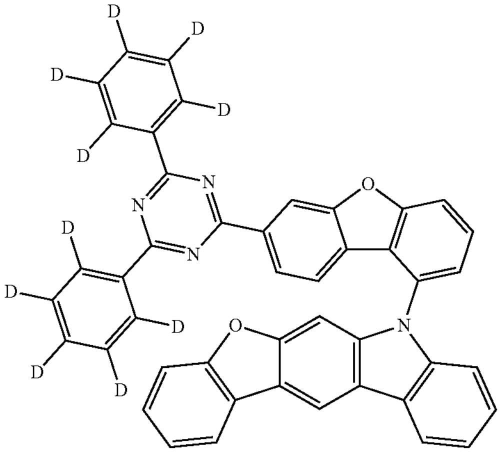
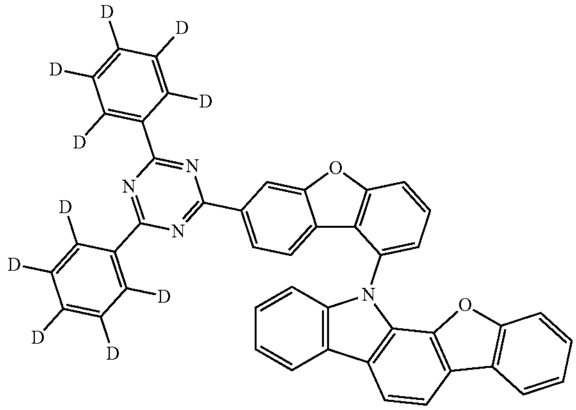
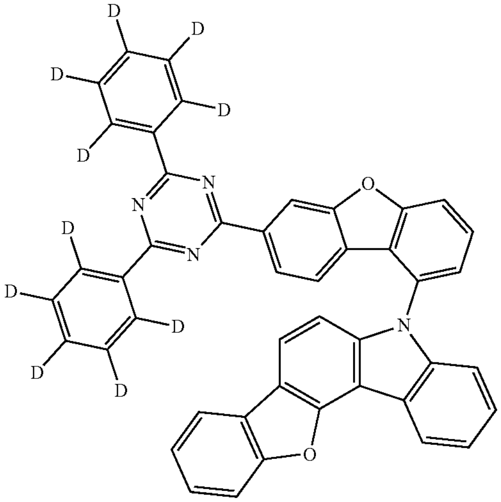
-continued -continued
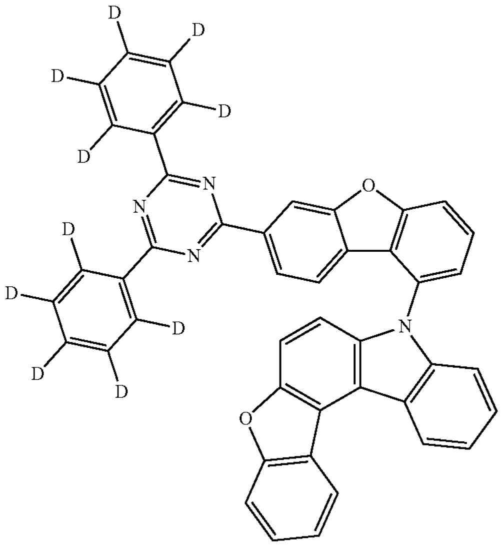
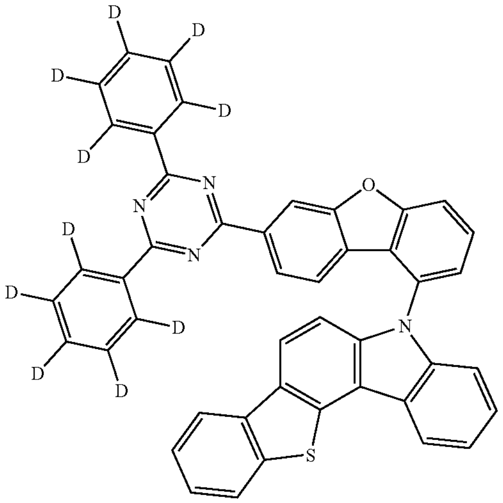
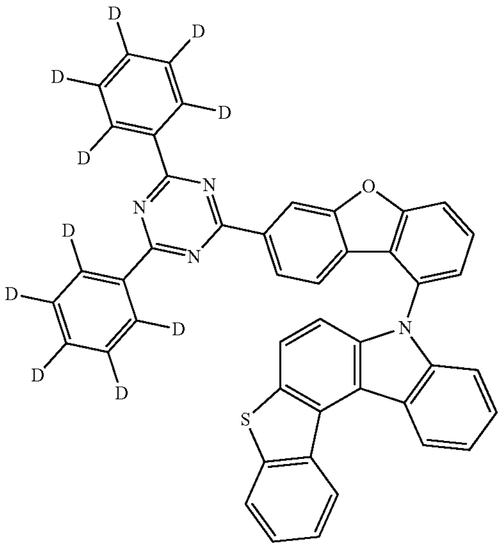
-continued
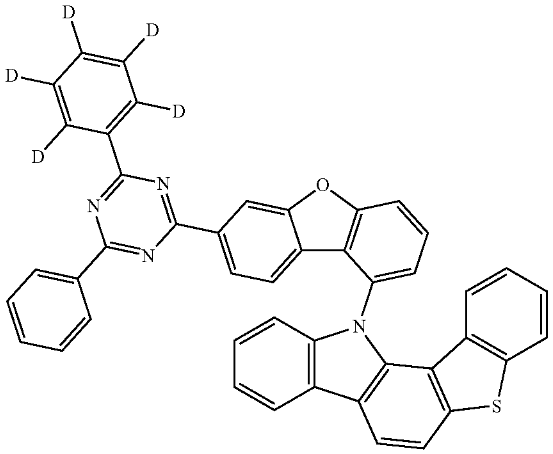
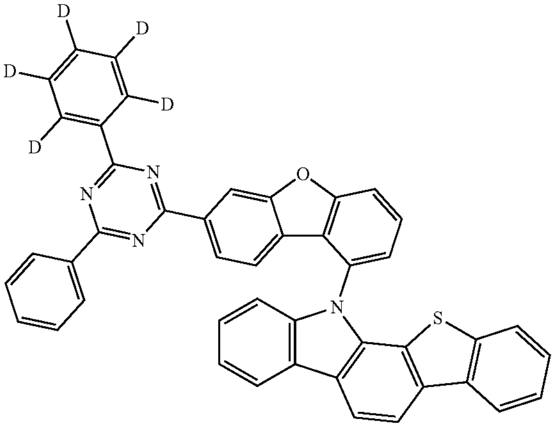
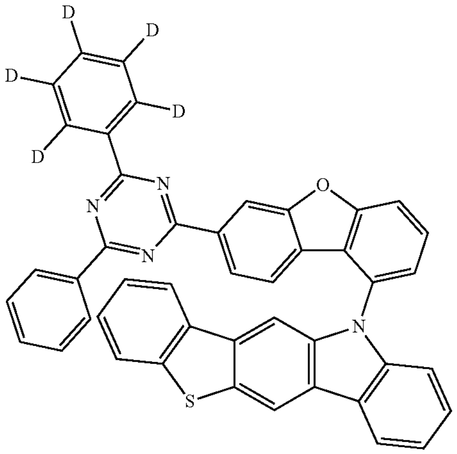

-continued
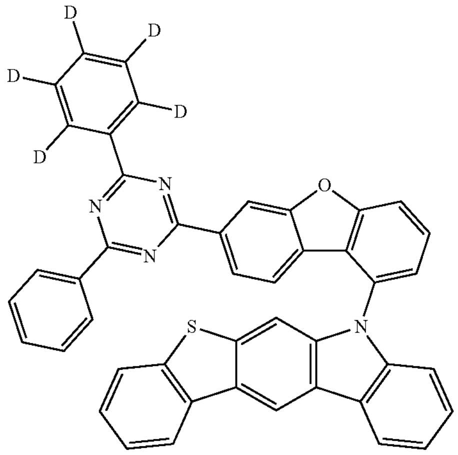
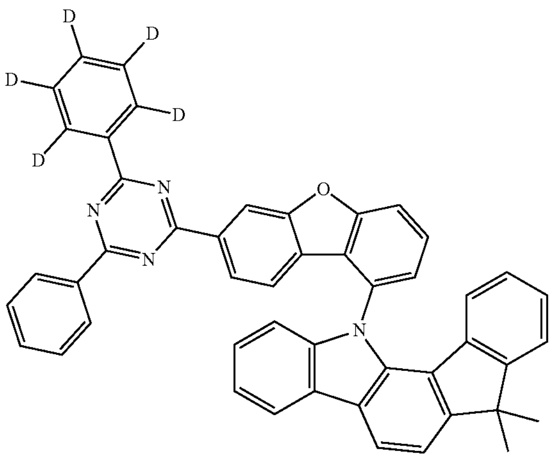
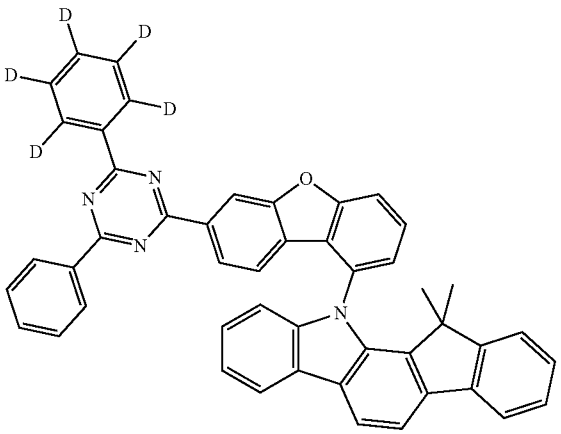
-continued
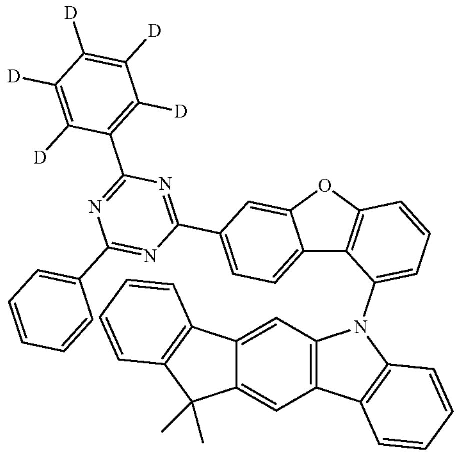
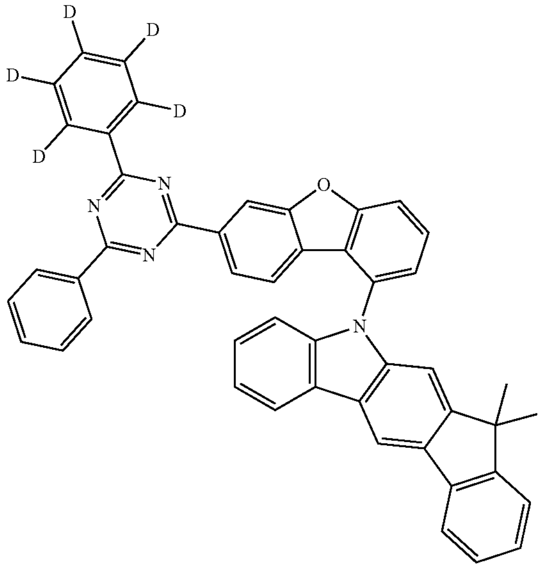
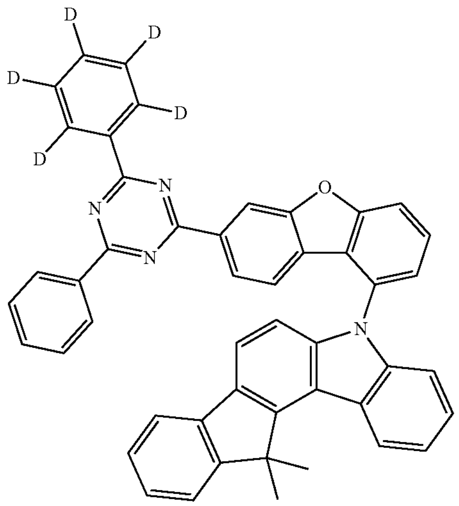

-continued
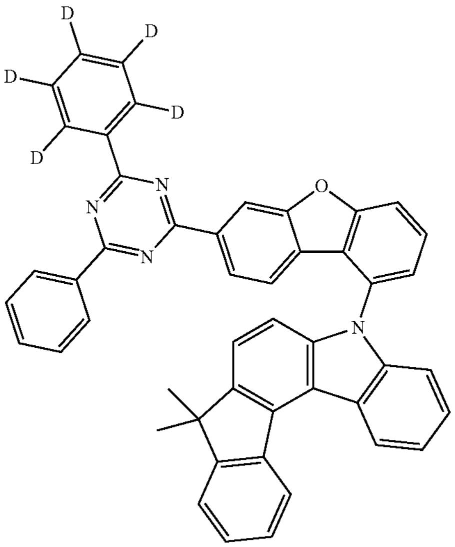
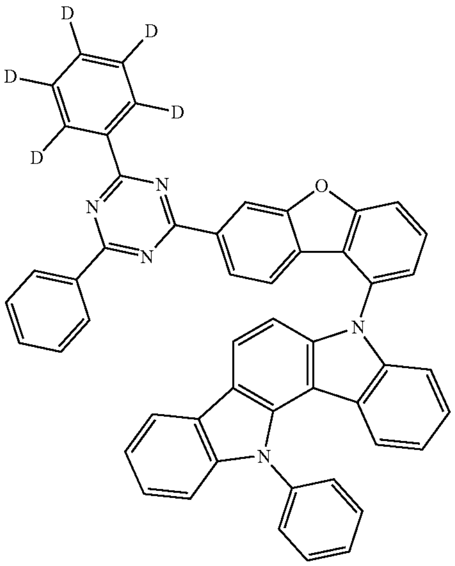
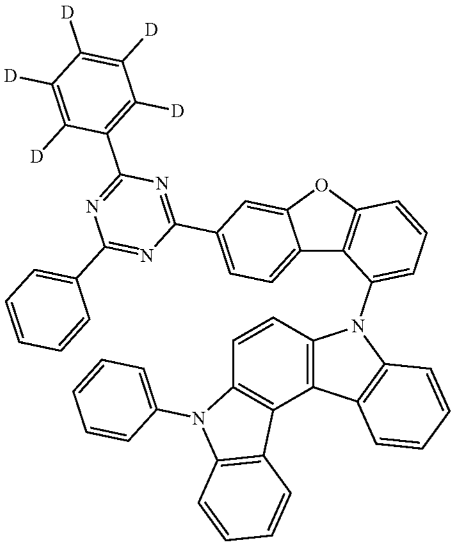
-continued
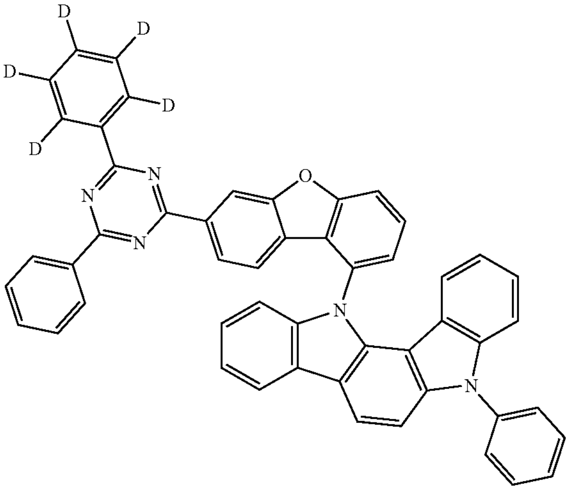
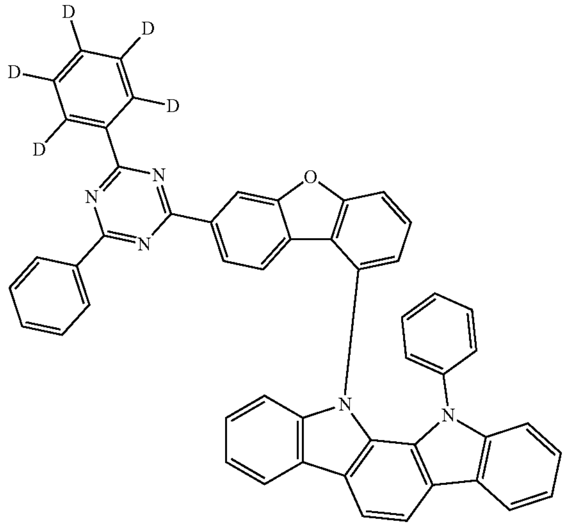
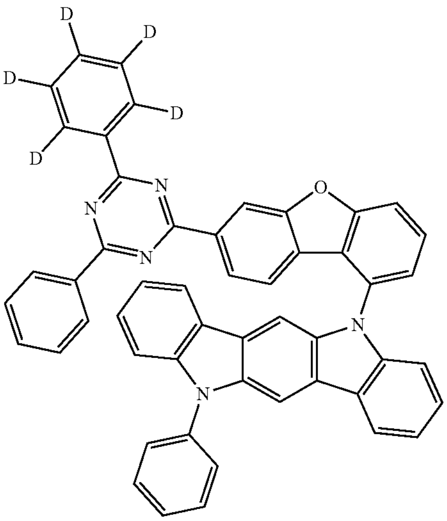

-continued
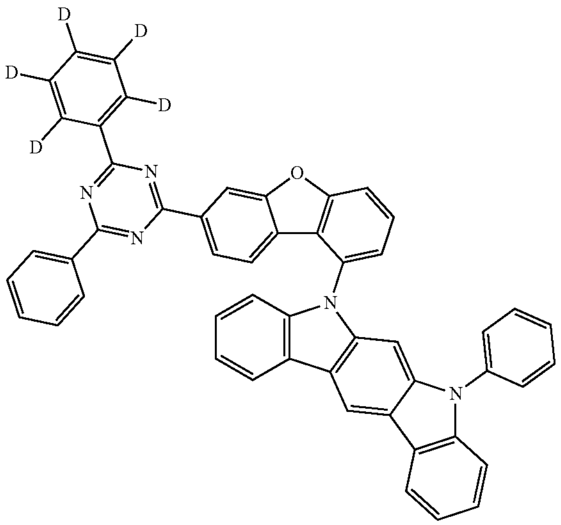
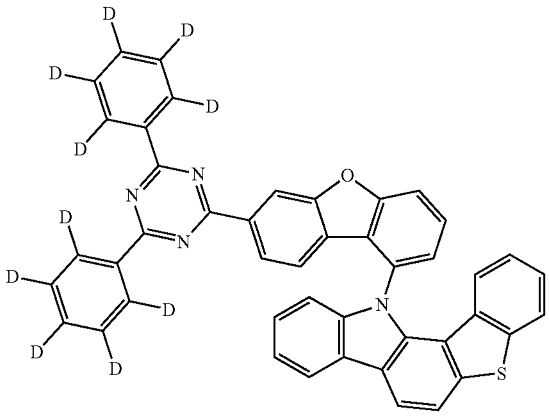
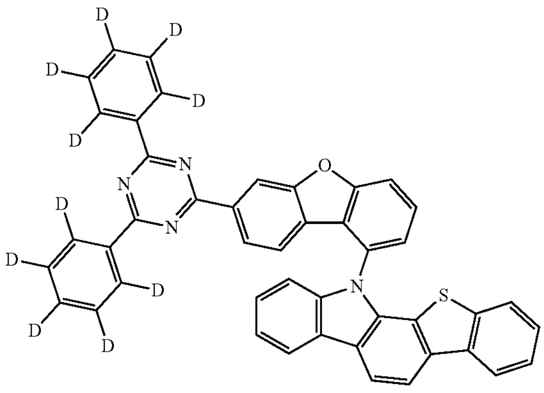
-continued
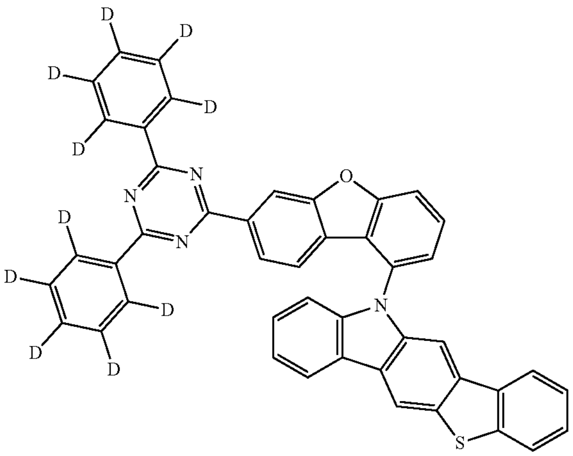
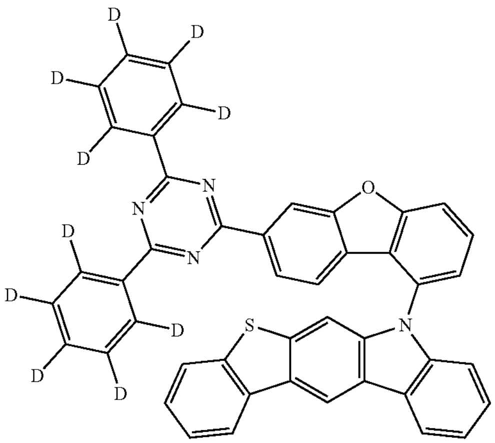
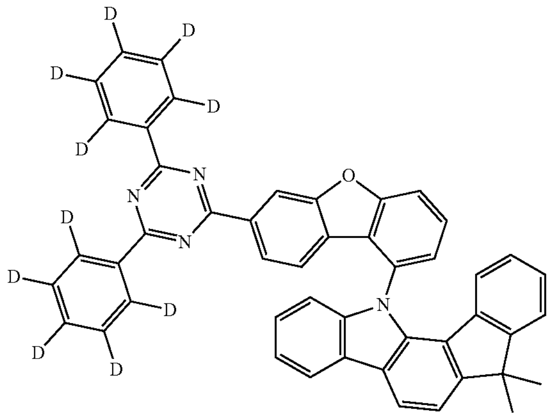
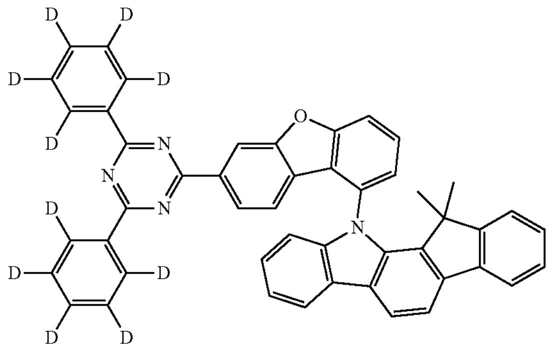

-continued
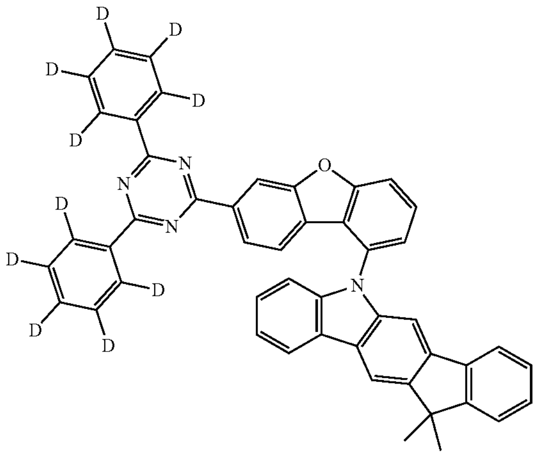
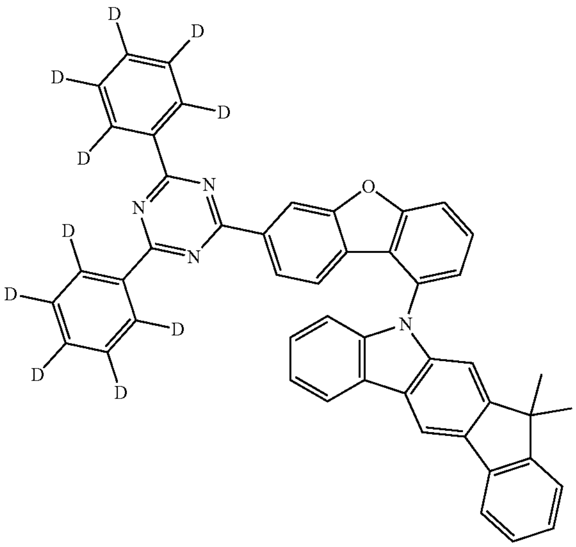
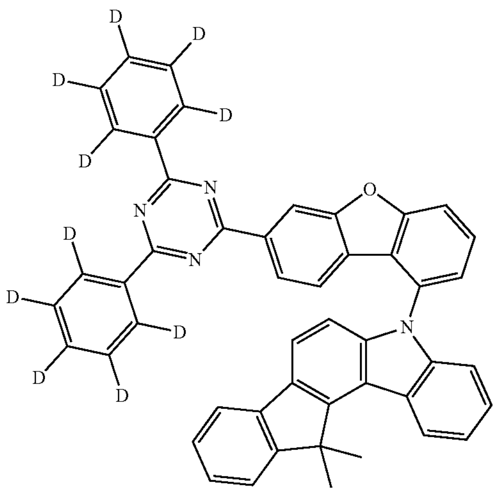
-continued
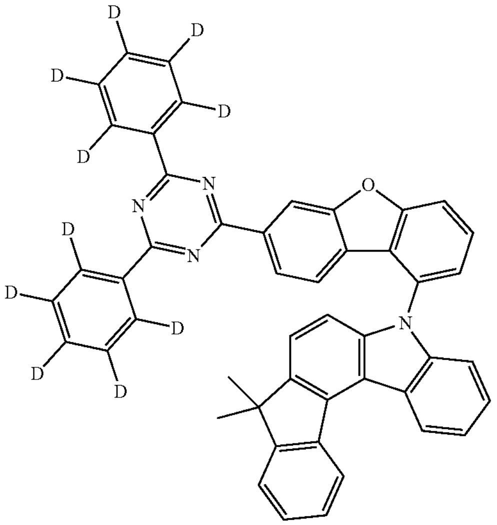
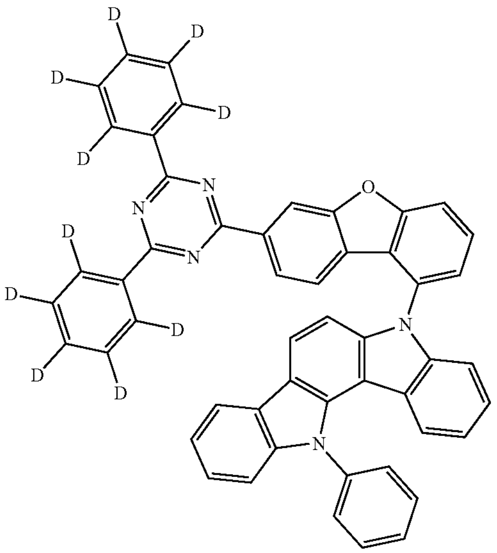
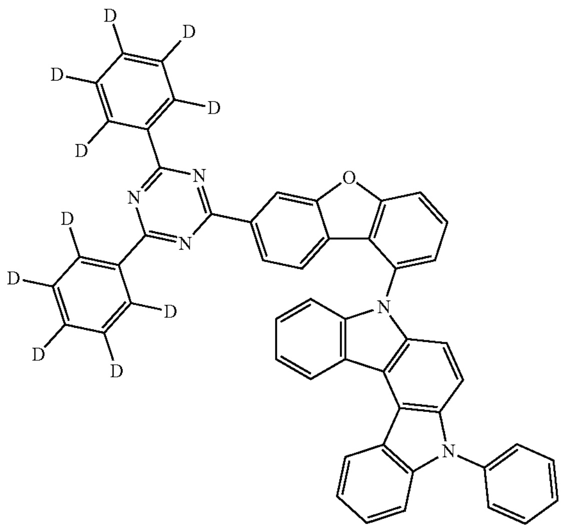

-continued
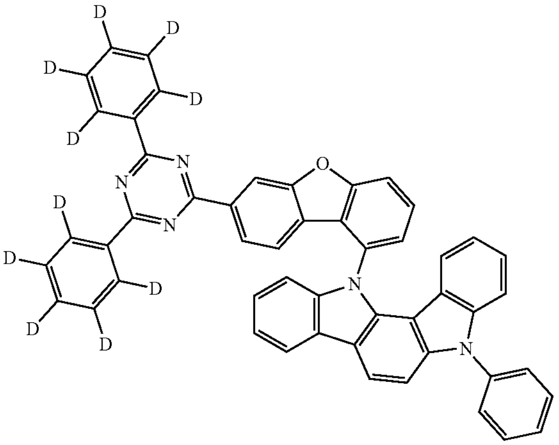
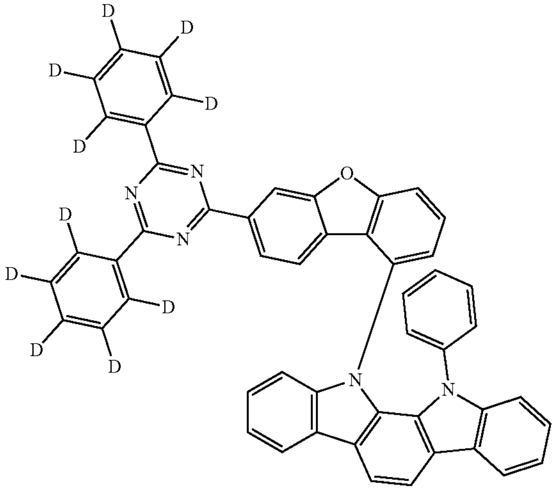
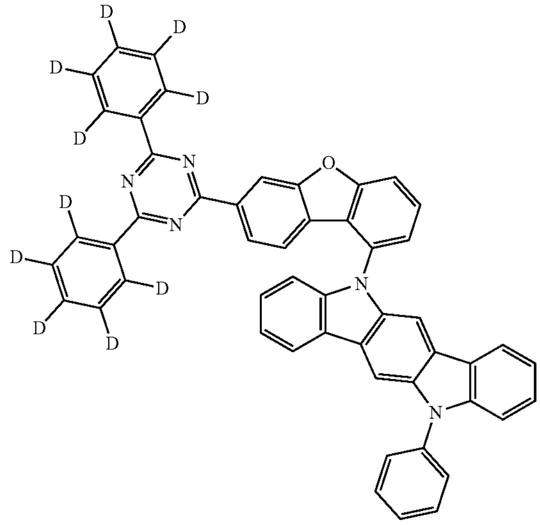
-continued
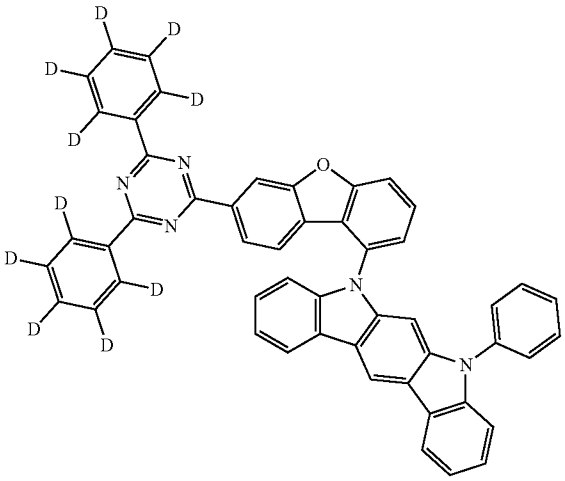
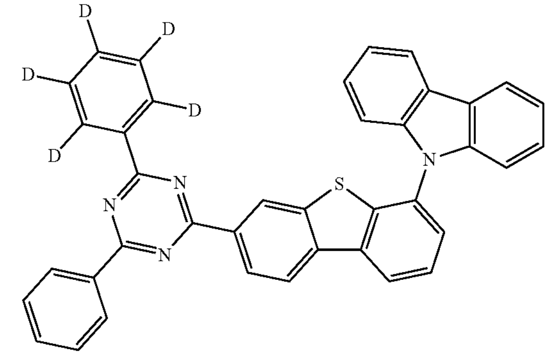
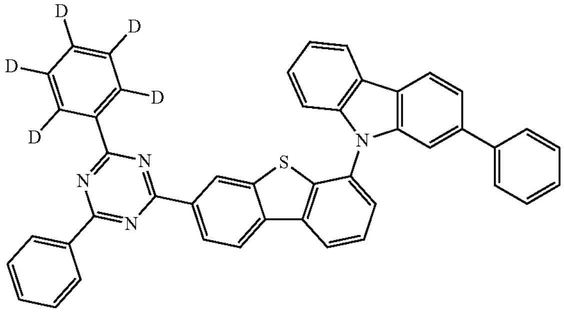
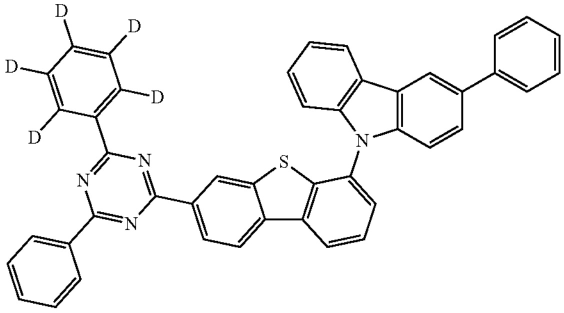

-continued
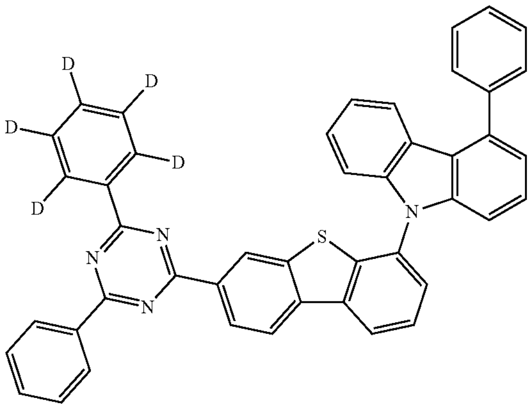
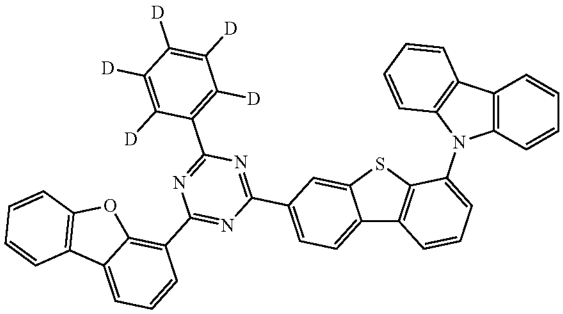
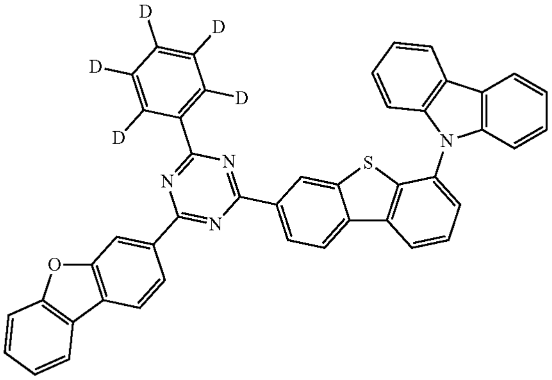
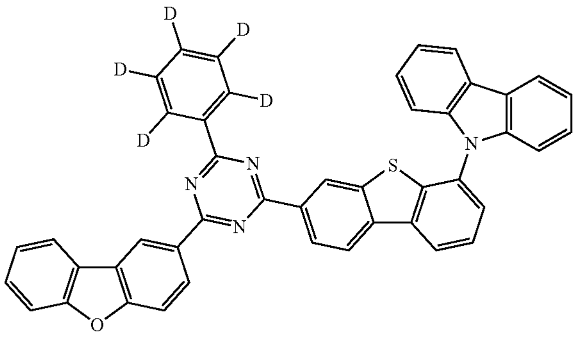
-continued
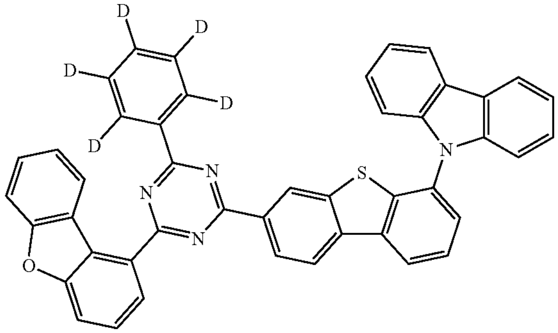
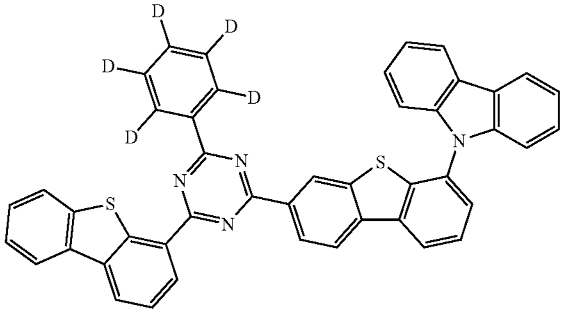
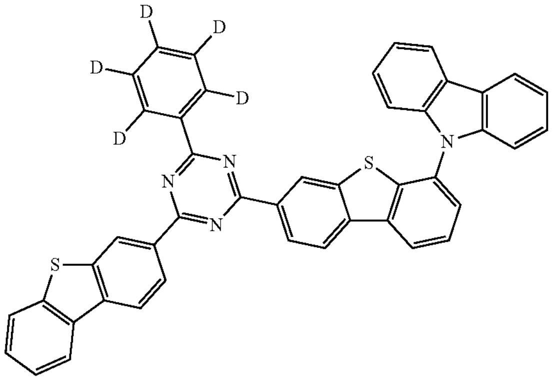
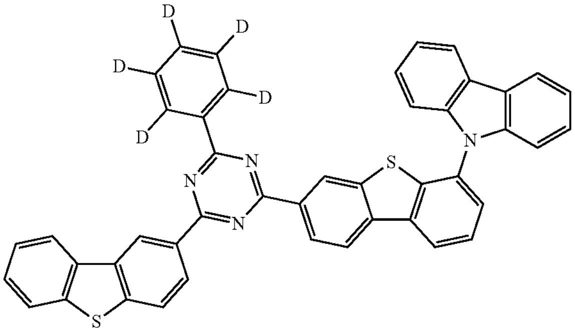
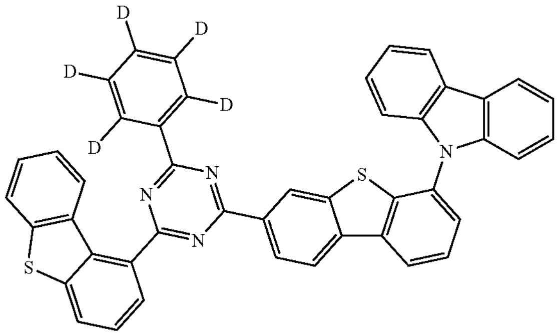

-continued
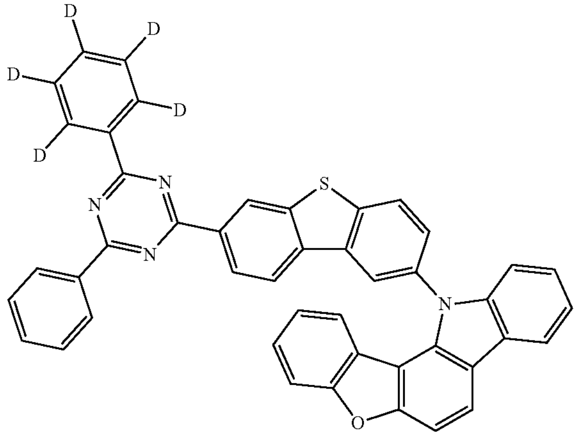
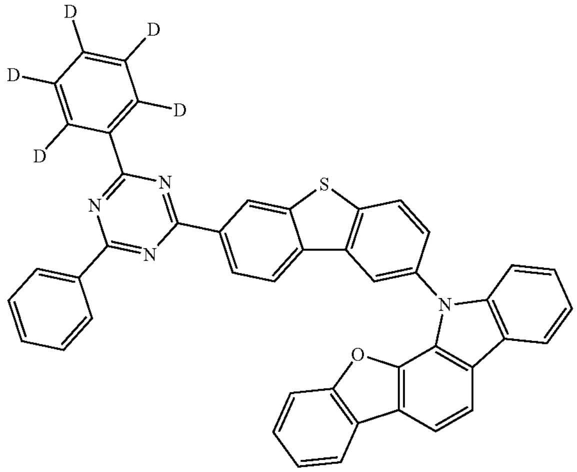
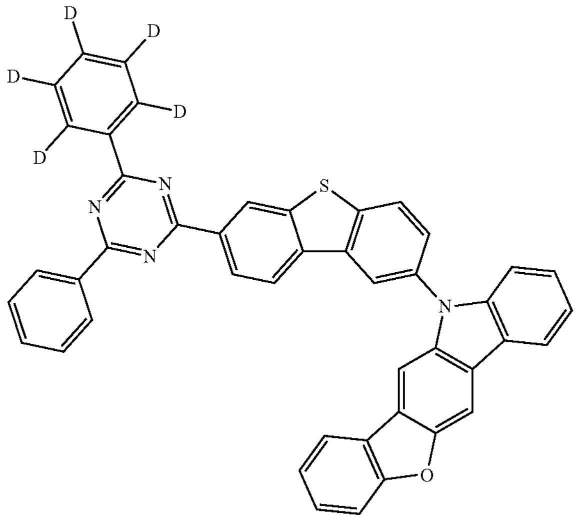
-continued
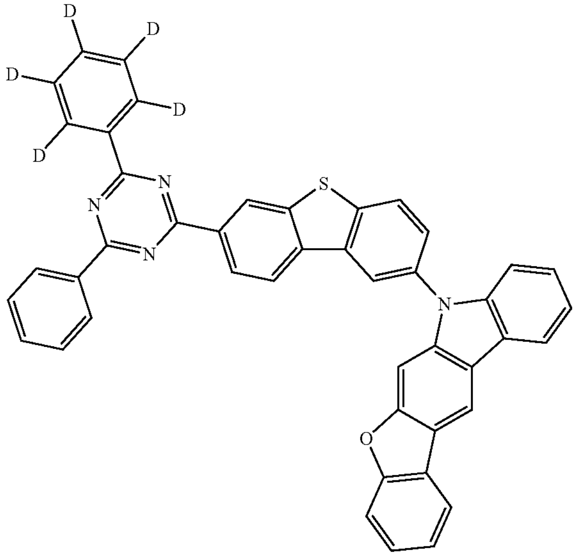
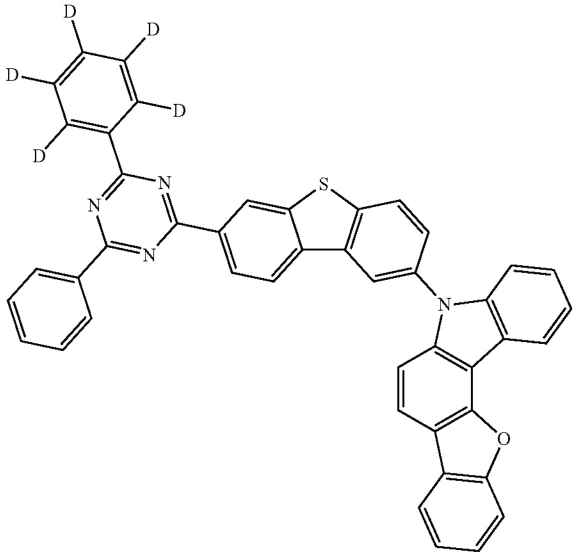
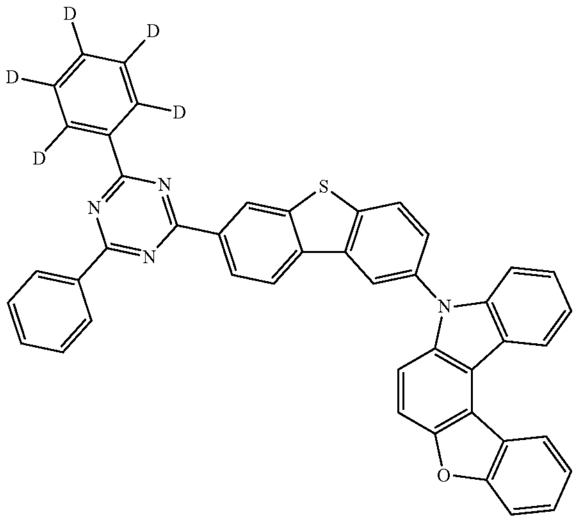

-continued
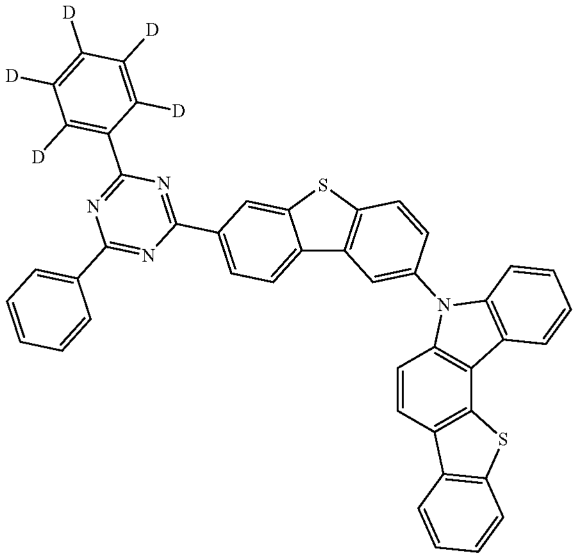
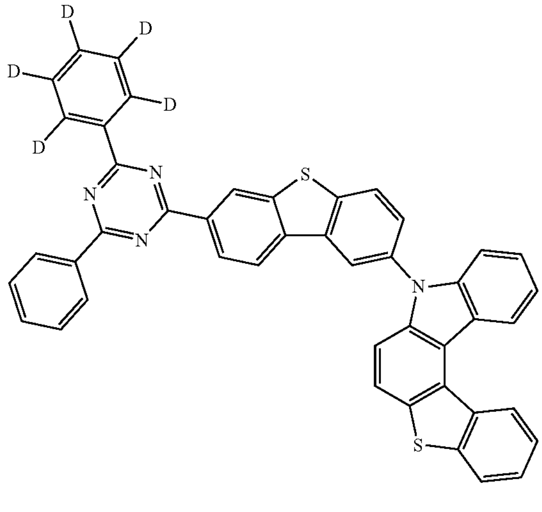
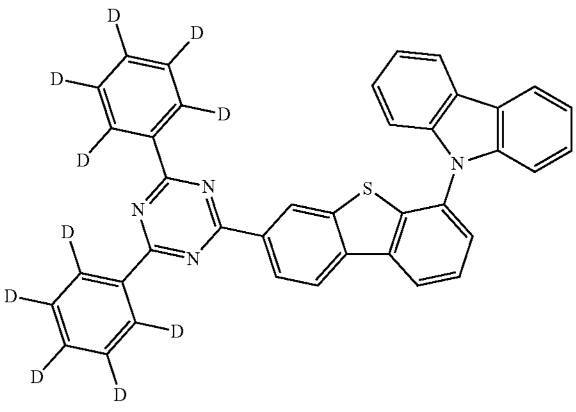
-continued
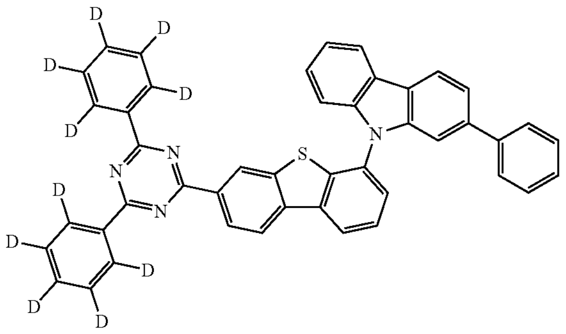
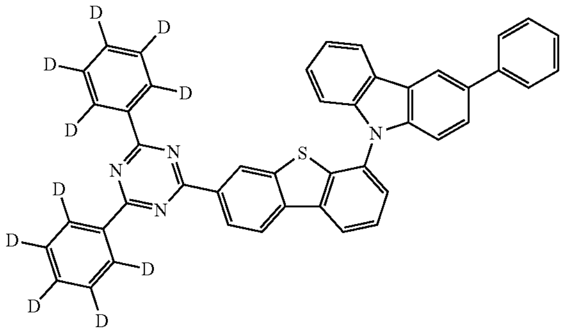
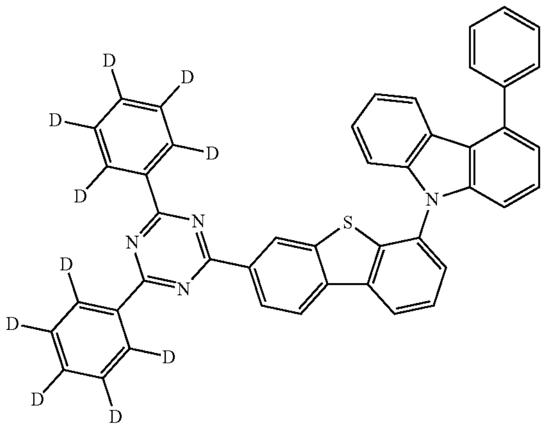
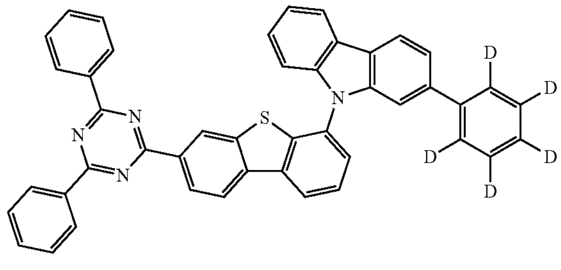
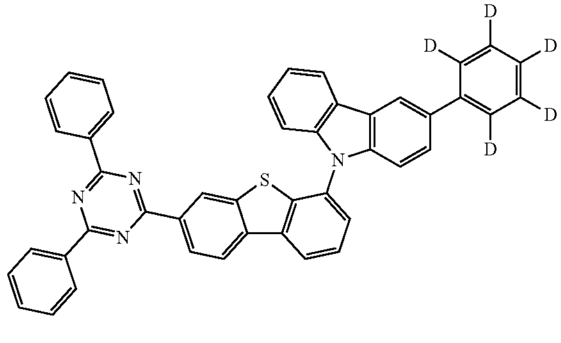

-continued
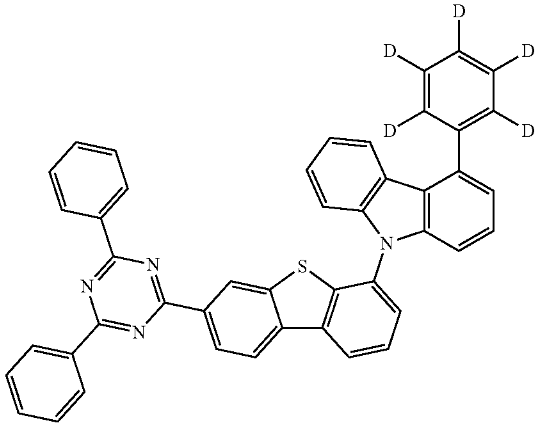
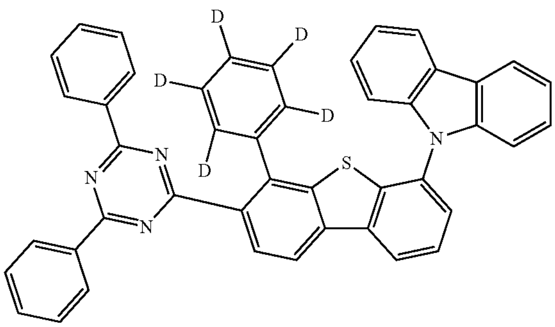
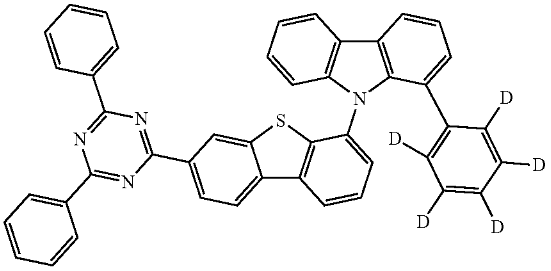
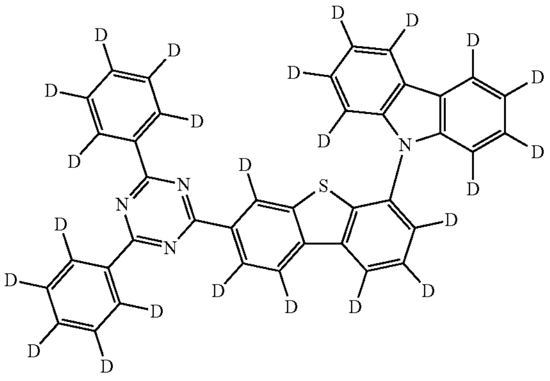
-continued
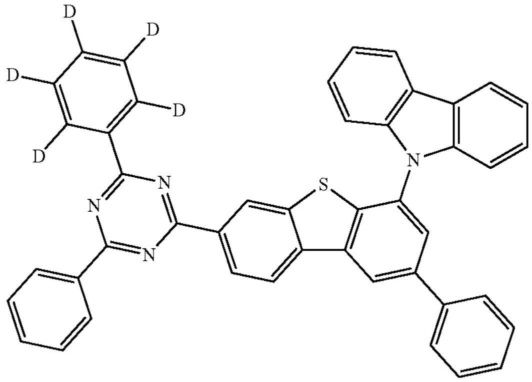
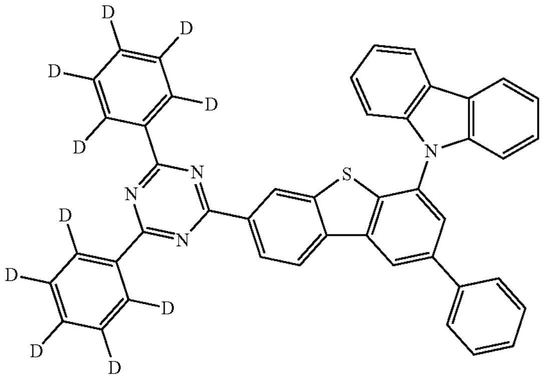
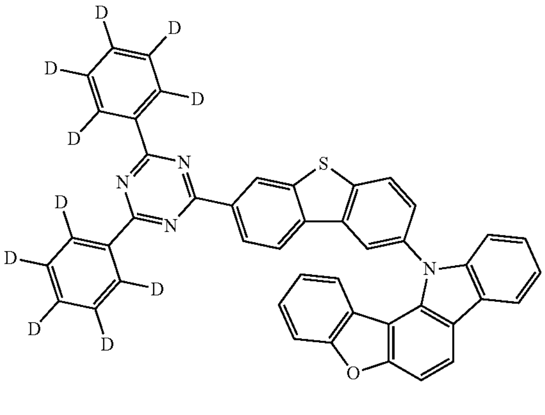
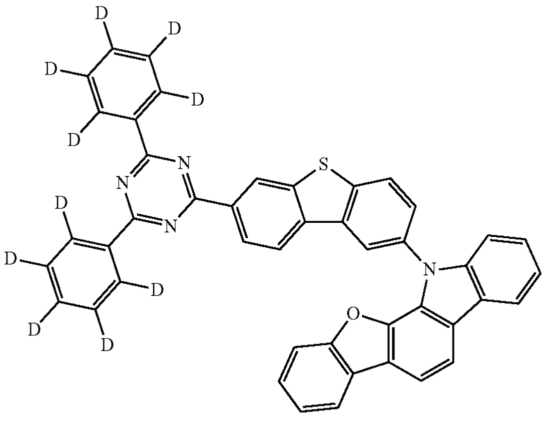

-continued
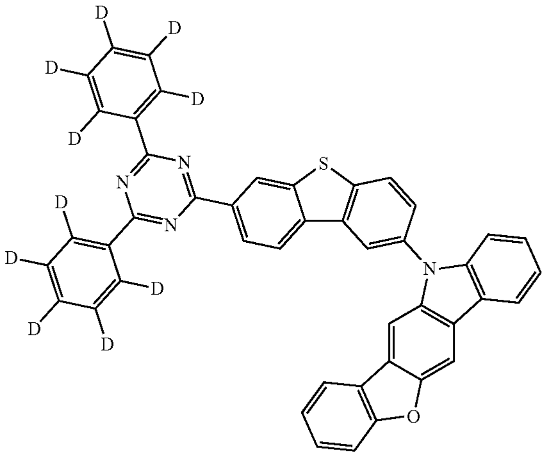
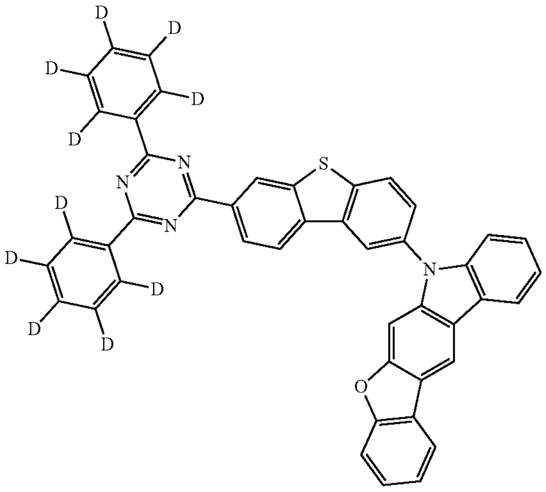
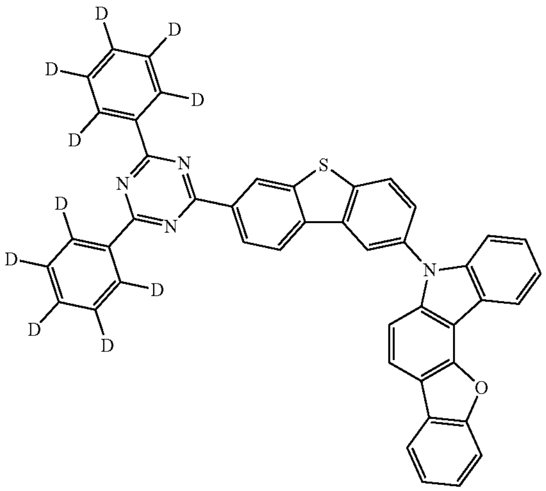
-continued
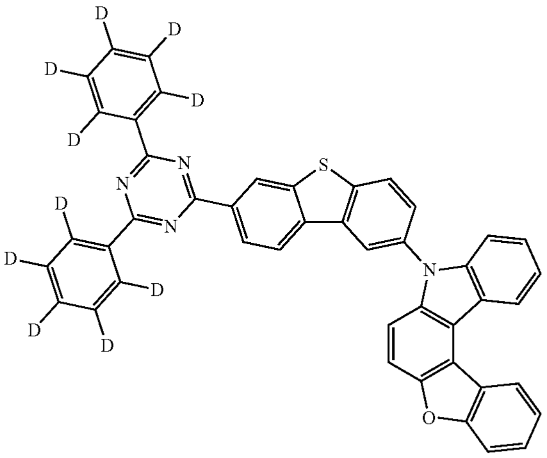
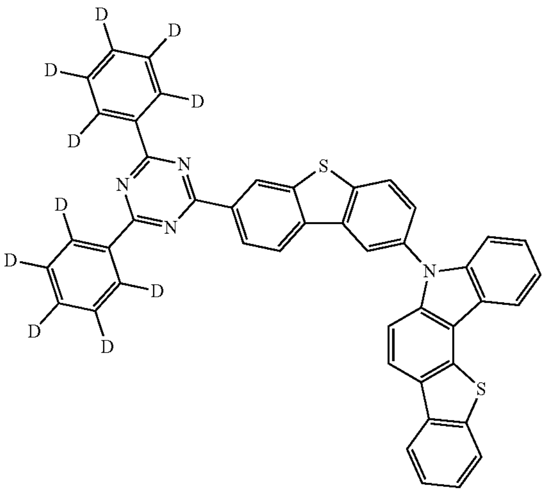
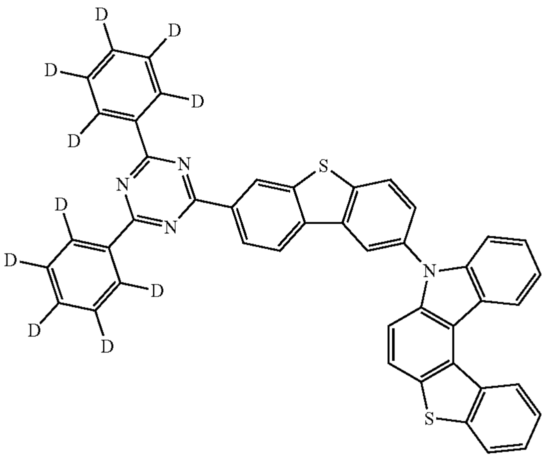

-continued
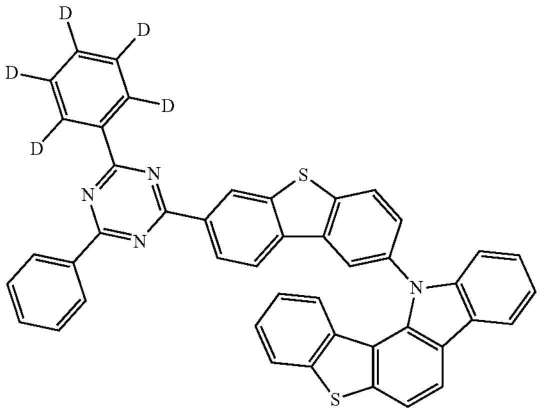
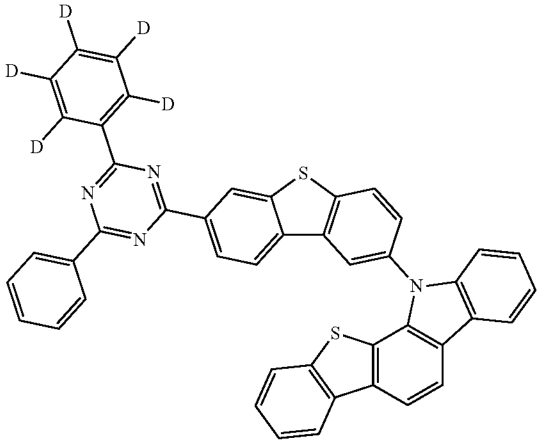
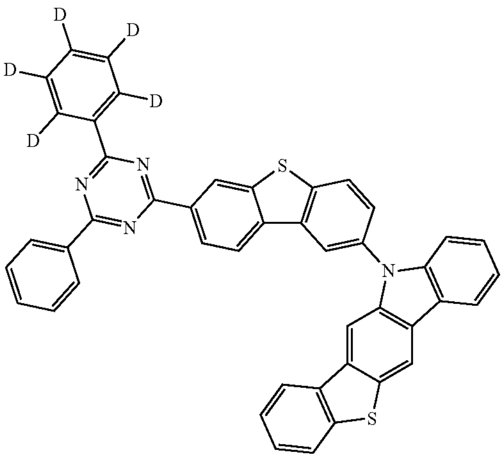
-continued
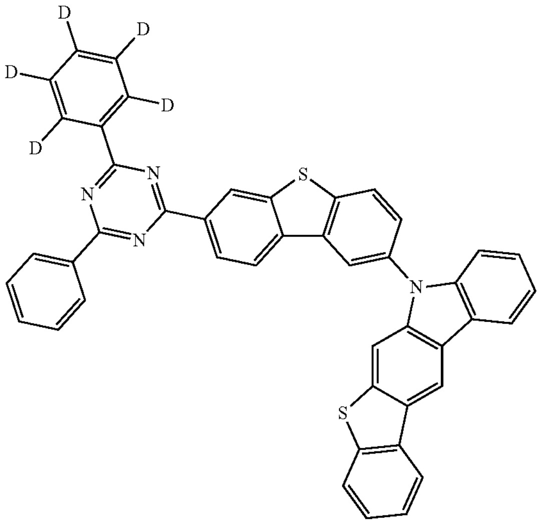
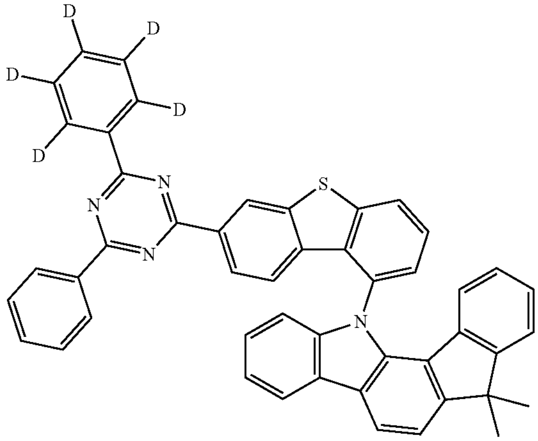
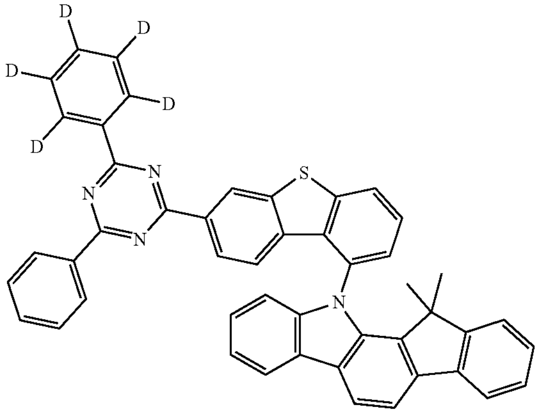

-continued
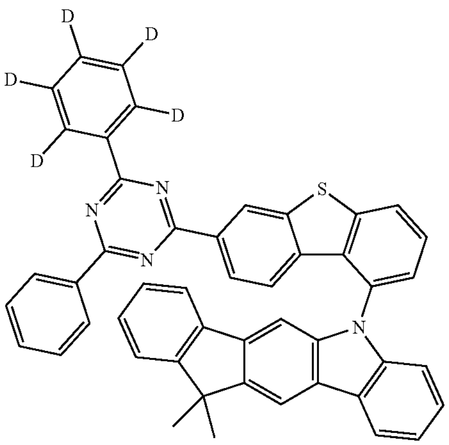
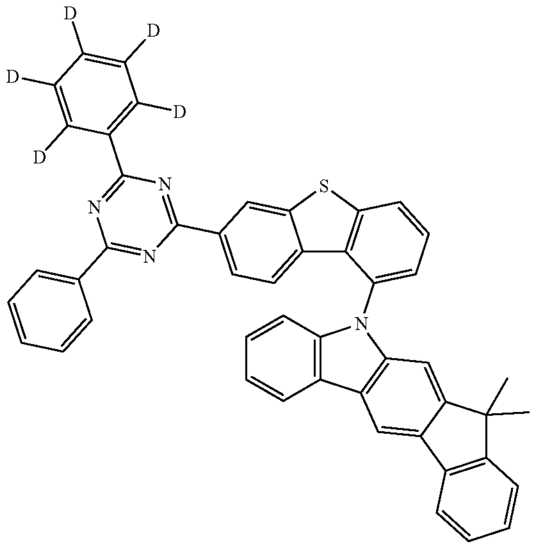
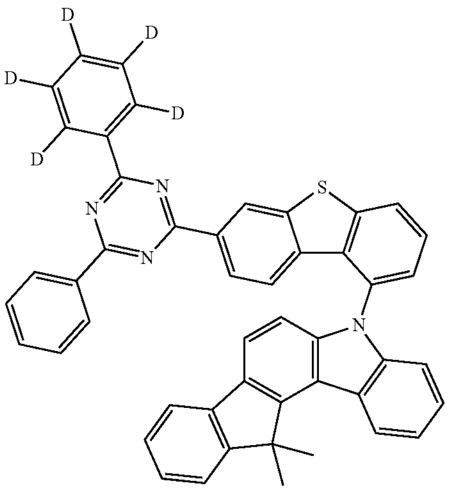
-continued
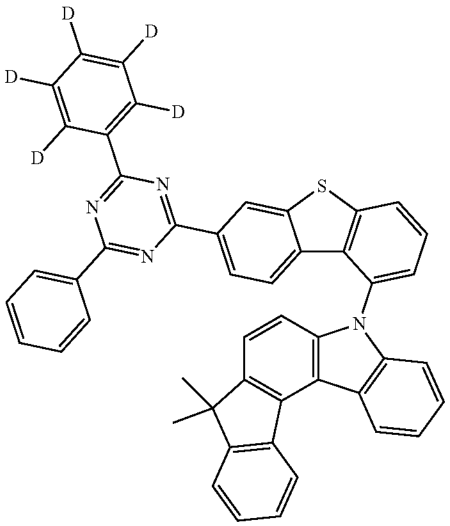
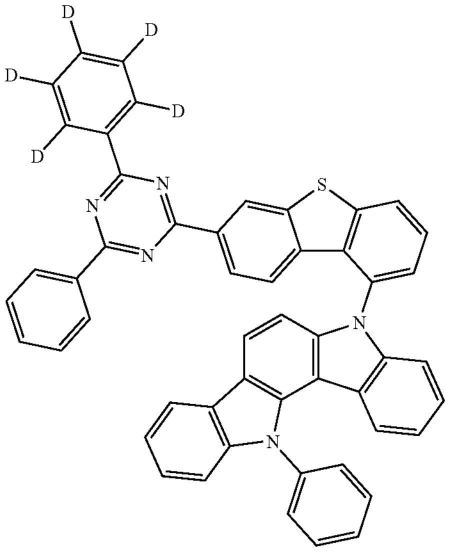
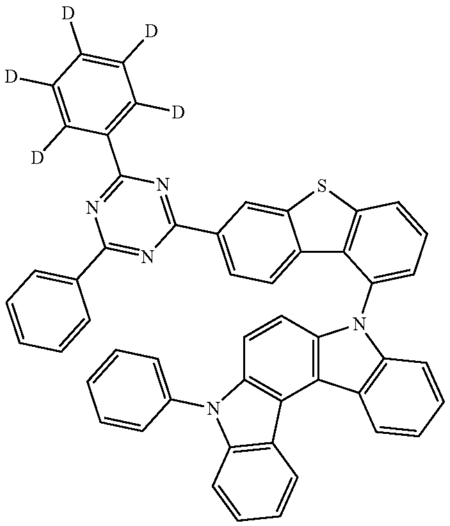

-continued
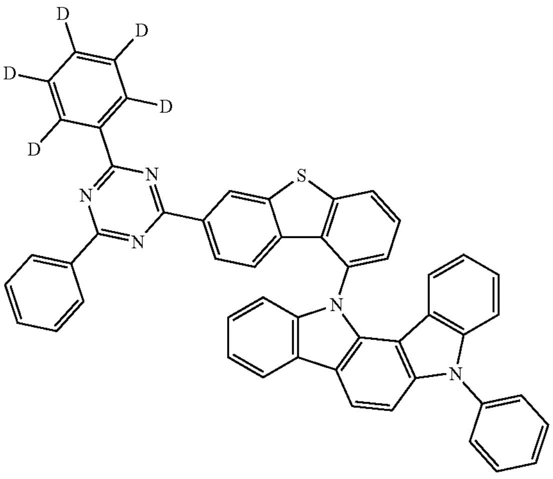
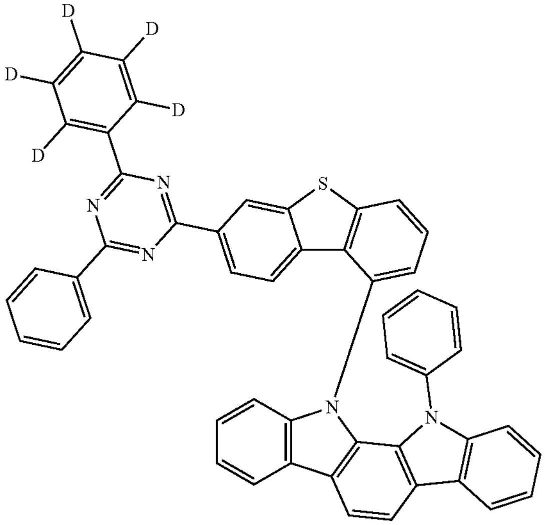
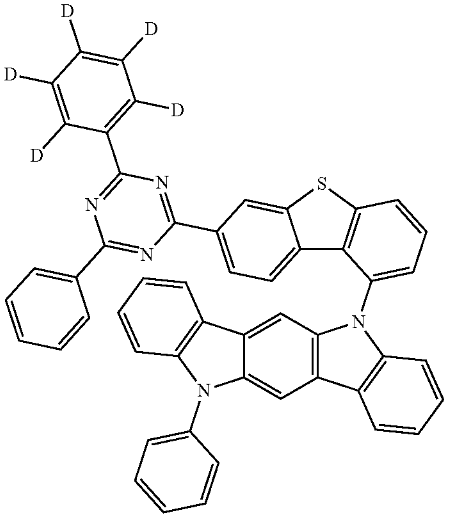
-continued
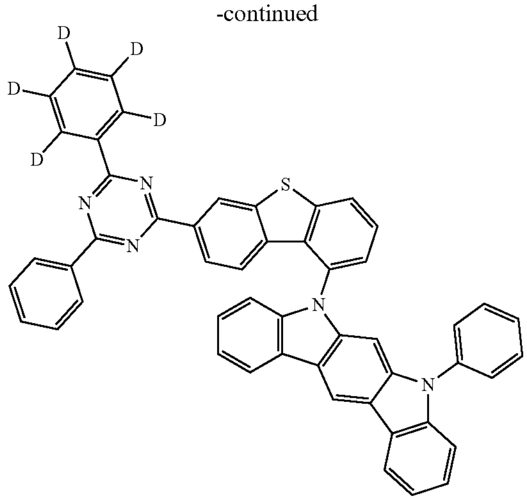
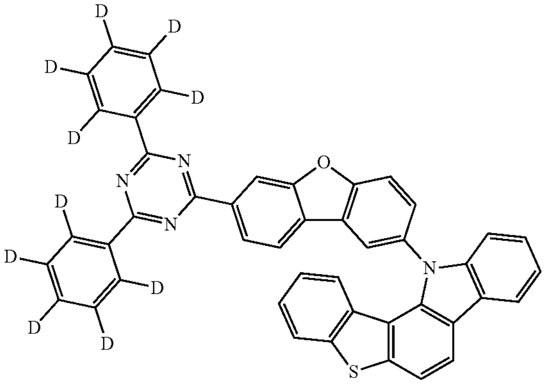
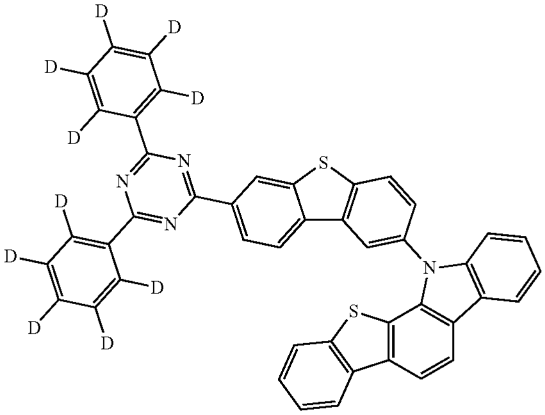
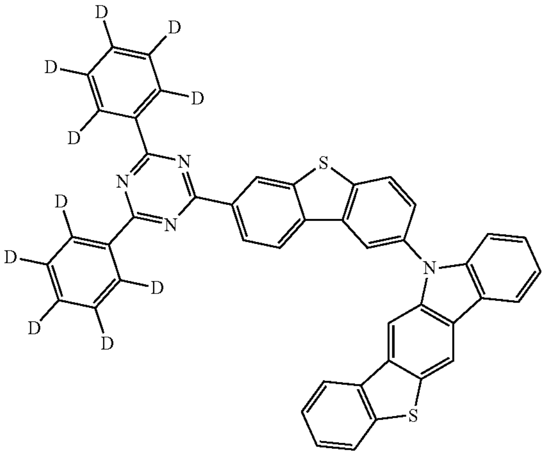

-continued
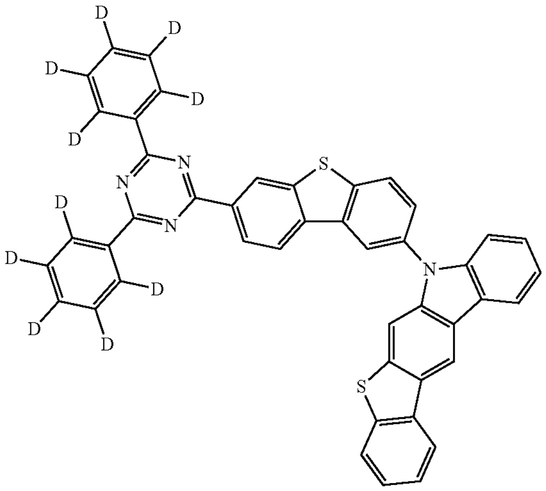
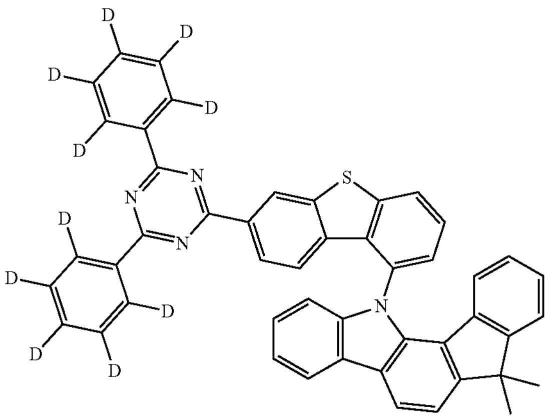
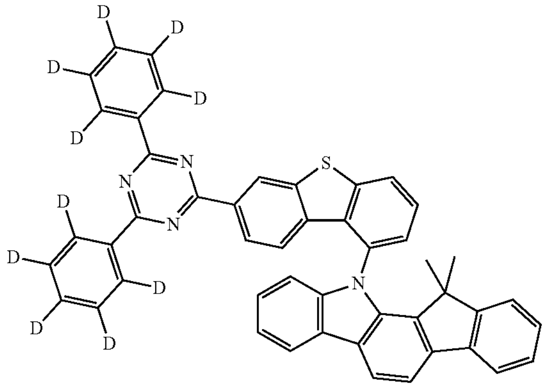
-continued
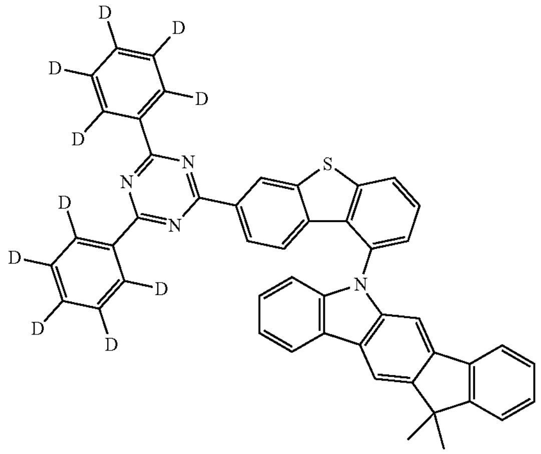
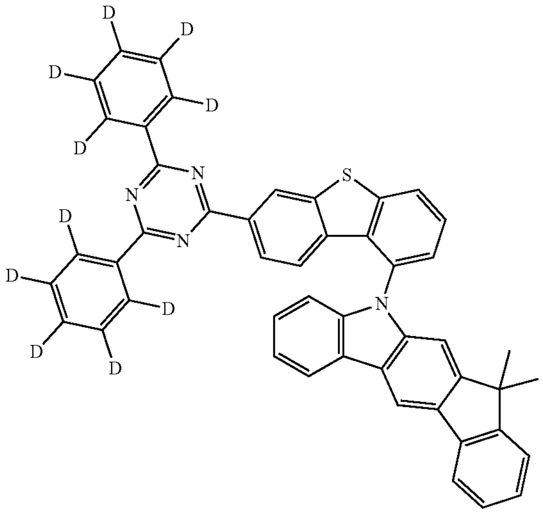
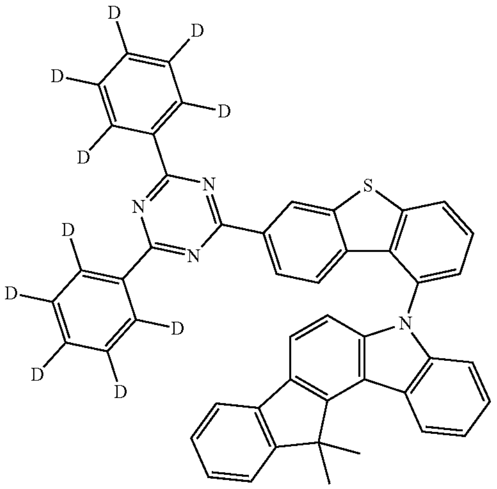

-continued
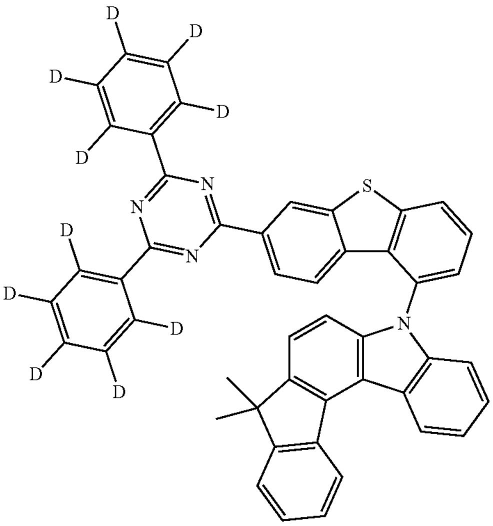
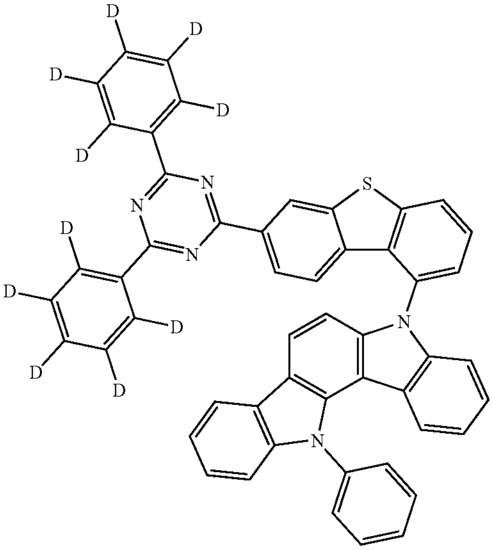
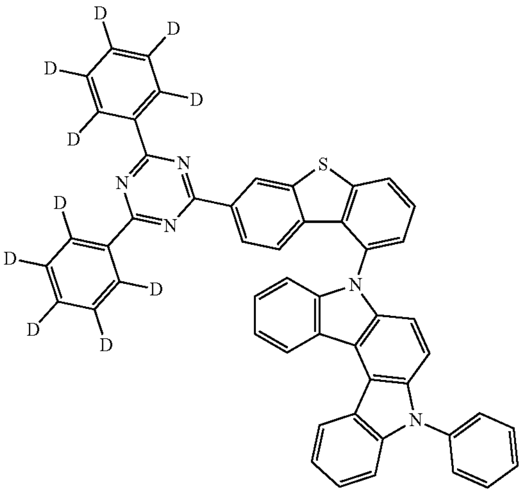
-continued
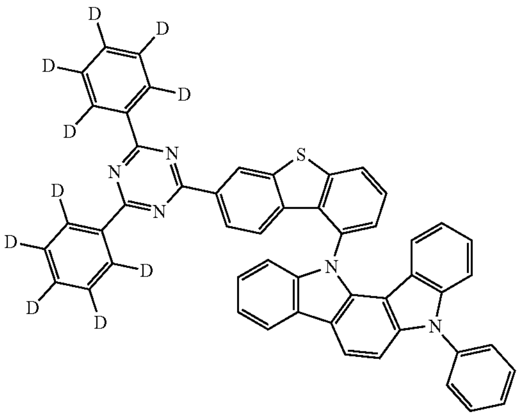
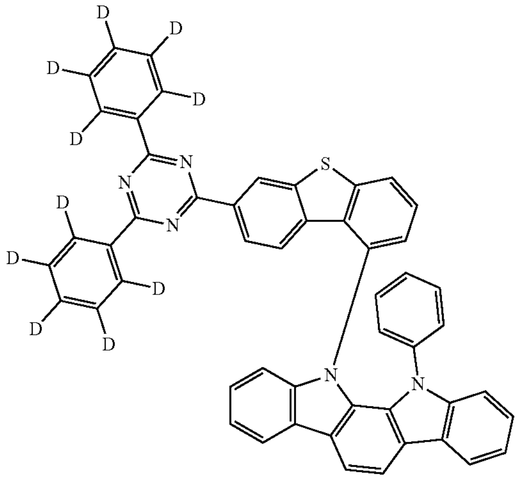
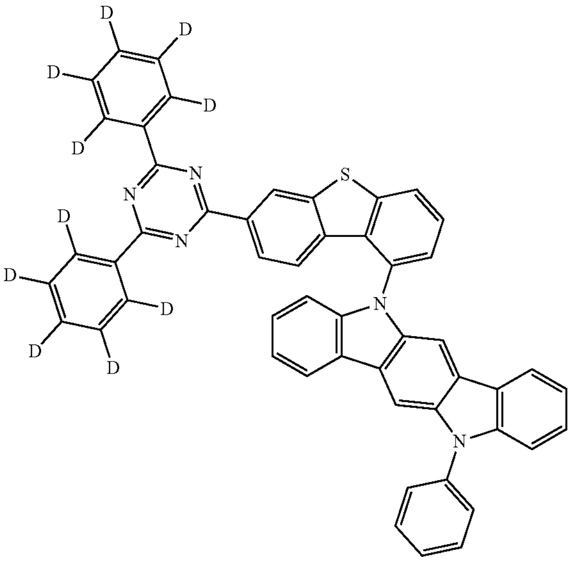

-continued
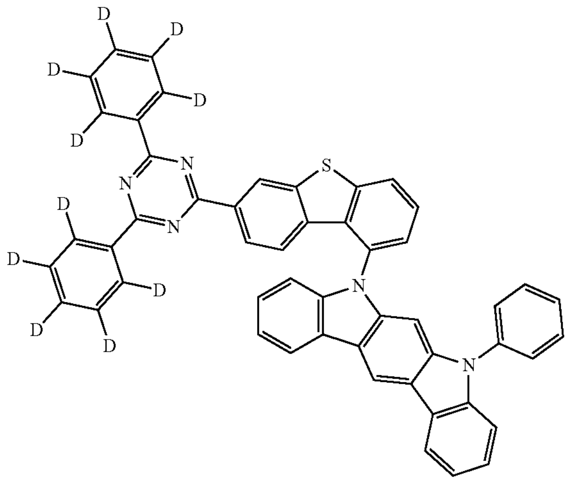
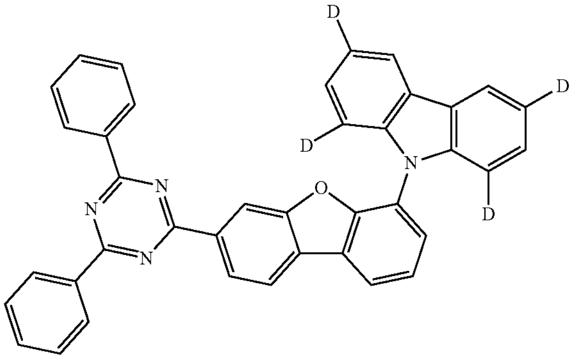
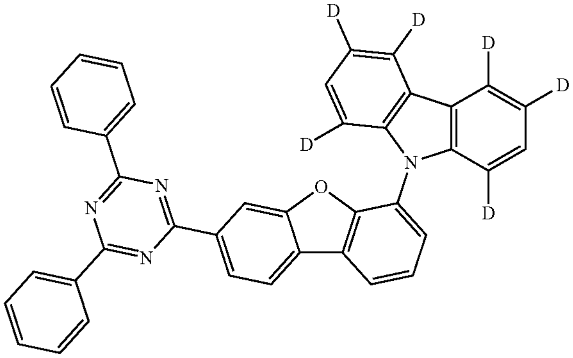
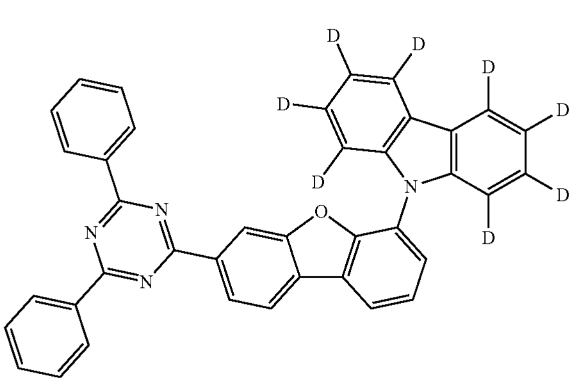
-continued
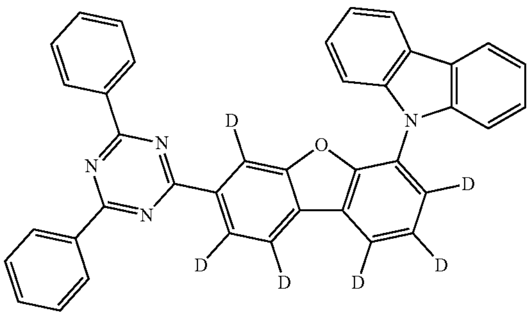
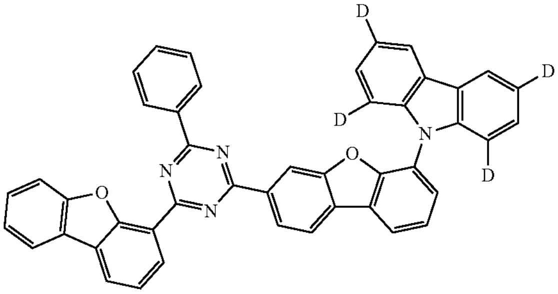
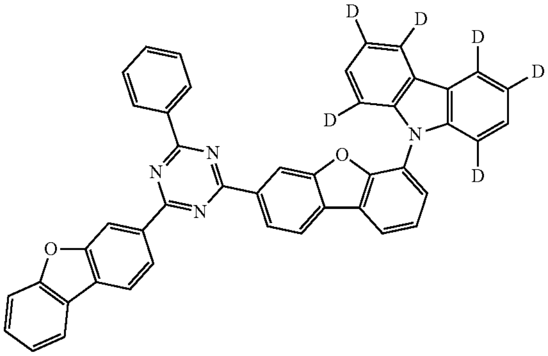
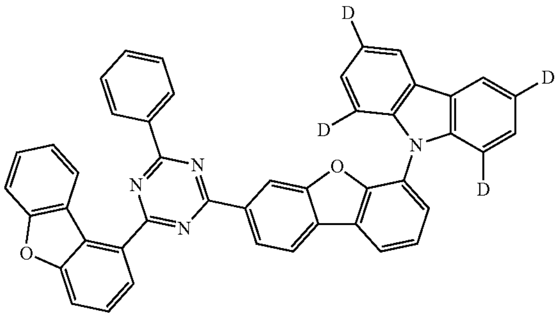
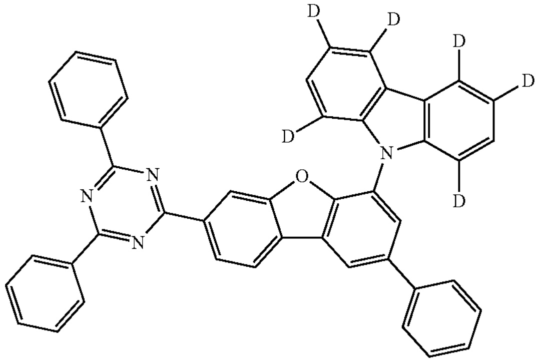

-continued
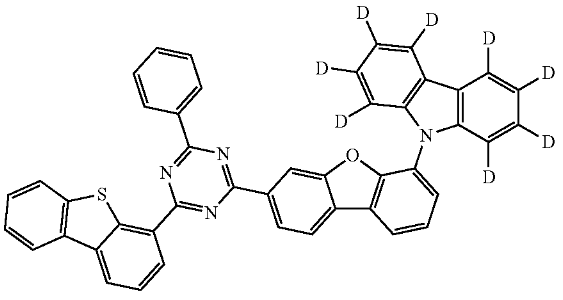
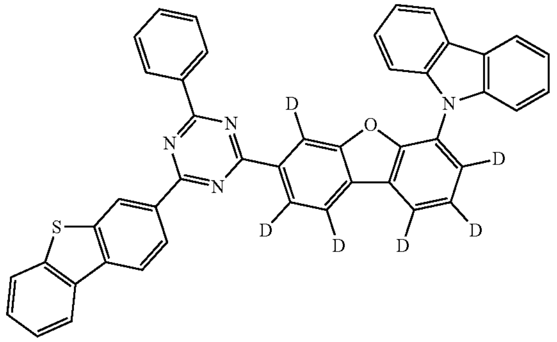
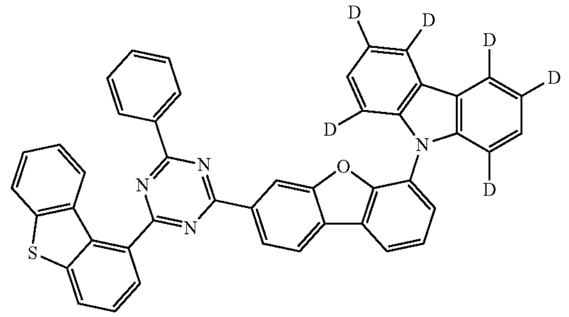
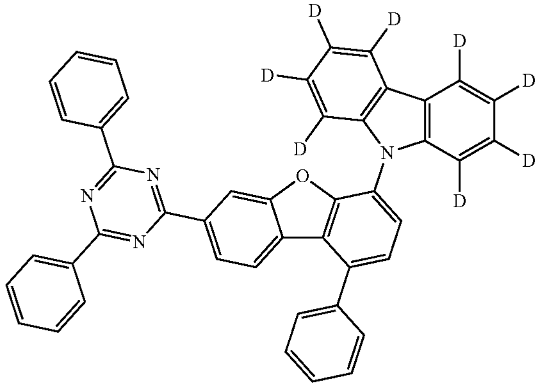
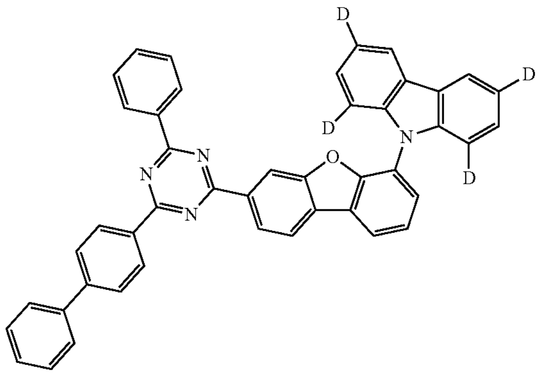
-continued
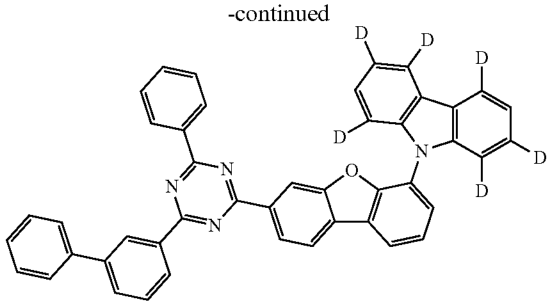
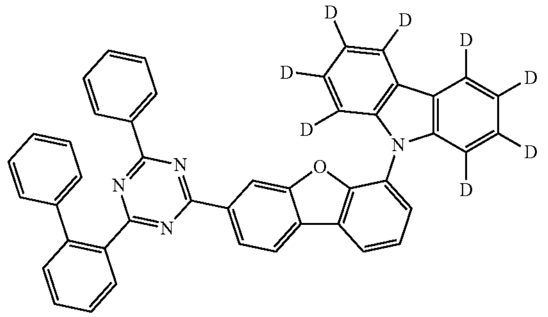
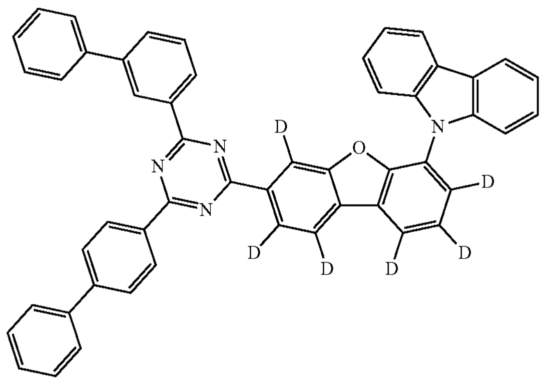
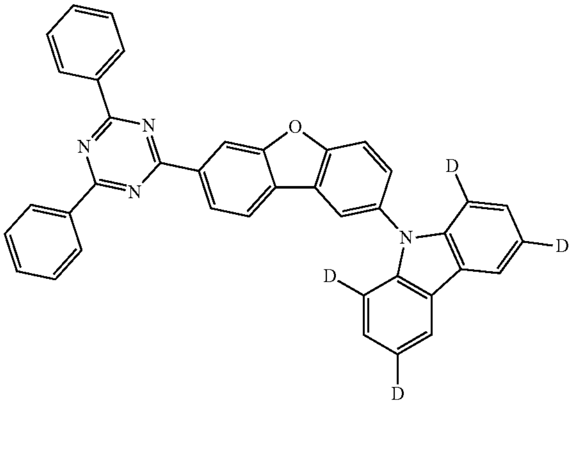

-continued
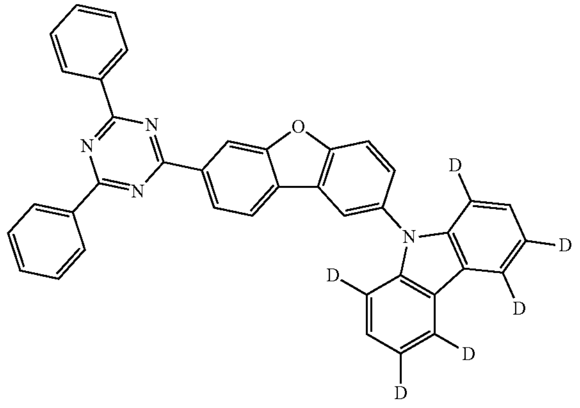
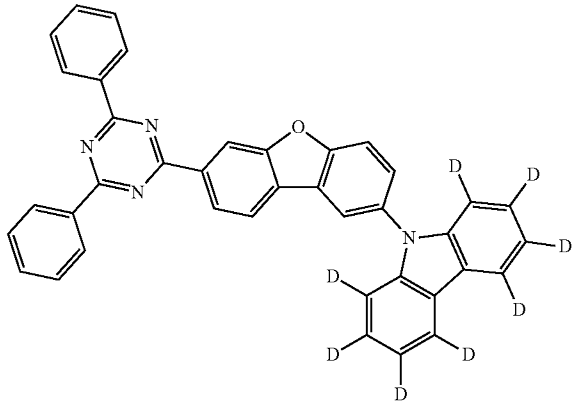
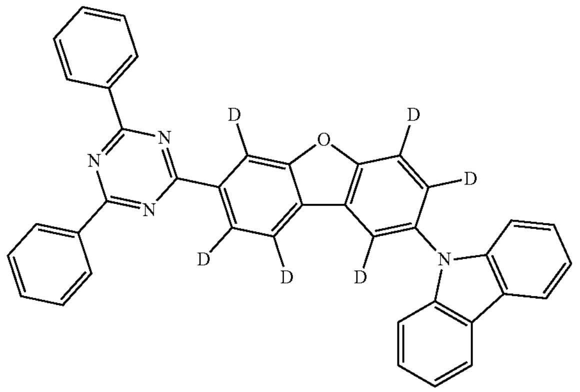
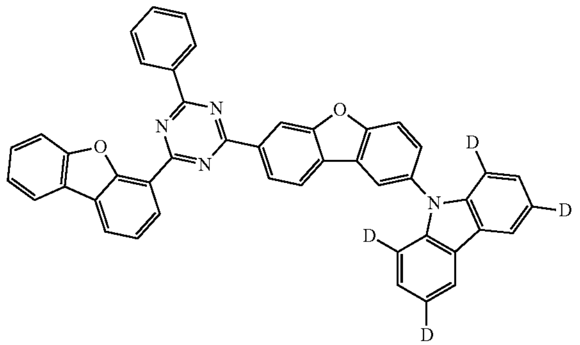
-continued
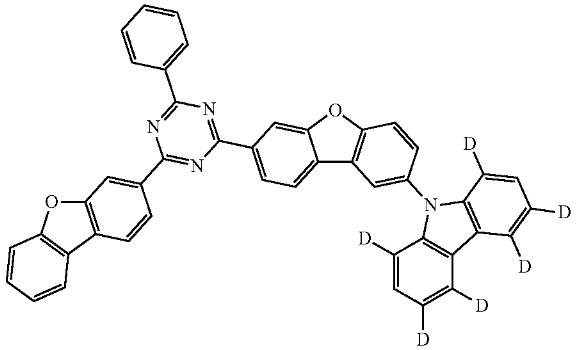
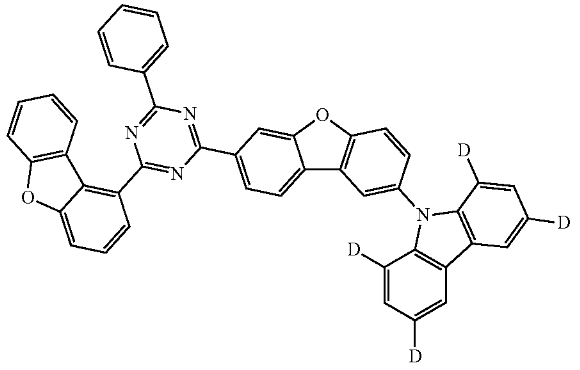
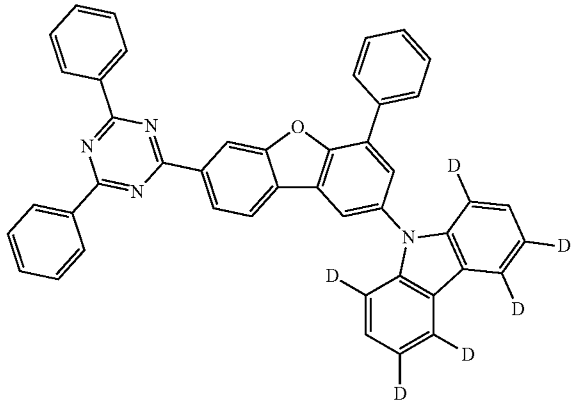
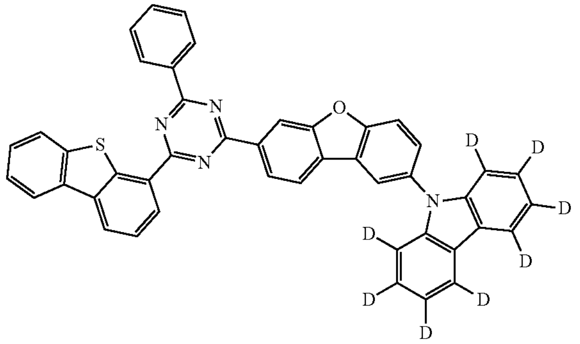

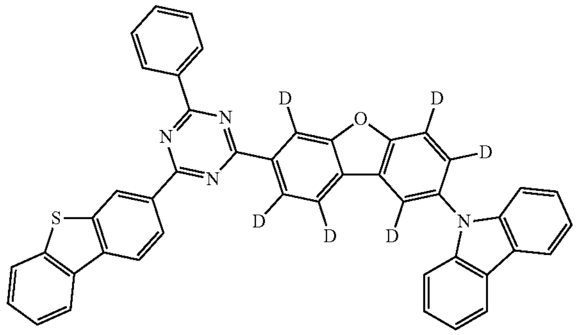
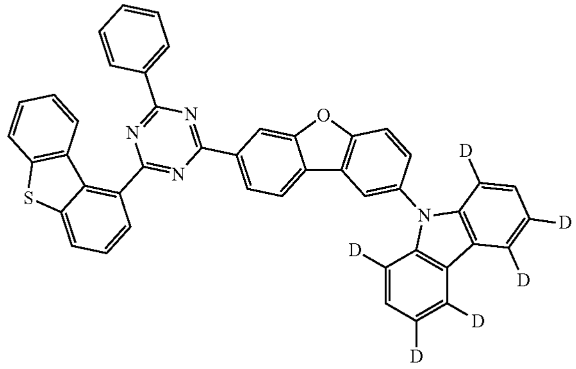
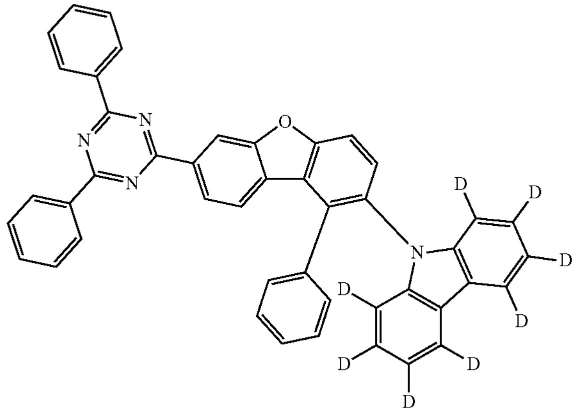
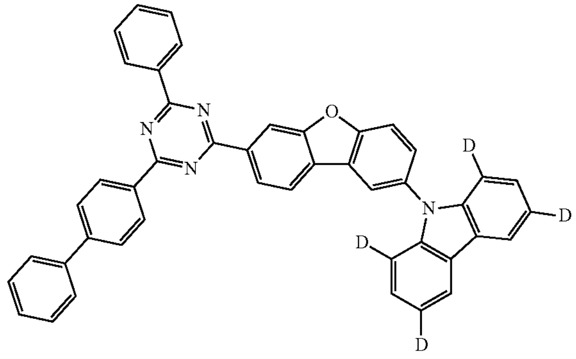
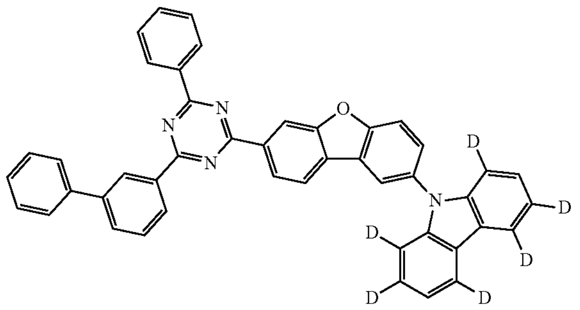
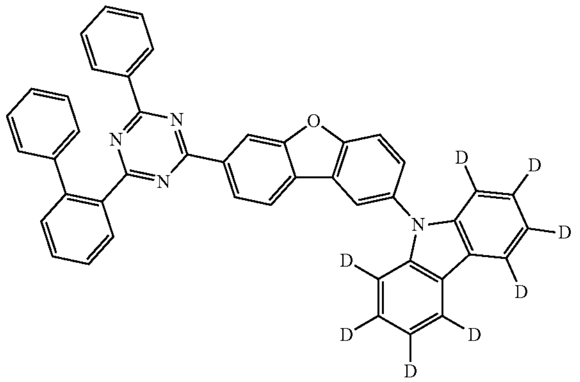
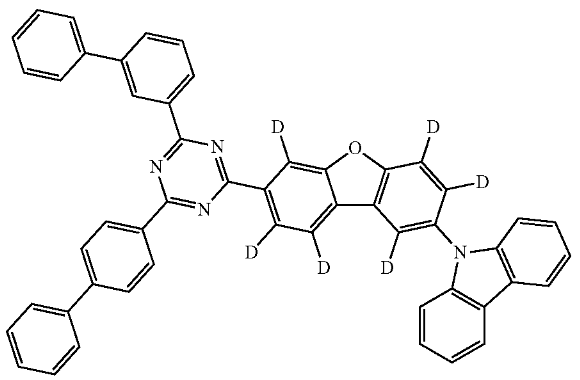
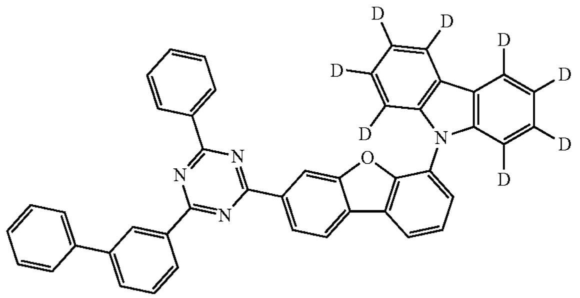

-continued
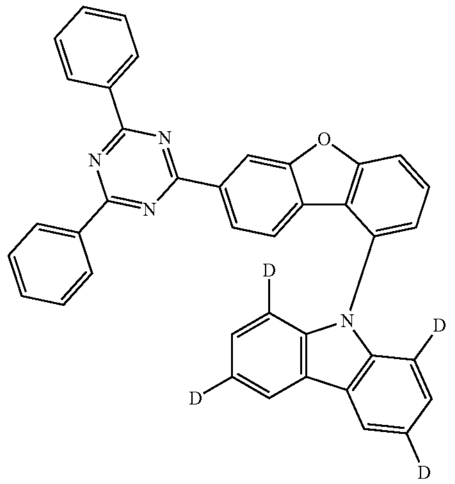
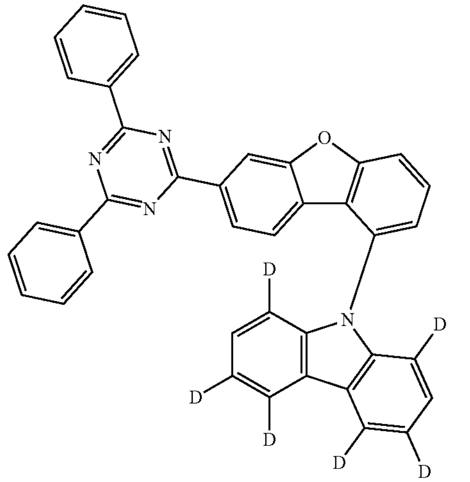
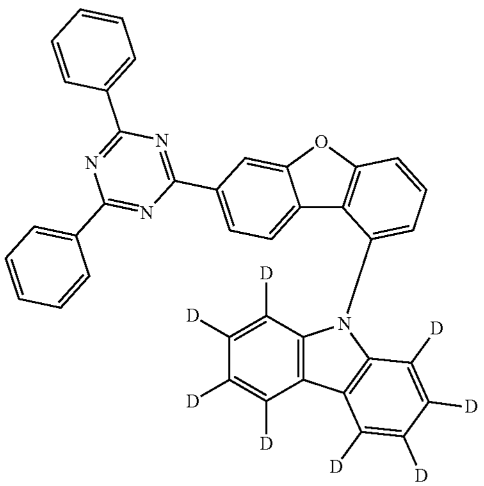
-continued
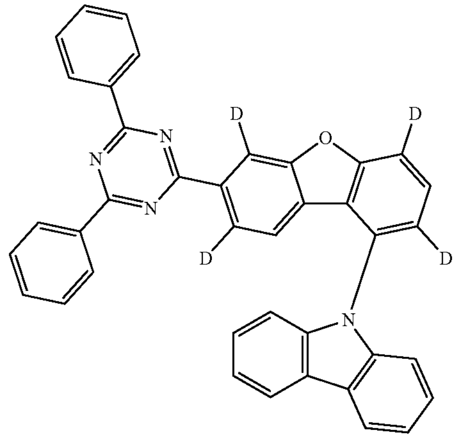
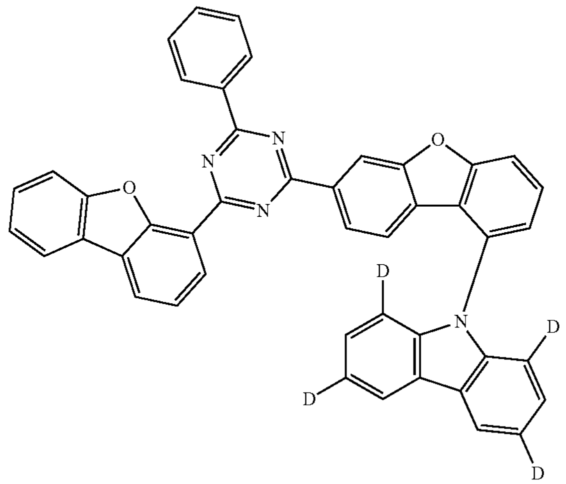
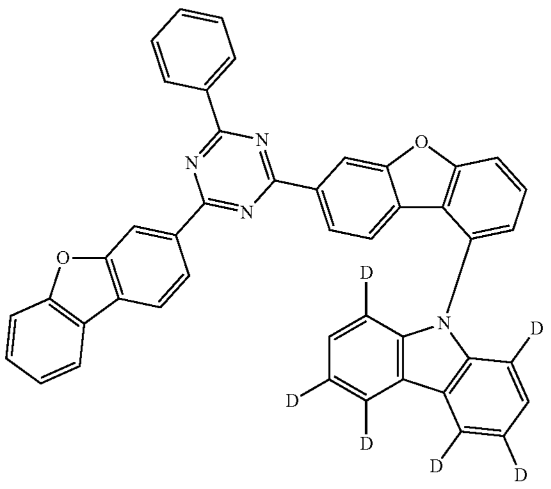

-continued
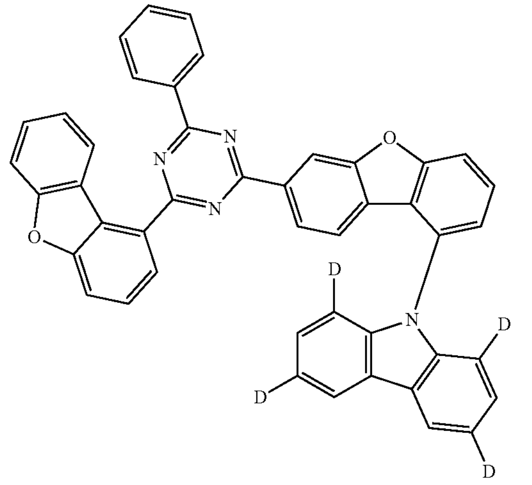
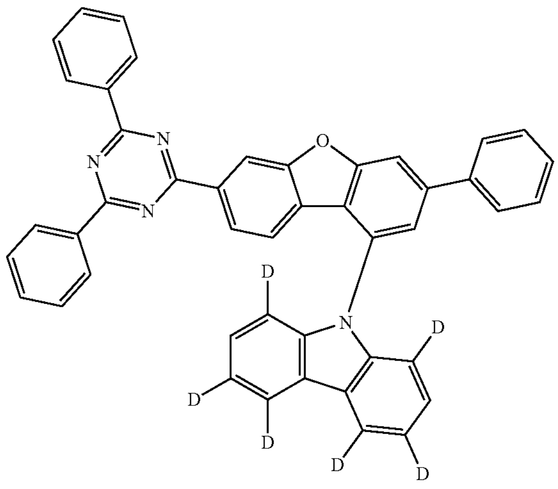
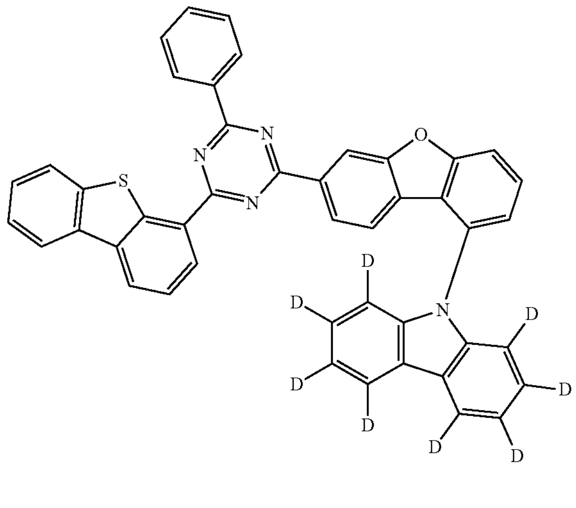
-continued
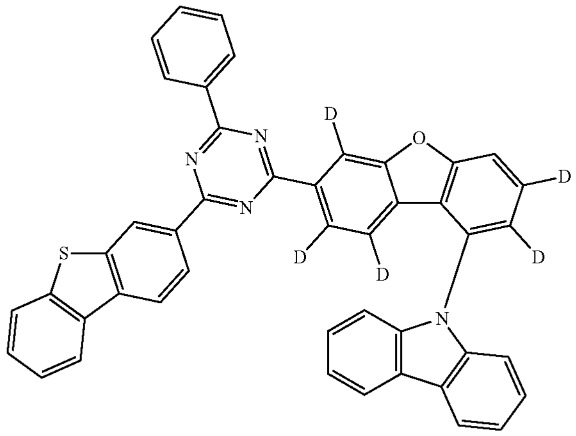
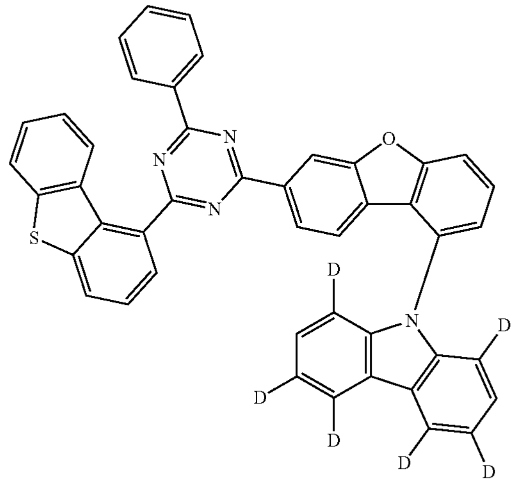
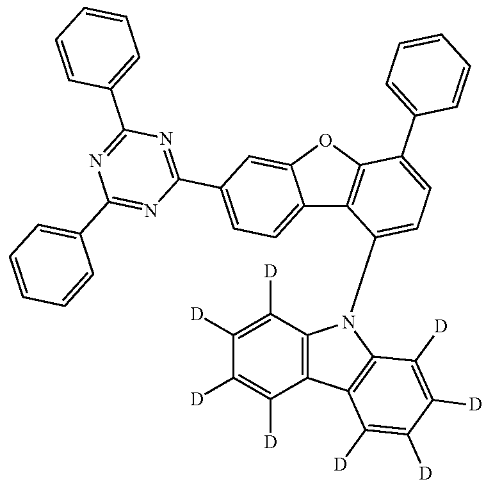

-continued
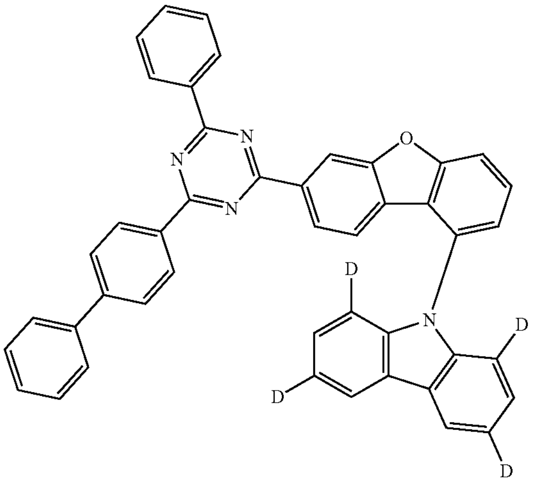
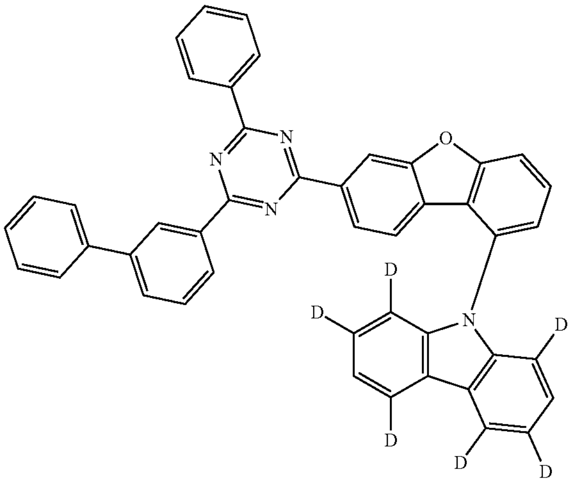
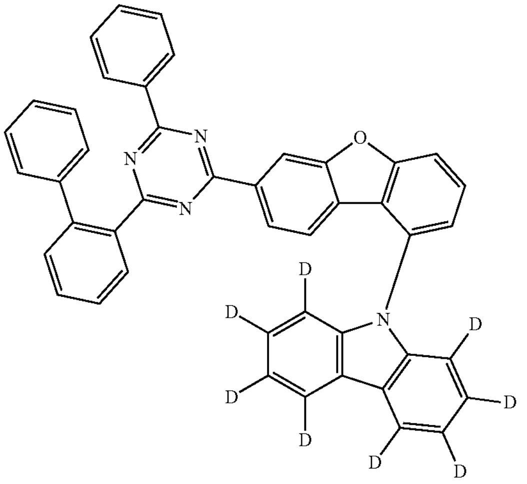
-continued
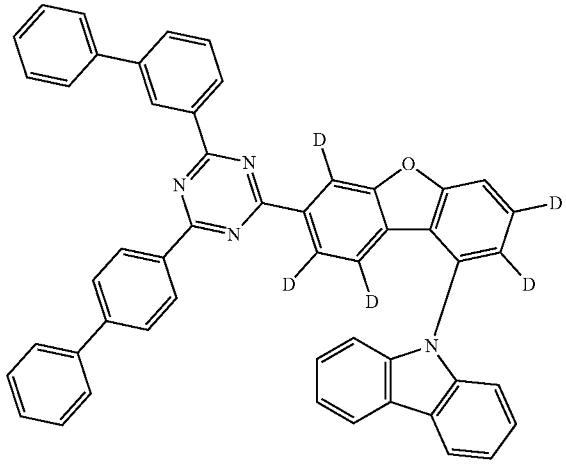
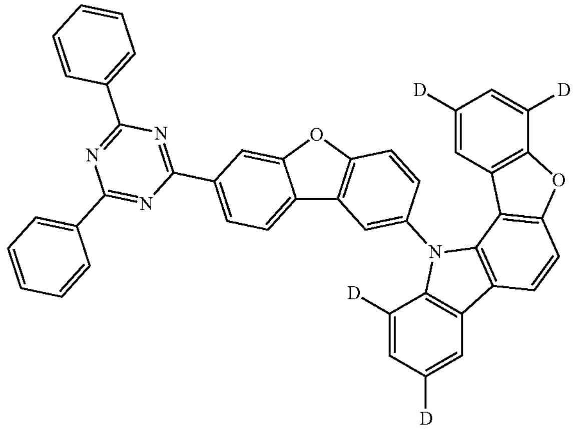
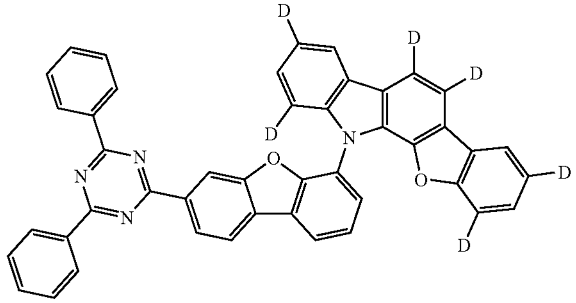
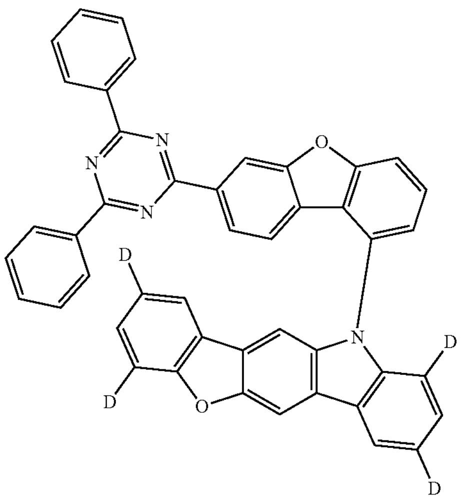

-continued
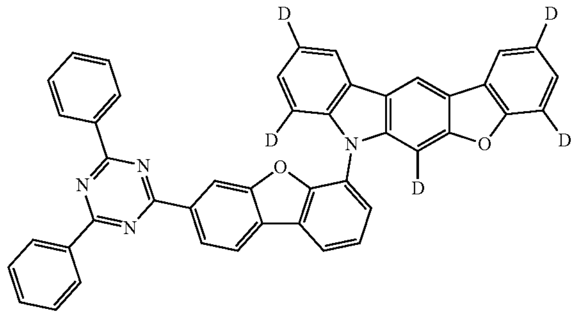
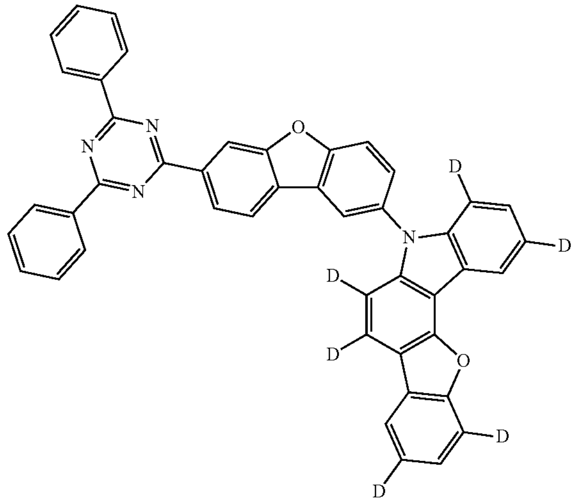
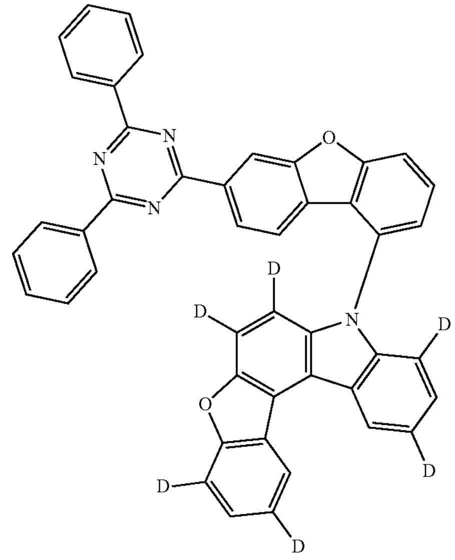
-continued
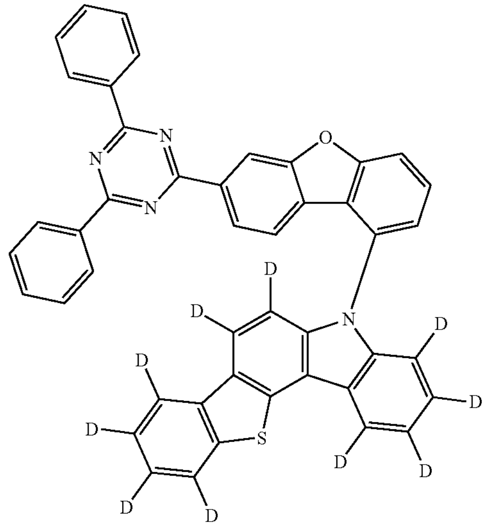
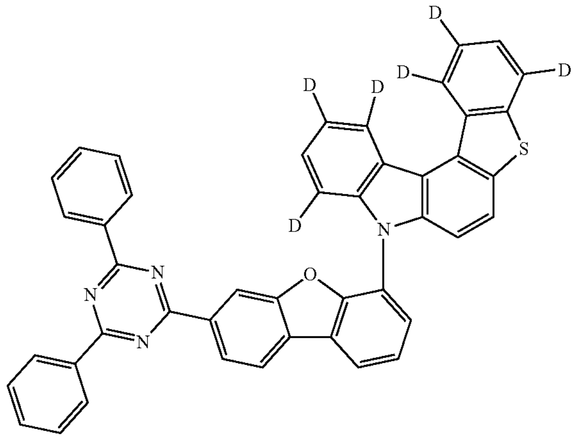
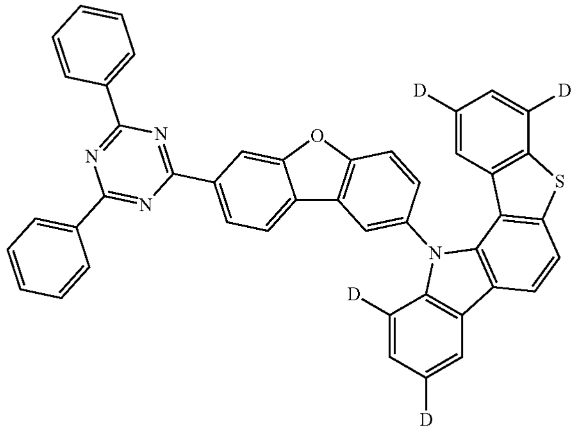

-continued
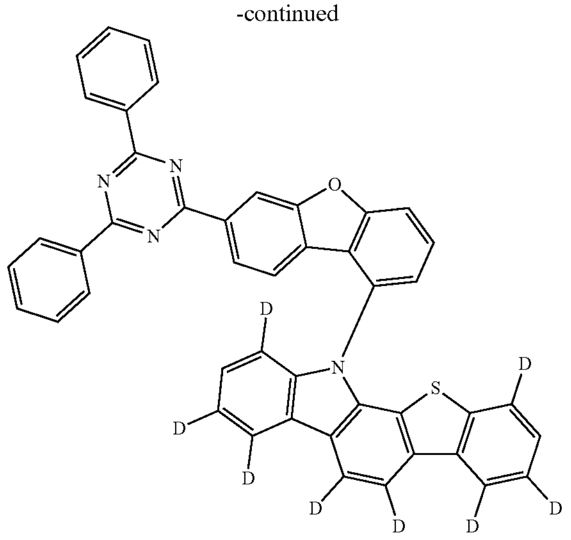
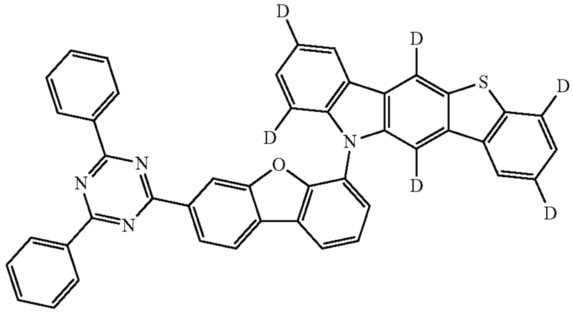
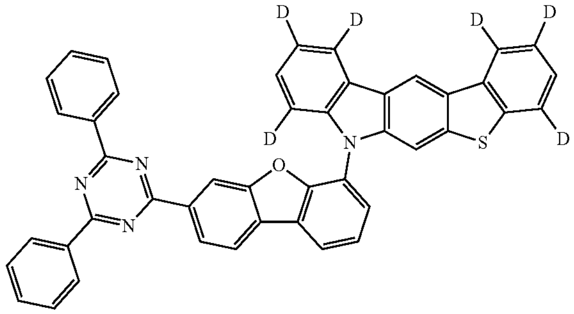
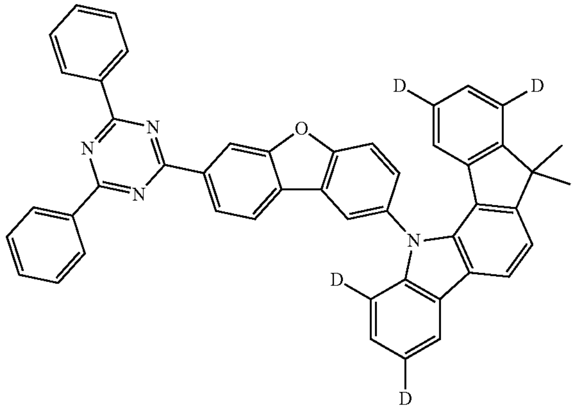
-continued
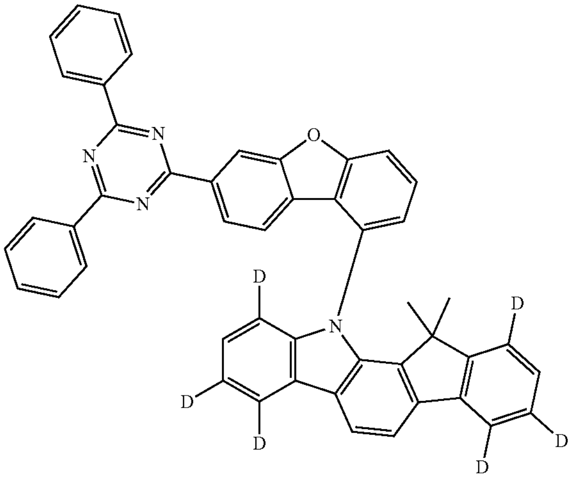
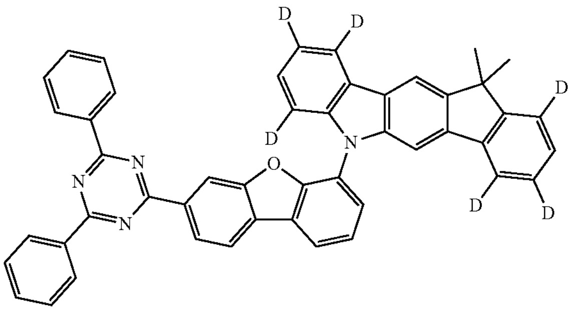
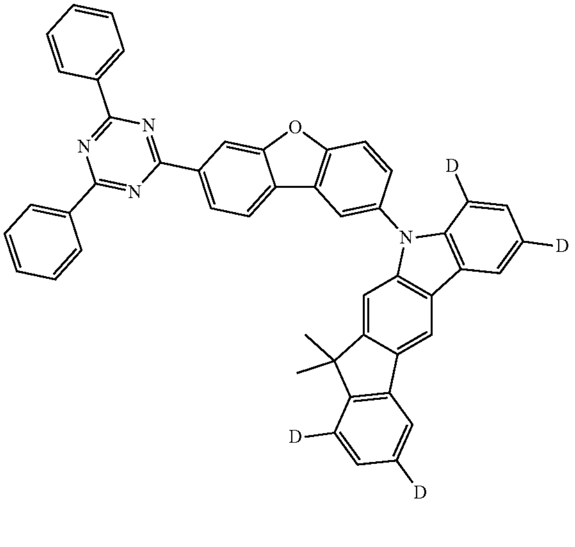

-continued
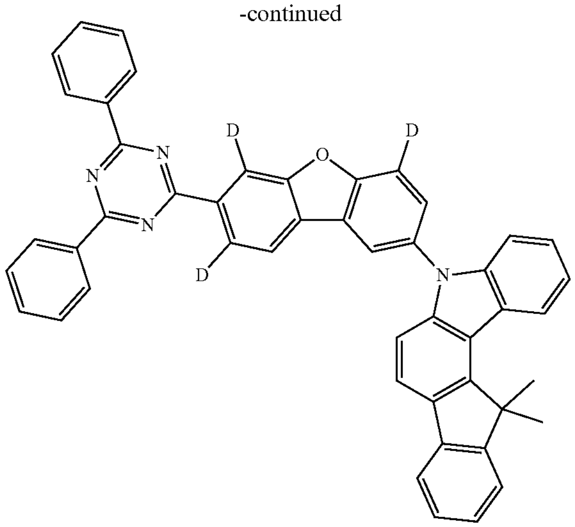
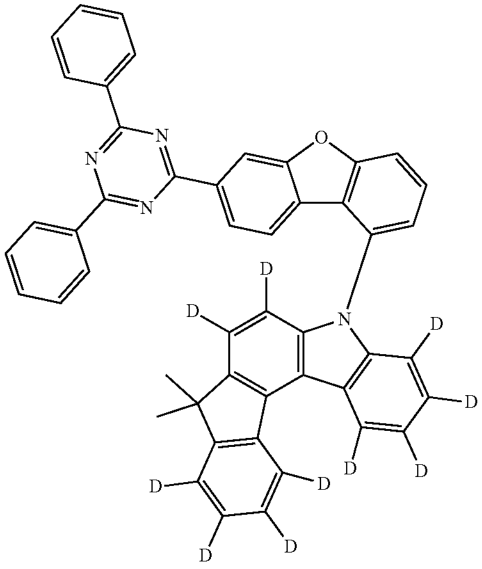
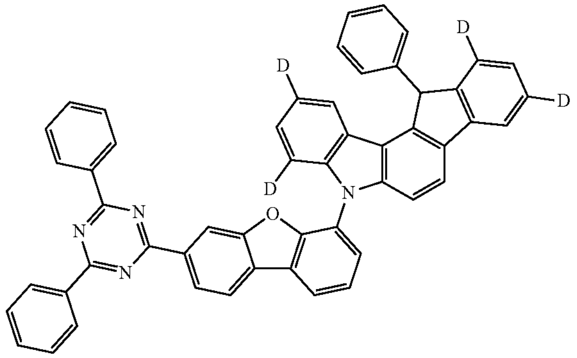
-continued
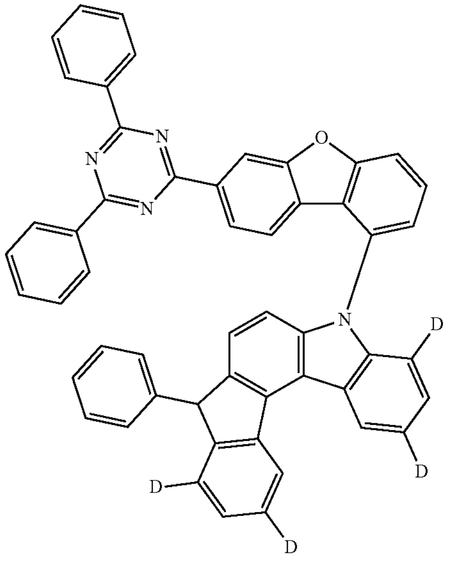
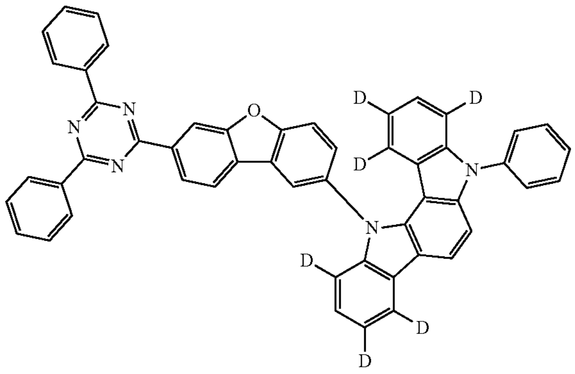
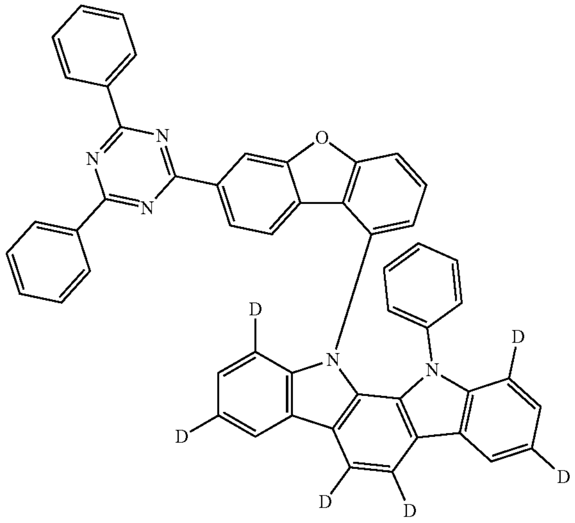

-continued
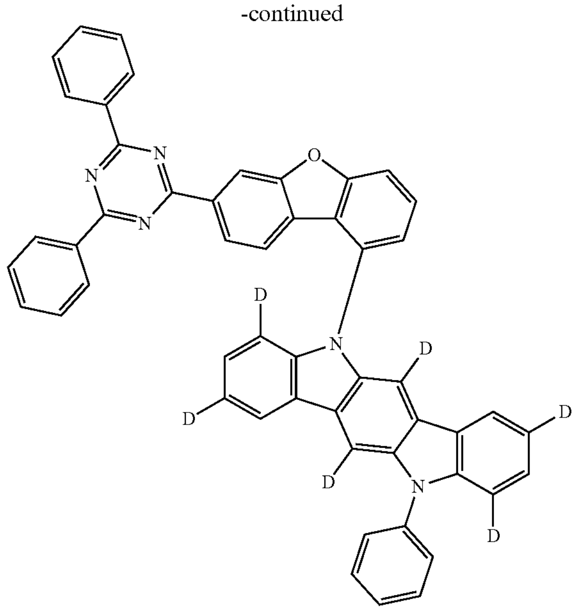
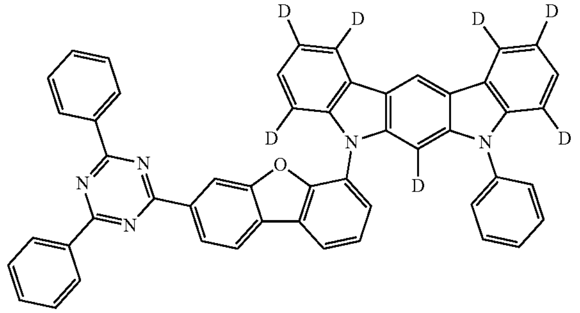
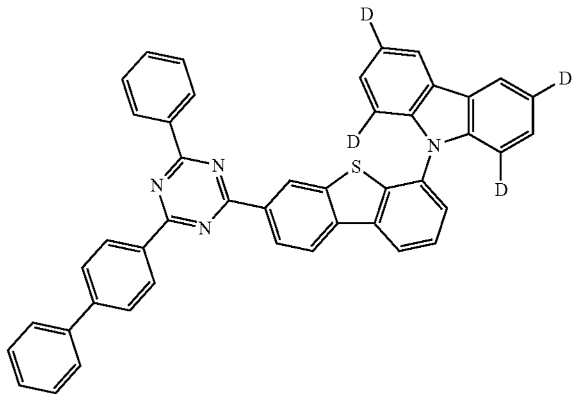
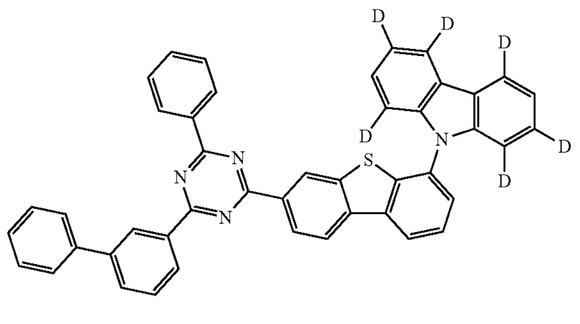
-continued
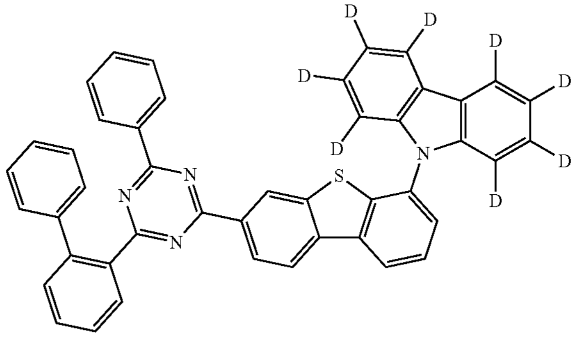
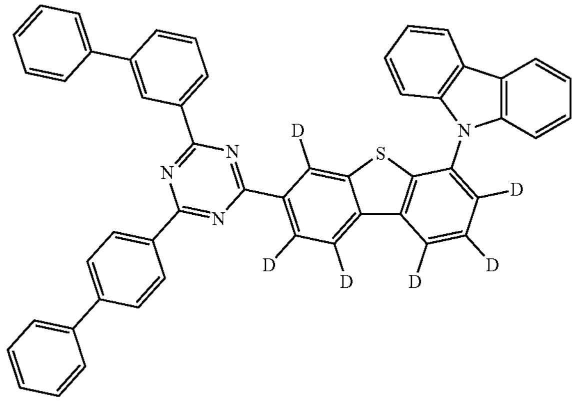
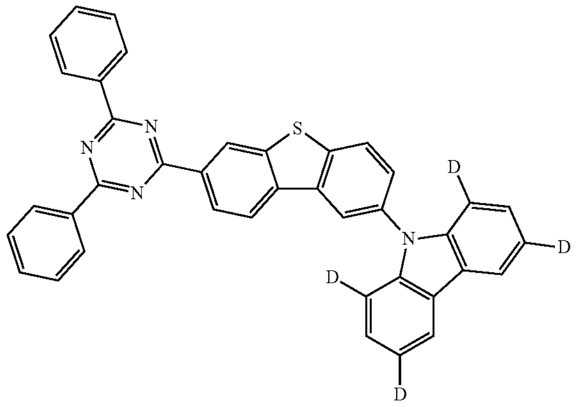
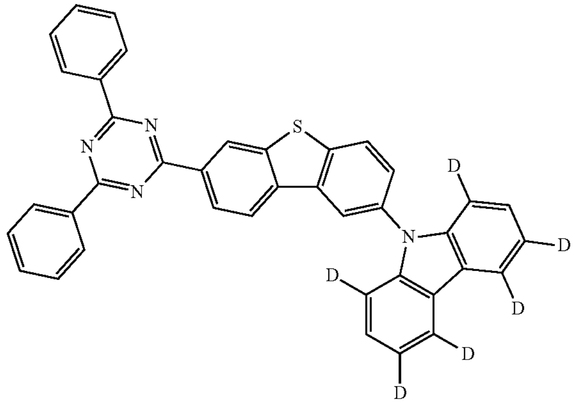

-continued
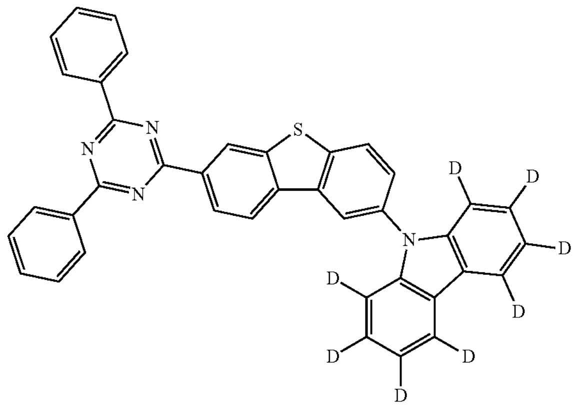
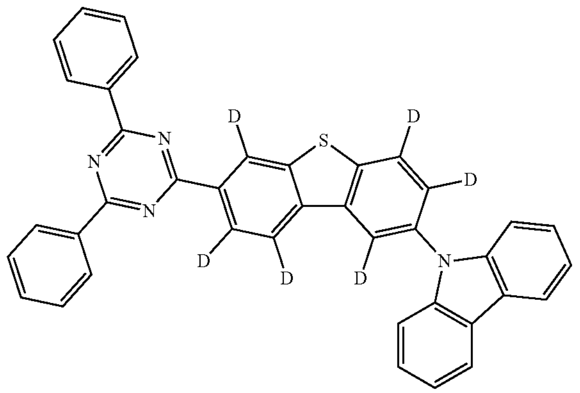
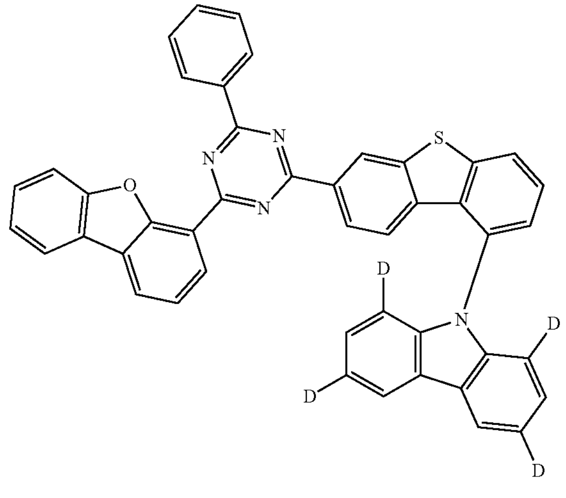
-continued
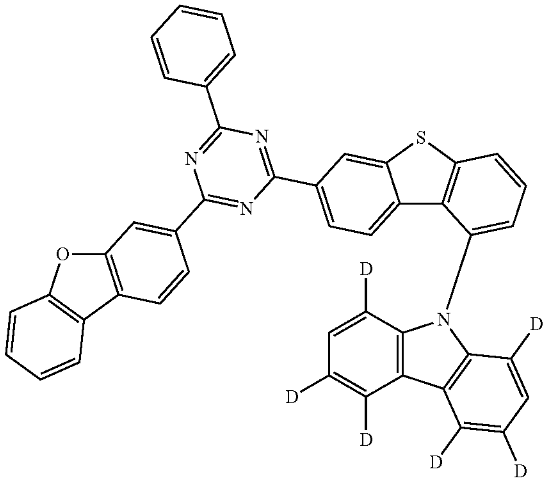
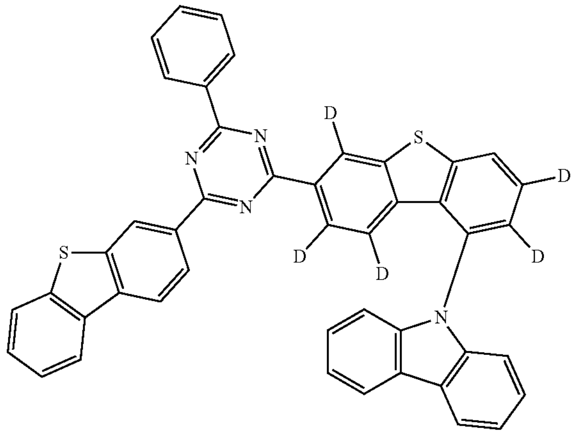
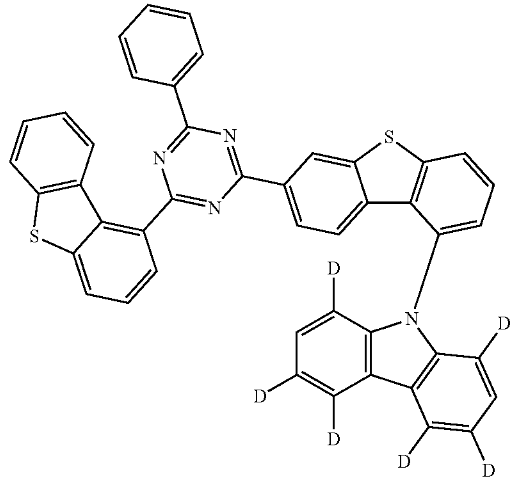

-continued

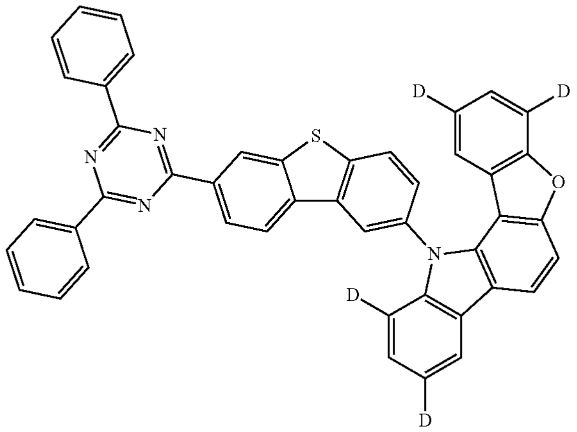

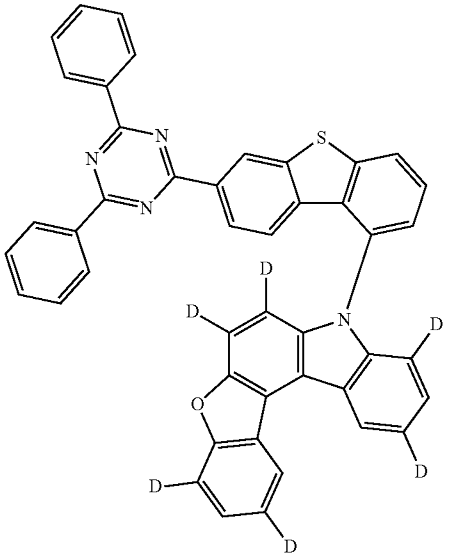

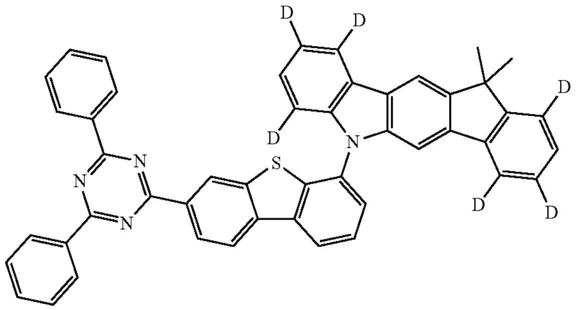

-continued

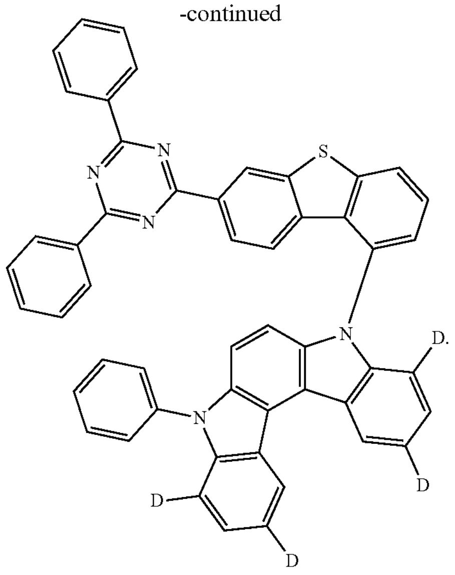

9. The organic light emitting device of claim 4, wherein the compound of Chemical Formula 1 is the following Chemical Formula 1-1 or Chemical Formula 1-2:

<Chemical Formula 1-1>

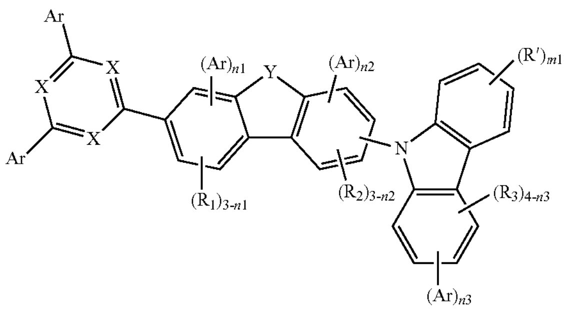

<Chemical Formula 1-2>

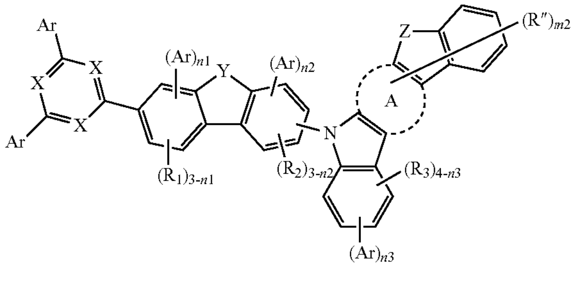

wherein in the Chemical Formulae 1-1 and 1-2:

X, Y, Ar, $R_1$, $R_2$, $R_3$, n1, n2, and n3 are as defined in claim 4;

A is a benzene ring;

Z is $C(R_5)_2$, O, S, or N—$(R_6)$;

each $R_5$ is independently a $C_{1-10}$ alkyl that is unsubstituted or substituted with deuterium, or a $C_{6-20}$ aryl that is unsubstituted or substituted with deuterium;

$R_6$ is a $C_{6-60}$ aryl that is unsubstituted or substituted with deuterium;

R' and R" are each independently hydrogen or deuterium;

m1 is an integer of 1 to 4; and m2 is an integer of 1 to 6, provided that at least one of Ar is phenyl substituted with five deuteriums, or at least one of $R_1$, $R_2$, $R_3$, R', and R" is deuterium.
10. The organic light emitting device of claim 4, wherein the compound of Chemical Formula 1 is any one compound selected from among the following compounds:
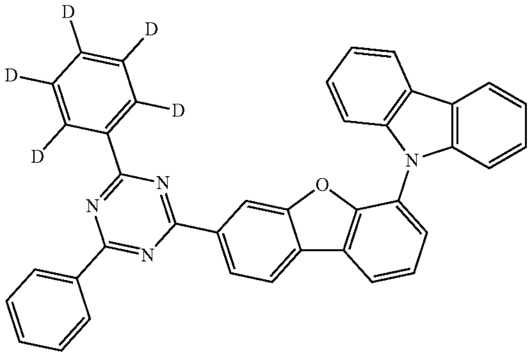
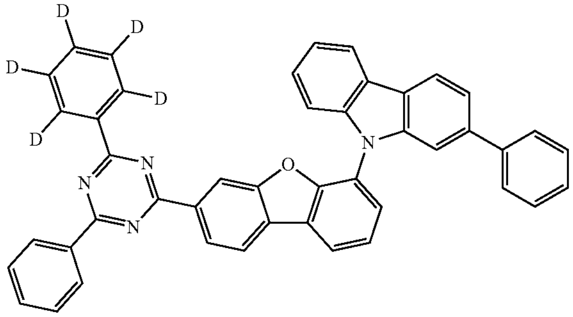
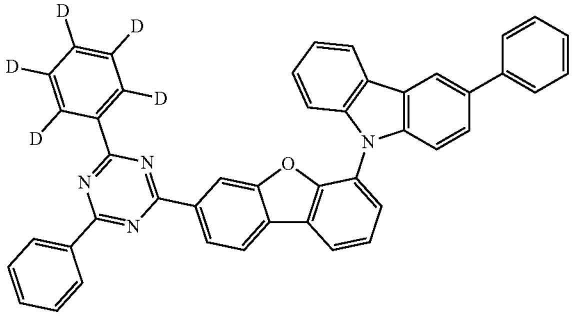
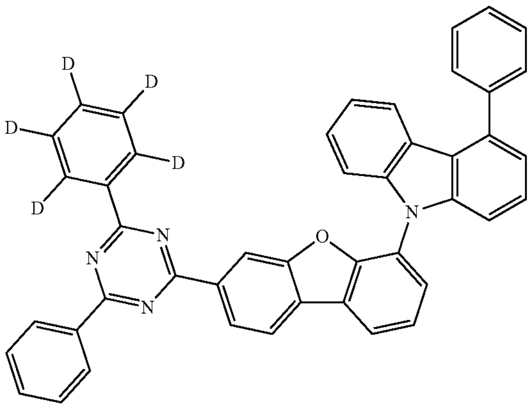
-continued
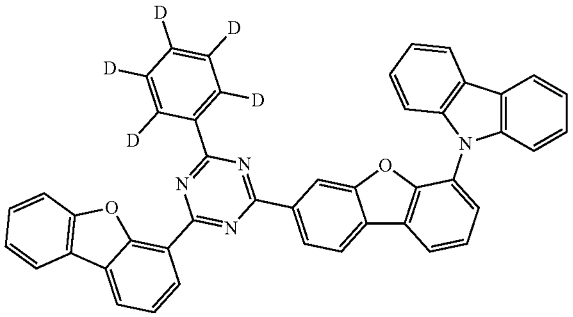
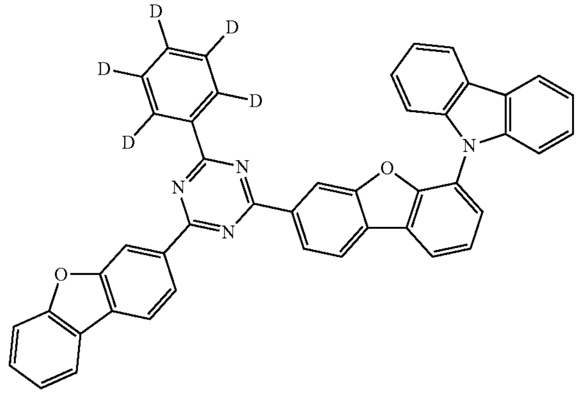
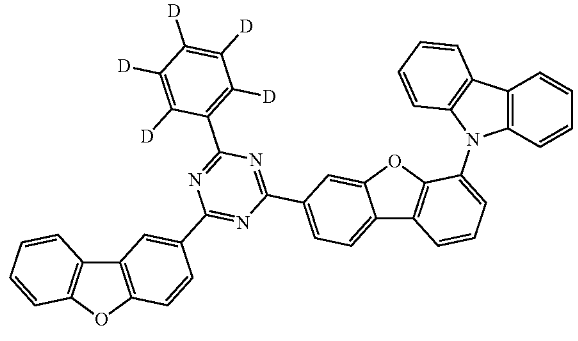
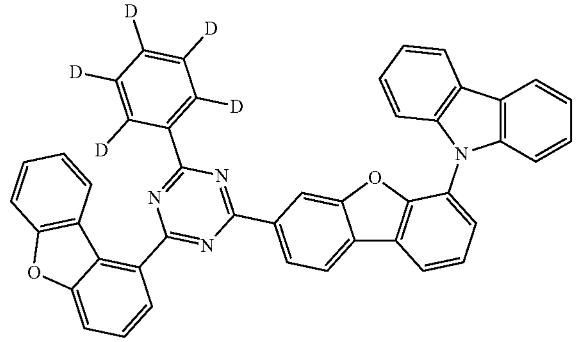
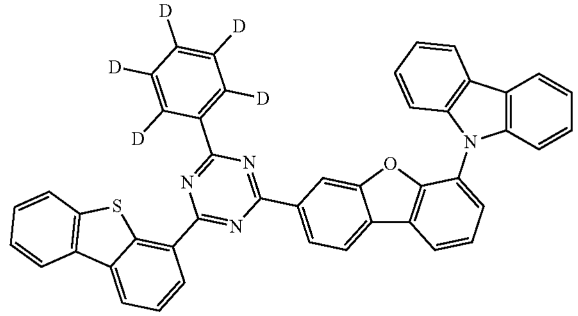

-continued
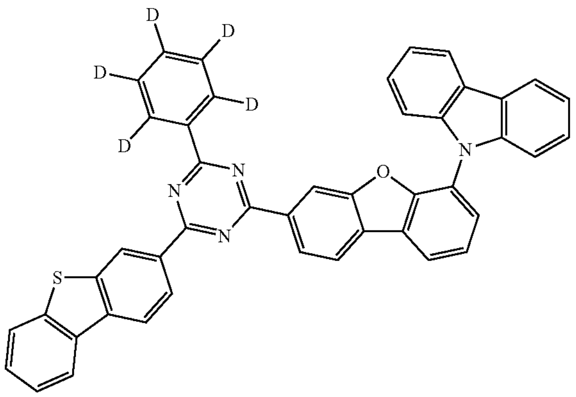
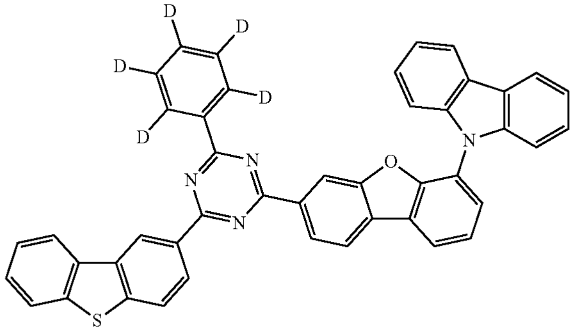
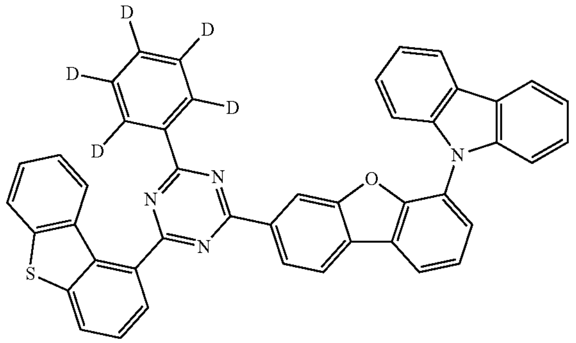
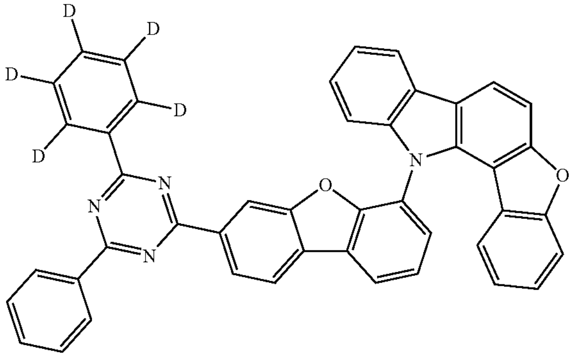
-continued
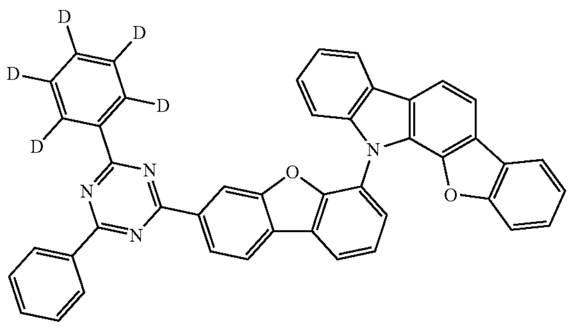
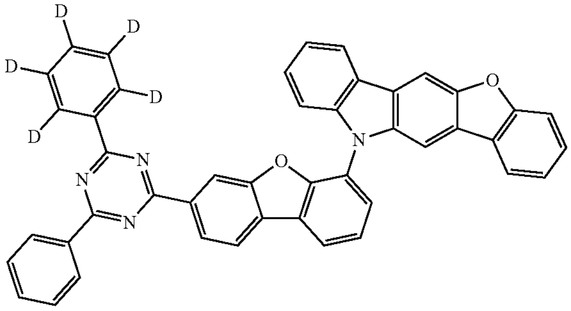
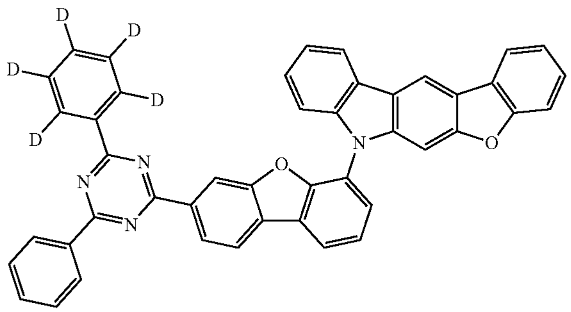
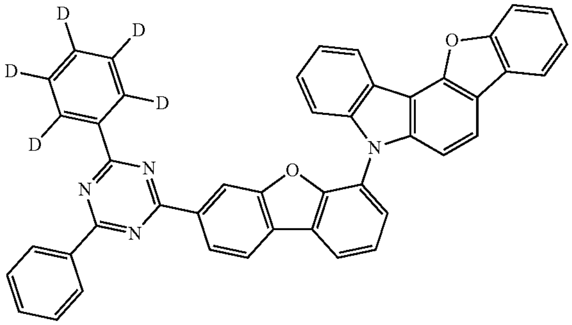
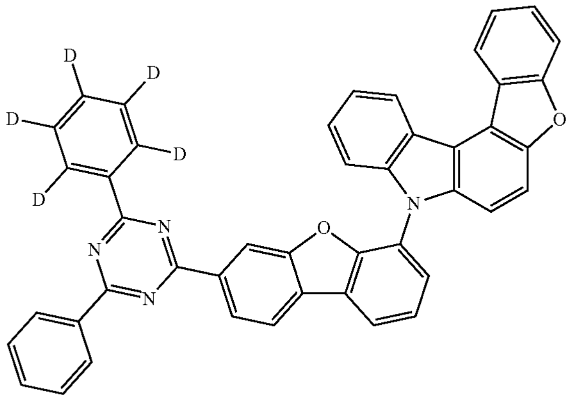

-continued
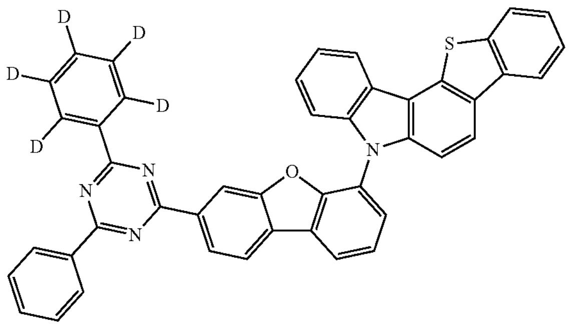
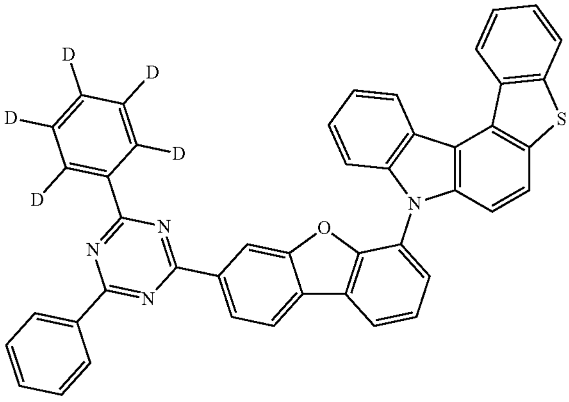
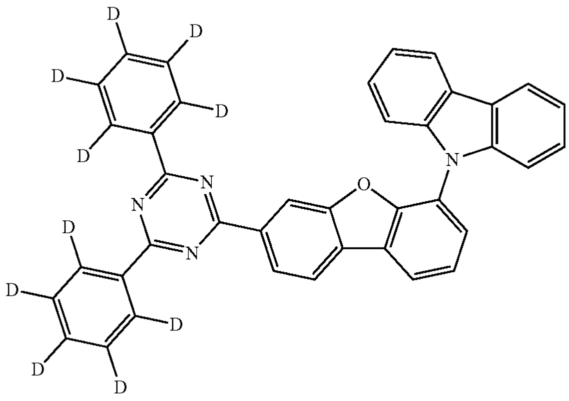
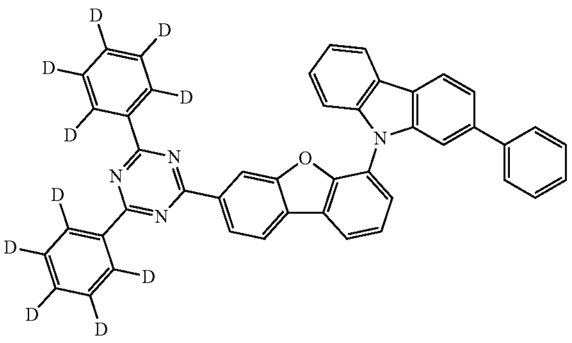
-continued
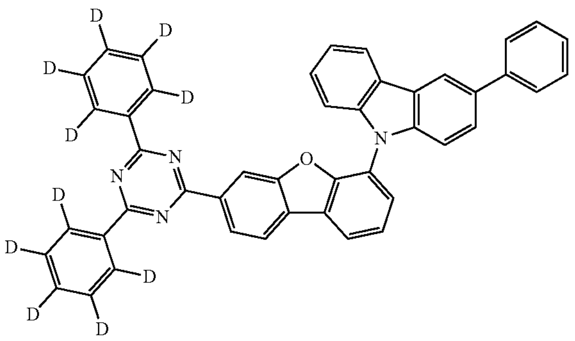
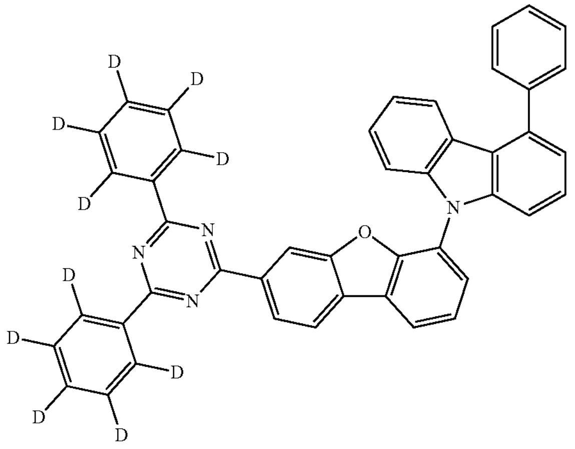
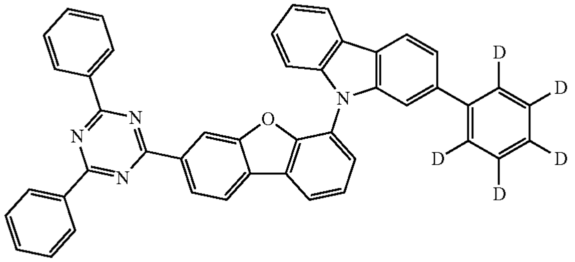
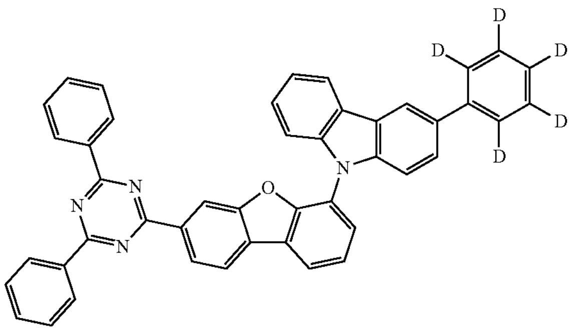

-continued
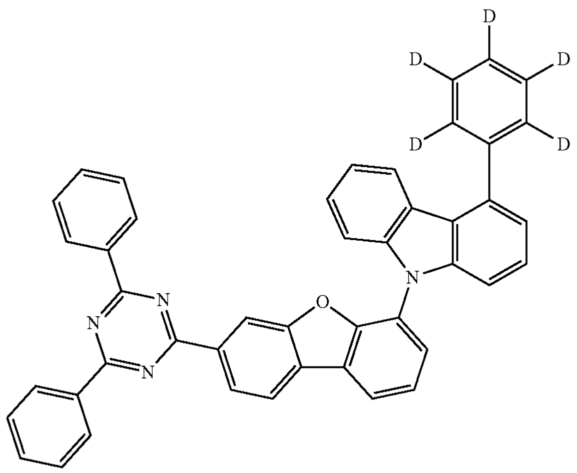
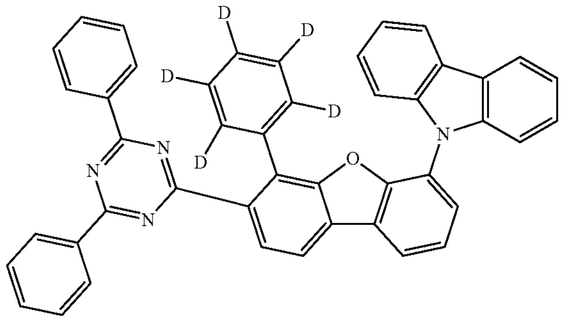
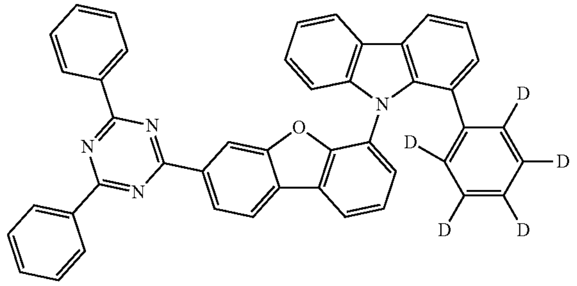
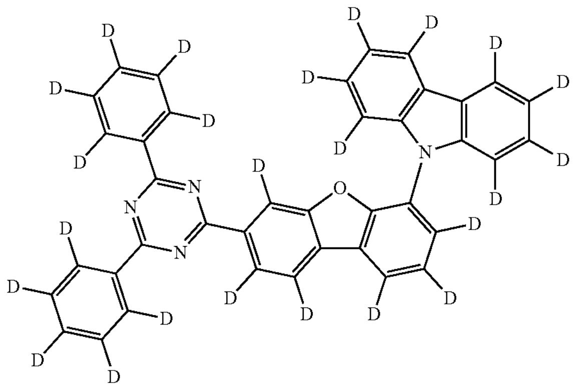
-continued
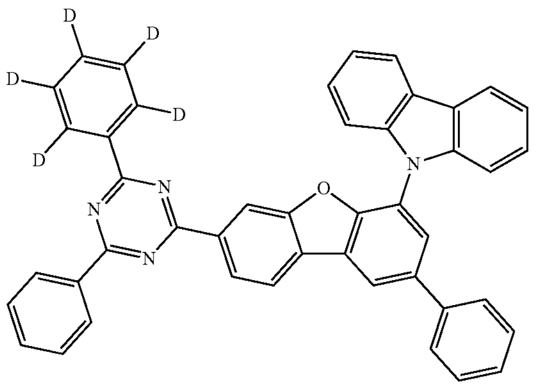
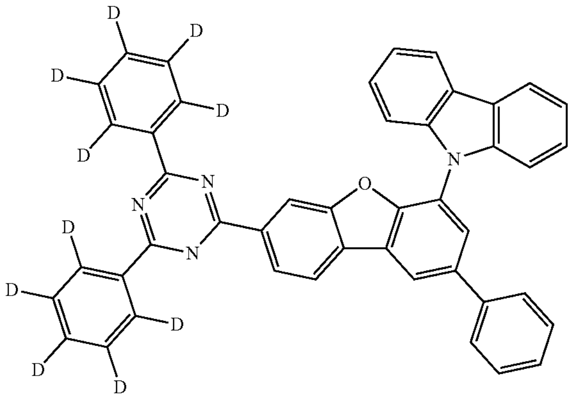
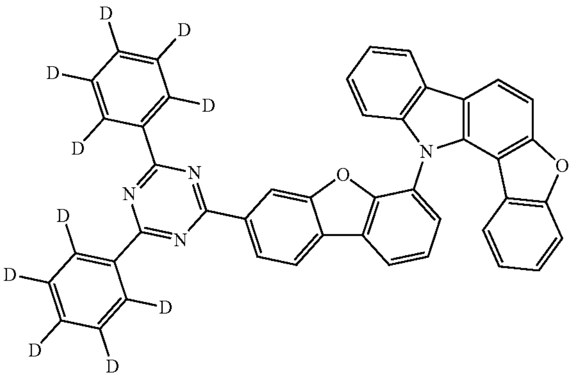
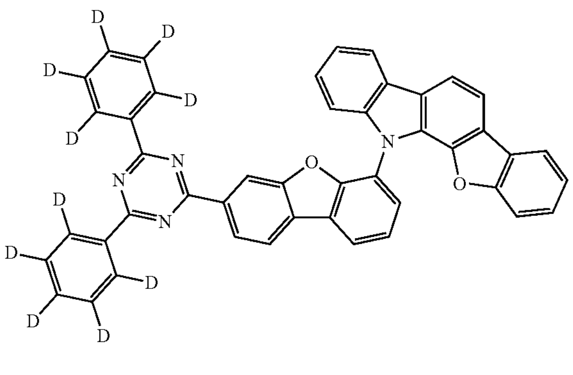

-continued
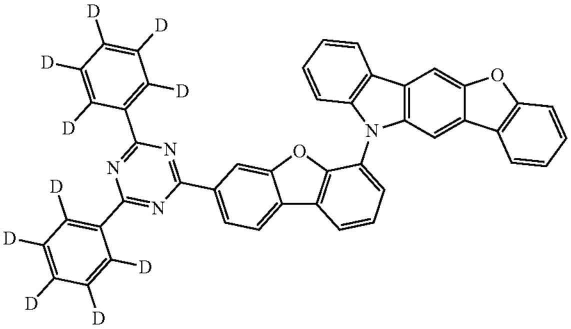
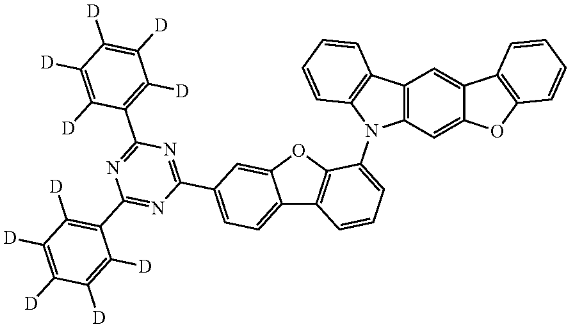
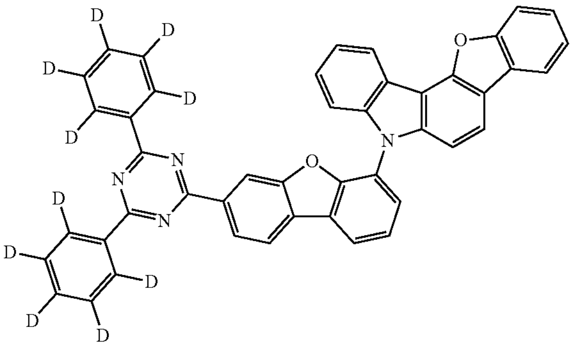
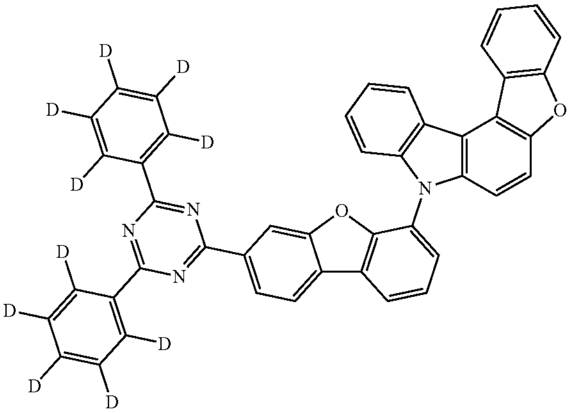
-continued
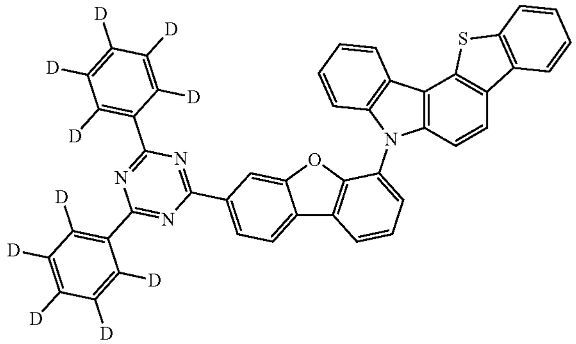
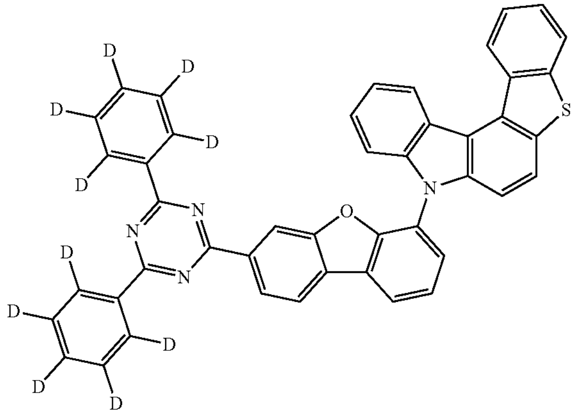
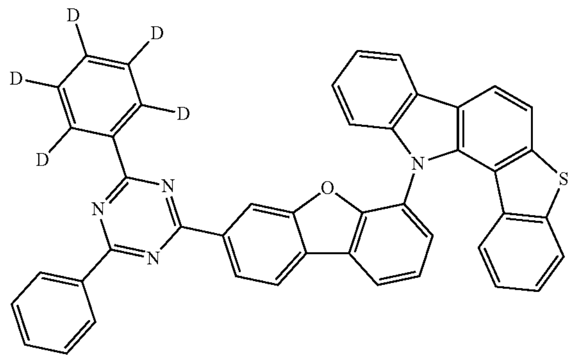
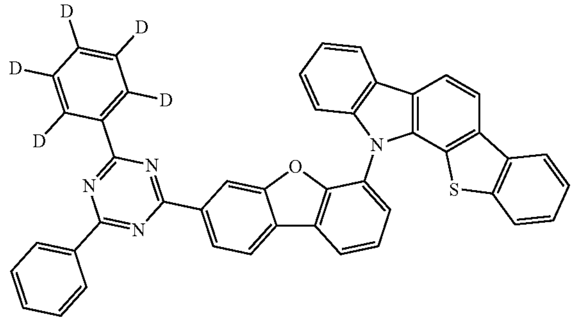

-continued
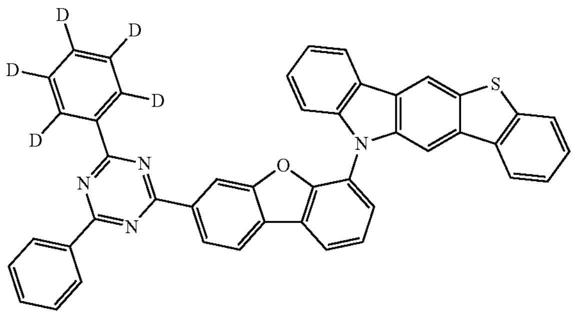
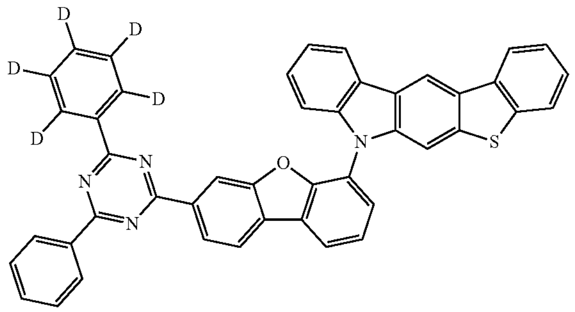
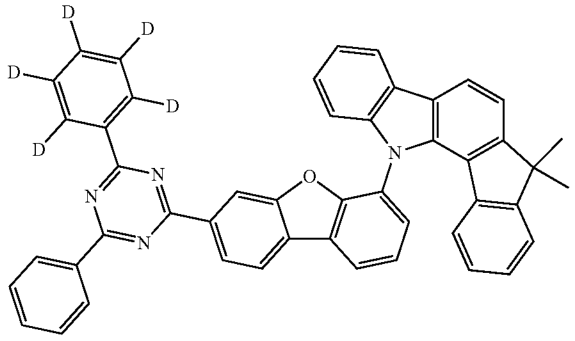
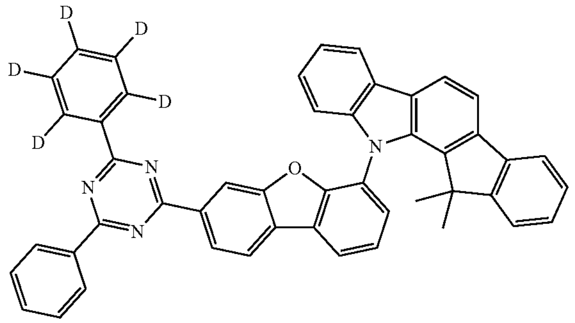
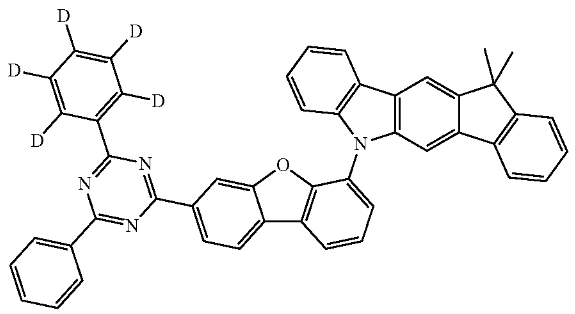
-continued
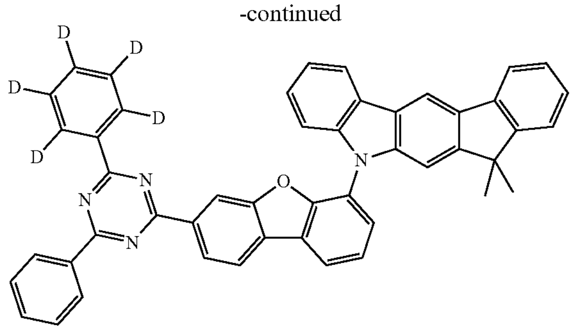
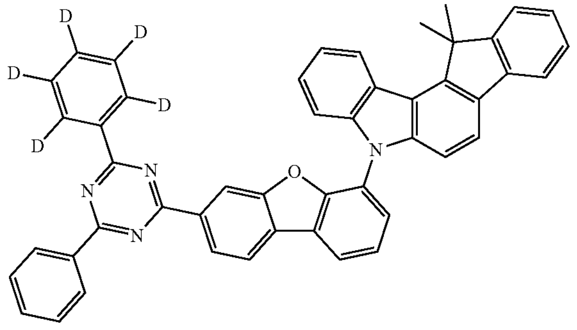
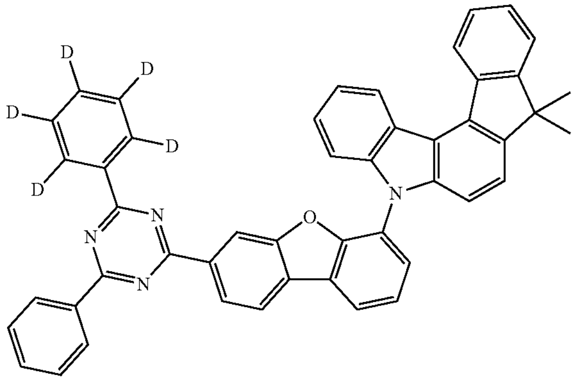
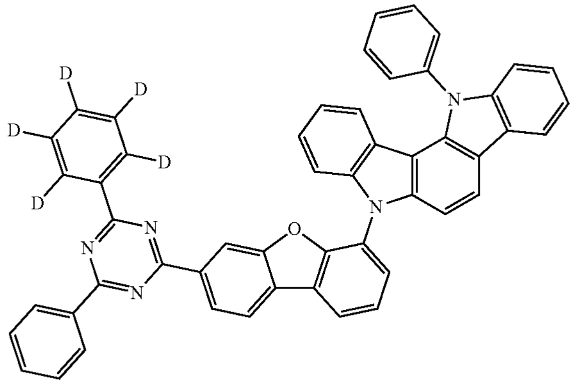
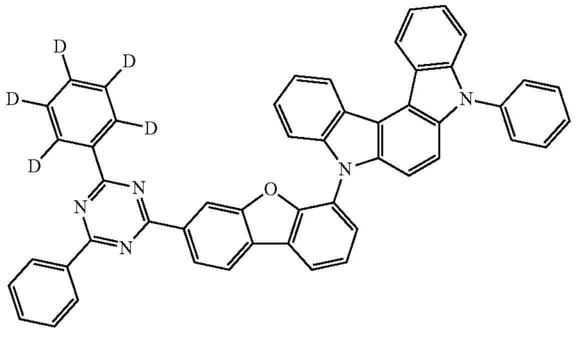

-continued
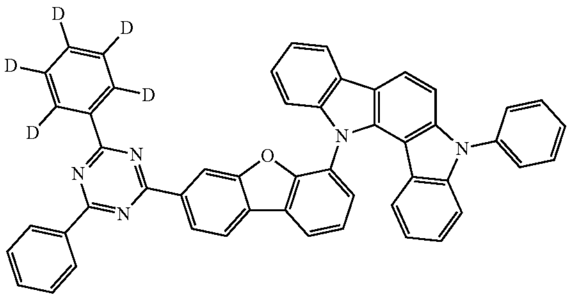
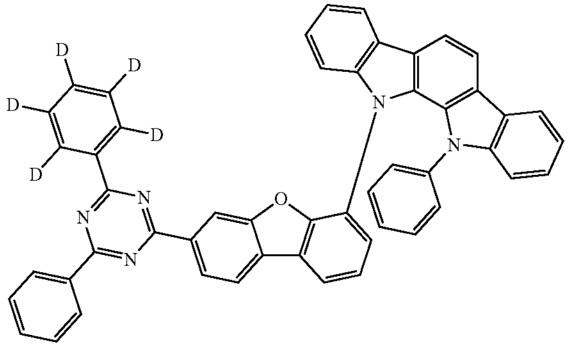
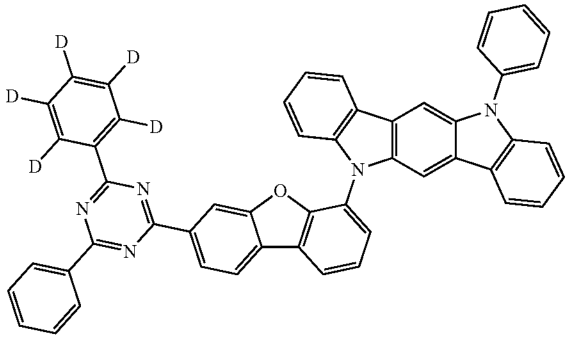
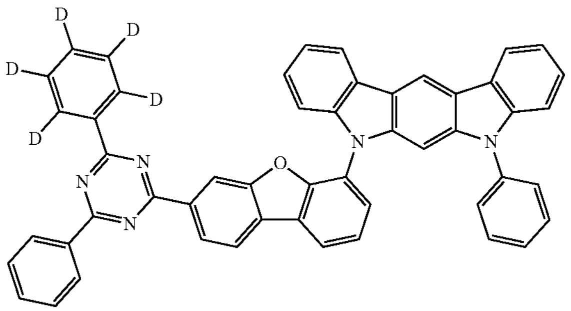
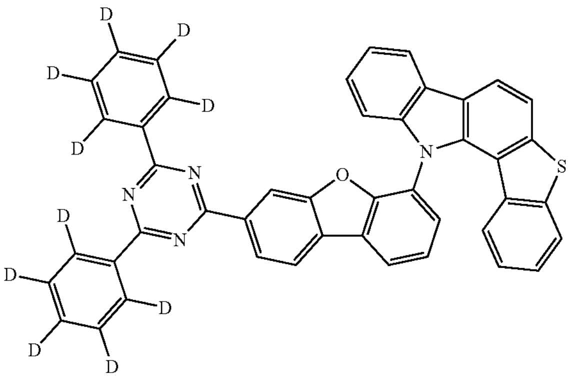
-continued
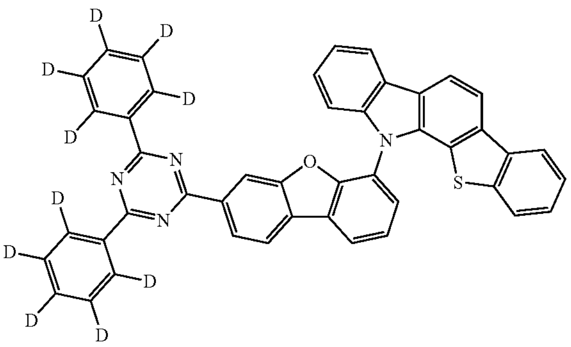
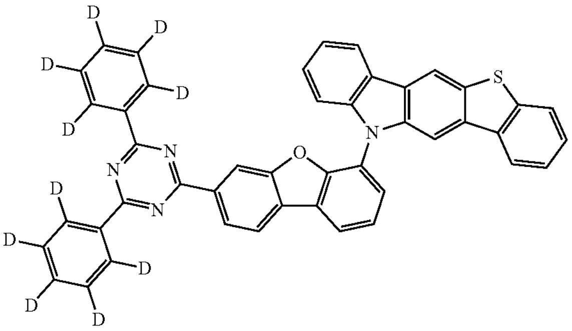
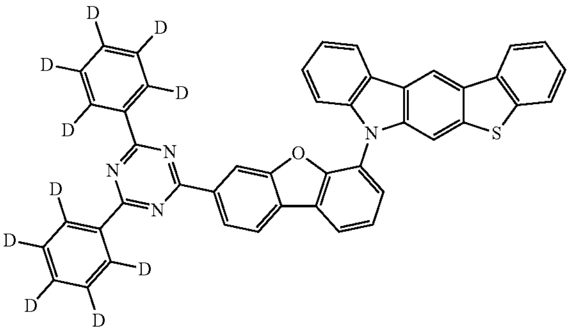
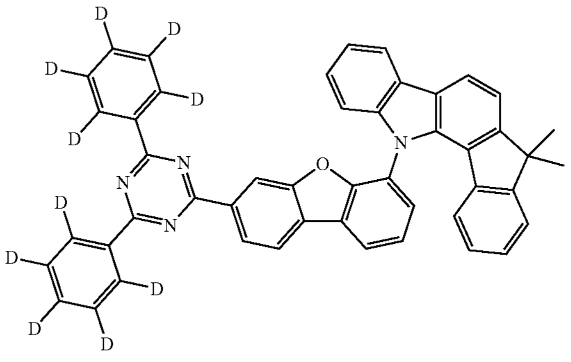
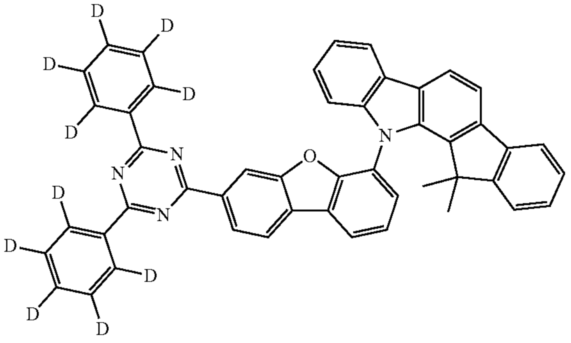

-continued
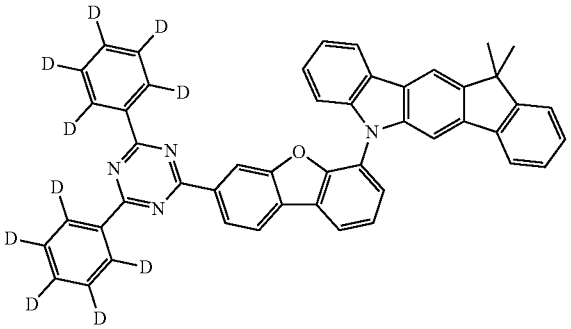
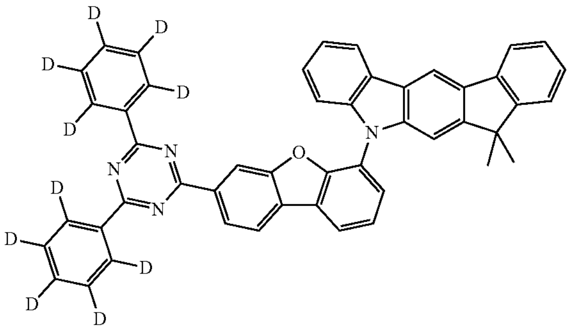
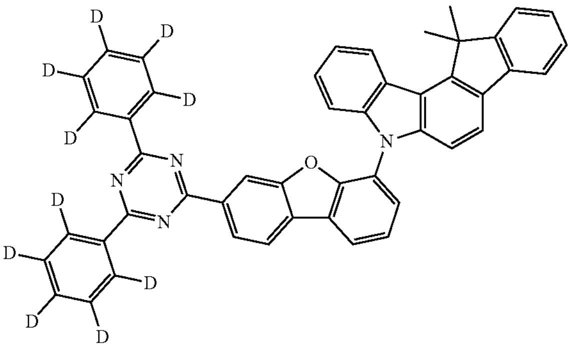
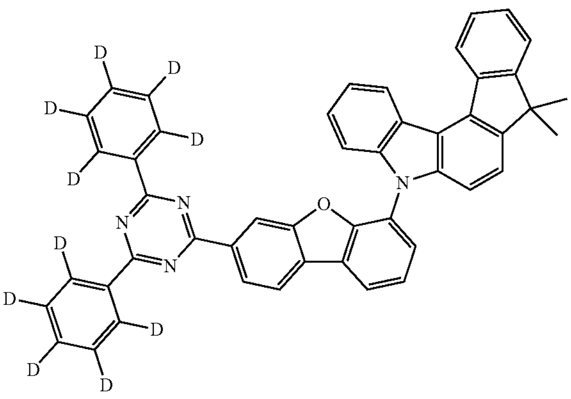
-continued
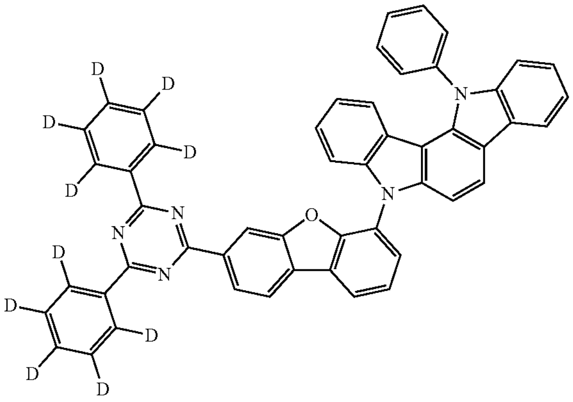
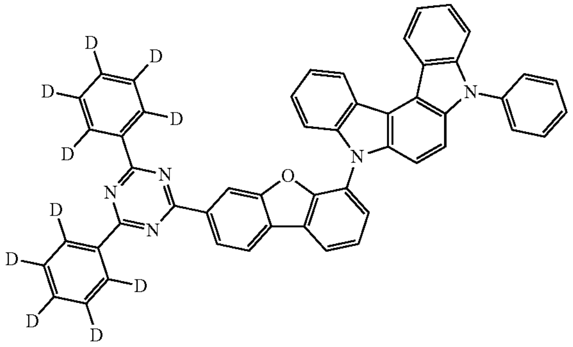
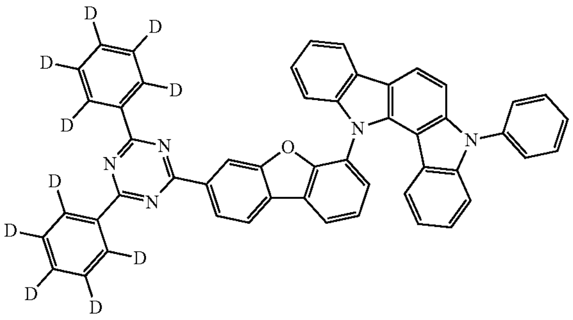
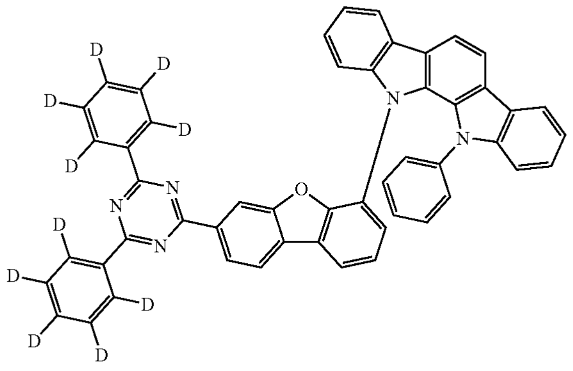

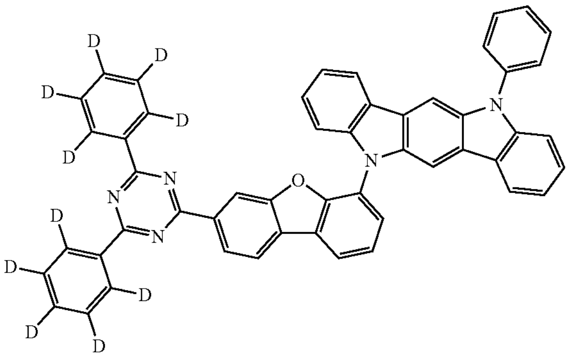
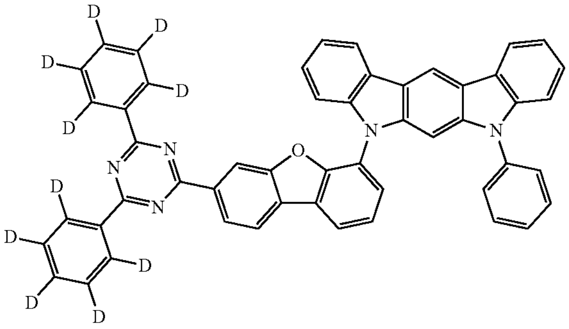
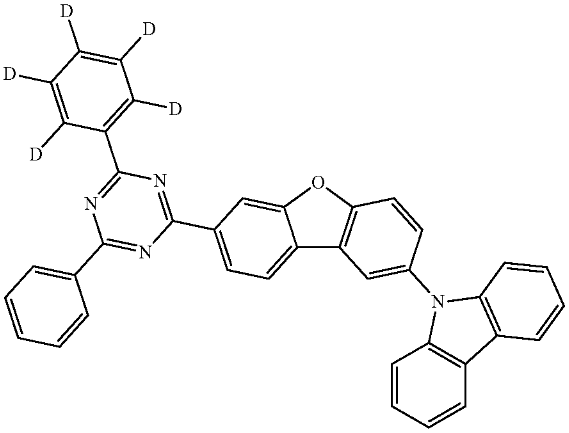
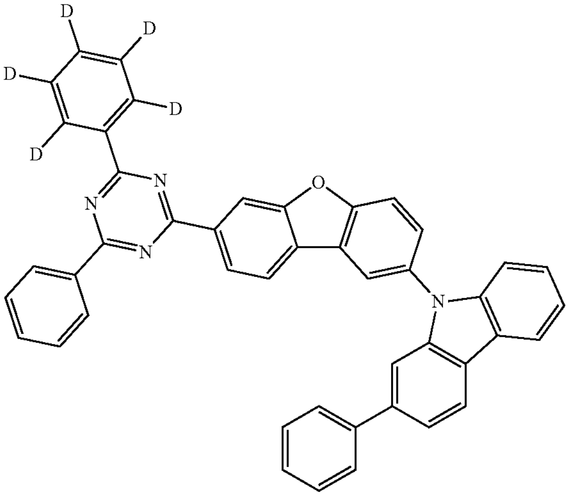
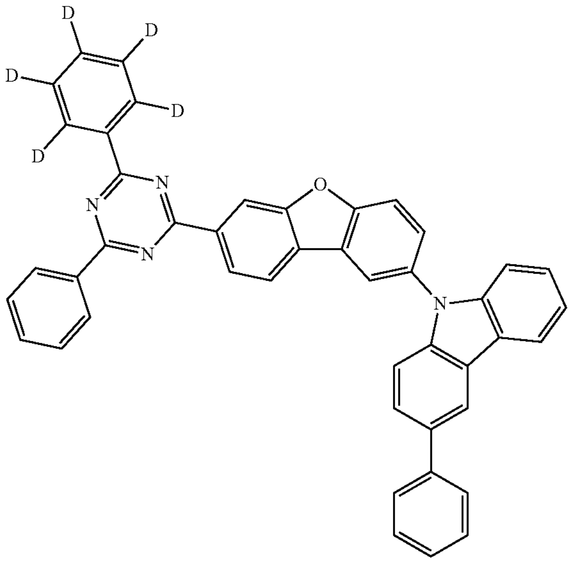
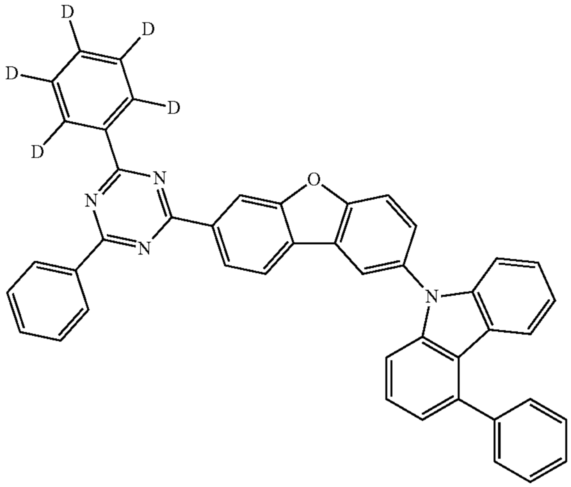
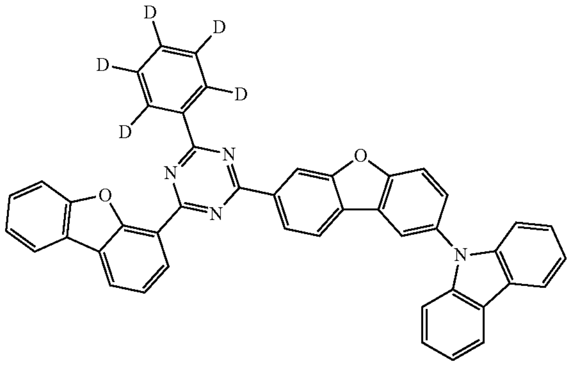

-continued
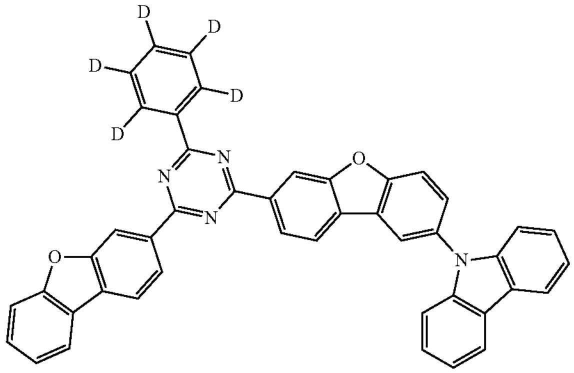
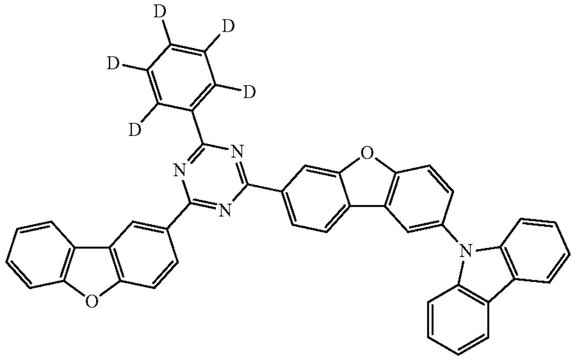
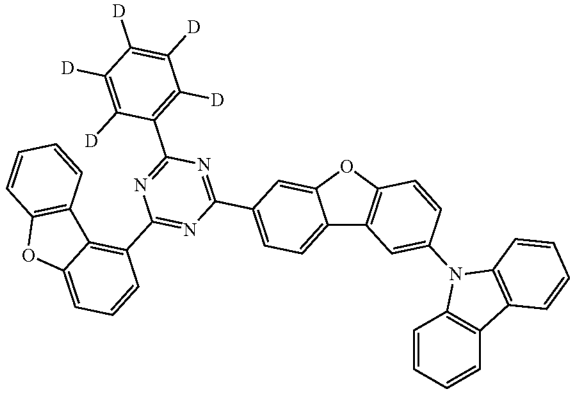
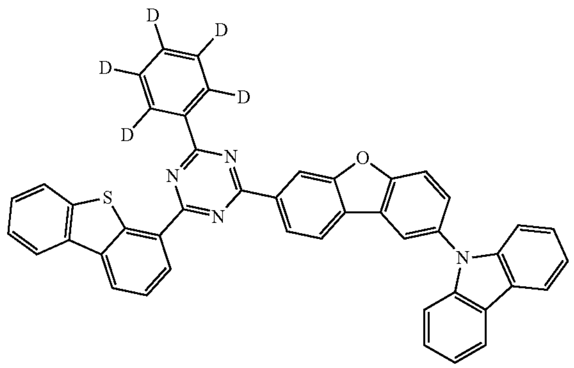
-continued
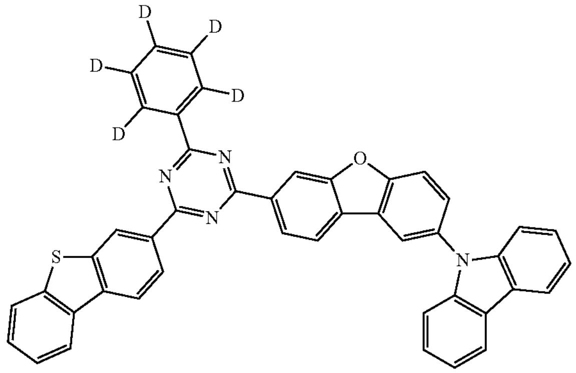
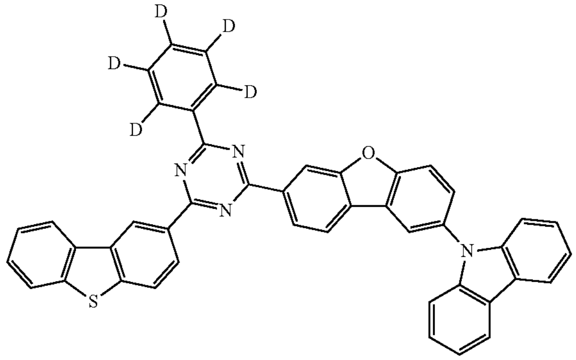
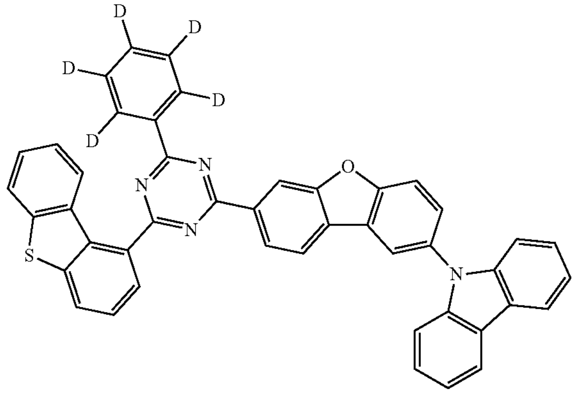
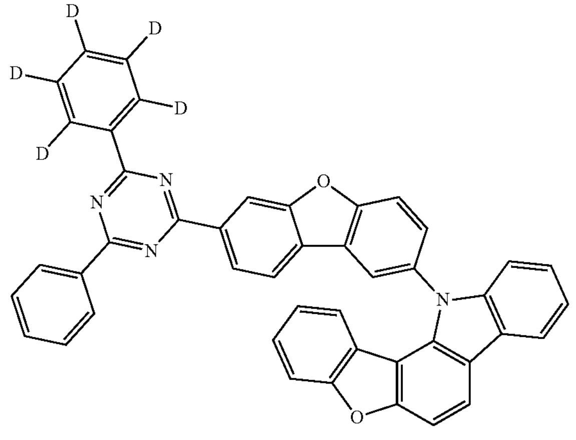

-continued
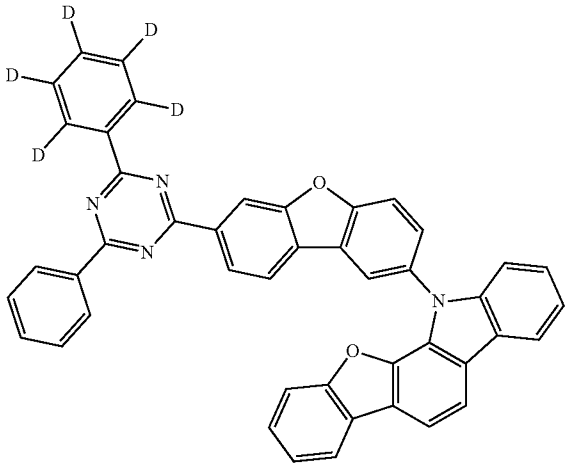
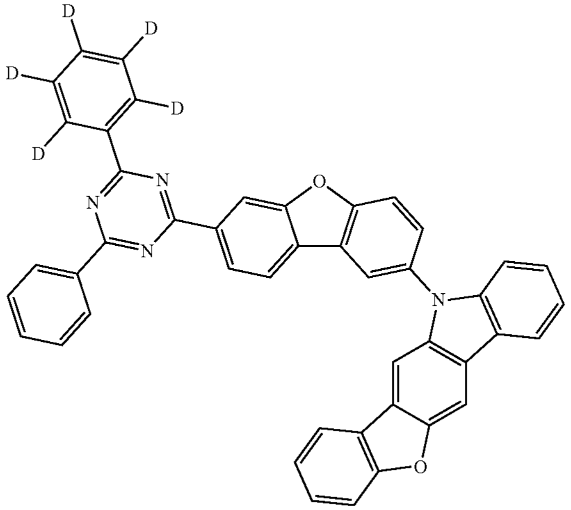
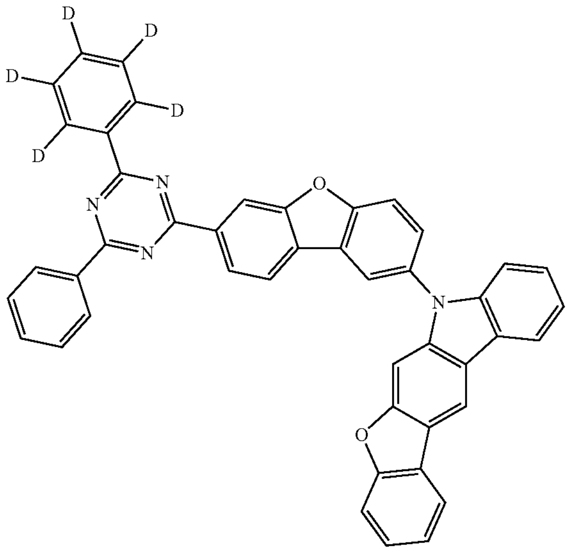
-continued
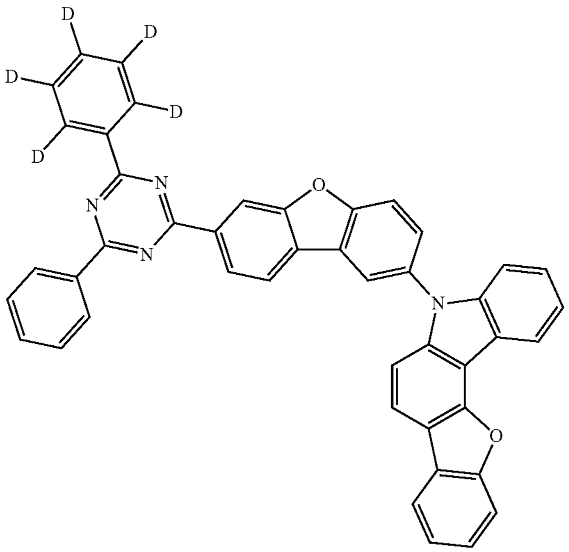
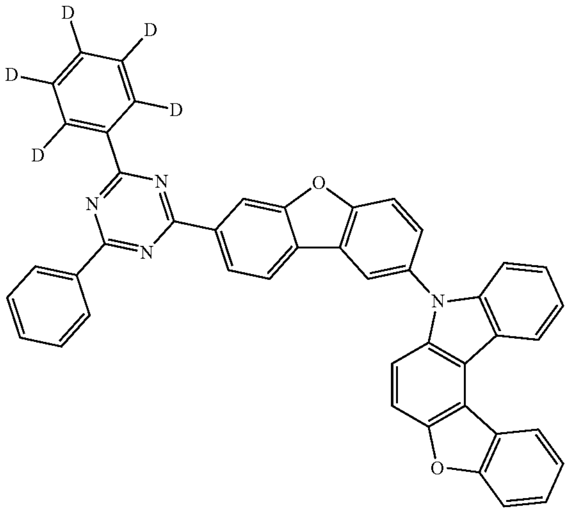
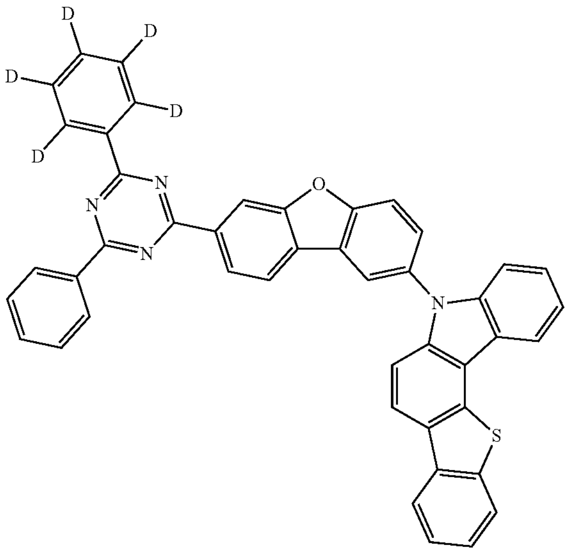

-continued
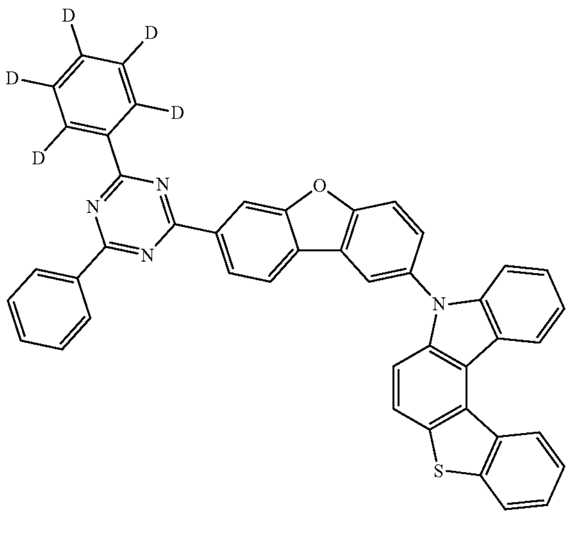
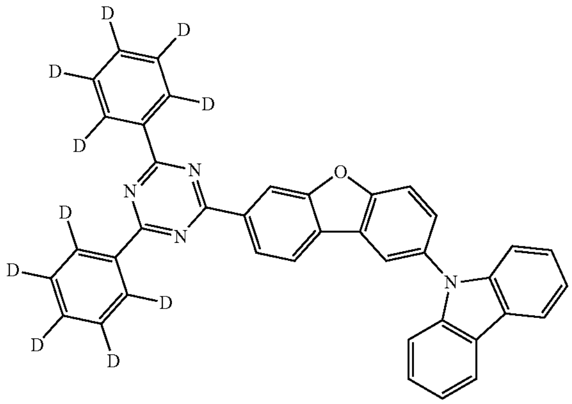
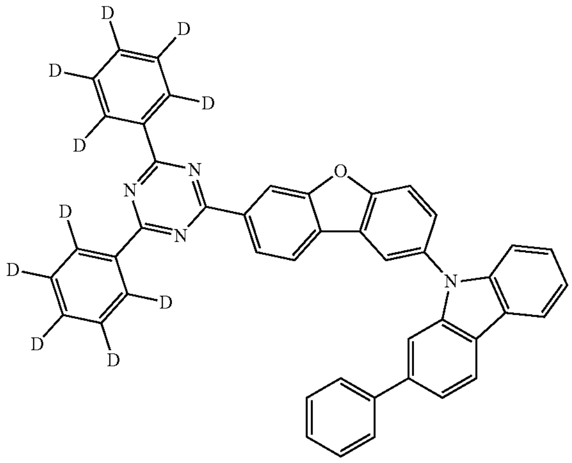
-continued
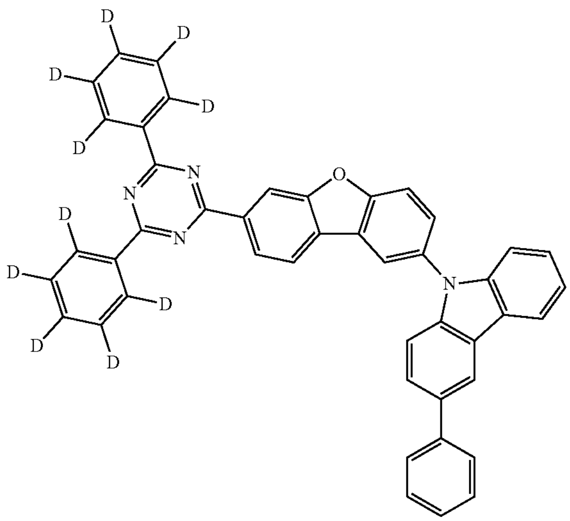
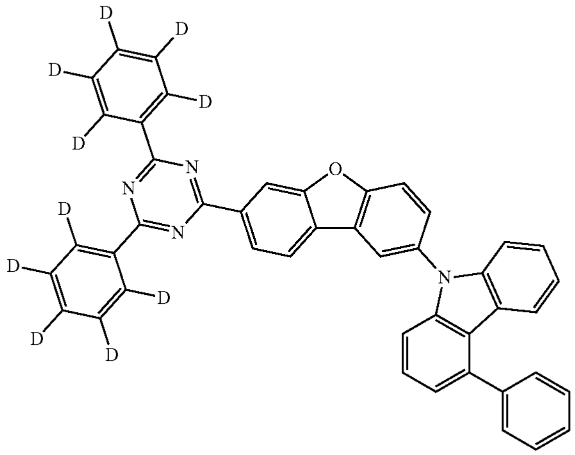
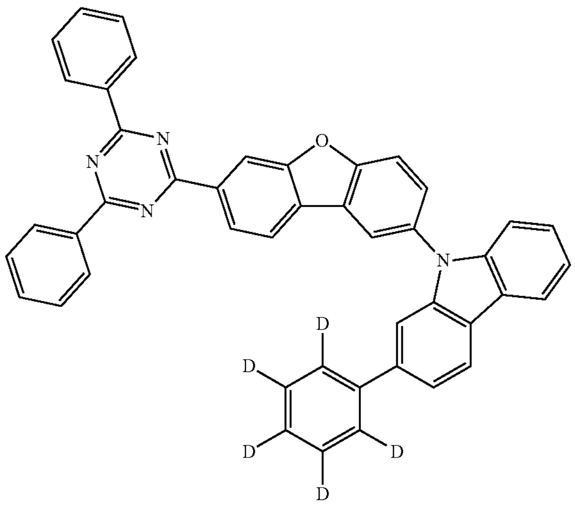

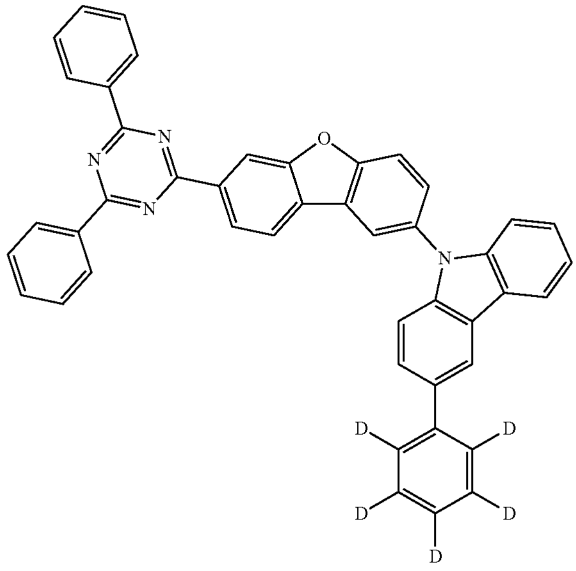
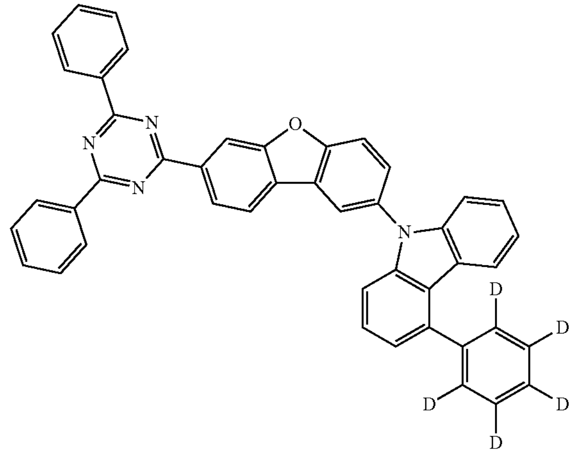
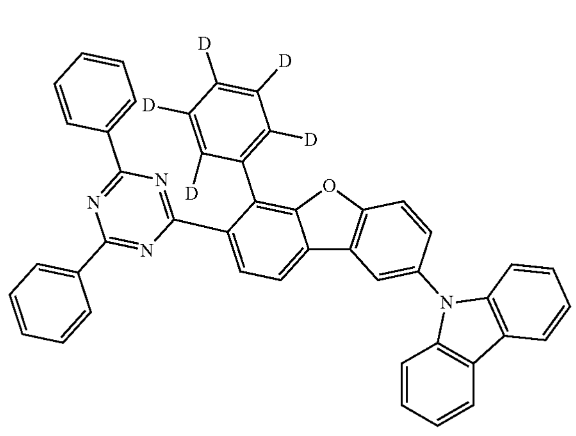
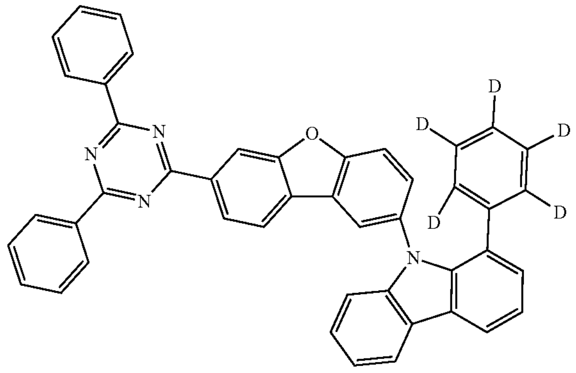
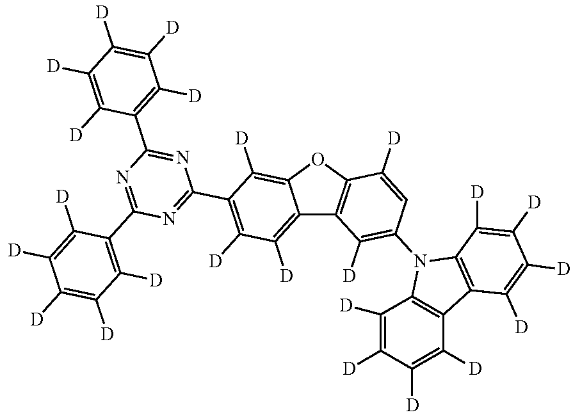
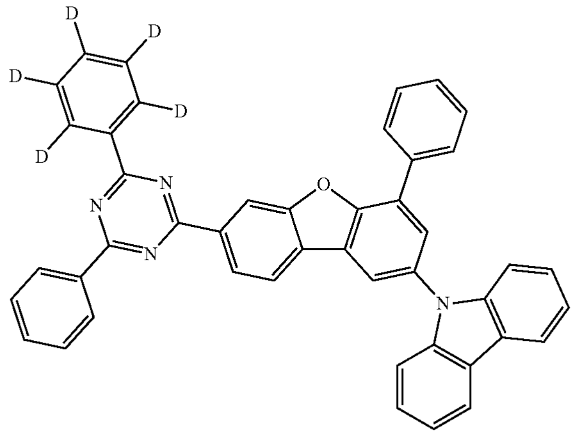
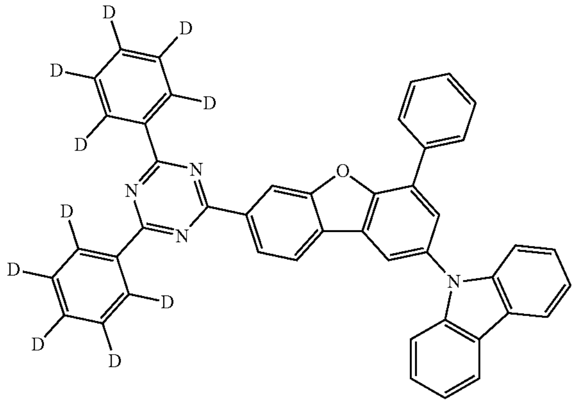

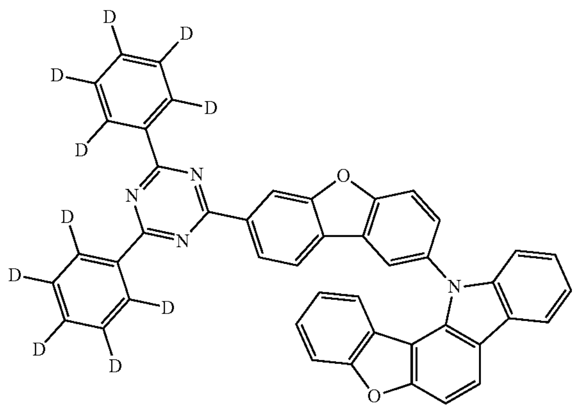
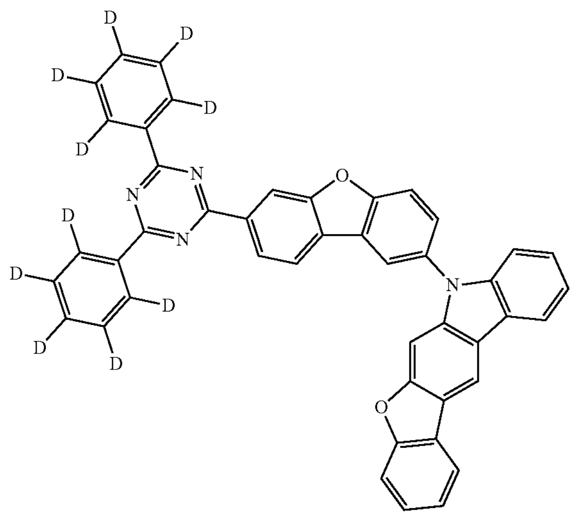
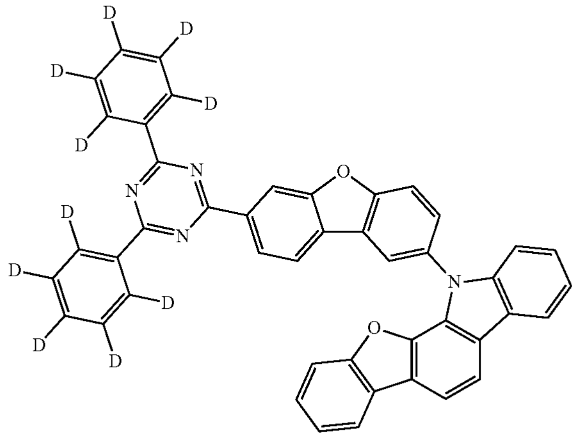
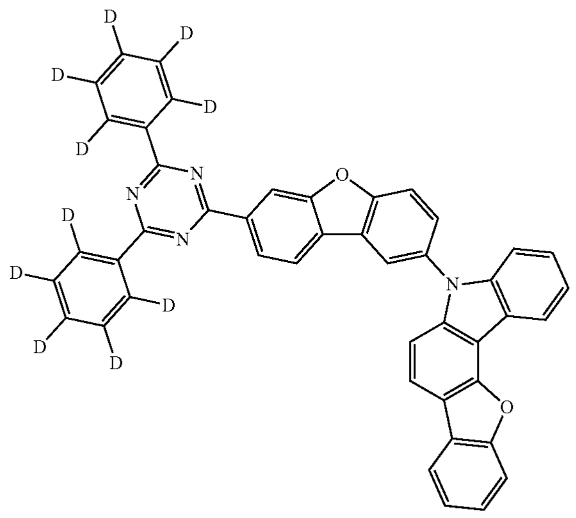
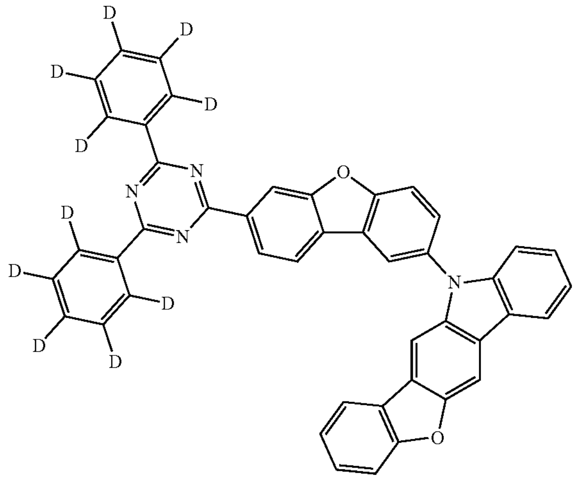
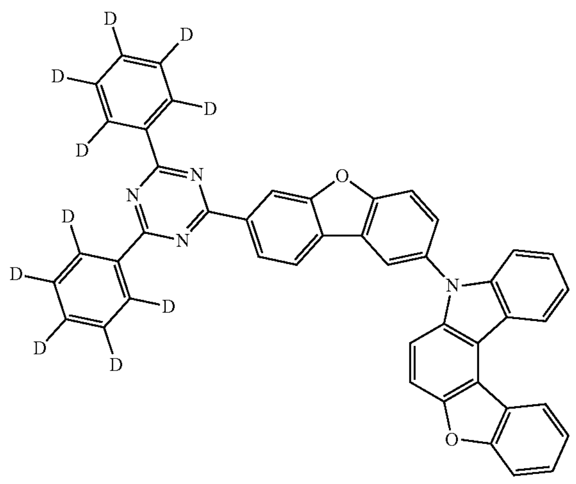

-continued
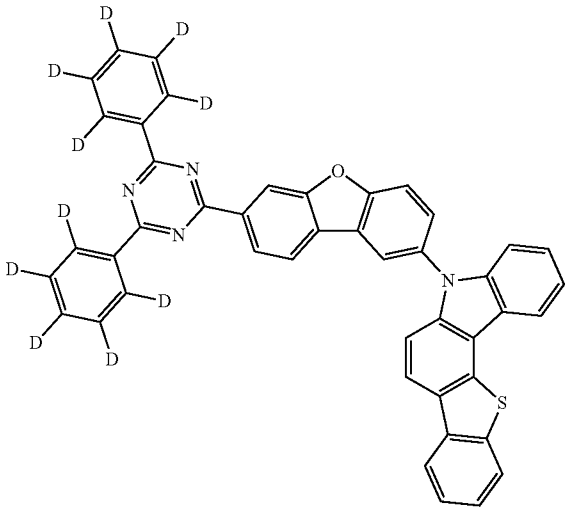
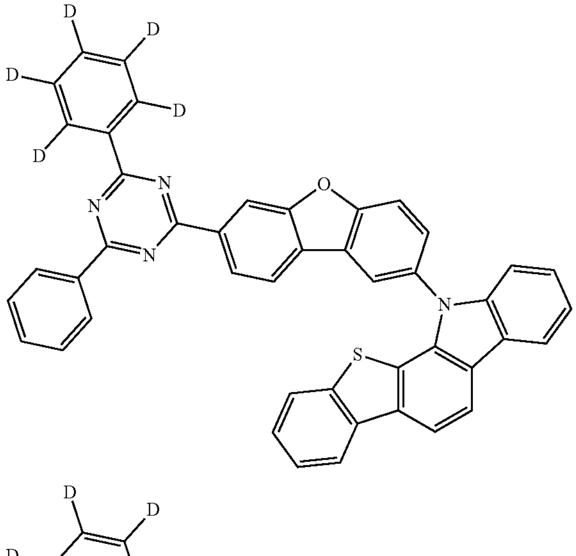
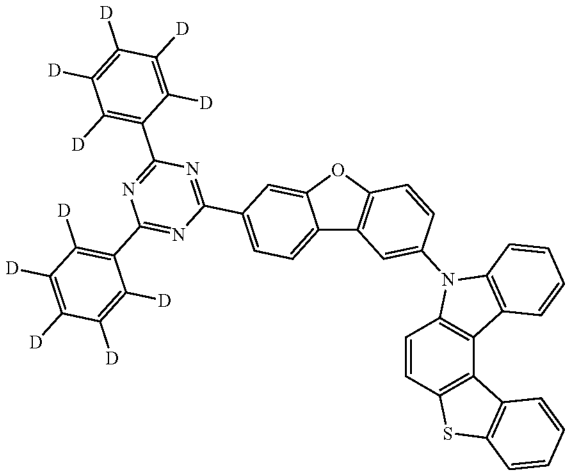
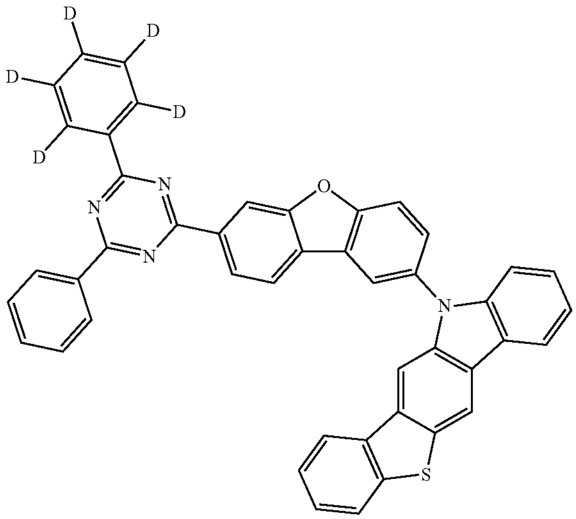
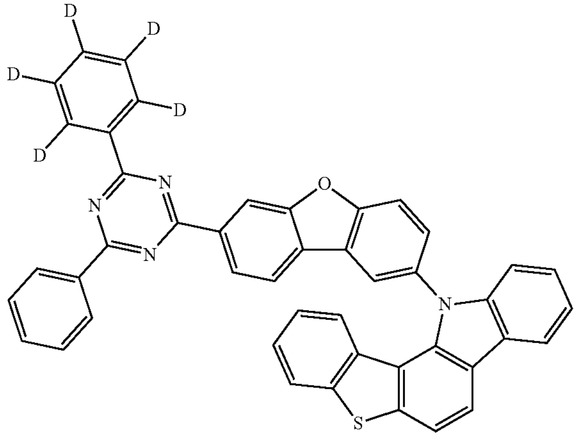
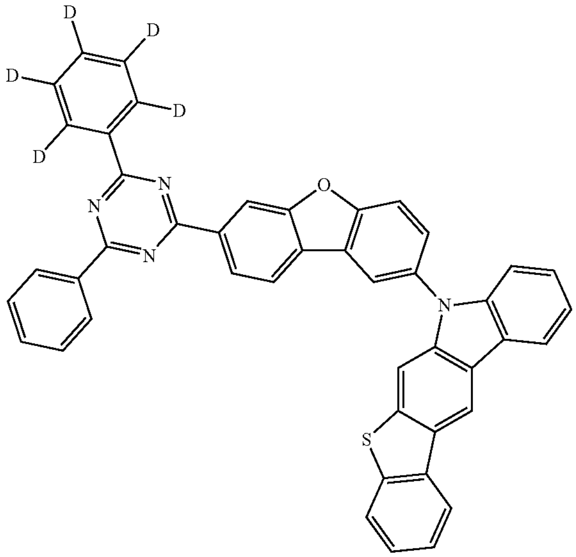 [SMILES: [2H]c1c([2H])c([2H])c(-c2nc(-c3ccccc3)nc(-c3ccc4c(c3)sc3ccc(-n5c6ccccc6c6cc7c(cc65)oc5ccccc57)cc34)n2)c([2H])c1[2H]]
-continued

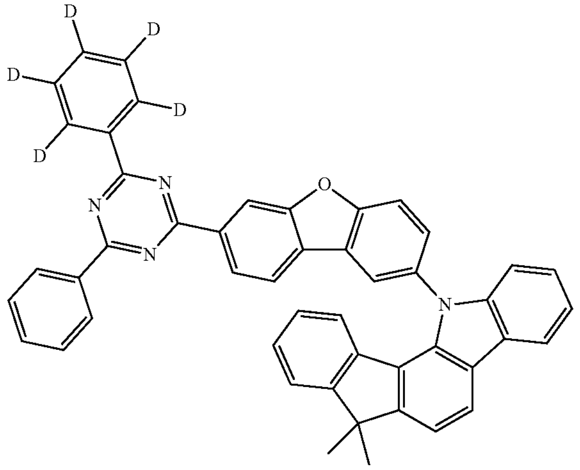
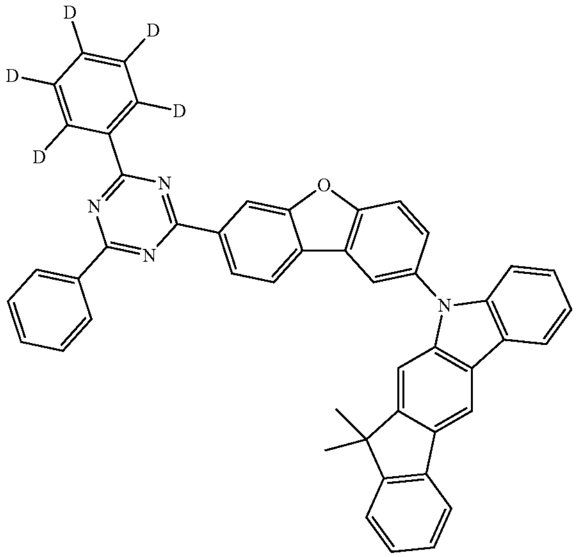
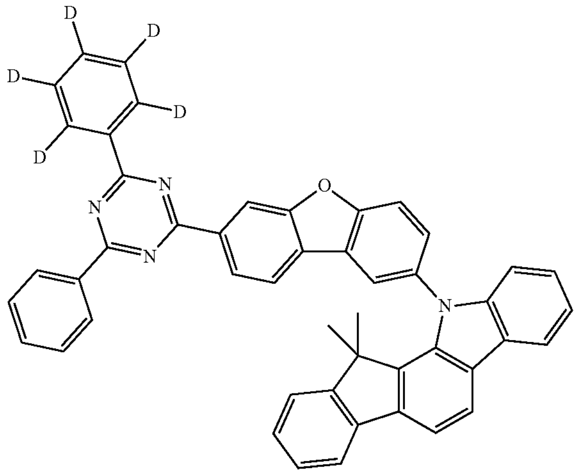
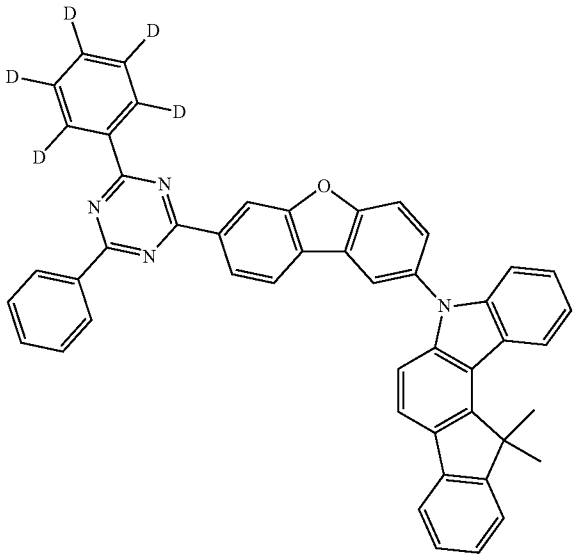
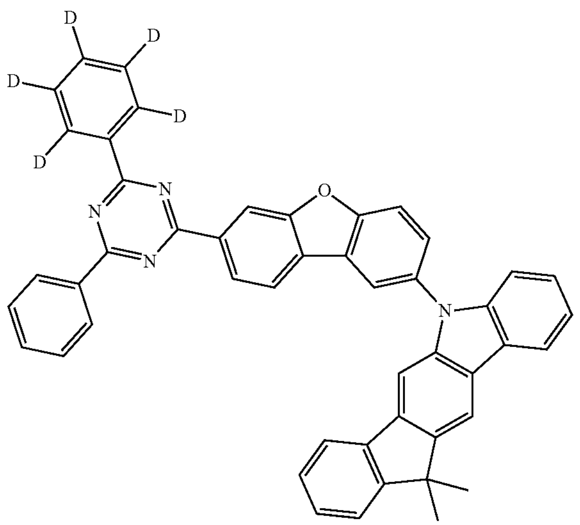
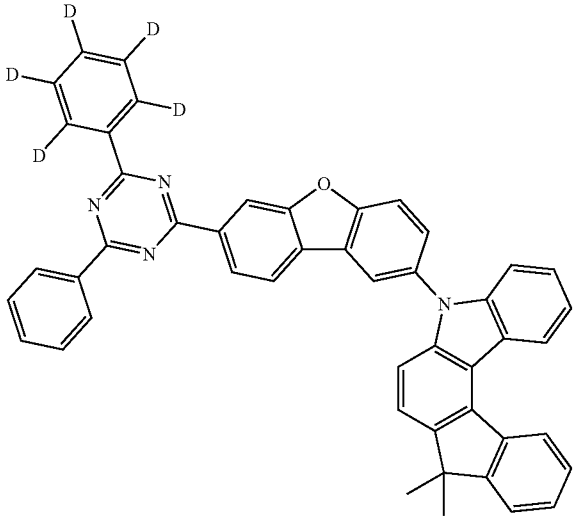

-continued
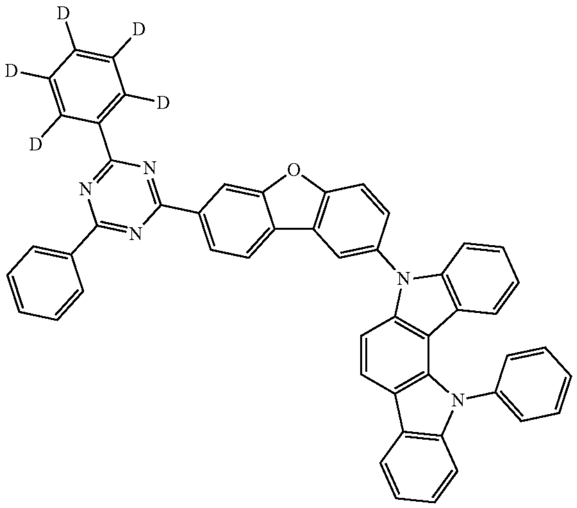
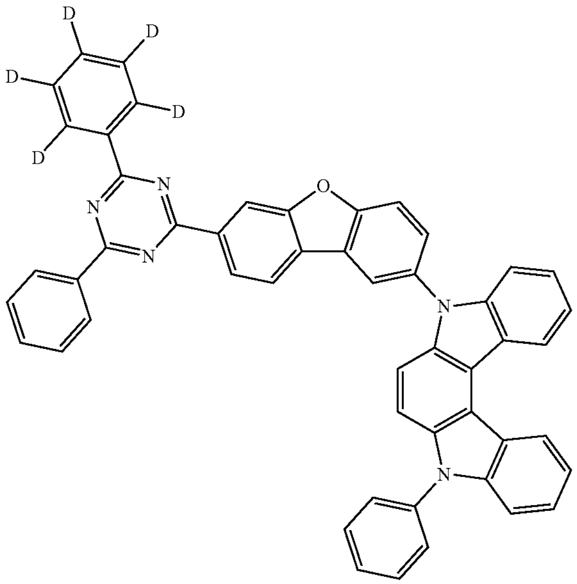
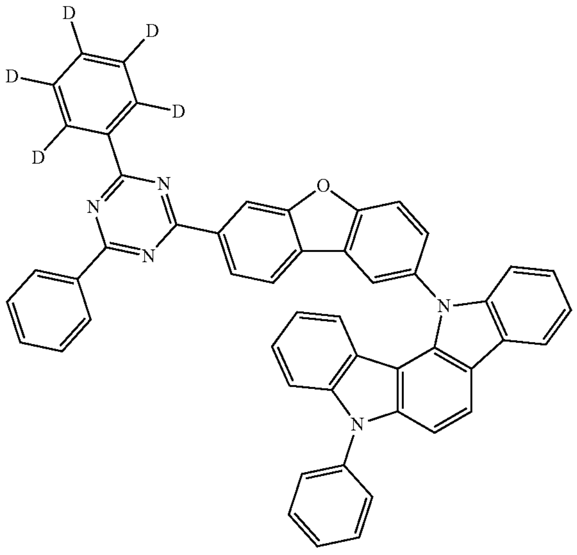
-continued
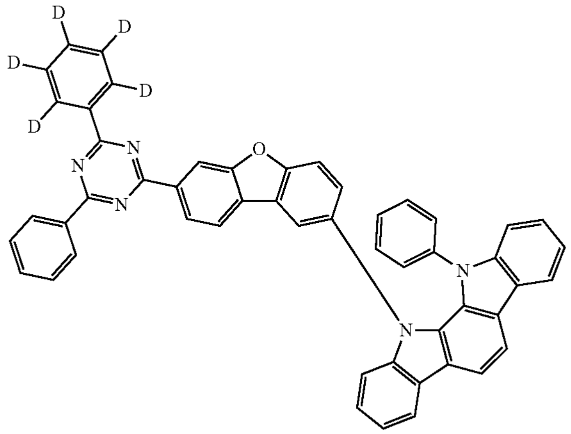
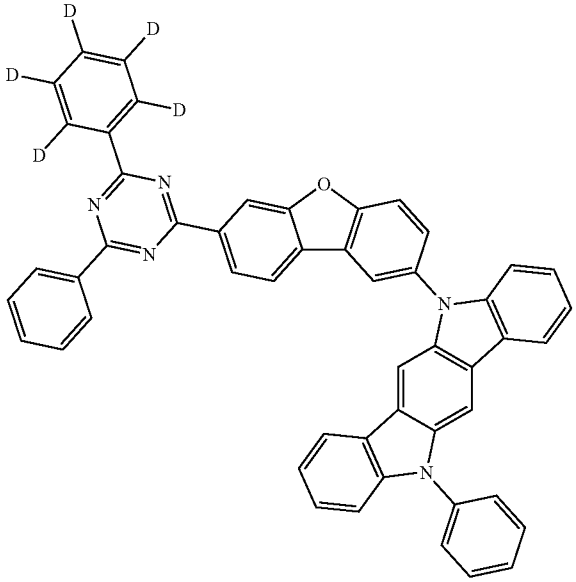
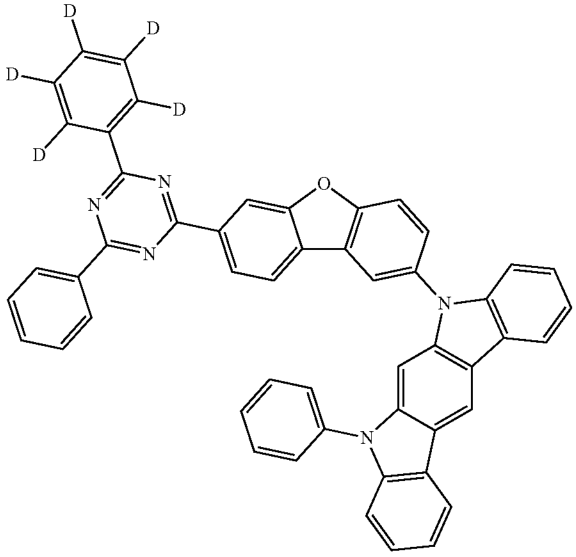

-continued
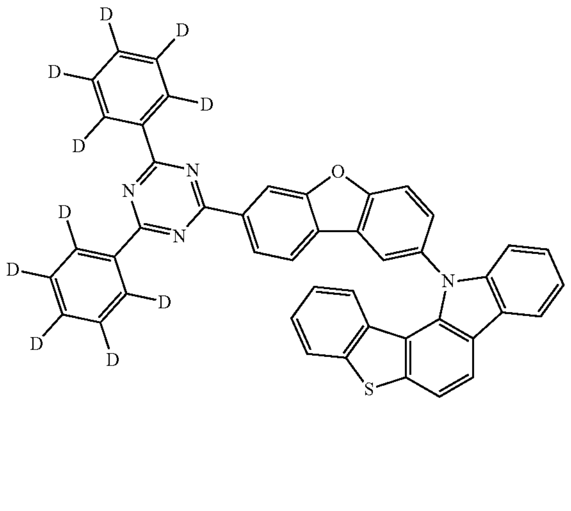
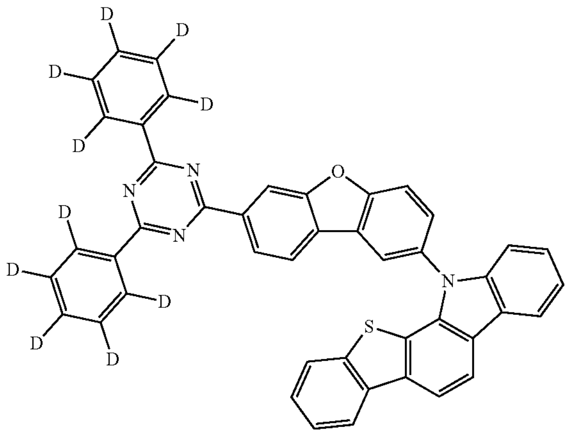
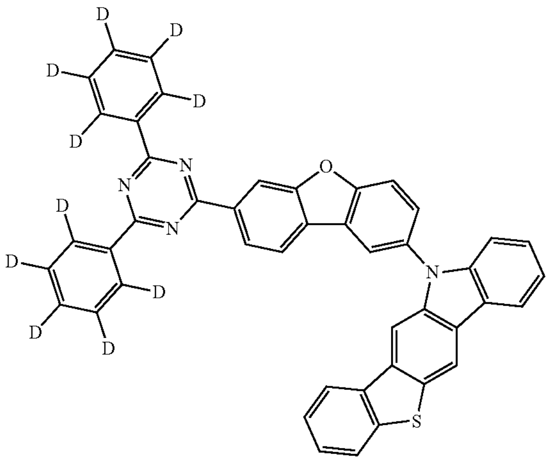
-continued
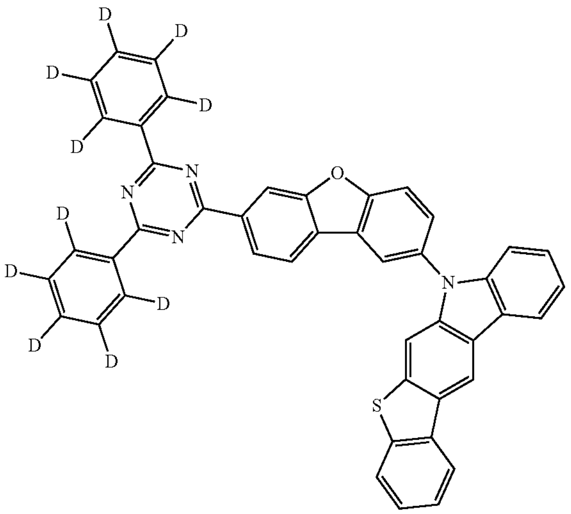
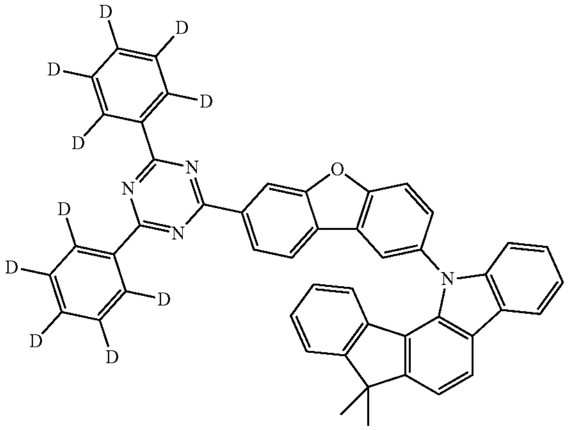
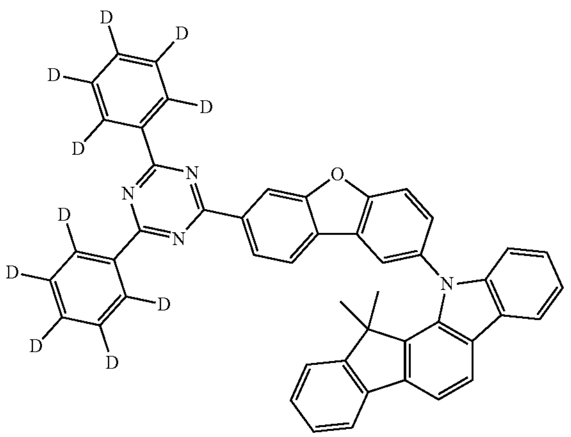

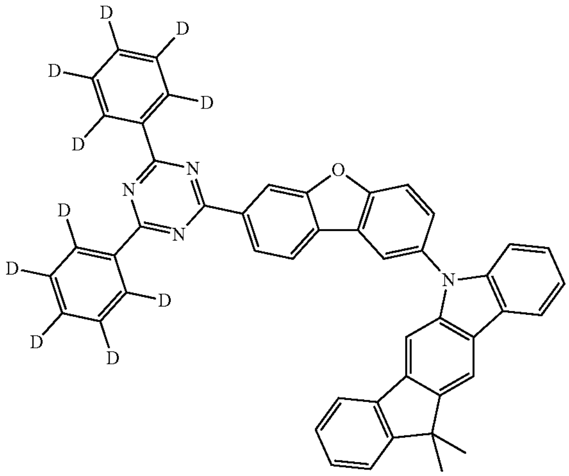
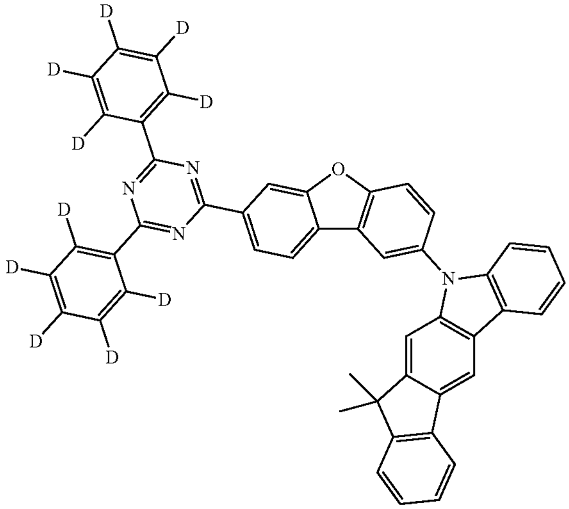
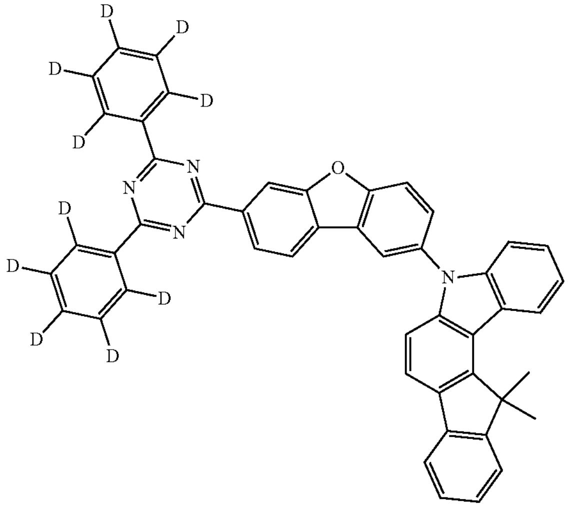
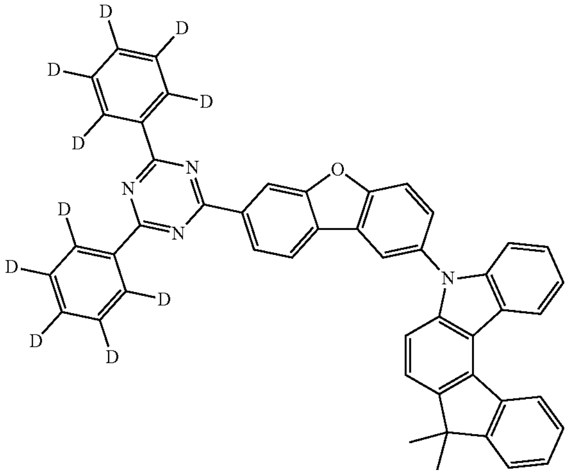
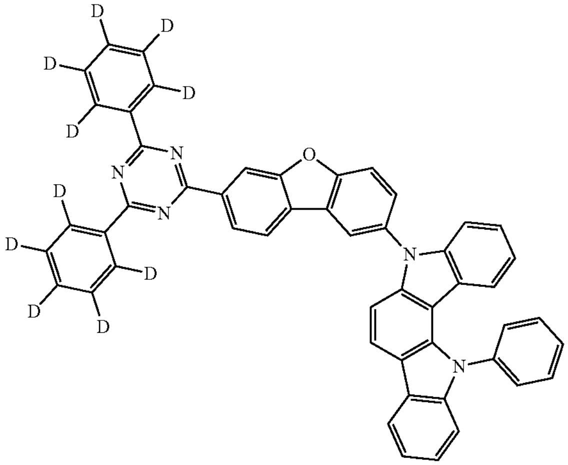
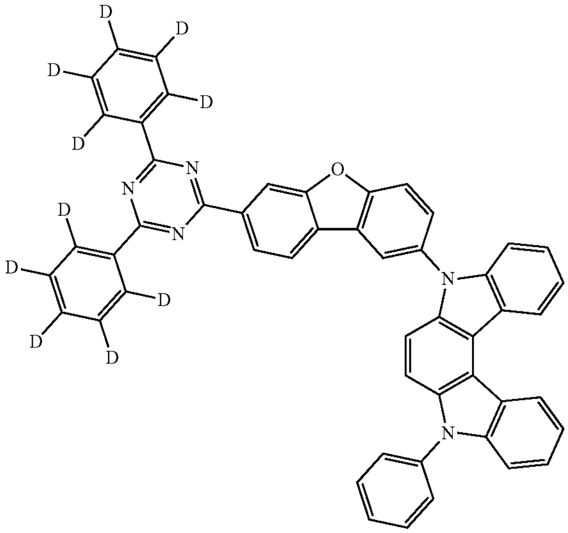

-continued
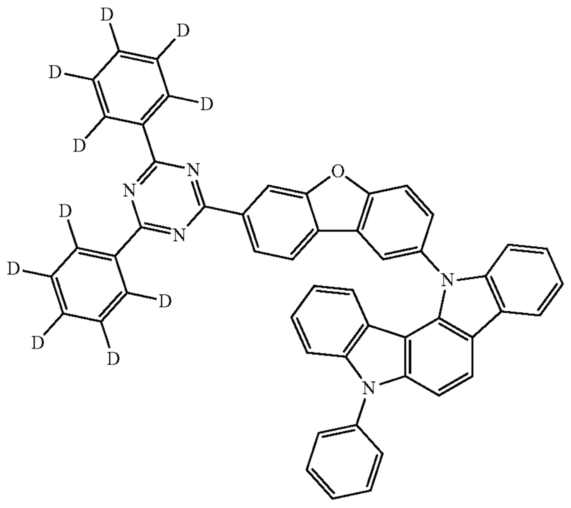
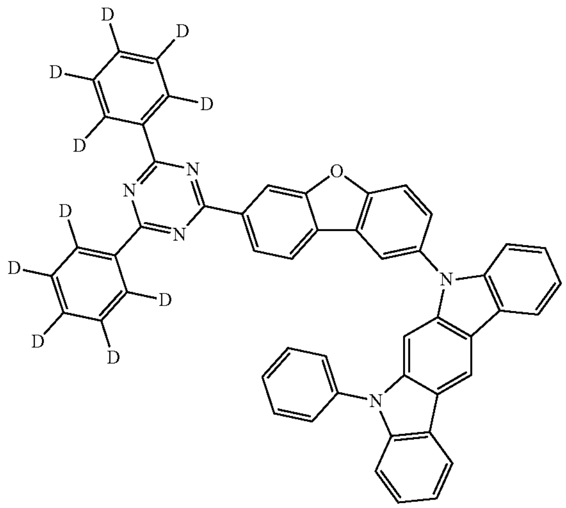
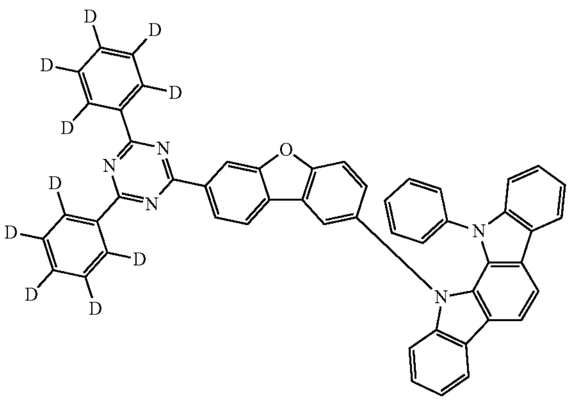
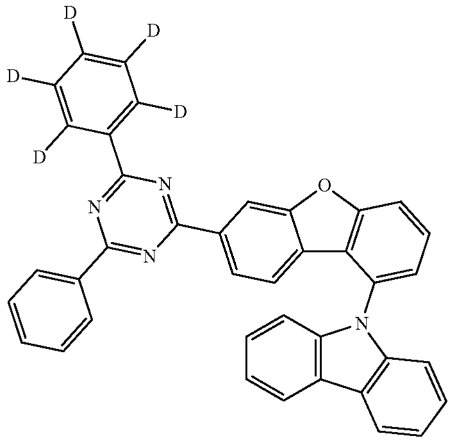
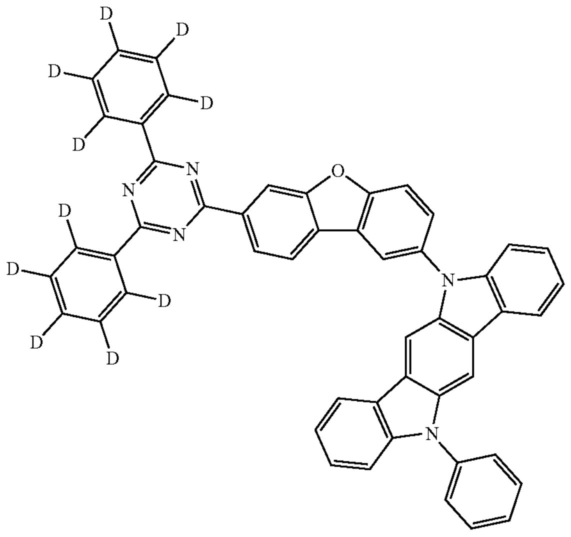
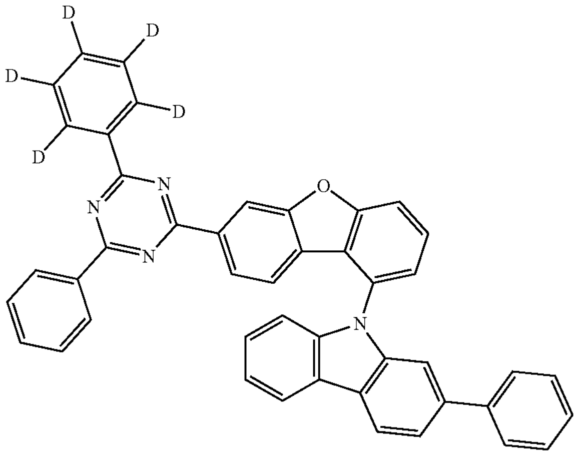
-continued -continued
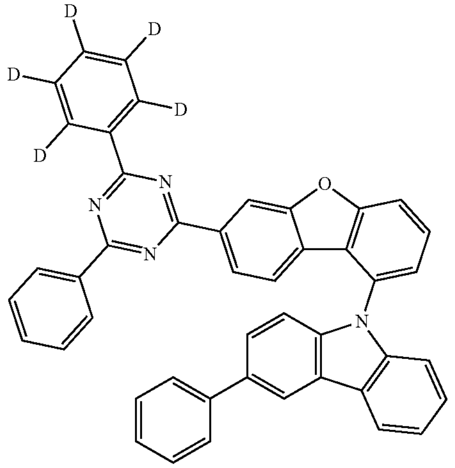
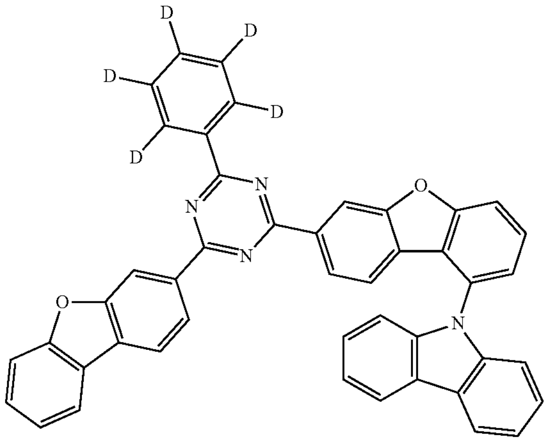
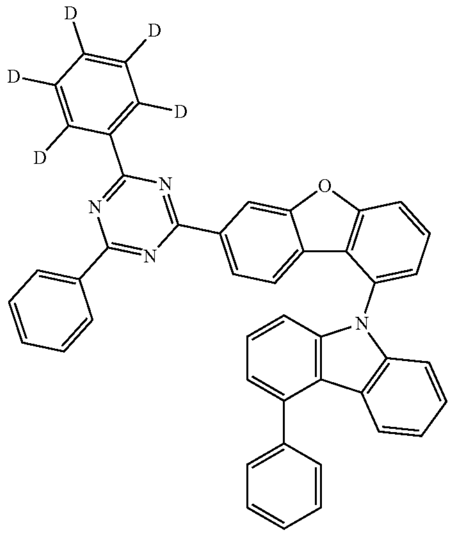
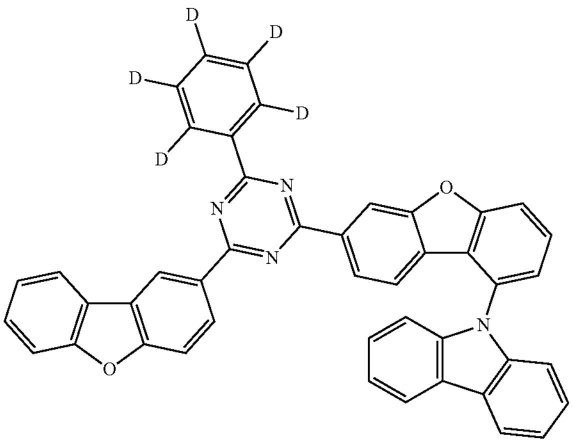
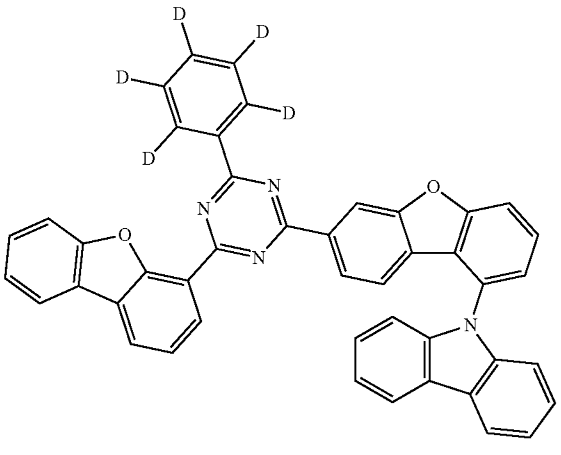
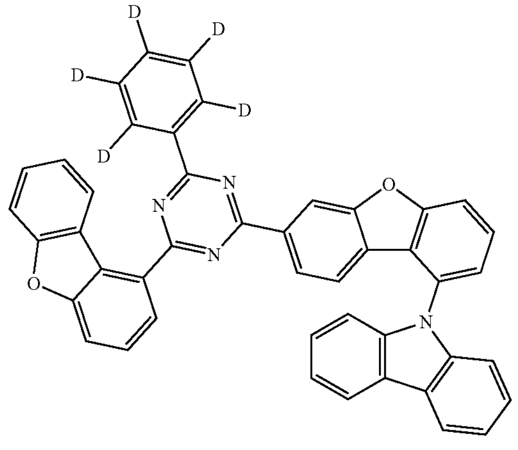

-continued
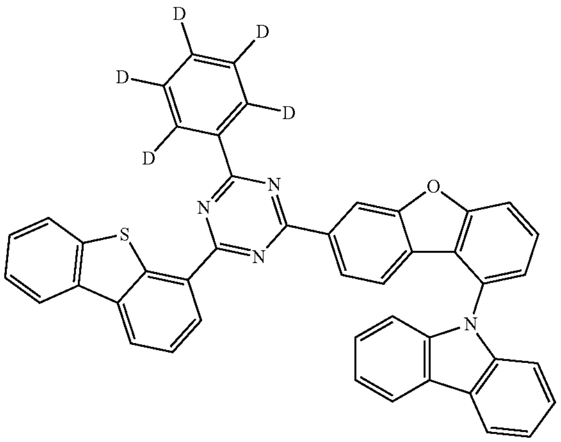
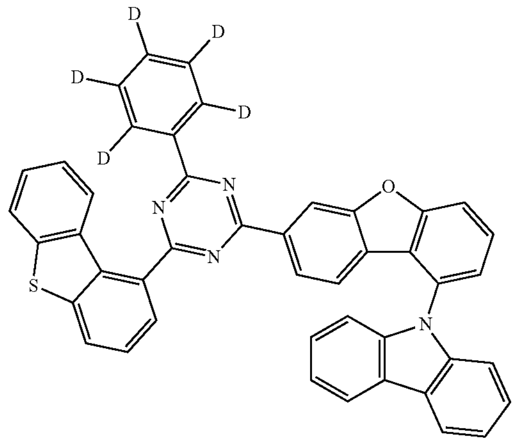
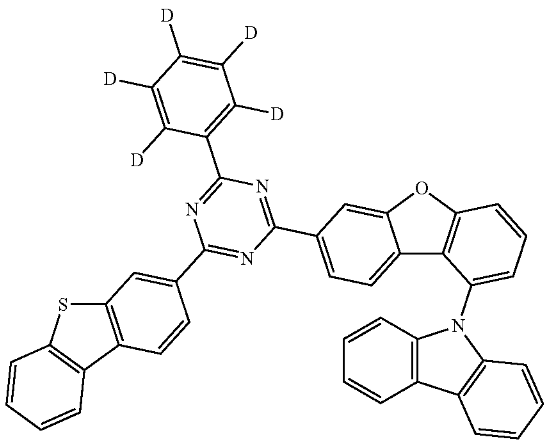
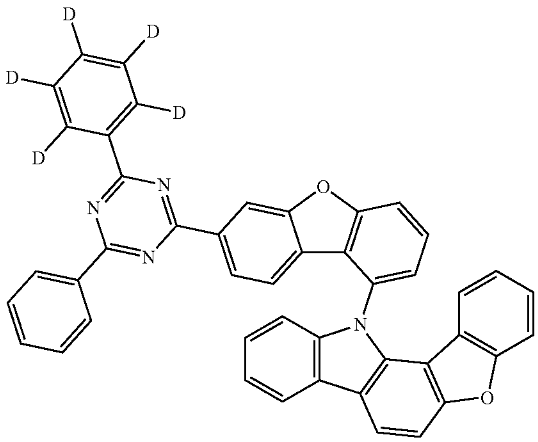
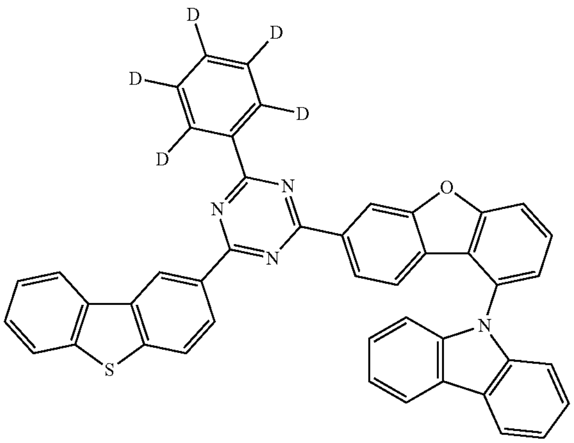
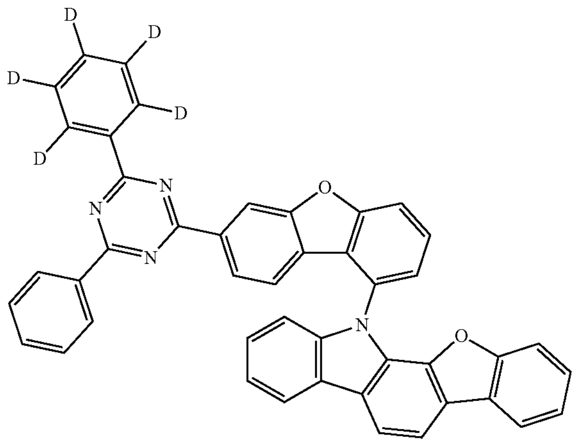
-continued -continued
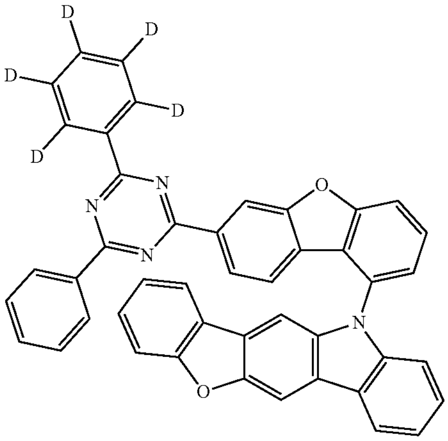
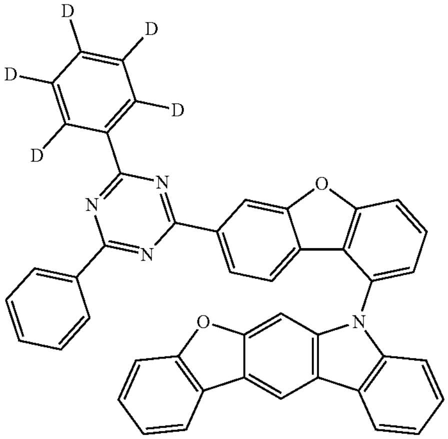
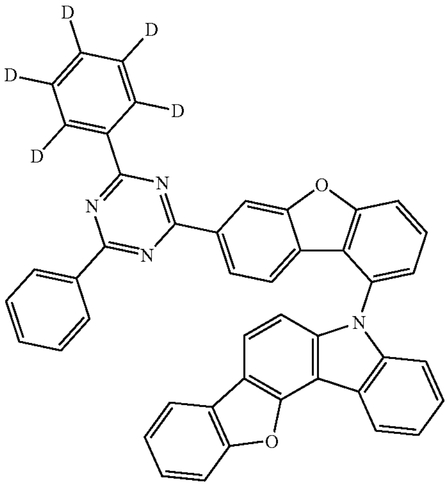
-continued
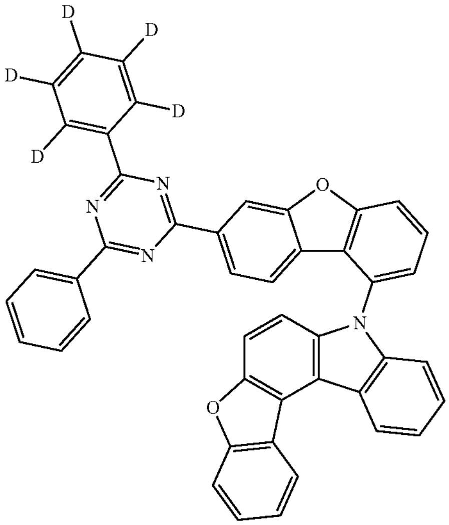
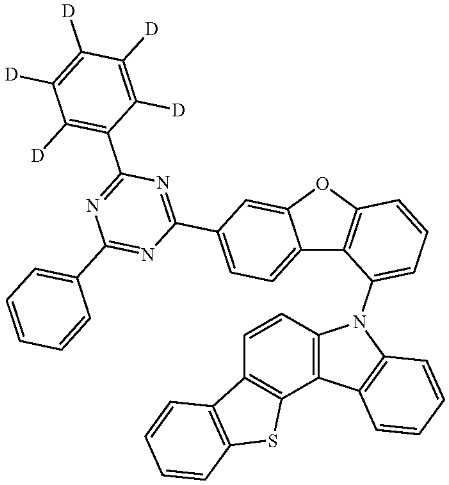
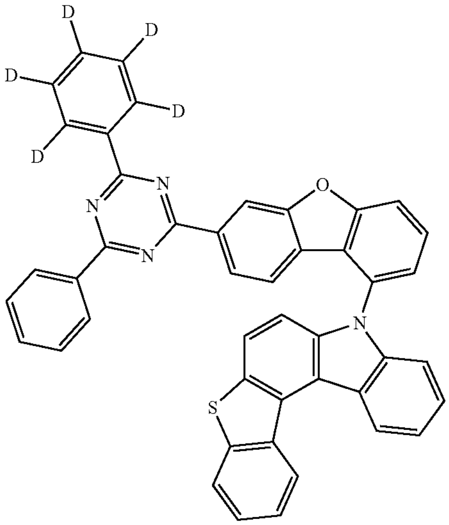

-continued
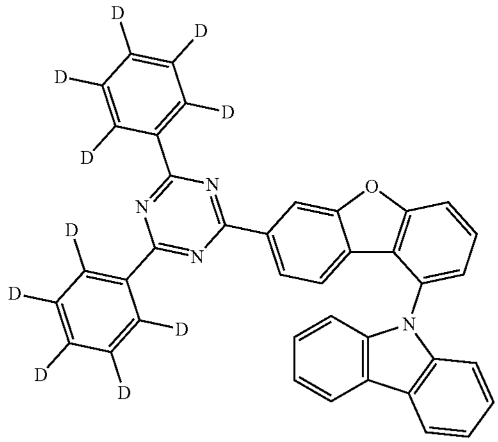
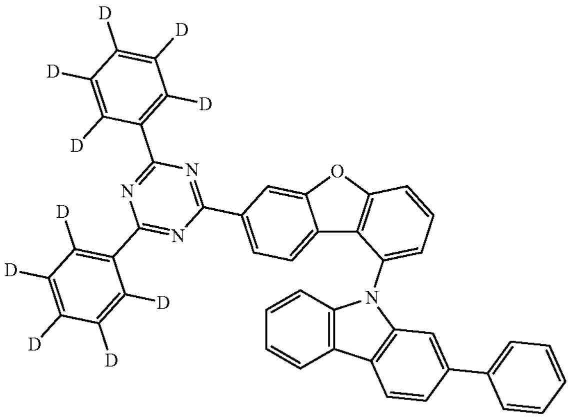
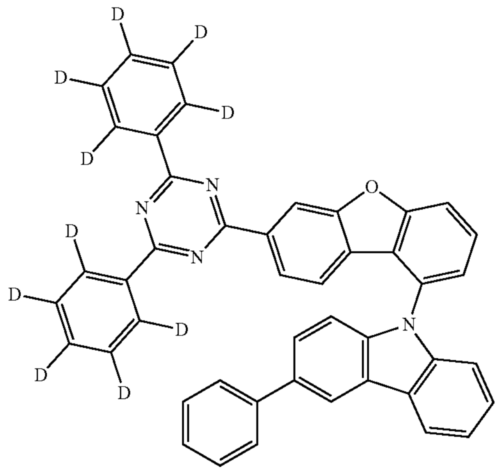
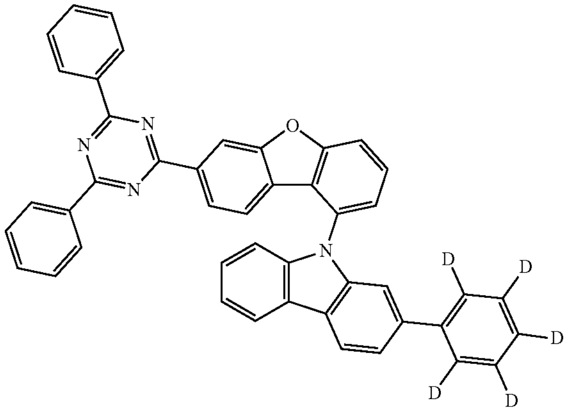
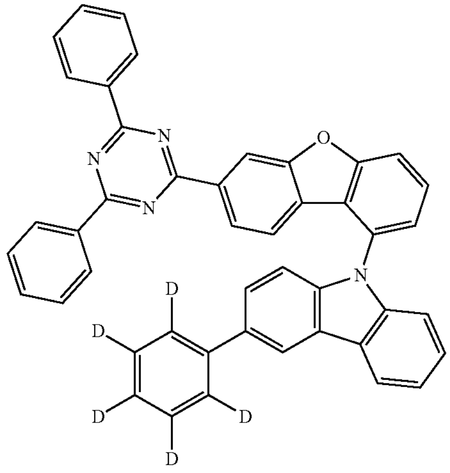
-continued
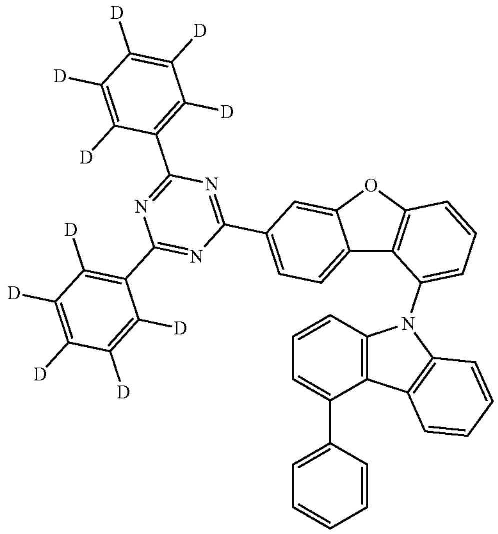

-continued
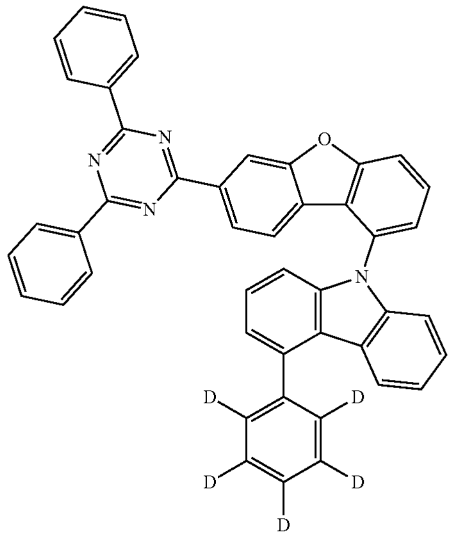
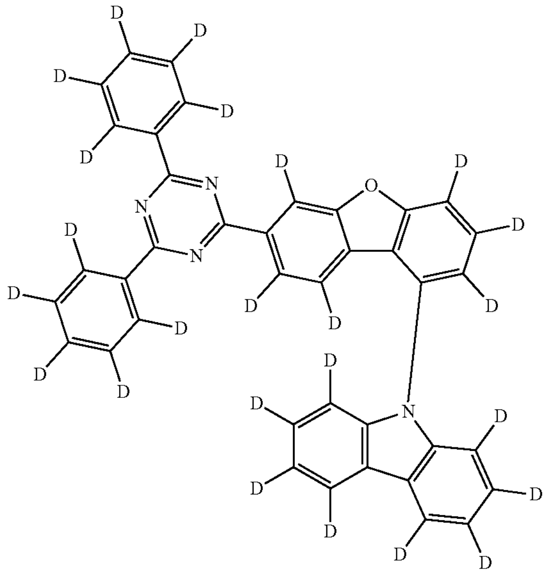
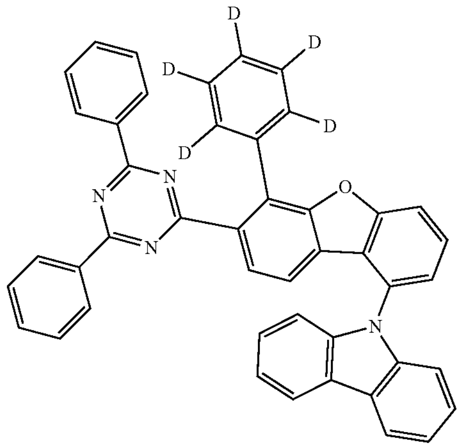
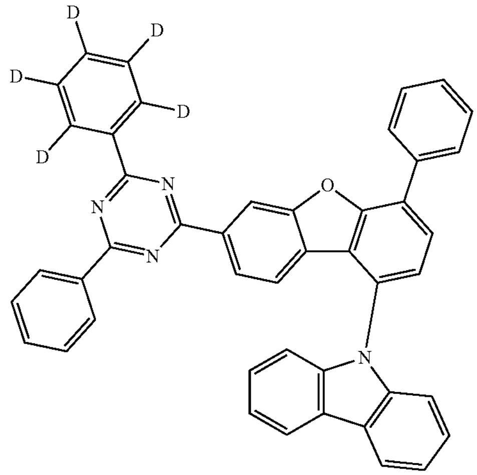
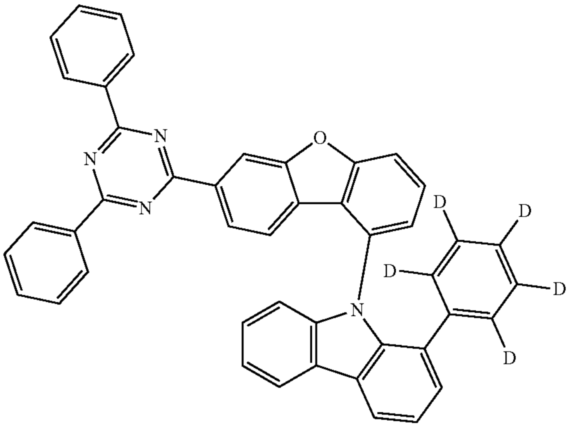
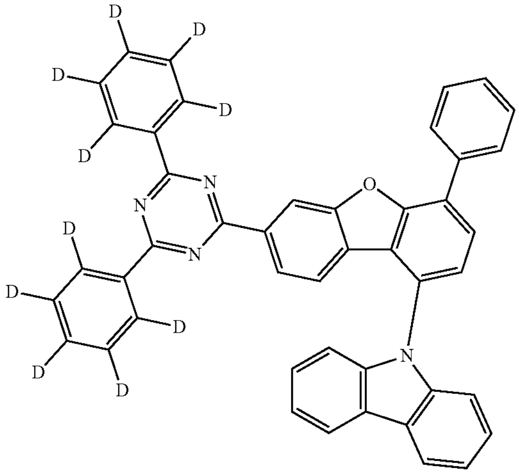
-continued

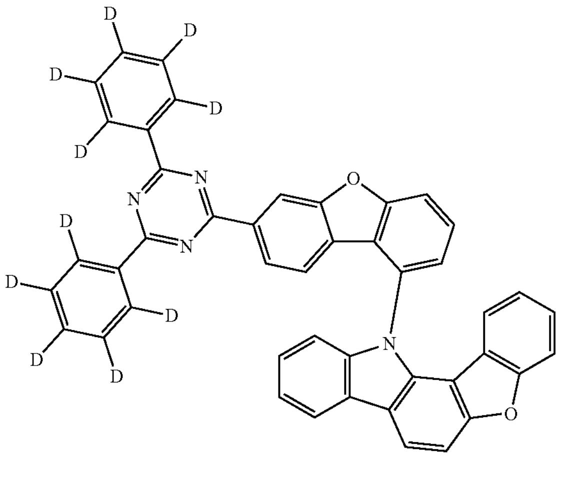
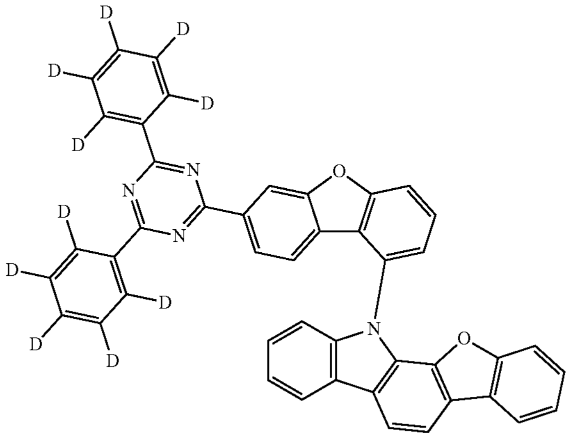
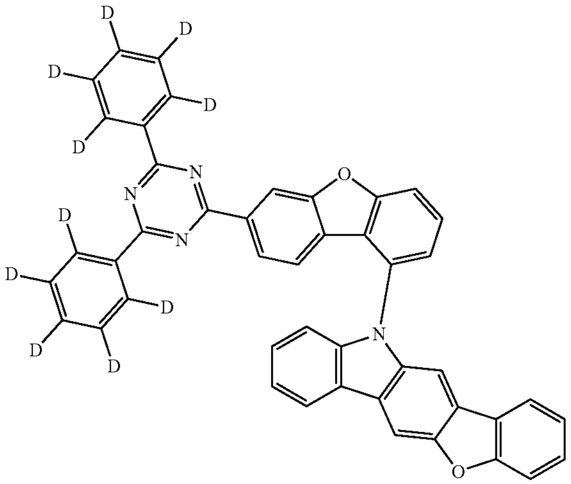
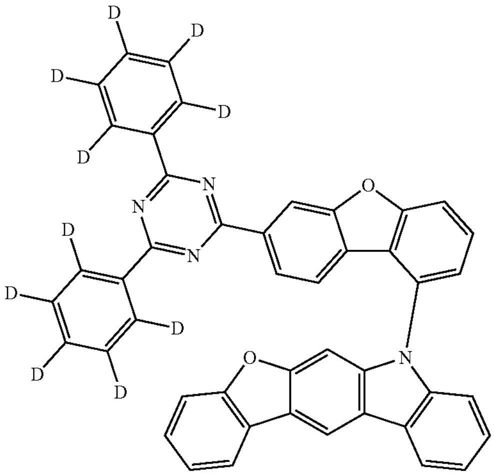
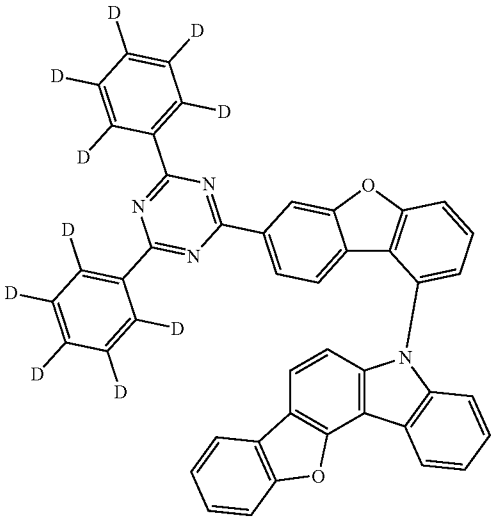
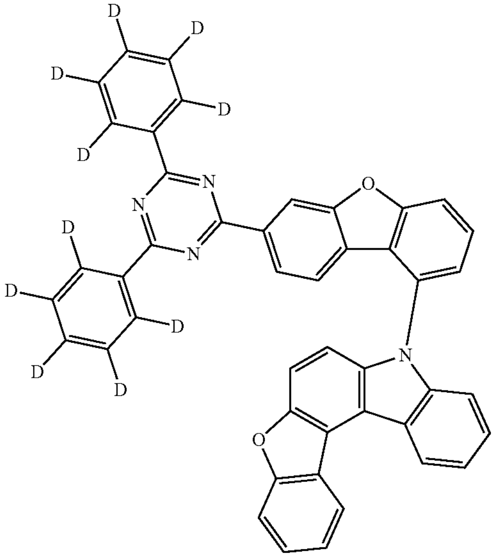

-continued
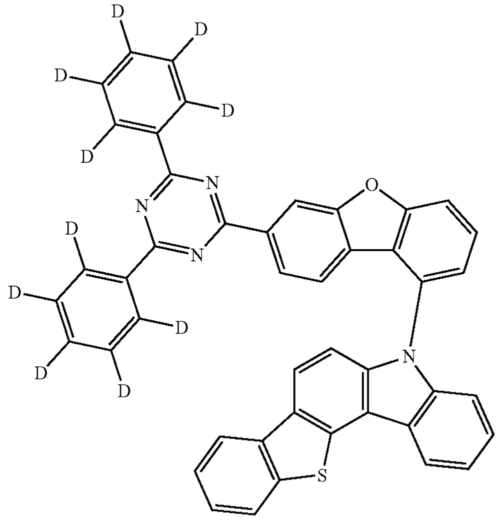
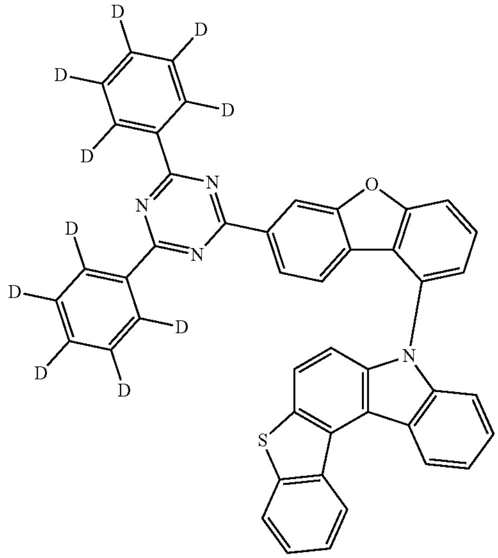
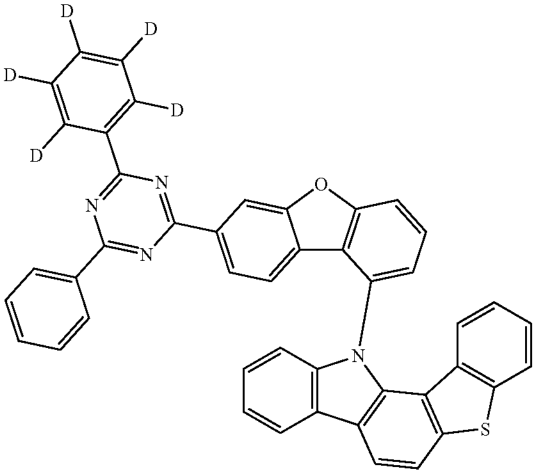
-continued
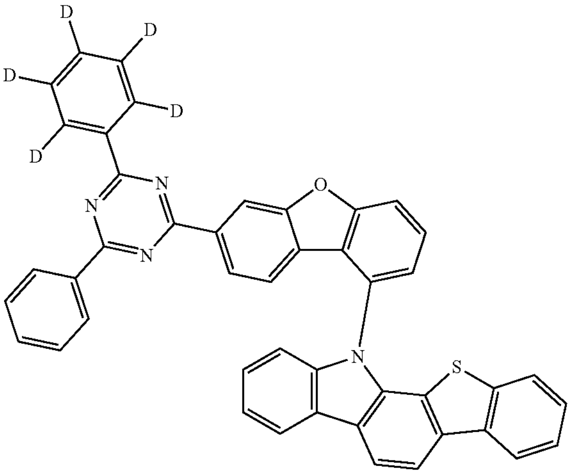
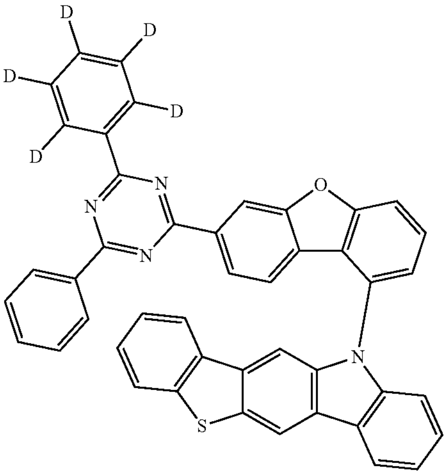
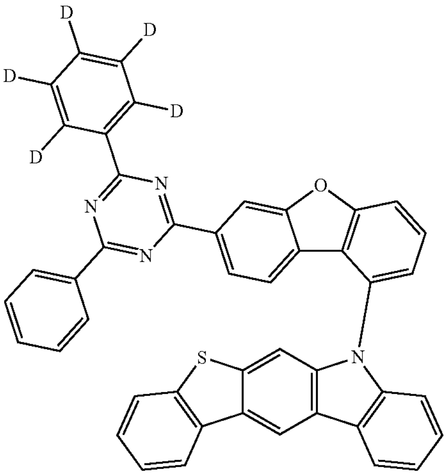

-continued
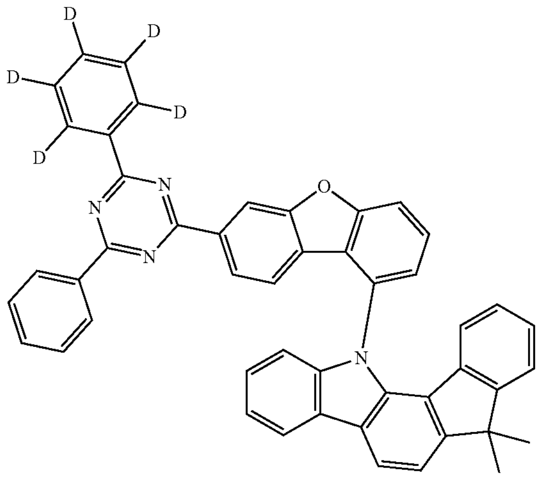
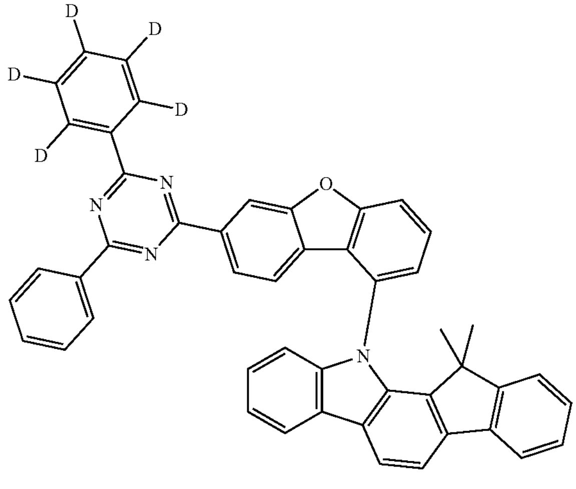
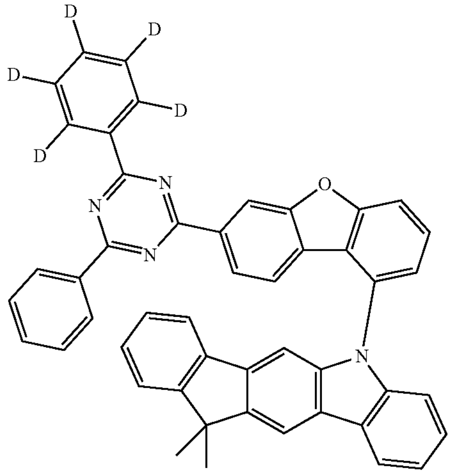
-continued
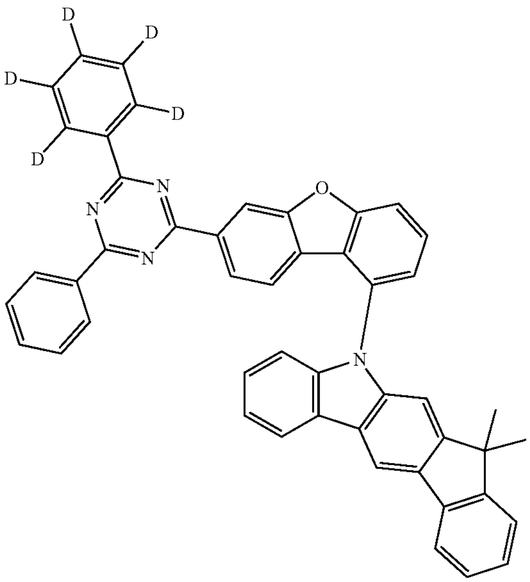
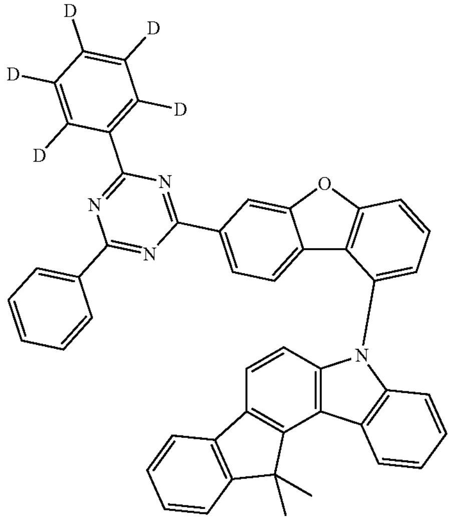
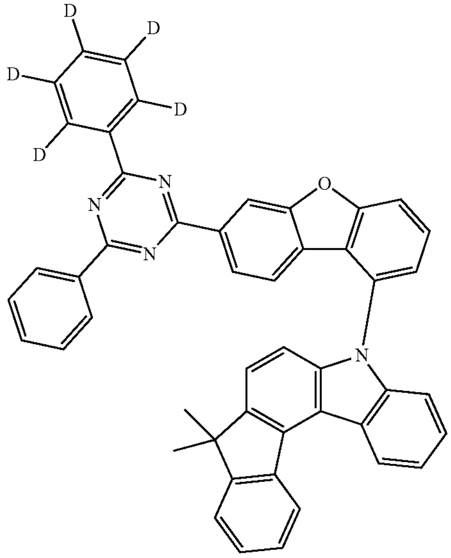

-continued
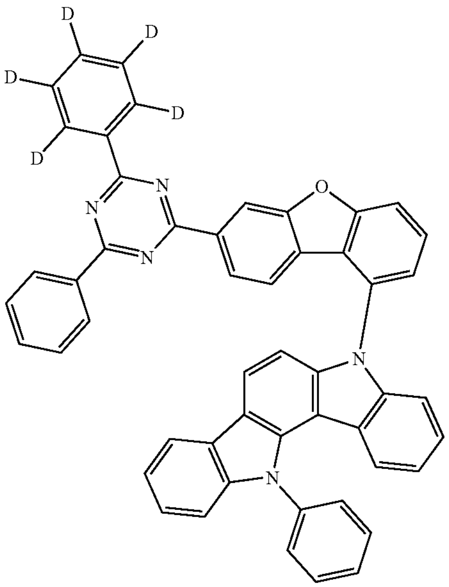
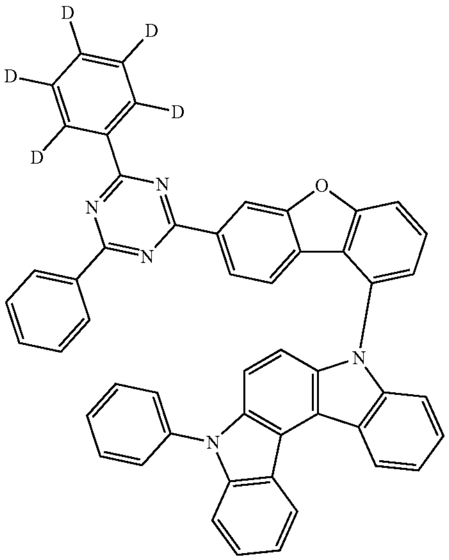
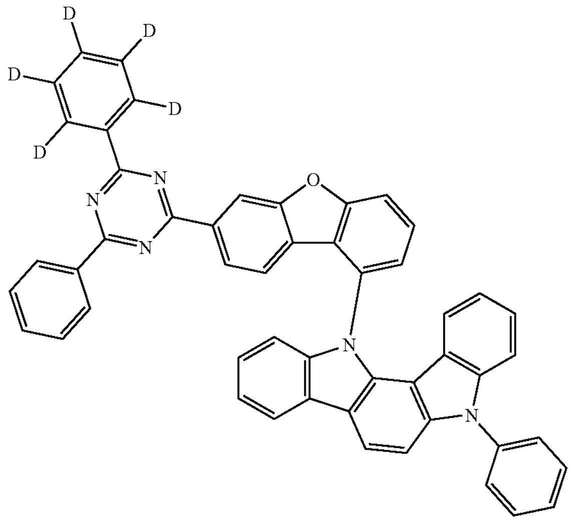
-continued
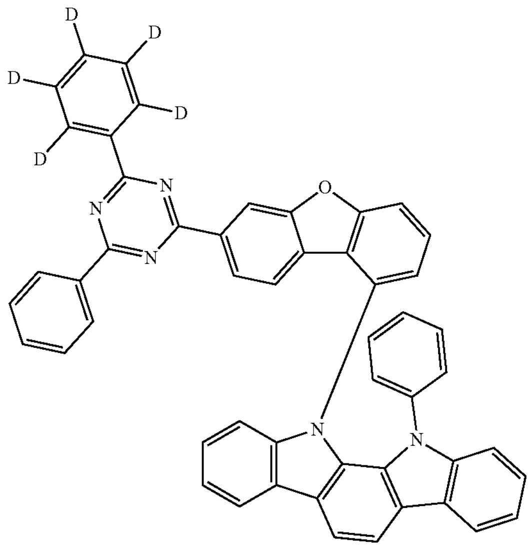
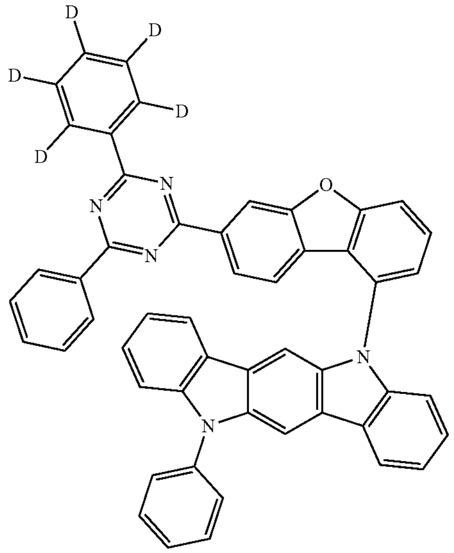
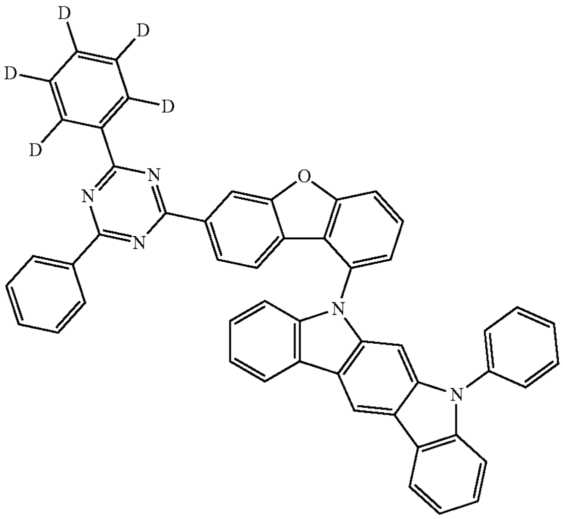

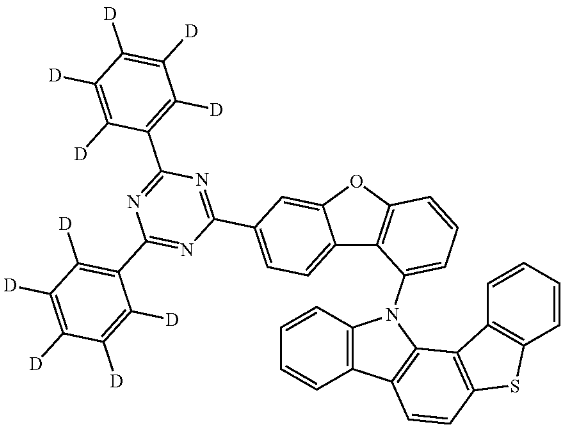
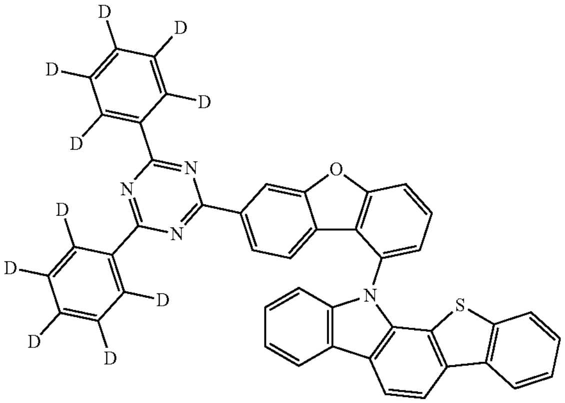
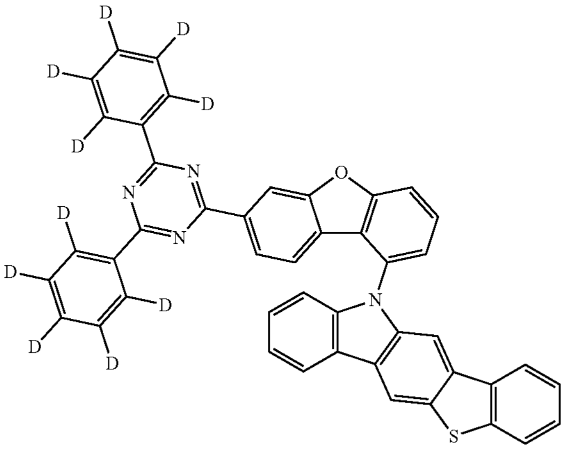
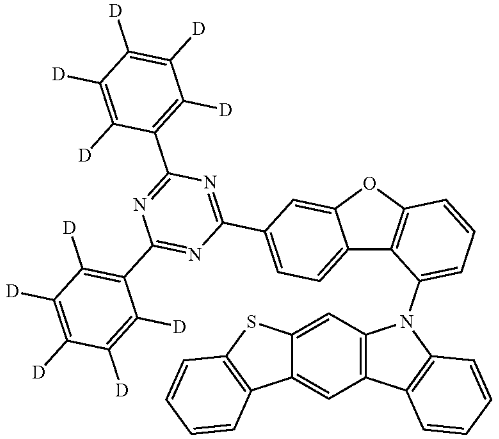
-continued
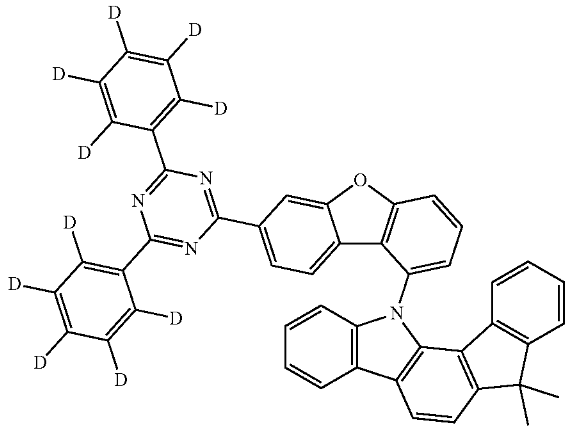
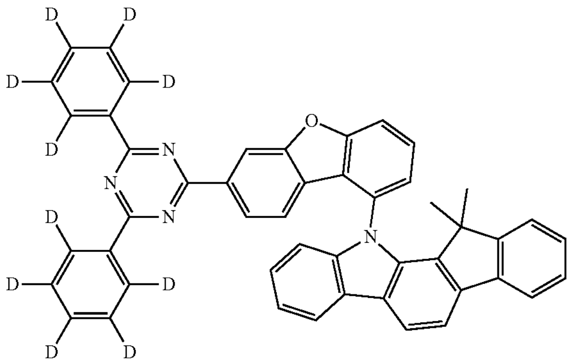
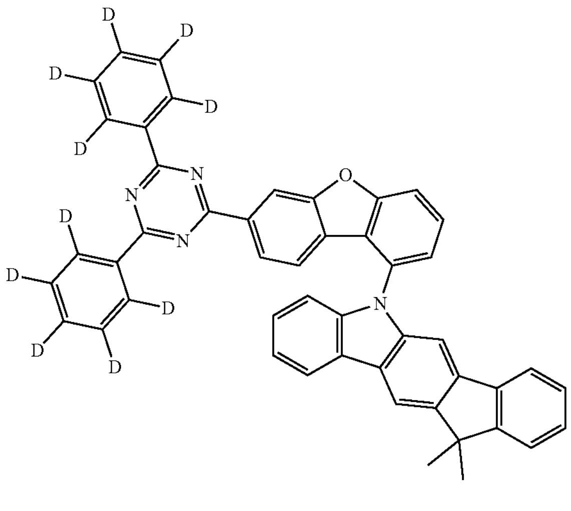

-continued
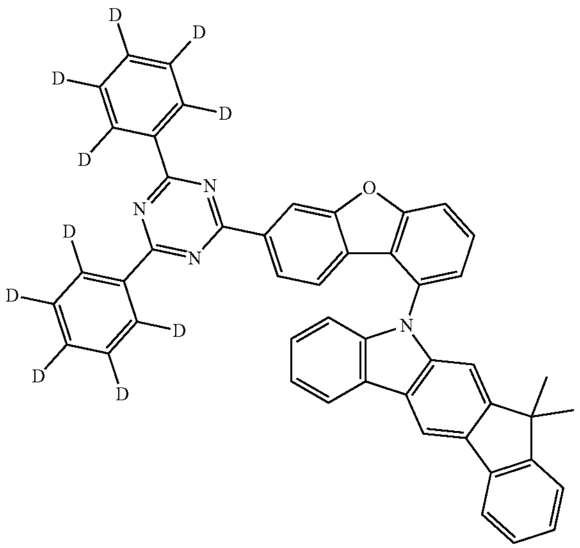
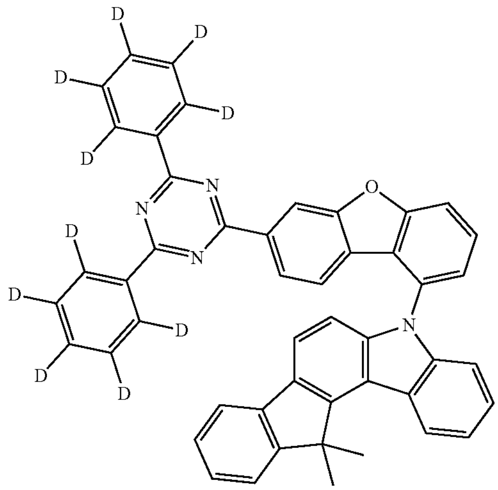
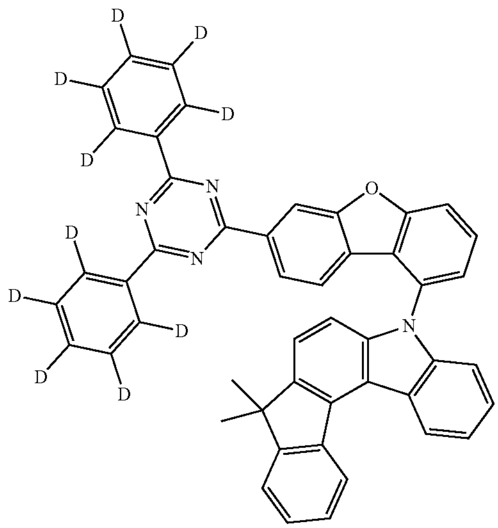
-continued
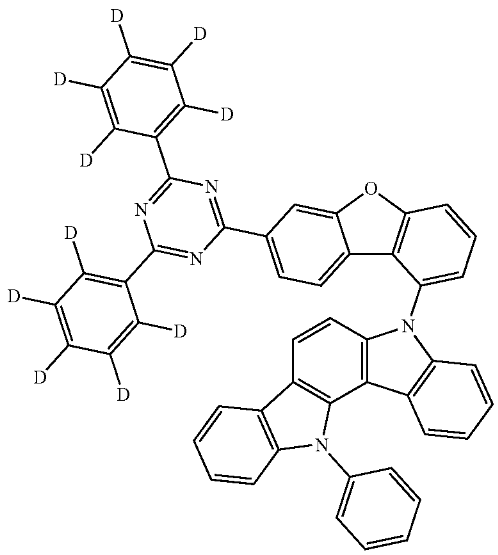
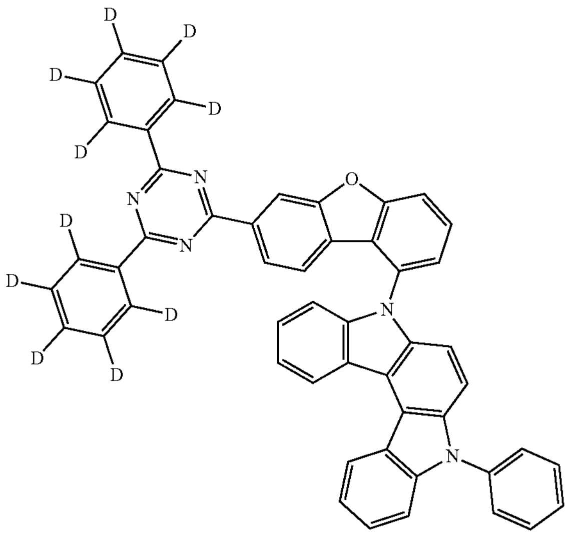
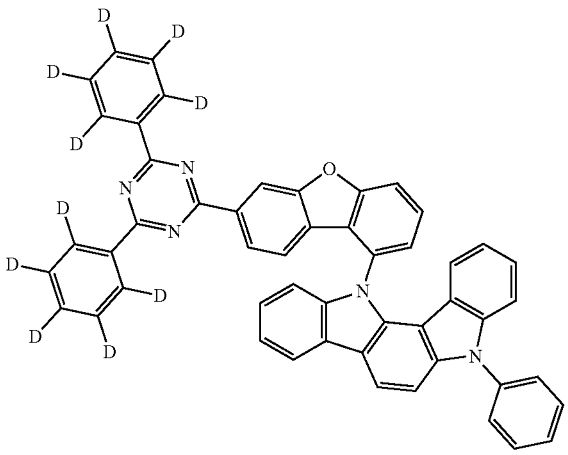

-continued
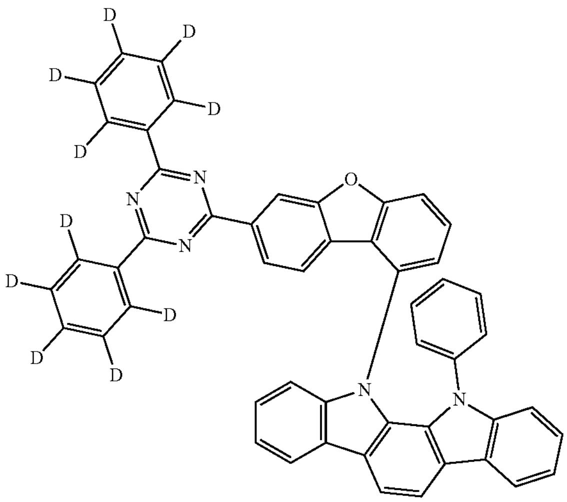
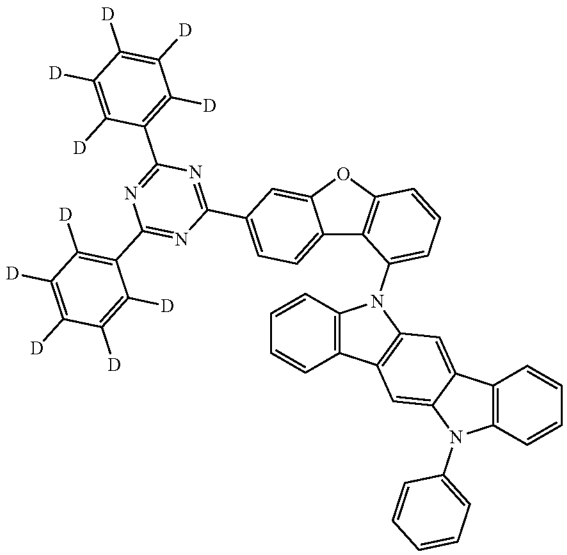
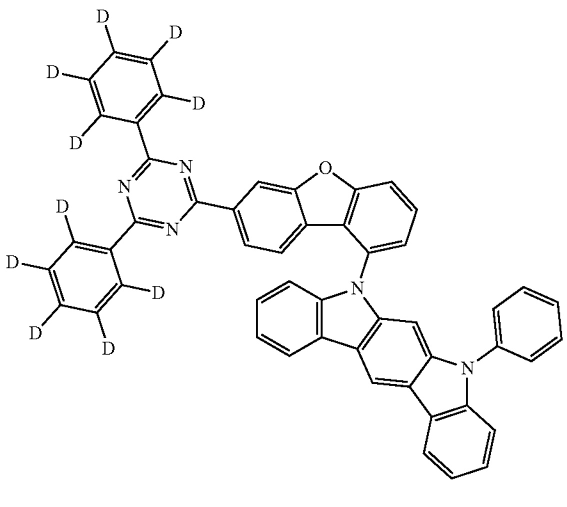
-continued
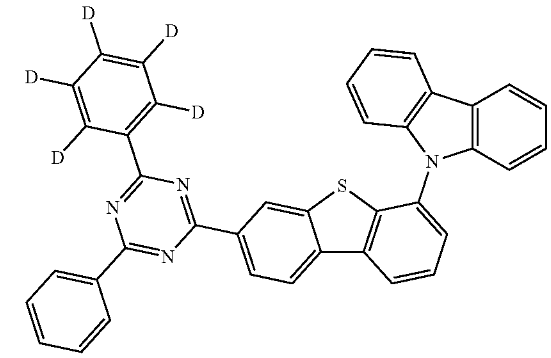
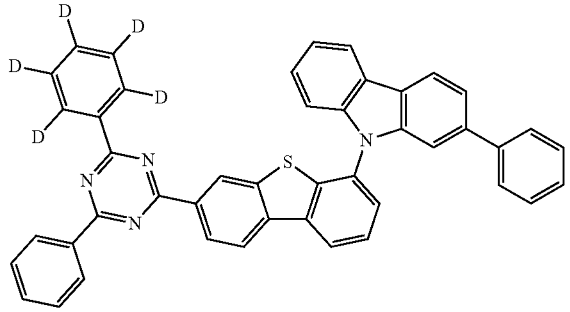
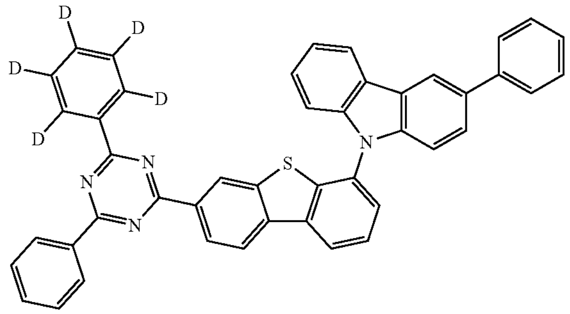
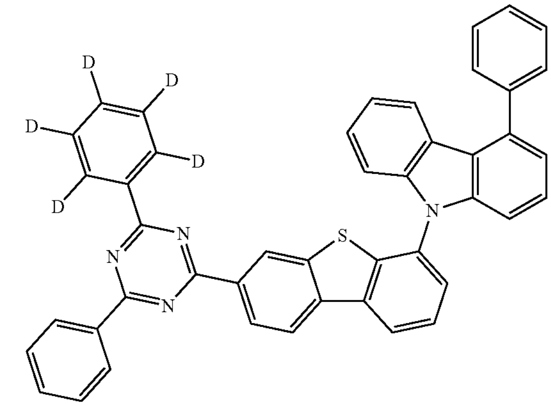
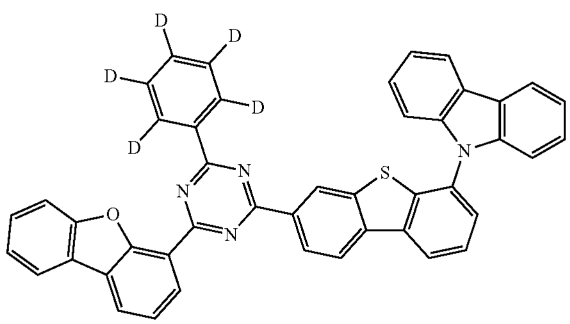

-continued
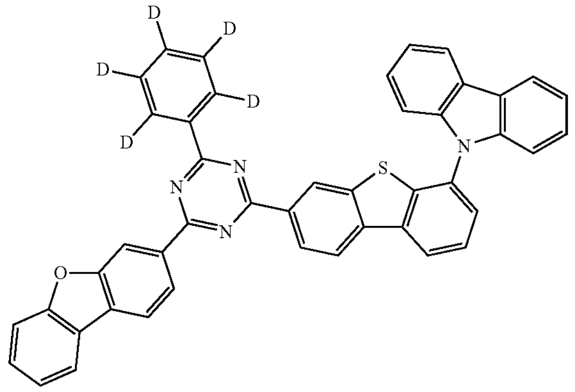
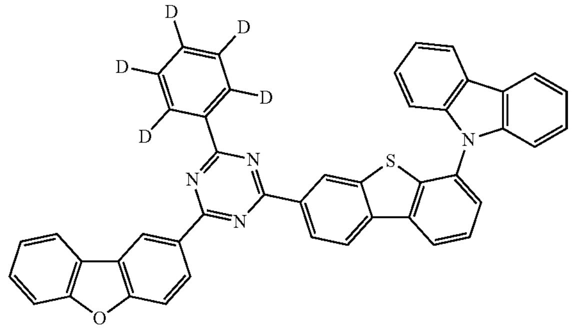
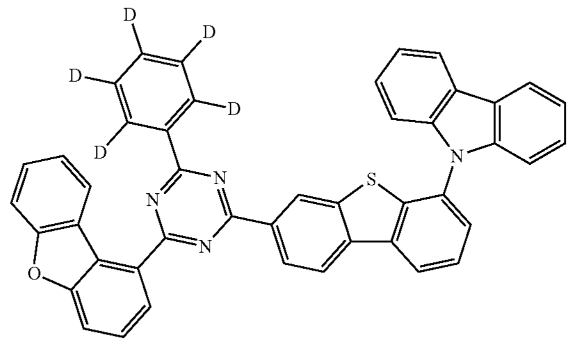
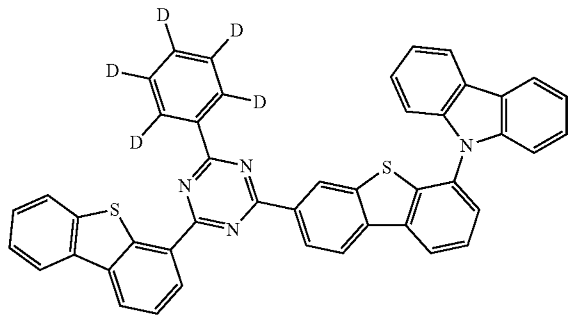
-continued
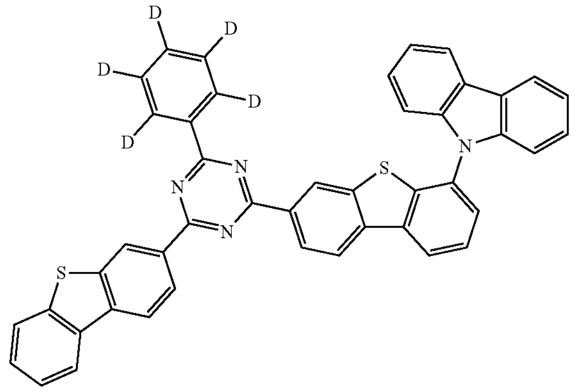
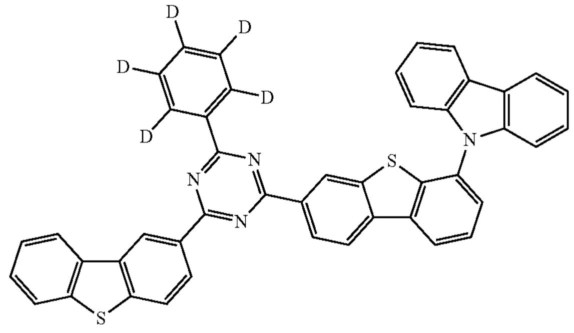
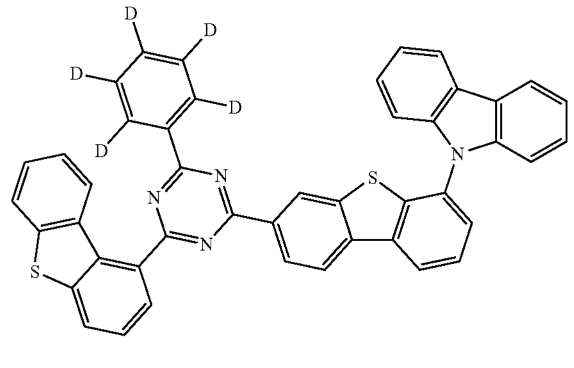
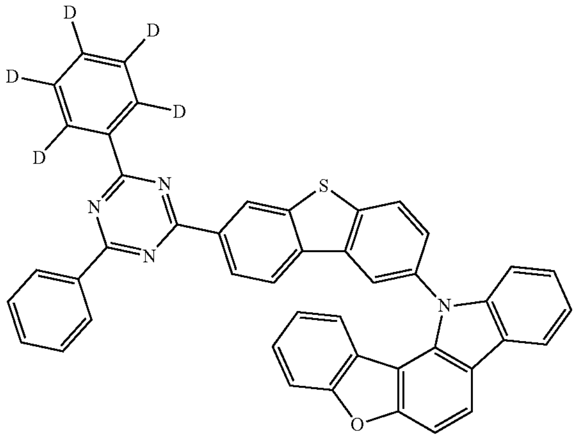

-continued
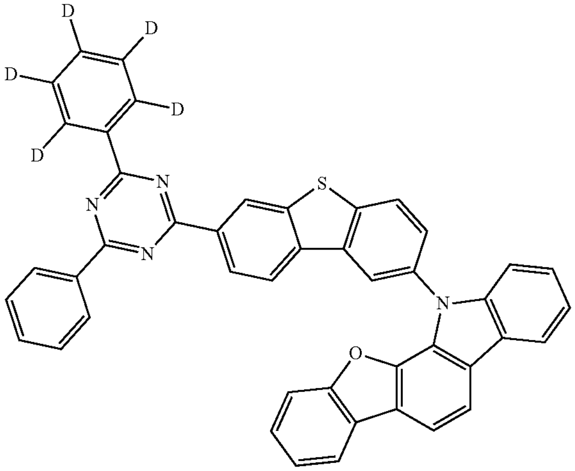
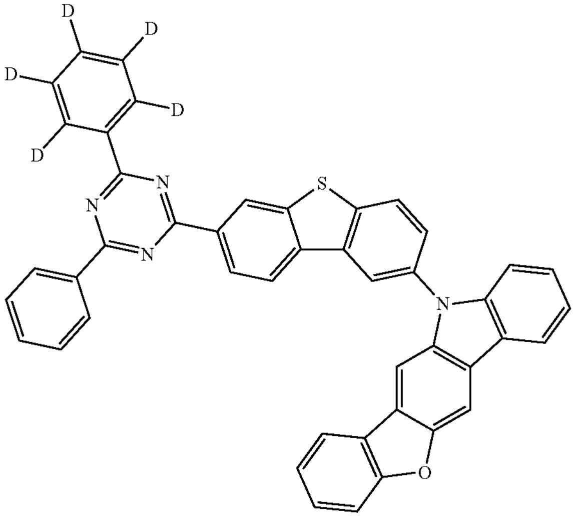
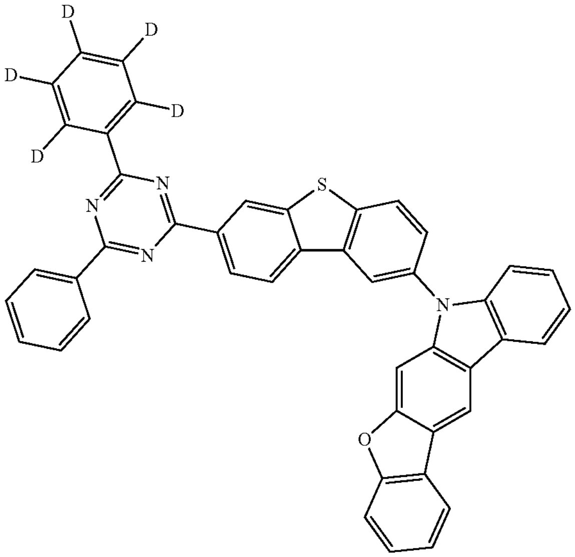
-continued
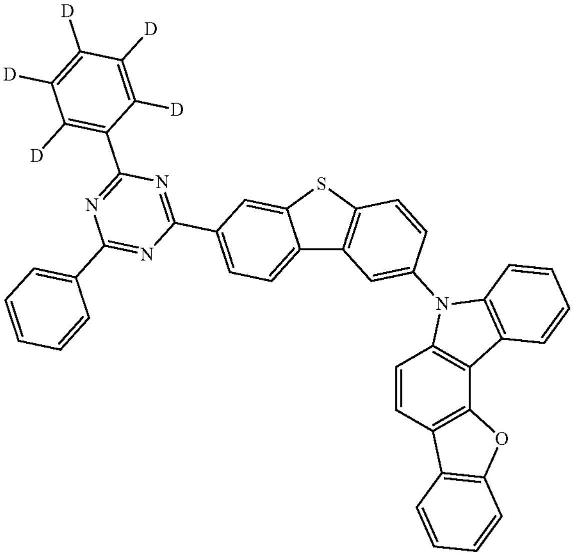
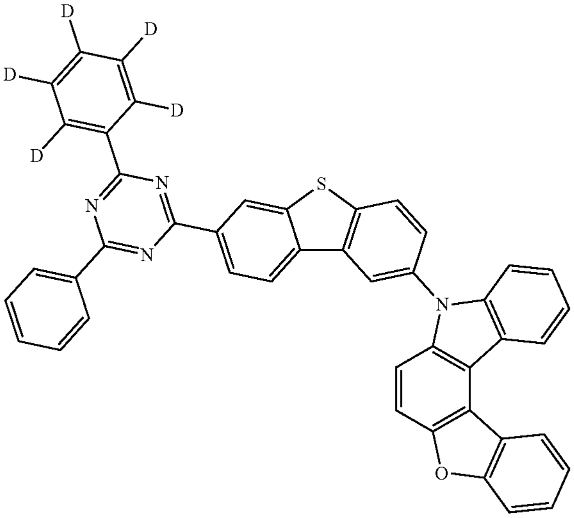
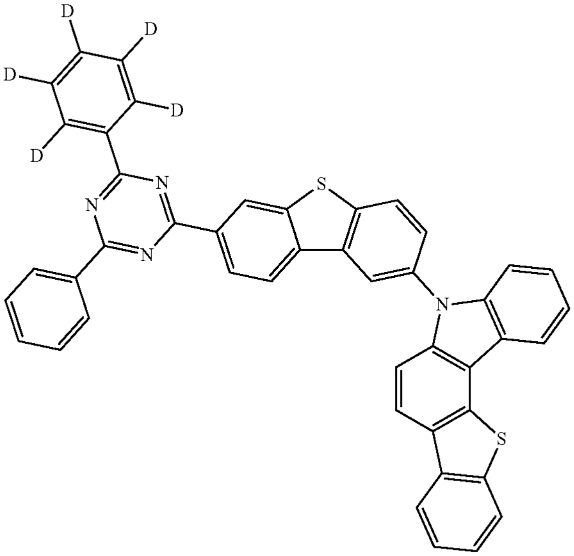

-continued
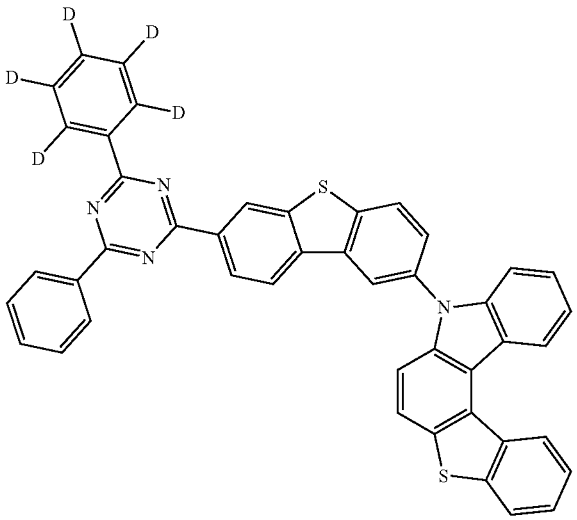
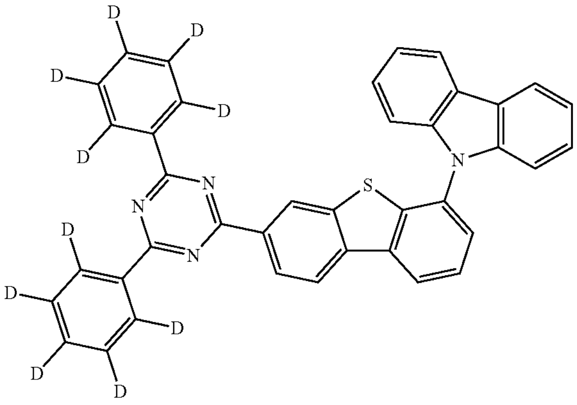
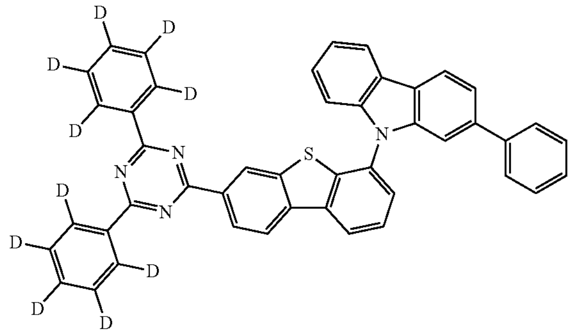
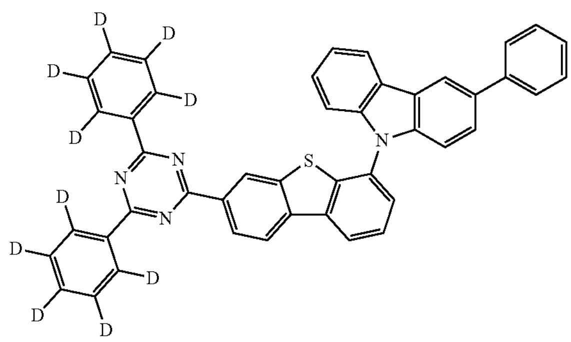
-continued
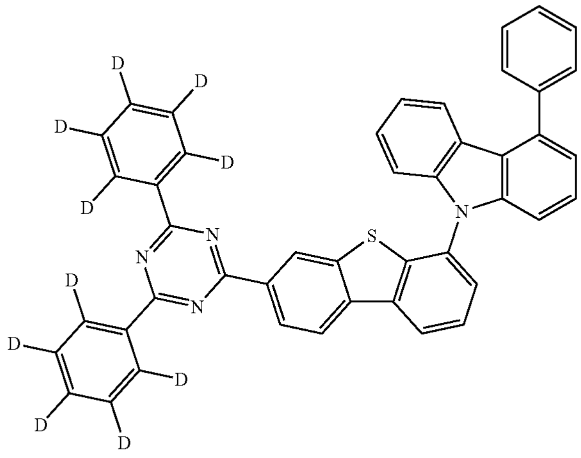
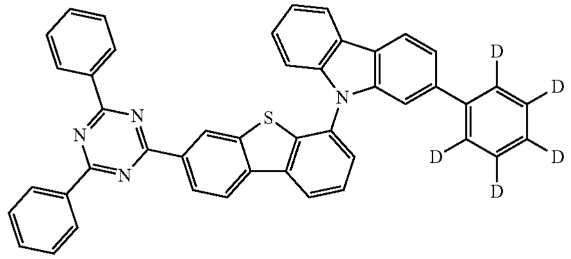
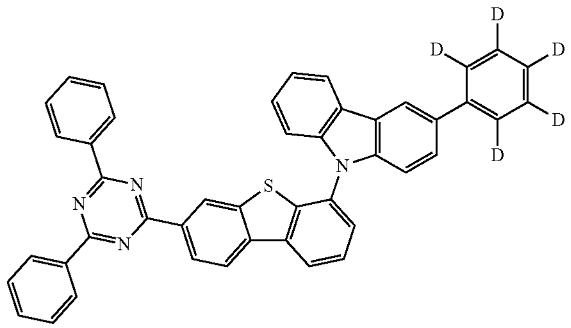
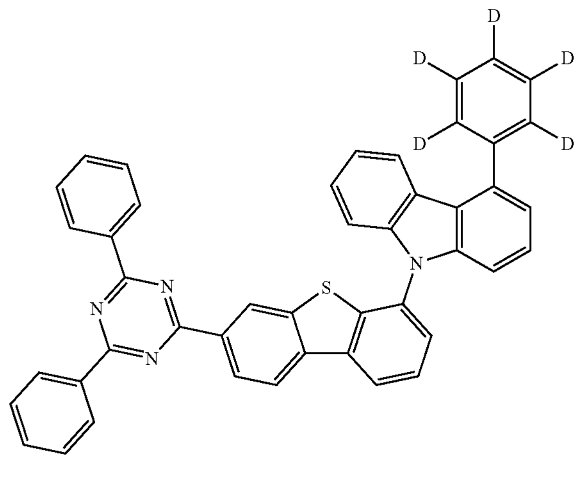

-continued
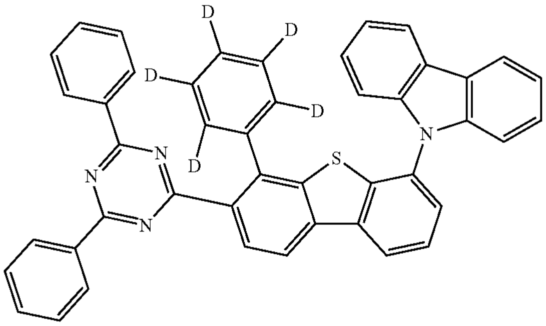
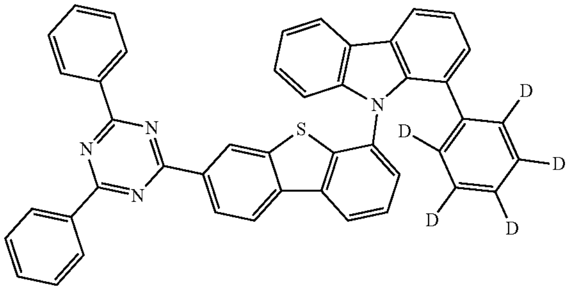
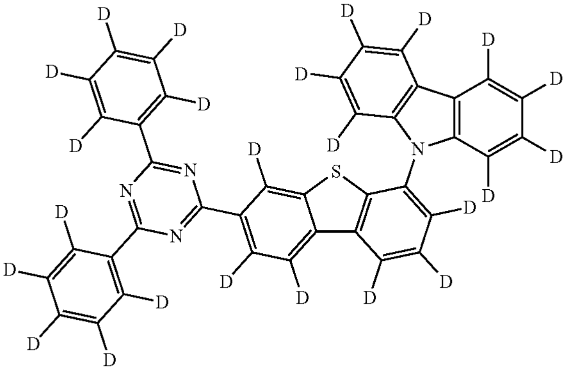
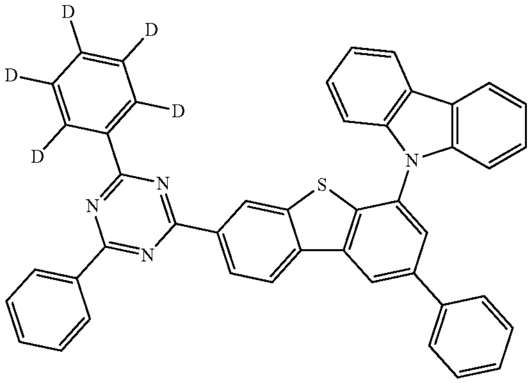
-continued
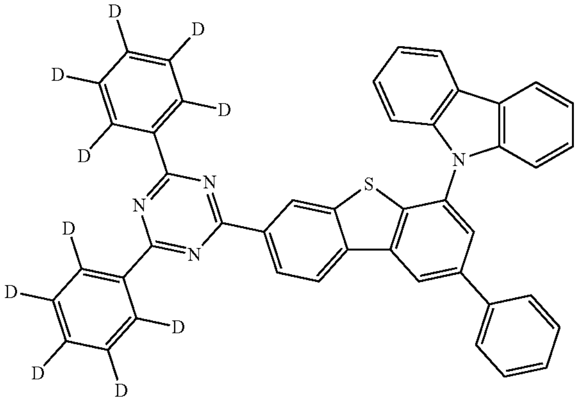
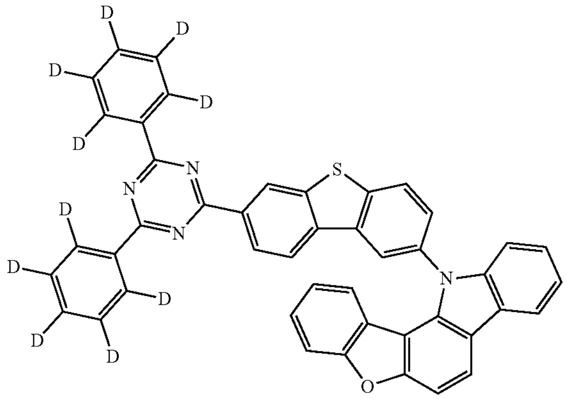
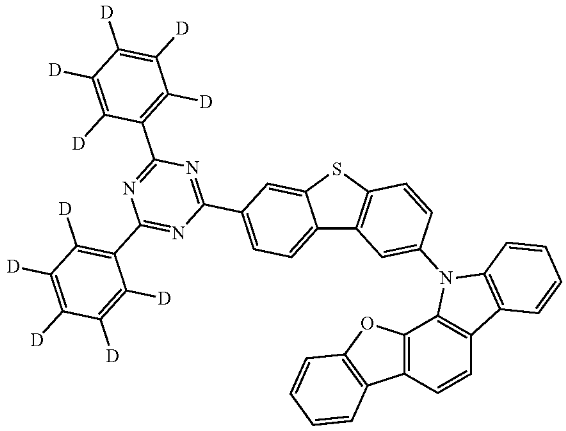
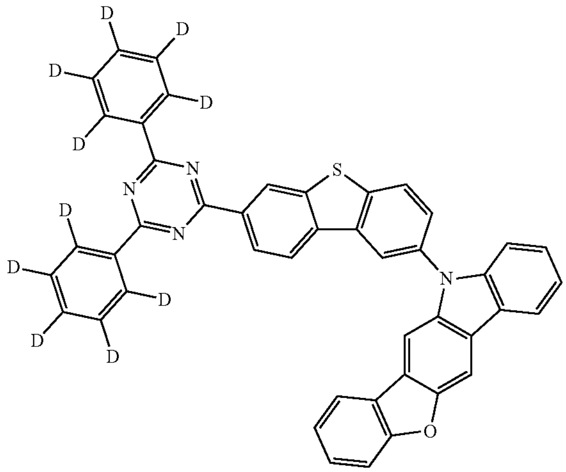

-continued
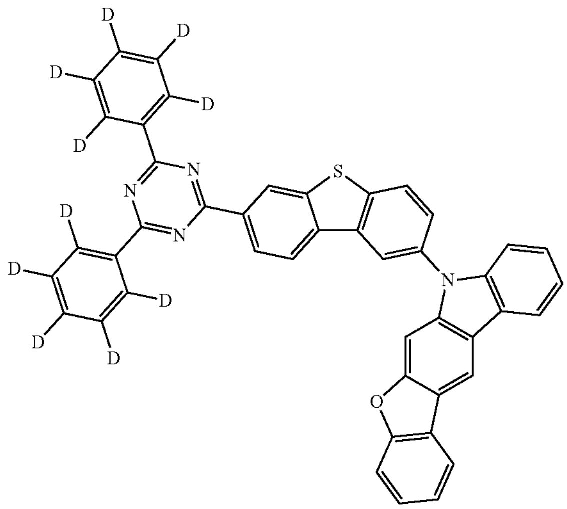
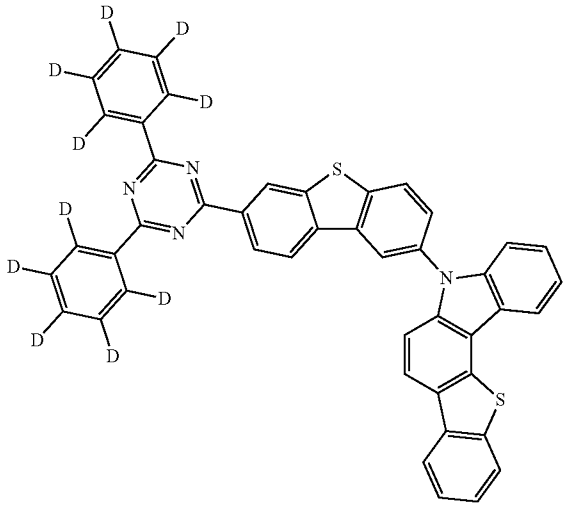
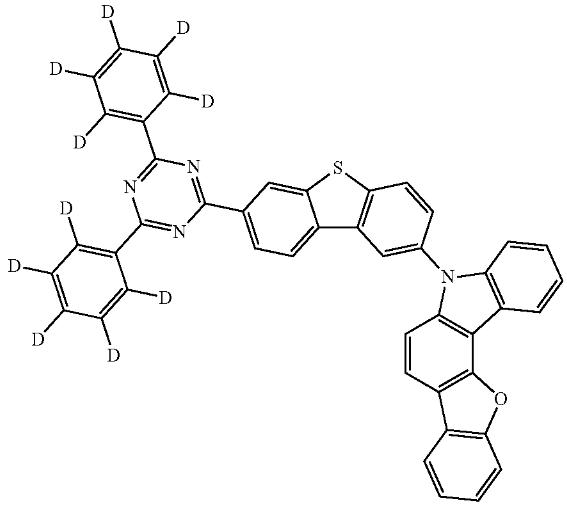
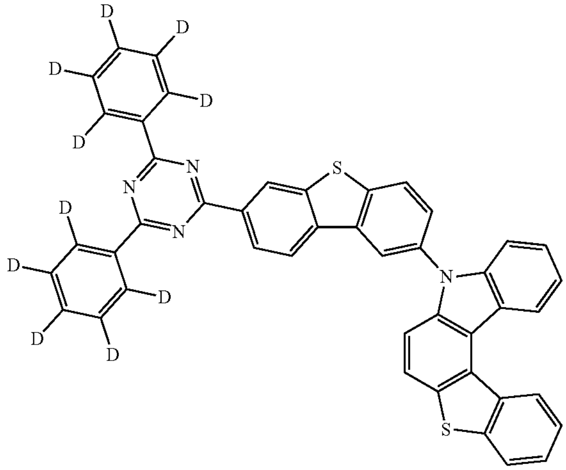
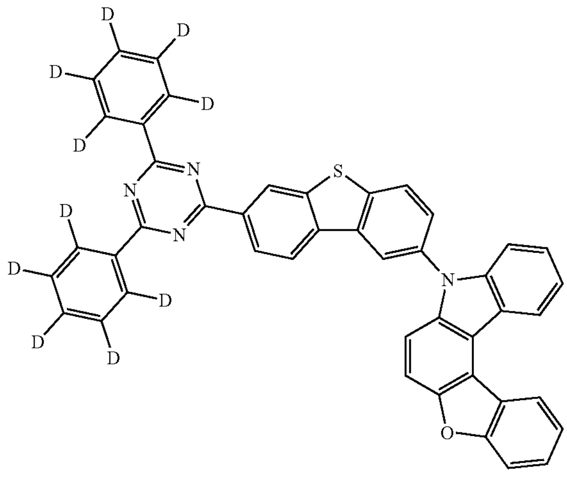
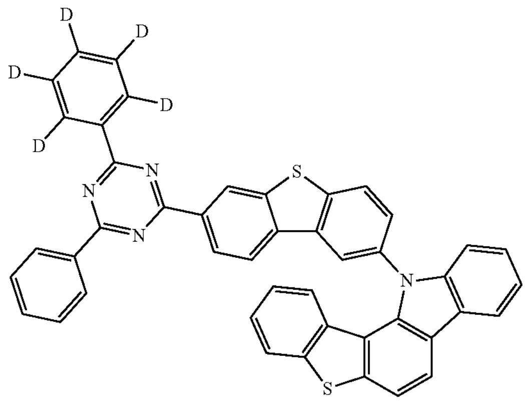

-continued
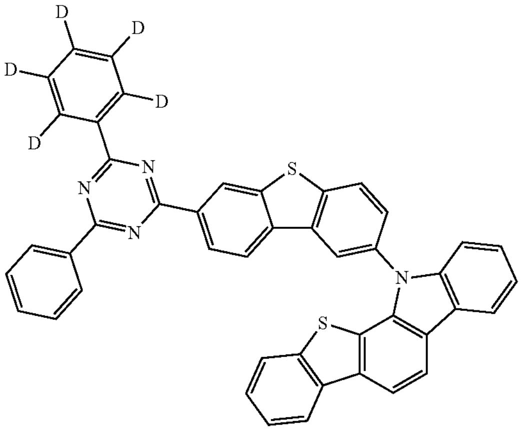
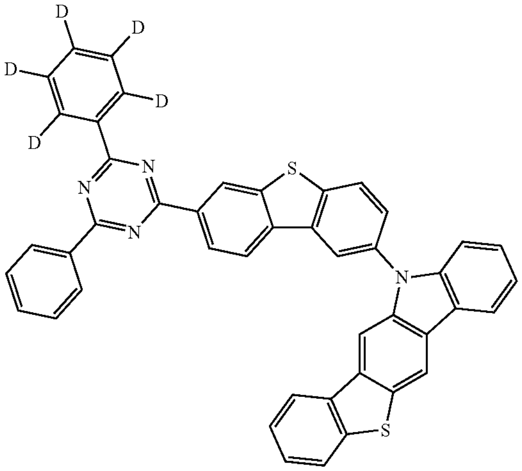
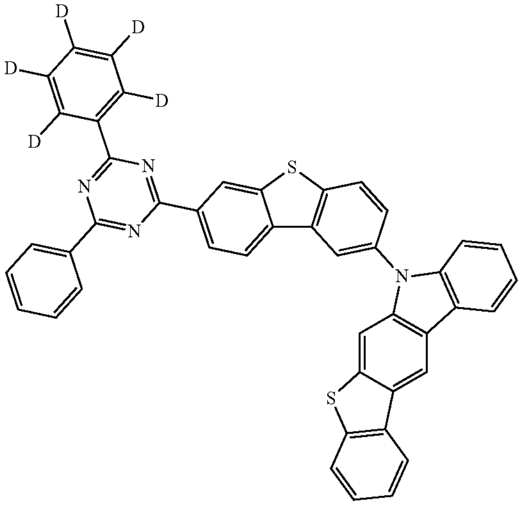
-continued
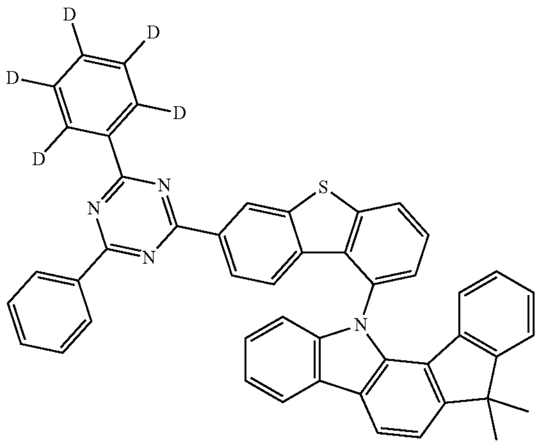
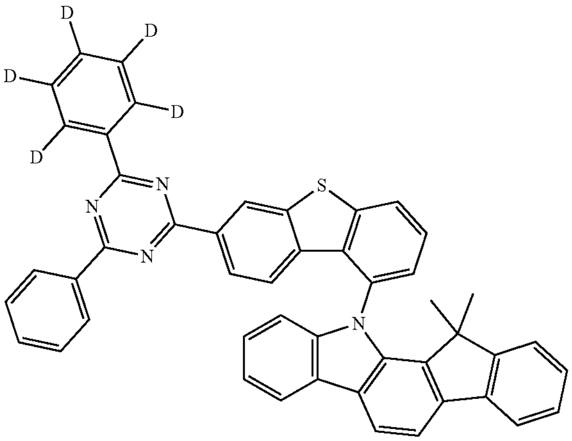
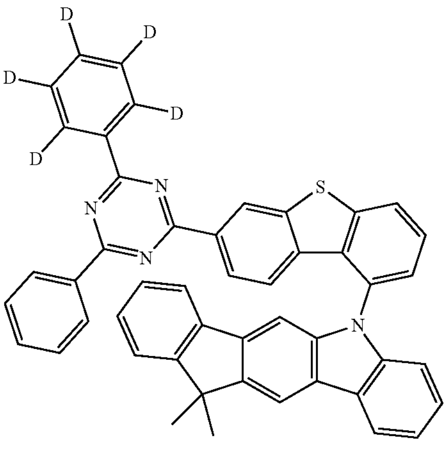

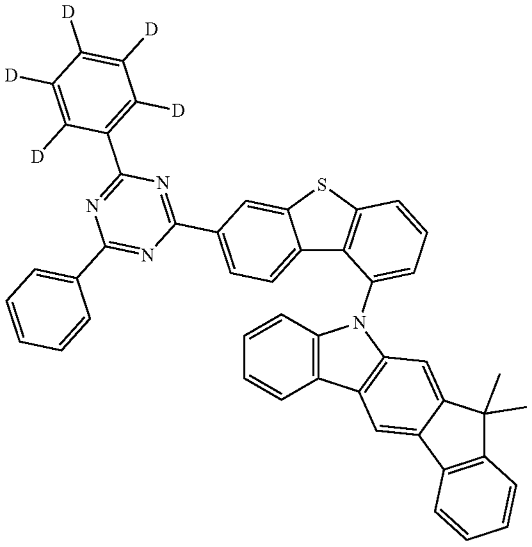
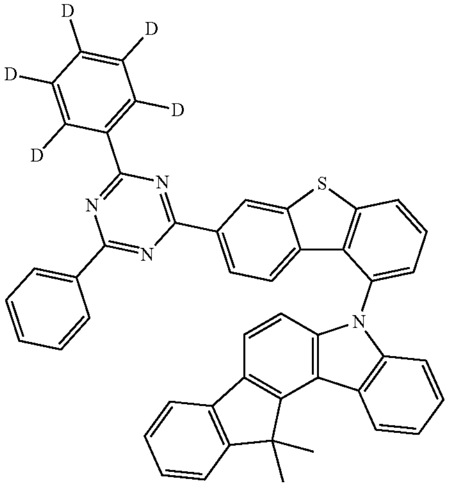
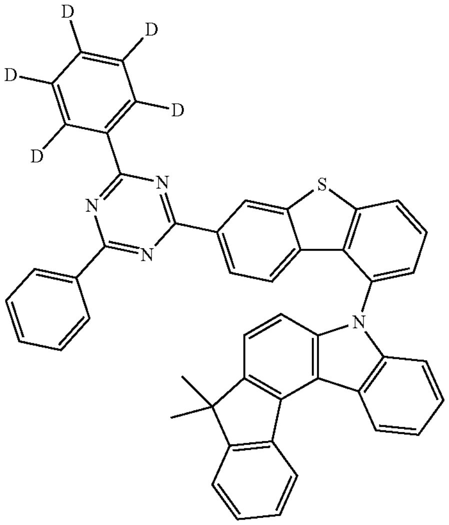
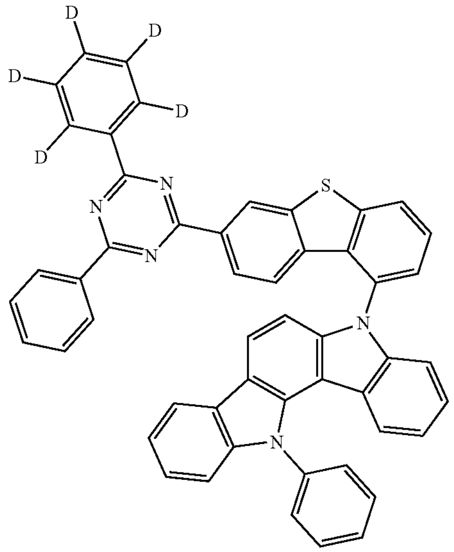
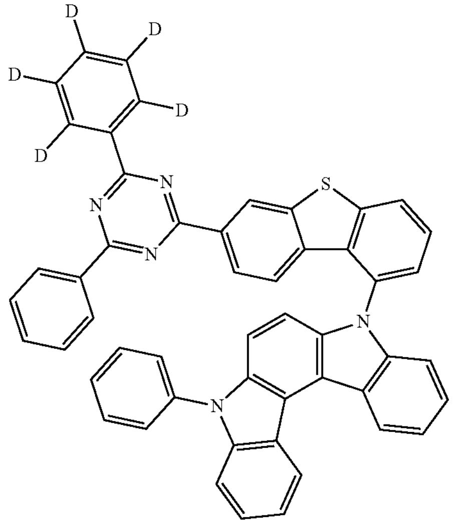 [SMILES: [2H]c1c([2H])c([2H])c(-c2nc(-c3ccccc3)nc(-c3ccc4c(c3)sc3cccc(-n5c6ccccc6c6c7c8ccccc8n(-c8ccccc8)c7ccc65)c34)n2)c([2H])c1[2H]]
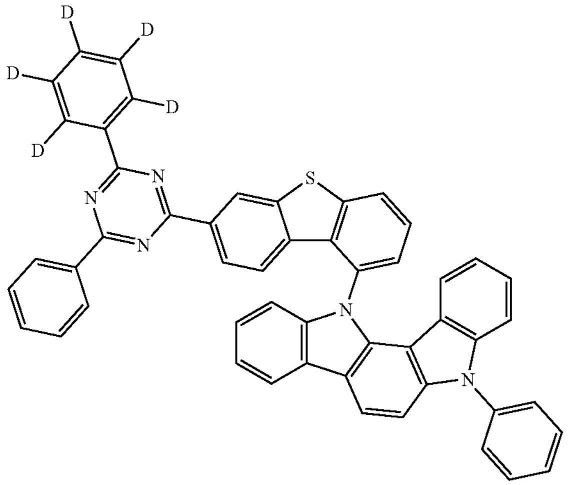

-continued
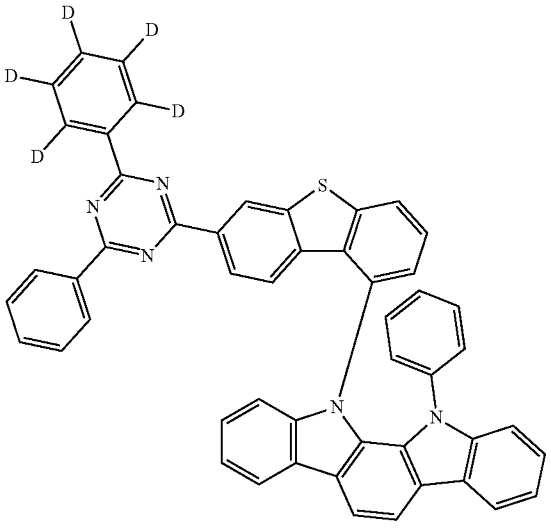
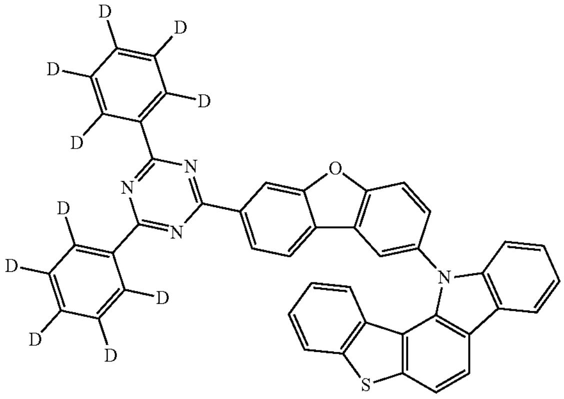
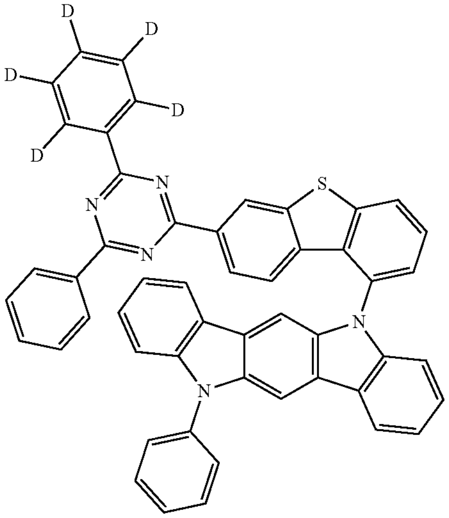
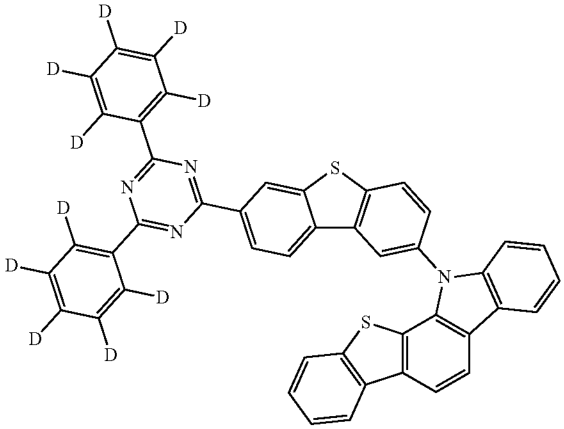
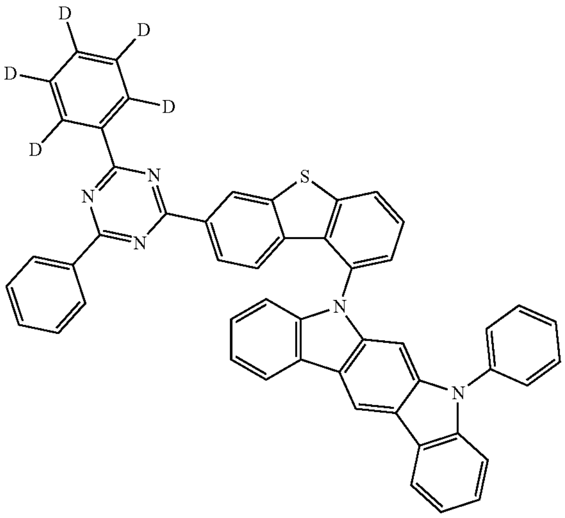 [SMILES: [2H]c1c([2H])c([2H])c(-c2nc(-c3ccccc3)nc(-c3ccc4c(c3)sc3cccc(-n5c6ccccc6c6cc7c8ccccc8n(-c8ccccc8)c7cc65)c34)n2)c([2H])c1[2H]]
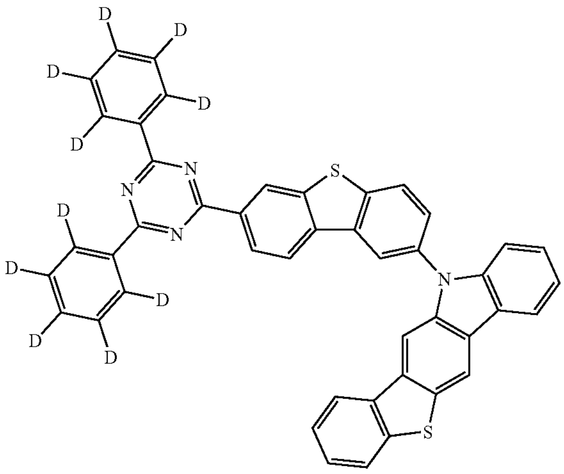
-continued -continued
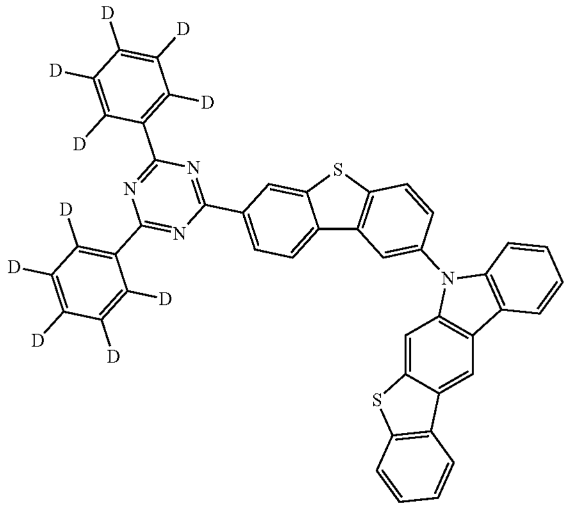
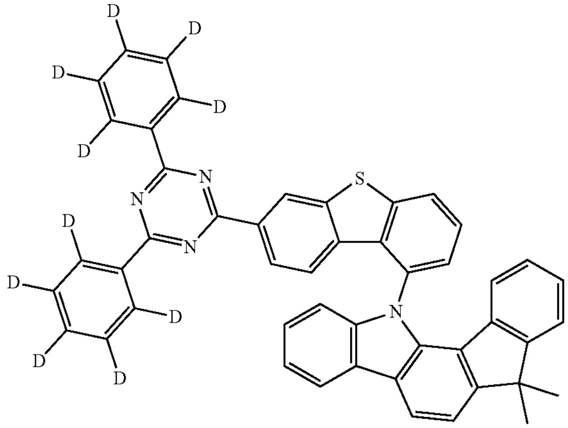
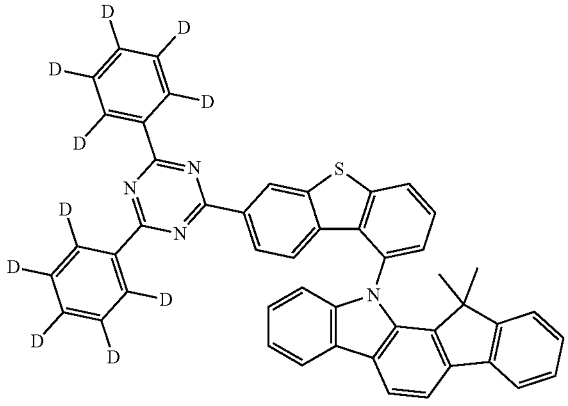
-continued
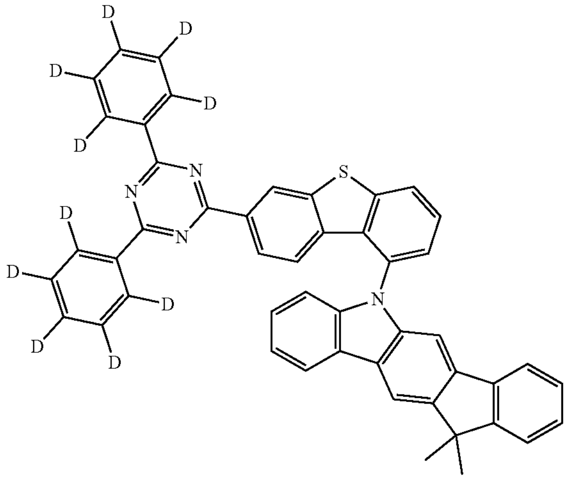
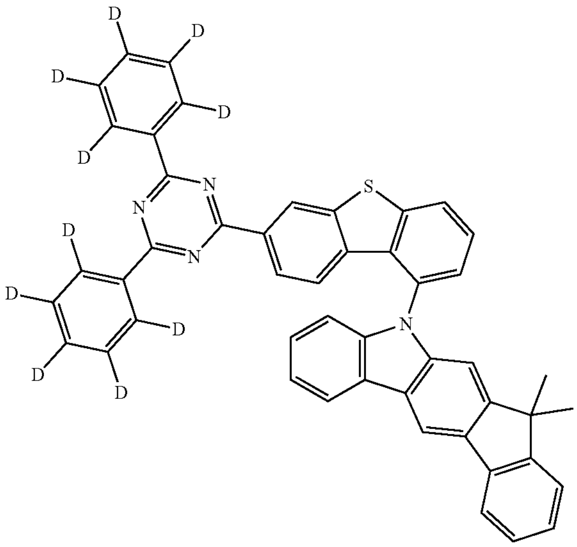
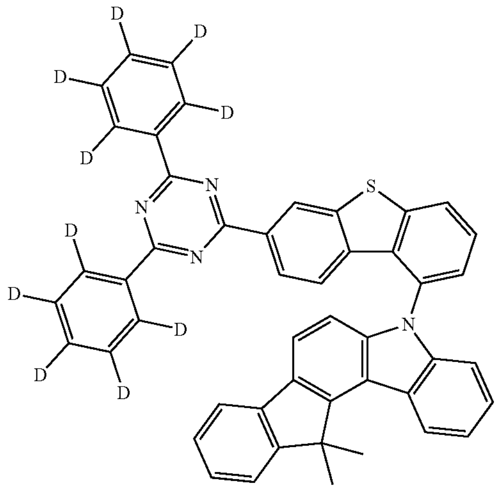

-continued
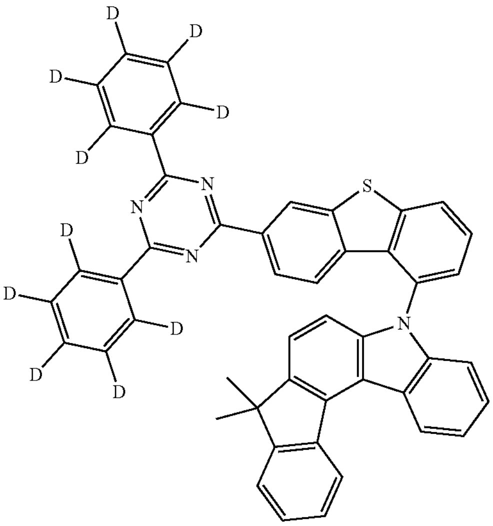
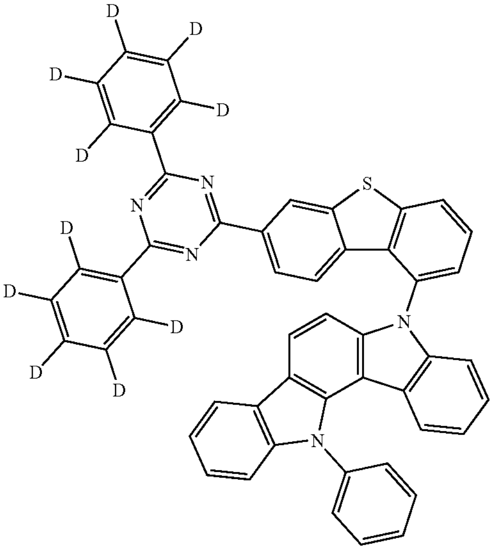
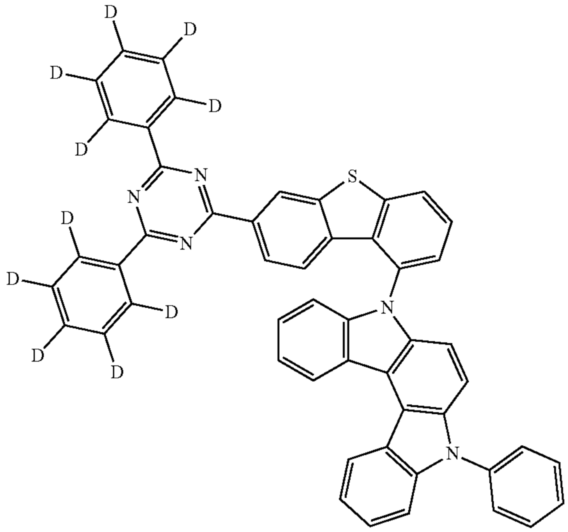 [SMILES: [2H]c1c([2H])c([2H])c(-c2nc(-c3ccc4c(c3)sc3cccc(-n5c6ccccc6c6c7c8ccccc8n(-c8ccccc8)c7ccc65)c34)nc(-c3c([2H])c([2H])c([2H])c([2H])c3[2H])n2)c([2H])c1[2H]]
-continued
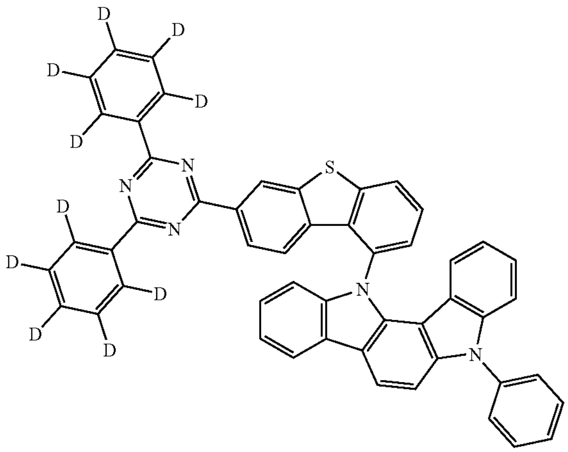
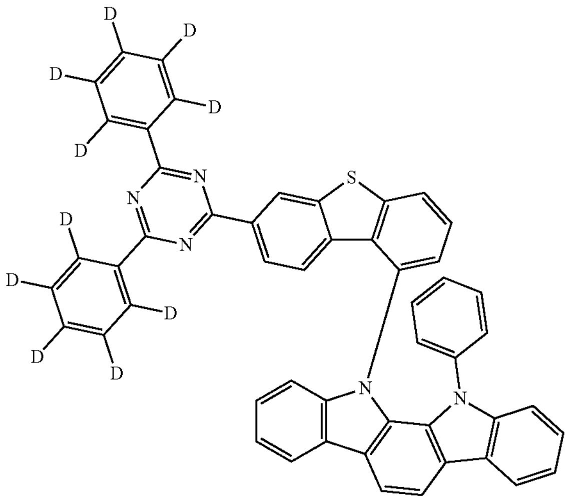
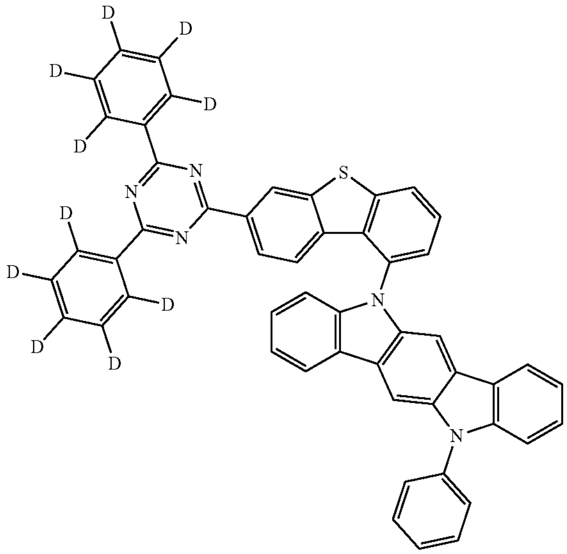

-continued
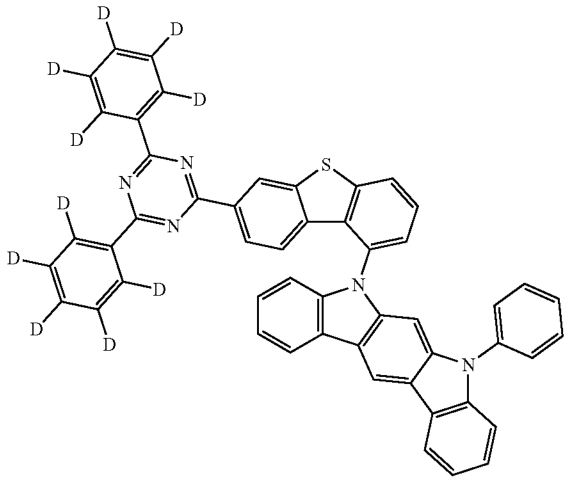 [SMILES: [2H]c1c([2H])c([2H])c(-c2nc(-c3ccc4c(c3)sc3cccc(-n5c6ccccc6c6cc7c8ccccc8n(-c8ccccc8)c7cc65)c34)nc(-c3c([2H])c([2H])c([2H])c([2H])c3[2H])n2)c([2H])c1[2H]]
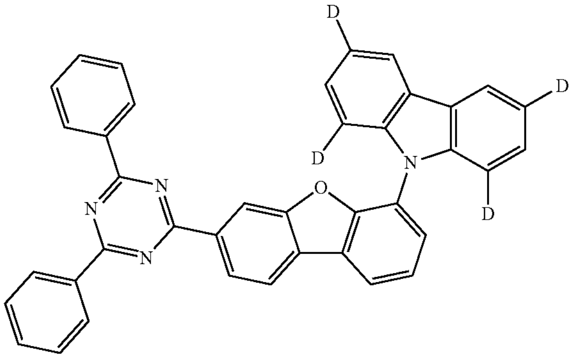
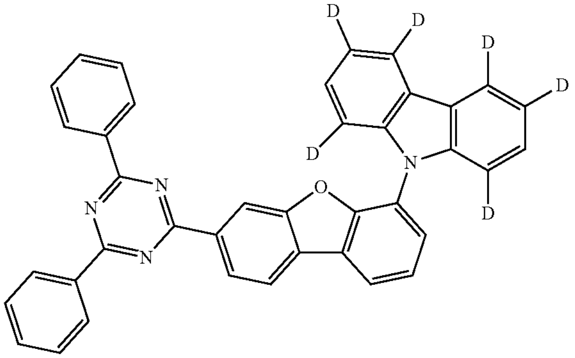
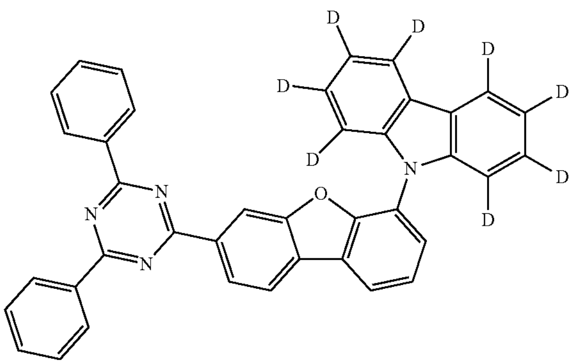
-continued
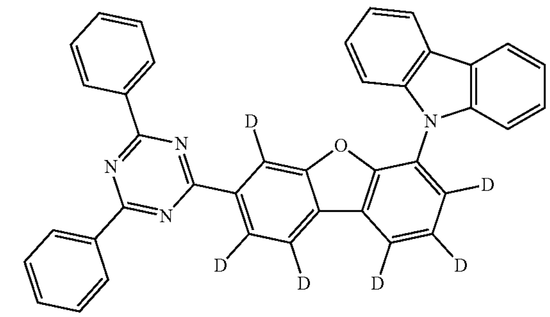
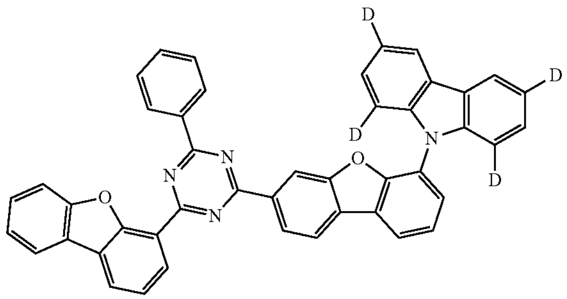
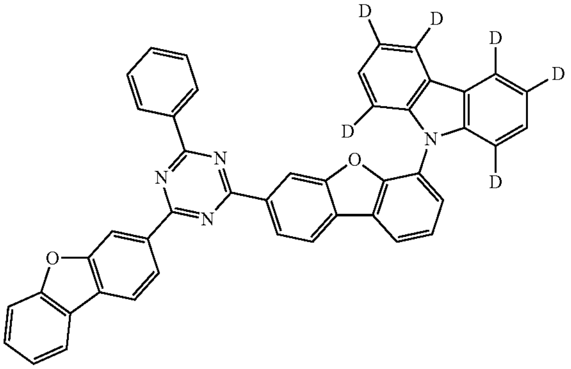
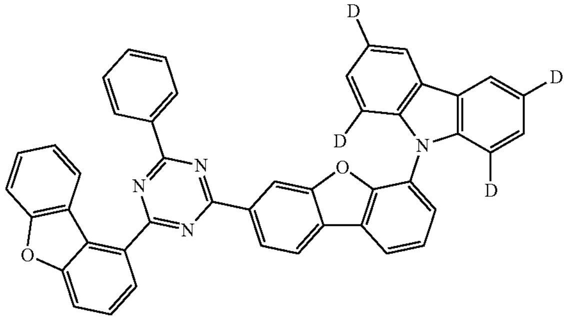
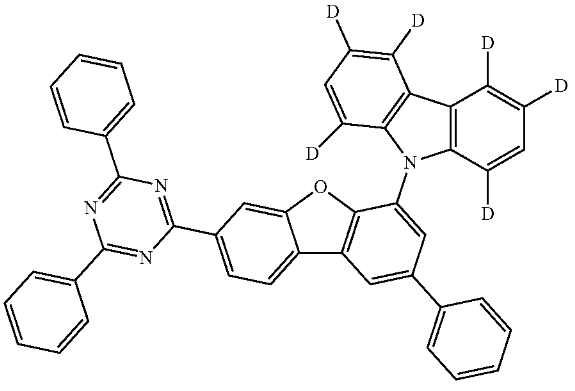

-continued
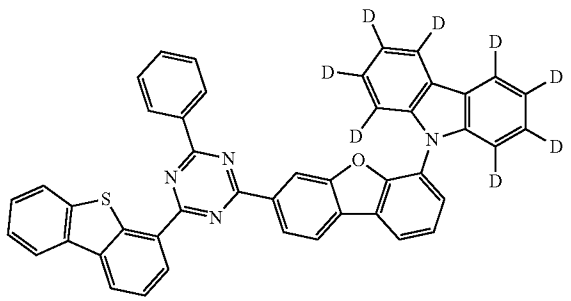
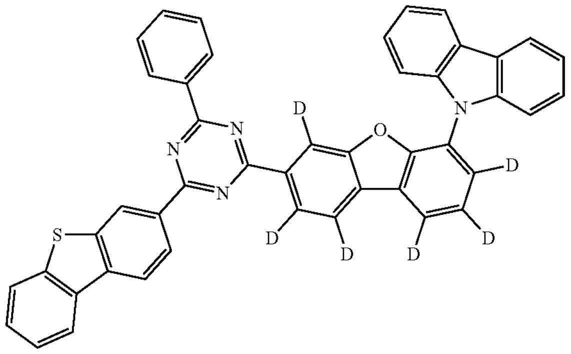
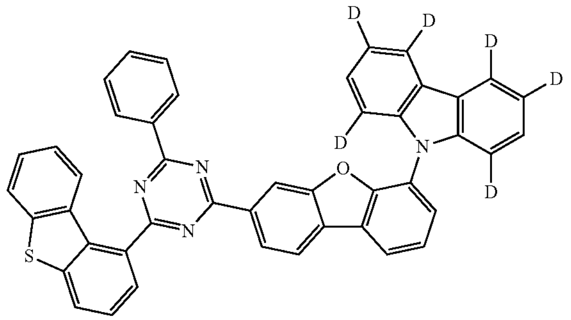
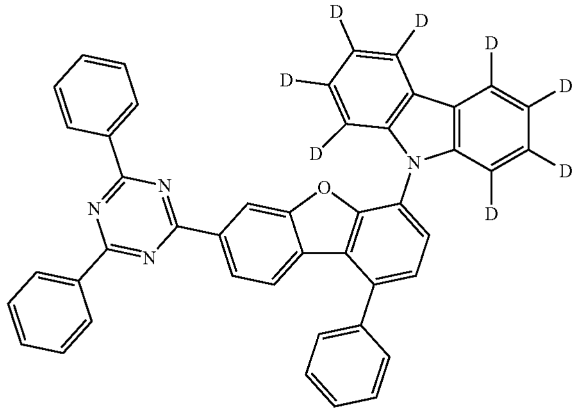
-continued
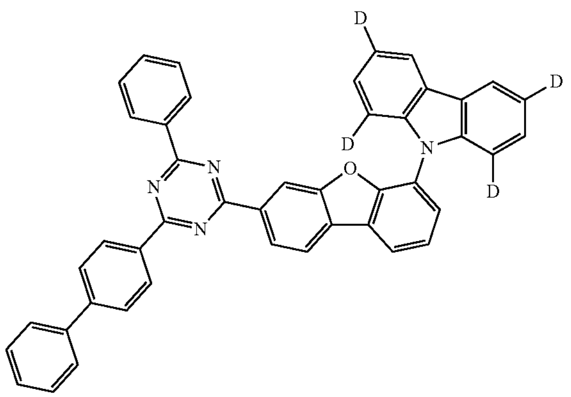
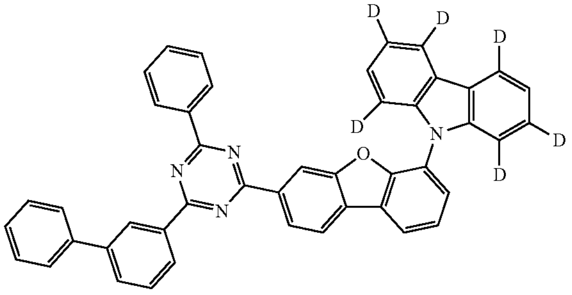
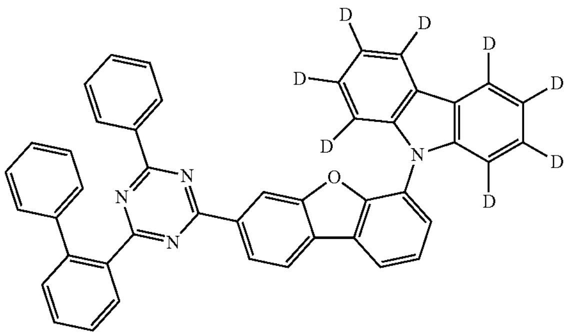
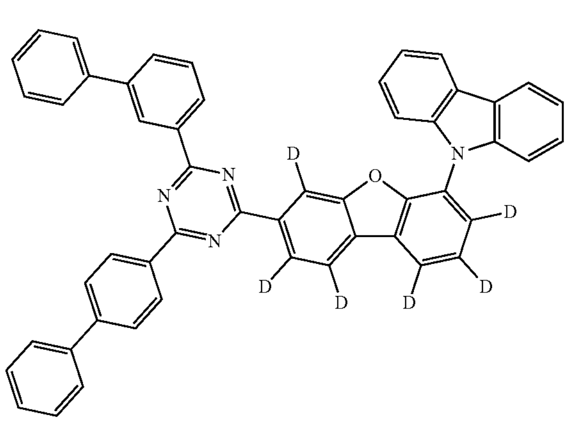

-continued
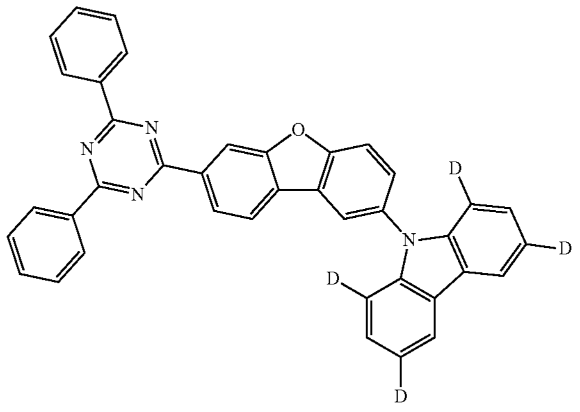
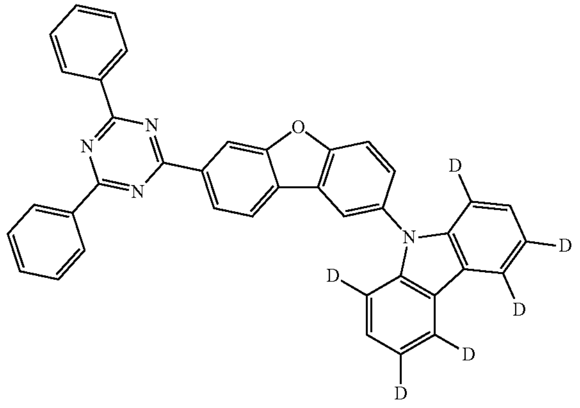
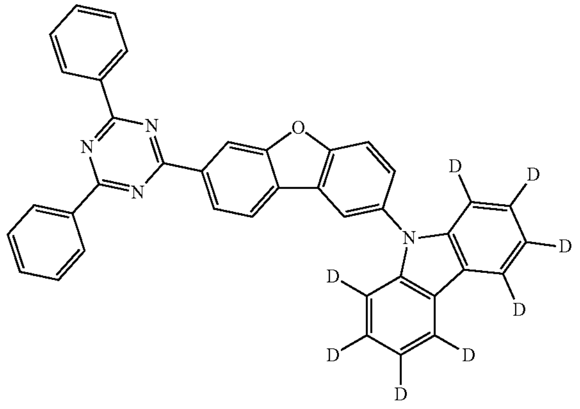
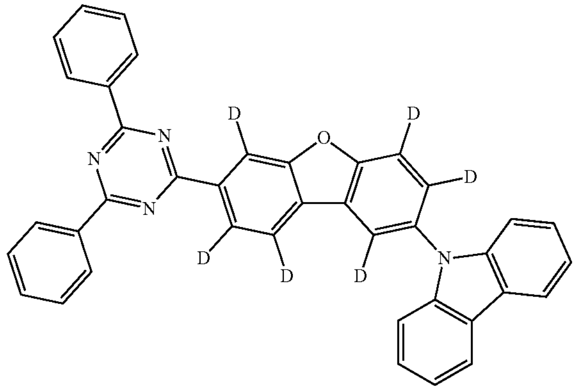
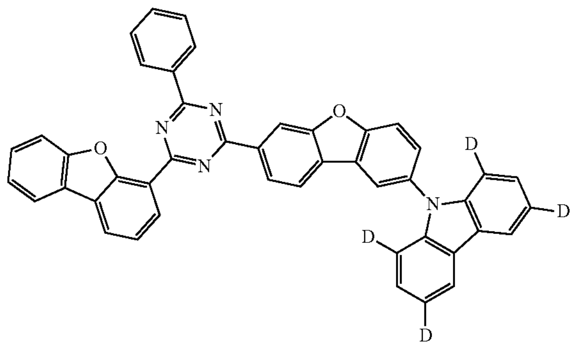
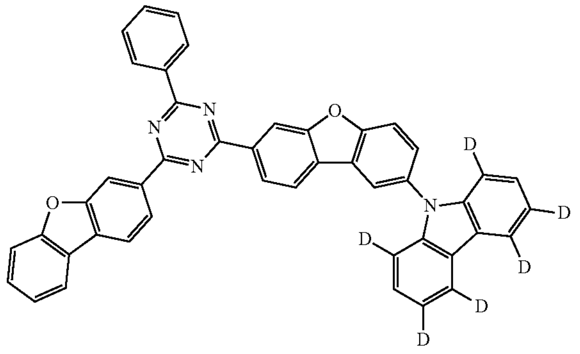
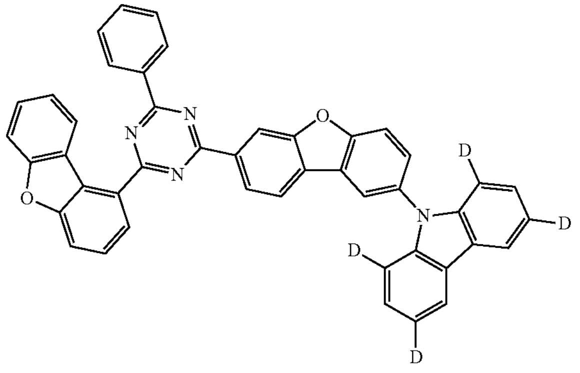
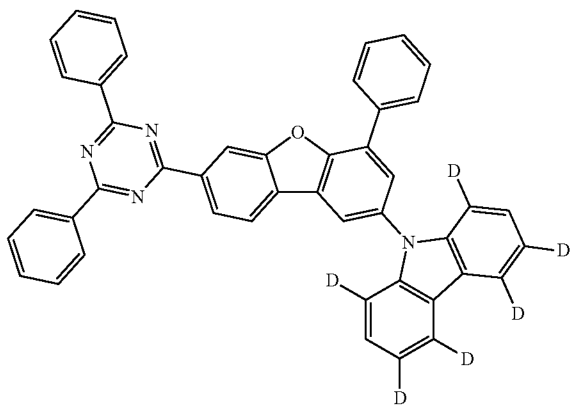

-continued
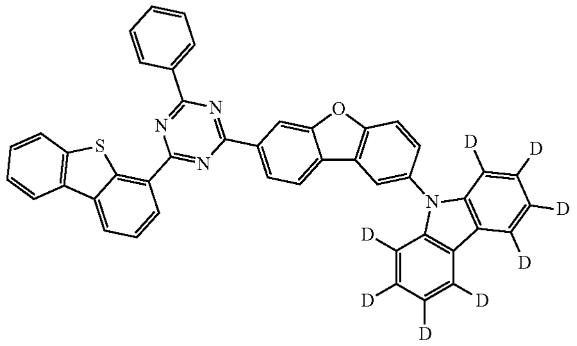
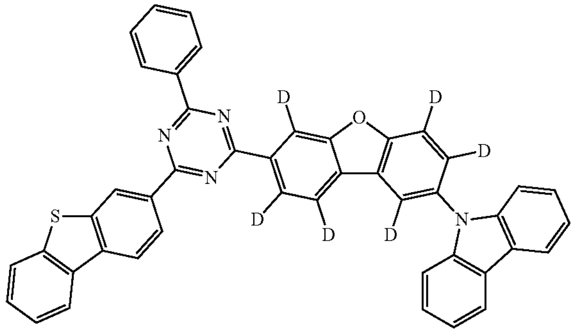
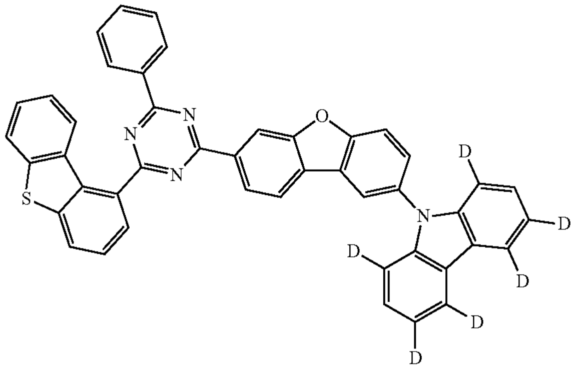
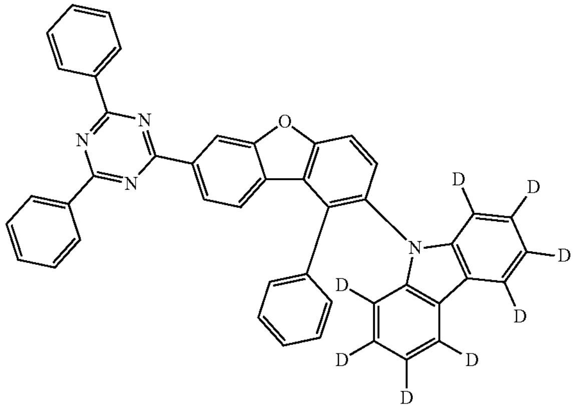
-continued
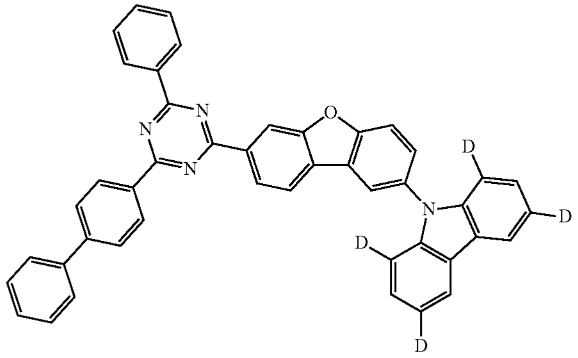
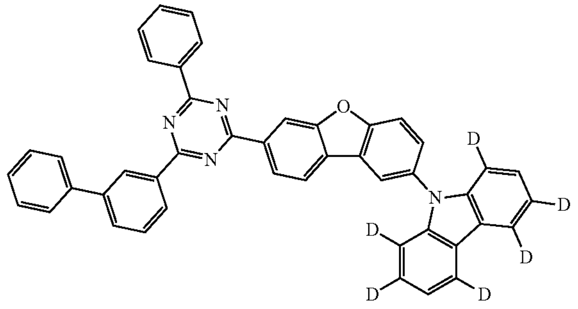
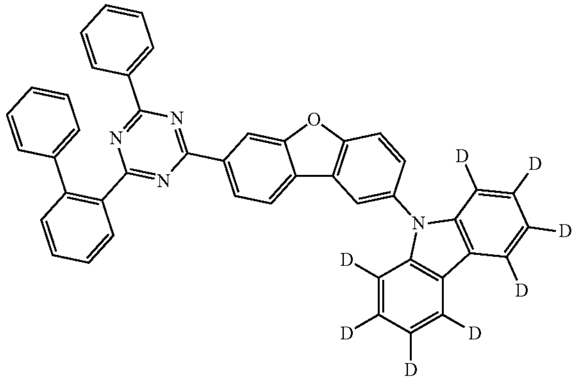
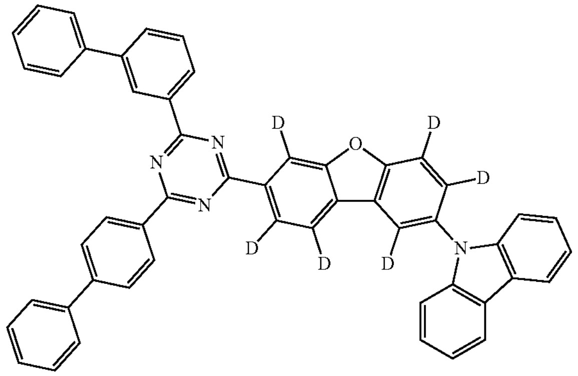
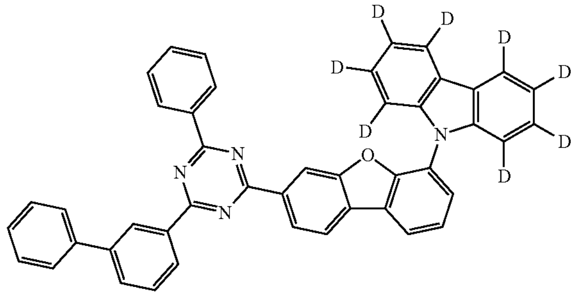

-continued
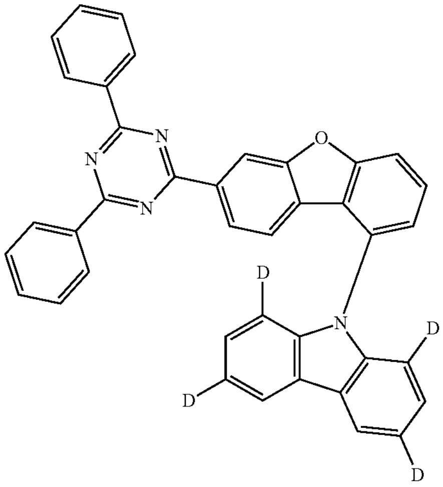
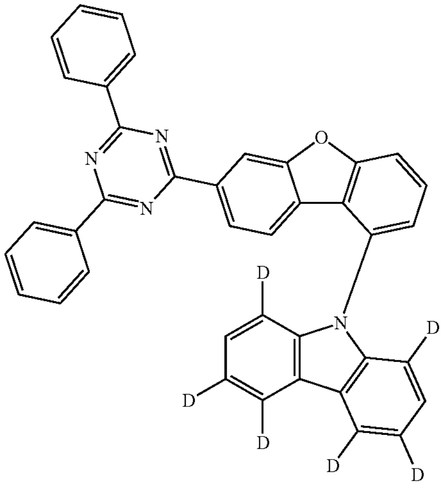
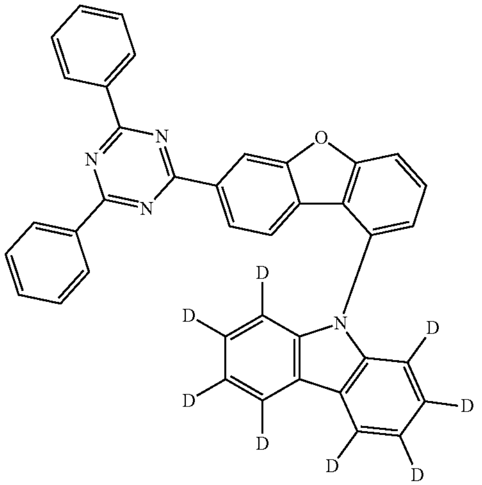
-continued
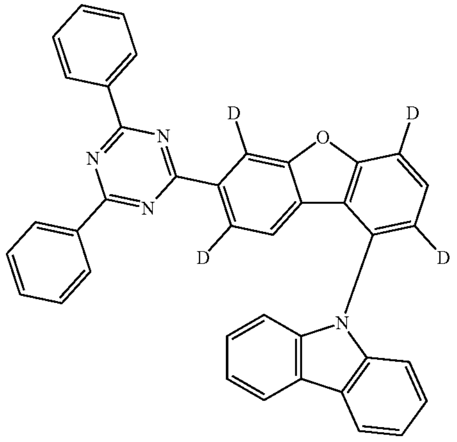
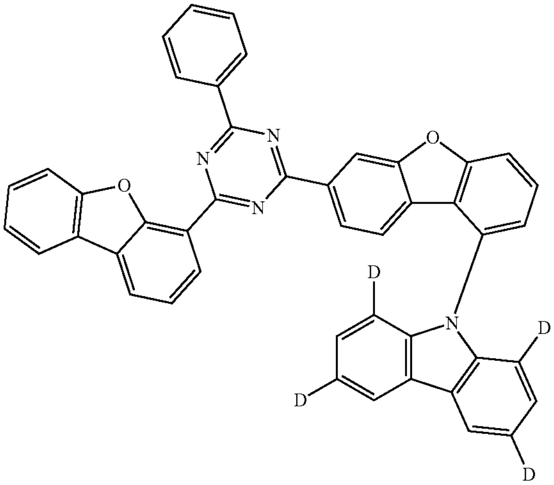
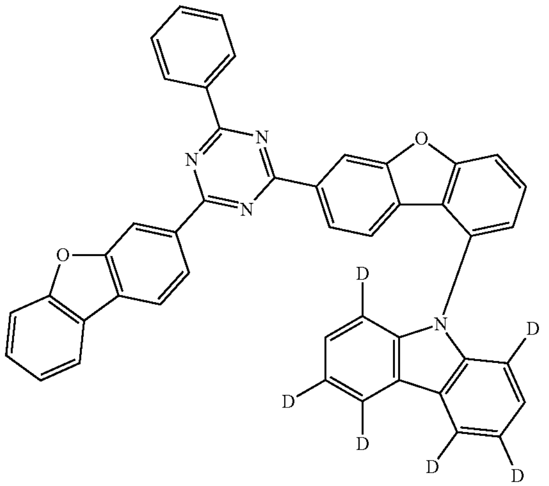

-continued
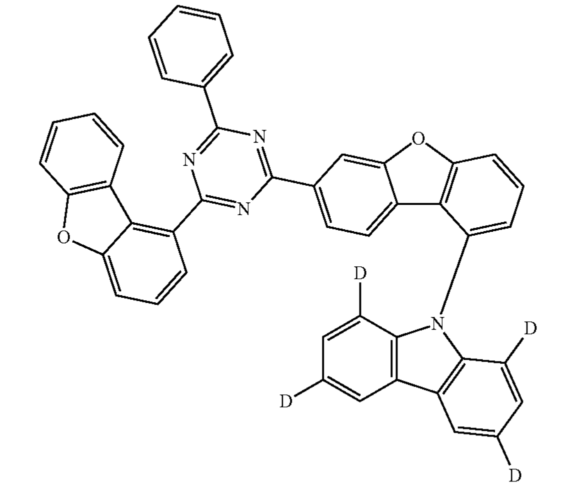
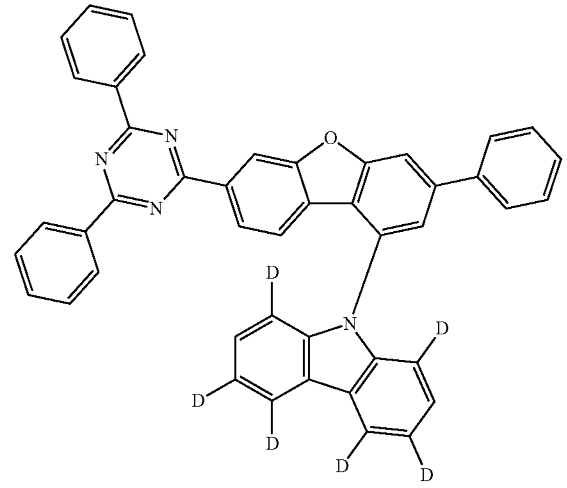
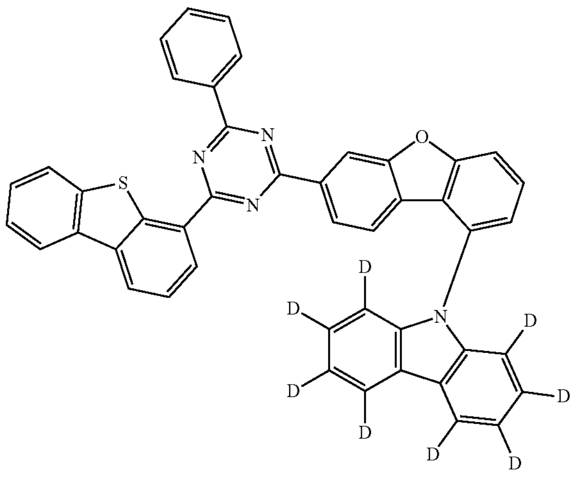
-continued
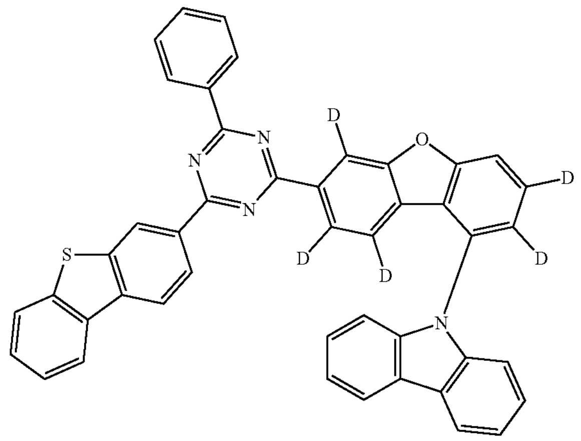
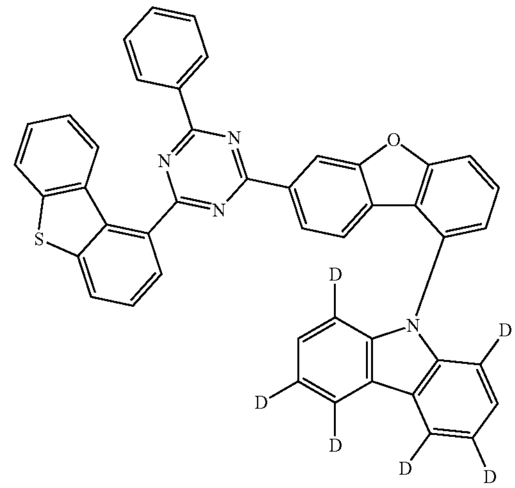
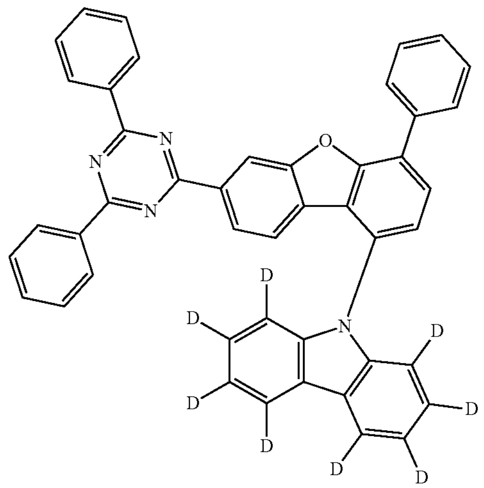

-continued
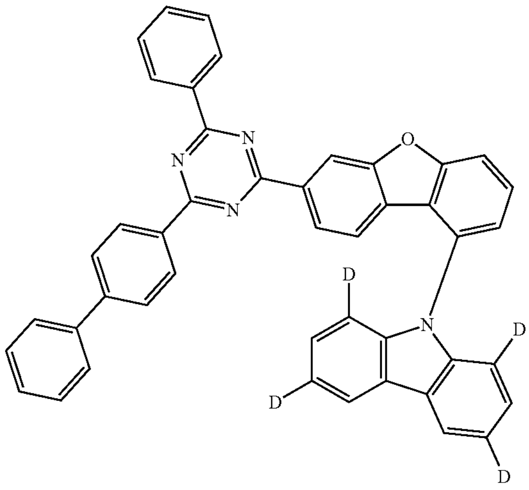
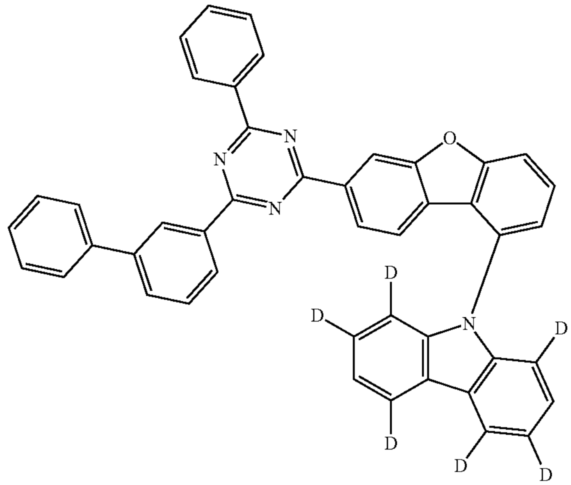
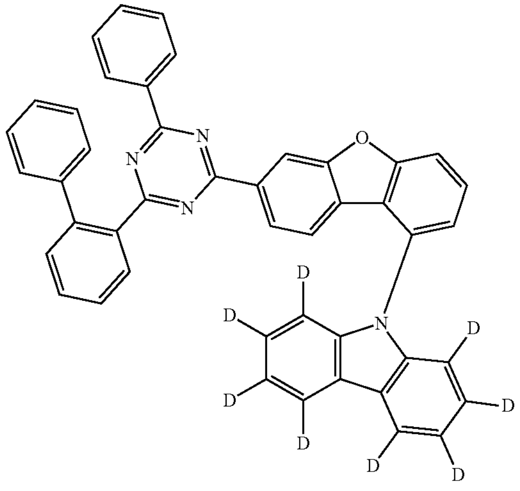
-continued
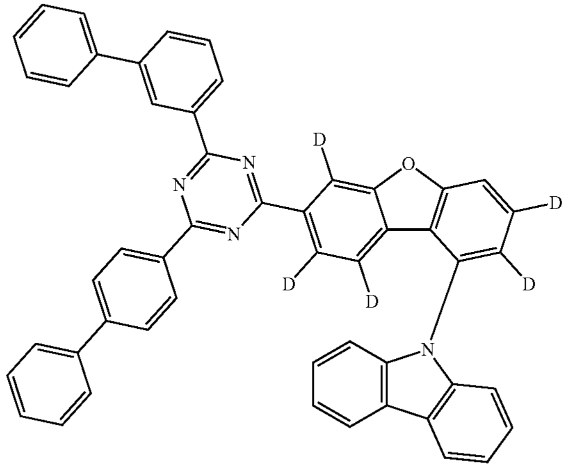
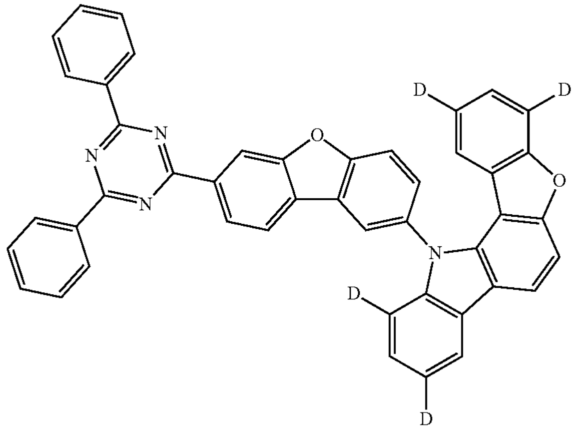
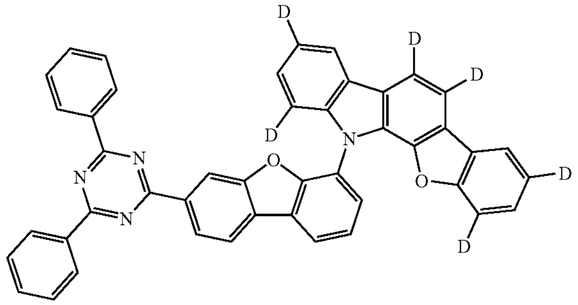
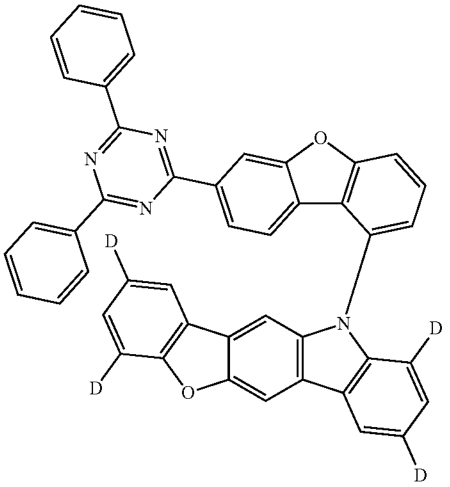

-continued
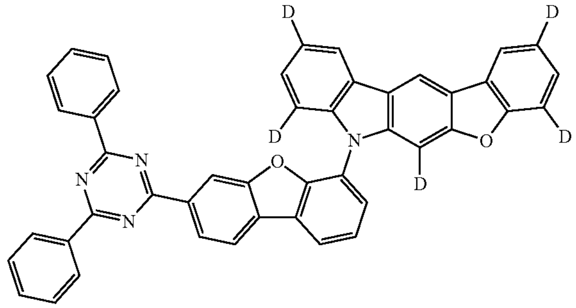
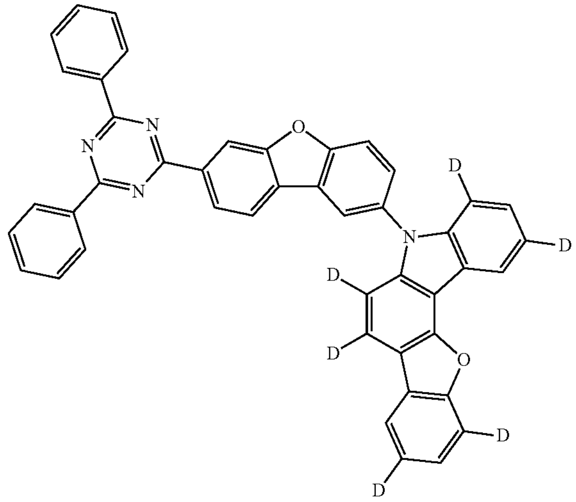
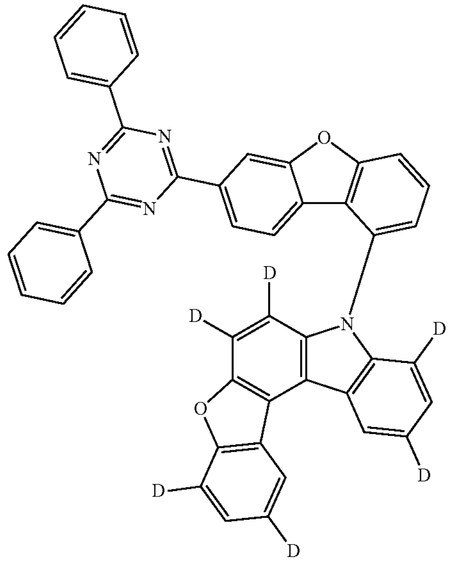
-continued
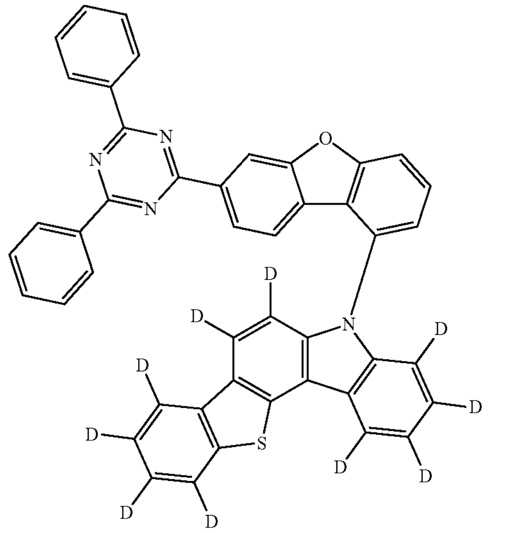
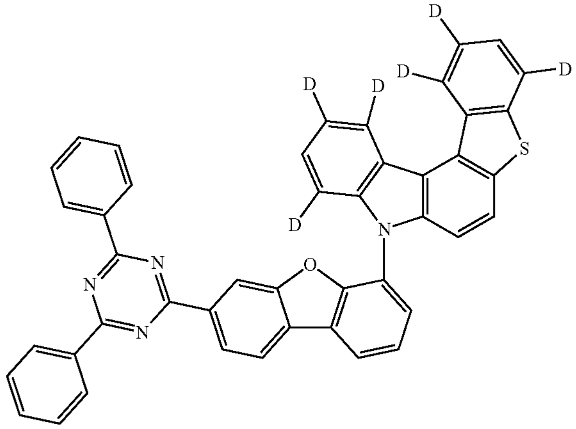
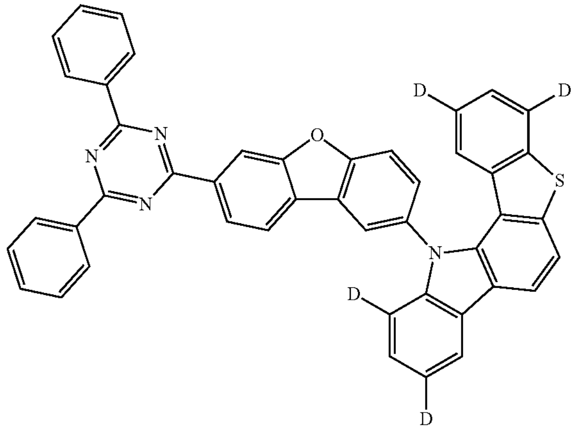

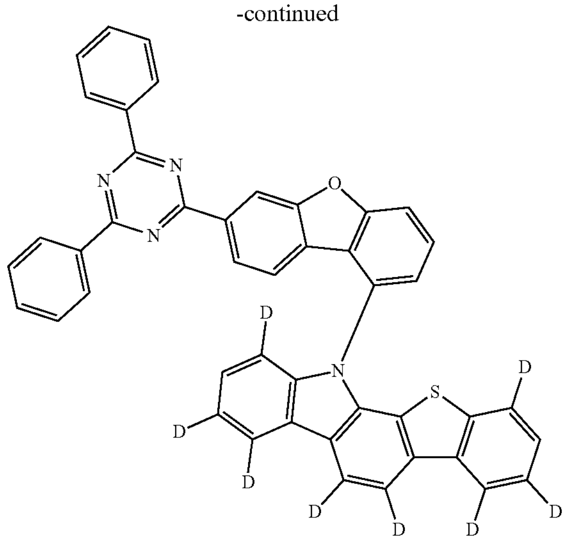
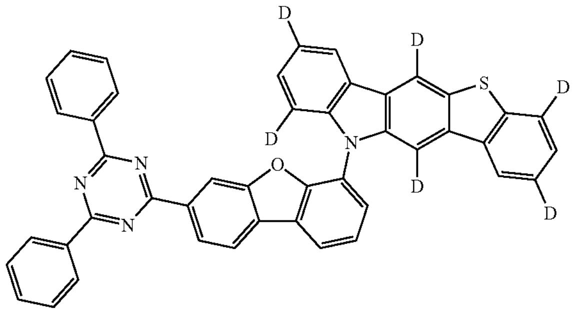
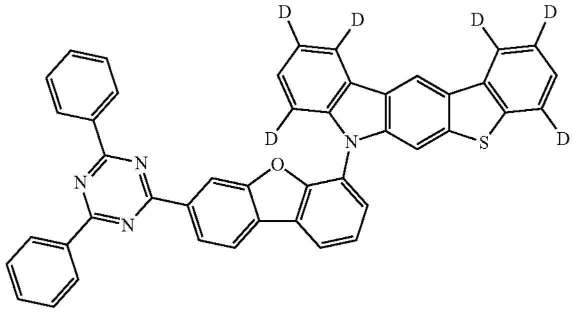
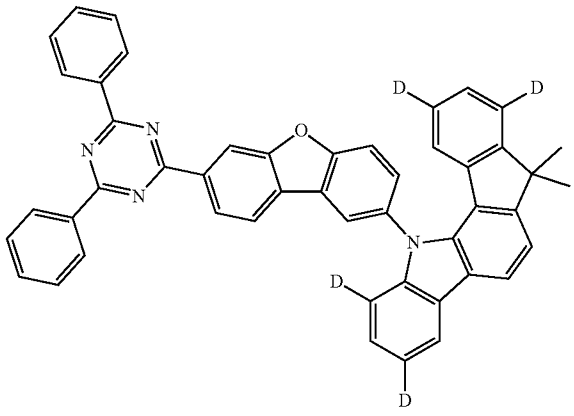
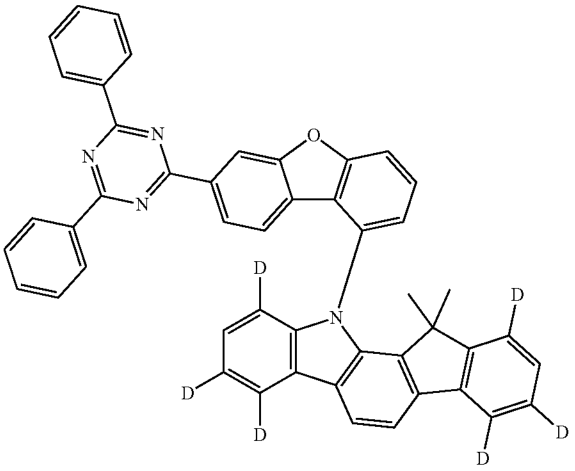
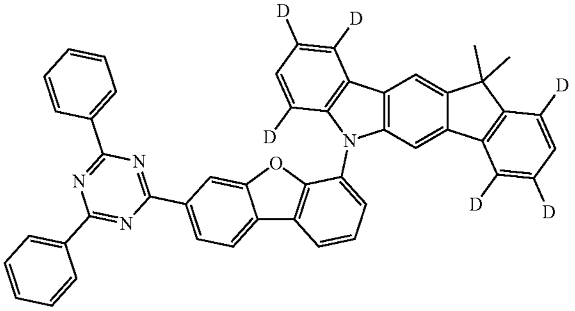
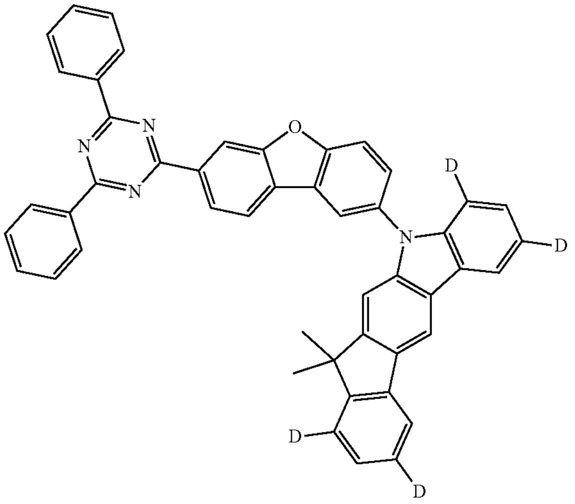

-continued
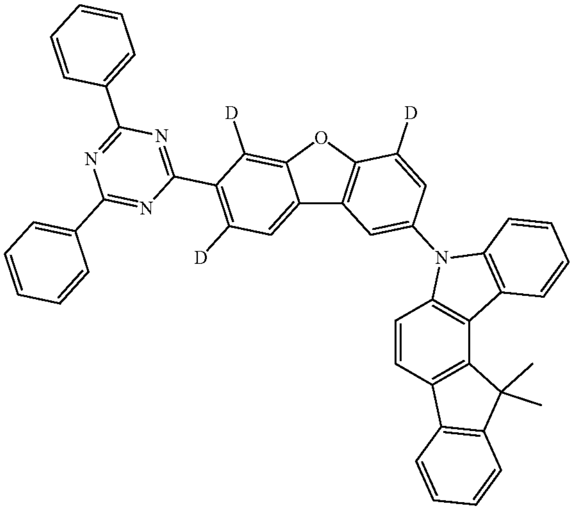
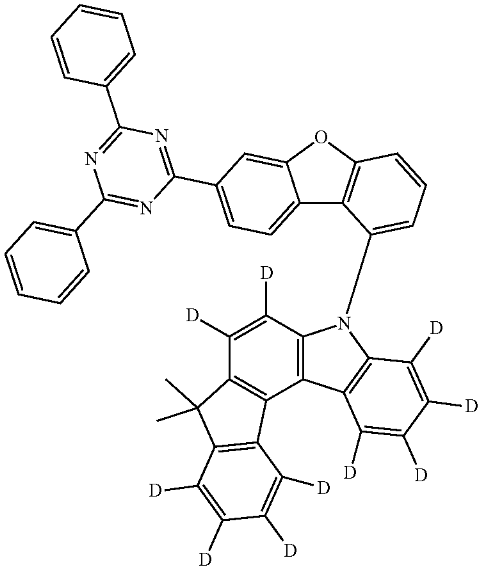
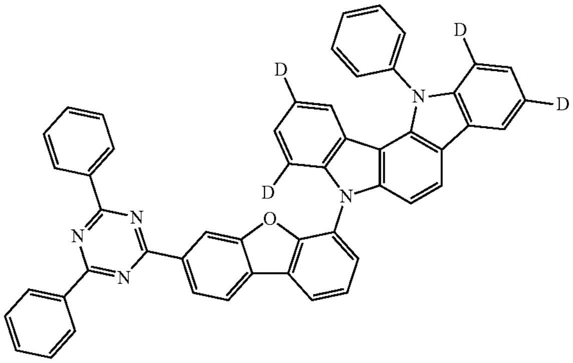
-continued
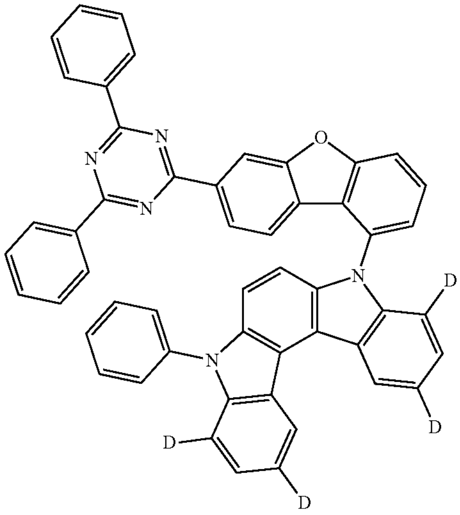
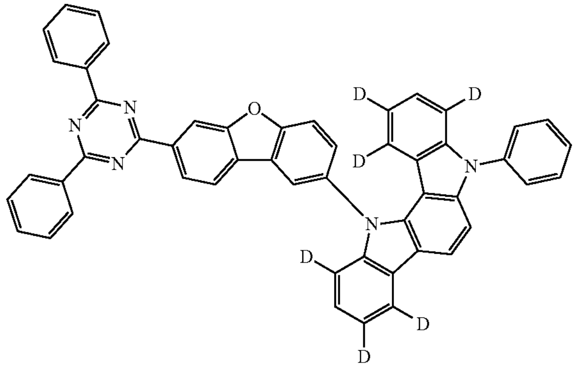
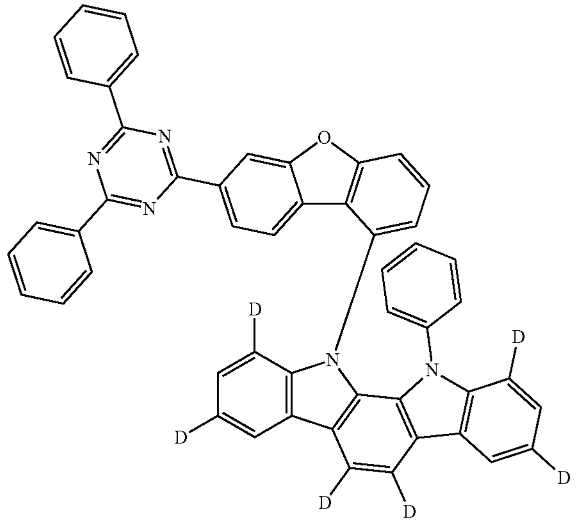

-continued
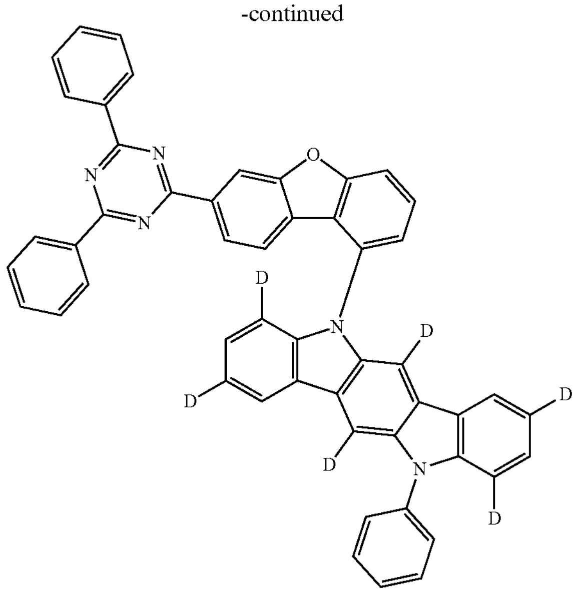
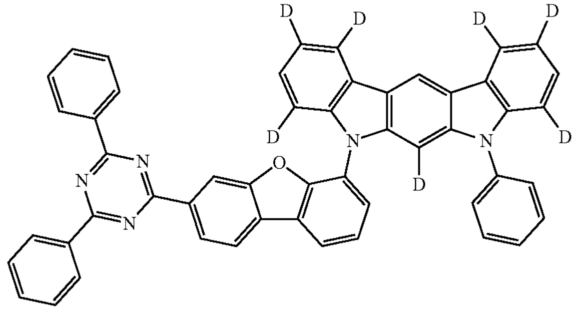
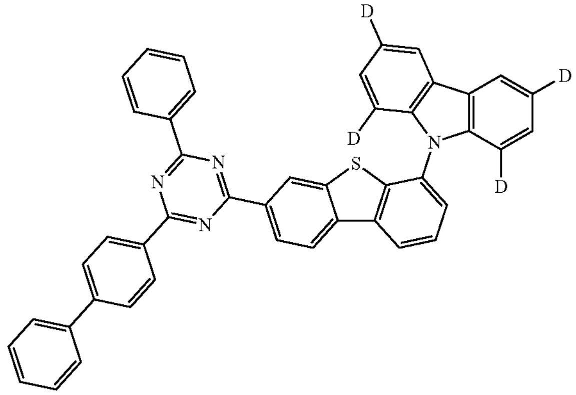
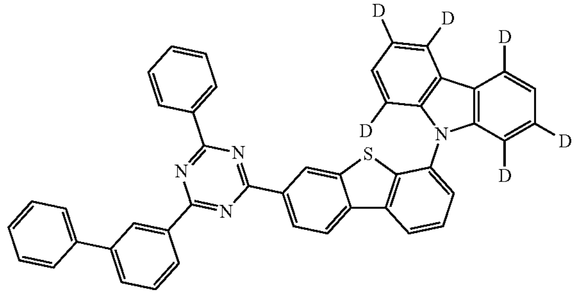
-continued
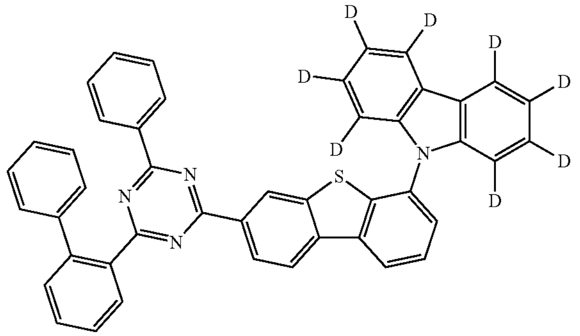
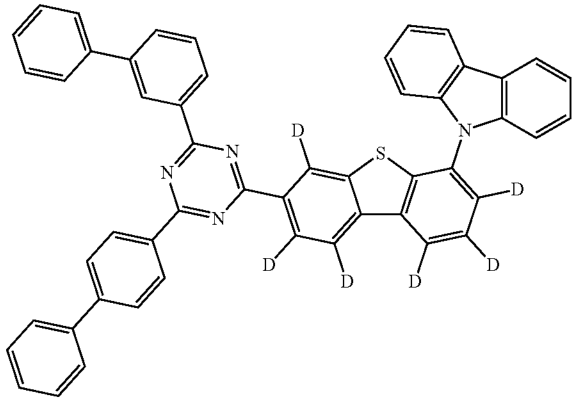
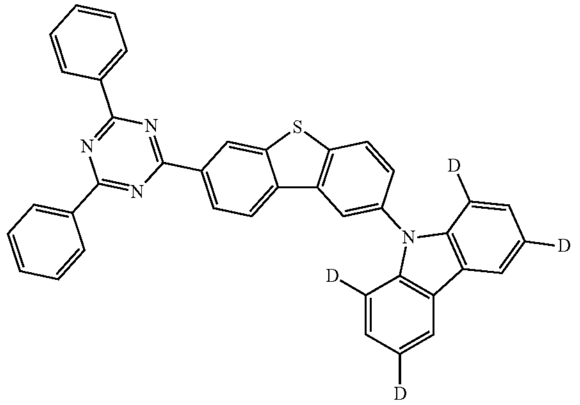
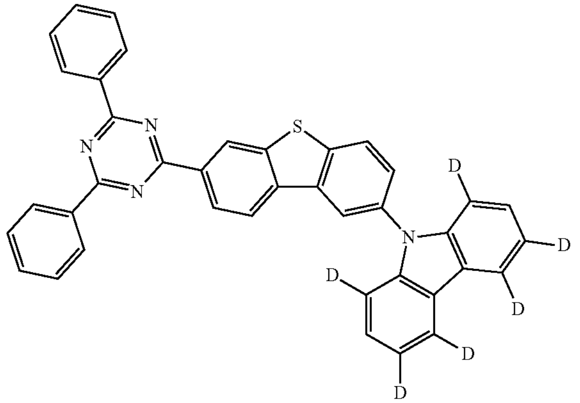

-continued
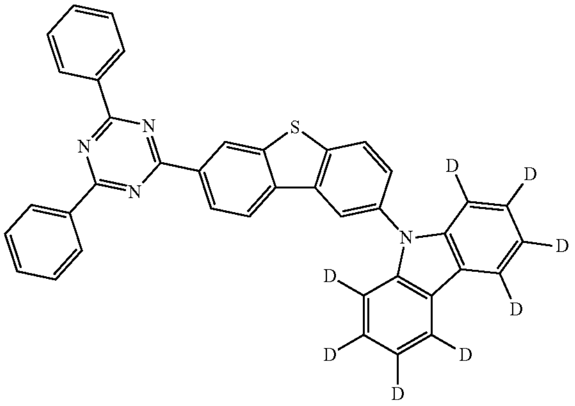
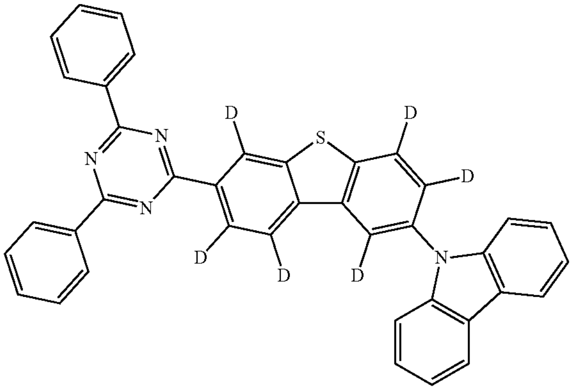
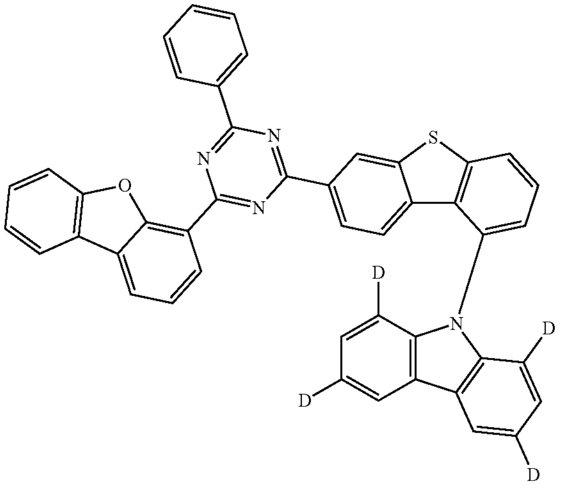
-continued
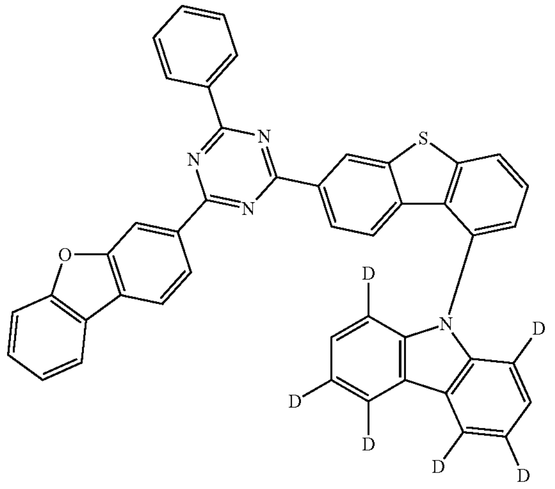
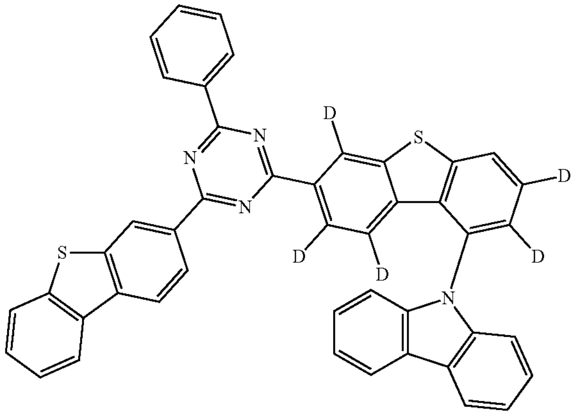
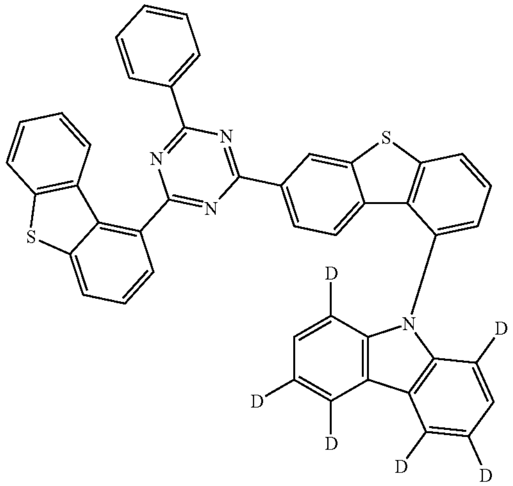

-continued

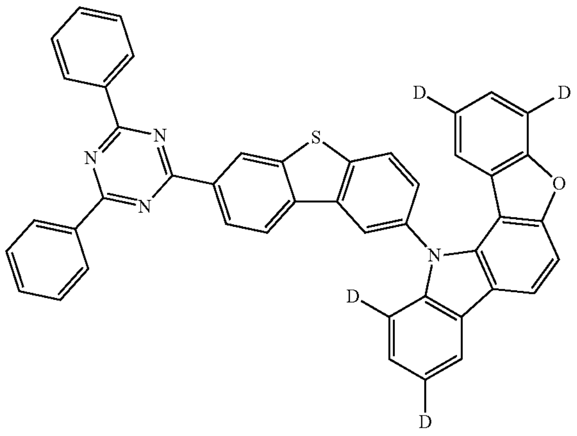

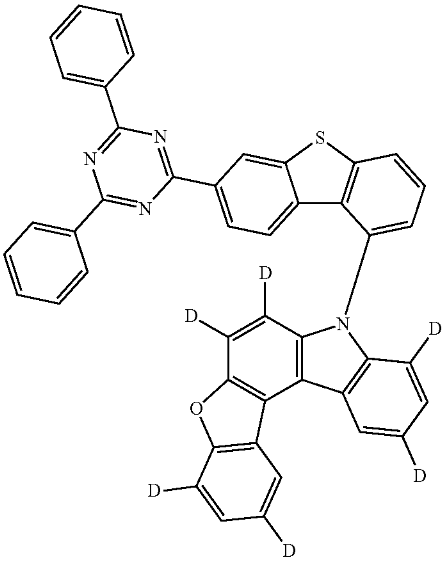

-continued

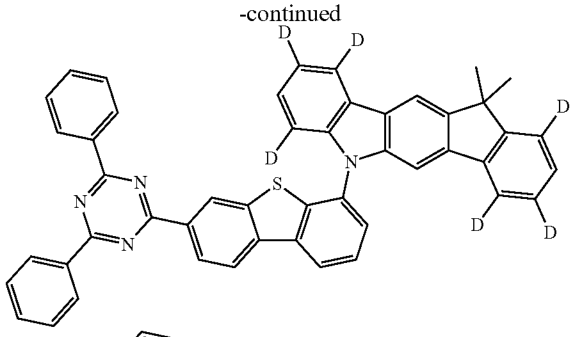

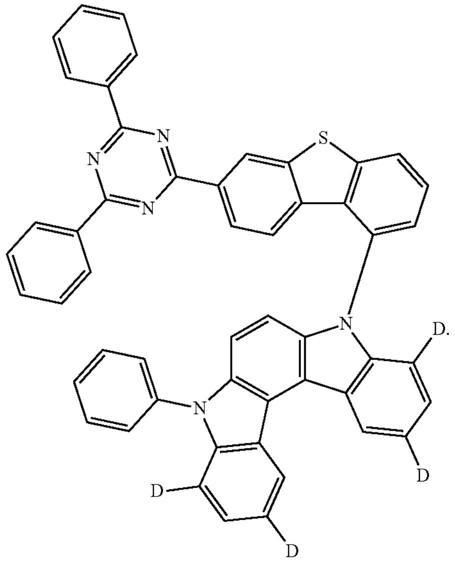

11. The organic light emitting device of claim 4, wherein each X is N.

12. The organic light emitting device of claim 9, wherein each $R_5$ is methyl or phenyl.

13. The organic light emitting device of claim 9, wherein each $R_6$ is phenyl.

14. The organic light emitting device of claim 7, wherein each $R_5$ is methyl or phenyl.

15. The organic light emitting device of claim 7, wherein each $R_6$ is phenyl.

* * * * *